United States Patent
Vechorkin et al.

(10) Patent No.: US 11,607,416 B2
(45) Date of Patent: Mar. 21, 2023

(54) BICYCLIC HETEROCYCLES AS FGFR INHIBITORS

(71) Applicant: Incyte Corporation, Wilmington, DE (US)

(72) Inventors: Oleg Vechorkin, Wilmington, DE (US); Minh Nguyen, Claymont, DE (US); Chao Qi, Newark, DE (US); Anlai Wang, Wilmington, DE (US); Michael Witten, Philadelphia, PA (US); Yao Xu, Wilmington, DE (US); Hai Fen Ye, Newark, DE (US); Ke Zhang, Wilmington, DE (US); Peng Zhao, Newark, DE (US); Wenqing Yao, Chadds Ford, PA (US)

(73) Assignee: Incyte Corporation, Wilmington, DE (US)

(*) Notice: Subject to any disclaimer, the term of this patent is extended or adjusted under 35 U.S.C. 154(b) by 195 days.

(21) Appl. No.: 17/070,160

(22) Filed: Oct. 14, 2020

(65) Prior Publication Data

US 2021/0106588 A1    Apr. 15, 2021

Related U.S. Application Data

(60) Provisional application No. 63/004,972, filed on Apr. 3, 2020, provisional application No. 62/914,766, filed on Oct. 14, 2019.

(51) Int. Cl.

| | |
|---|---|
| *A61K 31/5377* | (2006.01) |
| *A61P 35/00* | (2006.01) |
| *A61K 31/437* | (2006.01) |
| *A61K 31/496* | (2006.01) |
| *A61K 31/4995* | (2006.01) |
| *C07D 471/04* | (2006.01) |
| *C07D 519/00* | (2006.01) |

(52) U.S. Cl.
CPC ........ *A61K 31/5377* (2013.01); *A61K 31/437* (2013.01); *A61K 31/496* (2013.01); *A61K 31/4995* (2013.01); *A61P 35/00* (2018.01); *C07D 471/04* (2013.01); *C07D 519/00* (2013.01)

(58) Field of Classification Search
None
See application file for complete search history.

(56) References Cited

U.S. PATENT DOCUMENTS

| 850,370 A | 4/1907 | Hynes |
|---|---|---|
| 3,894,021 A | 7/1975 | Denzel et al. |
| 4,271,074 A | 6/1981 | Lohmann et al. |
| 4,339,267 A | 7/1982 | Levitt |
| 4,347,348 A | 8/1982 | Chemikhov et al. |
| 4,402,878 A | 9/1983 | D'Alelio et al. |
| 4,405,519 A | 9/1983 | D'Alelio et al. |
| 4,405,520 A | 9/1983 | D'Alelio et al. |
| 4,405,786 A | 9/1983 | D'Alelio et al. |
| 4,460,773 A | 7/1984 | Suzuki et al. |
| 4,874,803 A | 10/1989 | Baron et al. |
| 4,940,705 A | 7/1990 | Boshagen et al. |
| 5,159,054 A | 10/1992 | Keller |
| 5,240,941 A | 8/1993 | Bruneau |
| 5,480,887 A | 1/1996 | Hornback et al. |
| 5,521,184 A | 5/1996 | Zimmermann et al. |
| 5,536,725 A | 7/1996 | Cullen et al. |
| 5,541,324 A | 7/1996 | TenBrink et al. |
| 5,760,068 A | 6/1998 | Talley et al. |
| 5,783,577 A | 7/1998 | Houghten et al. |
| 5,845,025 A | 12/1998 | Garito et al. |
| 5,994,364 A | 11/1999 | Njoroge et al. |
| 6,465,484 B1 | 10/2002 | Bilodeau et al. |
| 6,998,408 B2 | 2/2006 | Pinto |
| 7,074,801 B1 | 7/2006 | Yoshida et al. |
| 7,125,880 B1 | 10/2006 | Chen |
| 7,488,802 B2 | 2/2009 | Collins et al. |
| 7,618,975 B2 | 11/2009 | Cai et al. |
| 7,642,255 B2 | 1/2010 | Sim |

(Continued)

FOREIGN PATENT DOCUMENTS

| CL | 2014003355 | 6/2015 |
|---|---|---|
| CL | 2015002628 | 8/2016 |

(Continued)

OTHER PUBLICATIONS

"Sabiosciences.com" [online]. "FGF Pathway," 2000-2012, [retrieved on Jun. 23, 2015], Retrieved from the Internet: URL <http://www.sabiosciences.com/pathway.php?sn=FGF_Signaling>, 3 pages.

(Continued)

*Primary Examiner* — Samantha L Shterengarts

(74) *Attorney, Agent, or Firm* — Fish & Richardson P.C.

(57) ABSTRACT

The present invention relates to bicyclic heterocycles, and pharmaceutical compositions of the same, that are inhibitors of the FGFR enzyme and are useful in the treatment of FGFR-associated diseases such as cancer.

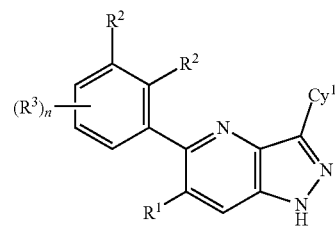

52 Claims, No Drawings

Specification includes a Sequence Listing.

(56) References Cited

U.S. PATENT DOCUMENTS

| | | |
|---|---|---|
| 7,648,973 B2 | 1/2010 | DeLuca et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,759,398 B2 | 1/2014 | Nelson |
| 8,754,114 B2 | 6/2014 | Yao et al. |
| 8,889,711 B2 | 11/2014 | Bedjeguelal |
| 9,266,892 B2 | 2/2016 | Zhuo et al. |
| 9,388,185 B2 | 7/2016 | Lu et al. |
| 9,533,954 B2 | 1/2017 | Yao et al. |
| 9,533,984 B2 | 1/2017 | Sun et al. |
| 9,580,423 B2 | 2/2017 | Lu et al. |
| 9,611,267 B2 | 4/2017 | Wu et al. |
| 9,708,318 B2 | 7/2017 | Lu et al. |
| 9,745,311 B2 | 8/2017 | Lu et al. |
| 9,801,889 B2 | 10/2017 | Lu et al. |
| 9,890,156 B2 | 2/2018 | Lu et al. |
| 10,016,348 B2 | 7/2018 | Lu et al. |
| 10,040,790 B2 | 8/2018 | Sun et al. |
| 10,131,667 B2 | 11/2018 | Wu et al. |
| 10,208,024 B2 | 2/2019 | Andrews et al. |
| 10,213,427 B2 | 2/2019 | Yao et al. |
| 10,214,528 B2 | 2/2019 | Lu et al. |
| 10,251,892 B2 | 4/2019 | Sokolsky et al. |
| 10,308,644 B2 | 6/2019 | Wu et al. |
| 10,350,240 B2 | 6/2019 | Gore et al. |
| 10,357,431 B2 | 7/2019 | Staric et al. |
| 10,450,313 B2 | 10/2019 | Lu et al. |
| 10,611,762 B2 | 4/2020 | Jia et al. |
| 10,632,126 B2 | 4/2020 | Lu et al. |
| 10,738,048 B2 | 8/2020 | Lu et al. |
| 10,813,930 B2 | 10/2020 | Yao et al. |
| 10,851,105 B2 | 12/2020 | Wu et al. |
| 10,947,230 B2 | 3/2021 | Sun et al. |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0127538 A1 | 7/2004 | Oinuma et al. |
| 2004/0204427 A1 | 10/2004 | Chen et al. |
| 2005/0009876 A1 | 1/2005 | Bhagwat et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0225286 A1 | 9/2007 | Ren et al. |
| 2007/0280943 A1 | 12/2007 | Friedman et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0216798 A1 | 8/2010 | Nakai et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0035153 A1 | 2/2012 | Saxty et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0210825 A1 | 8/2013 | Rehwinkel et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0194430 A1 | 7/2014 | Eis et al. |
| 2014/0228370 A1 | 8/2014 | Eis et al. |
| 2014/0243308 A1 | 8/2014 | Yao et al. |
| 2014/0288069 A1 | 9/2014 | Eis et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0038485 A1 | 2/2015 | Eis et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu et al. |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0260168 A1 | 9/2017 | Andrews et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0057486 A1 | 3/2018 | Wu et al. |
| 2018/0072718 A1 | 3/2018 | Liu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0244672 A1 | 8/2018 | Lu et al. |
| 2018/0273519 A1 | 9/2018 | Wu et al. |
| 2019/0040082 A1 | 2/2019 | Xiao et al. |
| 2019/0055237 A1 | 2/2019 | Pan et al. |
| 2019/0062327 A1 | 2/2019 | Sun et al. |
| 2019/0062345 A1 | 2/2019 | Xiao et al. |
| 2019/0071439 A1 | 3/2019 | Li et al. |
| 2019/0092767 A1 | 3/2019 | Li et al. |
| 2019/0127376 A1 | 5/2019 | Wu et al. |
| 2019/0127467 A1 | 5/2019 | Shah et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0240220 A1 | 8/2019 | Yao et al. |

(56) References Cited

U.S. PATENT DOCUMENTS

| | | |
|---|---|---|
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0300524 A1 | 10/2019 | Wu et al. |
| 2019/0337948 A1 | 11/2019 | Frietze et al. |
| 2019/0345170 A1 | 11/2019 | Wu et al. |
| 2020/0002338 A1 | 1/2020 | Jia et al. |
| 2020/0055853 A1 | 2/2020 | Ellies et al. |
| 2020/0095244 A1 | 3/2020 | Sun et al. |
| 2020/0255424 A1 | 8/2020 | Wu et al. |
| 2020/0270245 A1 | 8/2020 | Pan et al. |
| 2020/0277309 A1 | 9/2020 | Wu et al. |
| 2020/0306256 A1 | 10/2020 | Lu et al. |
| 2020/0377504 A1 | 12/2020 | Wu et al. |
| 2020/0399267 A1 | 12/2020 | Lu et al. |
| 2021/0009582 A1 | 1/2021 | Vechorkin et al. |
| 2021/0094935 A1 | 4/2021 | Vechorkin |

FOREIGN PATENT DOCUMENTS

| | | |
|---|---|---|
| CL | 2017000654 | 12/2017 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 20155017376 | 6/2015 |
| JP | 2018507214 | 3/2018 |
| JP | 2018511573 | 4/2018 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |
| WO | WO 2000/24744 | 5/2000 |
| WO | WO 2000/053595 | 9/2000 |
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |

(56) References Cited

FOREIGN PATENT DOCUMENTS

| | | |
|---|---|---|
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/64655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |

(56) References Cited

FOREIGN PATENT DOCUMENTS

| | | |
|---|---|---|
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2008/156712 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/085185 | 7/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148916 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |

(56) References Cited

FOREIGN PATENT DOCUMENTS

| | | |
|---|---|---|
| WO | WO 2010/064875 | 6/2010 |
| WO | WO 2010/067886 | 6/2010 |
| WO | WO 2010/067888 | 6/2010 |
| WO | WO 2010/075074 | 7/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |

(56) References Cited

FOREIGN PATENT DOCUMENTS

| | | |
|---|---|---|
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/028314 | 2/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/131627 | 6/2020 |
| WO | WO 2020/131674 | 6/2020 |

OTHER PUBLICATIONS

"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Arai et al., "Characterization of the cell or origin and propagation potential of the fibroblast growth factor 9-induced mouse model of lung adenocarcinoma," J. Pathol., Mar. 2015, 235(4): 593-605.
Arai et al., "Fibroblast growth factor receptor 2 tyrosine kinase fusions define a unique molecular subtype of cholangiocarcinoma," Hepatology, 2014, 59(4): 1427-1434.
Argentina Office Action in Argentina Application No. 20130102068, dated Jul. 17, 2020, 10 pages.
Argentina Office Action in Argentina Application No. 20140101651, dated Nov. 21, 2019, 5 pages.
Ash and Ash, "Handbook of Pharmaceutical Additives," Gower Publishing Company, 2007, 3rd ed, too voluminous to provide.
Atzrodt et al., "The Renaissance of H/D Exchange," Angew Chem Int Ed., 2007, 7744-7765.
Australian Office Action in Australian Application No. 2013287176, dated Sep. 12, 2017, 4 pages.
Australian Office Action in Australian Application No. 2014253798, dated Jul. 31, 2017, 4 pages.

(56) References Cited

OTHER PUBLICATIONS

Australian Office Action in Australian Application No. 2016219816, dated Aug. 26, 2019, 3 pages.
Australian Office Action in Australian Application No. 2016219822, dated Jul. 8, 2019, 4 pages.
Australian Office Action in Australian Application No. 2018208772, dated Jul. 1, 2018, 5 pages.
Australian Office Action in Australian Application No. 2019200066, dated Aug. 27, 2019, 6 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Bavin, "Polymorphism in Process Development," Chemistry & Industry, Society of Chemical Industry, Aug. 1989, 527-529.
Bazyl et al., "The selective ortho-methoxylation of pentafluorobenzoic acid—a new way to tetrafluorosalicylic acid and its derivatives," J Flour Chem., Feb. 11, 1999, 94(1):11-13.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 1977, 66(2):1-19.
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R)-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistiy, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growih Factor 1 (FGF-1) and FGF-2 Signaling Involved in ihe Invasive and Tumorigenic Behavior of Carchinoma Cells," Molecular Biology of ihe Cell, Oct. 2004, 15: 4725-4734.
Biocentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4; 14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J Combi Chem., 2003, 5:670.
Blom et al., Preparative LC-MS Purification: Improved Compound Specific Method Optimization, J Combi Chem. 2004, 6(6):874-883.
Blom, K., "Two-Pump at Column Dilution Configuration for Preparative LC-MS", J Combi Chem., 2002, 4:295.
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Borad et al., "Fibroblast growth factor receptor 2 fusions as a target for treating cholangiocarcinoma," Currrent opinion in Gastroenterology, May 2015, 31(3):264-268.
Brooks et al., "Fibroblast growth factor signaling: a new therapeutic opportunity in cancer," Clinical Cancer Research, 2012, 1-23.
Caira, "Crystalline Polymorphism of Organic Compounds,"Topics in Current Chemistry, Jan. 1, 1998, 198:163-208.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," PLOS ONE, Aug. 2015, 23 pages.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 1984-2017, dated Sep. 12, 2019, 9 pages.
Chilean Office Action in Chilean Application No. 2015-003089, dated Apr. 24, 2017, 13 pages (English Summary).
Chilean Office Action in Chilean Application No. 2015-003089, dated Jan. 23, 2018, 8 pages.

(56) References Cited

OTHER PUBLICATIONS

Chilean Office Action in Chilean Application No. 2122-2017, dated Apr. 22, 2019, 25 pages.
Chilean Office Action in Chilean Application No. 2122-2017, dated Nov. 15, 2019, 15 pages.
Chilean Office Action in Chilean Application No. 3355-2014, dated Jan. 18, 2017, 17 pages (with English translation).
Chilean Office Action in Chilean Application No. 3439-2019, dated Feb. 10, 2021, 26 pages.
Chilean Opposition in Chilean Application No. 3355-2014, dated Feb. 3, 2017, 3 pages (English translation only).
Chinese Office Action in Chinese Application No. 10874686.0, dated Oct. 8, 2019, 10 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Apr. 4, 2018, 10 pages (English Translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201680011332.7, dated Aug. 5, 2019, 14 pages.
Chinese Office Action in Chinese Application No. 201680011348.8, dated Aug. 2, 2019, 14 pages.
Chinese Office Action in Chinese Application No. 201710395346.X, dated Jan. 22, 2019, 17 pages.
Chinese Office Action in Chinese Application No. 201710395346.X, dated Sep. 9, 2019, 10 pages.
Chinese Office Action in Chinese Application No. 201710874686.0, dated Feb. 25, 2019, 17 pages.
Chng et al., "Translocation t(4; 14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Ciappetti and Geithlen "Molecular Variations Based on Isosteric Replacements," The Practice of Medicinal Chemistry, 2008, Chapter 15, pp. 290-341.
Cole et al., "Inhibition of FGFR2 and FGFR1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Nov. 29, 2018, 8 pages.
Colombian Office Action in Colombian Application No. NC2017/0008795, dated Aug. 16, 2019, 6 pages.
Colombian Office Action in Colombian Application No. NC2017/0008795, dated Aug. 29, 2017, 2 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2019/0009690, dated Jan. 22, 2020, 20 pages.
Cordovilla et al., "The Stille Reaction, 38 Years Later," ACS Catal., Apr. 17, 2015, 5(5):3040-3053.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Office Action in Costa Rican Application No. 2014-0577, dated Apr. 15, 2020, 18 pages.
Costa Rican Office Action in Costa Rican Application No. 2014-0577, dated Jun. 13, 2019, 17 pages.
Costa Rican Office Action in Costa Rican Application No. 2015-0578, dated Jun. 11, 2020, 15 pages.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.

(56) References Cited

OTHER PUBLICATIONS

Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
Eurasian Office Action in Eurasian Application No. 201590005, Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
European Communication pursuant to Article 94(3) EPC in European Application No. 13783125.1, dated Jan. 26, 2016, 4 pages.
European Office Action in European Application No. 18733045.1, dated Jan. 11, 2021, 5 pages.
European Office Action in European Application No. 20192679.7, dated Feb. 11, 2021, 7 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Faul et al., "FGF23 induces left ventricular hypertrophy," The Journal of Clinical Investigation, 2010, 1-16.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Feb. 2020, 135:109497.
Fukumoto and Yamashita, "FGF23 is a hormone-regulating phophate metabolism—Unique biological characteristics of FGF23," Bone, 2007, 1190-1195.
Furniss "Acidic/Basic characteristics for purification," Vogel's Textbook of Practical Organic Chemistry, 5th edition, 1989, 131-133, 135-143.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):o1741-o1742.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.

Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.
Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3):1540-1552.

(56) References Cited

OTHER PUBLICATIONS

Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications:Test Procedures and Acceptance Criteria for New Drug Substances and New Drug Products Chemical Substances," ICHTRRPHU, Oct. 6, 1999, 35 pages.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 9781/DELNP/2015, dated Jan. 18, 2019, 6 pages.
Indonesian Office Action in Indonesian Application No. P00201507153, dated Apr. 27, 2018, 5 pages (English Translation).
Indonesian Office Action in Indonesian Application No. PID201705977, dated Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, dated Jun. 25, 2013, 10 pages.
International Preliminary Report on Patentability in International Application No. PCT/US2013/045309, dated Dec. 24, 2014, 11 pages.
International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.

(56) References Cited

OTHER PUBLICATIONS

International Search Report and Written Opinion in International Application No. PCT/US2016/018787, dated Jun. 2, 2016, 12 pages.
International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/041104, dated Sep. 4, 2020, 14 pages.
International Search Report and Written Opinion in International Application. No. PCT/US2011/066473, dated Jun. 19, 2012, 15 pages.
International Search Report and Written Opinion in International Appln. No. PCT/US2020/063064, dated Feb. 12, 2021, 13 pages.
International Search Report and Written Opinion in International Appln. No. PCT/US2020/063038, dated Mar. 15, 2021, 16 pages.
International Search Report in International Application No. PCT/US2020/053436, dated Dec. 4, 2020, 15 pages.
International Search Report in Written Opinion in International Application No. PCT/US2020/055547, dated Jan. 11, 2021, 13 pages.
Invitation to Pay Additional Fees and, Where Applicable, Protest Fee in International Application No. PCT/US2013/045309, dated Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jackson et al., "8p11 Myeloproliferative syndrome: a review," Human Pathology, Apr. 1, 2010, 41:461-476.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Japanese Office Action in Japanese Application No. 2018-228352, dated Aug. 20, 2019, 6 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et. al., "Aurora kinase inhibitors based on the imidazo[1,2-a]pyrazine core: fluorine and deuterium incorporation improve oral absorption and exposure," J Med Chem., 2011, 54(1):201-210.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17:7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 28, 2020, 15 pages.
Kotha et al., "Recent applications of the Suzuki-Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.

(56) References Cited

OTHER PUBLICATIONS

Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS ONE, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)—mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.

(56) References Cited

OTHER PUBLICATIONS

New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 2433, dated Nov. 27, 2018, 13 pages.
Peruvian Office Action in Peruvian Application No. 1424, dated Mar. 12, 2021, 13 pages.
Philippine Office Action in Philippine Application No. 1/2017/501483, dated Dec. 12, 2019, 5 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Peruvian Office Action in Peruvian Application No. 1429, dated Mar. 19, 2021, 12 pages.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.

Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8; 13)(p11;q12) Myeloproliferative Syndrome," Blood, Sep. 1998, 92(5): 1735-1742.
Remington, "The Science and Practice of Pharmacy," Lippincott Williams & Wilkins, 2005, 21st edition Too voluminous to provide.
Remington's Pharmaceutical Sciences, 17th ed., Mack Publishing Company, Easton, Pa., 1985, p. 1418.
Renhowe et al., "Design, Structure-Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4; 14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Excipients," The Pharmaceutical Press and the American Pharmaceutical Association, 2009, 6th Edition, 917 pages.
Rowe et al., "Handbook of Pharmaceutical Additives," The Pharmaceutical Press and the American Pharmaceutical Association, 2009, 3rd ed., Too voluminous to provide.

(56) References Cited

OTHER PUBLICATIONS

Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-lllc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
STN Search Report dated Jan. 6, 2020, 88 pages.
STN International Search Report for CAS RN 2380276-25-3, dated Nov. 20, 2019, 11 pages.
STN Search Report, dated Sep. 11, 2019, 31 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (Carthamus tinctorius L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.

(56) References Cited

OTHER PUBLICATIONS

Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistiy Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.

Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Ukraine Office Action in Ukraine Application No. a201709220, dated Dec. 9, 2019, 11 pages.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
van Oers et al., "FGFR3 Mutations Indicate Better Survival in Invasive Upper Urinary Tract and Bladder Tumours," European Urology, 2009, 650-658.
Vatsveen et al., "FGFR3 is expressed and is important for survival in INA-6, a human myeloma cell line without a t(4;14)," Eur. J. Haematol., 83:5, Jul. 6, 2009, 471-476.
Vietnamese Office Action in Vietnamese Application No. 1-2015-00102, dated Mar. 18, 2015, 4 pages.
Vogt et al., "FGF23 and phosphate cardiovascular toxins in ckd," Toxins, Nov. 6, 2019, 11(11):647.
von Massenhausen et al., "Evaluation of FGFR3 as a Therapeutic Target in Head and Neck Squamous Cell Carcinoma," Targ. Oncol., 2016, 11: 631-642.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Wang et al., "The fibroblast growth factor receptor-4 Arg388 allele is associated with prostate cancer initiation and progression," Clin Cancer Res. 2004, 10:6169-6178.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale of Divergent Pathways," Nature Reviews, Sep. 2005, 5: 713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Xu et al. "Design, synthesis and biological evaluation of deuterated nintedanib for improving pharmacokinetic properties," J Label Compd Radiopharm., 2015, 58(7):308-312.
Ying et al., "Genome-wide screening for genetic alterations in esophageal cancer by aCGH identifies 11q13 amplification oncogenes associated with nodal metastasis," PLoS One, Jun. 25, 2012, 7:e39797.
Yu et al., "Analysis of the Biochemical Mechanisms for the Endocrine Actions of Fibroblast Growth Factor-23," Endocrinology, Nov. 2005, 146(11): 4647-4656.

(56) References Cited

OTHER PUBLICATIONS

Yu et al., "FGFR-4 Arg(3)(8)(8) enhances prostate cancer progression via extracellular signal-related kinase and serum response factor signaling," Clin Cancer Res., Jul. 2011, 17:4355-4366.

Zaid et al., "Identification of FGFR4 as a Potential Therapeutic Target for Advanced-Stage, High-Grade Serous Ovarian Cancer," Clin Cancer Res, 2013, 19(4): 809-820.

Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.

Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.

Zhang et al., "Enhanced FGFR signalling predisposes pancreatic cancer to the effect of a potent FGFR inhibitor in preclinical models," British Journal of Cancer, 2014, 110: 320-329.

Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.

Zhang et al., "Recent progress in therapeutic and diagnostic applications of lanthanides," Mini-Reviews in Medicinal Chemistry, 2011, 11(8):678-694.

Zhang et al., "Receptor Specificity of the Fibroblast Growth Factor Family," Journal of Biological Chemistry, Jun. 2006, 281(23): 15694-15700.

Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.

Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.

Zhao et al., "Homozygous Deletions and Chromosome Amplifications in Human Lung Carcinomas Revealed by Single Nucleotide Polymorphism Array Analysis," Cancer Res, Jul. 2005, 5561-5570.

Zhou et al., "A Structure-Guided Approach to Creating Covalent FGFR Inhibitors," Chemistry and Biology, Mar. 2010, 285-295.

Zhu et al., "Fibroblast growth factor receptor 3 inhibition by short hairpin RNAs leads to apoptosis in multiple myeloma," Mol Cancer Ther, May 2005, 787-798.

Zieger et al., "Role of Activating Fibroblast Growth Factor Receptor 3 Mutations in the Development of Bladder Tumors," Clin Cancer Res, Nov. 2005, 7709-7719.

Zingone et al., "Ectopic expression of wild-type FGFR3 cooperates with MYC to accelerate development of B-cell lineage neoplasms," Leukemia, 2010, 1171-1178.

SEQUENCE LISTING

<160> NUMBER OF SEQ ID NOS: 1

<210> SEQ ID NO 1
<211> LENGTH: 15
<212> TYPE: PRT
<213> ORGANISM: Artificial
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15

BICYCLIC HETEROCYCLES AS FGFR INHIBITORS

FIELD OF THE INVENTION

The present disclosure relates to bicyclic heterocycles, and pharmaceutical compositions of the same, that are inhibitors of the enzyme FGFR and are useful in the treatment of FGFR-associated diseases such as cancer.

BACKGROUND OF INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005, 16, 139-149). Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described (Reviewed in Knights and Cook, Pharmacology & Therapeutics, 2010, 125, 105-117; Turner and Grose, Nature Reviews Cancer, 2010, 10, 116-129). Large scale DNA sequencing of thousands of tumor samples has revealed that FGFR genes are altered in many cancers (Helsten et al. Clin Cancer Res. 2016, 22, 259-267). Some of these activating mutations are identical to germline mutations that lead to skeletal dysplasia syndromes (Gallo et al. Cytokine & Growth Factor Reviews 2015, 26, 425-449). Mechanisms that lead to aberrant ligand-dependent signaling in human disease include overexpression of FGFs and changes in FGFR splicing that lead to receptors with more promiscuous ligand binding abilities. Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, colorectal, endometrial, gastric, head and neck, kidney, lung, ovarian, prostate); hematopoietic malignancies (e.g., multiple myeloma, acute myelogenous leukemia, and myeloproliferative neoplasms); and other neoplasms (e.g., glioblastoma and sarcomas). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer, and the FGFR inhibitors described herein help address this need.

SUMMARY OF INVENTION

The present disclosure is directed to compounds having Formula (I):

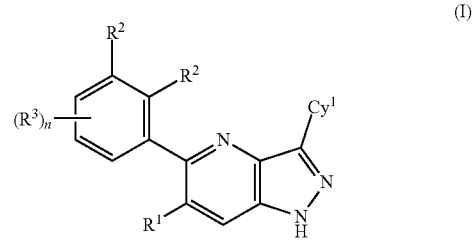

or pharmaceutically acceptable salts thereof, wherein constituent variables are defined herein.

The present disclosure is further directed to pharmaceutical compositions comprising a compound of Formula (I), or a pharmaceutically acceptable salt thereof, and at least one pharmaceutically acceptable carrier.

The present disclosure is further directed to methods of inhibiting an FGFR enzyme (e.g., an FGFR3 enzyme) comprising contacting the enzyme with a compound of Formula (I), or a pharmaceutically acceptable salt thereof.

The present disclosure is further directed to a method of treating a disease associated with abnormal activity or expression of an FGFR enzyme (e.g., an FGFR3 enzyme), comprising administering a compound of Formula (I), or a pharmaceutically acceptable salt thereof, to a patient in need thereof.

The present disclosure is further directed to compounds of Formula (I) for use in treating a disease associated with abnormal activity or expression of an FGFR enzyme (e.g., an FGFR3 enzyme).

The present disclosure is further directed to a method for treating a disorder mediated by an FGFR enzyme (e.g., an FGFR3 enzyme), or a mutant thereof, in a patient in need thereof, comprising the step of administering to said patient a compound of Formula (I), or pharmaceutically acceptable composition thereof.

The present disclosure is further directed to a method for treating a disorder mediated by an FGFR enzyme (e.g., an FGFR3 enzyme), or a mutant thereof, in a patient in need thereof, comprising the step of administering to the patient a compound of Formula (I), or a pharmaceutically acceptable salt thereof, or a composition comprising a compound of Formula (I), or a pharmaceutically acceptable salt thereof, in combination with another therapy or therapeutic agent as described herein.

Provided herein is also a method of treating cancer in a patient in need thereof comprising administering to the patient a therapeutically effective amount of Formula I wherein the cancer is characterized by an FGFR2 and/or FGFR3 alteration.

The present disclosure is further directed to the use of compounds of Formula (I) in the preparation of a medicament for use in therapy.

DETAILED DESCRIPTION

Compounds

In one aspect, the present disclosure provides compounds of Formula (I):

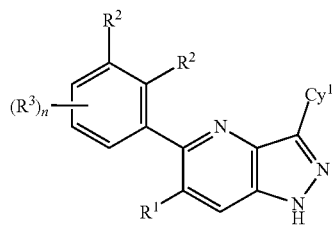

I or a pharmaceutically acceptable salt thereof, wherein:

$Cy^1$ is selected from phenyl and 5-6 membered heteroaryl; wherein each 5-6 membered heteroaryl has at least one ring-forming carbon atom and 1, 2, or 3 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1, 2, 3 or 4 substituents independently selected from $R^{10}$;

$R^1$ is selected from halo, $C_{1-6}$ alkyl, $C_{2-6}$ alkenyl, $C_{2-6}$ alkynyl, $C_{1-6}$ haloalkyl, $C_{3-6}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, $C_{1-6}$ alkylamino, di($C_{1-6}$alkyl)amino, $C_{1-6}$ alkylthio, $C_{1-6}$ alkylsulfonyl, $C_{1-6}$ alkylcarbonyl, and $C_{1-6}$ alkoxycarbonyl; wherein optionally one or more H atoms of the $C_{1-6}$ alkyl, $C_{2-6}$ alkenyl, $C_{2-6}$ alkynyl, $C_{1-6}$ haloalkyl, $C_{3-6}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, $C_{1-6}$ alkylamino, di($C_{1-6}$alkyl)amino, $C_{1-6}$ alkylthio, $C_{1-6}$ alkylsulfonyl, $C_{1-6}$ alkylcarbonyl, and $C_{1-6}$ alkoxycarbonyl are replaced by one or more D atoms;

each $R^2$ and $R^3$ are independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

or two adjacent $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming heteroatoms independently selected from N, O, and S; wherein a ring-forming carbon atom of each fused 5- or 6-membered heterocycloalkyl ring is optionally substituted by oxo to form a carbonyl group; and wherein the fused 5- or 6-membered cycloalkyl ring, and the fused 5- or 6-membered heterocycloalkyl ring are each optionally substituted with 1, 2, 3 or 4 substituents independently selected from $R^{21}$;

n is selected from 0, 1, 2, and 3;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-12 membered heterocycloalkyl, $C_{6-10}$ aryl, 5-10 membered heteroaryl, $C_{3-10}$ alkylene, 4-12 membered heterocycloalkyl-$C_{1-3}$alkylene, $C_{6-10}$ aryl-$C_{1-3}$ alkylene, 5-10 membered heteroaryl-$C_{1-3}$alkylene, halo, D, CN, $NO_2$, $OR^{a1}$ $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ alkylene, 4-10 membered heterocycloalkyl-$C_{1-3}$alkylene, $C_{6-10}$ alkylene, 5-10 membered heteroaryl-$C_{1-3}$alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, (O)$R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl, are each optionally substituted with 1, 2, 3, or 4 substituents independently selected from $R^g$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ alkylene, 4-10 membered heterocycloalkyl-$C_{1-3}$alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$ $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$ $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamoyl, di($C_{1-6}$alkyl)carbamyl, amino sulfonyl, $C_{1-6}$ alkylaminosulfonyl and di($C_{1-6}$ alkyl)aminosulfonyl;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamoyl, di($C_{1-6}$alkyl)carbamyl, amino sulfonyl, $C_{1-6}$ alkylaminosulfonyl and di($C_{1-6}$ alkyl)aminosulfonyl;

each $R^{a3}$, $R^{c3}$ and $R^{d3}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamoyl, di($C_{1-6}$alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$ alkyl)aminocarbonylamino.

In one aspect, the present disclosure provides compounds of Formula (I):

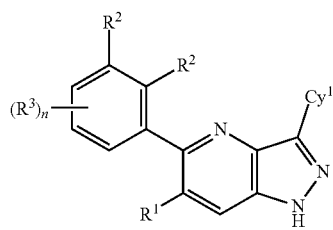

I or a pharmaceutically acceptable salt thereof, wherein:

$Cy^1$ is selected from phenyl, pyridinyl and pyrazolyl; wherein the phenyl pyridinyl and pyrazolyl are each optionally substituted with 1, 2, 3 or 4 substituents independently selected from $R^{10}$;

$R^1$ is selected from halo, $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$alkyl)amino; wherein any of the H atoms of the $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$alkyl)amino can be replaced by D atoms;

each $R^2$ and $R^3$ are independently selected from $C_{1-6}$ alkyl, $C_{2-6}$ alkenyl, $C_{1-6}$ haloalkyl, $C_{3-6}$ cycloalkyl, 4-6 membered heterocycloalkyl, halo, CN, $OR^{a2}$, $C(O)R^{b2}$, $C(O)NR^{c2}R^{d2}$, $C(O)OR^{a2}$, $NR^{c2}R^{d2}$, and $S(O)_2R^{b2}$; wherein said $C_{1-6}$ alkyl, $C_{2-6}$ alkenyl, $C_{3-6}$ cycloalkyl, and 4-6 membered heterocycloalkyl are each optionally substituted with 1, 2, 3, or 4 substituents independently selected from $R^{21}$;

or two adjacent $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming heteroatoms independently selected from O and N; wherein a ring-forming carbon atom of each fused 5- or 6-membered heterocycloalkyl ring is optionally substituted by oxo to form a carbonyl group; and wherein the fused 5- or 6-membered cycloalkyl ring, and the fused 5- or 6-membered heterocycloalkyl ring are each optionally substituted with 1, 2, 3 or 4 substituents independently selected from $R^{21}$;

n is selected from 0 and 1;

each $R^{10}$ is independently selected from $C_{1-6}$ alkyl, $C_{1-6}$ haloalkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a1}$, $C(O)R^{b1}$, $(O)NR^{c1}R^{d1}$, $C(O)OR^{a1}$; $NR^{c1}R^{d1}$; $NR^{c1}C(O)R^{b1}$, and $S(O)_2R^{b1}$; wherein said $C_{1-6}$ alkyl, $C_{3-10}$ cycloalkyl, 4-12 membered heterocycloalkyl, $C_{6-10}$ aryl, 5-10 membered heteroaryl, $C_{3-10}$ alkylene, 4-12 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $SR^{a3}$, $C(O)R^{b3}$, $C(O)NR^{c3}R^{d3}$, $C(O)OR^{a3}$; $NR^{c3}R^{d3}$, $NR^{c3}C(O)R^{b3}$, $NR^{c3}C(O)OR^{a3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{12}$;

each $R^{12}$ is independently selected from $C_{1-6}$ alkyl, $C_{1-6}$ haloalkyl, $C_{3-6}$ cycloalkyl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $S(O)_2R^{b5}$, and $S(O)_2NR^{c5}R^{d5}$; wherein said $C_{1-6}$ alkyl, $C_{3-6}$ cycloalkyl, and 4-7 membered heterocycloalkyl, are each optionally substituted with 1, 2, 3, or 4 substituents independently selected from $R^g$;

each $R^{21}$ is independently selected from $C_{1-6}$ alkyl, $C_{1-6}$ haloalkyl, halo, D, CN, $OR^{a4}$, $C(O)R^{b4}$, $(O)NR^{c4}R^{d4}$, $C(O))R^{a4}$, $NR^{c4}R^{d4}$, and $S(O)_2R^{b4}$; wherein said $C_{1-6}$ alkyl, is optionally substituted with 1, 2, or 3 substituents independently selected from $R^{22}$;

each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1 or 2 substituents independently selected from $R^g$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{b1}$ is independently selected from $C_{1-6}$ alkyl, $C_{1-6}$ haloalkyl, $C_{3-10}$ cycloalkyl, and 4-10 membered heterocycloalkyl, wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{a2}$, $R^{b2}$ and $R^{d2}$, is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, or 6-membered heterocycloalkyl group optionally substituted with 1, 2 or 3 substituents independently selected from $R^{21}$;

each $R^{b2}$ is independently selected from $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{21}$;

each $R^{a3}$, $R^{c3}$ and $R^{d3}$, is independently selected from H, $C_{1-6}$ alkyl, $C_{1-6}$ haloalkyl, $C_{3-6}$ cycloalkyl, and 4-7 membered heterocycloalkyl; wherein said $C_{1-6}$ alkyl $C_{3-6}$ cycloalkyl, and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{1-6}$ haloalkyl, $C_{3-6}$ cycloalkyl, and 4-7 membered heterocycloalkyl; wherein said $C_{1-6}$ alkyl $C_{3-6}$ cycloalkyl, and 4-7 membered heterocycloalkyl, are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^{22}$;

each $R^{b4}$ is independently selected from $C_{1-6}$ alkyl, and $C_{1-6}$ haloalkyl; wherein said $C_{1-6}$ alkyl is optionally substituted with 1, 2, 3, or 4 substituents independently selected from $R^{22}$;

each $R^{a5}$, $R^{c5}$ and $R^{d5}$, is independently selected from H, $C_{1-6}$ alkyl, and $C_{1-6}$ haloalkyl; wherein said $C_{1-6}$ alkyl, is optionally substituted with 1, 2, 3, or 4 substituents independently selected from $R^{g}$;

each $R^{b5}$ is independently selected from $C_{1-6}$ alkyl, and $C_{1-6}$ haloalkyl; wherein said $C_{1-6}$ alkyl is optionally substituted with 1, 2, 3, or 4 substituents independently selected from $R^{g}$;

each $R^{a6}$, $R^{b6}$ and $R^{d6}$, is independently selected from H, $C_{1-6}$ alkyl, and $C_{1-6}$ haloalkyl; wherein said $C_{1-6}$ alkyl, is optionally substituted with 1, 2, 3, or 4 substituents independently selected from $R^{g}$;

each $R^{b6}$ is independently selected from $C_{1-6}$ alkyl, and $C_{1-6}$ haloalkyl; wherein said $C_{1-6}$ alkyl, is optionally substituted with 1, 2, 3, or 4 substituents independently selected from $R^{g}$; and each $R^{g}$ is independently selected from OH, CN, halo, $C_{1-6}$ alkyl, $C_{1-6}$ haloalkyl, $C_{3-6}$ cycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, cyano-$C_{1-3}$ alkyl, $H_2N$—$C_{1-3}$ alkyl, amino, $C_{1-6}$ alkylamino, di($C_{1-6}$alkyl)amino, $C_{1-6}$alkylthio, $C_{1-6}$alkylsulfonyl, carboxy, $C_{1-6}$ alkylcarbonyl, $C_{1-6}$ alkoxycarbonyl, and $C_{1-6}$ alkylcarbonylamino.

In one aspect, the present disclosure provides compounds of Formula (I):

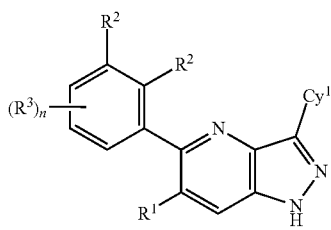

I or a pharmaceutically acceptable salt thereof, wherein:

$Cy^1$ is selected from phenyl, pyridine-3-yl and pyrazol-4-yl; wherein the phenyl, pyridine-3-yl and pyrazol-4-yl of $Cy^1$ are each optionally substituted with 1 substituent selected from $R^{10}$;

$R^1$ is selected from Cl, $C_{1-3}$ alkyl, $C_{1-3}$ haloalkyl, cyclopropyl, azedinyl, hydroxymethyl, $C_{1-3}$ alkoxy, $C_{1-3}$ haloalkoxy and $C_{1-3}$ alkylamino; wherein the $C_{1-3}$ alkyl, $C_{1-3}$ haloalkyl, cyclopropyl, azedinyl, hydroxymethyl, $C_{1-3}$ alkoxy, $C_{1-3}$ haloalkoxy and $C_{1-3}$ alkylamino are each optionally substituted with 1, 2, 3, 4, 5, 6, or 7 deuteriums;

each $R^2$ is independently selected from $C_{1-3}$ alkyl, $C_{1-3}$ haloalkyl, $C_{3-6}$ cycloalkyl, F, Cl, CN, and $OR^{a2}$; wherein said $C_{1-3}$ alkyl, and $C_{3-6}$ cycloalkyl, are each optionally substituted with 1, 2 or 3 substituents independently selected from $R^{21}$;

or the $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5- or 6-membered cycloalkyl ring, and the fused 5- or 6-membered heterocycloalkyl ring are each optionally substituted with 1 or 2 substituents independently selected from $R^{21}$;

n is 0;

each $R^{10}$ is independently selected from $C_{1-3}$ alkyl, $C_{1-3}$ haloalkyl, $C_{3-6}$ cycloalkyl, 4-10 membered heterocycloalkyl, 5-6 membered heteroaryl, 4-10 membered heterocycloalkyl-$C_{1-2}$ alkylene, 5-6 membered heteroaryl-$C_{1-2}$alkylene, F, Cl, D, CN, $OR^{a1}$, $C(O)NR^{c1}R^{d1}$, and $NR^{c1}R^{d1}$, wherein said $C_{1-3}$ alkyl, $C_{3-6}$ cycloalkyl, 4-10 membered heterocycloalkyl, 5-6 membered heteroaryl, 4-10 membered heterocycloalkyl-$C_{1-2}$ alkylene, and 5-6 membered heteroaryl-$C_{1-2}$ alkylene are each optionally substituted with 1 or 2 substituents independently selected from $R^{11}$;

each $R^{11}$ is independently selected from $C_{1-3}$ alkyl, $C_{1-3}$ haloalkyl, $C_{3-6}$ cycloalkyl, 4-10 membered heterocycloalkyl, 5-6 membered heteroaryl, F, Cl, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}S(O)_2R^{b3}$, $S(O)_2R^{b3}$, and $S(O)_2NR^{c3}R^{d3}$; wherein said $C_{1-3}$ alkyl, $C_{3-6}$ cycloalkyl, 4-10 membered heterocycloalkyl, and 5-6 membered heteroaryl, are each optionally substituted with 1 or 2 substituents independently selected from $R^{12}$;

each $R^{12}$ is independently selected from $C_{1-3}$ alkyl, $C_{1-3}$ haloalkyl, $C_{3-6}$ cycloalkyl, 4-7 membered heterocycloalkyl, F, Cl, D, CN, $OR^{a5}$, $C(O)R^{b5}$, $C(O)NR^{c5}R^{d5}$, and $NR^{c5}R^{d5}$; wherein said $C_{1-3}$ alkyl, $C_{3-6}$ cycloalkyl, and 4-7 membered heterocycloalkyl, are each optionally substituted with 1 substituent independently selected from $R^{g}$;

$R^{21}$ is independently selected from $C_{1-3}$ alkyl, F, Cl, D, CN, and $OR^{a4}$; wherein said $C_{1-3}$ alkyl, is optionally substituted with 1 or 2 substituents independently selected from $R^{22}$;

each $R^{22}$ is independently selected from F, Cl, D, CN, and $OR^{a6}$;

each $R^{a1}$, $R^{c1}$ and $R^{d1}$ is independently selected from H, $C_{1-3}$ alkyl, $C_{1-3}$ haloalkyl, and 4-6 membered heterocycloalkyl; wherein said $C_{1-3}$ alkyl, and 4-6 membered heterocycloalkyl, are each optionally substituted with 1 substituent independently selected from $R^{11}$;

each $R^{a2}$ is independently selected from H, $C_{1-3}$ alkyl, and $C_{1-3}$ haloalkyl;

each $R^{a3}$, $R^{c3}$ and $R^{d3}$, is independently selected from H, $C_{1-3}$ alkyl, $C_{1-3}$ haloalkyl, $C_{3-6}$ cycloalkyl, and 4-6 membered heterocycloalkyl; wherein said $C_{1-3}$ alkyl $C_{3-6}$ cycloalkyl, and 4-6 membered heterocycloalkyl are each optionally substituted with 1 or 2 substituents independently selected from $R^{12}$;

or any $R^{c3}$ and $R^{d3}$ attached to the same N atom, together with the N atom to which they are attached, form a 4-, 5- or 6-membered heterocycloalkyl group optionally substituted with 1 or 2 substituents independently selected from $R^{12}$;

each $R^{b3}$ is independently selected from $C_{1-3}$ alkyl, $C_{1-3}$ haloalkyl, $C_{3-6}$ cycloalkyl, and 4-6 membered heterocycloalkyl; wherein said $C_{1-3}$ alkyl $C_{3-6}$ cycloalkyl, and 4-6 membered heterocycloalkyl, are each optionally substituted with 1 or 2 substituents independently selected from $R^{12}$;

each $R^{a4}$ is independently selected from H, $C_{1-3}$ alkyl, and $C_{1-3}$ haloalkyl;

each $R^{a5}$, $R^{c5}$ and $R^{d5}$, is independently selected from H, $C_{1-3}$ alkyl, and $C_{1-3}$ haloalkyl; wherein said $C_{1-3}$ alkyl, is optionally substituted with 1 substituent independently selected from $R^g$;

each $R^{b5}$ is independently selected from $C_{1-3}$ alkyl, and $C_{1-3}$ haloalkyl; wherein said $C_{1-3}$ alkyl is optionally substituted with 1 substituents independently selected from $R^g$;

each $R^{a6}$ is independently selected from H, and $C_{1-3}$ alkyl; and each $R^g$ is independently selected from OH, CN, F, Cl, alkyl, and $C_{1-3}$ haloalkyl.

In some embodiments, $Cy^1$ is selected from phenyl, pyridinyl and pyrazolyl; wherein the phenyl, pyridinyl, and pyrazolyl are each optionally substituted with 1, 2, 3 or 4 substituents independently selected from $R^{10}$. In some embodiments, $Cy^1$ is selected from phenyl, pyridinyl and pyrazolyl; wherein the phenyl, pyridinyl, and pyrazolyl are each optionally substituted with 1 or 2 substituents independently selected from $R^{10}$. In some embodiments, $Cy^1$ is selected from phenyl, pyridinyl and pyrazolyl; wherein the phenyl, pyridinyl, and pyrazolyl are each optionally substituted with 1 substituent selected from $R^{10}$. In some embodiments, $Cy^1$ is selected from phenyl, pyridinyl and pyrazolyl; wherein the phenyl, pyridinyl, and pyrazolyl are each substituted with 1 substituent selected from $R^{10}$.

In some embodiments, $Cy^1$ is selected from phenyl, pyridin-3-yl and pyrazol-4-yl; wherein the phenyl, pyridin-3-yl, and pyrazol-4-yl are each optionally substituted with 1 substituent selected from $R^{10}$. In some embodiments, $Cy^1$ is selected from phenyl, pyridin-3-yl and pyrazol-4-yl; wherein the phenyl, pyridin-3-yl, and pyrazol-4-yl are each substituted with 1 substituent selected from $R^{10}$.

In some embodiments, $Cy^1$ is 5-6 membered heteroaryl optionally substituted with 1 or 2 substituents selected from $R^{10}$. In some embodiments, $Cy^1$ is selected from pyridin-3-yl and pyrazol-4-yl; wherein the pyridin-3-yl, and pyrazol-4-yl are each optionally substituted with 1 substituent selected from $R^{10}$.

In some embodiments, $Cy^1$ is pyrazol-4-yl optionally substituted with 1 or 2 substituents selected from $R^{10}$. In some embodiments, $Cy^1$ is selected from pyrazol-4-yl and pyridine-3-yl; wherein the pyrazol-4-yl and pyridin-3-yl are each optionally substituted with 1 or 2 substituents selected from $R^{10}$. In some embodiments, $Cy^1$ is pyridin-3-yl optionally substituted with 1 or 2 substituents selected from $R^{10}$. In some embodiments, $Cy^1$ is phenyl optionally substituted with 1 or 2 substituents selected from $R^{10}$.

In some embodiments, $R^1$ is selected from halo, $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$ alkyl)amino; wherein optionally one or more H atoms of the $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$ alkyl) amino are replaced by one or more D atoms.

In some embodiments, $R^1$ is selected from Cl, alkyl, $C_{1-3}$ haloalkyl, cyclopropyl, azetidinyl, hydroxymethyl, $C_{1-3}$ alkoxy, $C_{1-3}$ haloalkoxy and $C_{1-3}$ alkylamino; wherein optionally one or more H atoms of the $C_{1-3}$ alkyl, $C_{1-3}$ haloalkyl, cyclopropyl, azetidinyl, hydroxymethyl, $C_{1-3}$ alkoxy, $C_{1-3}$ haloalkoxy and $C_{1-3}$ alkylamino are replaced by one or more D atoms.

In some embodiments, $R^1$ is selected from Cl, $C_{1-2}$ alkyl, $C_{1-2}$ haloalkyl, cyclopropyl, hydroxymethyl, $C_{1-2}$ alkoxy, $C_{1-2}$ haloalkoxy and $C_{1-2}$ alkylamino; wherein optionally one or more H atoms of the $C_{1-2}$ alkyl, $C_{1-2}$ haloalkyl, cyclopropyl, hydroxymethyl, $C_{1-2}$ alkoxy, $C_{1-2}$ haloalkoxy and $C_{1-2}$ alkylamino are replaced by D atoms.

In some embodiments, $R^1$ is selected from Cl, $C_{1-2}$ alkyl, $C_{1-2}$ haloalkyl, hydroxymethyl, $C_{1-2}$ alkoxy, $C_{1-2}$ haloalkoxy and $C_{1-2}$ alkylamino; wherein optionally one or more H atoms of the $C_{1-2}$ alkyl, $C_{1-2}$ haloalkyl, hydroxymethyl, $C_{1-2}$ alkoxy, $C_{1-2}$ haloalkoxy and $C_{1-2}$ alkylamino are replaced by one or more D atoms.

In some embodiments, $R^1$ is selected from Cl, $CH_3$, $OCH_3$, $OCD_3$, $OCH_2CH_3$, $OCHF_2$, $NHCH_3$, $CHF_2$, and $CH_2OH$.

In some embodiments, $R^1$ is $C_{1-2}$ alkoxy. In some embodiments, $R^1$ is $OCH_3$. In some embodiments, $R^1$ is $OCD_3$.

In some embodiments, each $R^2$ and $R^3$ are independently selected from $C_{1-6}$ alkyl, $C_{2-6}$ alkenyl, $C_{1-6}$ haloalkyl, $C_{3-6}$ cycloalkyl, 4-6 membered heterocycloalkyl, halo, CN, $OR^{a2}$, $(O)R^{b2}$, $(O)NR^{c2}R^{d2}$, $C(O)OR^{a2}$, $NR^{c2}R^{d2}$, and $S(O)_2R^{b2}$; wherein said $C_{1-6}$ alkyl, $C_{2-6}$ alkenyl, $C_{3-6}$ cycloalkyl, and 4-6 membered heterocycloalkyl are each optionally substituted with 1, 2, 3, or 4 substituents independently selected from $R^{21}$.

In some embodiments, each $R^2$ is independently selected from $C_{1-6}$ alkyl, $C_{1-3}$ haloalkyl, $C_{3-6}$ cycloalkyl, halo, CN, and $OR^{a2}$; wherein said $C_{1-6}$ alkyl and $C_{3-6}$ cycloalkyl are each optionally substituted with 1, 2, 3, or 4 substituents independently selected from $R^{21}$.

In some embodiments, each $R^2$ is independently selected from $C_{1-6}$ alkyl, $C_{3-6}$ cycloalkyl, halo, and $OR^{a2}$; wherein said $C_{1-6}$ alkyl and $C_{3-6}$ cycloalkyl are each optionally substituted with 1, 2, 3, or 4 substituents independently selected from $R^{21}$.

In some embodiments, two adjacent $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming heteroatoms independently selected from O and N; wherein a ring-forming carbon atom of each fused 5- or 6-membered heterocycloalkyl ring is optionally substituted by oxo to form a carbonyl group; and wherein the fused 5- or 6-membered cycloalkyl ring, and the fused 5- or 6-membered heterocycloalkyl ring are each optionally substituted with 1, 2, 3 or 4 substituents independently selected from $R^{21}$.

In some embodiments, two adjacent $R^2$ substituents on the phenyl ring, taken together with the atoms to which they are attached, form a fused 5-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5-membered cycloalkyl ring, and the fused 5- or 6-membered heterocycloalkyl ring are each optionally substituted with 1 or 2 substituents independently selected from $R^{21}$.

In some embodiments, each $R^2$ is independently selected from $C_{3-6}$ cycloalkyl, $C_{1-2}$ alkyl, $C_{1-2}$ haloalkyl, F, Cl, CN, and $OR^{a2}$; wherein said $C_{1-2}$ alkyl is optionally substituted with 1 substituent selected from $R^{21}$.

In some embodiments, each $R^2$ is independently selected from $C_{1-3}$ alkyl, $C_{1-3}$ haloalkyl, F, Cl, CN, and $OR^{a2}$; wherein said $C_{1-6}$ alkyl is optionally substituted with 1 substituent selected from $R^{21}$.

In some embodiments, each $R^2$ is independently selected from $C_{1-2}$ alkyl, $C_{1-2}$ haloalkyl, F, Cl, CN, and $OR^{a2}$; wherein said $C_{1-2}$ alkyl is optionally substituted with 1 substituent selected from $R^{21}$.

In some embodiments, each $R^2$ is independently selected from $C_{1-3}$ alkyl, $C_{1-3}$ haloalkyl, $C_{3-6}$ cycloalkyl, F, Cl, CN, and $OR^{a2}$; wherein said $C_{1-3}$ alkyl, and $C_{3-6}$ cycloalkyl, are each optionally substituted with 1, 2 or 3 substituents independently selected from $R^{21}$.

In some embodiments, each $R^2$ is independently selected from $C_{1-2}$ alkyl and F; wherein said $C_{1-2}$ alkyl is optionally substituted with 1 substituent selected from $R^{21}$.

In some embodiments, each $R^2$ is independently selected from F, methyl, $CH_2CN$, and $CD_3$.

In some embodiments, each $R^2$ is independently selected from F, methyl, $CH_2CN$, cyclopropyl, and $CD_3$.

In some embodiments, each $R^2$ is independently selected from F, methyl, $CH_2CN$, $CD_3$, OH, $OCH_3$, and cyclopropyl.

In some embodiments, each $R^2$ is $C_{1-2}$ alkyl. In some embodiments, each $R^2$ is methyl.

In some embodiments, the $R^2$ substituents on the phenyl ring, taken together with the atoms to which they are attached, form a fused 5-membered cycloalkyl ring, or a fused 5-heterocycloalkyl ring; wherein the fused 5-membered heterocycloalkyl ring has at least one ring-forming carbon atom and 1 or 2 ring-forming O atoms; and wherein the fused 5-membered cycloalkyl ring and the fused 5-membered heterocycloalkyl ring are each optionally substituted with 1 or 2 substituents selected from $R^{21}$.

In some embodiments, the $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5- or 6-membered cycloalkyl ring, or the fused 5- or 6-membered heterocycloalkyl ring are each optionally substituted with 1 substituent selected from $R^{21}$.

In some embodiments, the $R^2$ substituents, taken together with the atoms to which they are attached, form a fused cyclopentyl group or a fused tetrahydrofuranyl group, each of which is optionally substituted with 1 or 2 substituents selected from $R^{21}$.

In some embodiments, the $R^2$ substituents, taken together with the atoms to which they are attached, form a fused cyclopentyl group, a fused tetrahydrofuranyl group, a fused 1,4-dioxanyl group, or a fused tetrahydropyranyl group, each of which is optionally substituted with 1 or 2 substituents selected from $R^{21}$.

In some embodiments, the $R^2$ substituents, taken together with the atoms to which they are attached, form a fused cyclopentyl group optionally substituted with 1 or 2 substituents independently selected from OH, CN, $CH_2OH$, and F.

In some embodiments, the $R^2$ substituents, taken together with the atoms to which they are attached, form a fused cyclopentyl group optionally substituted with 1 or 2 substituents independently selected from D, OH, CN, $CH_2OH$, and F.

In some embodiments, the $R^2$ substituents, taken together with the atoms to which they are attached, form a fused cyclopentyl group or a fused cyclohexyl group; wherein the fused cyclopentyl group and the fused cyclohexyl group have at least one ring-forming carbon atom and each optionally have 1 or 2 ring-forming O atoms; and wherein the fused cyclopentyl group and the fused cyclohexly group are each optionally substituted with 1 or 2 substituents independently selected from D, OH, CN, $CH_2OH$, and F.

In some embodiments, the $R^2$ substituents, taken together with the atoms to which they are attached, form a fused cyclopentyl group.

In some embodiments, n is selected from 0 and 1.

In some embodiments, n is 0. In some embodiments, n is 1.

In some embodiments, each $R^{10}$ is independently selected from $C_{1-6}$ alkyl, $C_{1-6}$ haloalkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene, 5-10 membered heteroaryl-$C_{1-3}$ alkylene halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $S(O)_2R^{b1}$; wherein said $C_{1-6}$ alkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$.

In some embodiments, each $R^{10}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$alkylene, 4-6 membered heterocycloalkyl-$C_{1-3}$alkylene, phenyl-$C_{1-3}$alkylene, 5-6 membered heteroaryl-$C_{1-3}$ alkylene halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $S(O)_2R^{b1}$; wherein said $C_{1-6}$ alkyl, $C_{3-6}$ cycloalkyl, 4-6 membered heterocycloalkyl, phenyl, 5-6 membered heteroaryl, $C_{3-6}$ cycloalkyl-$C_{1-3}$alkylene, 4-6 membered heterocycloalkyl-$C_{1-3}$alkylene, phenyl-$C_{1-3}$alkylene and 5-6 membered heteroaryl-$C_{1-3}$ alkylene are each optionally substituted with 1, 2, 3, or 4 substituents independently selected from $R^{11}$.

In some embodiments, each $R^{10}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$alkylene, 4-6 membered heterocycloalkyl-$C_{1-3}$alkylene, phenyl-$C_{1-3}$alkylene, 5-6 membered heteroaryl-$C_{1-3}$ alkylene halo, D, CN, $OR^{a1}$, $C(O)R^{b1}$, $C(O)NR^{c1}R^{d1}$, $C(O)OR^{a1}$, $NR^{c1}R^{d1}$ $NR^{c1}C(O)R^{b1}$, and $S(O)_2R^{b1}$; wherein said $C_{1-6}$ alkyl, $C_{3-6}$ cycloalkyl, 4-6 membered heterocycloalkyl, phenyl, 5-6 membered heteroaryl, $C_{3-6}$ cycloalkyl-$C_{1-3}$alkylene, 4-6 membered heterocycloalkyl-$C_{1-3}$alkylene, phenyl-$C_{1-3}$alkylene and 5-6 membered heteroaryl-$C_{1-3}$ alkylene are each optionally substituted with 1 or 2 substituents independently selected from $R^{11}$.

In some embodiments, each $R^{10}$ is independently selected from $C_{1-3}$ alkyl, $C_{1-3}$ haloalkyl, $C_{3-6}$ cycloalkyl, 4-10 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, $OR^{a1}$, $C(O)NR^{c1}R^{d1}$, and $NR^{c1}R^{d1}$; (wherein the $C_{1-3}$ alkyl, $C_{3-6}$ cycloalkyl, 4-10 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from $R^{11}$.

In some embodiments, each $R^{10}$ is independently selected from $C_{1-3}$ alkyl, $C_{1-3}$ haloalkyl, $C_{3-6}$ cycloalkyl, 4-10 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, C(O)NR$^{c1}$R$^{d1}$, and NR$^{c1}$R$^{d1}$; wherein the $C_{1-3}$ alkyl, $C_{3-6}$ cycloalkyl, 4-10 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from R$^{11}$.

In some embodiments, each R$^{10}$ is independently selected from $C_{1-3}$ alkyl, $C_{1-3}$ haloalkyl, OR$^{a1}$, $C_{3-6}$ cycloalkyl, 4-10 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, C(O)NR$^{c1}$R$^{d1}$, and NR$^{c1}$R$^{d1}$; wherein the $C_{1-3}$ alkyl, $C_{3-6}$ cycloalkyl, 4-10 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from R$^{11}$.

In some embodiments, each R$^{10}$ is independently selected from $C_{1-3}$ alkyl, $C_{1-3}$ haloalkyl, $C_{3-6}$ cycloalkyl, 4-10 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, C(O)NR$^{c1}$R$^{d1}$, and NR$^{c1}$R$^{d1}$; wherein the $C_{1-3}$ alkyl, $C_{3-6}$ cycloalkyl, 4-10 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 substituent selected from R$^{11}$, and optionally substituted with a second substituent selected from $C_{1-2}$ alkyl.

In some embodiments, each R$^{10}$ is independently selected from $C_{1-3}$ alkyl, $C_{1-3}$ haloalkyl, OR$^{a1}$, $C_{3-6}$ cycloalkyl, 4-10 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, C(O)NR$^{c1}$R$^{d1}$, and NR$^{c1}$R$^{d1}$; (wherein the $C_{1-3}$ alkyl, $C_{3-6}$ cycloalkyl, 4-10 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 substituent selected from R$^{11}$, and optionally substituted with a second substituent selected from $C_{1-2}$ alkyl.

In some embodiments, each R$^{10}$ is independently selected from $C_{1-3}$ alkyl, $C_{1-3}$ haloalkyl, $C_{3-6}$ cycloalkyl, 4-6 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, C(O)NR$^{c1}$R$^{d1}$, and NR$^{c1}$R$^{d1}$; wherein the $C_{1-3}$ alkyl, $C_{3-6}$ cycloalkyl, 4-6 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from R$^{11}$.

In some embodiments, each R$^{10}$ is independently selected from $C_{1-3}$ alkyl, $C_{1-3}$ haloalkyl, halo, D, CN, C(O)NR$^{c1}$R$^{d1}$, and NR$^{c1}$R$^{d1}$; wherein the $C_{1-3}$ alkyl is optionally substituted with 1 or 2 substituents independently selected from R$^{11}$.

In some embodiments, each R$^{10}$ is independently selected from $C_{3-6}$ cycloalkyl, 4-6 membered heterocycloalkyl, 5-6 membered heteroaryl, 4-6 membered heterocycloalkyl-$C_{1-2}$ alkylene, and 5-6 membered heteroaryl-$C_{1-2}$ alkylene; wherein the $C_{3-6}$ cycloalkyl, 4-6 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from R$^{11}$.

In some embodiments, each R$^{10}$ is independently selected from $C_{1-2}$ alkyl, $C_{1-2}$ haloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, 1-oxa-3,8-diazaspiro[4.5]decan-2-one, F, Cl, D, CN, and NR$^{c1}$R$^{d1}$; wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, and (pyridinyl)methyl are each optionally substituted with 1 or 2 substituents independently selected from R$^{11}$.

In some embodiments, each R$^{10}$ is independently selected from $C_{1-2}$ alkyl, $C_{3-6}$ cycloalkyl, halo, D, CN, OR$^{a1}$, C(O)NR$^{c1}$R$^{d1}$, NR$^{c1}$R$^{d1}$, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, thiomorpholinyl, 1-oxa-3,8-diazaspiro[4.5]decan-2-one, and hexahydropyrrolo[1,2-a]pyrazin-2(1H)-yl; wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, thiomorpholinyl, 1-oxa-3,8-diazaspiro[4.5]decan-2-one, and hexahydropyrrolo[1,2-a]pyrazin-2(1H)-yl are each optionally substituted with 1 or 2 substituents independently selected from R$^{11}$.

In some embodiments, each R$^{10}$ is independently selected from $C_{1-2}$ alkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, thiomorpholinyl, 1-oxa-3,8-diazaspiro[4.5]decan-2-one, and hexahydropyrrolo[1,2-a]pyrazin-2(1H)-yl, wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl) methyl, (triazolyl)methyl, thiomorpholinyl, 1-oxa-3,8-diazaspiro[4.5]decan-2-one, and hexahydropyrrolo[1,2-a]pyrazin-2(1H)-yl are each optionally substituted with 1 or 2 substituents independently selected from R$^{11}$ In some embodiments, when R$^{10}$ is 4-10 membered heterocycloalkyl, a heteroatom of the heterocycloalkyl ring is substituted with R$^{11}$ within acceptable valence. In some embodiments, when R$^{10}$ is 4-6 membered heterocycloalkyl, a heteroatom of the heterocycloalkyl ring is substituted with R$^{11}$ within acceptable valence. In some embodiments, an S atom of the heterocycloalkyl ring is substituted with NR. In some embodiments, an S atom of the heterocycloalkyl ring is substituted with NR and O.

In some embodiments, each R$^{10}$ is independently selected from $C_{1-2}$ alkyl, $C_{1-2}$ haloalkyl, F, Cl, D, CN, and NR$^{c1}$R$^{d1}$; wherein the $C_{1-2}$ alkyl is optionally substituted with 1 or 2 substituents independently selected from R$^{11}$.

In some embodiments, each R$^{10}$ is independently selected from $C_{1-2}$ alkyl, $C_{1-2}$ haloalkyl, F, Cl, D, CN, OR$^{a1}$, and NR$^{c1}$R$^{d1}$; wherein the $C_{1-2}$ alkyl is optionally substituted with 1 or 2 substituents independently selected from R$^{11}$.

In some embodiments, each R$^{10}$ is independently selected from $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazinyl)methyl, and 1-oxa-3,8-diazaspiro[4.5]decan-2-one; wherein the $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, and (pyridinyl)methyl are each optionally substituted with 1 or 2 substituents independently selected from $R^{11}$.

In some embodiments, each $R^{10}$ is independently selected from $C_{1-2}$ alkyl, $C_{1-2}$ haloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazinyl)methyl, 1-oxa-3,8-diazaspiro[4.5]decan-2-one, F, Cl, D, CN, $NR^{c1}R^{d1}$; wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, and (pyridinyl)methyl are each optionally substituted with 1 substituent selected from $R^{11}$, and optionally substituted with a second substituent selected from $C_{1-2}$ alkyl.

In some embodiments, each $R^{10}$ is independently selected from $C_{1-2}$ alkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, and 1-oxa-3,8-diazaspiro[4.5]decan-2-one; wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl and (triazolyl)methyl are each optionally substituted with 1 or 2 substituents independently selected from $R^{11}$.

In some embodiments, each $R^{10}$ is independently selected from $C_{1-2}$ alkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, and 1-oxa-3,8-diazaspiro[4.5]decan-2-one; wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl and (triazolyl)methyl are each optionally substituted with 1 substituent selected from $R^{11}$, and optionally substituted with a second substituent selected from $C_{1-2}$ alkyl.

In some embodiments, each $R^{10}$ is independently selected from methyl, (1-methyl-1H-1,2,4-triazol-5-yl)methyl, pyrrolidin-3-yl, pyrrolidin-1-yl, 1-ethylpyrrolidin-3-yl, 1-methylazetidin-3-yl, 1-ethylazetidin-3-yl, 4-acetylpiperazin-1-yl, 3-cyanocyclobutyl, 1-(dimethylcarbamoyl)piperidin-4-yl, 1-(methoxycarbonyl)piperidin-4-yl, 1-(methoxycarbonyl)azetidin-3-yl, 1-acetylazetidin-3-yl, 1-(methylsulfonyl)azetidin-3-yl, 1-(dimethylcarbamoyl)azetidin-3-yl, 1-(cyclopropanecarbonyl)azetidin-3-yl, pyridin-4-ylmethyl, 2-morpholinoethyl, cyclopropyl, 2-cyanoethyl, 2-hydroxyethyl, pyridin-4-yl, 4-hydroxycyclohexyl, 4-methylpiperazin-1-yl, 4-ethylpiperazin-1-yl, morpholino, 4-methyl-3-oxopiperazin-1-yl, 4-hydroxypiperidin-1-yl, (R)-3,4-dimethylpiperazin-1-yl, (1S,4S)-5-methyl-2,5-diazabicyclo[2.2.1]heptan-2-yl, 4-(dimethylcarbamoyl)piperidin-1-yl, 4-carboxy-4-methylpiperidin-1-yl, (1 S,4 S)-4-acetamidocyclohexyl, 2,4-dimethylpiperazin-1-yl, 4-(ethylcarbamoyl)piperazin-1-yl, 4-carbamoylpiperazin-1-yl, 4-isopropylpiperazin-1-yl, 4-ethylpiperazin-1-yl, 2-oxo-1-oxa-3,8-diazaspiro[4.5]decan-8-yl, pyridin-2-ylmethyl, 1-acetylpiperidin-4-yl), and 1-(methoxycarbonyl)piperidin-4-yl.

In some embodiments, each $R^{10}$ is independently selected from methyl, (1-methyl-1H-1,2,4-triazol-5-yl)methyl, pyrrolidin-3-yl, pyrrolidin-1-yl, 1-ethylpyrrolidin-3-yl, 1-methylazetidin-3-yl, 1-ethylazetidin-3-yl, 4-acetylpiperazin-1-yl, 3-cyanocyclobutyl, 1-(dimethylcarbamoyl)piperidin-4-yl, 1-(methoxycarbonyl)piperidin-4-yl, 1-(methoxycarbonyl)azetidin-3-yl, 1-acetylazetidin-3-yl, 1-(methylsulfonyl)azetidin-3-yl, 1-(dimethylcarbamoyl)azetidin-3-yl, 1-(cyclopropanecarbonyl)azetidin-3-yl, pyridin-4-ylmethyl, 2-morpholinoethyl, cyclopropyl, 2-cyanoethyl, 2-hydroxyethyl, pyridin-4-yl, 4-hydroxycyclohexyl, 4-methylpiperazin-1-yl, 4-ethylpiperazin-1-yl, morpholino, 4-methyl-3-oxopiperazin-1-yl, 4-hydroxypiperidin-1-yl, (R)-3,4-dimethylpiperazin-1-yl, (1S,4S)-5-methyl-2,5-diazabicyclo[2.2.1]heptan-2-yl, 4-(dimethylcarbamoyl)piperidin-1-yl, 4-carboxy-4-methylpiperidin-1-yl, (1S,4S)-4-acetamidocyclohexyl, 2,4-dimethylpiperazin-1-yl, 4-(ethylcarbamoyl)piperazin-1-yl, 4-carbamoylpiperazin-1-yl, 4-isopropylpiperazin-1-yl, 4-ethylpiperazin-1-yl, 2-oxo-1-oxa-3,8-diazaspiro[4.5]decan-8-yl, pyridin-2-ylmethyl, 1-acetylpiperidin-4-yl), 1-(methoxycarbonyl)piperidin-4-yl, (tetrahydrofuran-3-yl)oxy, 1-methyl-5-oxopyrrolidin-3-yl, 1-(2-hydroxypropanoyl)piperidin-4-yl, 1-(2-hydroxyacetyl)piperidin-4-yl, 4-carboxycyclohexyl, 3-amino-4-fluoropyrrolidin-1-yl, (7R,8aS)-7-hydroxyhexahydropyrrolo[1,2-a]pyrazin-2(1H)-yl, (7R,8aS)-7-hydroxyhexahydropyrrolo[1,2-a]pyrazin-2(1H)-yl, 4-imino-4-oxo-4$\lambda^6$-piperazin-1-yl, (2-hydroxy-N-methylacetamido)pyrrolidin-1-yl, 4-(2-hydroxyethyl)piperazin-1-yl, 2-methoxyethoxy, (tetrahydro-2H-pyran-4-yl)oxy, cyclopropyl, and 3-(2-hydroxy-N-methylacetamido)azetidin-1-yl.

In some embodiments, each $R^{10}$ is independently selected from 1-(2-hydroxyacetyl)pyrrolidin-3-yl, 1-acetylpiperidin-3-yl, 1-(3'-pyrrolidin-2'-one)pyrrolidin-3-yl, 1-(1'-methyl-(3'-pyrrolidin-2'-one))pyrrolidin-3-yl, 1-(2-propanamide)pyrrolidin-3-yl, 1-(methyl-L-prolyl)piperidin-4-yl, 1-(4-methylmorpholin-3-yl)pyrrolidin-3-yl, 3-cyanocyclobut-1-yl, 1-(hydroxymethylcarbonyl)azetidin-3-yl, 1-(2-(dimethylamino)ethanecarbonyl)azetidin-3-yl, 1-(dimethylamino-methyl-acetyl)azetidin-3-yl, 1-((1-methylazetidin-2-yl)carbonyl)azetidin-3-yl, 1-(2-(4-methylpiperazin-1-yl)ethan-1-one)azetidin-3-yl, 1-(2-(4-hydroxypiperazin-1-yl)ethan-1-one)azetidin-3-yl, 1-((1-methylazetidin-2-yl)carbonyl)azetidin-3-yl, 1-(hydroxy-methyl-acetyl)azetidin-3-yl, 1-((trans)-3-hydroxycyclobutylcarbonyl)azetidin-3-yl, 1-((cis)-3-hydroxycyclobutylcarbonyl)azetidin-3-yl, 1-((4-methylmorpholin-3-yl)carbonyl)azetidin-3-yl, 1-(hydroxyl-acetyl)pyrrolidin-3-yl, 1-((tetrahydrofuran-2-yl)carbonyl)azetidin-3-yl, 1-((tetrahydrofuran-3-yl)carbonyl)azetidin-3-yl, 1-(hydroxy-methyl-acetyl)pyrrolidin-3-yl, 1-(3-hydroxybutanoyl)azetidin-3-yl, 1-((–3-hydroxy-3-methylcyclobutyl)carbonyl)azetidin-3-yl, 1-(4-methylmorpholin-3-yl)carbonyl)pyrrolidin-3-yl, 1-((hydroxymethyl)cyclobutylcarbonyl)azetidin-3-yl, 1-((1-ethylazetidin-2-yl)carbonyl)azetidin-3-yl, 1-((1-(2-fluoroethyl)azetidin-2-yl)carbonyl)azetidin-3-yl, 1-((1-isopropylazetidin-2-yl)carbonyl)azetidin-3-yl, 1-((1-(2-fluoroethyl)azetidin-2-yl)carbonyl)pyrrolidin-3-yl, 1-((trans)-3-hydroxycyclobutylcarbonyl)pyrrolidin-3-yl, 1-((cis)-3-hydroxycyclobutylcarbonyl)pyrrolidin-3-yl, 1-((3-hydroxy-3-methylcyclobutyl)carbonyl)pyrrolidin-3-yl, 1-(2-methoxyethan-1-one)azetidin-3-yl, 1-(2-(dimethylamino)-2-methylpropan-1-one)azetidin-3-yl, 1-((cyclopropane-1-carbonitrile)carbonyl)azetidin-3-yl, 1-((ethan-1-ol)sulfonyl)azetidin-3-yl, 1-((N,N-dimethylethan-1-amine)sulfonyl)azetidin-3-yl, 1-((2-methoxyethyl)carboxylate)azetidin-3-yl, 1-((3-methoxycyclobutyl)carbonyl)azetidin-3-yl, 3-(2-hydroxy-N-methylacetamide)cyclopentyl, 3-(2-hydroxypropanamid)cyclopentyl, 3-(2-hydroxyacetamide)cyclopentyl, 3-(2-hydroxyethyl)-3-azabicyclo[3.1.0]hexan-1-yl, (4-hydroxypiperidin-1-yl)methyl, (2-oxa-5-azabicyclo[2.2.1]heptan-5-yl)methyl, 1-(morpholin-4-yl)ethyl, (5,6,7, 8-tetrahydro-[1,2,4]triazolo[1,5-a]pyrazine-7-yl)methyl, 1-(2-hydroxyethyl)piperidin-4-yl-4-carbonitrile, 1-(2-hydroxyacetyl)piperidin-4-yl-4-carbonitrile, 2-methoxyethylpiperazin-1-yl, 1-(tetrahydro-2H-pyran-4-carbonyl)piperidin-4-yl-4-d, 1-(2-methoxyacetyl)pyrrolidin-3-yl, 1-(tetrahydrofuran-2-carbonyl)pyrrolidin-3-yl, 3-(2-hydroxy-N-methylacetamide)azetidin-1-yl, 1-((tetrahydrofuran-2-yl)carbonyl)azetidin-3-yl, 1-((1-methylpiperidin-2-yl)carbonyl)azetidin-3-yl, 1-(2-(dimethylamino)ethan-1-one)azetidin-3-yl, 1-(3-hydroxypropan-1-one)azetidin-3-yl, 1-(2-hydroxyethan-1-one)azetidin-3-yl, 1-(2-hydroxypropan-1-one)azetidin-3-yl, 1-(2-hydroxy-N-methylacetamide)cyclobut-3-yl, 1-(2-hydroxyethan-1-one)-3-d-azetidin-3-yl, 1-carboxylatepiperidin-4-yl, 1-(morpholine-4-carbonyl)piperidin-4-yl, 1-acetylpyrrolidin-3-yl, 1-(morpholine-4-carbonyl)pyrrolidin-3-yl, cyanomethyl, 1-propanenitrile-azetidin-3-yl, 1-(2-methoxy-N-methylacetamide)cyclobut-3-yl, 1-(3-hydroxy-N-methylpropanamide)cyclobut-3-yl, 1-(2-hydroxy-N-methylpropanamide)cyclobut-3-yl, 1-(2-hydroxyethan-1-one)azabicyclo[3.1.0]hexan-3-yl, 1-((4-methylmorpholin-3-yl)carbonyl)azabicyclo[3.1.0]hexan-3-yl, 1-(tetrahydro-2H-pyran-4-yl)azabicyclo[3.1.0]hexan-3-yl, 1-(ethan-1-ol)azabicyclo[3.1.0]hexan-3-yl, 1-(4-methylmorpholine-3-carbonyl)-3-carbonitrile-pyrrolidin-3-yl, 1-(4-methylmorpholine-3-carbonyl)-4-carbonitrile-piperdin-4-yl, 1-(2-hydroxyacetyl)-3-carbonitrile-pyrrolidin-3-yl, (1,3-dimethylpiperazin-4-yl-2-one)methyl, and (2-oxa-5-azabicyclo[2.2.1]heptan-5-yl)methyl.

In some embodiments, each $R^{10}$ is independently selected from methyl, (1-methyl-1H-1,2,4-triazol-5-yl)methyl, pyrrolidin-3-yl, pyrrolidin-1-yl, 1-ethylpyrrolidin-3-yl, 1-methylazetidin-3-yl, 1-ethylazetidin-3-yl, 4-acetylpiperazin-1-yl, 3-cyanocyclobutyl, 1-(dimethylcarbamoyl)piperidin-4-yl, 1-(methoxycarbonyl)piperidin-4-yl, 1-(methoxycarbonyl)azetidin-3-yl, 1-acetylazetidin-3-yl, 1-(methylsulfonyl)azetidin-3-yl, 1-(dimethylcarbamoyl)azetidin-3-yl, 1-(cyclopropanecarbonyl)azetidin-3-yl, pyridin-4-ylmethyl, 2-morpholinoethyl, cyclopropyl, 2-cyanoethyl, 2-hydroxyethyl, pyridin-4-yl, 4-hydroxycyclohexyl, 4-methylpiperazin-1-yl, 4-ethylpiperazin-1-yl, morpholino, 4-methyl-3-oxopiperazin-1-yl, 4-hydroxypiperidin-1-yl, (R)-3,4-dimethylpiperazin-1-yl, (1S,4S)-5-methyl-2,5-diazabicyclo[2.2.1]heptan-2-yl, 4-(dimethylcarbamoyl)piperidin-1-yl, 4-carboxy-4-methylpiperidin-1-yl, (1S,4S)-4-acetamidocyclohexyl, 2,4-dimethylpiperazin-1-yl, 4-(ethylcarbamoyl)piperazin-1-yl, 4-carbamoylpiperazin-1-yl, 4-isopropylpiperazin-1-yl, 4-ethylpiperazin-1-yl, 2-oxo-1-oxa-3,8-diazaspiro[4.5]decan-8-yl, pyridin-2-ylmethyl, 1-acetylpiperidin-4-yl), 1-(methoxycarbonyl)piperidin-4-yl, (tetrahydrofuran-3-yl)oxy, 1-methyl-5-oxopyrrolidin-3-yl, 1-(2-hydroxypropanoyl)piperidin-4-yl, 1-(2-hydroxyacetyl)piperidin-4-yl, 4-carboxycyclohexyl, 3-amino-4-fluoropyrrolidin-1-yl, (7R,8aS)-7-hydroxyhexahydropyrrolo[1,2-a]pyrazin-2(1H)-yl, (7R,8aS)-7-hydroxyhexahydropyrrolo[1,2-a]pyrazin-2(1H)-yl, 4-imino-4-oxo-4$\lambda^6$-piperazin-1-yl, (2-hydroxy-N-methylacetamido)pyrrolidin-1-yl, 4-(2-hydroxyethyl)piperazin-1-yl, 2-methoxyethoxy, (tetrahydro-2H-pyran-4-yl)oxy, cyclopropyl, and 3-(2-hydroxy-N-methylacetamido)azetidin-1-yl, 1-(2-hydroxyacetyl)pyrrolidin-3-yl, 1-acetylpiperidin-3-yl, 1-(3'-pyrrolidin-2'-one)pyrrolidin-3-yl, 1-(1'-methyl-(3'-pyrrolidin-2'-one))pyrrolidin-3-yl, 1-(2-propanamide)pyrrolidin-3-yl, 1-(methyl-L-prolyl)piperidin-4-yl, 1-(4-methylmorpholin-3-yl)pyrrolidin-3-yl, 3-cyanocyclobut-1-yl, 1-(hydroxymethylcarbonyl)azetidin-3-yl, 1-(2-(dimethylamino)ethane-carbonyl)azetidin-3-yl, 1-(dimethylamino-methyl-acetyl)azetidin-3-yl, 1-((1-methylazetidin-2-yl)carbonyl)azetidin-3-yl, 1-(2-(4-methylpiperazin-1-yl)ethan-1-one)azetidin-3-yl, 1-(2-(4-hydroxypiperazin-1-yl)ethan-1-one)azetidin-3-yl, 1-((1-methylazetidin-2-yl)carbonyl)azetidin-3-yl, 1-(hydroxy-methyl-1-((trans)-3-hydroxycyclobutylcarbonyl)azetidin-3-yl, 1-((cis)-3-hydroxycyclobutylcarbonyl)azetidin-3-yl, 1-((4-methylmorpholin-3-yl)carbonyl)azetidin-3-yl, 1-(hydroxyl-acetyl)pyrrolidin-3-yl, 1-((tetrahydrofuran-2-yl)carbonyl)azetidin-3-yl, 1-((tetrahydrofuran-3-yl)carbonyl)azetidin-3-yl, 1-(hydroxy-methylacetyl)pyrrolidin-3-yl, 1-(3-hydroxybutanoyl)azetidin-3-yl, 1-((-3-hydroxy-3-methylcyclobutyl)carbonyl)azetidin-3-yl, 1-(4-methylmorpholin-3-yl)carbonyl)pyrrolidin-3-yl, 1-((hydroxymethyl)cyclobutylcarbonyl)azetidin-3-yl, 1-((1-ethylazetidin-2-yl)carbonyl)azetidin-3-yl, 1-((1-(2-fluoroethyl)azetidin-2-yl)carbonyl)azetidin-3-yl, 1-((1-isopropylazetidin-2-yl)carbonyl)azetidin-3-yl, 1-((1-(2-fluoroethyl)azetidin-2-yl)carbonyl)pyrrolidin-3-yl, 1-((trans)-3-hydroxycyclobutylcarbonyl)pyrrolidin-3-yl, 1-((cis)-3-hydroxycyclobutylcarbonyl)pyrrolidin-3-yl, 1-((3-hydroxy-3-methylcyclobutyl)carbonyl)pyrrolidin-3-yl, 1-(2-methoxyethan-1-one)azetidin-3-yl, 1-(2-(dimethylamino)-2-methylpropan-1-one)azetidin-3-yl, 1-((cyclopropane-1-carbonitrile)carbonyl)azetidin-3-yl, 1-((ethan-1-ol)sulfonyl)azetidin-3-yl, 1-((N,N-dimethylethan-1-amine) sulfonyl)azetidin-3-yl, 1-((2-methoxyethyl)carboxylate)azetidin-3-yl, 1-((3-methoxycyclobutyl)carbonyl)azetidin-3-yl, 3-(2-hydroxy-N-methylacetamide)cyclopentyl, 3-(2-hydroxypropanamid)cyclopentyl, 3-(2-hydroxyacetamide)cyclopentyl, 3-(2-hydroxyethyl)-3-azabicyclo[3.1.0]hexan-1-yl, (4-hydroxypiperidin-1-yl)methyl, (2-oxa-5-azabicyclo[2.2.1]heptan-5-yl)methyl, 1-(morpholin-4-yl)ethyl, (5,6,7,8-tetrahydro-[1,2,4]triazolo[1,5-a]pyrazine-7-yl)methyl, 1-(2-hydroxyethyl)piperidin-4-yl-4-carbonitrile, 1-(2-hydroxyacetyl)piperidin-4-yl-4-carbonitrile, 2-methoxyethylpiperazin-1-yl, 1-(tetrahydro-2H-pyran-4-carbonyl)piperidin-4-yl-4-d, 1-(2-methoxyacetyl)pyrrolidin-3-yl, 1-(tetrahydrofuran-2-carbonyl)pyrrolidin-3-yl, 3-(2-hydroxy-N-methylacetamide)azetidin-1-yl, 1-((tetrahydrofuran-2-yl)carbonyl)azetidin-3-yl, 1-((1-methylpiperidin-2-yl)carbonyl)azetidin-3-yl, 1-(2-(dimethylamino)ethan-1-one)azetidin-3-yl, 1-(3-hydroxypropan-1-one)azetidin-3-yl, 1-(2-hydroxyethan-1-one)azetidin-3-yl, 1-(2-hydroxypropan-1-one)azetidin-3-yl, 1-(2-hydroxy-N-methylacetamide)cyclobut-3-yl, 1-(2-hydroxyethan-1-one)-3-d-azetidin-3-yl, 1-carboxylatepiperidin-4-yl, 1-(morpholine-4-carbonyl)piperidin-4-yl, 1-acetylpyrrolidin-3-yl, 1-(morpholine-4-carbonyl)pyrrolidin-3-yl, cyanomethyl, 1-propanenitrile-azetidin-3-yl, 1-(2-methoxy-N-methylacetamide)cyclobut-3-yl, 1-(3-hydroxy-N-methylpropanamide)cyclobut-3-yl, 1-(2-hydroxy-N-methylpropanamide)cyclobut-3-yl, 1-(2-hydroxyethan-1-one)azabicyclo[3.1.0]hexan-3-yl, 1-((4-methylmorpholin-3-yl)carbonyl)azabicyclo[3.1.0]hexan-3-yl, 1-(tetrahydro-2H-pyran-4-yl)azabicyclo[3.1.0]hexan-3-yl, 1-(ethan-1-ol)azabicyclo[3.1.0]hexan-3-yl, 1-(4-methylmorpholine-3-carbonyl)-3-carbonitrile-pyrrolidin-3-yl, 1-(4-methylmorpholine-3-carbonyl)-4-carbonitrile-piperdin-4-yl, 1-(2-hydroxyacetyl)-3-carbonitrile-pyrrolidin-3-yl, (1,3-dimethylpiperazin-4-yl-2-one)methyl, and (2-oxa-5-azabicyclo[2.2.1]heptan-5-yl)methyl.

In some embodiments, each $R^{11}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{12}$.

In some embodiments, each $R^{11}$ is independently selected from $C_{1-6}$ alkyl, $C_{1-6}$ haloalkyl, $C_{3-6}$ cycloalkyl, 5-6 membered heteroaryl, 4-6 membered heterocycloalkyl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{3-6}$ cycloalkyl, 5-6 membered heteroaryl, and 4-6 membered heterocycloalkyl are each optionally substituted with 1, 2, or 3 substituents independently selected from $R^{12}$.

In some embodiments, each $R^{11}$ is independently selected from $C_{1-3}$ alkyl, $C_{1-3}$ haloalkyl, $C_{3-4}$ cycloalkyl, 5-6 membered heteroaryl, 4-6 membered heterocycloalkyl, halo, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, and $S(O)_2R^{b3}$; wherein said $C_{1-3}$ alkyl, $C_{3-4}$ cycloalkyl, 5-6 membered heteroaryl, and 4-6 membered heterocycloalkyl are each optionally substituted with 1 substituent selected from $R^{12}$.

In some embodiments, each $R^{11}$ is independently selected from $C_{1-3}$ alkyl, $C_{1-3}$ haloalkyl, $C_{3-4}$ cycloalkyl, 5-6 membered heteroaryl, 4-6 membered heterocycloalkyl, halo, D, CN, $OR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $S(O)_2R^{b3}$; and $NR^{c3}S(O)_2R^{b3}$ wherein said $C_{1-3}$ alkyl, $C_{3-4}$ cycloalkyl, 5-6 membered heteroaryl, and 4-6 membered heterocycloalkyl are each optionally substituted with 1 substituent selected from $R^{12}$.

In some embodiments, each $R^{11}$ is independently selected from halo, $C_{1-2}$ alkyl, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, and $S(O)_2R^{b3}$, wherein said $C_{1-2}$ alkyl is optionally substituted with $OR^{a5}$.

In some embodiments, each $R^{11}$ is independently selected from halo, $C_{1-2}$ alkyl, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $S(O)_2R^{b3}$, 1-methyl-pyrrolidin-3-yl-2-one, pyrrolidin-3-yl-2-one, 2-propanamide, $NR^{c3}S(O)_2R^{b3}$, D, and tetrahydropyran-4-yl, wherein said $C_{1-2}$ alkyl is optionally substituted with $OR^{a5}$.

In some embodiments, each $R^{11}$ is independently selected from $C_{1-3}$ alkyl, 4-10 membered heterocycloalkyl, F, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}S(O)_2R^{b3}$, and $S(O)_2R^{b3}$; wherein said $C_{1-3}$ alkyl, and 4-10 membered heterocycloalkyl, are each optionally substituted with 1 or 2 substituents independently selected from $R^{12}$.

In some embodiments, each $R^{11}$ is independently selected from $C_{1-2}$ alkyl, $C_{1-2}$ haloalkyl, F, Cl, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, and $S(O)_2R^{b3}$.

In some embodiments, each $R^{11}$ is independently selected from $C_{1-2}$ alkyl, CN, $OR^{a3}$, $C(O)R^{b3}$, $C(O)NR^{c3}R^{d3}$, $C(O)OR^{a3}$, $NR^{c3}C(O)R^{b3}$, and $S(O)_2R^{b3}$.

In some embodiments, each $R^{11}$ is independently selected from methyl, ethyl, isopropyl, CN, OH, oxo, (1-methyl-1H-1,2,4-triazol-5-yl)methyl, $C(O)CH_3$, $C(O)N(CH_3)_2$, $C(O)NH_2$, $C(O)NHCH_2CH_3$, $C(O)OCH_3$, $C(O)OH$, $NHC(O)CH_3$, $S(O)_2CH_3$, cyclopropanecarbonyl, pyridin-4-yl, pyridin-2-yl, and morpholino.

In some embodiments, each $R^{11}$ is independently selected from methyl, ethyl, isopropyl, CN, OH, oxo, (1-methyl-1H-1,2,4-triazol-5-yl)methyl, $C(O)CH_3$, $C(O)N(CH_3)_2$, $C(O)NH_2$, $C(O)NHCH_2CH_3$, $C(O)OCH_3$, $C(O)OH$, $NHC(O)CH_3$, $S(O)_2CH_3$, cyclopropanecarbonyl, pyridin-4-yl, pyridin-2-yl, morpholino, 2-hydroxypropanoyl, 2-hydroxyacetyl, 2-hydroxyethyl, F, $NH_2$, and $N(CH_3)C(O)CH_2OH$.

In some embodiments, each $R^{11}$ is independently selected from methyl, ethyl, isopropyl, CN, OH, D, oxo, (1-methyl-1H-1,2,4-triazol-5-yl)methyl, $C(O)CH_3$, $C(O)N(CH_3)_2$, $C(O)NH_2$, $C(O)NHCH_2CH_3$, $C(O)OCH_3$, $C(O)OH$, $NHC(O)CH_3$, $S(O)_2CH_3$, cyclopropanecarbonyl, pyridin-4-yl, pyridin-2-yl, and morpholino.

In some embodiments, each $R^{11}$ is independently selected from D, methyl, ethyl, isopropyl, CN, OH, oxo, (1-methyl-1H-1,2,4-triazol-5-yl)methyl, $CH_2CH_2OH$, $C(O)CH_3$, $C(O)N(CH_3)_2$, $C(O)NH_2$, $C(O)NHCH_2CH_3$, $C(O)CH_2CH_2N(CH_3)_2$, $C(O)CH(CH_3)N(CH_3)_2$, $C(O)OCH_3$, $C(O)CH_2OH$, $CH(CH_3)C(O)NH_2$, $C(O)OH$, $NHC(O)CH_3$, $S(O)_2CH_3$, cyclopropanecarbonyl, pyridin-4-yl, pyridin-2-yl, morpholino, 2-hydroxypropanoyl, 2-hydroxyacetyl, 2-hydroxyethyl, F, $NH_2$, $N(CH_3)C(O)CH_2OH$, 3'-pyrrolidin-2'-one, methyl-3'-pyrrolidin-2'-one, 1-methyl-prolyl, (4-methylmorpholin-3-yl)methyl-1-one, (1-methylazetidin-2-yl)methyl-1-one, 2-(4-methylpiperazin-1-yl)ethyl-1-one, 2-(4-hydroxypiperidin-1-yl)ethyl-1-one, 2-hydroxypropyl-1-one, (trans)-3-hydroxycyclobutyl)methyl-1-one, (cis)-3-hydroxycyclobutypmethyl-1-one, (4-methylmorpholin-3-yl)methyl-1-one, (tetrahydrofuran-2-yl)methyl-1-one, 2-hydroxypropyl-1-one, 3-hydroxybutyl-1-one, 3-hydroxy-3-methylcyclobutyl)methyl-1-one, (hydroxymethyl)cyclobutyl)methyl-one, (1-ethylazetidin-2-yl)methyl-1-one, (2-fluoroethyl)azetidin-2-yl)methyl-1-one, (1-isopropylazetidin-2-yl)methyl-1-one, 2-methoxyethyl-1-one, 2-(dimethylamino)-2-methylpropyl-1-one, (cyclopropane-1-carbonitrile)methyl-1-one, $S(O)_2CH_2CH_2OH$, $S(O)_2CH_2CH_2N(CH_3)_2$, 2-methoxyethyl-carboxyl, N-methylmethanesulfonamido, 2-hydroxy-N-methylacetamido, 2-hydroxypropanamido, tetrahydro-2H-pyran-4-methyl-1-one, 2-methoxyacetyl, 2-hydroxy-N-methylacetamido, tetrahydrofuran-2-methyl-1-one, (1-methylpiperidin-2-yl)methyl-1-one, 2-(dimethylamino)ethyl-1-one, 3-hydroxypropyl-1-one, methoxymethyl-carboxyl, morpholine-4-carbonyl, propylnitrile, 2-methoxy-N-methylacetamido, 3-hydroxy-N-methylpropanamido, 2-hydroxy-N-methylpropanamido, tetrahydro-2H-pyran-4-yl, and 1,3-dimethylpiperazinyl-2-one.

In some embodiments, each $R^{12}$ is independently selected from $C_{1-6}$ alkyl, $C_{1-6}$ haloalkyl, halo, D, CN, $OR^{a5}$, and $NR^{c5}R^{d5}$; wherein said $C_{1-6}$ alkyl is optionally substituted with 1, 2, 3, or 4 substituents independently selected from $R^g$.

In some embodiments, each $R^{12}$ is independently selected from $C_{1-6}$ alkyl, $C_{1-6}$ haloalkyl, $C_{3-6}$ cycloalkyl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $S(O)_2R^{b5}$, and $S(O)_2NR^{c5}R^{d5}$; wherein said $C_{1-6}$ alkyl, $C_{3-6}$ cycloalkyl, and 4-7 membered heterocycloalkyl, are each optionally substituted with 1, 2, 3, or 4 substituents independently selected from $R^g$.

In some embodiments, each $R^{12}$ is independently selected from $C_{1-3}$ alkyl, $C_{1-3}$ haloalkyl, $C_{3-6}$ cycloalkyl, 4-7 membered heterocycloalkyl, F, Cl, D, CN, $OR^{a5}$, $C(O)R^{b5}$, $C(O)NR^{c5}R^{d5}$, and $NR^{c5}R^{d5}$; wherein said $C_{1-3}$ alkyl, $C_{3-6}$ cycloalkyl, and 4-7 membered heterocycloalkyl, are each optionally substituted with 1 substituent independently selected from $R^g$.

In some embodiments, each $R^{12}$ is independently selected from $C_{1-3}$ alkyl, halo, D, and $OR^{a5}$.

In some embodiments, $R^{12}$ is methyl.

In some embodiments, $R^{12}$ is OH.

In some embodiments, each $R^{21}$ is independently selected from $C_{1-6}$ alkyl, $C_{1-6}$ haloalkyl, halo, D, CN, $OR^{a4}$, $C(O)R^{b4}$, $C(O)NR^{c4}R^{d4}$, $C(O)OR^{a4}$, $NR^{c4}R^{d4}$, and $S(O)_2R^{b4}$; wherein said $C_{1-6}$ alkyl is optionally substituted with 1, 2, or 3 substituents independently selected from $R^{22}$.

In some embodiments, each $R^{21}$ is independently selected from $C_{1-3}$ alkyl, halo, D, CN, and $OR^{a4}$; wherein said $C_{1-3}$ alkyl is optionally substituted with 1 or 2 substituents independently selected from $R^{22}$.

In some embodiments, each $R^{21}$ is independently selected from $C_{1-2}$ alkyl, F, Cl, D, CN, and $OR^{a4}$; wherein said $C_{1-2}$ alkyl is optionally substituted with 1 substituent selected from $R^{22}$.

In some embodiments, each $R^{21}$ is independently selected from $C_{1-2}$ alkyl, halo, D, CN, and $OR^{a4}$; wherein said $C_{1-3}$ alkyl is optionally substituted with 1 or 2 substituents independently selected from $R^{22}$.

In some embodiments, each $R^{21}$ is independently selected from $C_{1-3}$ alkyl, halo, D, CN, and $OR^{a4}$; wherein said $C_{1-3}$ alkyl, is optionally substituted with 1 or 2 substituents independently selected from $R^{22}$.

In some embodiments, each $R^{21}$ is independently selected from $C_{1-3}$ alkyl, F, Cl, D, CN, and $OR^{a4}$; wherein said $C_{1-3}$ alkyl, is optionally substituted with 1 or 2 substituents independently selected from $R^{22}$. In some embodiments, each $R^{21}$ is independently selected from $C_{1-2}$ alkyl, F, D, CN, and $OR^{a4}$; wherein said $C_{1-2}$ alkyl is optionally substituted with 1 substituent selected from $R^{22}$.

In some embodiments, each $R^{21}$ is independently selected from methyl, F, D, CN, and OH;

In some embodiments, each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl is optionally substituted with 1 or 2 substituents independently selected from $R^g$.

In some embodiments, each $R^{22}$ is independently selected from F, Cl, D, CN, and $OR^{a6}$.

In some embodiments, each $R^{22}$ is independently selected from halo, D, CN, and $OR^{a6}$.

In some embodiments, each $R^{22}$ is independently selected from F, Cl, CN, and $OR^{a6}$.

In some embodiments, $R^{22}$ is $OR^{a6}$. In some embodiments, $R^{22}$ is OH. In some embodiments, each $R^{22}$ is independently selected from F and Cl. In some embodiments, $R^{22}$ is CN.

In some embodiments, each $R^{a1}$, $R^{c1}$ and $R^{d1}$ is independently selected from H, $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{11}$.

In some embodiments, each $R^{a1}$, $R^{c1}$ and $R^{d1}$ is independently selected from H and $C_{1-6}$ alkyl.

In some embodiments, each $R^{a1}$, $R^{c1}$ and $R^{d1}$ is independently selected from H, $C_{1-6}$ alkyl, and 4-6 membered heterocycloalkyl.

In some embodiments, any $R^{c1}$ and $R^{d1}$ attached to the same N atom, together with the N atom to which they are attached, form a 4-, 5- or 6-membered heterocycloalkyl group optionally substituted with 1, 2, or 3 substituents independently selected from $R^{11}$.

In some embodiments, each $R^{c1}$ and $R^{d1}$ is independently selected from H, $C_{1-3}$ alkyl, and
$C_{1-3}$ haloalkyl.

In some embodiments, $R^{c1}$ and $R^{d1}$ is independently selected from H and $C_{1-2}$ alkyl.

In some embodiments, each $R^{b1}$ is independently selected from $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{11}$. In some embodiments, each $R^{b1}$ is independently selected from $C_{1-6}$ alkyl.

In some embodiments, each $R^{a2}$, $R^{c2}$ and $R^{d2}$, is independently selected from H, $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{21}$.

In some embodiments, each $R^{a2}$, $R^{c2}$ and $R^{d2}$, is independently selected from H and $C_{1-6}$ alkyl.

In some embodiments, each $R^{a2}$ is independently selected from H and $C_{1-3}$ alkyl.

In some embodiments, each $R^{a2}$ is independently selected from H and $C_{1-2}$ alkyl.

In some embodiments, any $R^{c2}$ and $R^{d2}$ attached to the same N atom, together with the N atom to which they are attached, form a 4-, 5-, or 6-membered heterocycloalkyl group optionally substituted with 1, 2 or 3 substituents independently selected from $R^{21}$.

In some embodiments, each $R^{b2}$ is independently selected from $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{21}$.

In some embodiments, each $R^{b2}$ is independently selected from $C_{1-6}$ alkyl.

In some embodiments, each $R^{a3}$, $R^{c3}$ and $R^{d3}$, is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1 or 2 substituents independently selected from $R^{12}$.

In some embodiments, each $R^{a3}$, $R^{c3}$ and $R^{d3}$, is independently selected from H, $C_{1-3}$ alkyl, $C_{1-3}$ haloalkyl, and $C_{3-5}$ cycloalkyl.

In some embodiments, each $R^{a3}$, $R^{c3}$ and $R^{d3}$, is independently selected from H and $C_{1-2}$ alkyl.

In some embodiments, any $R^{c3}$ and $R^{d3}$ attached to the same N atom, together with the N atom to which they are attached, form a 4-, 5- or 6-membered heterocycloalkyl group optionally substituted with 1 or 2 substituents independently selected from $R^{12}$.

In some embodiments, each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1 or 2 substituents independently selected from $R^{12}$.

In some embodiments, each $R^{b3}$ is independently selected from $C_{1-3}$ alkyl, $C_{1-3}$ haloalkyl, $C_{3-6}$ cycloalkyl, and 4-6 membered heterocycloalkyl; wherein said $C_{1-3}$ alkyl $C_{3-6}$ cycloalkyl, and 4-6 membered heterocycloalkyl, are each optionally substituted with 1 or 2 substituents independently selected from $R^{12}$.

In some embodiments, each $R^{b3}$ is independently selected from $C_{1-3}$ alkyl and $C_{3-5}$ cycloalkyl.

In some embodiments, each $R^{b3}$ is independently selected from $C_{1-2}$ alkyl and cyclopropyl. In some embodiments, each $R^{b3}$ is independently selected from $C_{1-2}$ alkyl.

In some embodiments, each $R^{a4}$, $R^{b4}$ and $R^{d4}$, is independently selected from H, $C_{1-6}$ alkyl, and $C_{1-6}$ haloalkyl; wherein said $C_{1-6}$ alkyl is optionally substituted with 1 or 2 substituents independently selected from $R^{22}$.

In some embodiments, each $R^{a4}$, $R^{b4}$ and $R^{d4}$, is independently selected from H, $C_{1-3}$ alkyl, and $C_{1-3}$ haloalkyl; wherein said $C_{1-3}$ alkyl is optionally substituted with 1 or 2 substituents independently selected from $R^{22}$.

In some embodiments, each $R^{a4}$ is independently selected from H and $C_{1-3}$ alkyl.

In some embodiments, $R^{a4}$ is independently selected from H and $C_{1-2}$ alkyl. In some embodiments, $R^{a4}$ is H.

In some embodiments, each $R^{b4}$ is independently selected from $C_{1-6}$ alkyl, and $C_{1-6}$ haloalkyl; wherein said $C_{1-6}$ alkyl is optionally substituted with 1 or 2 substituents independently selected from $R^{22}$. In some embodiments, each $R^{b4}$ is independently selected from $C_{1-6}$ alkyl.

In some embodiments, each $R^{a5}$, $R^{c5}$ and $R^{d5}$, is independently selected from H, $C_{1-6}$ alkyl, and $C_{1-6}$ haloalkyl; wherein said $C_{1-6}$ alkyl is optionally substituted with 1 or 2 substituents independently selected from $R^g$.

In some embodiments, $R^{a5}$ is selected from H and $C_{1-3}$ alkyl.

In some embodiments, each $R^{b5}$ is independently selected from $C_{1-6}$ alkyl, and $C_{1-6}$ haloalkyl; wherein said $C_{1-6}$ alkyl is optionally substituted with 1 or 2 substituents independently selected from $R^g$.

In some embodiments, each $R^{a6}$, $R^{b6}$ and $R^{d6}$, is independently selected from H, $C_{1-6}$ alkyl, and $C_{1-6}$ haloalkyl; wherein said $C_{1-6}$ alkyl is optionally substituted with 1 or 2 substituents independently selected from $R^g$.

In some embodiments, each $R^{a6}$ is independently selected from H and $C_{1-3}$ alkyl.

In some embodiments, $R^{a6}$ is independently selected from H and $C_{1-2}$ alkyl.

In some embodiments, each $R^{b6}$ is independently selected from $C_{1-6}$ alkyl, and $C_{1-6}$ haloalkyl; wherein said $C_{1-6}$ alkyl is optionally substituted with 1 or 2 substituents independently selected from $R^g$. In some embodiments, each $R^{b6}$ is independently selected from $C_{1-6}$ alkyl.

In some embodiments, each $R^g$ is independently selected from OH, CN, halo, $C_{1-6}$ alkyl, $C_{1-6}$ haloalkyl, $C_{3-6}$ cycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, $C_{1-6}$ alkylthio, $C_{1-6}$ alkylsulfonyl, carboxy, $C_{1-6}$ alkylcarbonyl, $C_{1-6}$ alkoxycarbonyl, and $C_{1-6}$ alkylcarbonylamino.

In some embodiments, each $R^g$ is independently selected from halo, $C_{1-6}$ alkyl, and $C_{1-6}$ haloalkyl.

In some embodiments, each $R^g$ is independently selected from OH, CN, F, Cl, alkyl, and $C_{1-3}$ haloalkyl.

In some embodiments the compound of Formula I is a compound of Formula Ia:

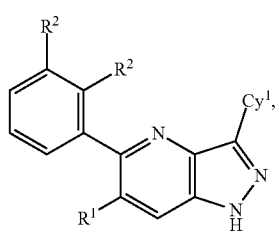

or a pharmaceutically acceptable salt thereof; wherein $Cy^1$, $R^1$, and each $R^2$ are as defined herein.

In some embodiments the compound of Formula I is a compound of Formula IIa:

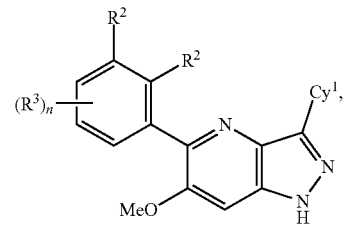

or a pharmaceutically acceptable salt thereof; wherein $Cy^1$, each $R^2$, $R^3$, and n are as defined herein.

In some embodiments the compound of Formula I is a compound of Formula

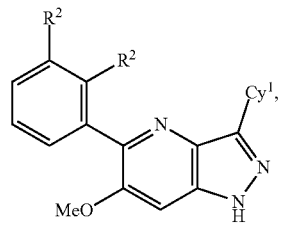

or a pharmaceutically acceptable salt thereof, wherein $Cy^1$ and each $R^2$ are as defined herein.

In some embodiments the compound of Formula I is a compound of Formula IIIa:

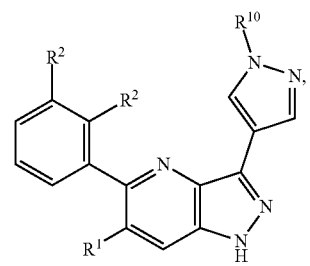

or a pharmaceutically acceptable salt thereof, wherein $R^1$, each $R^2$, and $R^{10}$ are as defined herein.

In some embodiments the compound of Formula I is a compound of Formula IIIb:

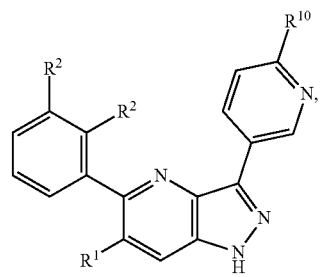

or a pharmaceutically acceptable salt thereof, wherein $R^1$, each $R^2$, and $R^{10}$ are as defined herein.

In some embodiments the compound of Formula I is a compound of Formula IIIc:

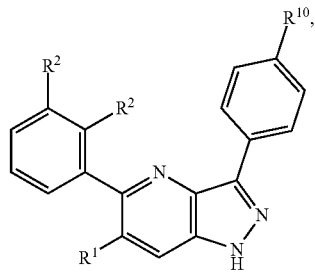

IIIc or a pharmaceutically acceptable salt thereof, wherein R¹, each R², and R¹⁰ are as defined herein.

In some embodiments the compound of Formula I is a compound of Formula IVa:

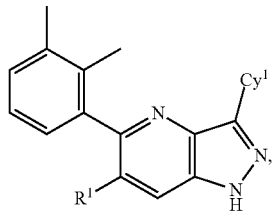

IVa or a pharmaceutically acceptable salt thereof, wherein Cy¹ and R¹ are as defined herein.

In some embodiments the compound of Formula I is a compound of Formula IVb:

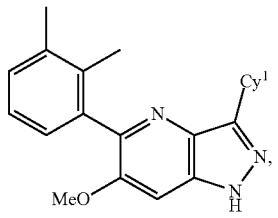

IVb or a pharmaceutically acceptable salt thereof, wherein Cy¹ is as defined herein.

In some embodiments the compound of Formula I is a compound of Formula Va:

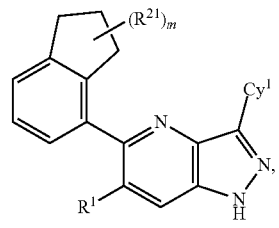

Va or a pharmaceutically acceptable salt thereof, wherein m is 0, 1 or 2; and wherein Cy¹, and R²¹ are as defined herein. In some embodiments, m is 0. In some embodiments, m is 1. In some embodiments, m is 2.

In some embodiments the compound of Formula I is a compound of Formula Vb:

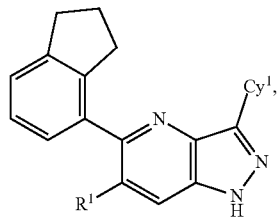

Vb or a pharmaceutically acceptable salt thereof, wherein Cy¹ and R¹ are as defined herein.

In some embodiments the compound of Formula I is a compound of Formula Vc:

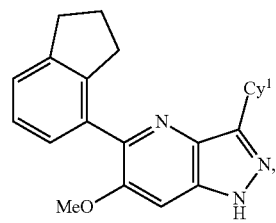

Vc or a pharmaceutically acceptable salt thereof, wherein Cy¹ is as defined herein.

In some embodiments the compound of Formula I is a compound of Formula VI:

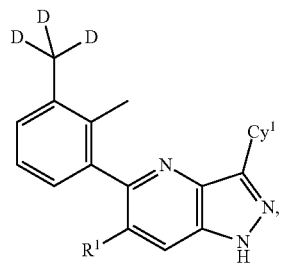

VI or a pharmaceutically acceptable salt thereof, wherein Cy¹ and R¹ are as defined herein.

In some embodiments, provided herein is a compound of Formula (I), or a pharmaceutically acceptable salt thereof, wherein:

Cy¹ is selected from phenyl, pyridinyl and pyrazolyl; wherein the phenyl pyridinyl and pyrazolyl are each optionally substituted with 1, 2, 3 or 4 substituents independently selected from $R^{10}$;

$R^1$ is selected from halo, $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$alkyl)amino; wherein optionally one or more H atoms of the $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$alkylamino, and di($C_{1-6}$alkyl)amino are replaced by one or more D atoms;

each $R^2$ and $R^3$ are independently selected from $C_{1-6}$ alkyl, $C_{2-6}$ alkenyl, $C_{1-6}$ haloalkyl, $C_{3-6}$ cycloalkyl, 4-6 membered heterocycloalkyl, halo, CN, $OR^{a2}$, $C(O)R^{b2}$, $C(O)NR^{c2}R^{d2}$, $C(O)OR^{a2}$, $NR^{c2}R^{d2}$, and $S(O)_2R^{b2}$; wherein said $C_{1-6}$ alkyl, $C_{2-6}$ alkenyl, $C_{3-6}$ cycloalkyl, and 4-6 membered heterocycloalkyl are each optionally substituted with 1, 2, 3, or 4 substituents independently selected from $R^{21}$;

or two adjacent $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming heteroatoms independently selected from O and N; wherein a ring-forming carbon atom of each fused 5- or 6-membered heterocycloalkyl ring is optionally substituted by oxo to form a carbonyl group; and wherein the fused 5- or 6-membered cycloalkyl ring, and the fused 5- or 6-membered heterocycloalkyl ring are each optionally substituted with 1, 2, 3 or 4 substituents independently selected from $R^{21}$;

n is selected from 0 and 1;

each $R^{10}$ is independently selected from $C_{1-6}$ alkyl, $C_{1-6}$ haloalkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^1$, and $S(O)_2R^{b1}$; wherein said $C_{1-6}$ alkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-6}$ cycloalkyl, 5-6 membered heteroaryl, 4-6 membered heterocycloalkyl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{3-6}$ cycloalkyl, 5-6 membered heteroaryl, and 4-6 membered heterocycloalkyl are each optionally substituted with 1, 2, or 3 substituents independently selected from $R^{12}$;

each $R^{12}$ is independently selected from $C_{1-6}$ alkyl, $C_{1-6}$ haloalkyl, halo, D, CN, $OR^{a5}$, and $NR^{c5}R^{d5}$; wherein said $C_{1-6}$ alkyl is optionally substituted with 1, 2, 3, or 4 substituents independently selected from $R^g$;

each $R^{21}$ is independently selected from $C_{1-6}$ alkyl, $C_{1-6}$ haloalkyl, halo, D, CN, $OR^{a4}$, $C(O)R^{b4}$, $C(O)NR^{c4}R^{d4}$, $C(O)OR^{a4}$, $NR^{c4}R^{d4}$ and $S(O)_2R^{b4}$; wherein said $C_{1-6}$ alkyl is optionally substituted with 1, 2, or 3 substituents independently selected from $R^{22}$;

each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl is optionally substituted with 1 or 2 substituents independently selected from $R^g$;

each $R^{a1}$, $R^{c1}$ and $R^{d1}$ is independently selected from H, $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{11}$;

or any $R^{c1}$ and $R^{d1}$ attached to the same N atom, together with the N atom to which they are attached, form a 4-, 5- or 6-membered heterocycloalkyl group optionally substituted with 1, 2, or 3 substituents independently selected from $R^{11}$;

each $R^{b1}$ is independently selected from $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{11}$;

each $R^{a2}$, $R^{c2}$ and $R^{d2}$, is independently selected from H, $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{21}$;

or any $R^{c2}$ and $R^{d2}$ attached to the same N atom, together with the N atom to which they are attached, form a 4-, 5-, or 6-membered heterocycloalkyl group optionally substituted with 1, 2 or 3 substituents independently selected from $R^{21}$;

each $R^{b2}$ is independently selected from $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{21}$;

each $R^{a3}$, $R^{c3}$ and $R^{d3}$, is independently selected from H, $C_{1-6}$ alkyl, $C_{1-6}$ haloalkyl, and $C_{3}$-6 cycloalkyl; wherein said $C_{1-6}$ alkyl and $C_{3-6}$ cycloalkyl, are each optionally substituted with 1 or 2 substituents independently selected from $R^{12}$;

each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1 or 2 substituents independently selected from $R^{12}$;

each $R^{a4}$, $R^{c4}$ and $R^{d4}$, is independently selected from H, $C_{1-6}$ alkyl, and $C_{1-6}$ haloalkyl; wherein said $C_{1-6}$ alkyl is optionally substituted with 1 or 2 substituents independently selected from $R^{22}$;

each $R^{b4}$ is independently selected from $C_{1-6}$ alkyl, and $C_{1-6}$ haloalkyl; wherein said $C_{1-6}$ alkyl is optionally substituted with 1 or 2 substituents independently selected from $R^{22}$;

each $R^{a5}$, $R^{c3}$ and $R^{d5}$, is independently selected from H, $C_{1-6}$ alkyl, and $C_{1-6}$ haloalkyl; wherein said $C_{1-6}$ alkyl is optionally substituted with 1 or 2 substituents independently selected from $R^g$;

each $R^{a6}$, $R^{b6}$ and $R^{d6}$, is independently selected from H, $C_{1-6}$ alkyl, and $C_{1-6}$ haloalkyl; wherein said $C_{1-6}$ alkyl is optionally substituted with 1 or 2 substituents independently selected from $R^g$;

and each $R^g$ is independently selected from OH, CN, halo, $C_{1-6}$ alkyl, $C_{1-6}$ haloalkyl, $C_{3-6}$ cycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, $C_{1-6}$ alkylthio, $C_{1-6}$ alkylsulfonyl, carboxy, $C_{1-6}$ alkylcarbonyl, $C_{1-6}$ alkoxycarbonyl, and $C_{1-6}$ alkylcarbonylamino.

In some embodiments, provided herein is a compound of Formula (I), or a pharmaceutically acceptable salt thereof, wherein:

$Cy^1$ is selected from phenyl, pyridin-3-yl and pyrazol-4-yl; wherein the phenyl, pyridin-3-yl and pyrazol-4-yl of $Cy^1$ are each optionally substituted with 1 substituent selected from $R^{10}$;

$R^1$ is selected from Cl, $C_{1-3}$ alkyl, $C_{1-3}$ haloalkyl, cyclopropyl, azetidinyl, hydroxymethyl, $C_{1-3}$ alkoxy, $C_{1-3}$ haloalkoxy and $C_{1-3}$ alkylamino; wherein optionally one or more H atoms of the $C_{1-3}$ alkyl, $C_{1-3}$ haloalkyl, cyclopropyl, azetidinyl, hydroxymethyl, $C_{1-3}$ alkoxy, $C_{1-3}$ haloalkoxy and $C_{1-3}$ alkylamino are replaced by one or more D atoms;

each $R^2$ is independently selected from $C_{1-3}$ alkyl, $C_{1-3}$ haloalkyl, F, Cl, CN, and $OR^{a2}$; wherein said $C_{1-6}$ alkyl is optionally substituted with 1 substituent selected from $R^{21}$;

or the $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5- or 6-membered cycloalkyl ring, or the fused 5- or 6-membered heterocycloalkyl ring are each optionally substituted with 1 substituent selected from $R^{21}$;

n is 0;

$R^{10}$ is independently selected from $C_{1-3}$ alkyl, $C_{1-3}$ haloalkyl, $C_{3-6}$ cycloalkyl, 4-10 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, $C(O)NR^{c1}R^{d1}$; and $NR^{c1}R^{d1}$; wherein the alkyl, $C_{3-6}$ cycloalkyl, 4-10 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from $R^{11}$;

each $R^{11}$ is independently selected from $C_{1-3}$ alkyl, $C_{1-3}$ haloalkyl, $C_{3-4}$ cycloalkyl, 5-6 membered heteroaryl, 4-6 membered heterocycloalkyl, halo, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)OR^{b3}$, and $S(O)_2R^{b3}$; wherein the $C_{1-3}$ alkyl, $C_{3-4}$ cycloalkyl, 5-6 membered heteroaryl, and 4-6 membered heterocycloalkyl are each optionally substituted with 1 substituent selected from $R^{12}$;

each $R^{12}$ is selected from alkyl, halo, D, and $OR^{a5}$;

each $R^{21}$ is independently selected from $C_{1-3}$ alkyl, halo, D, CN, and $OR^{a4}$; wherein said $C_{1-3}$ alkyl, is optionally substituted with 1 or 2 substituents independently selected from $R^{22}$;

each $R^{22}$ is independently selected from halo, D, CN, and $OR^{a6}$;

$R^{c1}$ and $R^{d1}$ are independently selected from H, $C_{1-3}$ alkyl, and $C_{1-3}$ haloalkyl;

each $R^{a2}$ is independently selected from H and alkyl;

each $R^{a3}$, $R^{c3}$ and $R^{d3}$, is independently selected from H, $C_{1-3}$ alkyl, $C_{1-3}$ haloalkyl, and $C_{3-5}$ cycloalkyl;

each $R^{b3}$ is independently selected from $C_{1-3}$ alkyl and $C_{3-5}$ cycloalkyl;

each $R^{a4}$ is independently selected from H and alkyl;

each $R^{a5}$ is selected from H and $C_{1-3}$ alkyl; and each $R^{ab}$ is independently selected from H and $C_{1-3}$ alkyl.

In some embodiments, provided herein is a compound of Formula (I), or a pharmaceutically acceptable salt thereof, wherein:

$Cy^1$ is selected from phenyl, pyridin-3-yl and pyrazol-4-yl; wherein the phenyl, pyridin-3-yl and pyrazol-4-yl of $Cy^1$ are each optionally substituted with 1 substituent selected from $R^{10}$;

$R^1$ is selected from Cl, $C_{1-3}$ alkyl, $C_{1-3}$ haloalkyl, cyclopropyl, azetidinyl, hydroxymethyl, $C_{1-3}$ alkoxy, $C_{1-3}$ haloalkoxy and $C_{1-3}$ alkylamino; wherein optionally one or more H atoms of the $C_{1-3}$ alkyl, $C_{1-3}$ haloalkyl, cyclopropyl, azetidinyl, hydroxymethyl, $C_{1-3}$ alkoxy, $C_{1-3}$ haloalkoxy and $C_{1-3}$ alkylamino are replaced by one or more D atoms;

each $R^2$ is independently selected from $C_{1-3}$ alkyl, $C_{1-3}$ haloalkyl, F, Cl, CN, and $OR^{a2}$; wherein said $C_{1-6}$ alkyl is optionally substituted with 1 substituent selected from $R^{21}$;

or the $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5- or 6-membered cycloalkyl ring, or the fused 5- or 6-membered heterocycloalkyl ring are each optionally substituted with 1 substituent selected from $R^{21}$;

n is 0;

$R^{10}$ is independently selected from $C_{1-3}$ alkyl, $C_{1-3}$ haloalkyl, $C_{3-6}$ cycloalkyl, 4-6 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, $C(O)NR^{c1}R^{d1}$; and $NR^{c1}R^{d1}$; wherein the alkyl, $C_{3-6}$ cycloalkyl, 4-6 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from $R^{11}$;

each $R^{11}$ is independently selected from $C_{1-3}$ alkyl, $C_{1-3}$ haloalkyl, $C_{3-4}$ cycloalkyl, 5-6 membered heteroaryl, 4-6 membered heterocycloalkyl, halo, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, and $S(O)_2R^{b3}$; wherein the $C_{1-3}$ alkyl, $C_{3-4}$ cycloalkyl, 5-6 membered heteroaryl, and 4-6 membered heterocycloalkyl are each optionally substituted with 1 substituent selected from $R^{12}$;

each $R^{12}$ is selected from alkyl, halo, D, and $OR^{a5}$;

each $R^{21}$ is independently selected from $C_{1-3}$ alkyl, halo, D, CN, and $OR^{a4}$; wherein said $C_{1-3}$ alkyl, is optionally substituted with 1 or 2 substituents independently selected from $R^{22}$;

each $R^{22}$ is independently selected from halo, D, CN, and $OR^{a6}$;

$R^{c1}$ and $R^{d1}$ are independently selected from H, $C_{1-3}$ alkyl, and $C_{1-3}$ haloalkyl;

each $R^{a2}$ is independently selected from H and $C_{1-3}$ alkyl;

each $R^{a3}$, $R^{c3}$ and $R^{d3}$, is independently selected from H, $C_{1-3}$ alkyl, $C_{1-3}$ haloalkyl, and $C_{3-5}$ cycloalkyl;

each $R^{b3}$ is independently selected from $C_{1-3}$ alkyl and $C_{3-5}$ cycloalkyl;

each $R^{a4}$ is independently selected from H and $C_{1-3}$ alkyl;

each $R^{a5}$ is selected from H and $C_{1-3}$ alkyl; and each $R^{a6}$ is independently selected from H and $C_{1-3}$ alkyl.

In some embodiments, provided herein is a compound of Formula (I), or a pharmaceutically acceptable salt thereof, wherein:

$Cy^1$ is selected from phenyl, pyridin-3-yl and pyrazol-4-yl; wherein the phenyl, pyridin-3-yl and pyrazol-4-yl of $Cy^1$ are each optionally substituted with 1 substituent selected from $R^{10}$;

$R^1$ is selected from Cl, $C_{1-2}$ alkyl, $C_{1-2}$ haloalkyl, cyclopropyl, hydroxymethyl, $C_{1-2}$ alkoxy, $C_{1-2}$ haloalkoxy and $C_{1-2}$ alkylamino; wherein optionally one or more H atoms of the $C_{1-2}$ alkyl, $C_{1-2}$ haloalkyl, cyclopropyl, hydroxymethyl, $C_{1-2}$ alkoxy, $C_{1-2}$ haloalkoxy and $C_{1-2}$ alkylamino are replaced by one or more D atoms;

each $R^2$ is independently selected from $C_{1-2}$ alkyl, $C_{1-2}$ haloalkyl, F, Cl, CN, and $OR^{a2}$; wherein said $C_{1-2}$ alkyl is optionally substituted with 1 substituent selected from $R^{21}$;

or the $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5- or 6-membered cycloalkyl ring, or the fused 5- or 6-membered heterocycloalkyl ring are each optionally substituted with 1 substituent selected from $R^{21}$;

n is 0;

$R^{10}$ is independently selected from $C_{1-2}$ alkyl, $C_{1-2}$ haloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl, (morpholinyl)ethyl, (pyridinyl)methyl, (triazolyl)methyl, 1-oxa-3,8-diazaspiro[4.5]decan-2-one, F, Cl, D, CN, $NR^{c1}R^{d1}$; wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl and (triazolyl)methyl are each optionally substituted with 1 or 2 substituents independently selected from $R^{11}$;

each $R^{11}$ is independently selected from $C_{1-2}$ alkyl, $C_{1-2}$ haloalkyl, F, Cl, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, and $S(O)_2R^{b3}$;

each $R^{21}$ is independently selected from $C_{1-2}$ alkyl, F, Cl, D, CN, and $OR^{a4}$; wherein said $C_{1-2}$ alkyl is optionally substituted with 1 substituent selected from $R^{22}$;

each $R^{22}$ is independently selected from F, Cl, CN, and $OR^{a6}$;

$R^{c1}$ and $R^{d1}$ is independently selected from H and $C_{1-2}$ alkyl;

each $R^{a2}$ is independently selected from H and $C_{1-2}$ alkyl;

each $R^{a3}$, $R^{c3}$ and $R^{d3}$, is independently selected from H and $C_{1-2}$ alkyl;

each $R^{b3}$ is independently selected from $C_{1-2}$ alkyl, and cyclopropyl;

each $R^{a4}$ is independently selected from H and $C_{1-2}$ alkyl; and each $R^{a6}$ is independently selected from H and $C_{1-2}$ alkyl.

In some embodiments, provided herein is a compound of Formula (I), or a pharmaceutically acceptable salt thereof, wherein:

$Cy^1$ is selected from phenyl, pyridin-3-yl and pyrazol-4-yl; wherein the phenyl, pyridin-3-yl and pyrazol-4-yl of $Cy^1$ are each substituted with 1 substituent selected from $R^{10}$;

$R^1$ is selected from Cl, $C_{1-2}$ alkyl, $C_{1-2}$ haloalkyl, hydroxymethyl, $C_{1-2}$ alkoxy, $C_{1-2}$ haloalkoxy and $C_{1-2}$ alkylamino; wherein optionally one or more H atoms of the $C_{1-2}$ alkyl, $C_{1-2}$ haloalkyl, hydroxymethyl, $C_{1-2}$ alkoxy, $C_{1-2}$ haloalkoxy and $C_{1-2}$ alkylamino are replaced by one or more D atoms;

each $R^2$ is independently selected from $C_{1-2}$ alkyl and F; wherein said $C_{1-2}$ alkyl is ach optionally substituted with 1 substituent selected from $R^{21}$;

or the $R^2$ substituents on the phenyl ring, taken together with the atoms to which they are attached, form a fused 5-membered cycloalkyl ring, or a fused 5-membered heterocycloalkyl ring; wherein each fused 5-membered heterocycloalkyl ring has at least one ring-forming carbon atom and 1 or 2 ring-forming O atoms; and wherein the fused 5-membered cycloalkyl ring and the fused 5-membered heterocycloalkyl ring are each optionally substituted with 1 or 2 substituents each independently selected from $R^{21}$;

n is 0;

$R^{10}$ is independently selected from $C_{1-2}$ alkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazinyl)methyl, and 1-oxa-3,8-diazaspiro[4.5]decan-2-one; wherein the $C_{1-2}$ alkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, and (pyridinyl)methyl are each optionally substituted with 1 or 2 substituents independently selected from $R^{11}$;

each $R^{11}$ is independently selected from $C_{1-2}$ alkyl, CN, $OR^{a3}$, $C(O)R^{b3}$, $C(O)NR^{c3}R^{d3}$, $C(O)OR^{a3}$, $NR^{c3}C(O)R^{b3}$, and $S(O)_2R^{b3}$;

each $R^{21}$ is independently selected from $C_{1-2}$ alkyl, F, D, CN, and $OR^{a4}$; wherein said $C_{1-2}$ alkyl is optionally substituted with 1 substituent selected from $R^{22}$;

each $R^{22}$ is $OR^{a6}$;

each $R^{a3}$, $R^{c3}$ and $R^{d3}$, is independently selected from H and $C_{1-2}$ alkyl;

each $R^{b3}$ is independently selected from $C_{1-2}$ alkyl, and cyclopropyl; and each $R^{ab}$ is independently selected from H and $C_{1-2}$ alkyl.

In some embodiments, provided herein is a compound of Formula (I), or a pharmaceutically acceptable salt thereof, wherein:

$Cy^1$ is selected from phenyl, pyridin-3-yl and pyrazol-4-yl; wherein the phenyl, pyridin-3-yl and pyrazol-4-yl of $Cy^1$ are each optionally substituted with 1 substituent selected from $R^{10}$;

$R^1$ is selected from Cl, $C_{1-2}$ alkyl, $C_{1-2}$ haloalkyl, cyclopropyl, hydroxymethyl, $C_{1-2}$ alkoxy, $C_{1-2}$ haloalkoxy and $C_{1-2}$ alkylamino; wherein optionally one or more H atoms of the $C_{1-2}$ alkyl, $C_{1-2}$ haloalkyl, cyclopropyl, hydroxymethyl, $C_{1-2}$ alkoxy, $C_{1-2}$ haloalkoxy and $C_{1-2}$ alkylamino are replaced by one or more D atoms;

each $R^2$ is independently selected from $C_{3-6}$ cycloalkyl, $C_{1-2}$ alkyl, $C_{1-2}$ haloalkyl, F, Cl, CN, and $OR^{a2}$; wherein said $C_{1-2}$ alkyl is optionally substituted with 1 substituent selected from $R^{21}$;

or the $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5- or 6-membered cycloalkyl ring, or the fused 5- or 6-membered heterocycloalkyl ring are each optionally substituted with 1 substituent selected from $R^{21}$;

n is 0;

$R^{10}$ is independently selected from $C_{1-2}$ alkyl, $C_{1-2}$ haloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, thiomorpholinyl, 1-oxa-3,8-diazaspiro[4.5]decan-2-one, hexahydropyrrolo[1,2-a]pyrazin-2(1H)-yl, F, Cl, D, CN, $OR^{a1}$, and $NR^{c1}R^{d1}$; wherein the $C_{1-2}$ alkyl, $C_{3-6}$ cycloalkyl, $C_{3-6}$ cycloalkyl, azetidinyl, pyrrolidinyl, piperidinyl, morpholinyl, piperazinyl, pyridinyl, piperazinonyl, diazabicyclo[2.2.1]heptanyl (morpholinyl)ethyl, (pyridinyl)methyl, (triazolyl)methyl, thiomorpholinyl, 1-oxa-3,8-diazaspiro[4.5]decan-2-one, and hexahydropyrrolo[1,2-a]pyrazin-2(1H)-yl are each optionally substituted with 1 or 2 substituents independently selected from $R^{11}$;

each $R^{11}$ is independently selected from $C_{1-2}$ alkyl, $C_{1-2}$ haloalkyl, F, Cl, D, CN, $C(O)R^{b3}$, $C(O)NR^{c3}R^{d3}$, $C(O)OR^{a3}$, $NR^{c3}R^{d3}$, $NR^{c3}C(O)R^{b3}$, and $S(O)_2R^{b3}$, wherein said $C_{1-2}$ alkyl is optionally substituted with $OR^{a5}$;

each $R^{21}$ is independently selected from $C_{1-2}$ alkyl, F, Cl, D, CN, and $OR^{a4}$; wherein said $C_{1-2}$ alkyl is optionally substituted with 1 substituent selected from $R^{22}$;

each $R^{22}$ is independently selected from F, Cl, CN, and $OR^{a6}$;

each $R^{a1}$, $R^{c1}$ and $R^{d1}$ are independently selected from H, $C_{1-2}$ alkyl, and 4-6 membered heterocycloalkyl;

each $R^{a2}$ is independently selected from H and $C_{1-2}$ alkyl;

each $R^{a3}$, $R^{c3}$ and $R^{d3}$, is independently selected from H and $C_{1-2}$ alkyl;

each $R^{b3}$ is independently selected from $C_{1-2}$ alkyl, and cyclopropyl;

each $R^{a4}$ is independently selected from H and $C_{1-2}$ alkyl;

each $R^{a5}$ is independently selected from H and $C_{1-2}$ alkyl; and each $R^{a6}$ is independently selected from H and $C_{1-2}$ alkyl.

In some embodiments, provided herein is a compound selected from:

5-(2,3-dimethylphenyl)-6-methoxy-3-(1-methyl-1H-pyrazol-4-yl)-1H-pyrazolo[4,3-b]pyridine;

5-(2,3-dihydro-1H-inden-4-yl)-6-methoxy-3-(1-methyl-1H-pyrazol-4-yl)-1H-pyrazolo[4,3-b]pyridine;

5-(2,3-dimethylphenyl)-6-methoxy-3-(1-((l-methyl-1H-1,2,4-triazol-5-yl)methyl)-1H-pyrazol-4-yl)-1H-pyrazolo[4,3-b]pyridine;

5-(2,3-dihydrobenzofuran-7-yl)-6-methoxy-3-(1-methyl-1H-pyrazol-4-yl)-1H-pyrazolo[4,3-b]pyridine;

2-(3-(6-methoxy-3-(1-methyl-1H-pyrazol-4-yl)-1H-pyrazolo[4,3-b]pyridin-5-yl)-2-methylphenyl)acetonitrile;

1-(4-(5-(6-(difluoromethoxy)-5-(2,3-dimethylphenyl)-1H-pyrazolo[4,3-b]pyridin-3-yl)pyridin-2-yl)piperazin-1-yl)ethan-1-one;

4-(6-methoxy-3-(1-methyl-1H-pyrazol-4-yl)-1H-pyrazolo[4,3-b]pyridin-5-yl)-2,3-dihydro-1H-inden-1-ol;

4-(6-methoxy-3-(1-methyl-1H-pyrazol-4-yl)-1H-pyrazolo[4,3-b]pyridin-5-yl)-2,3-dihydro-1H-indene-1-carbonitrile;

4-(6-methoxy-3-(1-methyl-1H-pyrazol-4-yl)-1H-pyrazolo[4,3-b]pyridin-5-yl)-2,3-dihydro-1H-inden-2-ol;

(4-(6-methoxy-3-(1-methyl-1H-pyrazol-4-yl)-1H-pyrazolo[4,3-b]pyridin-5-yl)-2,3-dihydro-1H-inden-1-yl)methanol;

2-fluoro-4-(6-methoxy-3-(1-methyl-1H-pyrazol-4-yl)-1H-pyrazolo[4,3-b]pyridin-5-yl)-2,3-dihydro-1H-inden-1-ol;

5-(2,3-dihydro-1H-inden-4-yl)-6-methoxy-3-(1-(pyrrolidin-3-yl)-1H-pyrazol-4-yl)-1H-pyrazolo[4,3-b]pyridine;

5-(2,3-dihydro-1H-inden-4-yl)-3-(1-(1-ethylpyrrolidin-3-yl)-1H-pyrazol-4-yl)-6-methoxy-1H-pyrazolo[4,3-b]pyridine;

3-(4-(5-(2,3-dihydro-1H-inden-4-yl)-6-methoxy-1H-pyrazolo[4,3-b]pyridin-3-yl)-1H-pyrazol-1-yl)cyclobutanecarbonitrile;

5-(2,3-dihydro-1H-inden-4-yl)-6-methoxy-3-(1-(1-methylazetidin-3-yl)-1H-pyrazol-4-yl)-1H-pyrazolo[4,3-b]pyridine;

5-(2,3-dihydro-1H-inden-4-yl)-3-(1-(1-ethylazetidin-3-yl)-1H-pyrazol-4-yl)-6-methoxy-1H-pyrazolo[4,3-b]pyridine;

4-(4-(5-(2,3-dihydro-1H-inden-4-yl)-6-methoxy-1H-pyrazolo[4,3-b]pyridin-3-yl)-1H-pyrazol-1-yl)-N,N-dimethylpiperidine-1-carboxamide;

methyl 4-(4-(5-(2,3-dihydro-1H-inden-4-yl)-6-methoxy-1H-pyrazolo[4,3-b]pyridin-3-yl)-1H-pyrazol-1-yl)piperidine-1-carboxylate;

methyl 3-(4-(5-(2,3-dihydro-1H-inden-4-yl)-6-methoxy-1H-pyrazolo[4,3-b]pyridin-3-yl)-1H-pyrazol-1-yl)azetidine-1-carboxylate;

1-(3-(4-(5-(2,3-dihydro-1H-inden-4-yl)-6-methoxy-1H-pyrazolo[4,3-b]pyridin-3-yl)-1H-pyrazol-1-yl)azetidin-1-yl)ethan-1-one;

5-(2,3-dihydro-1H-inden-4-yl)-6-methoxy-3-(1-(1-(methylsulfonyl)azetidin-3-yl)-1H-pyrazol-4-yl)-1H-pyrazolo[4,3-b]pyridine;

3-(4-(5-(2,3-dihydro-1H-inden-4-yl)-6-methoxy-1H-pyrazolo[4,3-b]pyridin-3-yl)-1H-pyrazol-1-yl)-N,N-dimethylazetidine-1-carboxamide;

cyclopropyl(3-(4-(5-(2,3-dihydro-1H-inden-4-yl)-6-methoxy-1H-pyrazolo[4,3-b]pyridin-3-yl)-1H-pyrazol-1-yl)azetidin-1-yl)methanone;

5-(2,3-dihydro-1H-inden-4-yl)-6-ethoxy-3-(1-methyl-1H-pyrazol-4-yl)-1H-pyrazolo[4,3-b]pyridine;

5-(2,3-dihydro-1H-inden-4-yl)-6-methoxy-3-(1-(pyridin-4-ylmethyl)-1H-pyrazol-4-yl)-1H-pyrazolo[4,3-b]pyridine;

4-(2-(4-(5-(2,3-dihydro-1H-inden-4-yl)-6-methoxy-1H-pyrazolo[4,3-b]pyridin-3-yl)-1H-pyrazol-1-yl)ethyl)morpholine;

3-(1-cyclopropyl-1H-pyrazol-4-yl)-5-(2,3-dihydro-1H-inden-4-yl)-6-methoxy-1H-pyrazolo[4,3-b]pyridine;

3-(4-(5-(2,3-dihydro-1H-inden-4-yl)-6-methoxy-1H-pyrazolo[4,3-b]pyridin-3-yl)-1H-pyrazol-1-yl)propanenitrile;

2-(4-(5-(2,3-dihydro-1H-inden-4-yl)-6-methoxy-1H-pyrazolo[4,3-b]pyridin-3-yl)-1H-pyrazol-1-yl)ethan-1-ol;

5-(2,3-dihydro-1H-inden-4-yl)-6-methoxy-3-(1-(pyridin-4-yl)-1H-pyrazol-4-yl)-1H-pyrazolo[4,3-b]pyridine;

(trans)-4-(4-(5-(2,3-dihydro-1H-inden-4-yl)-6-methoxy-1H-pyrazolo[4,3-b]pyridin-3-yl)-1H-pyrazol-1-yl)cyclohexan-1-ol;

5-(2,3-dimethylphenyl)-N-methyl-3-(1-methyl-1H-pyrazol-4-yl)-1H-pyrazolo[4,3-b]pyridin-6-amine;

6-(difluoromethyl)-5-(2,3-dihydro-1H-inden-4-yl)-3-(1-methyl-1H-pyrazol-4-yl)-1H-pyrazolo[4,3-b]pyridine;

(5-(2,3-dihydro-1H-inden-4-yl)-3-(1-methyl-1H-pyrazol-4-yl)-1H-pyrazolo[4,3-b]pyridin-6-yl)methanol;

5-(2,3-dihydro-1H-inden-4-yl)-N-methyl-3-(1-methyl-1H-pyrazol-4-yl)-1H-pyrazolo[4,3-b]pyridin-6-amine;

(5-(2,3-dimethylphenyl)-3-(1-methyl-1H-pyrazol-4-yl)-1H-pyrazolo[4,3-b]pyridin-6-yl)methanol;

4-(6-chloro-3-(1-methyl-1H-pyrazol-4-yl)-1H-pyrazolo[4,3-b]pyridin-5-yl)-2,3-dihydro-1H-inden-2-ol;

5-(2,3-dimethylphenyl)-6-methyl-3-(1-methyl-1H-pyrazol-4-yl)-1H-pyrazolo[4,3-b]pyridine;

5-(2,3-dimethylphenyl)-6-methoxy-3-(6-(4-methylpiperazin-1-yl)pyridin-3-yl)-1H-pyrazolo[4,3-b]pyridine;

5-(2,3-dimethylphenyl)-3-(6-(4-ethylpiperazin-1-yl)pyridin-3-yl)-6-methoxy-1H-pyrazolo[4,3-b]pyridine;

1-(4-(5-(5-(2,3-dimethylphenyl)-6-methoxy-1H-pyrazolo[4,3-b]pyridin-3-yl)pyridin-2-yl)piperazin-1-yl)ethan-1-one;

4-(5-(5-(2,3-dimethylphenyl)-6-methoxy-1H-pyrazolo[4,3-b]pyridin-3-yl)pyridin-2-yl)morpholine;

4-(5-(5-(2,3-dimethylphenyl)-6-methoxy-1H-pyrazolo[4,3-b]pyridin-3-yl)pyridin-2-yl)-1-methylpiperazin-2-one;

1-(5-(5-(2,3-dimethylphenyl)-6-methoxy-1H-pyrazolo[4,3-b]pyridin-3-yl)pyridin-2-yl)piperidin-4-ol;

(R)-5-(2,3-dimethylphenyl)-3-(6-(3,4-dimethylpiperazin-1-yl)pyridin-3-yl)-6-methoxy-1H-pyrazolo[4,3-b]pyridine;

5-(2,3-dimethylphenyl)-6-(methoxy-d3)-3-(6-(4-methylpiperazin-1-yl)pyridin-3-yl)-1H-pyrazolo[4,3-b]pyridine;

5-(2,3-dimethylphenyl)-6-methoxy-3-(6-((1S,4S)-5-methyl-2,5-diazabicyclo[2.2.1]heptan-2-yl)pyridin-3-yl)-1H-pyrazolo[4,3-b]pyridine;

1-(5-(5-(2,3-dimethylphenyl)-6-methoxy-1H-pyrazolo[4,3-b]pyridin-3-yl)pyridin-2-yl)-N,N-dimethylpiperidine-4-carboxamide;

1-(5-(5-(2,3-dimethylphenyl)-6-methoxy-1H-pyrazolo[4,3-b]pyridin-3-yl)pyridin-2-yl)-4-methylpiperidine-4-carboxylic acid;

3-(4-(5-(2-fluoro-3-methylphenyl)-6-methoxy-1H-pyrazolo[4,3-b]pyridin-3-yl)-1H-pyrazol-1-yl)-N,N-dimethylazetidine-1-carboxamide;
N-((cis)-4-(4-(5-(2,3-dihydro-1H-inden-4-yl)-6-methoxy-1H-pyrazolo[4,3-b]pyridin-3-yl)-1H-pyrazol-1-yl)cyclohexyl)acetamide;
5-(2,3-dihydro-1H-inden-4-yl)-3-(6-(2,4-dimethylpiperazin-1-yl)pyridin-3-yl)-6-methoxy-1H-pyrazolo[4,3-b]pyridine;
2-(3-(3-(6-(4-acetylpiperazin-1-yl)pyridin-3-yl)-6-methoxy-1H-pyrazolo[4,3-b]pyridin-5-yl)-2-methylphenyl)acetonitrile;
2-(3-(6-methoxy-3-(6-morpholinopyridin-3-yl)-1H-pyrazolo[4,3-b]pyridin-5-yl)-2-methylphenyl)acetonitrile;
5-(2,3-dihydro-1H-inden-4-yl)-6-methoxy-3-(6-(pyrrolidin-1-yl)pyridin-3-yl)-1H-pyrazolo[4,3-b]pyridine;
4-(5-(5-(2,3-dihydro-1H-inden-4-yl)-6-methoxy-1H-pyrazolo[4,3-b]pyridin-3-yl)pyridin-2-yl)morpholine;
4-(5-(5-(2,3-dihydro-1H-inden-4-yl)-6-methoxy-1H-pyrazolo[4,3-b]pyridin-3-yl)pyridin-2-yl)-N-ethylpiperazine-1-carboxamide;
4-(5-(5-(2,3-dihydro-1H-inden-4-yl)-6-methoxy-1H-pyrazolo[4,3-b]pyridin-3-yl)pyridin-2-yl)piperazine-1-carboxamide;
1-(4-(4-(5-(2,3-dihydro-1H-inden-4-yl)-6-methoxy-1H-pyrazolo[4,3-b]pyridin-3-yl)phenyl)piperazin-1-yl)ethan-1-one;
5-(2,3-dihydro-1H-inden-4-yl)-3-(4-(4-isopropylpiperazin-1-yl)phenyl)-6-methoxy-1H-pyrazolo[4,3-b]pyridine;
5-(2,3-dihydro-1H-inden-4-yl)-3-(4-(4-ethylpiperazin-1-yl)phenyl)-6-methoxy-1H-pyrazolo[4,3-b]pyridine;
1-(4-(5-(5-(2,3-dihydro-1H-inden-4-yl)-6-methoxy-1H-pyrazolo[4,3-b]pyridin-3-yl)pyridin-2-yl)piperazin-1-yl)ethan-1-one;
8-(5-(5-(2,3-dimethylphenyl)-6-methoxy-1H-pyrazolo[4,3-b]pyridin-3-yl)pyridin-2-yl)-1-oxa-3,8-diazaspiro[4.5]decan-2-one;
5-(2,3-dimethylphenyl)-6-methoxy-3-(1-(pyridin-2-ylmethyl)-1H-pyrazol-4-yl)-1H-pyrazolo[4,3-b]pyridine;
3-(1-cyclopropyl-1H-pyrazol-4-yl)-5-(2,3-dimethylphenyl)-6-methoxy-1H-pyrazolo[4,3-b]pyridine;
6-methoxy-5-(2-methyl-3-(methyl-d3)phenyl)-3-(6-(4-methylpiperazin-1-yl)pyridin-3-yl)-1H-pyrazolo[4,3-b]pyridine;
1-(4-(4-(5-(2,3-dimethylphenyl)-6-methoxy-1H-pyrazolo[4,3-b]pyridin-3-yl)-1H-pyrazol-1-yl)piperidin-1-yl)ethan-1-one;
methyl 4-(4-(5-(2,3-dimethylphenyl)-6-methoxy-1H-pyrazolo[4,3-b]pyridin-3-yl)-1H-pyrazol-1-yl)piperidine-1-carboxylate;
methyl 3-(4-(5-(2,3-dimethylphenyl)-6-methoxy-1H-pyrazolo[4,3-b]pyridin-3-yl)-1H-pyrazol-1-yl)azetidine-1-carboxylate; and
3-(4-(5-(2,3-dimethylphenyl)-6-methoxy-1H-pyrazolo[4,3-b]pyridin-3-yl)-1H-pyrazol-1-yl)-N,N-dimethylazetidine-1-carboxamide;
or a pharmaceutically acceptable salt of any of the aforementioned.

In some embodiments, provided herein is a compound selected from:
2-fluoro-4-(6-methoxy-3-(1-methyl-1H-pyrazol-4-yl)-1H-pyrazolo[4,3-b]pyridin-5-yl)-2,3-dihydro-1H-inden-1-ol;
5-(2,3-dimethylphenyl)-6-methoxy-3-(6-(4-methylpiperazin-1-yl)pyridin-3-yl)-1H-pyrazolo[4,3-b]pyridine;
4-(6-methoxy-3-(6-((tetrahydrofuran-3-yl)oxy)pyridin-3-yl)-1H-pyrazolo[4,3-b]pyridin-5-yl)-2,3-dihydro-1H-inden-2-ol;
4-(6-methoxy-3-(1-methyl-1H-pyrazol-4-yl)-1H-pyrazolo[4,3-b]pyridin-5-yl) 2,3-dihydro-1H-inden-2-d-2-ol;
4-(6-methoxy-3-(6-(1-methyl-5-oxopyrrolidin-3-yl)pyridin-3-yl)-1H-pyrazolo[4,3-b]pyridin-5-yl)-2,3-dihydro-1H-indene-1-carbonitrile;
(S)-1-(4-(5-(5-(2,3-dimethylphenyl)-6-methoxy-1H-pyrazolo[4,3-b]pyridin-3-yl)pyridin-2-yl)piperidin-1-yl)-2-hydroxypropan-1-one;
1-(4-(5-(5-(2,3-dimethylphenyl)-6-methoxy-1H-pyrazolo[4,3-b]pyridin-3-yl)pyridin-2-yl)piperidin-1-yl)-2-hydroxyethan-1-one;
4-(5-(5-(2,3-dimethylphenyl)-6-methoxy-1H-pyrazolo[4,3-b]pyridin-3-yl)pyridin-2-yl)cyclohexane-1-carboxylic acid;
(3S,4R)-1-(5-(5-(2,3-dimethylphenyl)-6-methoxy-1H-pyrazolo[4,3-b]pyridin-3-yl)pyridin-2-yl)-4-fluoropyrrolidin-3-amine;
(2S)-1-(4-(5-(5-(2-fluoro-2,3-dihydro-1H-inden-4-yl)-6-methoxy-1H-pyrazolo[4,3-b]pyridin-3-yl)pyridin-2-yl)piperidin-1-yl)-2-hydroxypropan-1-one;
1-(4-(5-(5-(2-fluoro-2,3-dihydro-1H-inden-4-yl)-6-methoxy-1H-pyrazolo[4,3-b]pyridin-3-yl)pyridin-2-yl)piperidin-1-yl)-2-hydroxyethan-1-one;
(7R,8aS)-2-(5-(5-(2-fluoro-2,3-dihydro-1H-inden-4-yl)-6-methoxy-1H-pyrazolo[4,3-b]pyridin-3-yl)pyridin-2-yl)octahydropyrrolo[1,2-a]pyrazin-7-ol;
5-(2-fluoro-2,3-dihydro-1H-inden-4-yl)-6-methoxy-3-(1-methyl-1H-pyrazol-4-yl)-1H-pyrazolo[4,3-b]pyridine;
(7S,8aR)-2-(5-(5-(2,3-dimethylphenyl)-6-methoxy-1H-pyrazolo[4,3-b]pyridin-3-yl)pyridin-2-yl)octahydropyrrolo[1,2-a]pyrazin-7-ol;
4-(5-(5-(2,3-dimethylphenyl)-6-methoxy-1H-pyrazolo[4,3-b]pyridin-3-yl)pyridin-2-yl)-1-imino-1$\lambda^6$-thiomorpholine 1-oxide;
(7R,8aS)-2-(5-(5-(2,3-dimethylphenyl)-6-methoxy-1H-pyrazolo[4,3-b]pyridin-3-yl)pyridin-2-yl)octahydropyrrolo[1,2-a]pyrazin-7-ol;
(S)—N-(1-(5-(5-(2,3-dimethylphenyl)-6-methoxy-1H-pyrazolo[4,3-b]pyridin-3-yl)pyridin-2-yl)pyrrolidin-3-yl)-2-hydroxy-N-methylacetamide;
2-(3-(3-(6-(4-(2-hydroxyethyl)piperazin-1-yl)pyridin-3-yl)-6-methoxy-1H-pyrazolo[4,3-b]pyridin-5-yl)-2-methylphenyl)acetonitrile;
(7R,8aS)-2-(5-(6-methoxy-5-(3-methoxy-2-methylphenyl)-1H-pyrazolo[4,3-b]pyridin-3-yl)pyridin-2-yl)octahydropyrrolo[1,2-a]pyrazin-7-ol;
(7R,8aS)-2-(5-(5-(2,3-dihydrobenzo[b][1,4]dioxin-5-yl)-6-methoxy-1H-pyrazolo[4,3-b]pyridin-3-yl)pyridin-2-yl)octahydropyrrolo[1,2-a]pyrazin-7-ol;
(7R,8aS)-2-(5-(5-(2-cyclopropylphenyl)-6-methoxy-1H-pyrazolo[4,3-b]pyridin-3-yl)pyridin-2-yl)octahydropyrrolo[1,2-a]pyrazin-7-ol;
(7R,8aS)-2-(5-(5-(chroman-5-yl)-6-methoxy-1H-pyrazolo[4,3-b]pyridin-3-yl)pyridin-2-yl)octahydropyrrolo[1,2-a]pyrazin-7-ol;
(7R,8aS)-2-(5-(5-(2-fluoro-3-methylphenyl)-6-methoxy-1H-pyrazolo[4,3-b]pyridin-3-yl)pyridin-2-yl)octahydropyrrolo[1,2-a]pyrazin-7-ol;
4-(6-methoxy-3-(6-(2-methoxyethoxy)pyridin-3-yl)-1H-pyrazolo[4,3-b]pyridin-5-yl)-2,3-dihydro-1H-inden-2-ol;
4-(6-methoxy-3-(6-((tetrahydro-2H-pyran-4-yl)oxy)pyridin-3-yl)-1H-pyrazolo[4,3-b]pyridin-5-yl)-2,3-dihydro-1H-inden-2-ol;
4-(3-(6-cyclopropylpyridin-3-yl)-6-methoxy-1H-pyrazolo[4,3-b]pyridin-5-yl)-2,3-dihydro-1H-inden-2-ol; and N-(1-(5-(5-(2,3-dimethylphenyl)-6-methoxy-1H-pyrazolo[4,3-b]pyridin-3-yl)pyridin-2-yl)azetidin-3-yl)-2-hydroxy-N-methylacetamide;

or a pharmaceutically acceptable salt of any of the aforementioned.

In some embodiments, provided herein is a compound selected from:

1-(4-(5-(5-(2,3-Dihydro-1H-inden-4-yl)-6-methoxy-1H-pyrazolo[4,3-b]pyridin-3-yl)pyridin-2-yl)piperidin-1-yl)ethan-1-one;

1-(4-(5-(5-(2,3-Dihydro-1H-inden-4-yl)-6-methoxy-1H-pyrazolo[4,3-b]pyridin-3-yl)pyridin-2-yl)piperidin-1-yl)-2-hydroxyethan-1-one;

1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)-2-hydroxyethan-1-one (Peak 1);

1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)-2-hydroxyethan-1-one (Peak 2);

1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)ethan-1-one (Peak 1);

1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)ethan-1-one (Peak 2);

3-(5-(5-(2,3-Dihydro-1H-inden-4-yl)-6-methoxy-1H-pyrazolo[4,3-b]pyridin-3-yl)pyridin-2-yl)-[1,3'-bipyrrolidin]-2'-one (Peak 1);

3-(5-(5-(2,3-Dihydro-1H-inden-4-yl)-6-methoxy-1H-pyrazolo[4,3-b]pyridin-3-yl)pyridin-2-yl)-1'-methyl-[1,3'-bipyrrolidin]-2'-one (Peak 1);

2-(3-(5-(5-(2,3-Dihydro-1H-inden-4-yl)-6-methoxy-1H-pyrazolo[4,3-b]pyridin-3-yl)pyridin-2-yl)pyrrolidin-1-yl)propanamide (Peak 1);

5-(2,3-Dihydro-1H-inden-4-yl)-6-methoxy-3-(6-(1-(methyl-L-prolyl)piperidin-4-yl)pyridin-3-yl)-1H-pyrazolo[4,3-b]pyridine;

(3-(5-(5-(2,3-Dihydro-1H-inden-4-yl)-6-methoxy-1H-pyrazolo[4,3-b]pyridin-3-yl)pyridin-2-yl)pyrrolidin-1-yl)((R)-4-methylmorpholin-3-yl)methanone (Peak 2);

4-(6-Methoxy-3-(6-(4-methylpiperazin-1-yl)pyridin-3-yl)-1H-pyrazolo[4,3-b]pyridin-5-yl)-2,3-dihydro-1H-indene-1-carbonitrile;

4-(3-(1-(3-Cyanocyclobutyl)-1H-pyrazol-4-yl)-6-methoxy-1H-pyrazolo[4,3-b]pyridin-5-yl)-2,3-dihydro-1H-indene-1-carbonitrile;

4-(3-(1-(1-Acetylpiperidin-4-yl)-1H-pyrazol-4-yl)-6-methoxy-1H-pyrazolo[4,3-b]pyridin-5-yl)-2,3-dihydro-1H-indene-1-carbonitrile;

4-(3-(6-(4-Hydroxycyclohexyl)pyridin-3-yl)-6-methoxy-1H-pyrazolo[4,3-b]pyridin-5-yl)-2,3-dihydro-1H-indene-1-carbonitrile;

4-(3-(6-(4-(2-Hydroxyethyl)piperazin-1-yl)pyridin-3-yl)-6-methoxy-1H-pyrazolo[4,3-b]pyridin-5-yl)-2,3-dihydro-1H-indene-1-carbonitrile;

4-(3-(6-(1-(2-Hydroxyacetyl)piperidin-4-yl)pyridin-3-yl)-6-methoxy-1H-pyrazolo[4,3-b]pyridin-5-yl)-2,3-dihydro-1H-indene-1-carbonitrile;

1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxyethan-1-one;

1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-3-(dimethylamino)propan-1-one;

(S)-1-(3-(4-(5-(2,3-dihydro-1H-inden-4-yl)-6-methoxy-1H-pyrazolo[4,3-b]pyridin-3-yl)-1H-pyrazol-1-yl)azetidin-1-yl)-2-(dimethylamino)propan-1-one;

(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-methylazetidin-2-yl)methanone;

1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(4-methylpiperazin-1-yl)ethan-1-one;

1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(4-hydroxypiperidin-1-yl)ethan-1-one;

(R)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-methylazetidin-2-yl)methanone;

(R)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxypropan-1-one;

(S)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxypropan-1-one;

(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((trans)-3-hydroxycyclobutyl)methanone;

(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((cis)-3-hydroxycyclobutyl)methanone;

(R)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(4-methylmorpholin-3-yl)methanone;

(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(4-methylmorpholin-3-yl)methanone;

(S)-1-(3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxyethan-1-one;

(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(tetrahydrofuran-2-yl)methanone;

(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(tetrahydrofuran-3-yl)methanone;

(R)-1-((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxypropan-1-one;

(S)-1-((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxypropan-1-one;

(R)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-3-hydroxybutan-1-one;

(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1r,3r)-3-hydroxy-3-methylcyclobutyl)methanone;

(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1s,3s)-3-hydroxy-3-methylcyclobutyl)methanone;

((R)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((S)-4-methylmorpholin-3-yl)methanone;

((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((R)-4-methylmorpholin-3-yl)methanone;

(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-(hydroxymethyl)cyclobutyl)methanone;

(S)-(3-(4-(5-(2,3-dihydro-1H-inden-4-yl)-6-methoxy-1H-pyrazolo[4,3-b]pyridin-3-yl)-1H-pyrazol-1-yl)azetidin-1-yl)(1-ethylazetidin-2-yl)methanone;

(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-(2-fluoroethyl)azetidin-2-yl)methanone;

(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-isopropylazetidin-2-yl)methanone;

((S)-3-(4-(5-(2,3-dihydro-1H-inden-4-yl)-6-methoxy-1H-pyrazolo[4,3-b]pyridin-3-yl)-1H-pyrazol-1-yl)pyrrolidin-1-yl)((S)-1-(2-fluoroethyl)azetidin-2-yl)methanone;

((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((trans)-3-hydroxycyclobutyl)methanone;

((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((cis)-3-hydroxycyclobutyl)methanone;

((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((1s,3r)-3-hydroxy-3-methylcyclobutyl)methanone;

1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-methoxyethan-1-one;

1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(dimethylamino)-2-methylpropan-1-one;

1-(3-(4-(5-(2,3-Dihydro-1H-inden-4-yl)-6-methoxy-1H-pyrazolo[4,3-b]pyridin-3-yl)-1H-pyrazol-1-yl)azetidine-1-carbonyl)cyclopropane-1-carbonitrile;

2-((3-(4-(5-(2,3-Dihydro-1H-inden-4-yl)-6-methoxy-1H-pyrazolo[4,3-b]pyridin-3-yl)-1H-pyrazol-1-yl)azetidin-1-yl)sulfonyl)ethan-1-01;

2-((3-(4-(5-(2,3-Dihydro-1H-inden-4-yl)-6-methoxy-1H-pyrazolo[4,3-b]pyridin-3-yl)-1H-pyrazol-1-yl)azetidin-1-yl)sulfonyl)-N,N-dimethylethan-1-amine;

2-Methoxyethyl 3-(4-(5-(2,3-dihydro-1H-inden-4-yl)-6-methoxy-1H-pyrazolo[4,3-b]pyridin-3-yl)-1H-pyrazol-1-yl)azetidine-1-carboxylate;

(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1s,3s)-3-methoxycyclobutyl)methanone;

N-(3-(5-(5-(2,3-Dihydro-1H-inden-4-yl)-6-methoxy-1H-pyrazolo[4,3-b]pyridin-3-yl)pyridin-2-yl)cyclopentyl)-N-methylmethanesulfonamide;

N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxy-N-methylacetamide (Peak 1);

(2S)—N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxypropanamid;

N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxyacetamide;

2-(1-(4-(5-(2,3-Dihydro-1H-inden-4-yl)-6-methoxy-1H-pyrazolo[4,3-b]pyridin-3-yl)phenyl)-3-azabicyclo[3.1.0]hexan-3-yl)ethan-1-ol;

4-(3-(4-((1R,5S)-3-(2-Hydroxyethyl)-3-azabicyclo[3.1.0]hexan-1-yl)phenyl)-6-methoxy-1H-pyrazolo[4,3-b]pyridin-5-yl)-2,3-dihydro-1H-indene-1-carbonitrile;

1-((5-(5-(2,3-Dihydro-1H-inden-4-yl)-6-methoxy-1H-pyrazolo[4,3-b]pyridin-3-yl)pyridin-2-yl)methyl)piperidin-4-ol;

5-((5-(5-(2,3-Dihydro-1H-inden-4-yl)-6-methoxy-1H-pyrazolo[4,3-b]pyridin-3-yl)pyridin-2-yl)methyl)-2-oxa-5-azabicyclo[2.2.1]heptane;

4-(1-(5-(5-(2,3-Dihydro-1H-inden-4-yl)-6-methoxy-1H-pyrazolo[4,3-b]pyridin-3-yl)pyridin-2-yl)ethyl)morpholine;

7-((5-(5-(2,3-Dihydro-1H-inden-4-yl)-6-methoxy-1H-pyrazolo[4,3-b]pyridin-3-yl)pyridin-2-yl)methyl)-5,6,7,8-tetrahydro-[1,2,4]triazolo[1,5-a]pyrazine;

4-(5-(5-(2,3-Dihydro-1H-inden-4-yl)-6-methoxy-1H-pyrazolo[4,3-b]pyridin-3-yl)pyridin-2-yl)-1-(2-hydroxyethyl)piperidine-4-carbonitrile;

4-(5-(5-(2,3-Dihydro-1H-inden-4-yl)-6-methoxy-1H-pyrazolo[4,3-b]pyridin-3-yl)pyridin-2-yl)-1-(2-hydroxyacetyl)piperidine-4-carbonitrile;

2-(3-(6-Methoxy-3-(6-(4-(2-methoxyethyl)piperazin-1-yl)pyridin-3-yl)-1H-pyrazolo[4,3-b]pyridin-5-yl)-2-methylphenyl)acetonitrile;

4-(6-Methoxy-3-(1-(1-(tetrahydro-2H-pyran-4-carbonyl)piperidin-4-yl-4-d)-1H-pyrazol-4-yl)-1H-pyrazolo[4,3-b]pyridin-5-yl)-2,3-dihydro-1H-indene-1-carbonitrile;

4-(6-Methoxy-3-(1-((S)-1-(2-methoxyacetyl)pyrrolidin-3-yl)-1H-pyrazol-4-yl)-1H-pyrazolo[4,3-b]pyridin-5-yl)-2,3-dihydro-1H-indene-1-carbonitrile;

4-(6-Methoxy-3-(1-((S)-1-((S)-tetrahydrofuran-2-carbonyl)pyrrolidin-3-yl)-1H-pyrazol-4-yl)-1H-pyrazolo[4,3-b]pyridin-5-yl)-2,3-dihydro-1H-indene-1-carbonitrile;

(7R,8aS)-2-(5-(5-(2,3-Dihydro-1H-inden-4-yl)-6-methoxy-1H-pyrazolo[4,3-b]pyridin-3-yl)pyridin-2-yl)octahydropyrrolo[1,2-a]pyrazin-7-ol;

N-(1-(5-(5-(2,3-Dihydro-1H-inden-4-yl)-6-methoxy-1H-pyrazolo[4,3-b]pyridin-3-yl)pyridin-2-yl)azetidin-3-yl)-2-hydroxy-N-methylacetamide;

(3-(5-(5-(2,3-Dihydro-1H-inden-4-yl)-6-methoxy-1H-pyrazolo[4,3-b]pyridin-3-yl)pyridin-2-yl)azetidin-1-yl)(tetrahydrofuran-2-yl)methanone;

(S)-(3-(5-(5-(2,3-Dihydro-1H-inden-4-yl)-6-methoxy-1H-pyrazolo[4,3-b]pyridin-3-yl)pyridin-2-yl)azetidin-1-yl)(1-methylpiperidin-2-yl)methanone;

1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-(dimethylamino)ethan-1-one;

1-(3-(5-(5-(2,3-Dihydro-1H-inden-4-yl)-6-methoxy-1H-pyrazolo[4,3-b]pyridin-3-yl)pyridin-2-yl)azetidin-1-yl)-3-hydroxypropan-1-one;

1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-hydroxyethan-1-one;

(S)-1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-hydroxypropan-1-one;

N-(3-(5-(5-(2,3-Dihydro-1H-inden-4-yl)-6-methoxy-1H-pyrazolo[4,3-b]pyridin-3-yl)pyridin-2-yl)cyclobutyl)-2-hydroxy-N-methylacetamide;

1-(3-(5-(5-(2,3-Dihydro-1H-inden-4-yl)-6-methoxy-1H-pyrazolo[4,3-b]pyridin-3-yl)pyridin-2-yl)azetidin-1-yl-3-d)-2-hydroxyethan-1-one;

Methyl 4-(5-(5-(1-Cyano-2,3-dihydro-1H-inden-4-yl)-6-methoxy-1H-pyrazolo[4,3-b]pyridin-3-yl)pyridin-2-yl)piperidine-1-carboxylate;

4-(6-Methoxy-3-(6-(1-(morpholine-4-carbonyl)piperidin-4-yl)pyridin-3-yl)-1H-pyrazolo[4,3-b]pyridin-5-yl)-2,3-dihydro-1H-indene-1-carbonitrile, Peak 2;

4-(3-(6-(1-Acetylpiperidin-4-yl)pyridin-3-yl)-6-methoxy-1H-pyrazolo[4,3-b]pyridin-5-yl)-2,3-dihydro-1H-indene-1-carbonitrile, Peak 2;

4-(3-(6-(1-Acetylpyrrolidin-3-yl)pyridin-3-yl)-6-methoxy-1H-pyrazolo[4,3-b]pyridin-5-yl)-2,3-dihydro-1H-indene-1-carbonitrile;

4-(6-Methoxy-3-(6-(1-(morpholine-4-carbonyl)pyrrolidin-3-yl)pyridin-3-yl)-1H-pyrazolo[4,3-b]pyridin-5-yl)-2,3-dihydro-1H-indene-1-carbonitrile;

4-(3-(1-(Cyanomethyl)-1H-pyrazol-4-yl)-6-methoxy-1H-pyrazolo[4,3-b]pyridin-5-yl)-2,3-dihydro-1H-indene-1-carbonitrile;

4-(6-Methoxy-3-(6-(4-methylpiperazin-1-yl)pyridin-3-yl)-1H-pyrazolo[4,3-b]pyridin-5-yl)-2,3-dihydro-1H-indene-1-carbonitrile;

3-(3-(5-(5-(2,3-Dihydro-1H-inden-4-yl)-6-methoxy-1H-pyrazolo[4,3-b]pyridin-3-yl)pyridin-2-yl)azetidin-1-yl)propanenitrile;

N-(3-(5-(5-(2,3-Dihydro-1H-inden-4-yl)-6-methoxy-1H-pyrazolo[4,3-b]pyridin-3-yl)pyridin-2-yl)cyclobutyl)-2-methoxy-N-methylacetamide;

N-(3-(5-(5-(2,3-Dihydro-1H-inden-4-yl)-6-methoxy-1H-pyrazolo[4,3-b]pyridin-3-yl)pyridin-2-yl)cyclobutyl)-3-hydroxy-N-methylpropanamide;

(S)—N-(3-(5-(5-(2,3-Dihydro-1H-inden-4-yl)-6-methoxy-1H-pyrazolo[4,3-b]pyridin-3-yl)pyridin-2-yl)cyclobutyl)-2-hydroxy-N-methylpropanamide;

1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one;

(R) 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one, two enantiomers;

(S) 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one, two enantiomers;

(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)((R)-4-methylmorpholin-3-yl)methanone;

5-(2,3-Dihydro-1H-inden-4-yl)-6-methoxy-3-(6-(3-(tetrahydro-2H-pyran-4-yl)-3-azabicyclo[3.1.0]hexan-1-yl)pyridin-3-yl)-1H-pyrazolo[4,3-b]pyridine 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol;

(R) 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol, two enantiomers;

(S) 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol, two enantiomers;

3-(5-(5-(2,3-Dihydro-1H-inden-4-yl)-6-methoxy-1H-pyrazolo[4,3-b]pyridin-3-yl)pyridin-2-yl)-1-((R)-4-methylmorpholine-3-carbonyl)pyrrolidine-3-carbonitrile;

(R)-4-(5-(5-(2,3-Dihydro-1H-inden-4-yl)-6-methoxy-1H-pyrazolo[4,3-b]pyridin-3-yl)pyridin-2-yl)-1-(4-methylmorpholine-3-carbonyl)piperidine-4-carbonitrile;

1-(1-(4-(5-(2,3-Dihydro-1H-inden-4-yl)-6-methoxy-1H-pyrazolo[4,3-b]pyridin-3-yl)-1H-pyrazol-1-yl)-3-azabicyclo[3.1.0]hexan-3-yl)-2-hydroxyethan-1-one;

3-(5-(5-(2,3-Dihydro-1H-inden-4-yl)-6-methoxy-1H-pyrazolo[4,3-b]pyridin-3-yl)pyridin-2-yl)-1-(2-hydroxyacetyl)pyrrolidine-3-carbonitrile;

(S)-4-((5-(5-(2,3-Dihydro-1H-inden-4-yl)-6-methoxy-1H-pyrazolo[4,3-b]pyridin-3-yl)pyridin-2-yl)methyl)-1,3-dimethylpiperazin-2-one; and (1R,4R)-5-((5-(5-(2,3-Dihydro-1H-inden-4-yl)-6-methoxy-1H-pyrazolo[4,3-b]pyridin-3-yl)pyridin-2-yl)methyl)-2-oxa-5-azabicyclo[2.2.1]heptane;

or a pharmaceutically acceptable salt of any of the aforementioned.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub combination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. A single divalent substituent, e.g., oxo, can replace two hydrogen atoms.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. An alkyl group formally corresponds to an alkane with one C—H bond replaced by the point of attachment of the alkyl group to the remainder of the compound. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, the term "$C_{i-j}$ alkylene," employed alone or in combination with other terms, means a saturated divalent linking hydrocarbon group that may be straight-chain or branched, having i to j carbons. In some embodiments, the alkylene group contains from 1 to 4 carbon atoms, from 1 to 3 carbon atoms, or from 1 to 2 carbon atoms. Examples of alkylene moieties include, but are not limited to, chemical groups such as methylene, ethylene, 1,1-ethylene, 1,2-ethylene, 1,3-propylene, 1,2-propylene, 1,1-propylene, isopropylene, and the like.

As used herein, "alkenyl," employed alone or in combination with other terms, refers to a straight-chain or branched hydrocarbon group corresponding to an alkyl group having one or more carbon-carbon double bonds. An alkenyl group formally corresponds to an alkene with one C—H bond replaced by the point of attachment of the alkenyl group to the remainder of the compound. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to a straight-chain or branched hydrocarbon group corresponding to an alkyl group having one or more carbon-carbon triple bonds. An alkynyl group formally corresponds to an alkyne with one C—H bond replaced by the point of attachment of the alkyl group to the remainder of the compound. In some embodiments, the alkynyl moiety contains 2 to 6 or 2 to 4 carbon atoms. Example alkynyl groups include, but are not limited to, ethynyl, propyn-1-yl, propyn-2-yl, and the like.

As used herein, "halo" or "halogen", employed alone or in combination with other terms, includes fluoro, chloro, bromo, and iodo. In some embodiments, halo is F or Cl. In some embodiments, halo is F.

As used herein, the term "haloalkyl," employed alone or in combination with other terms, refers to an alkyl group in which one or more of the hydrogen atoms has been replaced by a halogen atom, having up to the full valency of halogen atom substituents, which may either be the same or different. In some embodiments, the halogen atoms are fluoro atoms. In some embodiments, the alkyl group has 1 to 6, 1 to 4, or 1 to 3 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. In some embodiments, the alkyl group has 1 to 6, 1 to 4, or 1 to 3 carbon atoms. Example alkoxy groups include methoxy, ethoxy, propoxy (e.g., n-propoxy and isopropoxy), t-butoxy, and the like. In some embodiments, alkoxy is methoxy.

As used herein, "haloalkoxy," employed alone or in combination with other terms, refers to a group of formula —O-(haloalkyl). In some embodiments, the alkyl group has 1 to 6, 1 to 4, or 1 to 3 carbon atoms. An example haloalkoxy group is —$OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —N(alkyl)$_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio," employed alone or in combination with other terms, refers to a group of formula —S-alkyl. In some embodiments, the alkyl group has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. A cycloalkyl group containing a fused aromatic ring can be attached through any ring-forming atom including a ring-forming atom of the fused aromatic ring. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members, or 3 to 6 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus, and which has 4-14 ring members, 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or polycyclic (e.g., having 2, 3 or 4 fused, bridged, or spiro rings) or spirocyclic ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or 3 to 8 ring forming atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, an S atom in the ring of the heterocycloalkyl group can be oxidized to form an imino-$\lambda^6$-sulfanone group (i.e., the S atom is substituted with an =O group and an =NH group). In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring. In some embodiments, the heterocycloalkyl is a 4-7 membered heterocycloalkyl moiety having carbon and 1, 2, or 3 heteroatoms independently selected from N, O and S. In some embodiments, the heterocycloalkyl is 4-10 membered heterocycloalkyl moiety having carbon and 1, 2, or 3 heteroatoms independently selected from N, O and S.

As used herein, the term "aryl," employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl.

As used herein, the term "genetic alterations" employed alone or in combination with other terms, refers to mutations, fusions, rearrangements (translocations, deletions, inversions) and amplifications of genes.

As used herein, the term "heteroaryl" or "heteroaromatic" employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl, pyridone, or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In one embodiment the heteroaryl group is a 5 to 10 membered heteroaryl group. In another embodiment the heteroaryl group is a 5 to 6 membered heteroaryl group. In some embodiments, the heteroaryl is a 5-6 membered heteroaryl moiety having carbon and 1, 2, or 3 heteroatoms independently selected from N, O and S. In some embodiments, the heteroaryl is a 5-10 membered heteroaryl moiety having carbon and 1, 2, or 3 heteroatoms independently selected from N, O and S. In some embodiments, the heteroaryl has 5-6 ring atoms and 1 or 2 heteroatom ring members independently selected from nitrogen, sulfur and oxygen. In some embodiments, no more than 2 heteroatoms of a 5-membered heteroaryl moiety are N.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (5)-configuration. In compounds with more than one chiral centers, each of the chiral centers in the compound may be independently (R) or (5), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers, and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., in the form of hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The following abbreviations may be used herein: AcOH (acetic acid); $Ac_2O$ (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography mass spectrometry); m (multiplet); M (molar); mCPBA (3-chloroperoxybenzoic acid); $MgSO_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaHCO_3$ (sodium bicarbonate); NaOH (sodium hydroxide); $Na_2SO_4$ (sodium sulfate); $NH_4Cl$ (ammonium chloride); $NH_4OH$ (ammonium hydroxide); NIS (N-iodosuccinimide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), $POCl_3$ (phosphoryl chloride); RP-HPLC (reverse phase high performance liquid chromatography); s (singlet); SEM (2-trimethylsilylethoxymethyl); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

Synthesis

Compounds of the invention, including salts thereof, can be prepared using known organic synthesis techniques and according to various possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of formula (I) with a variety of substitution at position $Cy^1$ can be prepared, using a process as illustrated in Scheme 1. In the process depicted in Scheme 1, the halo substituent in compounds of formula 1-1 can undergo a cross-coupling reaction, including Suzuki (Tetrahedron 2002, 58, 9633-9695) (e.g., in the presence of a palladium catalyst, such as Xphos Pd G2, and a base, such as potassium phosphate), Negishi (ACS Catalysis 2016, 6, 1540-1552) or Stille (ACS Catalysis 2015, 5, 3040-3053) (e.g., in the presence of a palladium(0) catalyst, such as tetrakis(triphenylphosphine)palladium(0)), and others, to give compounds of formula 1-2. A protective group in the compounds of formula 1-2 can be removed in acidic conditions (e.g., in the presence of TFA or HCl) to give compounds of formula 1-3. These compounds can be further halogenated with one of the halogenation agents (e.g., NIS or iodine), followed by NH protection with a suitable protecting group (e.g., Boc), to afford compounds of formula 1-4. A cross-coupling reaction of 1-4, including Suzuki (e.g., in the presence of a palladium catalyst, such as Xphos Pd G2, and a base, such as potassium phosphate), Negishi or Stille (e.g., in the presence of a palladium(0) catalyst, such as tetrakis(triphenylphosphine)palladium(0)), followed by deprotection of the protective group, affords compounds of formula (I).

Scheme 1

-continued

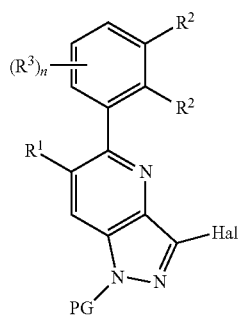

1-4

| 1) Cross-coupling
| 2) NH deprotection

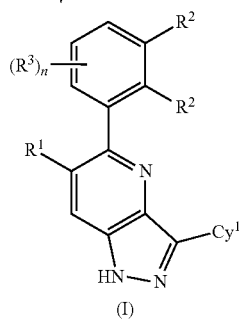

(I)

Alternatively, the compounds of formula (I) can be prepared, using a process as illustrated in Scheme 2. A protective group in the compounds of formula 1-1 can be removed in acidic conditions (e.g., in the presence of TFA or HCl) to give compounds of formula 2-1. These compounds can be iodinated with one of the iodination agents (e.g., NIS or iodine), followed by NH protection with a suitable protecting group (e.g., Boc), to afford compounds of formula 2-2. A cross-coupling reaction of 2-2, including Suzuki (e.g., in the presence of a palladium catalyst, such as Pd(dppf)Cl$_2$, and a base, such as potassium phosphate), results in the formation of the compounds of formula 2-3. The second cross-coupling reaction of 2-3, including Suzuki (e.g., in the presence of a palladium catalyst, such as Xphos Pd G2, and a base, such as potassium phosphate), Negishi or Stille (e.g., in the presence of a palladium(0) catalyst, such as tetrakis(triphenylphosphine)palladium(0)), followed by deprotection of the protective group, affords compounds of formula (I).

Scheme 2

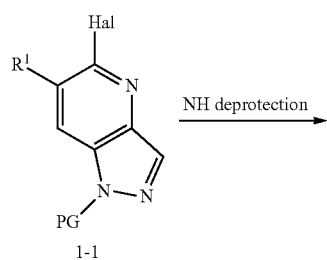

1-1

NH deprotection →

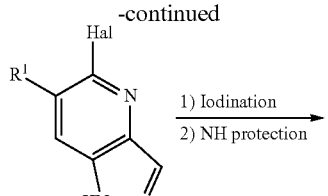

2-1

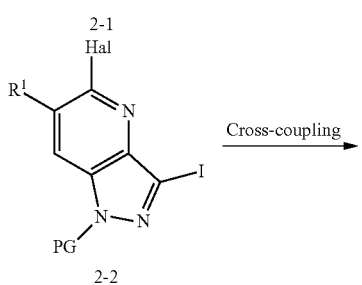

2-2

Cross-coupling →

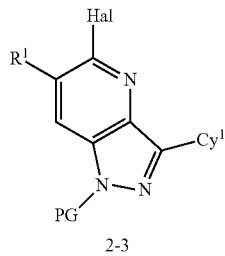

2-3

| 1) Cross-coupling
| 2) NH deprotection

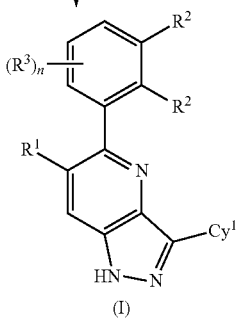

(I)

Methods of Use

Compounds of the present disclosure can inhibit the activity of the FGFR enzyme. For example, compounds of the present disclosure can be used to inhibit activity of an FGFR enzyme in a cell or in an individual or patient in need of inhibition of the enzyme by administering an inhibiting amount of one or more compounds of the present disclosure to the cell, individual, or patient. Compounds of the present disclosure can be used to inhibit activity of the FGFR3 enzyme in a cell or in an individual or patient in need of inhibition of the enzyme by administering an inhibiting amount of one or more compounds of the present disclosure to the cell, individual, or patient. Compounds of the present disclosure can be used to inhibit activity of the FGFR2 enzyme in a cell or in an individual or patient in need of inhibition of the enzyme by administering an inhibiting amount of one or more compounds of the present disclosure to the cell, individual, or patient. Compounds of the present disclosure can be used to inhibit the activity of an FGFR3 and an FGFR2 enzyme in a cell or in an individual or patient in need of inhibition of the enzyme by administering an inhibiting amount of a compound of the disclosure to the cell, individual, or patient.

In some embodiments, the compounds of the disclosure have selective inhibitory activity for the enzyme FGFR3 over FGFR1. In some embodiments, the selectivity of the compounds of the disclosure for FGFR3 over FGFR1 is 10-fold to 25-fold, or 25-fold to 50-fold. In some embodiments, the compounds of the disclosure have selective inhibitory activity for the enzyme FGFR3 over FGFR4. In some embodiments, the selectivity of the compounds of the disclosure for FGFR3 over FGFR4 is 10-fold to 25-fold, 25-fold to 50-fold, or 50-fold to 100-fold. In some embodiments, the compounds of the disclosure have selective inhibitory activity for the enzyme FGFR3 over FGFR2. In some embodiments, the selectivity of the compounds of the disclosure for FGFR3 over FGFR2 is 1.5-fold to 2-fold, or 2-fold to 3-fold.

In some embodiments, the inhibitory activity of the compounds of Examples 1 through 98 for FGFR3 over the inhibitory activity of the compounds of US2018/0072718 for FGFR3 is 10-fold or more, e.g., 50-fold, 100-fold, 250-fold, 500-fold, 750-fold, 1000-fold, etc.

In some embodiments, the compounds of the present disclosure have selective inhibitory activity for the enzyme FGFR3 over FGFR1. Without being bound to a particular theory, it is believed that FGFR1 is associated with certain side effects such as FGFR1-driven hypophosphatemia. Compounds of the present disclosure can be advantageous over nonselective FGFR inhibitors (e.g., compounds that have similar inhibitory activity against, for example, both FGFR1 and FGFR3) because the compounds of the present disclosure have the potential for little or no FGFR1-driven hypophosphatemia side effects, and potentially allow for higher maximum dosage while avoiding side effects associated with FGFR1.

In some embodiments, the compounds of the disclosure have selective inhibitory activity for the enzyme FGFR2 over FGFR1. In some embodiments, the selectivity of the compounds of the disclosure for FGFR2 over FGFR1 is 10-fold to 25-fold, or 25-fold to 50-fold. In some embodiments, the compounds of the disclosure have selective inhibitory activity for the enzyme FGFR2 over FGFR4. In some embodiments, the selectivity of the compounds of the disclosure for FGFR2 over FGFR4 is 10-fold to 25-fold, 25-fold to 50-fold, or 50-fold to 100-fold.

As FGFR inhibitors, the compounds of the present disclosure are useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

In some embodiments, cancers that are treatable using the compounds of the present disclosure are selected from adenocarcinoma, bladder cancer, breast cancer, cervical cancer, cholangiocarcinoma, colorectal cancer, endometrial cancer, esophageal cancer, gall bladder cancer, gastric cancer, glioma, head and neck cancer, hepatocellular cancer, kidney cancer, liver cancer, lung cancer, melanoma, ovarian cancer, pancreatic cancer, prostate cancer, rhabdomyosarcoma, skin cancer, thyroid cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, and Burkett's lymphoma.

In some embodiments, cancers that are treatable using the compounds of the present disclosure are selected from hepatocellular cancer, bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

In some embodiments, said cancer is selected from adenocarcinoma, bladder cancer, breast cancer, cervical cancer, cholangiocarcinoma, endometrial cancer, gastric cancer, glioma, head and neck cancer, lung cancer, ovarian cancer, leukemia, and multiple myeloma.

In some embodiments, cancers that are treatable using the compounds of the present disclosure are selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

A cancer characterized by an FGFR2 and/or FGFR3 alteration includes bladder cancers (FGFR3 mutation or fusion), cholangiocarcinoma (FGFR2 fusion) and gastric cancer (FGFR2 amplification).

Compounds of the invention can be used to treat cancer patients with FGFR2/3 alterations, including mutations, fusion, rearrangement, and amplification. FGFR2/3 alterations were found in a subset of cholangiocarcinoma, urothelial carcinoma, multiple myeloma, gastric adenocarcinoma, glioma, endometrial carcinoma, ovarian carcinoma, cervical cancer, lung cancer and breast cancer. Moreover, the compounds of the invention can be used to target patients progressing on pan-FGFR inhibitor treatment due to acquirement of gatekeeper mutations (V555M/L/F/I in FGFR3, V564M/L/F/I in FGFR2). Also Compounds of the invention can be used to treat cancer where FGFR2/3 signaling is involved in the resistance to other targeted therapies, for example, it has the potential to overcome resistance to CDK4/6 inhibitors in ER positive breast cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome), myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound described herein includes the administration of a compound described herein to an individual or patient, such as a human, having FGFR, as well as, for example, introducing a compound described herein into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e. arresting further development of the pathology and/or symptomatology) or ameliorating the disease; for example, ameliorating a disease, condition or disorder in an individual who is experiencing or displaying the pathology or symptomatology of the disease, condition or disorder (i.e. reversing the pathology and/or symptomatology) such as decreasing the severity of disease.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of FGFR-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the FGFR inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (Ruxolitinib, additional JAK1/2 and JAK1-selective, baricitinib or INCB39110), Pim kinase inhibitors (e.g., LGH447, INCB053914 and SGI-1776), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), inhibitors of BTK such as ibrutinib, c-MET inhibitors (e.g., capmatinib), an ALK2 inhibitor (e.g., INCB00928); or combinations thereof.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptupurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, CDK2, and CDK4/6 kinase inhibitors such as, for example, those described in WO 2006/056399 can be used in combination with the treatment methods and regimens of the present disclosure for treatment of cancers and solid tumors. Other agents such as therapeutic antibodies can be used in combination with the treatment methods and regimens of the present disclosure for treatment of cancers and solid tumors. The one or more additional pharmaceutical agents can be administered to a patient simultaneously or sequentially.

The treatment methods as disclosed herein can be used in combination with one or more other enzyme/protein/receptor inhibitors therapies for the treatment of diseases, such as cancer and other diseases or disorders described herein. For example, the treatment methods and regimens of the present disclosure can be combined with one or more inhibitors of the following kinases for the treatment of cancer: Akt1, Akt2, Akt3, BCL2, CDK2, CDK4/6, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the treatment methods and regimens of the present disclosure for treatment of cancer include an FGFR inhibitor (FGFR1, FGFR2, FGFR3 or FGFR4, e.g., pemigatinib (INCB54828), INCB62079), an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib or niraparib), a JAK inhibitor (JAK1 and/or JAK2, e.g., ruxolitinib, baricitinib, itacitinib (INCB39110), an LSD1 inhibitor (e.g., INCB59872 and INCB60003), a TDO inhibitor, a PI3K-delta inhibitor (e.g., INCB50465 and INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHPT/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the treatment methods described herein are combined with administration of a PI3Kδ inhibitor. In some embodiments, the treatment methods described herein are combined with administration of a JAK inhibitor. In some embodiments, the treatment methods described herein are combined with administration of a JAK1 or JAK2 inhibitor (e.g., baricitinib or ruxolitinib). In some embodiments, the treatment methods described herein are combined with administration of a JAK1 inhibitor. In some embodiments, the treatment methods described herein are combined with administration of a JAK1 inhibitor, which is selective over JAK2.

Example antibodies that can be administered in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be administered to a patient in combination with the treatment methods of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The treatment methods and regimens of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epacadostat, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the treatment methods of the disclosure can be used in combination with a chemotherapeutic in the treatment of cancer, and may improve the treatment response as compared to the response to the chemotherapeutic agent alone, without exacerbation of its toxic effects. In some embodiments, the treatment methods of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining treatment methods of the present disclosure with an additional agent.

The agents can be combined with Compound 1 and/or antibody that binds to human PD-1 or human PD-L1, or antigen-binding fragment thereof, of the present treatment methods in a single or continuous dosage form, or the agents can be administered simultaneously or sequentially as separate dosage forms.

In some embodiments, a corticosteroid such as dexamethasone is administered to a patient in combination with the treatment methods of the disclosure where the dexamethasone is administered intermittently as opposed to continuously.

The treatment methods described herein can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The treatment methods described herein can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the treatment methods and regimens of the present disclosure can be used in combination with tumor specific antigen such as heat shock proteins isolated from tumor tissue itself. In some embodiments, the treatment methods described herein can be combined with dendritic cells immunization to activate potent anti-tumor responses.

The treatment methods and regimens of the present disclosure can be used in combination with bispecific macrocyclic peptides that target Fc alpha or Fc gamma receptor-expressing effectors cells to tumor cells. The treatment methods and regimens of the present disclosure can also be combined with macrocyclic peptides that activate host immune responsiveness.

In some further embodiments, the treatment methods of the disclosure are combined with administration of other therapeutic agents to a patient prior to, during, and/or after a bone marrow transplant or stem cell transplant. The treatment methods and regimens of the present disclosure can be used in combination with bone marrow transplant for the treatment of a variety of tumors of hematopoietic origin.

When more than one pharmaceutical agents is administered to a patient, as discussed in any of the above embodiments, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012 (retifanlimab). In some embodiments, the anti-PD1 antibody is SHR-1210. Other anti-cancer agent(s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the inhibitor of an immune checkpoint molecule is an inhibitor of CD19, e.g., an anti-CD19 antibody. In some embodiments, the anti-CD19 antibody is tafasitamab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDOL TDO, or arginase. Examples of IDO1 inhibitors include epacadostat, NLG919, BMS-986205, PF-06840003, IOM2983, RG-70099 and LY338196.

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, $CD_{47}$, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (IBI308), AB122 (GLS-010), AMP-224, AMP-514/MEDI-0680, BMS936559, JTX-4014, BGB-108, SHR-1210, MEDI4736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217, 149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008166712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MEDI1873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDOL TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with antihormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, compounds described herein can be administered in the form of pharmaceutical compositions which refers to a combination of one or more compounds described herein, and at least one pharmaceutically acceptable carrier or excipient. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, one or more compounds described herein in combination with one or more pharmaceutically acceptable carriers or excipients. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is suitable for topical administration.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from, for example, about 5 mg to about 1000 mg, about 5 mg to about 100 mg, about 100 mg to about 500 mg or about 10 to about 30 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S.
Food and Drug Administration.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 ug/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid pre-formulation composition containing a homogeneous mixture of one or more compounds described herein. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of the compounds in a pharmaceutical composition can vary depending upon a number of factors including dosage, chemical characteristics (e.g., hydrophobicity), and the route of administration. For example, compounds of the present disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Compounds described herein can also be formulated in combination with one or more additional active ingredients, which can include any pharmaceutical agent such as anti-viral agents, vaccines, antibodies, immune enhancers, immune suppressants, anti-inflammatory agents and the like.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating FGFR3 protein in tissue samples, including human, and for identifying FGFR3 ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes FGFR binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium) $^{11}C$, $^{13}C$, $^{14}C$, $^{13}N$, $^{15}N$, $^{15}$O, $^{17}$O, $^{18}$O, $^{18}$F, $^{35}$S, $^{36}$Cl, $^{82}$Br, $^{75}$Br, $^{76}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —CD$_3$ being substituted for —CH$_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro adenosine receptor labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind an FGFR3 protein by monitoring its concentration variation when contacting with the FGFR3, through tracking of the labeling. For example, a test compound (labeled) can be evaluated for its ability to reduce binding of another compound which is known to bind to a FGFR3 protein (i.e., standard compound). Accordingly, the ability of a test compound to compete with the standard compound for binding to the FGFR3 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of FGFR-associated diseases or disorders, such as cancer and other diseases referred to herein which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of FGFR3 as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters)(Bridge $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1. 5-(2,3-Dimethylphenyl)-6-methoxy-3-(1-methyl-1H-pyrazol-4-yl)-1H-pyrazolo[4,3-b]pyridine

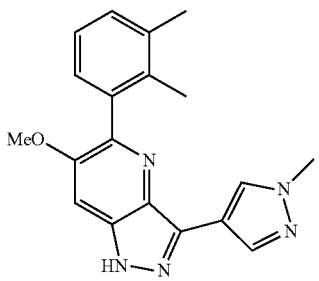 [SMILES: COc1cc2[nH]nc(-c3cnn(C)c3)c2nc1-c1cccc(C)c1C]

Step 1. 6-Bromo-1-trityl-1H-pyrazolo[4,3-b]pyridine

NaH (60% in mineral oil, 2.46 g, 61.6 mmol) was slowly added at 0° C. to a solution of 6-bromo-1H-pyrazolo[4,3-b]pyridine (10.16 g, 51.3 mmol) in DMF (70 ml). After stirring at r.t. for 20 min, (chloromethanetriyl)tribenzene (15.73 g, 56.4 mmol) was slowly added and the reaction mixture was stirred at r.t. for 1 h. Then water was added and the precipitated product was collected by filtration, washed with water and air dried. It was used in the next step without further purification. LC-MS calculated for $C_{25}H_{19}BrN_3$ $(M+H)^+$: m/z=440.1 and 442.1; found 440.0 and 442.0.

Step 2. 6-Methoxy-1-trityl-1H-pyrazolo[4,3-b]pyridine

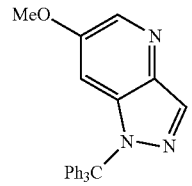

A mixture of 6-bromo-1-trityl-1H-pyrazolo[4,3-b]pyridine (25.0 g, 56.8 mmol), cesium carbonate (25.9 g, 79 mmol), methanol (6.89 ml, 170 mmol) and 'BuXPhos Pd G3 (1.52 g, 1.7 mmol) in toluene (150 ml) was heated at 80° C. for 1 h. After cooling to r.t., the reaction mixture was filtered, the solvent evaporated in vacuo and crude material was purified by Biotage Isolera. LCMS calculated for $C_{26}H_{22}N_3O$ $(M+H)^+$: m/z=392.2; Found: 392.1.

Step 3. 6-Methoxy-1-trityl-1H-pyrazolo[4,3-b]pyridine 4-oxide

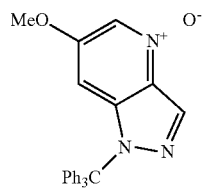

m-CPBA (14.5 g, 64.6 mmol) was slowly added at 0° C. to a solution of 6-methoxy-1-trityl-1H-pyrazolo[4,3-b]pyridine (16.8 g, 43.0 mmol) in DCM (150 ml). After stirring at r.t. overnight, the reaction was quenched with $Na_2S_2O_3$ solution and 1M NaOH solution. After stirring at r.t. for 30 min, the organic phase was separated and washed 3 times with 1M NaOH solution and 2 times with brine solution. Then the organic phase was dried over sodium sulfate, filtered and the solvent was removed in vacuo. The resultant product was used in the next step without further purification. LC-MS calculated for $C_{26}H_{22}N_3O_2$ $(M+H)^+$: m/z=408.2; found 408.2.

Step 4. 5-Chloro-6-methoxy-1-trityl-1H-pyrazolo[4,3-b]pyridine

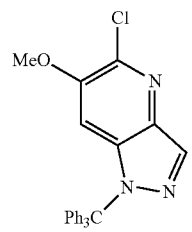

A solution of oxalyl chloride (5.36 ml, 61.3 mmol) in DCM was slowly added at 0° C. to a solution of 6-methoxy-1-trityl-1H-pyrazolo[4,3-b]pyridine 4-oxide (16.65 g, 40.9 mmol) and DIPEA (14.27 ml, 82 mmol) in DCM (100 ml). After stirring at 0° C. for 1 h, the reaction was diluted with DCM and carefully quenched with water. The organic phase was separated, washed 3 times with water, 2 times with saturated NaHCO₃ solution, 2 times with brine and was dried over sodium sulfate. After removing the solvent in vacuo, the resultant product was used in the next step without further purification. LC-MS calculated for C₂₆H₂₁ClN₃O (M+H)⁺: m/z=426.1; found 426.2.

Step 5. 5-Chloro-6-methoxy-1H-pyrazolo[4,3-b]pyridine

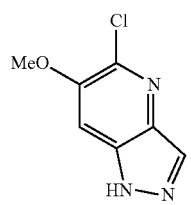 [SMILES: COc1cc2[nH]ncc2nc1Cl]

TFA (29 ml, 376 mmol) and water (1.35 ml, 75 mmol) were added to a solution of 5-chloro-6-methoxy-1-trityl-1H-pyrazolo[4,3-b]pyridine (16 g, 37.6 mmol) in DCM (75 ml). After stirring at r.t. for 30 min, CH₃CN and water were added and the DCM was evaporated in vacuo. The precipitated solid was filtered off. The reaction mixture was further diluted with water and was washed 3 times with EtOAc/hexane 1:1 mixture. The water phase was separated and all solvents were removed in vacuo. The residue was redissolved in DCM and was neutralized with NaHCO₃ solution. The organic phase was further washed 2 times with NaHCO₃ solution, brine, and then dried over sodium sulfate. The solvent was evaporated in vacuo. The resultant crude product was used in the next step without further purification. LC-MS calculated for C₇H₇ClN₃O (M+H)⁺: m/z=184.0; found 184.1.

Step 6. tert-Butyl 5-chloro-3-iodo-6-methoxy-1H-pyrazolo[4,3-b]pyridine-1-carboxylate

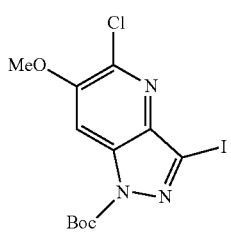 [SMILES: COc1cc2c(nc1Cl)c(I)nn2C(=O)OC(C)(C)C]

NIS (6.87 g, 30.6 mmol) was added to a solution of 5-chloro-6-methoxy-1H-pyrazolo[4,3-b]pyridine (5.5 g, 30.0 mmol) in DMF (60 ml). After stirring at 60° C. for 2 h, the reaction mixture was cooled to r.t., and triethylamine (6.26 ml, 44.9 mmol) and Boc-anhydride (8.17 g, 37.4 mmol) were added. After additional stirring at r.t. for 1 h, water was added and the precipitated product was collected by filtration. The solid product was air dried and used in the next step without further purification. LC-MS calculated for C₁₂H₁₄ClIN₃O₃ (M+H)⁺: m/z=410.0; found 410.1.

Step 7. tert-Butyl 5-chloro-6-methoxy-3-(1-methyl-1H-pyrazol-4-yl)-1H-pyrazolo[4,3-b]pyridine-1-carboxylate tert-Butyl 5-chloro-3-iodo-6-methoxy-1H-pyrazolo[4,3-b]pyridine-1-carboxylate (8.73 g, 21.31 mmol), 1-methyl-4-(4,4,5,5-tetramethyl-1,3,2-dioxaborolan-2-yl)-1H-pyrazole (5.32 g, 25.6 mmol), PdCl₂(dppf)-CH₂Cl₂ adduct (3.48 g, 4.26 mmol) and potassium phosphate (6.79 g, 32.0 mmol) were placed in a flask and the flask was evacuated and backfilled with N₂ three times. Then 1,4-dioxane (150 ml) and water (15 ml) were added and the reaction was stirred at 80° C. for 1 h. After cooling to r.t., water was added and the desired product was extracted with EtOAc. The organic phase was washed with brine, dried over sodium sulfate and the solvent was evaporated in vacuo. Crude material was purified by Biotage Isolera. LCMS calculated for C₁₆H₁₉ClN₅O₃ (M+H)⁺: m/z=364.1; Found: 364.0.

Step 8. 5-(2,3-Dimethylphenyl)-6-methoxy-3-(1-methyl-1H-pyrazol-4-yl)-1H-pyrazolo[4,3-b]pyridine tert-Butyl 5-chloro-6-methoxy-3-(1-methyl-1H-pyrazol-4-yl)-1H-pyrazolo[4,3-b]pyridine-1-carboxylate (8 mg, 0.022 mmol), (2,3-dimethylphenyl)boronic acid (4.95 mg, 0.033 mmol), chloro(2-dicyclohexylphosphino-2',4',6'-triisopropyl-1,1'-biphenyl)[2-(2'-amino-1,1'-biphenyl)]palladium (1.7 mg, 2.2 µmol) and potassium phosphate (9.34 mg, 0.044 mmol) were placed in a vial and the vial was evacuated and backfilled with N₂ three times. After 1,4-dioxane (1 ml) and water (100 µl) were added, the reaction mixture was stirred at 100° C. for 1 h. Then the reaction was filtered, and the solvents were evaporated in vacuo. DCM (1 ml) and TFA (0.5 ml) were added and the reaction mixture was stirred at r.t. for 30 min. It was then diluted with CH₃CN and water and purified with prep-LCMS (XBridge C18 column, eluting with a gradient of acetonitrile/water containing 0.1% TFA, at flow rate of 60 mL/min). The product was isolated as the TFA salt. LCMS calculated for C₁₉H₂₀N₅O (M+H)⁺: m/z=334.2; Found: 334.2. ¹H NMR (500 MHz, DMSO-d6) δ 8.27 (s, 1H), 8.00 (s, 1H), 7.45 (s, 1H), 7.25-7.20 (m, 1H), 7.19-7.14 (t, J=7.5 Hz, 1H), 7.12-7.09 (m, 1H), 3.89 (s, 3H), 3.82 (s, 3H), 2.31 (s, 3H), 1.96 (s, 3H) ppm.

Example 2. 5-(2,3-Dihydro-1H-inden-4-yl)-6-methoxy-3-(1-methyl-1H-pyrazol-4-yl)-1H-pyrazolo[4,3-b]pyridine

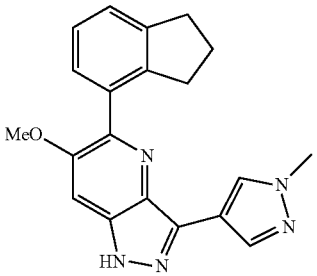 [SMILES: COc1cc2[nH]nc(-c3cnn(C)c3)c2nc1-c1cccc2c1CCC2]

This compound was prepared according to the procedures described in Example 1, using 2-(2,3-dihydro-1H-inden-4-yl)-4,4,5,5-tetramethyl-1,3,2-dioxaborolane instead of (2,3-dimethylphenyl)boronic acid as starting material. The product was isolated as the TFA salt. LCMS calculated for $C_{20}H_{20}N_5O$ $(M+H)^+$: m/z=346.2; Found: 346.2. $^1$H NMR (500 MHz, DMSO-d6) δ 8.34-8.29 (s, 1H), 8.09-8.01 (s, 1H), 7.51-7.44 (s, 1H), 7.30-7.25 (m, 2H), 7.25-7.19 (m, 1H), 3.94-3.90 (s, 3H), 3.90-3.84 (s, 3H), 2.99-2.91 (t, J=7.4 Hz, 2H), 2.85-2.75 (t, J=7.4 Hz, 2H), 2.02-1.91 (p, J=7.4 Hz, 2H) ppm.

Example 3. 5-(2,3-Dimethylphenyl)-6-methoxy-3-(1-((1-methyl-1H-1,2,4-triazol-5-yl)methyl)-1H-pyrazol-4-yl)-1H-pyrazolo[4,3-b]pyridine

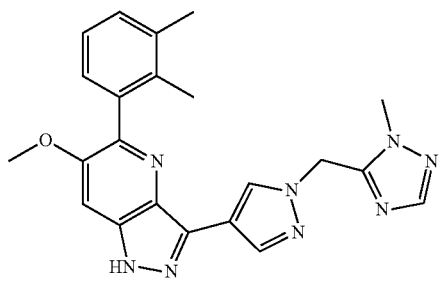 [SMILES: COc1cc2[nH]nc(-c3cnn(Cc4ncnn4C)c3)c2nc1-c1cccc(C)c1C]

Step 1. 5-(2,3-Dimethylphenyl)-6-methoxy-1-(4-methoxybenzyl)-3-(1H-pyrazol-4-yl)-1H-pyrazolo[4,3-b]pyridine

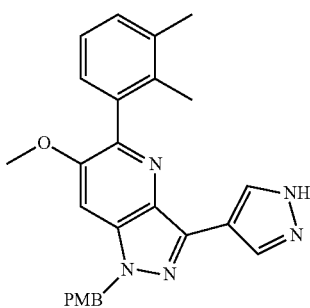

To a solution of 5-(2,3-dimethylphenyl)-3-iodo-6-methoxy-1-(4-methoxybenzyl)-1H-pyrazolo[4,3-b]pyridine (Example 69, 100 mg, 0.2 mmol) in 1,4-dioxane (3 mL) and water (0.3 mL) were added 4-(4,4,5,5-tetramethyl-1,3,2-dioxaborolan-2-yl)-1H-pyrazole (118 mg, 0.4 mmol), potassium phosphate (128 mg, 0.6 mmol), and [1,1'-bis(diphenylphosphino)ferrocene]-dichloropalladium(II) (1:1) (16 mg, 0.02 mmol). The reaction was purged with $N_2$ and stirred at 80° C. for 2 h. After this time it was cooled to r.t. and diluted with EtOAc. It was then washed sequentially with water, sat. NaCl solution and dried over $Na_2SO_4$. The organic phases were filtered and concentrated to dryness. The residue was purified by Biotage Isolera to afford the desired product. LC-MS calculated for $C_{26}H_{26}N_5O_2$ (M+H)+: m/z=440.2; found 440.2.

Step 2. 5-(2,3-Dimethylphenyl)-6-methoxy-3-(1-((1-methyl-1H-1,2,4-triazol-5-yl)methyl)-1H-pyrazol-4-yl)-1H-pyrazolo[4,3-b]pyridine To a solution of 5-(2,3-dimethylphenyl)-6-methoxy-1-(4-methoxybenzyl)-3-(1H-pyrazol-4-yl)-1H-pyrazolo[4,3-b]pyridine (90 mg, 0.2 mmol) in acetonitrile (3 mL) were added 5-(chloromethyl)-1-methyl-1H-1,2,4-triazole (70 mg, 0.53 mmol) and cesium carbonate (400 mg, 1.23 mmol). The reaction was stirred at 80° C. for 12 h. After this time it was cooled to r.t. and diluted with EtOAc. It was then washed sequentially with water, sat. NaCl solution and dried over $Na_2SO_4$. The organic phases were filtered and concentrated to dryness. The residue was dissolved in TFA (1 ml) and heated to 80° C. for 1 h. The reaction mixture was then diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{22}H_{23}N_8O$ $(M+H)^+$: m/z=415.2; found 415.2. $^1$H NMR (600 MHz, DMSO-d6) δ 8.55-8.45 (s, 1H), 8.14-8.03 (s, 1H), 7.93-7.82 (s, 1H), 7.52-7.42 (s, 1H), 7.25-7.21 (d, J=7.5 Hz, 1H), 7.19-7.14 (t, J=7.5 Hz, 1H), 7.13-7.08 (d, J=7.5 Hz, 1H), 5.75-5.60 (s, 2H), 3.91-3.86 (s, 2H), 3.86-3.76 (s, 3H), 2.34-2.27 (s, 3H), 2.01-1.90 (s, 3H) ppm.

Example 4. 5-(2,3-Dihydrobenzofuran-7-yl)-6-methoxy-3-(1-methyl-1H-pyrazol-4-yl)-1H-pyrazolo[4,3-b]pyridine

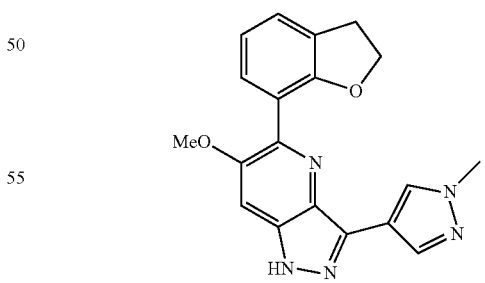

This compound was prepared according to the procedures described in Example 1, using (2,3-dihydrobenzofuran-7-yl)boronic acid instead of (2,3-dimethylphenyl)boronic acid as starting material. The product was isolated as the TFA salt. LCMS calculated for $C_{19}H_{18}N_5O_2$ $(M+H)^+$: m/z=348.1; Found: 348.1. $^1$H NMR (500 MHz, DMSO-d6) δ 8.33-8.29 (s, 1H), 8.06-8.02 (s, 1H), 7.45-7.40 (s, 1H), 7.31-7.25 (d, J=5.8 Hz, 1H), 7.21-7.16 (d, J=6.3 Hz, 1H), 6.96-6.86 (t, J=7.5 Hz, 1H), 4.54-4.44 (t, J=8.7 Hz, 2H), 3.94-3.90 (s, 3H), 3.87-3.82 (s, 3H), 3.29-3.20 (t, J=8.7 Hz, 2H) ppm.

Intermediate 1. 2-(2-Methyl-3-(4,4,5,5-tetramethyl-1,3,2-dioxaborolan-2-yl)phenyl)acetonitrile

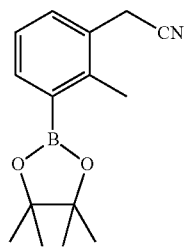 [SMILES: Cc1c(CC#N)cccc1B1OC(C)(C)C(C)(C)O1]

To a mixture of 4,4,5,5,4',4',5',5'-octamethyl-[2,2]bi[[1,3,2]dioxaborolanyl] (1.28 g, 5.1 mmol), potassium acetate (0.57 g, 5.83 mmol) and [1,1'-bis(diphenylphosphino)ferrocene]dichloropalladium(II), complex with dichloromethane (1:1) (0.318 g, 0.389 mmol) under nitrogen was added a solution of 2-(3-iodo-2-methylphenyl)acetonitrile (1 g, 3.89 mmol) in 1,4-dioxane (30 mL). The reaction mixture was stirred under nitrogen at 100° C. for 3 days. After cooling to room temperature, the mixture was diluted with DCM and filtered. The filtrate was concentrated in vacuo and the resultant residue was purified by Biotage Isolera to give the desired product.

Example 5. 2-(3-(6-Methoxy-3-(1-methyl-1H-pyrazol-4-yl)-1H-pyrazolo[4,3-b]pyridin-5-yl)-2-methylphenyl)acetonitrile

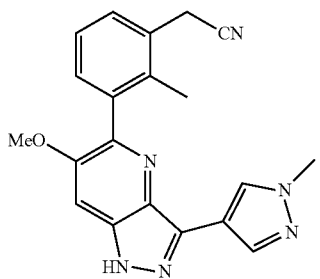 [SMILES: COc1cc2[nH]nc(-c3cnn(C)c3)c2nc1-c1cccc(CC#N)c1C]

This compound was prepared according to the procedures described in Example 1, using 2-(2-methyl-3-(4,4,5,5-tetramethyl-1,3,2-dioxaborolan-2-yl)phenyl)acetonitrile (Intermediate 1) instead of (2,3-dimethylphenyl)boronic acid as starting material. The product was isolated as the TFA salt. LCMS calculated for $C_{20}H_{19}N_6O$ (M+H)$^+$: m/z=359.2; Found: 359.2. $^1$H NMR (500 MHz, DMSO-d6) δ 8.33-8.22 (s, 1H), 8.05-7.95 (s, 1H), 7.53-7.48 (s, 1H), 7.47-7.41 (d, J=6.8 Hz, 1H), 7.36-7.30 (t, J=7.6 Hz, 1H), 7.30-7.25 (d, J=6.2 Hz, 1H), 4.13-4.05 (s, 2H), 3.92-3.87 (s, 3H), 3.85-3.80 (s, 3H), 2.08-2.01 (s, 3H) ppm.

Intermediate 2. 4-(4,4,5,5-Tetramethyl-1,3,2-dioxaborolan-2-yl)-2,3-dihydro-1H-inden-1-ol

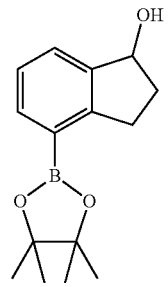 [SMILES: CC1(C)OB(c2cccc3c2CCC3O)OC1(C)C]

To a mixture of 4,4,5,5,4',4',5',5'-octamethyl-[2,2]bi[[1,3,2]dioxaborolanyl] (626 mg, 2.46 mmol), potassium acetate (322 mg, 3.29 mmol) and [1,1'-bis(diphenylphosphino)ferrocene]dichloropalladium(II), complex with dichloromethane (1:1) (201 mg, 0.246 mmol) under nitrogen was added a solution of 4-bromo-2,3-dihydro-1H-inden-1-ol (350 mg, 1.643 mmol) in 1,4-dioxane (15 mL). The reaction mixture was stirred under nitrogen at 100° C. overnight. After cooling to room temperature, the mixture was diluted with DCM and filtered. The filtrate was concentrated in vacuo and the resultant residue was purified by Biotage Isolera to give the desired product.

Example 6. 1-(4-(5-(6-(Difluoromethoxy)-5-(2,3-dimethylphenyl)-1H-pyrazolo[4,3-b]pyridin-3-yl)pyridin-2-yl)piperazin-1-yl)ethan-1-one

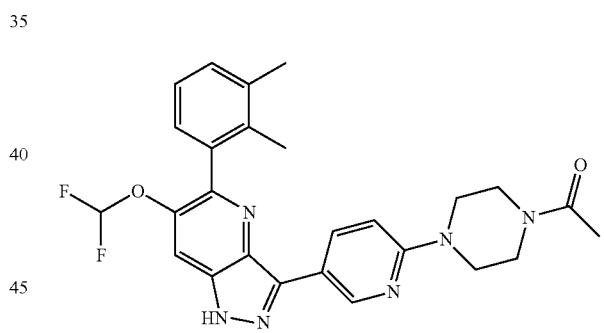

Step 1. 1-Trityl-1H-pyrazolo[4,3-b]pyridin-6-ol

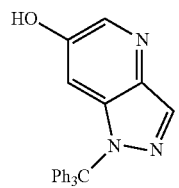

A mixture of 6-bromo-1-trityl-1H-pyrazolo[4,3-b]pyridine (Example 1, step 1; 20 g, 45.4 mmol), KOH (12.74 g, 227 mmol), and $^t$BuXPhos Pd G3 (0.727 g, 0.908 mmol) in 1,4-dioxane (100 mL) water (100 mL) was heated at 100° C. for 3 h. After this time it was cooled to r.t., diluted with water and extracted with EtOAc. The combined organic phases were washed with sat. aq. NaCl, dried over Na$_2$SO$_4$, filtered and concentrated to dryness. The crude material was used in next step without further purification. LCMS calculated for C$_{25}$H$_{20}$N$_3$O (M+H)$^+$: m/z=378.2; Found: 378.1.

Step 2. 6-(Difluoromethoxy)-1-trityl-1H-pyrazolo[4,3-b]pyridine

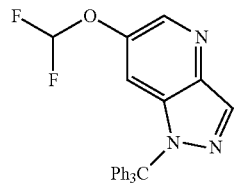

To a mixture of 1-trityl-1H-pyrazolo[4,3-b]pyridin-6-ol (17 g, 45 mmol) and KOH (12.62 g, 225 mmol) in acetonitrile (100 mL) and water (10 mL) was added diethyl (bromodifluoromethyl)-phosphonate (16.02 ml, 90 mmol) at 0° C. After addition, the reaction was stirred at r.t. overnight. Water was then added and the product was extracted with EtOAc. The organic phase was washed with brine, dried over sodium sulfate and the solvent was evaporated in vacuo. Crude material was purified by Biotage Isolera. LCMS calculated for C$_{26}$H$_{20}$F2N$_3$O (M+H)$^+$: m/z=428.2; Found: 428.2.

Step 3. 5-Chloro-6-(difluoromethoxy)-1-trityl-1H-pyrazolo[4,3-b]pyridine

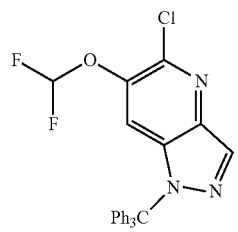

3-Chlorobenzoperoxoic acid (7.64 g, 33.2 mmol) was slowly added at 0° C. to a solution of 6-(difluoromethoxy)-1-trityl-1H-pyrazolo[4,3-b]pyridine (7.1 g, 16.61 mmol) in DCM (100 mL). After stirring at r.t. overnight, the reaction was treated with Na$_2$S$_2$O$_3$ solution and 1M NaOH solution. After stirring at r.t. for 30 min, the organic phase was separated and washed 3 times with 1M NaOH solution and 2 times with brine solution. The organic phase was dried over sodium sulfate, filtered and the solvent was removed in vacuo.

The resultant product was dissolved in DCM (100 mL). To this solution DIEA (7.25 ml, 41.5 mmol) and oxalyl chloride (2.91 ml, 33.2 mmol) were added sequentially at 0° C. The reaction mixture was allowed to warm to r.t. and stirred at this temperature overnight. The reaction mixture was diluted with DCM and carefully treated with water. The organic phase was separated, washed 3 times with water, 2 times with saturated NaHCO$_3$ solution, 2 times with brine and dried over sodium sulfate. After removing the solvent in vacuo, crude material was purified by Biotage Isolera. LCMS calculated for C$_{26}$H$_{19}$ClF$_2$N$_3$O (M+H)$^+$: m/z=462.1; Found: 462.1.

Step 4. 6-(Difluoromethoxy)-5-(2,3-dimethylphenyl)-1H-pyrazolo[4,3-b]pyridine

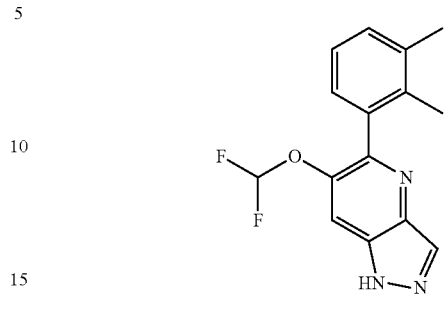

5-Chloro-6-(difluoromethoxy)-1-trityl-1H-pyrazolo[4,3-b]pyridine (2.2 g, 4.76 mmol), (2,3-dimethylphenyl)boronic acid (1.072 g, 7.14 mmol), chloro(2-dicyclohexylphosphino-2',4',6'-triisopropyl-1,1'-biphenyl)[2-(2'-amino-1,1'-biphenyl)]palladium (0.38 g, 0.47 mmol) and K$_3$PO$_4$ (2.1 g, 9.53 mmol) were placed in a flask and the flask was evacuated and backfilled with N$_2$ three times. After 1,4-dioxane (20 mL) and water (2 mL) were added, the reaction mixture was stirred at 100° C. for 1 h. After cooling to r.t., water was added and the desired product was extracted with EtOAc. The organic phase was washed with brine, dried over sodium sulfate and the solvent was evaporated in vacuo.

Crude material was dissolved in TFA (2 mL), DCM (10 mL), and water (2 mL). After stirring at r.t. for 30 min, CH$_3$CN and water were added and the DCM was evaporated in vacuo. The precipitated solid was filtered off. The reaction mixture was further diluted with water and washed 3 times with EtOAc/hexane 1:1 mixture. The water phase was separated and all solvents were removed in vacuo. The residue was dissolved in DCM and neutralized with NaHCO$_3$ solution. The organic phase was washed 2 times with NaHCO$_3$ solution, 1 time with brine, dried over sodium sulfate and concentrated in vacuo. The resultant crude product was used in the next step without further purification. LC-MS calculated for C$_{15}$H$_{14}$F$_2$N$_3$O (M+H)$^+$: m/z=290.1; found 290.1.

Step 5. 6-(Difluoromethoxy)-5-(2,3-dimethylphenyl)-3-iodo-1-(4-methoxybenzyl)-1H-pyrazolo[4,3-b]pyridine

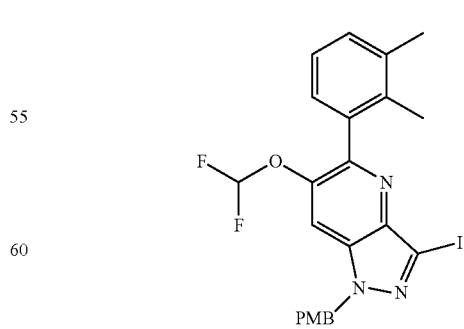

1-Iodopyrrolidine-2,5-dione (1.5 g, 6.57 mmol) was added to a solution of 6-(difluoromethoxy)-5-(2,3-dimethylphenyl)-1H-pyrazolo[4,3-b]pyridine (1.9 g, 6.57 mmol) in DMF (25 mL). After stirring at 80° C. for 1 h, the reaction mixture was cooled to r.t., and Cs$_2$CO$_3$ (5.35 g, 16.42 mmol) and 1-(chloromethyl)-4-methoxybenzene (1.714 ml, 13.14 mmol) were added. After additional stirring at 80° C. for 1 h, water was added and the desired product was extracted with EtOAc. The organic phase was washed with brine, dried over sodium sulfate and the solvent was evaporated in vacuo. Crude material was purified by Biotage Isolera. LCMS calculated for C$_{23}$H$_{21}$F$_2$IN$_3$O$_2$ (M+H)$^+$: m/z=536.1; Found: 536.1.

Step 6. 1-(4-(5-(6-(Difluoromethoxy)-5-(2,3-dimethylphenyl)-1H-pyrazolo[4,3-b]pyridin-3-yl)pyridin-2-yl)piperazin-1-yl)ethan-1-one A solution of 6-(difluoromethoxy)-5-(2,3-dimethylphenyl)-3-iodo-1-(4-methoxybenzyl)-1H-pyrazolo[4,3-b]pyridine (27 mg, 0.050 mmol), 1-(4-(5-(4,4,5,5-tetramethyl-1,3,2-dioxaborolan-2-yl)pyridin-2-yl)piperazin-1-yl)ethan-1-one (56 mg, 0.17 mmol), Xphos Pd G2 (4 mg, 5 µmol), potassium phosphate (44 mg, 0.21 mmol) in water (0.100 ml) and dioxane (1 ml) was heated to 80° C. for 2 h. After this time it was cooled to r.t., diluted with water and extracted with EtOAc. The combined organic phases were washed with sat. aq. NaCl and dried over Na$_2$SO$_4$, then filtered and concentrated to dryness. The residue was dissolved in triflic acid (0.5 mL). The mixture was stirred at r.t. for 1 h, diluted with CH$_3$CN and purified by prep-LCMS (XBridge C18 column, eluting with a gradient of acetonitrile/water containing 0.1% TFA, at flow rate of 60 mL/min). The product was isolated as the TFA salt. LCMS calculated for C$_{26}$H$_{27}$F$_2$N$_6$O$_2$ (M+H)+: m/z=493.2; found 493.3. $^1$H NMR (500 MHz, DMSO-d6) δ 13.47 (s, 1H), 9.16 (d, J=2.2 Hz, 1H), 8.50 (dd, J=9.0, 2.4 Hz, 1H), 7.91 (s, 1H), 7.46-7.01 (m, 5H), 3.66-3.58 (m, 8H), 2.35 (s, 3H), 2.05 (s, 3H), 2.02 (s, 3H) ppm.

Example 7 and Example 8. 4-(6-Methoxy-3-(1-methyl-1H-pyrazol-4-yl)-1H-pyrazolo[4,3-b]pyridin-5-yl)-2,3-dihydro-1H-inden-1-ol, two enantiomers peak 1 peak 2

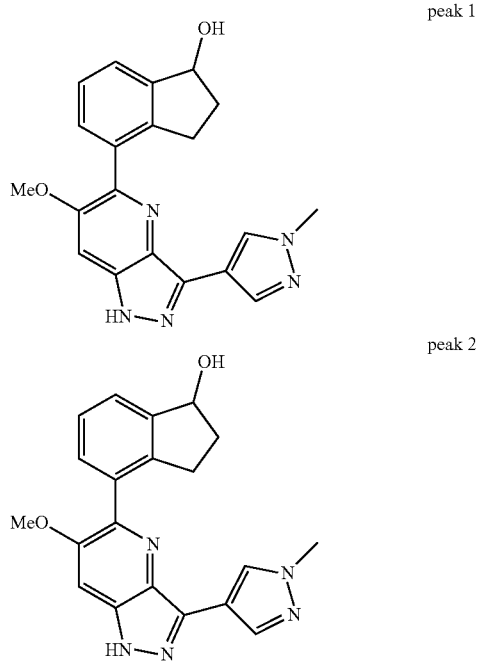

tert-Butyl 5-chloro-6-methoxy-3-(1-methyl-1H-pyrazol-4-yl)-1H-pyrazolo[4,3-b]pyridine-1-carboxylate (35 mg, 0.096 mmol), 4-(4,4,5,5-tetramethyl-1,3,2-dioxaborolan-2-yl)-2,3-dihydro-1H-inden-1-ol (32 mg, 0.12 mmol), chloro (2-dicyclohexylphosphino-2',4',6'-triisopropyl-1,1'-biphenyl)[2-(2'-amino-1,1'-biphenyl)]palladium (15 mg, 0.02 mmol) and potassium phosphate (30 mg, 0.14 mmol) were placed in a vial and the vial was evacuated and backfilled with N$_2$ three times. After 1,4-dioxane (2 ml) and water (200 µl) were added, the reaction mixture was stirred at 100° C. for 1 h. After cooling to room temperature, the mixture was diluted with DCM and filtered. The filtrate was concentrated in vacuo and the resultant residue was purified by Biotage Isolera.

The purified material was redissolved in 1,4-dioxane (2 ml) and water (2 ml). After addition of cesium carbonate (31.3 mg, 0.096 mmol) and morpholine (0.3 ml) the reaction mixture was heated at 100° C. for 2 h. After cooling to room temperature, the mixture was diluted with DCM washed with brine, dried over sodium sulfate and the solvents were evaporated in vacuo.

Then, the two enantiomers were separated with chiral prep-HPLC (Phenomenex Lux 5 um Amylose-1, 21.2×250 mm, eluting with 25% EtOH in hexanes, at flow rate of 20 mL/min, t$_{R, peak 1}$=15.4 min t$_{R, peak 2}$=17.6 min). After the solvents were evaporated in vacuo, both enantiomers were purified by prep-LCMS (XBridge C18 column, eluting with a gradient of acetonitrile/water containing 0.1% TFA, at flow rate of 60 mL/min). The products were isolated as TFA salts.

Example 7. Peak 1: LCMS calculated for C$_{20}$H$_{20}$N$_5$O$_2$ (M+H)$^+$: m/z=362.2; Found: 362.2. $^1$H NMR (500 MHz, DMSO-d6) δ 8.32-8.25 (s, 1H), 8.07-8.00 (s, 1H), 7.49-7.44 (s, 1H), 7.41-7.38 (d, J=7.3 Hz, 1H), 7.38-7.35 (d, J=7.5 Hz, 1H), 7.33-7.28 (m, 1H), 5.18-5.09 (t, J=6.7 Hz, 1H), 3.95-3.88 (s, 3H), 3.88-3.82 (s, 3H), 2.87-2.75 (m, 1H), 2.75-2.65 (m, 1H), 2.35-2.28 (m, 1H), 1.83-1.68 (m, 1H) ppm.

Example 8. Peak 2: LCMS calculated for C$_{20}$H$_{20}$N$_5$O$_2$ (M+H)$^+$: m/z=362.2; Found: 362.2. $^1$H NMR (500 MHz, DMSO-d6) δ 8.33-8.28 (s, 1H), 8.06-8.02 (s, 1H), 7.49-7.45 (s, 1H), 7.42-7.38 (d, J=7.2 Hz, 1H), 7.38-7.35 (m, 1H), 7.33-7.28 (m, 1H), 5.19-5.07 (t, J=6.7 Hz, 1H), 3.93-3.89 (s, 3H), 3.89-3.85 (s, 3H), 2.86-2.75 (m, 1H), 2.75-2.66 (m, 1H), 2.36-2.22 (m, 1H), 1.82-1.67 (m, 1H) ppm.

Example 9. 4-(6-Methoxy-3-(1-methyl-1H-pyrazol-4-yl)-1H-pyrazolo[4,3-b]pyridin-5-yl)-2,3-dihydro-1H-indene-1-carbonitrile

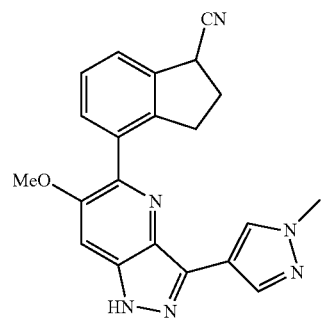 [SMILES: COc1cc2[nH]nc(-c3cnn(C)c3)c2nc1-c1cccc2c1CCC2C#N]

Methanesulfonyl chloride (5 mg, 0.04 mmol) was added to a solution of triethylamine (6.04 µl, 0.043 mmol) and tert-butyl 5-(1-hydroxy-2,3-dihydro-1H-inden-4-yl)-6- methoxy-3-(1-methyl-1H-pyrazol-4-yl)-1H-pyrazolo[4,3-b]pyridine-1-carboxylate (Intermediate from Example 8, 10 mg, 0.022 mmol) in DCM (1 ml). After stirring at r.t. for 30 min, the reaction mixture was filtered through a pad of silica gel, the filter was washed with DCM and methanol, the organic fractions were combined and the solvent was evaporated in vacuo. The resultant residue was dissolved in DMF (1 ml), and potassium cyanide (2.82 mg, 0.043 mmol) and 18-crown-6 (11 mg, 0.043 mmol) were added. The reaction mixture was stirred at 80° C. for 2 h before water was added and the desired product was extracted with DCM. The organic phase was washed with brine and the solvent was evaporated in vacuo. The resultant material was dissolved in DCM (1 ml) and TFA (0.5 ml), and the reaction mixture was stirred at r.t. for 30 min. It was then diluted with CH$_3$CN and water and purified with prep-LCMS (XBridge C18 column, eluting with a gradient of acetonitrile/water containing 0.1% TFA, at flow rate of 60 mL/min). The product was isolated as the TFA salt. LCMS calculated for C$_{21}$H$_{19}$N$_6$O (M+H)$^+$: m/z=371.2; Found: 371.2.

Intermediate 3. 4-(4,4,5,5-Tetramethyl-1,3,2-dioxaborolan-2-yl)-2,3-dihydro-1H-inden-2-ol

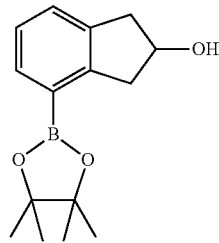 [SMILES: CC1(C)OB(c2cccc3c2CC(O)C3)OC1(C)C]

This compound was prepared according to the procedures described in Intermediate 2, using 4-bromo-2,3-dihydro-1H-inden-2-ol instead of 4-bromo-2,3-dihydro-1H-inden-1-ol as starting material.

Example 10. 4-(6-Methoxy-3-(1-methyl-1H-pyrazol-4-yl)-1H-pyrazolo[4,3-b]pyridin-5-yl)-2,3-dihydro-1H-inden-2-ol peak 2

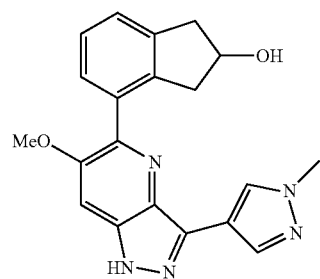

tert-Butyl 5-chloro-6-methoxy-3-(1-methyl-1H-pyrazol-4-yl)-1H-pyrazolo[4,3-b]pyridine-1-carboxylate (35 mg, 0.096 mmol), 4-(4,4,5,5-tetramethyl-1,3,2-dioxaborolan-2-yl)-2,3-dihydro-1H-inden-2-ol (32 mg, 0.12 mmol), chloro (2-dicyclohexylphosphino-2',4',6'-triisopropyl-1,1'-biphenyl)[2-(2'-amino-1,1'-biphenyl)]palladium (15 mg, 0.02 mmol) and potassium phosphate (30 mg, 0.14 mmol) were placed in a vial and the vial was evacuated and backfilled with N$_2$ three times. After 1,4-dioxane (2 ml) and water (200 μl) were added, the reaction mixture was stirred at 100° C. for 1 h. After cooling to room temperature, the mixture was diluted with DCM and filtered. The filtrate was concentrated in vacuo and the resultant residue was purified by Biotage Isolera.

The two enantiomers were separated with chiral prep-HPLC (Phenomenex LUX Cellulose-1 Sum 21.2×250 mm, eluting with 20% IPA (containing 2 mM NH$_3$) in hexanes, at flow rate of 65 mL/min, t$_{R,peak 1}$=6.5 min, t$_{R,peak 2}$=7.5 min). Peak 2 was collected and the solvents were evaporated in vacuo. The resultant material was redissolved in 1,4-dioxane (2 ml) and water (2 ml). After addition of cesium carbonate (31.3 mg, 0.096 mmol) and morpholine (0.3 ml) the reaction mixture was heated at 100° C. for 2 h. After cooling to room temperature, the mixture was diluted with CH$_3$CN and purified by prep-LCMS (XBridge C18 column, eluting with a gradient of acetonitrile/water containing 0.1% TFA, at flow rate of 60 mL/min). The product was isolated as the TFA salt. LCMS calculated for C$_{20}$H$_{20}$N$_5$O$_2$ (M+H)$^+$: m/z=362.2; Found: 362.2. $^1$H NMR (500 MHz, DMSO-d6) δ 8.35-8.29 (s, 1H), 8.08-8.03 (s, 1H), 7.48-7.45 (s, 1H), 7.34-7.28 (d, J=7.2 Hz, 1H), 7.29-7.25 (m, 1H), 7.25-7.20 (m, 1H), 4.52-4.45 (m, 1H), 3.94-3.90 (s, 3H), 3.89-3.84 (s, 3H), 3.21-3.11 (dd, J=16.0, 6.0 Hz, 1H), 3.09-3.00 (dd, J=16.4, 5.9 Hz, 1H), 2.88-2.78 (dd, J=16.0, 3.6 Hz, 1H), 2.71-2.64 (dd, J=16.4, 3.6 Hz, 1H) ppm.

Intermediate 4. (4-(4,4,5,5-Tetramethyl-1,3,2-dioxaborolan-2-yl)-2,3-dihydro-1H-inden-1-yl)methanol

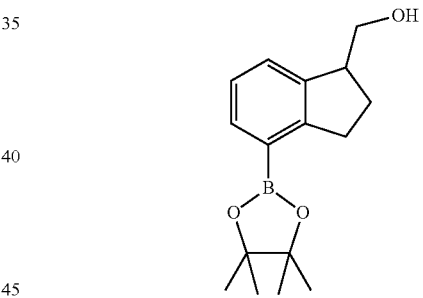

Step 1.
(4-Bromo-2,3-dihydro-1H-inden-1-yl)methanol

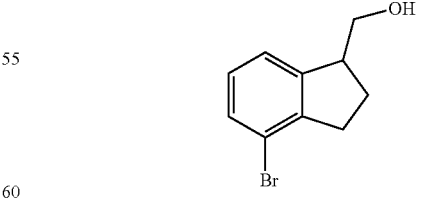

A 1M THF solution of LiHMDS (29.6 ml, 29.6 mmol) was slowly added to a suspension of (methoxymethyl)triphenylphosphonium chloride (10.15 g, 29.6 mmol) in THF (150 ml) at 0° C. After this solution was stirring at 0° C. for 1 h, a solution of 4-bromo-2,3-dihydro-1H-inden-1-one (5.0 g, 23.7 mmol) in THF (20 ml) was slowly added and the reaction mixture was stirred at r.t. for 2 h. The reaction was then quenched with water and the product was extracted with EtOAc. The combined organic phases were washed with brine, dried over anhydrous Na$_2$SO$_4$ and concentrated. The crude product was purified by Biotage Isolera.

A 1M DCM solution of BBr$_3$ (21.2 ml, 21.2 mmol) was added to a solution of the above purified material in DCM (50 ml) at −78° C. After stirring at that temperature for 1 h, the reaction was quenched with water and the product was extracted with DCM. The organic phase was dried over sodium sulfate and the solvent was evaporated in vacuo. The crude product was purified by Biotage Isolera.

NaBH$_4$ (0.630 g, 16.7 mmol) was added to a solution of the resultant above material in a mixture of THF (15 ml) and MeOH (15 ml). After the reaction mixture was stirred at r.t. for 1 h, water was added. The desired product was extracted with EtOAc, the organic phase was washed with brine, dried over sodium sulfate and the solvents were evaporated in vacuo. The resultant crude product was used in the next step without further purification.

Step 2. (4-(4,4,5,5-Tetramethyl-1,3,2-dioxaborolan-2-yl)-2,3-dihydro-1H-inden-1-yl)methanol This compound was prepared according to the procedures described in Intermediate 2, using (4-bromo-2,3-dihydro-1H-inden-1-yl)methanol instead of 4-bromo-2,3-dihydro-1H-inden-1-ol as starting material.

Example 11 and Example 12. (4-(6-Methoxy-3-(1-methyl-1H-pyrazol-4-yl)-1H-pyrazolo[4,3-b]pyridin-5-yl)-2,3-dihydro-1H-inden-1-yl)methanol, two enantiomers

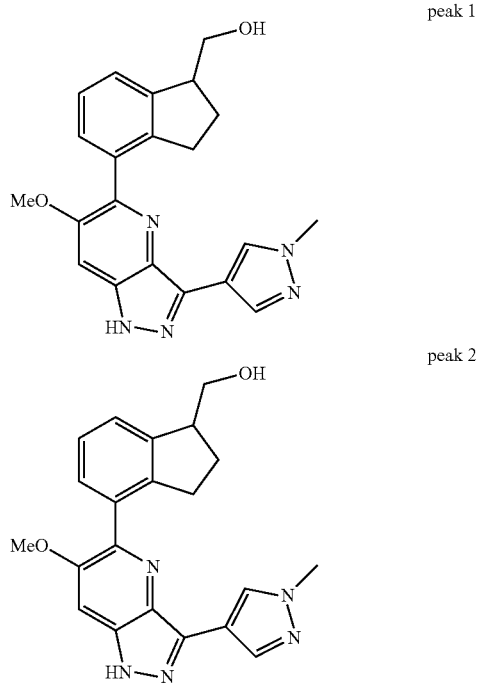

peak 1 peak 2

These compounds were prepared according to the procedures described in Example 7, using (4-(4,4,5,5-tetramethyl-1,3,2-dioxaborolan-2-yl)-2,3-dihydro-1H-inden-1-yl)methanol (Intermediate 4) instead of 4-(4,4,5,5-tetramethyl-1,3,2-dioxaborolan-2-yl)-2,3-dihydro-1H-inden-1-ol as starting material.

The two enantiomers were separated with chiral prep-HPLC (Phenomenex Lux 5um Amylose-1, 21.2×250 mm, eluting with 60% EtOH in hexanes, at flow rate of 20 mL/min, t$_{R, peak 1}$=4.2 min t$_{R, peak 2}$=7.6 min). After the solvents were evaporated in vacuo, both enantiomers were purified by prep-LCMS (XBridge C18 column, eluting with a gradient of acetonitrile/water containing 0.1% TFA, at flow rate of 60 mL/min). The products were isolated as TFA salts.

Example 11. Peak 1: LCMS calculated for C$_{21}$H$_{22}$N$_5$O$_2$ (M+H)$^+$: m/z=376.2; Found: 376.2. $^1$H NMR (500 MHz, DMSO-d6) δ 8.34-8.28 (s, 1H), 8.07-8.00 (s, 1H), 7.49-7.45 (s, 1H), 7.36-7.34 (d, J=7.4 Hz, 1H), 7.31-7.28 (d, J=7.5 Hz, 1H), 7.27-7.20 (t, J=7.5 Hz, 1H), 3.95-3.89 (s, 3H), 3.89-3.84 (s, 3H), 3.74-3.66 (dd, J=10.4, 5.8 Hz, 1H), 3.58-3.51 (dd, J=10.4, 7.3 Hz, 1H), 3.34-3.20 (p, J=6.9 Hz, 1H), 2.83-2.74 (t, J=7.5 Hz, 2H), 2.23-2.06 (dq, J=14.6, 7.3 Hz, 1H), 1.87-1.71 (dq, J=14.4, 7.6 Hz, 1H) ppm.

Example 12. Peak 2: LCMS calculated for C$_{21}$H$_{22}$N$_5$O$_2$ (M+H)$^+$: m/z=376.2; Found: 376.2. $^1$H NMR (500 MHz, DMSO-d6) δ 8.34-8.29 (s, 1H), 8.09-8.01 (s, 1H), 7.48-7.44 (s, 1H), 7.37-7.34 (d, J=7.3 Hz, 1H), 7.32-7.27 (d, J=7.4 Hz, 1H), 7.25-7.20 (t, J=7.5 Hz, 1H), 3.94-3.87 (s, 3H), 3.88-3.83 (s, 3H), 3.74-3.67 (dd, J=10.4, 5.8 Hz, 1H), 3.58-3.50 (dd, J=10.4, 7.3 Hz, 1H), 3.35-3.23 (p, J=6.8 Hz, 1H), 2.86-2.68 (t, J=7.4 Hz, 2H), 2.19-2.05 (dq, J=14.5, 7.2 Hz, 1H), 1.86-1.73 (m, 1H) ppm.

Intermediate 5. 2-Fluoro-4-(4,4,5,5-tetramethyl-1,3,2-dioxaborolan-2-yl)-2,3-dihydro-1H-inden-1-ol

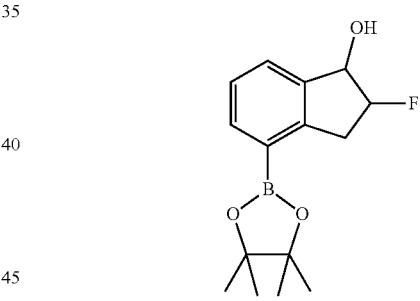

Step 1.
4-Bromo-2-fluoro-2,3-dihydro-1H-inden-1-ol

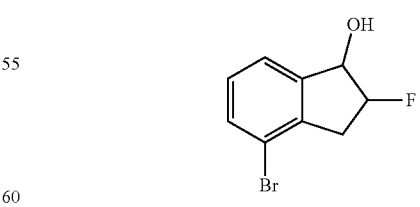

Selectfluor (671 mg, 1.9 mmol) was added to a solution of 4-bromo-2,3-dihydro-1H-inden-1-one (200 mg, 0.948 mmol) in acetonitrile (15 ml). After the reaction mixture was stirred at reflux overnight, the solvent was evaporated in vacuo and the crude material was purified by Biotage Isolera.

NaBH₄ (62 mg, 1.6 mmol) was added to a solution of the above purified material in a mixture of THF (2 ml) and MeOH (2 ml). After the reaction mixture was stirred at r.t. for 1 h, water was added. The desired product was extracted with EtOAc, the organic phase was washed with brine, dried over sodium sulfate and the solvents were evaporated in vacuo. The resultant crude product was used in the next step without further purification.

Step 2. 2-Fluoro-4-(4,4,5,5-tetramethyl-1,3,2-dioxaborolan-2-yl)-2,3-dihydro-1H-inden-1-ol This compound was prepared according to the procedures described in Intermediate 2, using 4-bromo-2-fluoro-2,3-dihydro-1H-inden-1-ol instead of 4-bromo-2,3-dihydro-1H-inden-1-ol as starting material. Intermediate 5 was isolated as a cis-isomer with only traces of trans isomer.

Example 13. 2-Fluoro-4-(6-methoxy-3-(1-methyl-1H-pyrazol-4-yl)-1H-pyrazolo[4,3-b]pyridin-5-yl)-2,3-dihydro-1H-inden-1-ol peak 2

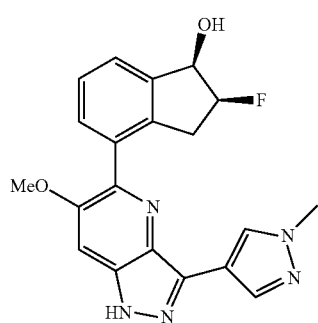

This compound was prepared according to the procedures described in Example 7, using 2-fluoro-4-(4,4,5,5-tetramethyl-1,3,2-dioxaborolan-2-yl)-2,3-dihydro-1H-inden-1-ol (Intermediate 5) instead of 4-(4,4,5,5-tetramethyl-1,3,2-dioxaborolan-2-yl)-2,3-dihydro-1H-inden-1-ol as starting material.

The two enantiomers were separated with chiral prep-HPLC (Phenomenex Lux Sum Amylose-1, 21.2×250 mm, eluting with 35% EtOH in hexanes, at flow rate of 20 mL/min, $t_{R,\ peak\ 1}$=7.8 min, $t_{R,\ peak\ 2}$=9.8 min). Peak 2 was collected. After the solvents were evaporated in vacuo, the product was purified by prep-LCMS (XBridge C18 column, eluting with a gradient of acetonitrile/water containing 0.1% TFA, at flow rate of 60 mL/min). The product was isolated as the TFA salt. LCMS calculated for $C_{20}H_{19}FN_5O_2$, (M+H)⁺: m/z=380.2; Found: 380.2. ¹H NMR (500 MHz, DMSO-d6) δ 8.35-8.31 (s, 1H), 8.07-8.04 (s, 1H), 7.51-7.47 (s, 1H), 7.48-7.44 (m, 1H), 7.43-7.34 (m, 2H), 5.28-5.13 (m, 1H), 5.13-5.07 (m, 1H), 3.94-3.89 (s, 3H), 3.89-3.86 (s, 3H), 3.24-3.06 (ddd, J=35.5, 17.3, 4.1 Hz, 1H), 2.97-2.86 (dd, J=22.2, 17.0 Hz, 1H) ppm. Single crystal x-ray was performed on Intermediate 5, which is a cis-isomer, and its absolute stereochemistry was determined, confirming the absolute stereochemistry of the title compound.

The preparation of tert-butyl 5-chloro-6-methoxy-3-(1-methyl-1H-pyrazol-4-yl)-1H-pyrazolo[4,3-b]pyridine-1-carboxylate, which is used as a starting material in this Example, is described below:

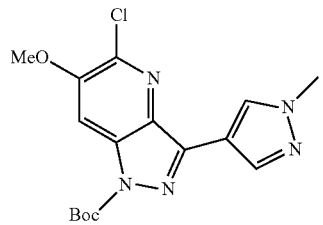 [SMILES: COc1cc2c(nc1Cl)c(-c1cnn(C)c1)nn2C(=O)OC(C)(C)C]

Step 1. 6-Bromo-1-trityl-1H-pyrazolo[4,3-b]pyridine

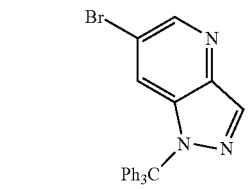

NaH (60% in mineral oil, 2.46 g, 61.6 mmol) was slowly added at 0° C. to a solution of 6-bromo-1H-pyrazolo[4,3-b]pyridine (10.16 g, 51.3 mmol) in DMF (70 ml). After stirring at r.t. for 20 min, (chloromethanetriyl)tribenzene (15.73 g, 56.4 mmol) was slowly added and the reaction mixture was stirred at r.t. for 1 h. Then water was added and the precipitated product was collected by filtration, washed with water and air dried. It was used in the next step without further purification. LC-MS calculated for $C_{25}H_{19}BrN_3$ (M+H)⁺: m/z=440.1 and 442.1; found 440.0 and 442.0.

Step 2. 6-Methoxy-1-trityl-1H-pyrazolo[4,3-b]pyridine

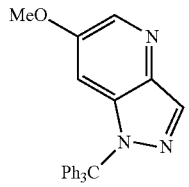

A mixture of 6-bromo-1-trityl-1H-pyrazolo[4,3-b]pyridine (25.0 g, 56.8 mmol), cesium carbonate (25.9 g, 79 mmol), methanol (6.89 ml, 170 mmol) and ᵗBuXPhos Pd G3 (1.52 g, 1.7 mmol) in toluene (150 ml) was heated at 80° C. for 1 h. After cooling to r.t., the reaction mixture was filtered, the solvent evaporated in vacuo and crude material was purified by Biotage Isolera. LCMS calculated for $C_{26}H_{22}N_3O$ (M+H)⁺: m/z=392.2; Found: 392.1.

Step 3. 6-Methoxy-1-trityl-1H-pyrazolo[4,3-b]pyridine 4-oxide

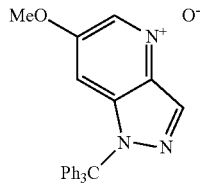

m-CPBA (14.5 g, 64.6 mmol) was slowly added at 0° C. to a solution of 6-methoxy-1-trityl-1H-pyrazolo[4,3-b]pyridine (16.8 g, 43.0 mmol) in DCM (150 ml). After stirring at r.t. overnight, the reaction was quenched with $Na_2S_2O_3$ solution and 1M NaOH solution. After stirring at r.t. for 30 min, the organic phase was separated and washed 3 times with 1M NaOH solution and 2 times with brine solution. Then the organic phase was dried over sodium sulfate, filtered and the solvent was removed in vacuo. The resultant product was used in the next step without further purification. LC-MS calculated for $C_{26}H_{22}N_3O_2$ $(M+H)^+$: m/z=408.2; found 408.2.

Step 4. 5-Chloro-6-methoxy-1-trityl-1H-pyrazolo[4,3-b]pyridine

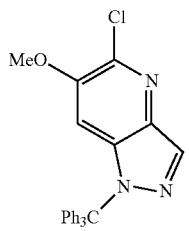

A solution of oxalyl chloride (5.36 ml, 61.3 mmol) in DCM was slowly added at 0° C. to a solution of 6-methoxy-1-trityl-1H-pyrazolo[4,3-b]pyridine 4-oxide (16.65 g, 40.9 mmol) and DIPEA (14.27 ml, 82 mmol) in DCM (100 ml). After stirring at 0° C. for 1 h, the reaction was diluted with DCM and carefully quenched with water. The organic phase was separated, washed 3 times with water, 2 times with saturated $NaHCO_3$ solution, 2 times with brine and was dried over sodium sulfate. After removing the solvent in vacuo, the resultant product was used in the next step without further purification. LC-MS calculated for $C_{26}H_{21}ClN_3O$ $(M+H)^+$: m/z=426.1; found 426.2.

Step 5. 5-Chloro-6-methoxy-1H-pyrazolo[4,3-b]pyridine

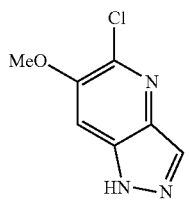 [SMILES: COc1cc2[nH]ncc2nc1Cl]

TFA (29 ml, 376 mmol) and water (1.35 ml, 75 mmol) were added to a solution of 5-chloro-6-methoxy-1-trityl-1H-pyrazolo[4,3-b]pyridine (16 g, 37.6 mmol) in DCM (75 ml). After stirring at r.t. for 30 min, $CH_3CN$ and water were added and the DCM was evaporated in vacuo. The precipitated solid was filtered off. The reaction mixture was further diluted with water and was washed 3 times with EtOAc/hexane 1:1 mixture. The water phase was separated and all solvents were removed in vacuo. The residue was redissolved in DCM and was neutralized with $NaHCO_3$ solution. The organic phase was further washed 2 times with $NaHCO_3$ solution, brine, and then dried over sodium sulfate. The solvent was evaporated in vacuo. The resultant crude product was used in the next step without further purification. LC-MS calculated for $C_7H_7ClN_3O$ $(M+H)^+$: m/z=184.0; found 184.1.

Step 6. tert-Butyl 5-chloro-3-iodo-6-methoxy-1H-pyrazolo[4,3-b]pyridine-1-carboxylate

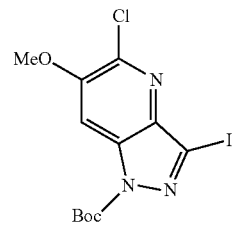 [SMILES: COc1cc2c(nc1Cl)c(I)nn2C(=O)OC(C)(C)C]

NIS (6.87 g, 30.6 mmol) was added to a solution of 5-chloro-6-methoxy-1H-pyrazolo[4,3-b]pyridine (5.5 g, 30.0 mmol) in DMF (60 ml). After stirring at 60° C. for 2 h, the reaction mixture was cooled to r.t., and triethylamine (6.26 ml, 44.9 mmol) and Boc-anhydride (8.17 g, 37.4 mmol) were added. After additional stirring at r.t. for 1 h, water was added and the precipitated product was collected by filtration. The solid product was air dried and used in the next step without further purification. LC-MS calculated for $C_{12}H_{14}ClIN_3O_3$ $(M+H)^+$: m/z=410.0; found 410.1.

Step 7. tert-Butyl 5-chloro-6-methoxy-3-(1-methyl-1H-pyrazol-4-yl)-1H-pyrazolo[4,3-b]pyridine-1-carboxylate

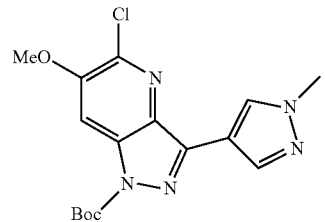 [SMILES: COc1cc2c(nc1Cl)c(-c1cnn(C)c1)nn2C(=O)OC(C)(C)C]

tert-Butyl 5-chloro-3-iodo-6-methoxy-1H-pyrazolo[4,3-b]pyridine-1-carboxylate (8.73 g, 21.31 mmol), 1-methyl-4-(4,4,5,5-tetramethyl-1,3,2-dioxaborolan-2-yl)-1H-pyrazole (5.32 g, 25.6 mmol), $PdCl_2$(dppf)-$CH_2Cl_2$ adduct (3.48 g, 4.26 mmol) and potassium phosphate (6.79 g, 32.0 mmol) were placed in a flask and the flask was evacuated and backfilled with $N_2$ three times. Then 1,4-dioxane (150 ml) and water (15 ml) were added and the reaction was stirred at 80° C. for 1 h. After cooling to r.t., water was added and the desired product was extracted with EtOAc. The organic phase was washed with brine, dried over sodium sulfate and the solvent was evaporated in vacuo. Crude material was purified by Biotage Isolera. LCMS calculated for $C_{16}H_{19}ClN_5O_3$ (M+H)$^+$: m/z=364.1; Found: 364.0.

Example 14. 5-(2,3-Dihydro-1H-inden-4-yl)-6-methoxy-3-(1-(pyrrolidin-3-yl)-1H-pyrazol-4-yl)-1H-pyrazolo[4,3-b]pyridine

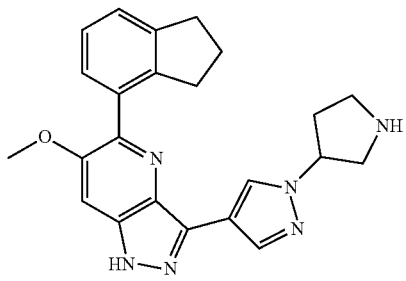 [SMILES: COc1cc2[nH]nc(-c3cnn(C4CCNC4)c3)c2nc1-c1cccc2c1CCC2]

Step 1. 5-(2,3-Dihydro-1H-inden-4-yl)-6-methoxy-1-trityl-1H-pyrazolo[4,3-b]pyridine

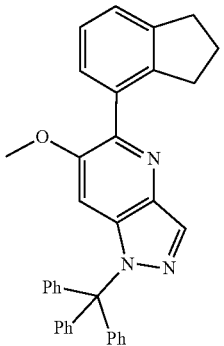 [SMILES: COc1cc2c(cnn2C(c2ccccc2)(c2ccccc2)c2ccccc2)nc1-c1cccc2c1CCC2]

5-Chloro-6-methoxy-1-trityl-1H-pyrazolo[4,3-b]pyridine (Example 1, Step 4, 0.50 g, 1.174 mmol), 2-(2,3-dihydro-1H-inden-4-yl)-4,4,5,5-tetramethyl-1,3,2-dioxaborolane (0.32 g, 1.31 mmol), chloro(2-dicyclohexylphosphino-2',4',6'-triisopropyl-1,1'-biphenyl)[2-(2'-amino-1,1'-biphenyl)] palladium (102 mg, 0.13 mmol) and potassium phosphate (274 mg, 1.3 mmol) were placed in a vial and the vial was evacuated and backfilled with $N_2$ three times. After 1,4-dioxane (10 ml) and water (1 ml) were added, the reaction mixture was stirred at 80° C. for 2 hrs. After cooling to r.t., water was added and the desired product was extracted with EtOAc. The organic phase was washed with brine, dried over sodium sulfate and the solvent was evaporated in vacuo. Crude material was purified by Biotage Isolera to give a white solid (0.59 g, 99%). LCMS calculated for $C_{35}H_{30}N_3O$ (M+H)$^+$: m/z=508.2; found 508.1.

Step 2. 5-(2,3-Dihydro-1H-inden-4-yl)-6-methoxy-1H-pyrazolo[4,3-b]pyridine

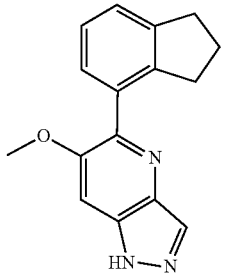 [SMILES: COc1cc2[nH]ncc2nc1-c1cccc2c1CCC2]

5-(2,3-Dihydro-1H-inden-4-yl)-6-methoxy-1-trityl-1H-pyrazolo[4,3-b]pyridine (0.58 g, 1.143 mmol) in a mixture of DCM (10 ml) and TFA (4 ml) was stirred at r.t. for 1 h. The reaction was then concentrated in vacuo, dissolved in DCM and neutralized with NaHCO$_3$ solution. The organic phase was separated, dried over sodium sulfate and concentrated in vacuo. Crude material was purified by Biotage Isolera to give a white solid (0.2 g, 66%). LCMS calculated for $C_{16}H_{16}N_3O$ (M+H)$^+$: m/z=266.1; found 266.1.

Step 3. tert-Butyl 5-(2,3-dihydro-1H-inden-4-yl)-3-iodo-6-methoxy-1H-pyrazolo[4,3-b]pyridine-1-carboxylate

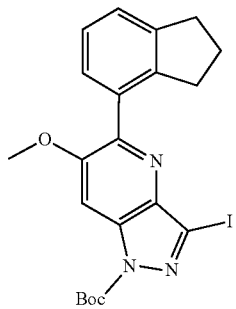 [SMILES: COc1cc2c(nc1-c1cccc3c1CCC3)c(I)nn2C(=O)OC(C)(C)C]

NIS (0.220 g, 0.978 mmol) was added to a solution of 5-(2,3-dihydro-1H-inden-4-yl)-6-methoxy-1H-pyrazolo[4,3-b]pyridine (0.20 g, 0.754 mmol) in DMF (10 ml). After stirring at 80° C. for 2 h, the reaction mixture was cooled to r.t., and triethylamine (0.3 ml, 2.2 mmol) and Boc-anhydride (0.411 g, 1.885 mmol) were added. After additional stirring at r.t. for 1 h, water was added and the precipitated product was collected by filtration and air dried. Crude material was purified by Biotage Isolera to give a white solid (0.29 g, 78%). LCMS calculated for $C_{21}H_{23}IN_3O_3$ (M+H)$^+$: m/z=492.1; found 492.1.

Step 4. 5-(2,3-Dihydro-1H-inden-4-yl)-6-methoxy-3-(1-(pyrrolidin-3-yl)-1H-pyrazol-4-yl)-1H-pyrazolo[4,3-b]pyridine tert-Butyl 5-(2,3-dihydro-1H-inden-4-yl)-3-iodo-6-methoxy-1H-pyrazolo[4,3-b]pyridine-1-carboxylate (0.10 g, 0.204 mmol), (1-(1-(tert-butoxycarbonyl)pyrrolidin-3-yl)-1H-pyrazol-4-yl)boronic acid (0.114 g, 0.407 mmol), chloro(2-dicyclohexylphosphino-2',4',6'-triisopropyl-1,1'- biphenyl)[2-(2'-amino-1,1'-biphenyl)]palladium (17 mg, 22 mop and potassium phosphate (40 mg, 0.18 mmol) were placed in a vial and the vial was evacuated and backfilled with N₂ three times. After 1,4-dioxane (3 ml) and water (300 µl) were added, the reaction mixture was stirred at 80° C. for 2 hrs. The reaction was then filtered, and the solvents were evaporated in vacuo. 4N solution of HCl in dioxane (2 ml) was added to the resultant residue and the reaction mixture was stirred at r.t. for 1 h. The mixture was then diluted with CH₃CN and water and purified with prep-LCMS (XBridge C18 column, eluting with a gradient of acetonitrile/water containing 0.1% TFA, at flow rate of 60 mL/min). The product was isolated as the TFA salt. LCMS calculated for $C_{23}H_{25}N_6O$ (M+H)⁺: m/z=401.1; Found: 401.1.

Example 15. 5-(2,3-Dihydro-1H-inden-4-yl)-3-(1-(1-ethylpyrrolidin-3-yl)-1H-pyrazol-4-yl)-6-methoxy-1H-pyrazolo[4,3-b]pyridine

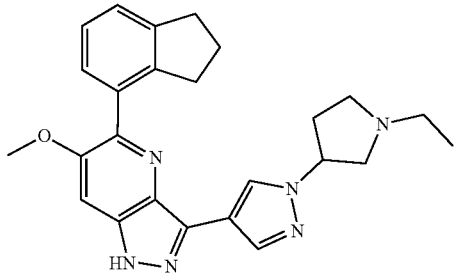 [SMILES: CCN1CCC(n2cc(-c3n[nH]c4cc(OC)c(-c5cccc6c5CCC6)nc34)cn2)C1]

Acetaldehyde (11 mg, 0.24 mmol) and sodium triacetoxyborohydride (25 mg, 0.12 mmol) were added to a solution of 5-(2,3-dihydro-1H-inden-4-yl)-6-methoxy-3-(1-(pyrrolidin-3-yl)-1H-pyrazol-4-yl)-1H-pyrazolo[4,3-b]pyridine (25 mg, 0.062 mmol) and one drop of acetic acid in DCE (1 ml). After stirring at r.t. overnight, the reaction was then diluted with CH₃CN and water and purified with prep-LCMS (XBridge C18 column, eluting with a gradient of acetonitrile/water containing 0.1% TFA, at flow rate of 60 mL/min). The product was isolated as the TFA salt. LCMS calculated for $C_{25}H_{29}N_6O$ (M+H)⁺: m/z=429.1; Found: 429.1.

Example 16. 3-(4-(5-(2,3-Dihydro-1H-inden-4-yl)-6-methoxy-1H-pyrazolo[4,3-b]pyridin-3-yl)-1H-pyrazol-1-yl)cyclobutanecarbonitrile

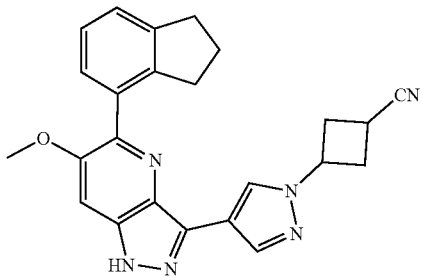 [SMILES: COc1cc2[nH]nc(-c3cnn(C4CC(C#N)C4)c3)c2nc1-c1cccc2c1CCC2]

This compound was prepared according to the procedures described in Example 14, using 3-(4-(4,4,5,5-tetramethyl-1,3,2-dioxaborolan-2-yl)-1H-pyrazol-1-yl)cyclobutane-1-carbonitrile instead of (1-(1-(tert-butoxycarbonyl)pyrrolidin-3-yl)-1H-pyrazol-4-yl)boronic acid as starting material. The product was isolated as the TFA salt. LCMS calculated for $C_{24}H_{23}N_6O$ (M+H)⁺: m/z=411.2; Found: 411.2. ¹H NMR (500 MHz, DMSO-d6) δ 8.44-8.37 (s, 1H), 8.20-8.15 (s, 1H), 7.50-7.44 (s, 1H), 7.32-7.27 (m, 2H), 7.25-7.20 (t, J=7.4 Hz, 1H), 5.39-5.27 (p, J=8.0 Hz, 1H), 3.92-3.82 (s, 3H), 3.02-2.88 (m, 4H), 2.85-2.73 (m, 4H), 2.06-1.91 (p, J=7.4 Hz, 3H) ppm.

Example 17. 5-(2,3-Dihydro-1H-inden-4-yl)-6-methoxy-3-(1-(1-methylazetidin-3-yl)-1H-pyrazol-4-yl)-1H-pyrazolo[4,3-b]pyridine

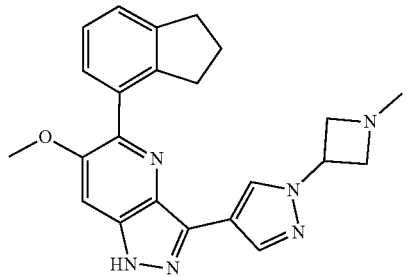

Step 1. tert-Butyl 3-(1-(1-(tert-butoxycarbonyl)azetidin-3-yl)-1H-pyrazol-4-yl)-5-(2,3-dihydro-1H-inden-4-yl)-6-methoxy-1H-pyrazolo[4,3-b]pyridine-1-carboxylate

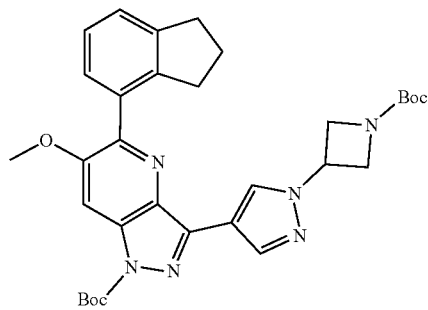 [SMILES: COc1cc2c(nc1-c1cccc3c1CCC3)c(-c1cnn(C3CN(C(=O)OC(C)(C)C)C3)c1)nn2C(=O)OC(C)(C)C]

This compound was prepared according to the procedures described in Example 14, using tert-butyl 3-(4-(4,4,5,5-tetramethyl-1,3,2-dioxaborolan-2-yl)-1H-pyrazol-1-yl)azetidine-1-carboxylate instead of (1-(1-(tert-butoxycarbonyl) pyrrolidin-3-yl)-1H-pyrazol-4-yl)boronic acid as starting material. LCMS calculated for $C_{32}H_{39}N_6O_5$ (M+H)⁺: m/z=587.3; Found: 587.3.

Step 2. 3-(1-(Azetidin-3-yl)-1H-pyrazol-4-yl)-5-(2,3-dihydro-M-inden-4-yl)-6-methoxy-M-pyrazolo[4,3-b]pyridine

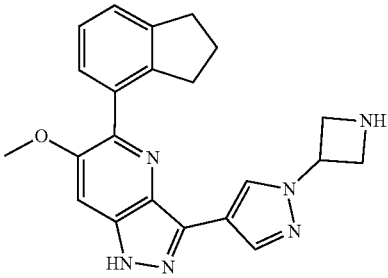 [SMILES: COc1cc2[nH]nc(-c3cnn(C4CNC4)c3)c2nc1-c1cccc2c1CCC2]

A solution of tert-butyl 3-(1-(1-(tert-butoxycarbonyl)azetidin-3-yl)-1H-pyrazol-4-yl)-5-(2,3-dihydro-1H-inden-4-yl)-6-methoxy-1H-pyrazolo[4,3-b]pyridine-1-carboxylate (0.14 g, 0.239 mmol) in a mixture of DCM (2 ml) and TFA (2 ml) was stirred at r.t. for 2 hrs. The solvent was then evaporated in vacuo and the crude product was directly used in the next step without further purification. LCMS calculated for $C_{22}H_{23}N_6O$ (M+H)$^+$: m/z=387.2; Found: 387.2.

Step 3. 5-(2,3-dihydro-1H-inden-4-yl)-6-methoxy-3-(1-(1-methylazetidin-3-yl)-1H-pyrazol-4-yl)-1H-pyrazolo[4,3-b]pyridine Formaldehyde solution (0.02 ml) and sodium triacetoxyborohydride (25 mg, 0.12 mmol) were added to a solution of 3-(1-(azetidin-3-yl)-1H-pyrazol-4-yl)-5-(2,3-dihydro-1H-inden-4-yl)-6-methoxy-1H-pyrazolo[4,3-b]pyridine (24 mg, 0.062 mmol) and one drop of acetic acid in DCE (1 ml). After stirring at r.t. overnight, the reaction was then diluted with CH$_3$CN and water and purified with prep-LCMS (XBridge C18 column, eluting with a gradient of acetonitrile/water containing 0.1% TFA, at flow rate of 60 mL/min). The product was isolated as the TFA salt. LCMS calculated for $C_{23}H_{25}N_6O$ (M+H)$^+$: m/z=401.2; Found: 401.2. $^1$H NMR (500 MHz, DMSO-d6) δ 12.97-12.91 (s, 1H), 8.50-8.39 (s, 1H), 8.16-8.10 (s, 1H), 7.51-7.45 (s, 1H), 7.33-7.27 (m, 2H), 7.26-7.18 (m, 1H), 5.16-5.00 (dt, J=13.6, 6.7 Hz, 1H), 3.90-3.83 (s, 3H), 3.75-3.65 (t, J=7.5 Hz, 2H), 3.45-3.36 (m, 2H), 3.01-2.89 (t, J=7.3 Hz, 2H), 2.88-2.77 (t, J=7.4 Hz, 2H), 2.36-2.29 (s, 3H), 2.03-1.90 (dt, J=14.8, 7.4 Hz, 2H) ppm.

Example 18. 5-(2,3-Dihydro-1H-inden-4-yl)-3-(1-(1-ethylazetidin-3-yl)-1H-pyrazol-4-yl)-6-methoxy-1H-pyrazolo[4,3-b]pyridine

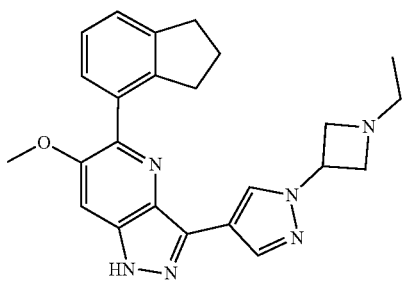 [SMILES: CCN1CC(n2cc(-c3n[nH]c4cc(OC)c(-c5cccc6c5CCC6)nc34)cn2)C1]

This compound was prepared according to the procedures described in Example 17, using acetaldehyde instead of formaldehyde as starting material. The product was isolated as the TFA salt. LCMS calculated for $C_{24}H_{27}N_6O$ (M+H)$^+$: m/z=415.2; Found: 415.2.

Example 19. 4-(4-(5-(2,3-Dihydro-1H-inden-4-yl)-6-methoxy-1H-pyrazolo[4,3-b]pyridin-3-yl)-1H-pyrazol-1-yl)-N,N-dimethylpiperidine-1-carboxamide

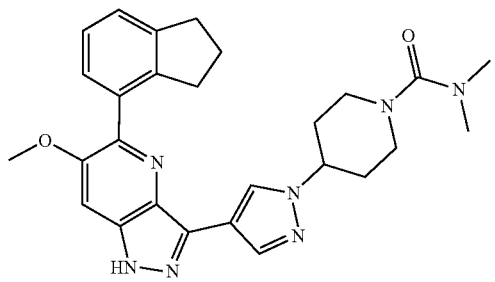

Step 1. 5-(2,3-Dihydro-1H-inden-4-yl)-3-iodo-6-methoxy-1-(4-methoxybenzyl)-1H-pyrazolo[4,3-b]pyridine

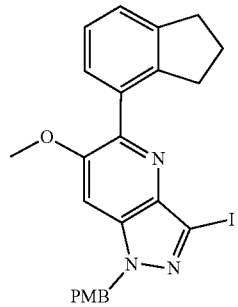

1-(Chloromethyl)-4-methoxybenzene (0.149 g, 0.951 mmol) was added to mixture of 5-(2,3-dihydro-1H-inden-4-yl)-3-iodo-6-methoxy-1H-pyrazolo[4,3-b]pyridine (Example 14, Step 3, 0.31 g, 0.792 mmol) and cesium carbonate (500 mg, 1.54 mmol) in DMF (5 ml). After stirring at 80° C. for 1 h, the reaction was diluted with DCM and washed with water and brine. The organic phase was dried over sodium sulfate and the solvent was evaporated in vacuo. Crude material was purified by Biotage Isolera (0.40, 99%). LCMS calculated for $C_{24}H_{23}IN_3O_2$ (M+H)$^+$: m/z=512.1; Found: 512.1.

Step 2. 5-(2,3-Dihydro-1H-inden-4-yl)-6-methoxy-1-(4-methoxybenzyl)-3-(1-(piperidin-4-yl)-1H-pyrazol-4-yl)-1H-pyrazolo[4,3-b]pyridine

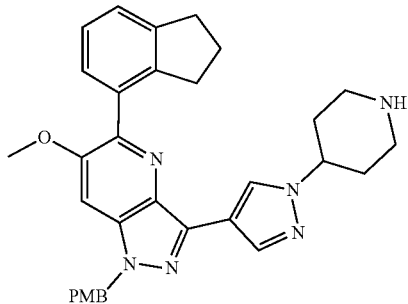

5-(2,3-Dihydro-1H-inden-4-yl)-3-iodo-6-methoxy-1-(4-methoxybenzyl)-1H-pyrazolo[4,3-b]pyridine (0.200 g, 0.391 mmol), tert-butyl 4-(4-(4,4,5,5-tetramethyl-1,3,2-dioxaborolan-2-yl)-1H-pyrazol-1-yl)piperidine-1-carboxylate (0.177 g, 0.469 mmol), chloro(2-dicyclohexylphosphino-2',4',6'-triisopropyl-1,1'-biphenyl)[2-(2'-amino-1,1'-biphenyl)] palladium (17 mg, 22 µmol) and potassium phosphate (100 mg, 0.44 mmol) were placed in a vial and the vial was evacuated and backfilled with $N_2$ three times. After 1,4-dioxane (3 ml) and water (300 µl) were added, the reaction mixture was stirred at 100° C. for 1 h. Then the reaction was filtered, and the solvents were evaporated in vacuo. After purification by Biotage Isolera, DCM (1 ml) and TFA (1 ml) were added to the purified material and the reaction mixture was stirred at r.t. for 1 h. The reaction mixture was then diluted with DCM and neutralized with $NaHCO_3$ solution. The product was extracted with DCM, and organic phase was dried over sodium sulfate and concentrated in vacuo. The resultant product was used in the next step without further purification. LCMS calculated for $C_{32}H_{35}N_6O_2$ $(M+H)^+$: m/z=535.2; Found: 535.2.

Step 3. 4-(4-(5-(2,3-Dihydro-1H-inden-4-yl)-6-methoxy-1H-pyrazolo[4,3-b]pyridin-3-yl)-1H-pyrazol-1-yl)-N,N-dimethylpiperidine-1-carboxamide

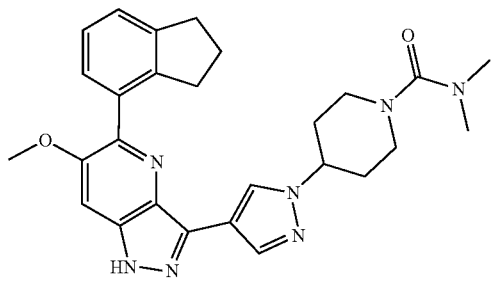

To a solution of 5-(2,3-dihydro-1H-inden-4-yl)-6-methoxy-1-(4-methoxybenzyl)-3-(1-(piperidin-4-yl)-1H-pyrazol-4-yl)-1H-pyrazolo[4,3-b]pyridine (10 mg, 0.019 mmol) in 1,4-dioxane (0.5 ml) and $Et_3N$ (0.02 ml) was added dimethylcarbamic chloride (10 mg, 0.094 mmol). After stirring at r.t. for 1 h, the reaction was concentrated in vacuo. TFA (1 ml) was added to the crude material and the resultant solution was heated at 100° C. for 2 hrs. The reaction was then diluted with $CH_3CN$ and water and purified with prep-LCMS (XBridge C18 column, eluting with a gradient of acetonitrile/water containing 0.1% TFA, at flow rate of 60 mL/min). The product was isolated as the TFA salt. LCMS calculated for $C_{27}H_{32}N_7O_2$ $(M+H)^+$: m/z=486.2; Found: 486.2.

Example 20. Methyl 4-(4-(5-(2,3-dihydro-1H-inden-4-yl)-6-methoxy-1H-pyrazolo[4,3-b]pyridin-3-yl)-1H-pyrazol-1-yl)piperidine-1-carboxylate

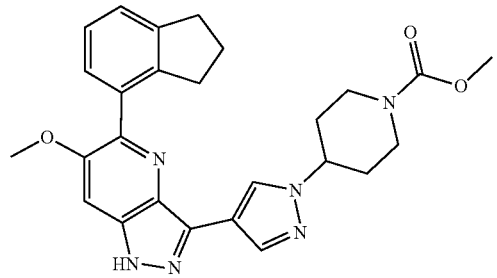

This compound was prepared according to the procedures described in Example 19, using methyl chloroformate instead of dimethylcarbamic chloride. The product was isolated as the TFA salt. LC-MS calculated for $C_{26}H_{29}N_6O_3$ $(M+H)^+$: m/z=473.2; Found: 473.2.

Example 21. Methyl 3-(4-(5-(2,3-dihydro-1H-inden-4-yl)-6-methoxy-1H-pyrazolo[4,3-b]pyridin-3-yl)-1H-pyrazol-1-yl)azetidine-1-carboxylate

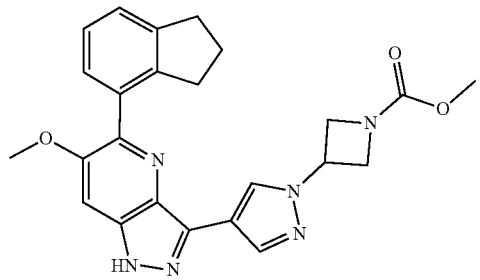

Step 1. 3-(1-(Azetidin-3-yl)-1H-pyrazol-4-yl)-5-(2,3-dihydro-1H-inden-4-yl)-6-methoxy-1-(4-methoxybenzyl)-1H-pyrazolo[4,3-b]pyridine

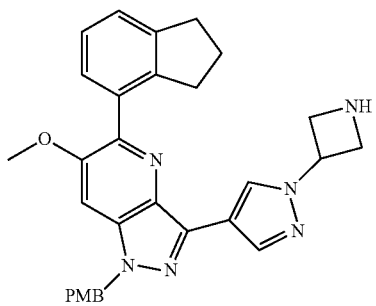

This compound was prepared according to the procedures described in Example 19, using tert-butyl 3-(4-(4,4,5,5-tetramethyl-1,3,2-dioxaborolan-2-yl)-1H-pyrazol-1-yl)azetidine-1-carboxylate instead of tert-butyl 4-(4-(4,4,5,5-tetramethyl-1,3,2-dioxaborolan-2-yl)-1H-pyrazol-1-yl)piperidine-1-carboxylate. LC-MS calculated for $C_{30}H_{31}N_6O_2$ (M+H)$^+$: m/z=507.2; found: 507.2.

Step 2. Methyl 3-(4-(5-(2,3-dihydro-1H-inden-4-yl)-6-methoxy-1H-pyrazolo[4,3-b]pyridin-3-yl)-1H-pyrazol-1-yl)azetidine-1-carboxylate This compound was prepared according to the procedures described in Example 19, using 3-(1-(azetidin-3-yl)-1H-pyrazol-4-yl)-5-(2,3-dihydro-1H-inden-4-yl)-6-methoxy-1-(4-methoxybenzyl)-1H-pyrazolo[4,3-b]pyridine instead of 5-(2,3-dihydro-1H-inden-4-yl)-6-methoxy-1-(4-methoxybenzyl)-3-(1-(piperidin-4-yl)-1H-pyrazol-4-yl)-1H-pyrazolo[4,3-b]pyridine, and using methyl chloroformate instead of dimethylcarbamic chloride. The product was isolated as the TFA salt. LC-MS calculated for $C_{24}H_{25}N_6O_3$ (M+H)$^+$: m/z=445.1; found: 445.1.

Example 22. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)ethan-1-one

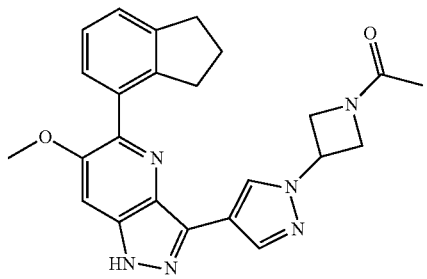 [SMILES: COc1cc2[nH]nc(-c3cnn(C4CN(C(C)=O)C4)c3)c2nc1-c1cccc2c1CCC2]

This compound was prepared according to the procedures described in Example 21, using acetyl chloride instead of methyl chloroformate. The product was isolated as the TFA salt. LC-MS calculated for $C_{24}H_{25}N_6O_2$ (M+H)$^+$: m/z=429.1; found: 429.1.

Example 23. 5-(2,3-Dihydro-1H-inden-4-yl)-6-methoxy-3-(1-(1-(methylsulfonyl)azetidin-3-yl)-1H-pyrazol-4-yl)-1H-pyrazolo[4,3-b]pyridine

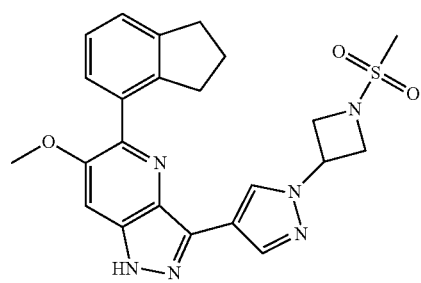 [SMILES: COc1cc2[nH]nc(-c3cnn(C4CN(S(C)(=O)=O)C4)c3)c2nc1-c1cccc2c1CCC2]

This compound was prepared according to the procedures described in Example 21, using methane sulfonyl chloride instead of methyl chloroformate. The product was isolated as the TFA salt. LC-MS calculated for $C_{23}H_{25}N_6O_3S$ (M+H)$^+$: m/z=465.1; found: 465.1.

Example 24. 3-(4-(5-(2,3-Dihydro-1H-inden-4-yl)-6-methoxy-1H-pyrazolo[4,3-b]pyridin-3-yl)-1H-pyrazol-1-yl)-N,N-dimethylazetidine-1-carboxamide

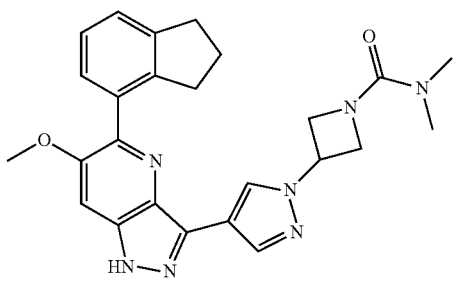

This compound was prepared according to the procedures described in Example 21, using dimethylcarbamic chloride instead of methyl chloroformate. The product was isolated as the TFA salt. LC-MS calculated for $C_{25}H_{28}N_7O_2$ (M+H)$^+$: m/z=458.1; found: 458.1.

Example 25. Cyclopropyl(3-(4-(5-(2,3-dihydro-1H-inden-4-yl)-6-methoxy-1H-pyrazolo[4,3-b]pyridin-3-yl)-1H-pyrazol-1-yl)azetidin-1-yl)methanone

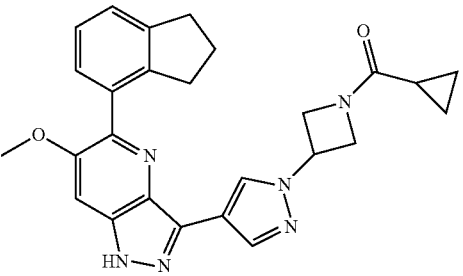 [SMILES: COc1cc2[nH]nc(-c3cnn(C4CN(C(=O)C5CC5)C4)c3)c2nc1-c1cccc2c1CCC2]

This compound was prepared according to the procedures described in Example 21, using cyclopropanecarbonyl chloride instead of methyl chloroformate. The product was isolated as the TFA salt. LC-MS calculated for $C_{26}H_{27}N_6O_2$ (M+H)$^+$: m/z=455.1; found: 455.1. $^1$H NMR (500 MHz, DMSO-d6) δ 8.52-8.44 (s, 1H), 8.26-8.16 (s, 1H), 7.51-7.43 (s, 1H), 7.31-7.25 (m, 2H), 7.25-7.18 (t, J=7.4 Hz, 1H), 5.52-5.41 (m, 1H), 4.75-4.69 (m, 1H), 4.60-4.52 (m, 1H), 4.36-4.26 (t, J=9.1 Hz, 1H), 4.21-4.11 (dd, J=10.1, 5.1 Hz, 1H), 3.90-3.84 (s, 3H), 3.01-2.93 (t, J=7.4 Hz, 2H), 2.85-2.77 (t, J=7.4 Hz, 2H), 2.03-1.90 (p, J=7.4 Hz, 2H), 1.66-1.53 (m, 1H), 0.82-0.70 (m, 4H) ppm.

Example 26. 5-(2,3-Dihydro-1H-inden-4-yl)-6-ethoxy-3-(1-methyl-1H-pyrazol-4-yl)-1H-pyrazolo[4,3-b]pyridine

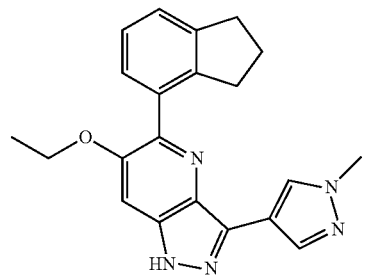 [SMILES: CCOc1cc2[nH]nc(-c3cnn(C)c3)c2nc1-c1cccc2c1CCC2]

Step 1. 6-Ethoxy-1-trityl-1H-pyrazolo[4,3-b]pyridine

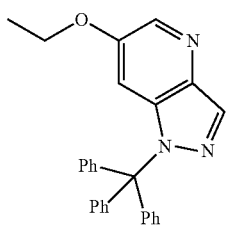 [SMILES: CCOc1cnc2cnn(C(c3ccccc3)(c3ccccc3)c3ccccc3)c2c1]

A mixture of 6-bromo-1-trityl-1H-pyrazolo[4,3-b]pyridine (2.5 g, 5.7 mmol), cesium carbonate (2.6 g, 8 mmol), ethanol (0.7 ml, 12 mmol) and ᵗBuXPhos Pd G3 (0.15 g, 0.17 mmol) in toluene (30 ml) was heated at 80° C. for 1 h. After cooling to r.t., the reaction mixture was filtered, solvent evaporated in vacuo and crude material was purified by Biotage Isolera. LC-MS calculated for $C_{27}H_{24}N_3O$ $(M+H)^+$: m/z=406.1; found 406.1.

Step 2. 6-Ethoxy-1-trityl-1H-pyrazolo[4,3-b]pyridine 4-oxide

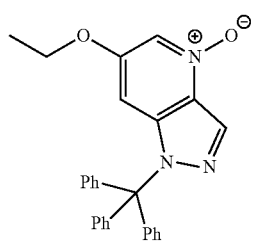 [SMILES: CCOc1cc2c(cnn2C(c2ccccc2)(c2ccccc2)c2ccccc2)[n+]([O-])c1]

To a solution of 6-ethoxy-1-trityl-1H-pyrazolo[4,3-b]pyridine (1.08 g, 2.66 mmol) in 10 mL of DCM at 0° C. was added 3-chlorobenzoperoxoic acid (1.5 g, 6.52 mmol). The reaction was stirred at r.t. for 2 hrs. The reaction mixture was diluted with DCM and the organic phase was washed with $Na_2S_2O_3$ solution, followed by $NaHCO_3$ solution. After the solvent was concentrated in vacuo, the crude material was purified by Biotage Isolera to give a white solid (0.80 g, 71%). LC-MS calculated for $C_{27}H_{24}N_3O_2$ $(M+H)^+$: m/z=422.1; found 422.1.

Step 3. 5-Chloro-6-ethoxy-1-trityl-1H-pyrazolo[4,3-b]pyridine

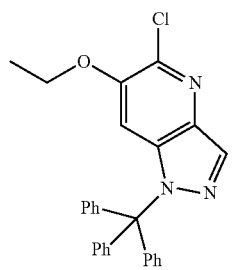 [SMILES: CCOc1cc2c(cnn2C(c2ccccc2)(c2ccccc2)c2ccccc2)nc1Cl]

To a solution of 6-ethoxy-1-trityl-1H-pyrazolo[4,3-b]pyridine 4-oxide (0.80 g, 1.9 mmol) in 20 ml of DCM was added 1.0 ml of $Et_3N$. The mixture was cooled to 0° C. in an ice bath, and oxalyl chloride (0.60 g, 4.7 mmol) was slowly added. The reaction mixture was stirred at 0° C. for 1 hr, before being neutralized with $NaHCO_3$ solution. The organic phase was separated, dried over sodium sulfate and concentrated in vacuo. The crude material was purified by Biotage Isolera to give a white solid (0.26 g, 31%). LC-MS calculated for $C_{27}H_{23}ClN_3O$ $(M+H)^+$: m/z=440.2; found 440.2.

Step 4. 5-(2,3-Dihydro-1H-inden-4-yl)-6-ethoxy-1H-pyrazolo[4,3-b]pyridine

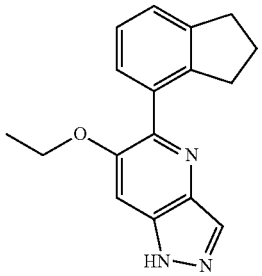 [SMILES: CCOc1cc2[nH]ncc2nc1-c1cccc2c1CCC2]

This compound was prepared according to the procedures described in Example 14, using 5-chloro-6-ethoxy-1-trityl-1H-pyrazolo[4,3-b]pyridine instead of 5-chloro-6-methoxy-1-trityl-1H-pyrazolo[4,3-b]pyridine. LC-MS calculated for $C_{17}H_{18}N_3O$ $(M+H)^+$: m/z=280.1; found 280.1.

Step 5. tert-Butyl 5-(2,3-dihydro-1H-inden-4-yl)-6-ethoxy-3-iodo-1H-pyrazolo[4,3-b]pyridine-1-carboxylate

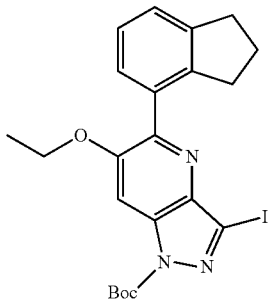 [SMILES: CCOc1cc2c(nc1-c1cccc3c1CCC3)c(I)nn2C(=O)OC(C)(C)C]

This compound was prepared according to the procedures described in Example 21, step 2, using 5-(2,3-dihydro-1H-inden-4-yl)-6-ethoxy-1H-pyrazolo[4,3-b]pyridine instead of 5-(2,3-dihydro-1H-inden-4-yl)-6-methoxy-1H-pyrazolo[4,3-b]pyridine. LC-MS calculated for $C_{22}H_{25}IN_3O_3$ $(M+H)^+$: m/z=506.1; found 506.1.

Step 6. 5-(2,3-Dihydro-1H-inden-4-yl)-6-ethoxy-3-(1-methyl-1H-pyrazol-4-yl)-1H-pyrazolo[4,3-b]pyridine A mixture of 1-methyl-4-(4,4,5,5-tetramethyl-1,3,2-dioxaborolan-2-yl)-1H-pyrazole (20 mg, 0.096 mmol), tert-butyl 5-(2,3-dihydro-1H-inden-4-yl)-6-ethoxy-3-iodo-1H-pyrazolo[4,3-b]pyridine-1-carboxylate (7 mg, 0.014 mmol), X-Phos Pd G2 (4 mg, 0.001 mmol) and $K_3PO_4$ (10 mg, 0.05 mmol) was combined with dioxane (1 ml) and water (0.1 ml) and the reaction mixture was heated at 80° C. for 2 hrs. After cooling to r.t., the reaction was filtered and 2 mL of 4N HCl in dioxane was added. The reaction mixture was stirred at r.t. for an additional 1 hr before it was concentrated in vacuo. The residue was then dissolved in a mixture of $CH_3CN$ and water, and the product was purified with prep-LCMS (XBridge C18 column, eluting with a gradient of acetonitrile/water containing 0.1% TFA, at flow rate of 60 mL/min). The product was isolated as the TFA salt. LC-MS calculated for $C_{21}H_{22}N_5O$ $(M+H)^+$: m/z=360.1; found: 360.1.

Example 27. 5-(2,3-Dihydro-1H-inden-4-yl)-6-methoxy-3-(1-(pyridin-4-ylmethyl)-1H-pyrazol-4-yl)-1H-pyrazolo[4,3-b]pyridine

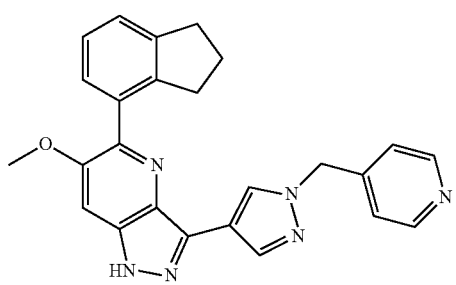 [SMILES: COc1cc2[nH]nc(-c3cnn(Cc4ccncc4)c3)c2nc1-c1cccc2c1CCC2]

This compound was prepared according to the procedures described in Example 14, using 4-((4-(4,4,5,5-tetramethyl-1,3,2-dioxaborolan-2-yl)-1H-pyrazol-1-yl)methyl)pyridine instead of (1-(1-(tert-butoxycarbonyl)pyrrolidin-3-yl)-1H-pyrazol-4-yl)boronic acid as starting material. The product was isolated as the TFA salt. LC-MS calculated for $C_{25}H_{23}N_6O$ $(M+H)^+$: m/z=423.1; found: 423.1.

Example 28. 4-(2-(4-(5-(2,3-Dihydro-1H-inden-4-yl)-6-methoxy-1H-pyrazolo[4,3-b]pyridin-3-yl)-1H-pyrazol-1-yl)ethyl)morpholine

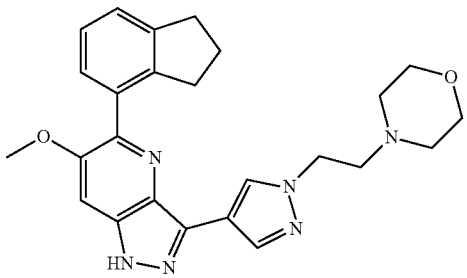 [SMILES: COc1cc2[nH]nc(-c3cnn(CCN4CCOCC4)c3)c2nc1-c1cccc2c1CCC2]

This compound was prepared according to the procedures described in Example 14, using 4-(2-(4-(4,4,5,5-tetramethyl-1,3,2-dioxaborolan-2-yl)-1H-pyrazol-1-yl)ethyl)morpholine instead of (1-(1-(tert-butoxycarbonyl)pyrrolidin-3-yl)-1H-pyrazol-4-yl)boronic acid as starting material. The product was isolated as the TFA salt. LC-MS calculated for $C_{25}H_{29}N_6O_2$ $(M+H)^+$: m/z=445.1; found: 445.1.

Example 29. 3-(1-Cyclopropyl-1H-pyrazol-4-yl)-5-(2,3-dihydro-1H-inden-4-yl)-6-methoxy-1H-pyrazolo[4,3-b]pyridine

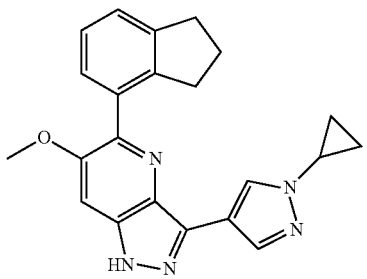 [SMILES: COc1cc2[nH]nc(-c3cnn(C4CC4)c3)c2nc1-c1cccc2c1CCC2]

This compound was prepared according to the procedures described in Example 14, using 1-cyclopropyl-4-(4,4,5,5-tetramethyl-1,3,2-dioxaborolan-2-yl)-1H-pyrazole instead of (1-(1-(tert-butoxycarbonyl)pyrrolidin-3-yl)-1H-pyrazol-4-yl)boronic acid as starting material. The product was isolated as the TFA salt. LC-MS calculated for $C_{22}H_{22}N_5O$ $(M+H)^+$: m/z=372.1; found: 372.1.

Example 30. 3-(4-(5-(2,3-Dihydro-1H-inden-4-yl)-6-methoxy-1H-pyrazolo[4,3-b]pyridin-3-yl)-1H-pyrazol-1-yl)propanenitrile

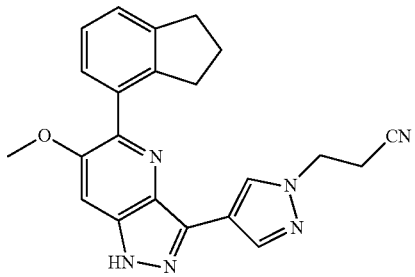 [SMILES: COc1cc2[nH]nc(-c3cnn(CCC#N)c3)c2nc1-c1cccc2c1CCC2]

This compound was prepared according to the procedures described in Example 14, using 3-(4-(4,4,5,5-tetramethyl-1,3,2-dioxaborolan-2-yl)-1H-pyrazol-1-yl)propanenitrile instead of (1-(1-(tert-butoxycarbonyl)pyrrolidin-3-yl)-1H-pyrazol-4-yl)boronic acid as starting material. The product was isolated as the TFA salt. LC-MS calculated for $C_{22}H_{21}N_6O$ $(M+H)^+$: m/z=385.1; found: 385.1.

Example 31. 2-(4-(5-(2,3-Dihydro-1H-inden-4-yl)-6-methoxy-1H-pyrazolo[4,3-b]pyridin-3-yl)-1H-pyrazol-1-yl)ethan-1-ol

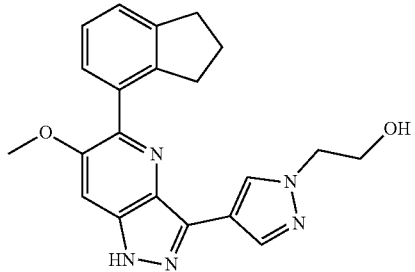 [SMILES: COc1cc2[nH]nc(-c3cnn(CCO)c3)c2nc1-c1cccc2c1CCC2]

This compound was prepared according to the procedures described in Example 14, using 2-(4-(4,4,5,5-tetramethyl-1,3,2-dioxaborolan-2-yl)-1H-pyrazol-1-yl)ethan-1-ol instead of (1-(1-(tert-butoxycarbonyl)pyrrolidin-3-yl)-1H-pyrazol-4-yl)boronic acid as starting material. The product was isolated as the TFA salt. LC-MS calculated for $C_{21}H_{22}N_5O_2$ $(M+H)^+$: m/z=376.1; found: 376.1. $^1H$ NMR (500 MHz, DMSO-d6) δ 8.38-8.30 (s, 1H), 8.11-8.04 (s, 1H), 7.50-7.42 (s, 1H), 7.33-7.26 (m, 2H), 7.25-7.17 (m, 1H), 4.29-4.17 (t, J=5.5 Hz, 2H), 3.92-3.83 (s, 3H), 3.79-3.73 (t, J=5.5 Hz, 2H), 3.00-2.91 (t, J=7.3 Hz, 2H), 2.84-2.78 (t, J=7.4 Hz, 2H), 2.07-1.92 (p, J=7.5 Hz, 2H) ppm.

Example 32. 5-(2,3-Dihydro-1H-inden-4-yl)-6-methoxy-3-(1-(pyridin-4-yl)-1H-pyrazol-4-yl)-1H-pyrazolo[4,3-b]pyridine

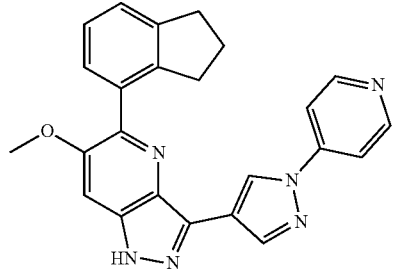 [SMILES: COc1cc2[nH]nc(-c3cnn(-c4ccncc4)c3)c2nc1-c1cccc2c1CCC2]

This compound was prepared according to the procedures described in Example 14, using 4-(4-(4,4,5,5-tetramethyl-1,3,2-dioxaborolan-2-yl)-1H-pyrazol-1-yl) pyridine instead of (1-(1-(tert-butoxycarbonyl)pyrrolidin-3-yl)-1H-pyrazol-4-yl)boronic acid as starting material. The product was isolated as the TFA salt. LC-MS calculated for $C_{24}H_{21}N_6O$ $(M+H)^+$: m/z=409.1; found: 409.1.

Example 33. (trans)-4-(4-(5-(2,3-Dihydro-1H-inden-4-yl)-6-methoxy-1H-pyrazolo[4,3-b]pyridin-3-yl)-1H-pyrazol-1-yl)cyclohexan-1-ol

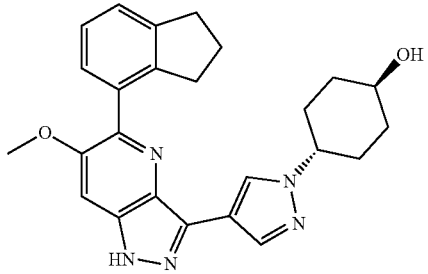 [SMILES: COc1cc2[nH]nc(-c3cnn([C@H]4CC[C@H](O)CC4)c3)c2nc1-c1cccc2c1CCC2]

This compound was prepared according to the procedures described in Example 14, using ((trans)-4-((tert-butyldimethylsilyl)oxy)cyclohexyl)-4-(4,4,5,5-tetramethyl-1,3,2-dioxaborolan-2-yl)-1H-pyrazole instead of (1-(1-(tert-butoxycarbonyl)pyrrolidin-3-yl)-1H-pyrazol-4-yl)boronic acid as starting material. The product was isolated as the TFA salt. LC-MS calculated for $C_{25}H_{28}N_5O_2$ $(M+H)^+$: m/z=430.1; found: 430.1.

Example 34. 5-(2,3-Dimethylphenyl)-N-methyl-3-(1-methyl-1H-pyrazol-4-yl)-1H-pyrazolo[4,3-b]pyridin-6-amine

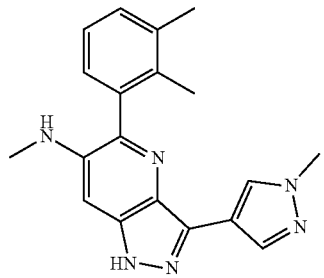

Step 1. 6-Bromo-3-iodo-1H-pyrazolo[4,3-b]pyridine

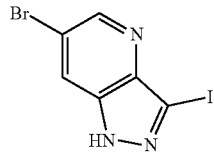

To a solution of 6-bromo-1H-pyrazolo[4,3-b]pyridine (8.0 g, 40.4 mmol) in 60 ml of DMF was added 1-iodopyrrolidine-2,5-dione (7.69 g, 44.4 mmol), and the reaction mixture was stirred at r.t for 2 h. The mixture was poured into water (300 ml) and was stirred for another 10 min. The resulting solid was collected by filtration and was washed with water. It was air-dried and used in the next step without further purification. LC-MS calculated for $C_6H_4BrIN_3$ (M+H)$^+$: m/z=323.9; found 323.9.

Step 2. 6-Bromo-3-iodo-1-trityl-1H-pyrazolo[4,3-b]pyridine

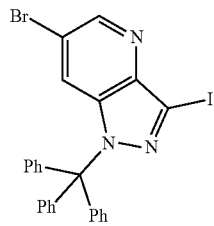 [SMILES: Brc1cnc2c(I)nn(C(c3ccccc3)(c3ccccc3)c3ccccc3)c2c1]

To a suspension of NaH (1.63 g, 40.8 mmol) in DMF (100 ml) at 0° C. was added a solution of 6-bromo-3-iodo-1H-pyrazolo[4,3-b]pyridine (12.0 g, 37.0 mmol) in 20 ml of DMF dropwise. After the addition was complete, the reaction mixture was warmed to r.t and stirred at that temperature for 30 min. The mixture was then cooled back to 0° C. and treated with a solution of (chloromethanetriyl)tribenzene (11.4 g, 40.8 mmol) in 20 ml of DMF. The reaction mixture was stirred at r.t for 2 h. Water was then added and the product was extracted with DCM. The organic phase was concentrated in vacuo. The resultant solid was collected by filtration and air-dried. LC-MS calculated for $C_{25}H_{18}BrIN_3$ (M+H)$^+$: m/z=566.0; found: 566.0.

Step 3. 6-Bromo-3-(1-methyl-1H-pyrazol-4-yl)-1-trityl-1H-pyrazolo[4,3-b]pyridine

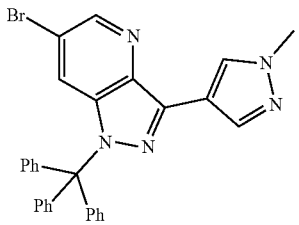 [SMILES: Cn1cc(-c2nn(C(c3ccccc3)(c3ccccc3)c3ccccc3)c3cc(Br)cnc23)cn1]

6-Bromo-3-iodo-1-trityl-1H-pyrazolo[4,3-b]pyridine (5.0 g, 8.83 mmol), 1-methyl-4-(4,4,5,5-tetramethyl-1,3,2-dioxaborolan-2-yl)-1H-pyrazole (1.837 g, 8.83 mmol), PdCl$_2$(dppf)-CH$_2$Cl$_2$ adduct (0.7 g, 0.883 mmol) and potassium phosphate (2.81 g, 13.25 mmol) were placed in a round bottom flask and it was evacuated and backfilled with N$_2$ three times. Then 1,4-dioxane (100 ml) and water (10 ml) were added and the reaction was stirred at 70° C. for 1 h. Water was then added and the product was extracted with EtOAc. The solution was washed with brine, dried and concentrated. The residue was purified by Biotage Isolera to afford the desired product. LC-MS calculated for $C_{29}H_{23}BrN_5$ (M+H)$^+$: m/z=520.2; found: 520.2.

Step 4. N-Methyl-3-(1-methyl-1H-pyrazol-4-yl)-1-trityl-1H-pyrazolo[4,3-b]pyridin-6-amine

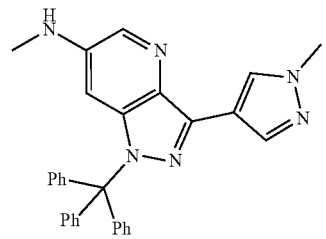

A microwave vial containing 6-bromo-3-(1-methyl-1H-pyrazol-4-yl)-1-trityl-1H-pyrazolo[4,3-b]pyridine (0.460 g, 0.884 mmol), chloro(2-dicyclohexylphosphino-2',6'-di-i-propoxy-1,1'-biphenyl)(2'-amino-1,1'-biphenyl-2-yl)palladium(II) (0.069 g, 0.088 mmol) and cesium carbonate (0.576 g, 1.768 mmol) was sealed and evacuated and backfilled with nitrogen three times. 1,4-Dioxane (12 ml) and a solution of methanamine (1.105 ml, 2.210 mmol) were added. The reaction mixture was heated to 100° C. for 2 h. Then water was added and the product was extracted with EtOAc. The combined organic phases were washed with brine, dried and concentrated. The residue was purified by Biotage Isolera to afford the desired product. LC-MS calculated for $C_{30}H_{27}N_6$ (M+H)$^+$: m/z=471.2; found 471.2.

Step 5. 5-Bromo-N-methyl-3-(1-methyl-1H-pyrazol-4-yl)-1-trityl-1H-pyrazolo[4,3-b]pyridin-6-amine

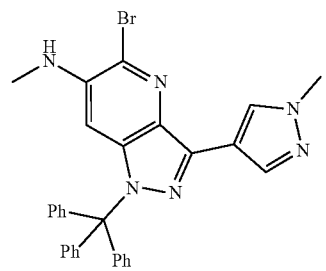

To a solution of N-methyl-3-(1-methyl-1H-pyrazol-4-yl)-1-trityl-1H-pyrazolo[4,3-b]pyridin-6-amine (300 mg, 0.638 mmol) in DMF (5 ml) was added NBS (125 mg, 0.701 mmol). The reaction mixture was stirred at r.t for 2 h and then treated with water. The product was extracted with DCM. The organic phase was washed with water and brine, dried over Na$_2$SO$_4$, and concentrated. The residue was purified by Biotage Isolera to afford the desired product. LC-MS calculated for $C_{30}H_{26}BrN_6$ (M+H)$^+$: m/z=549.2; found 549.2.

Step 6. 5-(2,3-Dimethylphenyl)-N-methyl-3-(1-methyl-1H-pyrazol-4-yl)-1-trityl-1H-pyrazolo[4,3-b]pyridin-6-amine

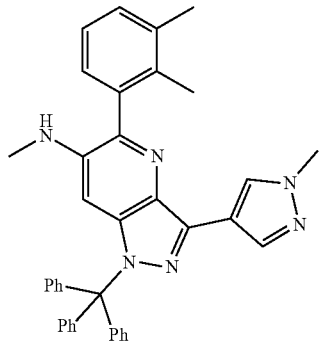

5-Bromo-N-methyl-3-(1-methyl-1H-pyrazol-4-yl)-1-trityl-1H-pyrazolo[4,3-b]pyridin-6-amine (100 mg, 0.182 mmol), (2,3-dimethylphenyl)boronic acid (0.030 g, 0.200 mmol), Cs$_2$CO$_3$ (0.089 g, 0.273 mmol), Xphos PdG2 (3.46 mg, 9.10 μmol), were placed in a vial and the vial was evacuated and backfilled with nitrogen three times. 1,4-Dioxane (5 ml) and water (1.25 ml) were added and the reaction mixture was stirred at 70° C. for 1 hr. The reaction mixture was quenched with water and the product was extracted with ethyl acetate. The organic phase was washed with water and brine, dried over sodium sulfate and concentrated. The residue was purified by Biotage Isolera to afford the desired product. LC-MS calculated for $C_{38}H_{35}N_6$ (M+H)$^+$: m/z=575.2; found: 575.2.

Step 7. 5-(2,3-Dimethylphenyl)-N-methyl-3-(1-methyl-1H-pyrazol-4-yl)-1H-pyrazolo[4,3-b]pyridin-6-amine 5-(2,3-Dimethylphenyl)-N-methyl-3-(1-methyl-1H-pyrazol-4-yl)-1-trityl-1H-pyrazolo[4,3-b]pyridin-6-amine (0.060 g, 0.100 mmol) was dissolved in 2 ml of methylene chloride and 2 ml of TFA was added. The reaction mixture was stirred at r.t for 1 hr. Most of the solvent was removed in vacuo and the residue was treated with water. The product was extracted with ethyl acetate, and neutralized to pH-7 with saturated NaHCO$_3$ solution. The organic phase was separated, washed with water and brine, dried over sodium sulfate and concentrated. The residue was purified by prep-LCMS (XBridge C18 column, eluting with a gradient of acetonitrile/water containing 0.1% TFA, at flow rate of 60 mL/min). The product was isolated as the TFA salt. LC-MS calculated for $C_{19}H_{21}N_6$ (M+H)$^+$: m/z=333.2; found: 333.2. $^1$H NMR (500 MHz, DMSO-d6) δ 8.25-8.19 (s, 1H), 7.98-7.94 (s, 1H), 7.31-7.26 (d, J=7.4 Hz, 1H), 7.25-7.20 (t, J=7.5 Hz, 1H), 7.12-7.05 (d, J=6.1 Hz, 1H), 6.80-6.73 (s, 1H), 3.91-3.86 (s, 3H), 2.75-2.68 (s, 3H), 2.36-2.31 (s, 3H), 1.99-1.88 (s, 3H) ppm.

Example 35. 6-(Difluoromethyl)-5-(2,3-dihydro-1H-inden-4-yl)-3-(1-methyl-1H-pyrazol-4-yl)-1H-pyrazolo[4,3-b]pyridine

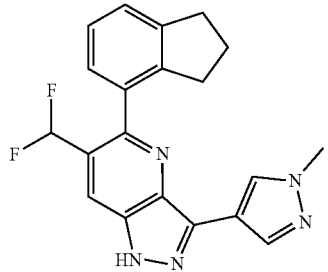 [SMILES: Cn1cc(-c2n[nH]c3cc(C(F)F)c(-c4cccc5c4CCC5)nc23)cn1]

Step 1. 6-Bromo-5-chloro-2-methylpyridin-3-amine

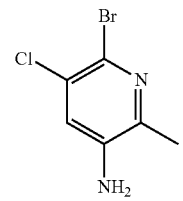

NBS (6.51 g, 36.6 mmol) was added to a solution of 5-chloro-2-methylpyridin-3-amine (4.97 g, 34.9 mmol) in DMF (349 ml). After stirring at r.t. for 30 min, water was added and precipitated product was collected by filtration and dried overnight in the air. The crude product was used in the next step without further purification. LCMS calculated for $C_6H_7N_2BrCl$ (M+H)$^+$: m/z=221.0; found 221.0.

Step 2. N-(6-Bromo-5-chloro-2-methylpyridin-3-yl)acetamide

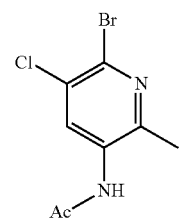

To a solution of 6-bromo-5-chloro-2-methylpyridin-3-amine (7.0 g, 31.6 mmol) in acetic acid (79 mL) was added acetic anhydride (3.73 ml, 39.5 mmol). The reaction was stirred at 50° C. for 1 h, water was then added and the precipitated product was collected by filtration. It was used in the next step without further purification. LCMS calculated for $C_8H_9N_2BrClO$ (M+H)$^+$: m/z=263.0; found 263.0.

Step 3. 1-(5-Bromo-6-chloro-1H-pyrazolo[4,3-b]pyridin-1-yl)ethan-1-one

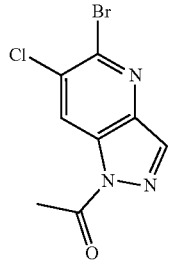

To a suspension of N-(6-bromo-5-chloro-2-methylpyridin-3-yl)acetamide (7.2 g, 27.3 mmol) in toluene (137 ml) were added acetic anhydride (7.73 ml, 82 mmol), potassium acetate (3.22 g, 32.8 mmol) and isopentyl nitrite (5.87 ml, 43.7 mmol). The reaction mixture was heated at 100° C. for 2 h before dilution with EtOAc. The mixture was washed with sat. NaHCO$_3$ and brine, dried over Na$_2$SO$_4$. The solvent was removed under vacuum to afford the brown solid as the crude product which was used directly in next step without purification. LCMS calculated for C$_8$H$_6$N$_3$BrClO (M+H)$^+$: m/z=274.0; found 274.0.

Step 4. 5-Bromo-6-chloro-1H-pyrazolo[4,3-b]pyridine

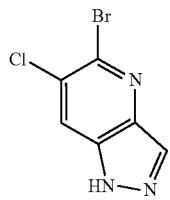 [SMILES: Clc1cc2[nH]ncc2nc1Br]

To a solution of 1-(5-bromo-6-chloro-1H-pyrazolo[4,3-b]pyridin-1-yl)ethan-1-one (7 g, 25.5 mmol) in THF (31.9 ml) and methanol (31.9 ml) was added 1M solution of sodium hydroxide (38.3 ml, 38.3 mmol). The mixture was stirred at 50° C. for 1 h. After completion, most of solvent was evaporated before 1N HCl (40 mL) was added, followed by 200 mL of water. Brown solid slowly formed during stirring of the reaction. The crude product was collected by filtration and used in the next step without further purification. LCMS calculated for C$_6$H$_4$N$_3$BrCl (M+H)$^+$: m/z=232.0; found 232.0.

Step 5. 5-Bromo-6-chloro-3-iodo-1H-pyrazolo[4,3-b]pyridine

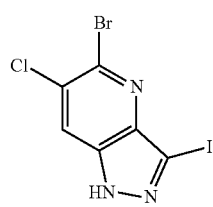 [SMILES: Clc1cc2[nH]nc(I)c2nc1Br]

To a solution of 5-bromo-6-chloro-1H-pyrazolo[4,3-b]pyridine (4.0 g, 17.2 mmol) in 30 ml of DMF was added 1-iodopyrrolidine-2,5-dione (4.3 g, 19.0 mmol), and the reaction mixture was stirred at r.t for 2 h. The mixture was poured into water (200 mL) and stirred for another 10 min. The resulting solid was filtered and air-dried. The resultant material was used in the next step without further purification. LC-MS calculated for C$_6$H$_3$BrClIN$_3$ (M+H)$^+$: m/z=358.0; found 358.0.

Step 6. 5-Bromo-6-chloro-3-iodo-1-((2-(trimethylsilyl)ethoxy)methyl)-1H-pyrazolo[4,3-b]pyridine

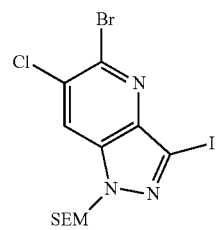 [SMILES: C[Si](C)(C)CCOCn1nc(I)c2nc(Br)c(Cl)cc21]

To a suspension of 5-bromo-6-chloro-3-iodo-1H-pyrazolo[4,3-b]pyridine (5.0 g, 14.0 mmol) in DMF (40 ml) at 0° C. was added 60% NaH (0.72 g, 18.0 mmol). After the addition was complete, the reaction was warmed to r.t and stirred at r.t. for 30 min. The mixture was cooled back to 0° C. when a solution of (2-(chloromethoxy)ethyl)trimethylsilane (3.0 g, 18.0 mmol) in 10 mL of DMF was added. The reaction was stirred at r.t for 2 h. Water was added to the reaction mixture and the product was extracted with DCM. The organic phase was separated, dried over sodium sulfate and the solvents were evaporated in vacuo. The residue was purified by Biotage Isolera to afford the desired product. LC-MS calculated for C$_{12}$H$_{17}$BrClIN$_3$OSi(M+H)$^+$: m/z=488.2; found: 488.2.

Step 7. 5-Bromo-6-chloro-3-(1-methyl-1H-pyrazol-4-yl)-1-((2-(trimethylsilyl)ethoxy)methyl)-1H-pyrazolo[4,3-b]pyridine

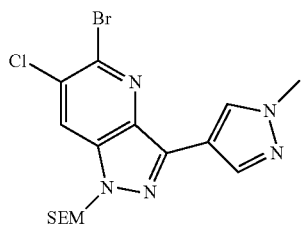 [SMILES: Cn1cc(-c2nn(COCC[Si](C)(C)C)c3cc(Cl)c(Br)nc23)cn1]

5-Bromo-6-chloro-3-iodo-1-((2-(trimethylsilyl)ethoxy)methyl)-1H-pyrazolo[4,3-b]pyridine (1.50 g, 3.07 mmol), 1-methyl-4-(4,4,5,5-tetramethyl-1,3,2-dioxaborolan-2-yl)-1H-pyrazole (0.652 g, 3.13 mmol), PdCl$_2$(dppf)-CH$_2$Cl$_2$ adduct (0.251 g, 0.307 mmol) and potassium phosphate (912 mg, 4.30 mmol) were placed in a vial and the vial was evacuated and backfilled with N$_2$ three times. 1,4-Dioxane (10 ml) and water (2.0 ml) were added and the reaction was stirred at 65° C. for 1 h. Then water was added and the product was extracted with EtOAc. The solution was washed with brine, dried and concentrated. The residue was purified by Biotage Isolera to afford the desired product. LC-MS calculated for $C_{16}H_{22}BrCl_5OSi$ (M+H)+: m/z=442.2; found: 442.2.

Step 8. 6-Chloro-5-(2,3-dihydro-1H-inden-4-yl)-3-(1-methyl-1H-pyrazol-4-yl)-1-((2-(trimethylsilyl)ethoxy)methyl)-1H-pyrazolo[4,3-b]pyridine

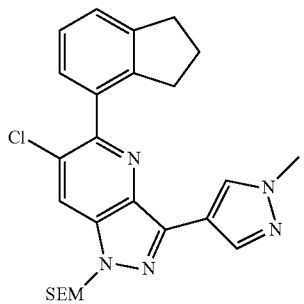 [SMILES: Cn1cc(-c2nn(COCC[Si](C)(C)C)c3cc(Cl)c(-c4cccc5c4CCC5)nc23)cn1]

5-Bromo-6-chloro-3-(1-methyl-1H-pyrazol-4-yl)-1-((2-(trimethylsilyl)ethoxy)methyl)-1H-pyrazolo[4,3-b]pyridine (700 mg, 1.58 mmol), 2-(2,3-dihydro-1H-inden-4-yl)-4,4,5,5-tetramethyl-1,3,2-dioxaborolane (463 mg, 1.9 mmol), ᵗBuXPhos Pd G3 (175 mg, 0.22 mmol) and potassium phosphate (0.356 ml, 4.30 mmol) were placed in a vial and the vial was evacuated and backfilled with $N_2$ three times. 1,4-Dioxane (10 ml) and water (2.0 ml) were added and reaction was stirred at 80° C. for 1 h. Then water was added and the product was extracted with EtOAc. The organic phase was washed with brine, dried and concentrated. The residue was purified by Biotage Isolera to afford the desired product. LC-MS calculated for $C_{25}H_{31}ClN_5OSi$ (M+H)+: m/z=480.2; found: 480.2.

Step 9. 5-(2,3-Dihydro-1H-inden-4-yl)-3-(1-methyl-1H-pyrazol-4-yl)-1-((2-(trimethylsilyl)ethoxy)methyl)-6-vinyl-1H-pyrazolo[4,3-b]pyridine

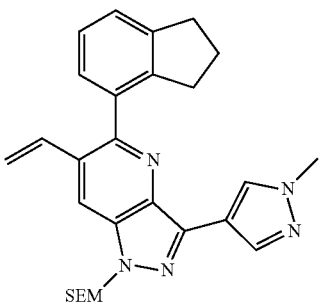 [SMILES: C=Cc1cc2c(nc1-c1cccc3c1CCC3)c(-c1cnn(C)c1)nn2COCC[Si](C)(C)C]

6-Chloro-5-(2,3-dihydro-1H-inden-4-yl)-3-(1-methyl-1H-pyrazol-4-yl)-1-((2-(trimethylsilyl)ethoxy)methyl)-1H-pyrazolo[4,3-b]pyridine (200 mg, 0.42 mmol), 4,4,5,5-tetramethyl-2-vinyl-1,3,2-dioxaborolane (83 mg, 0.542 mmol), $Cs_2CO_3$ (271 mg, 0.833 mmol) and Xphos Pd G2 (31.7 mg, 0.083 mmol) were placed in a vial and the vial was evacuated and backfilled with $N_2$ three times. 1,4-Dioxane (5 ml) and water (1 ml) were added and the reaction was stirred at 75° C. for 1 h. Then water was added and the product was extracted with EtOAc. The organic phase was washed with brine, dried over sodium sulfate and concentrated. The residue was purified by Biotage Isolera to afford the desired product. LC-MS calculated for $C_{27}H_{34}N_5OSi$ (M+H)+: m/z=472.2; found: 472.2.

Step 10. 5-(2,3-Dihydro-1H-inden-4-yl)-3-(1-methyl-1H-pyrazol-4-yl)-1-((2-(trimethylsilyl)ethoxy)methyl)-1H-pyrazolo[4,3-b]pyridine-6-carbaldehyde

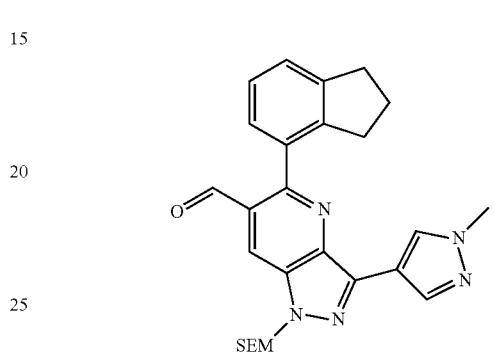

To a mixture of 5-(2,3-dihydro-1H-inden-4-yl)-3-(1-methyl-1H-pyrazol-4-yl)-1-((2-(trimethylsilyl)ethoxy)methyl)-6-vinyl-1H-pyrazolo[4,3-b]pyridine (0.250 g, 0.530 mmol) and sodium periodate (0.57 g, 2.65 mmol) in tetrahydrofuran (5 ml) and water (1.5 ml), was added osmium (VIII) oxide, 4% in water (0.337 g, 0.053 mmol). The reaction mixture was stirred at r.t. for 1 hour. It was quenched with saturated sodium thiosulfate solution. The product was extracted with DCM (×3). The combined extracts were washed with water, brine, dried over sodium sulfate and concentrated. The crude material was used to the next step without further purification. LC-MS calculated for $C_{26}H_{32}N_5O_2Si$ (M+H)+: m/z=474.2; found: 474.2.

Step 11. 6-(Difluoromethyl)-5-(2,3-dihydro-1H-inden-4-yl)-3-(1-methyl-1H-pyrazol-4-yl)-1H-pyrazolo[4,3-b]pyridine To a solution of 5-(2,3-dihydro-1H-inden-4-yl)-3-(1-methyl-1H-pyrazol-4-yl)-1-((2-(trimethylsilyl)ethoxy)methyl)-1H-pyrazolo[4,3-b]pyridine-6-carbaldehyde (20 mg, 0.042 mmol) in methylene chloride (2 mL) was added by diethylaminosulfur trifluoride (11.22 µl, 0.084 mmol). After stirring at r.t. overnight, $NaHCO_3$ solution was added and the product was extracted with DCM, organic phase was washed with brine, dried over $Na_2SO_4$ and concentrated. The resultant residue was redissolved in 50% of TFA in $CH_2Cl_2$. After stirring at r.t. for 30 min, the solvents were evaporated and aqueous ammonia was added. After stirring at r.t. for additional 30 min, the reaction was diluted with $CH_3CN$ and water and purified with prep-LCMS (XBridge C18 column, eluting with a gradient of acetonitrile/water containing 0.1% TFA, at flow rate of 60 mL/min). The product was isolated as the TFA salt. LC-MS calculated for $C_{20}H_{18}F_2N_5$ (M+H)+: m/z=366.2; found: 366.2.

Example 36. (5-(2,3-Dihydro-1H-inden-4-yl)-3-(1-methyl-1H-pyrazol-4-yl)-1H-pyrazolo[4,3-b]pyridin-6-yl)methanol

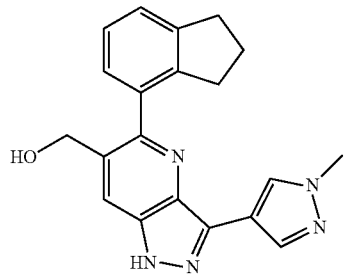 [SMILES: Cn1cc(-c2n[nH]c3cc(CO)c(-c4cccc5c4CCC5)nc23)cn1]

To a solution of 5-(2,3-dihydro-1H-inden-4-yl)-3-(1-methyl-1H-pyrazol-4-yl)-1-((2-(trimethylsilyl)ethoxy)methyl)-1H-pyrazolo[4,3-b]pyridine-6-carbaldehyde (Example 35, step 10) (20 mg, 0.042 mmol) in THF (2.0 ml) and MeOH (1.0 ml) was added sodium borohydride (8 mg, 0.21 mmol) at 0° C. After stirring at r.t for 1 h, NaHCO₃ solution was added and the product was extracted with EtOAc. The organic phase was washed with brine, dried over $Na_2SO_4$ and concentrated in vacuo. The resultant residue was dissolved in 50% of TFA in $CH_2Cl_2$. After stirring at r.t. for 30 min, the solvents were evaporated and aqueous ammonia was added. After stirring at r.t. for additional 30 min, the reaction was diluted with $CH_3CN$ and water and purified with prep-LCMS (XBridge C18 column, eluting with a gradient of acetonitrile/water containing 0.1% TFA, at flow rate of 60 mL/min). The product was isolated as the TFA salt. LC-MS calculated for $C_{20}H_{20}N_5O$ (M+H)⁺: m/z=346.2; found: 346.2.

Example 37. 5-(2,3-Dihydro-1H-inden-4-yl)-N-methyl-3-(1-methyl-1H-pyrazol-4-yl)-1H-pyrazolo[4,3-b]pyridin-6-amine

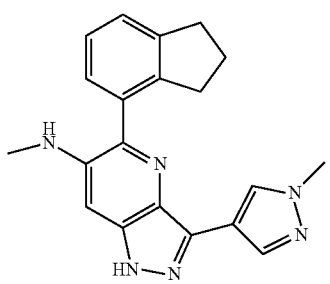

This compound was prepared according to the procedure described in Example 34, using 2-(2,3-dihydro-1H-inden-4-yl)-4,4,5,5-tetramethyl-1,3,2-dioxaborolane instead of (2,3-dimethylphenyl)boronic acid. The product was isolated as the TFA salt. LC-MS calculated for $C_{20}H_{21}N_6$ (M+H)⁺: m/z=345.2; found 345.2.

Example 38. (5-(2,3-Dimethylphenyl)-3-(1-methyl-1H-pyrazol-4-yl)-1H-pyrazolo[4,3-b]pyridin-6-yl)methanol

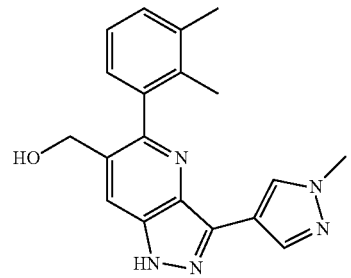 [SMILES: Cc1cccc(-c2nc3c(-c4cnn(C)c4)n[nH]c3cc2CO)c1C]

This compound was prepared according to the procedure described in Examples 35 and 36, using (2,3-dimethylphenyl)boronic acid instead of 2-(2,3-dihydro-1H-inden-4-yl)-4,4,5,5-tetramethyl-1,3,2-dioxaborolane. The product was isolated as the TFA salt. LC-MS calculated for $C_{19}H_{20}N_5O$ (M+H)⁺: m/z=334.2; found 334.2. ¹H NMR (500 MHz, DMSO-d6) δ 8.34-8.26 (s, 1H), 8.08-8.05 (s, 1H), 8.05-8.01 (s, 1H), 7.29-7.23 (d, J=7.4 Hz, 1H), 7.23-7.16 (t, J=7.5 Hz, 1H), 7.08-7.00 (d, J=6.1 Hz, 1H), 4.36-4.17 (m, 2H), 3.95-3.87 (s, 3H), 2.38-2.28 (s, 3H), 1.92-1.81 (s, 3H) ppm.

Example 39. 4-(6-Chloro-3-(1-methyl-1H-pyrazol-4-yl)-1H-pyrazolo[4,3-b]pyridin-5-yl)-2,3-dihydro-1H-inden-2-ol

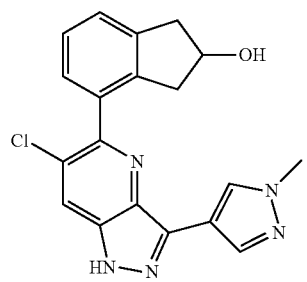 [SMILES: Cn1cc(-c2n[nH]c3cc(Cl)c(-c4cccc5c4CC(O)C5)nc23)cn1]

Step 1. 6-Bromo-5-chloro-2-methylpyridin-3-amine

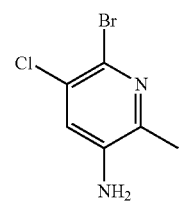

NBS (10.4 g, 58.4 mmol) was added to a solution of 5-chloro-2-methylpyridin-3-amine (7.9 g, 55.6 mmol) in DMF (100 ml). After stirring at r.t. for 10 min, water was added and the precipitated product was collected by filtration. The resultant product was washed with water and air dried. It was used in the next step without further purification. LC-MS calculated for $C_6H_7BrCl_2$ $(M+H)^+$: m/z=221.0 and 223.0; found 221.0 and 223.0.

Step 2.
N-(6-Bromo-5-chloro-2-methylpyridin-3-yl)acetamide

Acetic anhydride (6.3 ml, 66.3 mmol) was added to a solution of 6-bromo-5-chloro-2-methylpyridin-3-amine (11.75 g, 53.1 mmol) in acetic acid (130 ml). After stirring at 50° C. for 1 h, water was added and the precipitated product was collected by filtration. The resultant product was washed with water and air dried. It was used in the next step without further purification. LC-MS calculated for $C_8H_9BrClN_2O$ $(M+H)^+$: m/z=263.0 and 265.0; found 263.0 and 265.0.

Step 3. 1-(5-Bromo-6-chloro-1H-pyrazolo[4,3-b]pyridin-1-yl)ethan-1-one

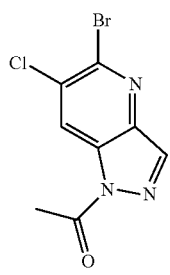

To a suspension of N-(6-bromo-5-chloro-2-methylpyridin-3-yl)acetamide (12.7 g, 48.2 mmol) in toluene (120 ml) were added acetic anhydride (13.6 ml, 145 mmol), potassium acetate (5.7 g, 57.8 mmol) and isopentyl nitrite (10.4 ml, 77 mmol). After heating at 110° C. for 2 h, the reaction mixture was cooled down to r.t. and EtOAc was added. Then organic phase was washed with $NaHCO_3$ solution, dried over sodium sulfate, filtered, and the solvent was removed in vacuo. The resultant crude product was purified by Biotage Isolera to give the desired compound.

Step 4. 5-Bromo-6-chloro-1H-pyrazolo[4,3-b]pyridine

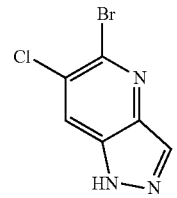 [SMILES: Clc1cc2[nH]ncc2nc1Br]

Potassium carbonate (7.40 g, 53.6 mmol) was added to a solution of 1-(5-bromo-6-chloro-1H-pyrazolo[4,3-b]pyridin-1-yl)ethan-1-one (13.37 g, 48.7 mmol) in methanol (100 ml). After stirring at 60° C. for 1 h, water was added and the precipitated product was collected by filtration. The resultant product was washed with water and air dried. It was used in the next step without further purification. LC-MS calculated for $C_6H_4BrClN_3$ $(M+H)^+$: m/z=232.0 and 234.0; found 232.0 and 234.0.

Step 5. tert-Butyl 5-bromo-6-chloro-3-iodo-1H-pyrazolo[4,3-b]pyridine-1-carboxylate

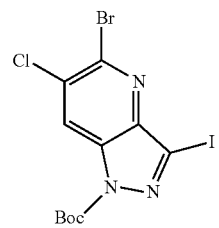 [SMILES: CC(C)(C)OC(=O)n1nc(I)c2nc(Br)c(Cl)cc21]

NIS (4.95 g, 22 mmol) was added to a solution of 5-bromo-6-chloro-1H-pyrazolo[4,3-b]pyridine (5 g, 21.55 mmol) in DMF (50 ml). After stirring at 60° C. for 2 h, the reaction mixture was cooled down to r.t., and triethylamine (6.26 ml, 44.9 mmol) and Boc-anhydride (8.17 g, 37.4 mmol) were added. After additional stirring at r.t. for 1 h, water was added and the precipitated solid was collected by filtration and air dried. The resultant product was used in the next step without further purification. LC-MS calculated for $C_{11}H_{11}BrClIN_3O_2$ $(M+H)^+$: m/z=457.9 and 459.9; found 457.9 and 459.9.

Step 6. tert-Butyl 5-bromo-6-chloro-3-(1-methyl-1H-pyrazol-4-yl)-1H-pyrazolo[4,3-b]pyridine-1-carboxylate

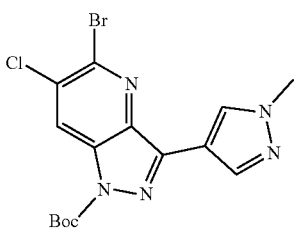 [SMILES: Cn1cc(-c2nn(C(=O)OC(C)(C)C)c3cc(Cl)c(Br)nc23)cn1]

tert-Butyl 5-bromo-6-chloro-3-iodo-1H-pyrazolo[4,3-b]pyridine-1-carboxylate (5.36 g, 11.69 mmol), 1-methyl-4-(4,4,5,5-tetramethyl-1,3,2-dioxaborolan-2-yl)-1H-pyrazole (2.48 g, 11.92 mmol), PdCl$_2$(dppf)-CH$_2$Cl$_2$ adduct (0.96 g, 1.17 mmol) and potassium phosphate (3.47 g, 16.37 mmol) were placed in a flask and the flask was evacuated and backfilled with N$_2$ three times. Then 1,4-dioxane (100 ml) and water (10 ml) were added and the reaction was stirred at 80° C. for 1 h. After cooling to r.t., water was added and the desired product was extracted with EtOAc. The organic phase was washed with brine, dried over sodium sulfate and the solvent was removed in vacuo. Crude material was purified by Biotage Isolera. LC-MS calculated for C$_{15}$H$_{16}$BrClN$_5$O$_2$ (M+H)$^+$: m/z=412.0 and 414.0; found 412.0 and 414.0.

Step 7. 4-(6-Chloro-3-(1-methyl-1H-pyrazol-4-yl)-1H-pyrazolo[4,3-b]pyridin-5-yl)-2,3-dihydro-1H-inden-2-ol

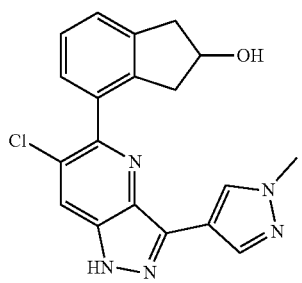

peak 2 tert-Butyl 5-bromo-6-chloro-3-(1-methyl-1H-pyrazol-4-yl)-1H-pyrazolo[4,3-b]pyridine-1-carboxylate (265 mg, 0.642 mmol), 4-(4,4,5,5-tetramethyl-1,3,2-dioxaborolan-2-yl)-2,3-dihydro-1H-inden-2-ol (175 mg, 0.674 mmol), chloro[tri-tert-butylphosphine)-2-(2-aminobiphenyl)] palladium(II) (33.0 mg, 0.064 mmol) and potassium phosphate (204 mg, 0.963 mmol) were placed in a vial and the vial was evacuated and backfilled with N$_2$ three times. After 1,4-dioxane (4 ml) and water (400 µl) were added, the reaction mixture was stirred at 80° C. for 1 h. The mixture was cooled to room temperature, diluted with DCM and filtered. The filtrate was concentrated in vacuo and the resultant residue was purified by Biotage Isolera. The resultant purified material was dissolved in 1,4-dioxane (6 ml) and water (6 ml). After the addition of cesium carbonate (313 mg, 0.96 mmol) and morpholine (1 ml), the reaction mixture was heated at 100° C. for 2 h. The mixture was cooled to room temperature, diluted with DCM, washed with brine, dried over sodium sulfate, and the solvents were removed in vacuo. The two enantiomers of the product were separated with chiral SFC-PR-2 (Phenomenex LUX i-Cellulose-5 Sum 21.2×250 mm, eluting with 30% of IPA in CO$_2$, at flow rate of 60 mL/min, t$_{R, peak 1}$=8.2 min, t$_{R, peak 2}$=9.9 min). After the solvent was evaporated in vacuo, peak 2 was purified by prep-LCMS (XBridge C18 column, eluting with a gradient of acetonitrile/water containing 0.1% TFA, at flow rate of 60 mL/min. The product was isolated as the TFA salt. LC-MS calculated for C$_{19}$H$_{17}$ClN$_5$O (M+H)$^+$: m/z=366.1; found 366.1.

Example 40. 5-(2,3-Dimethylphenyl)-6-methyl-3-(1-methyl-1H-pyrazol-4-yl)-1H-pyrazolo[4,3-b]pyridine

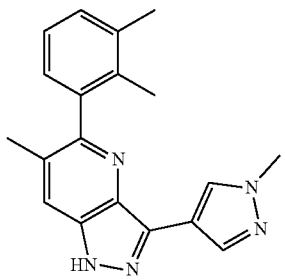

To a vial were added tert-butyl 6-chloro-5-(2,3-dimethylphenyl)-3-(1-methyl-1H-pyrazol-4-yl)-1H-pyrazolo[4,3-b]pyridine-1-carboxylate (20 mg, 0.046 mmol, prepared in a similar way to Example 35, step 1-8), 2,4,6-trimethyl-1,3,5,2,4,6-trioxatriborinane (11 mg, 0.09 mmol), Cs$_2$CO$_3$ (30 mg, 0.091 mmol), XPhos PdG2 (4 mg, 0.009 mmol). The vial was sealed then evacuated and backfilled with N$_2$ three times. After toluene (1.0 ml) and water (0.2 ml) were added, the reaction mixture was heated at 75° C. for 1 h. Then water was added and the product was extracted with EtOAc. The organic phase was washed with brine, dried over sodium sulfate and concentrated. The resultant residue was dissolved in 50% of TFA in CH$_2$Cl$_2$. After stirring at r.t. for 30 min, the reaction was diluted with CH$_3$CN and water and purified with prep-LCMS (XBridge C18 column, eluting with a gradient of acetonitrile/water containing 0.1% TFA, at flow rate of 60 mL/min). The product was isolated as the TFA salt. LC-MS calculated for C$_{19}$H$_{20}$N$_5$ (M+H)$^+$: m/z=318.2; found: 318.2.

Example 41. 5-(2,3-Dimethylphenyl)-6-methoxy-3-(6-(4-methylpiperazin-1-yl)pyridin-3-yl)-1H-pyrazolo[4,3-b]pyridine

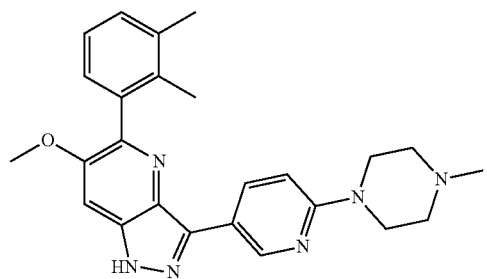

A solution of tert-butyl 5-(2,3-dimethylphenyl)-3-iodo-6-methoxy-1H-pyrazolo[4,3-b]pyridine-1-carboxylate (Example 66, 25 mg, 0.052 mmol), 1-methyl-4-(5-(4,4,5,5-tetramethyl-1,3,2-dioxaborolan-2-yl)pyridin-2-yl)piperazine (47.4 mg, 0.156 mmol), Xphos Pd G2 (4.10 mg, 5.22 µmol), potassium phosphate (44.3 mg, 0.209 mmol) in water (0.100 ml) and dioxane (1 ml) was heated to 80° C. for 20 hrs. After this time it was cooled to r.t., diluted with water and extracted with EtOAc. The combined organic phases were washed with sat. aq. NaCl and dried over Na$_2$SO$_4$, then filtered and concentrated to dryness. The residue was then dissolved in DCM (1 mL) and TFA (1 mL) was added. The mixture was stirred at r.t. for 1 h and purified by prep-LCMS (XBridge C18 column, eluting with a gradient of acetonitrile/water containing 0.1% TFA, at flow rate of 60 mL/min). The product was isolated as the TFA salt. LCMS calculated for $C_{25}H_{29}N_6O$ (M+H)$^+$: m/z=429.2; found 429.0. $^1$H NMR (500 MHz, DMSO-d6) δ 10.02 (s, 1H), 9.21 (d, J=2.3 Hz, 1H), 8.50 (dd, J=9.0, 2.3 Hz, 1H), 7.52 (s, 1H), 7.23 (d, J=7.1 Hz, 1H), 7.17 (t, J=7.5 Hz, 1H), 7.13-7.05 (m, 2H), 4.46 (d, J=13.2 Hz, 2H), 3.84 (s, 3H), 3.57-3.46 (m, 2H), 3.25-3.02 (m, 4H), 2.85 (s, 3H), 2.32 (s, 3H), 1.98 (s, 3H) ppm.

Alternative Synthesis of 5-(2,3-Dimethylphenyl)-6-methoxy-3-(6-(4-methylpiperazin-1-yl)pyridin-3-yl)-1H-pyrazolo[4,3-b]pyridine Step 1. 6-Bromo-1-trityl-1H-pyrazolo[4,3-b]pyridine

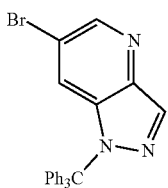

NaH (60% in mineral oil, 2.46 g, 61.6 mmol) was slowly added at 0° C. to a solution of 6-bromo-1H-pyrazolo[4,3-b]pyridine (10.16 g, 51.3 mmol) in DMF (70 ml). After stirring at r.t. for 20 min, (chloromethanetriyl)tribenzene (15.73 g, 56.4 mmol) was slowly added and the reaction mixture was stirred at r.t. for 1 h. Then water was added and the precipitated product was collected by filtration, washed with water and air dried. It was used in the next step without further purification. LC-MS calculated for $C_{25}H_{19}BrN_3$ (M+H)$^+$: m/z=440.1 and 442.1; found 440.0 and 442.0.

Step 2. 6-Methoxy-1-trityl-1H-pyrazolo[4,3-b]pyridine

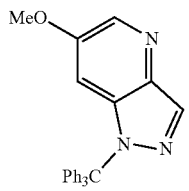

A mixture of 6-bromo-1-trityl-1H-pyrazolo[4,3-b]pyridine (25.0 g, 56.8 mmol), cesium carbonate (25.9 g, 79 mmol), methanol (6.89 ml, 170 mmol) and $^t$BuXPhosPd G3 (1.52 g, 1.7 mmol) in toluene (150 ml) was heated at 80° C. for 1 h. After cooling to r.t., the reaction mixture was filtered, the solvent evaporated in vacuo and the crude material was purified by Biotage Isolera. LCMS calculated for $C_{26}H_{22}N_3O$ (M+H)$^+$: m/z=392.2; Found: 392.1.

Step 3. 6-Methoxy-1-trityl-1H-pyrazolo[4,3-b]pyridine 4-oxide

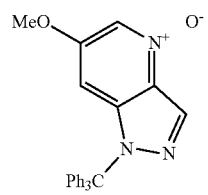

m-CPBA (14.5 g, 64.6 mmol) was slowly added at 0° C. to a solution of 6-methoxy-1-trityl-1H-pyrazolo[4,3-b]pyridine (16.8 g, 43.0 mmol) in DCM (150 ml). After stirring at r.t. overnight, the reaction was treated with $Na_2S_2O_3$ solution and 1M NaOH solution. After stirring at r.t. for 30 min, the organic phase was separated and washed 3 times with 1M NaOH solution and 2 times with brine solution. Then the organic phase was dried over sodium sulfate, filtered and the solvent was removed in vacuo. The resultant product was used in the next step without further purification. LC-MS calculated for $C_{26}H_{22}N_3O_2$ (M+H)$^+$: m/z=408.2; found 408.2.

Step 4. 5-Chloro-6-methoxy-1-trityl-1H-pyrazolo[4,3-b]pyridine

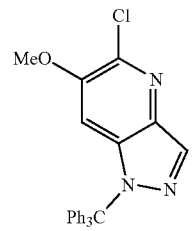

A solution of oxalyl chloride (5.36 ml, 61.3 mmol) in DCM was slowly added at 0° C. to a solution of 6-methoxy-1-trityl-1H-pyrazolo[4,3-b]pyridine 4-oxide (16.65 g, 40.9 mmol) and DIPEA (14.27 ml, 82 mmol) in DCM (100 ml). After stirring at 0° C. for 1 h, the reaction was diluted with DCM and carefully treated with water. The organic phase was separated, washed 3 times with water, 2 times with saturated $NaHCO_3$ solution, 2 times with brine and was dried over sodium sulfate. After removing the solvent in vacuo, the resultant product was used in the next step without further purification. LC-MS calculated for $C_{26}H_{21}ClN_3O$ (M+H)$^+$: m/z=426.1; found 426.2.

Step 5. 5-(2,3-Dimethylphenyl)-6-methoxy-1-trityl-1H-pyrazolo[4,3-b]pyridine

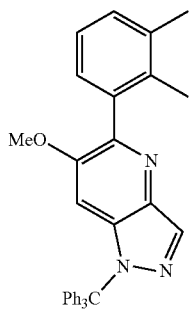

A mixture of 5-chloro-6-methoxy-1-trityl-1H-pyrazolo[4,3-b]pyridine (11.29 g, 26.5 mmol), (2,3-dimethylphenyl)boronic acid (11.93 g, 80 mmol), XphosPd G2 (4.17 g, 5.30 mmol), and potassium phosphate (22.51 g, 106 mmol) in dioxane (100 ml) and water (10 ml) was heated to 85° C. for 2 hrs. After this time the solution was cooled to r.t., diluted with water and extracted with EtOAc. The combined organic phases were washed with sat. aq. NaCl, dried over $Na_2SO_4$, filtered, and concentrated to dryness. The obtained crude was used directly in the next step. LCMS calculated for $C_{34}H_{30}N_3O$ $(M+H)^+$: m/z=496.2; found 496.4.

Step 6. 5-(2,3-Dimethylphenyl)-6-methoxy-1H-pyrazolo[4,3-b]pyridine

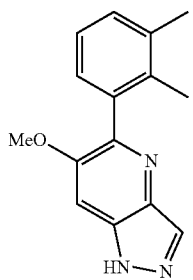 [SMILES: COc1cc2[nH]ncc2nc1-c1cccc(C)c1C]

To a solution of 5-(2,3-dimethylphenyl)-6-methoxy-1-trityl-1H-pyrazolo[4,3-b]pyridine (13 g, 26.2 mmol) in 100 mL $CH_2Cl_2$ was added TFA (40 ml) and water (2 ml) and the resulting solution was stirred at r.t. After 1.5 hrs, 250 mL solution of $MeCN:H_2O$ (1:1) was added. The mixture was stirred for additional 10 min and the organic solvent was removed in vacuo. The precipitated solid was filtered off and the filtrate was washed 3 times with 200 mL EtOAc/hexanes (1:1). The aqueous phase was separated and concentrated. The obtained crude was then taken up in 100 mL $CH_2Cl_2$ and 100 mL $H_2O$. The mixture was neutralized with aq. $NH_4OH$. The organic phase was separated and washed 2 times with water. The obtained organic phase was then dried over $Na_2SO_4$, filtered and concentrated to obtain the desired product. LCMS calculated for $C_{15}H_{16}N_3O$ $(M+H)^+$: m/z=254.1; found 254.2.

Step 7. tert-Butyl 5-(2,3-dimethylphenyl)-3-iodo-6-methoxy-1H-pyrazolo[4,3-b]pyridine-1-carboxylate

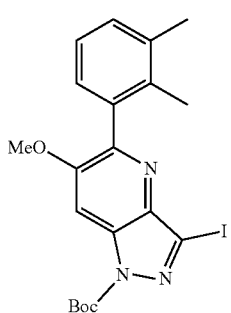 [SMILES: COc1cc2c(nc1-c1cccc(C)c1C)c(I)nn2C(=O)OC(C)(C)C]

N-Iodosuccinimide (20.38 g, 91 mmol) was added to a solution of 5-(2,3-dimethylphenyl)-6-methoxy-1H-pyrazolo[4,3-b]pyridine (15.3 g, 60.4 mmol) in DMF (100 ml). After stirring at 60° C. for 4 hrs, the reaction mixture was cooled to r.t., and N,N-diisopropylethylamine (31.6 ml, 181 mmol) and di-tert-butyl dicarbonate (39.5 g, 181 mmol) were added. The resulting reaction mixture was then stirred at r.t. for 1.5 hrs. The reaction mixture was then treated with water, extracted with EtOAc, washed with brine. The combined organic phases were washed 3 times with water and concentrated. The crude was taken up in MeOH (ca. 150 mL) and the precipitated solid was collected by filtration and dried to obtain the desired product. LCMS calculated for $C_{20}H_{23}IN_3O_3$ $(M+H)^+$: m/z=480.1; found 480.2.

Step 8. 5-(2,3-Dimethylphenyl)-6-methoxy-3-(6-(4-methylpiperazin-1-yl)pyridin-3-yl)-1H-pyrazolo[4,3-b]pyridine A solution of tert-butyl 5-(2,3-dimethylphenyl)-3-iodo-6-methoxy-1H-pyrazolo[4,3-b]pyridine-1-carboxylate (25 mg, 0.052 mmol), 1-methyl-4-(5-(4,4,5,5-tetramethyl-1,3,2-dioxaborolan-2-yl)pyridin-2-yl)piperazine (47.4 mg, 0.156 mmol), XphosPd G2 (4.10 mg, 5.22 µmol), potassium phosphate (44.3 mg, 0.209 mmol) in water (0.1 ml) and dioxane (1 ml) was heated to 80° C. for 20 hrs. After this time it was cooled to r.t., diluted with water and the product was extracted with EtOAc. The combined organic phases were washed with sat. aq. NaCl, dried over $Na_2SO_4$, filtered, and concentrated to dryness. The residue was then dissolved in DCM (1 mL) and TFA (1 mL) was added. The mixture was stirred at r.t. for 1 h and purified by prep-LCMS (XBridge C18 column, eluting with a gradient of acetonitrile/water containing 0.1% TFA, at flow rate of 60 mL/min). The title compound was isolated as the TFA salt. LCMS calculated for $C_{25}H_{29}N_6O$ $(M+H)^+$: m/z=429.2; found 429.0.

$^1$H NMR (500 MHz, DMSO-d6) δ 10.02 (s, 1H), 9.21 (d, J=2.3 Hz, 1H), 8.50 (dd, J=9.0, 2.3 Hz, 1H), 7.52 (s, 1H), 7.23 (d, J=7.1 Hz, 1H), 7.17 (t, J=7.5 Hz, 1H), 7.13-7.05 (m, 2H), 4.46 (d, J=13.2 Hz, 2H), 3.84 (s, 3H), 3.57-3.46 (m, 2H), 3.25-3.02 (m, 4H), 2.85 (s, 3H), 2.32 (s, 3H), 1.98 (s, 3H) ppm.

Example 42. 5-(2,3-Dimethylphenyl)-3-(6-(4-ethylpiperazin-1-yl)pyridin-3-yl)-6-methoxy-1H-pyrazolo[4,3-b]pyridine

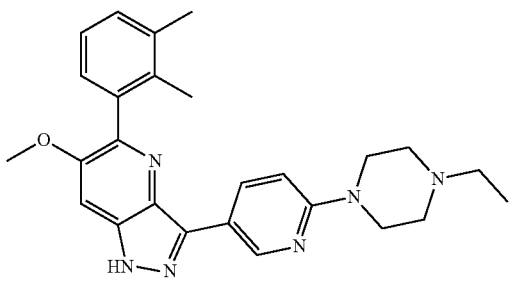 [SMILES: CCN1CCN(c2ccc(-c3n[nH]c4cc(OC)c(-c5cccc(C)c5C)nc34)cn2)CC1]

This compound was prepared according to the procedure described in Example 41, using 1-ethyl-4-(5-(4,4,5,5-tetramethyl-1,3,2-dioxaborolan-2-yl)pyridin-2-yl)piperazine instead of 1-methyl-4-(5-(4,4,5,5-tetramethyl-1,3,2-dioxaborolan-2-yl)pyridin-2-yl)piperazine. The product was isolated as the TFA salt. LC-MS calculated for $C_{26}H_{31}N_6O$ $(M+H)^+$: m/z=443.3; found 443.4.

Example 43. 1-(4-(5-(5-(2,3-Dimethylphenyl)-6-methoxy-1H-pyrazolo[4,3-b]pyridin-3-yl)pyridin-2-yl)piperazin-1-yl)ethan-1-one

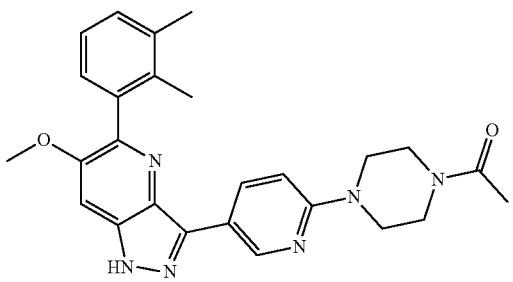 [SMILES: COc1cc2[nH]nc(-c3ccc(N4CCN(C(C)=O)CC4)nc3)c2nc1-c1cccc(C)c1C]

This compound was prepared according to the procedure described in Example 41, using 1-(4-(5-(4,4,5,5-tetramethyl-1,3,2-dioxaborolan-2-yl)pyridin-2-yl)piperazin-1-yl)ethan-1-one instead of 1-methyl-4-(5-(4,4,5,5-tetramethyl-1,3,2-dioxaborolan-2-yl)pyridin-2-yl)piperazine. The product was isolated as the TFA salt. LC-MS calculated for $C_{26}H_{29}N_6O_2$ $(M+H)^+$: m/z=457.2; found 457.1.

Example 44. 4-(5-(5-(2,3-Dimethylphenyl)-6-methoxy-1H-pyrazolo[4,3-b]pyridin-3-yl)pyridin-2-yl)morpholine

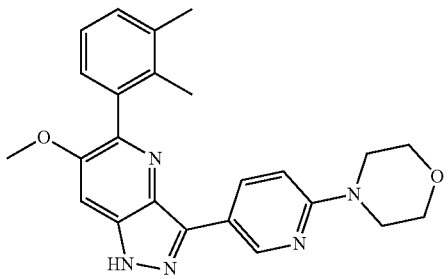 [SMILES: COc1cc2[nH]nc(-c3ccc(N4CCOCC4)nc3)c2nc1-c1cccc(C)c1C]

This compound was prepared according to the procedure described in Example 41, using 4-(5-(4,4,5,5-tetramethyl-1,3,2-dioxaborolan-2-yl)pyridin-2-yl)morpholine instead of 1-methyl-4-(5-(4,4,5,5-tetramethyl-1,3,2-dioxaborolan-2-yl)pyridin-2-yl)piperazine. The product was isolated as the TFA salt. LC-MS calculated for $C_{24}H_{26}N_5O_2$ $(M+H)^+$: m/z=416.2; found 416.1.

Example 45. 4-(5-(5-(2,3-Dimethylphenyl)-6-methoxy-1H-pyrazolo[4,3-b]pyridin-3-yl)pyridin-2-yl)-1-methylpiperazin-2-one

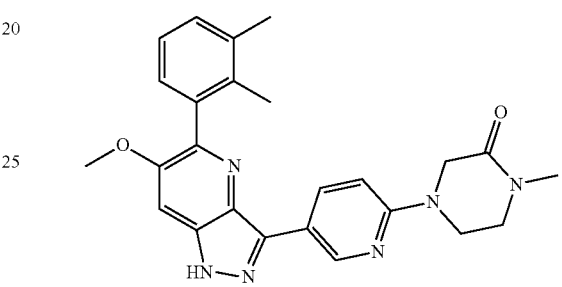

Step 1. 5-(2,3-Dimethylphenyl)-3-(6-fluoropyridin-3-yl)-6-methoxy-1H-pyrazolo[4,3-b]pyridine

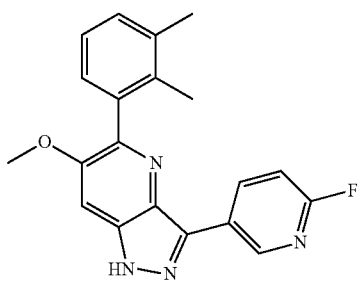 [SMILES: COc1cc2[nH]nc(-c3ccc(F)nc3)c2nc1-c1cccc(C)c1C]

A solution of tert-butyl 5-(2,3-dimethylphenyl)-3-iodo-6-methoxy-1H-pyrazolo[4,3-b]pyridine-1-carboxylate (150 mg, 0.313 mmol), (6-fluoropyridin-3-yl)boronic acid (132 mg, 0.939 mmol), Xphos Pd G2 (24.62 mg, 0.031 mmol) and potassium phosphate (266 mg, 1.25 mmol) in dioxane (5 ml) and water (0.500 ml) was heated to 80° C. for 12 hrs. After this time it was cooled to r.t., diluted with water and extracted with EtOAc. The combined organic phases were washed with sat. aq. NaCl, dried with $Na_2SO_4$, then filtered and concentrated to dryness. The residue was then dissolved in DCM (2 mL) and TFA (2 mL) was added. The mixture was stirred at r.t. for 1 h and purified by silica gel chromatography to afford the desired product. LCMS calculated for $C_{20}H_{18}FN_4O$ $(M+H)^+$: m/z=349.1; found 349.1.

Step 2. 4-(5-(5-(2,3-Dimethylphenyl)-6-methoxy-1H-pyrazolo[4,3-b]pyridin-3-yl)pyridin-2-yl)-1-methylpiperazin-2-one A solution of 5-(2,3-dimethylphenyl)-3-(6-fluoropyridin-3-yl)-6-methoxy-1H-pyrazolo[4,3-b]pyridine (20 mg, 0.057 mmol), 1-methylpiperazin-2-one hydrochloride (25.9 mg, 0.172 mmol), and N,N-diisopropylethylamine (100 µl, 0.574 mmol) in DMSO (0.5 ml) was heated to 120° C. for 20 hrs. The mixture was cooled to r.t. and purified by prep-LCMS (XBridge C18 column, eluting with a gradient of acetonitrile/water containing 0.1% TFA, at flow rate of 60 mL/min). The product was isolated as the TFA salt. LCMS calculated for $C_{25}H_{27}N_6O_2$ (M+H)$^+$: m/z=443.2; found 443.2.

Example 46. 1-(5-(5-(2,3-Dimethylphenyl)-6-methoxy-1H-pyrazolo[4,3-b]pyridin-3-yl)pyridin-2-yl)piperidin-4-ol

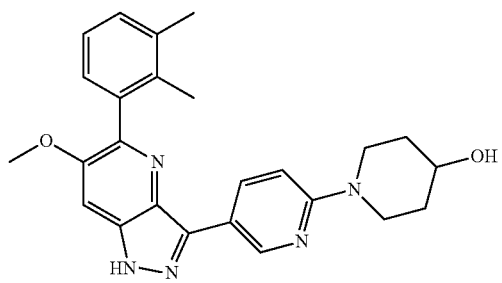 [SMILES: COc1cc2[nH]nc(-c3ccc(N4CCC(O)CC4)nc3)c2nc1-c1cccc(C)c1C]

This compound was prepared according to the procedure described in Example 45, using piperidin-4-ol instead of 1-methylpiperazin-2-one hydrochloride. The product was isolated as the TFA salt. LC-MS calculated for $C_{25}H_{28}N_5O_2$ (M+H)$^+$: m/z=430.2; found 430.2.

Example 47. (R)-5-(2,3-Dimethylphenyl)-3-(6-(3,4-dimethylpiperazin-1-yl)pyridin-3-yl)-6-methoxy-1H-pyrazolo[4,3-b]pyridine

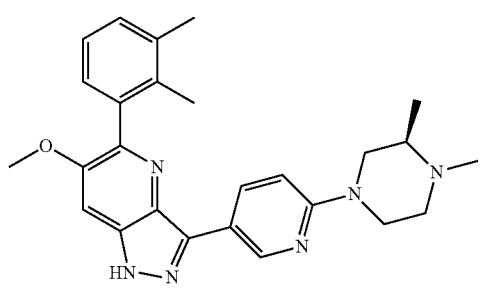

This compound was prepared according to the procedure described in Example 45, using (R)-1,2-dimethylpiperazine dihydrochloride instead of 1-methylpiperazin-2-one hydrochloride. The product was isolated as the TFA salt. LC-MS calculated for $C_{26}H_{31}N_6O$ (M+H)$^+$: m/z=443.3; found 443.4.

Example 48. 5-(2,3-Dimethylphenyl)-6-(methoxy-d3)-3-(6-(4-methylpiperazin-1-yl)pyridin-3-yl)-1H-pyrazolo[4,3-b]pyridine

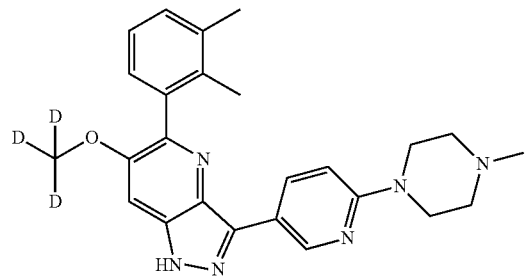 [SMILES: [2H]C([2H])([2H])Oc1cc2[nH]nc(-c3ccc(N4CCN(C)CC4)nc3)c2nc1-c1cccc(C)c1C]

Step 1. 6-(Methoxy-d3)-1-trityl-1H-pyrazolo[4,3-b]pyridine

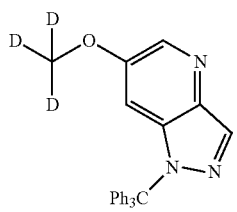

A mixture of 6-bromo-1-trityl-1H-pyrazolo[4,3-b]pyridine (Example 1, step 1; 10.0 g, 22.7 mmol), cesium carbonate (11.10 g, 34.1 mmol), methanol-d$_4$ (6.89 ml) and $^t$BuXPhos Pd G3 (0.18 g, 0.22 mmol) in toluene (70 ml) was heated at 80° C. for 1 h. After cooling to r.t. the reaction mixture was filtered, the solvent evaporated in vacuo and the crude material was purified by Biotage Isolera. LCMS calculated for $C_{26}H_{19}D_3N_3O$ (M+H)$^+$: m/z=395.2; Found: 395.2.

Step 2. 6-(Methoxy-d3)-1-trityl-1H-pyrazolo[4,3-b]pyridine 4-oxide

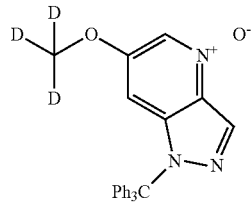

3-Chlorobenzoperoxoic acid (9.33 g, 40.6 mmol) was slowly added at 0° C. to a solution of 6-(methoxy-d3)-1-trityl-1H-pyrazolo[4,3-b]pyridine (8 g, 20.28 mmol) in DCM (100 mL). After stirring at r.t. overnight, the reaction was treated with Na$_2$S$_2$O$_3$ solution and 1M NaOH solution. After stirring at r.t. for 30 min, the organic phase was separated and washed 3 times with 1M NaOH solution and 2 times with brine solution. The organic phase was dried over sodium sulfate, filtered and the solvent was removed in vacuo. The resultant product was used in the next step without further purification. LC-MS calculated for $C_{26}H_{19}D_3N_3O_2$ (M+H)⁺: m/z=411.2; found 411.2.

Step 3. 5-Chloro-6-(methoxy-d3)-1-trityl-1H-pyrazolo[4,3-b]pyridine

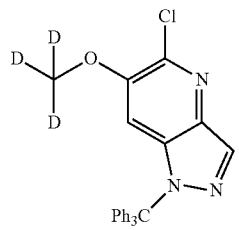

A solution of oxalyl chloride (2.65 ml, 30.3 mmol) in DCM was slowly added at 0° C. to a solution of 6-(methoxy-d3)-1-trityl-1H-pyrazolo[4,3-b]pyridine 4-oxide (8.3 g, 20.22 mmol) and DIEA (10.59 mL, 60.7 mmol) in DCM (100 ml). After stirring at 0° C. for 1 h, the reaction was diluted with DCM and carefully treated with water. The organic phase was separated, washed 3 times with water, 2 times with saturated NaHCO₃ solution, 2 times with brine and dried over sodium sulfate. After removing the solvent in vacuo, the resultant product was used in the next step without further purification. LC-MS calculated for $C_{26}H_{18}D_3ClN_3O$ (M+H)⁺: m/z=429.1; found 429.2.

Step 4. 5-(2,3-Dimethylphenyl)-6-(methoxy-d3)-1-trityl-1H-pyrazolo[4,3-b]pyridine

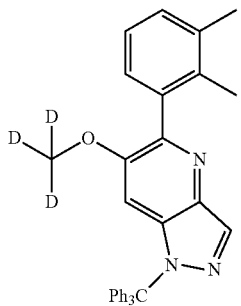

5-Chloro-6-(methoxy-d3)-1-trityl-1H-pyrazolo[4,3-b]pyridine (1.1 g, 2.56 mmol), (2,3-dimethylphenyl)boronic acid (0.577 g, 3.85 mmol), chloro(2-dicyclohexylphosphino-2',4',6'-triisopropyl-1,1'-biphenyl)[2-(2'-amino-1,1'-biphenyl)]palladium (0.205 g, 0.256 mmol) and K₃PO₄ (1.1 g, 5.13 mmol) were placed in a flask and the flask was evacuated and backfilled with N₂ three times. After 1,4-dioxane (10 mL) and water (1 mL) were added, the reaction mixture was stirred at 100° C. for 1 h. After cooling to r.t., water was added and the desired product was extracted with EtOAc. The organic phase was washed with brine, dried over sodium sulfate and the solvent was evaporated in vacuo. Crude material was purified by Biotage Isolera. LCMS calculated for $C_{34}H_{27}D_3N_3O$ (M+H)⁺: m/z=499.3; Found: 499.2.

Step 5. 5-(2,3-Dimethylphenyl)-6-(methoxy-d3)-1H-pyrazolo[4,3-b]pyridine

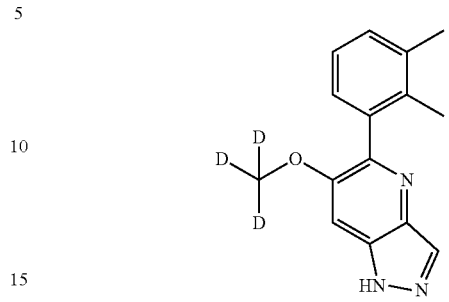

TFA (10 mL) and water (1 mL) were added to a solution of 5-(2,3-dimethylphenyl)-6-(methoxy-d3)-1-trityl-1H-pyrazolo[4,3-b]pyridine (1.0 g, 2.0 mmol) in DCM (10 mL). After stirring at r.t. for 30 min, CH₃CN and water were added and DCM was evaporated in vacuo. The precipitated solid was filtered off. The reaction mixture was further diluted with water and was washed 3 times with EtOAc/hexane 1:1 mixture. The water phase was separated and all solvents were removed in vacuo. The residue was dissolved in DCM and neutralized with NaHCO₃ solution. The organic phase was further washed 2 times with NaHCO₃ solution, brine, then dried over sodium sulfate. The solvent was evaporated in vacuo. The resultant crude product was used in the next step without further purification. LC-MS calculated for $C_{15}H_{13}D_3N_3O$ (M+H)⁺: m/z=257.1; found 257.1.

Step 6. 5-(2,3-Dimethylphenyl)-3-iodo-6-(methoxy-d3)-1-(4-methoxybenzyl)-1H-pyrazolo[4,3-b]pyridine

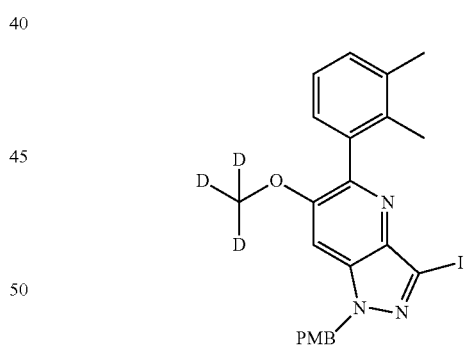

1-Iodopyrrolidine-2,5-dione (614 mg, 2.73 mmol) was added to a solution of 5-(2,3-dimethylphenyl)-6-(methoxy-d3)-1H-pyrazolo[4,3-b]pyridine (700 mg, 2.73 mmol) in DMF (5 mL). After stirring at 80° C. for 1 h, the reaction mixture was cooled to r.t., and Cs₂CO₃ (1.7 g, 5.46 mmol) and 1-(chloromethyl)-4-methoxybenzene (535 µl, 4.10 mmol) were added. After additional stirring at 80° C. for 1 h, water was added and the desired product was extracted with EtOAc. The organic phase was washed with brine, dried over sodium sulfate and the solvent was evaporated in vacuo. Crude material was purified by Biotage Isolera. LCMS calculated for $C_{23}H_{20}D_3IN_3O_2$ (M+H)⁺: m/z=503.1; Found: 503.1.

Step 7. 5-(2,3-Dimethylphenyl)-6-(methoxy-d3)-3-(6-(4-methylpiperazin-1-yl)pyridin-3-yl)-1H-pyrazolo[4,3-b]pyridine A solution of 5-(2,3-dimethylphenyl)-3-iodo-6-(methoxy-d3)-1-(4-methoxybenzyl)-1H-pyrazolo[4,3-b]pyridine (25 mg, 0.050 mmol), 1-methyl-4-(5-(4,4,5,5-tetramethyl-1,3,2-dioxaborolan-2-yl)pyridin-2-yl)piperazine (47.4 mg, 0.156 mmol), Xphos Pd G2 (4.10 mg, 5.22 µmol), potassium phosphate (44.3 mg, 0.209 mmol) in water (0.100 mL) and 1,4-dioxane (1 mL) was heated to 80° C. for 2 h. The reaction mixture was then cooled to r.t., diluted with water and extracted with EtOAc. The combined organic phases were washed with sat. aq. NaCl, dried over $Na_2SO_4$, filtered, and concentrated to dryness. The residue was then dissolved in triflic acid (0.5 mL). The mixture was stirred at r.t. for 1 h, diluted with $CH_3CN$ and purified by prep-LCMS (XBridge C18 column, eluting with a gradient of acetonitrile/water containing 0.1% TFA, at flow rate of 60 mL/min). The product was isolated as the TFA salt. LCMS calculated for $C_{25}H_{26}D_3N_6O$ $(M+H)+$: m/z=432.2; found 432.3.

Example 49. 5-(2,3-Dimethylphenyl)-6-methoxy-3-(6-((1S,4S)-5-methyl-2,5-diazabicyclo[2.2.1]heptan-2-yl)pyridin-3-yl)-1H-pyrazolo[4,3-b]pyridine

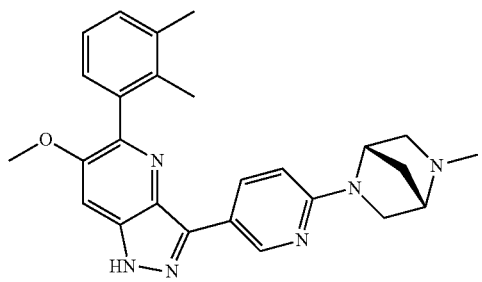

This compound was prepared according to the procedure described in Example 45, using (1S,4S)-2-methyl-2,5-diazabicyclo[2.2.1]heptane dihydrobromide instead of 1-methylpiperazin-2-one hydrochloride. The product was isolated as the TFA salt. LC-MS calculated for $C_{26}H_{29}N_6O$ $(M+H)^+$: m/z=441.2; found 441.3.

Example 50. 1-(5-(5-(2,3-Dimethylphenyl)-6-methoxy-1H-pyrazolo[4,3-b]pyridin-3-yl)pyridin-2-yl)-N,N-dimethylpiperidine-4-carboxamide

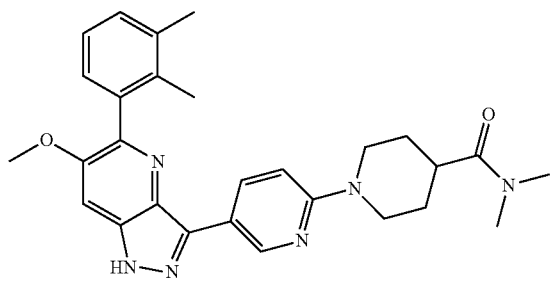

This compound was prepared according to the procedure described in Example 45, using N,N-dimethylpiperidine-4-carboxamide instead of 1-methylpiperazin-2-one hydrochloride. The product was isolated as the TFA salt. LC-MS calculated for $C_{28}H_{33}N_6O_2$ $(M+H)^+$: m/z=485.3; found 485.3.

Example 51. 1-(5-(5-(2,3-Dimethylphenyl)-6-methoxy-1H-pyrazolo[4,3-b]pyridin-3-yl)pyridin-2-yl)-4-methylpiperidine-4-carboxylic acid

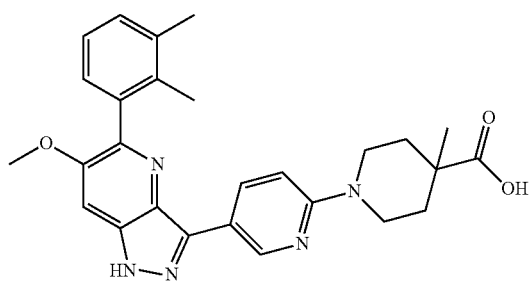 [SMILES: COc1cc2[nH]nc(-c3ccc(N4CCC(C)(C(=O)O)CC4)nc3)c2nc1-c1cccc(C)c1C]

Step 1. tert-Butyl 1-(5-(5-(2,3-dimethylphenyl)-6-methoxy-1H-pyrazolo[4,3-b]pyridin-3-yl)pyridin-2-yl)-4-methylpiperidine-4-carboxylate

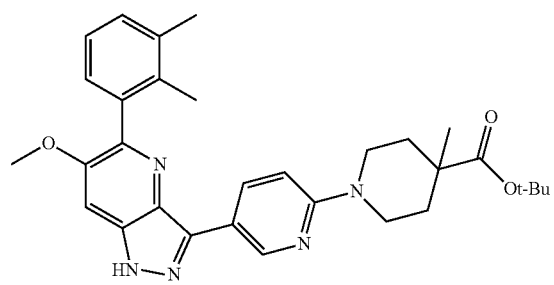 [SMILES: COc1cc2[nH]nc(-c3ccc(N4CCC(C)(C(=O)OC(C)(C)C)CC4)nc3)c2nc1-c1cccc(C)c1C]

This compound was prepared according to the procedure described in Example 45, using tert-butyl 4-methylpiperidine-4-carboxylate hydrochloride instead of 1-methylpiperazin-2-one hydrochloride. LCMS calculated for $C_{31}H_{38}N_5O_3(M+H)^+$: m/z=528.3; found 528.5.

Step 2. 1-(5-(5-(2,3-Dimethylphenyl)-6-methoxy-1H-pyrazolo[4,3-b]pyridin-3-yl)pyridin-2-yl)-4-methylpiperidine-4-carboxylic acid This compound was prepared by treating tert-butyl 1-(5-(5-(2,3-dimethylphenyl)-6-methoxy-1H-pyrazolo[4,3-b]pyridin-3-yl)pyridin-2-yl)-4-methylpiperidine-4-carboxylate with TFA in DCM, followed by purification by prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{30}N_5O_3$ $(M+H)^+$: m/z=472.2; found 472.4.

Example 52. 3-(4-(5-(2-Fluoro-3-methylphenyl)-6-methoxy-1H-pyrazolo[4,3-b]pyridin-3-yl)-1H-pyrazol-1-yl)-N,N-dimethylazetidine-1-carboxamide

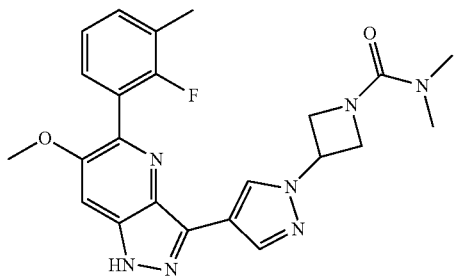

Step 1. 5-(2-Fluoro-3-methylphenyl)-6-methoxy-1-trityl-1H-pyrazolo[4,3-b]pyridine

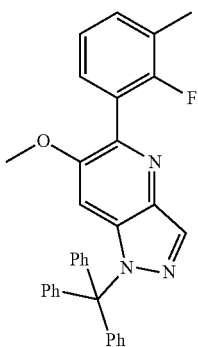 [SMILES: COc1cc2c(cnn2C(c2ccccc2)(c2ccccc2)c2ccccc2)nc1-c1cccc(C)c1F]

5-chloro-6-methoxy-1-trityl-1H-pyrazolo[4,3-b]pyridine (Example 14, Step 4; 0.50 g, 1.174 mmol), (2-fluoro-3-methylphenyl)boronic acid (0.217 g, 1.41 mmol), chloro(2-dicyclohexylphosphino-2',4',6'-triisopropyl-1,1'-biphenyl)[2-(2'-amino-1,1'-biphenyl)]palladium (0.094 g, 0.117 mmol) and potassium phosphate (0.498 g, 2.348 mmol) were placed in a flask and the flask was evacuated and backfilled with $N_2$ three times. After 1,4-dioxane (5 ml) and water (500 µl) were added, the reaction mixture was stirred at 100° C. for 1 h. After this time it was cooled to r.t., diluted with water and extracted with EtOAc three times. The combined organic phases were washed with sat. NaCl, dried with $Na_2SO_4$, filtered and concentrated to dryness. The residue was purified by silica gel chromatography to afford the desired product. LC-MS calculated for $C_{33}H_{27}FN_3O$ (M+H)$^+$: m/z=500.2; found 500.2.

Step 2. 5-(2-Fluoro-3-methylphenyl)-6-methoxy-1H-pyrazolo[4,3-b]pyridine

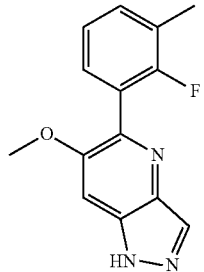 [SMILES: COc1cc2[nH]ncc2nc1-c1cccc(C)c1F]

TFA (1.2 ml, 16 mmol) and water (0.03 ml, 1.6 mmol) were added to a solution of 5-(2-fluoro-3-methylphenyl)-6-methoxy-1-trityl-1H-pyrazolo[4,3-b]pyridine (400 mg, 0.80 mmol) in DCM (2 mL). After stirring at r.t. for 30 min, $CH_3CN$ and water were added and DCM was evaporated in vacuo. Precipitated solid was filtered off. The reaction mixture was further diluted with water and was washed 3 times with EtOAc/hexane 1:1 mixture. The water phase was separated and all solvents were removed in vacuo. The residue was dissolved in DCM and neutralized with $NaHCO_3$ solution. The organic phase was further washed 2 times with $NaHCO_3$ solution, brine, then dried and the solvent evaporated in vacuo. The resultant crude product was used in the next step without further purification. LC-MS calculated for $C_{14}H_{13}FN_3O$ (M+H)$^+$: m/z=258.1; found 258.2.

Step 3. 5-(2-Fluoro-3-methylphenyl)-3-iodo-6-methoxy-1-(4-methoxybenzyl)-1H-pyrazolo[4,3-b]pyridine

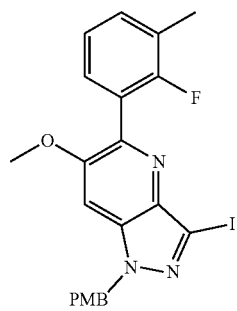

To a solution of 5-(2-fluoro-3-methylphenyl)-6-methoxy-1H-pyrazolo[4,3-b]pyridine (200 mg, 0.777 mmol) in DMF (2 mL) was added 1-iodopyrrolidine-2,5-dione (192 mg, 0.855 mmol). The reaction was warmed up to 80° C. and stirred at that temperature for 1 h. After this time the reaction mixture was cooled to r.t, and 1-(chloromethyl)-4-methoxybenzene (146 mg, 0.933 mmol) and $Cs_2CO_3$ (380 mg, 1.166 mmol) were added. The reaction mixture was stirred at 90° C. for 1 h. After this time it was cooled to r.t., diluted with water and extracted with EtOAc three times. The combined organic phases were washed with sat. NaCl, dried over $Na_2SO_4$, filtered and concentrated to dryness. The residue was purified by Biotage Isolera to afford the desired product. LC-MS calculated for $C_{22}H_{20}IFN_3O_2$ (M+H)$^+$: m/z=504.1; found 504.0.

Step 4. tert-Butyl 3-(4-(5-(2-fluoro-3-methylphenyl)-6-methoxy-1-(4-methoxybenzyl)-1H-pyrazolo[4,3-b]pyridin-3-yl)-1H-pyrazol-1-yl)azetidine-1-carboxylate

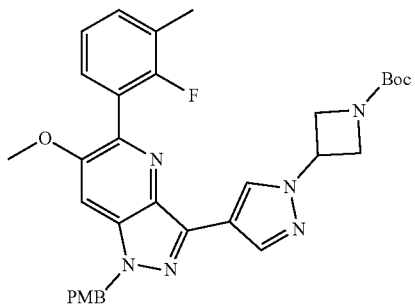

To a solution of 5-(2-fluoro-3-methylphenyl)-3-iodo-6-methoxy-1-(4-methoxybenzyl)-1H-pyrazolo[4,3-b]pyridine (320 mg, 0.636 mmol) in 1,4-dioxane (2 mL) and water (0.4 mL) was added tert-butyl 3-(4-(4,4,5,5-tetramethyl-1,3,2-dioxaborolan-2-yl)-1H-pyrazol-1-yl)azetidine-1-carboxylate (266 mg, 0.763 mmol), potassium phosphate (270 mg, 1.272 mmol), and [dichloro[1,1'-bis(diphenylphosphino)ferrocene]palladium (II) dichloromethane adduct (51.9 mg, 0.064 mmol. The reaction was degassed with $N_2$ and stirred at 80° C. for 2 h. After this time it was cooled to r.t., diluted with EtOAc, washed sequentially with water, sat. NaCl and dried over $Na_2SO_4$. The organic phases were filtered and concentrated to dryness. The residue was purified by Biotage Isolera to afford the desired product. LC-MS calculated for $C_{33}H_{36}FN_6O_4$ (M+H)$^+$: m/z=599.3; found 599.3.

Step 5. 3-(4-(5-(2-Fluoro-3-methylphenyl)-6-methoxy-1H-pyrazolo[4,3-b]pyridin-3-yl)-1H-pyrazol-1-yl)-N,N-dimethylazetidine-1-carboxamide To a solution of tert-butyl 3-(4-(5-(2-fluoro-3-methylphenyl)-6-methoxy-1-(4-methoxybenzyl)-1H-pyrazolo[4,3-b]pyridin-3-yl)-1H-pyrazol-1-yl)azetidine-1-carboxylate (20 mg, 0.033 mmol) in DCM (1 ml) was added 0.5 ml of TFA. The reaction was stirred for 1 h before concentration to dryness. The crude material was dissolved in DCM (1 ml), to which was then added TEA (9.31 µl, 0.067 mmol) and dimethylcarbamic chloride (3.95 mg, 0.037 mmol). The reaction mixture was stirred at r.t. for 1 h, followed by adding 0.5 ml of triflic acid. After additional stirring at r.t. for 2 h, the reaction was diluted with water and MeOH, then purified by prep-LCMS (XBridge C18 column, eluting with a gradient of acetonitrile/water containing 0.1% TFA, at flow rate of 60 mL/min). The product was isolated as the TFA salt. LCMS calculated for $C_{23}H_{25}FN_7O_2$ (M+H)$^+$: m/z=450.2; found 450.2.

Example 53. N-((cis)-4-(4-(5-(2,3-Dihydro-1H-inden-4-yl)-6-methoxy-1H-pyrazolo[4,3-b]pyridin-3-yl)-1H-pyrazol-1-yl)cyclohexyl)acetamide

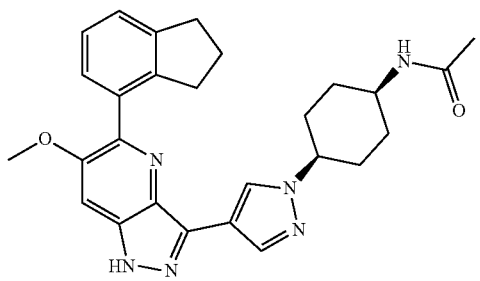 [SMILES: COc1cc2[nH]nc(-c3cnn([C@H]4CC[C@@H](NC(C)=O)CC4)c3)c2nc1-c1cccc2c1CCC2]

Step 1. 5-(2,3-Dihydro-1H-inden-4-yl)-6-methoxy-1-trityl-1H-pyrazolo[4,3-b]pyridine

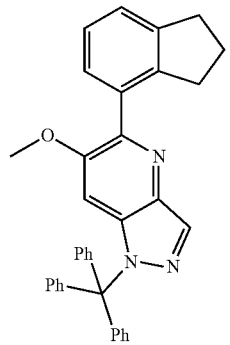 [SMILES: COc1cc2c(cnn2C(c2ccccc2)(c2ccccc2)c2ccccc2)nc1-c1cccc2c1CCC2]

5-Chloro-6-methoxy-1-trityl-1H-pyrazolo[4,3-b]pyridine (Example 14, Step 4; 0.50 g, 1.174 mmol), 2-(2,3-dihydro-1H-inden-4-yl)-4,4,5,5-tetramethyl-1,3,2-dioxaborolane (0.344 g, 1.409 mmol), chloro(2-dicyclohexylphosphino-2',4',6'-triisopropyl-1,1'-biphenyl)[2-(2'-amino-1,1'-biphenyl)]palladium (0.094 g, 0.117 mmol) and potassium phosphate (0.498 g, 2.348 mmol) were placed in a vial and the vial was evacuated and backfilled with $N_2$ three times. After 1,4-dioxane (5 ml) and water (500 µl) were added, the reaction mixture was stirred at 100° C. for 1 h. After this time it was cooled to r.t., diluted with water and extracted with EtOAc three times. The combined organic phases were washed with sat. NaCl, dried with $Na_2SO_4$, filtered and concentrated to dryness. The residue was purified by Biotage Isolera to afford the desired product. LC-MS calculated for $C_{35}H_{30}N_3O$ (M+H)$^+$: m/z=508.2; found 508.2.

Step 2. 5-(2,3-Dihydro-1H-inden-4-yl)-6-methoxy-1H-pyrazolo[4,3-b]pyridine

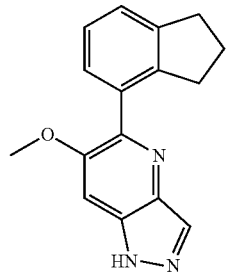 [SMILES: COc1cc2[nH]ncc2nc1-c1cccc2c1CCC2]

TFA (1.23 ml, 16 mmol) and water (0.028 ml, 1.6 mmol) were added to a solution of 5-(2-fluoro-3-methylphenyl)-6-methoxy-1-trityl-1H-pyrazolo[4,3-b]pyridine (400 mg, 0.80 mmol) in DCM (2 mL). After stirring at r.t. for 30 min, $CH_3CN$ and water were added and DCM was evaporated in vacuo. Precipitated solid was filtered off. The reaction mixture was further diluted with water and was washed 3 times with EtOAc/hexane 1:1 mixture. The water phase was separated and all solvents were removed in vacuo. The residue was dissolved in DCM and neutralized with $NaHCO_3$ solution. The organic phase was further washed 2 times with $NaHCO_3$ solution, brine, then dried and the solvent was evaporated in vacuo. The resultant crude product was used in the next step without further purification. LC-MS calculated for $C_{16}H_{16}N_3O$ (M+H)$^+$: m/z=266.1; found 266.1.

Step 3. 5-(2,3-Dihydro-1H-inden-4-yl)-3-iodo-6-methoxy-1-(4-methoxybenzyl)-1H-pyrazolo[4,3-b]pyridine

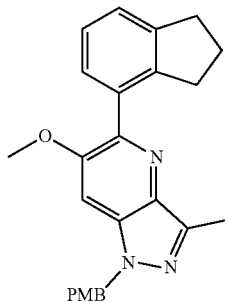

To a solution of 5-(2,3-dihydro-1H-inden-4-yl)-6-methoxy-1H-pyrazolo[4,3-b]pyridine (190 mg, 0.74 mmol) in DMF (2 mL) was added 1-iodopyrrolidine-2,5-dione (180 mg, 0.81 mmol). The reaction was warmed up to 80° C. and stirred at that temperature for 1 h. After this time the reaction mixture was cooled to r.t and 1-(chloromethyl)-4-methoxybenzene (131 mg, 0.90 mmol) and $Cs_2CO_3$ (380 mg, 1.166 mmol) were added. The reaction mixture was stirred at 90° C. for 1 h. After this time it was cooled to r.t., diluted with water and extracted with EtOAc three times. The combined organic phases were washed with sat. NaCl, dried with $Na_2SO_4$, filtered and concentrated to dryness. The residue was purified by Biotage Isolera to afford the desired product. LC-MS calculated for $C_{24}H_{23}IN_3O_2$ (M+H)$^+$: m/z=512.1; found 512.0.

Step 4. 5-(2,3-Dihydro-1H-inden-4-yl)-6-methoxy-1-(4-methoxybenzyl)-3-0H-pyrazol-4-yl)-1H-pyrazolo[4,3-b]pyridine

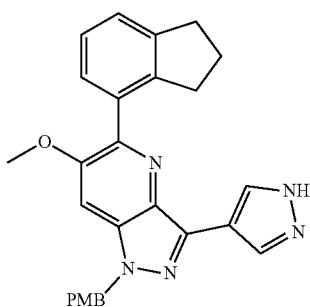

To a solution of 5-(2,3-dihydro-1H-inden-4-yl)-3-iodo-6-methoxy-1-(4-methoxybenzyl)-1H-pyrazolo[4,3-b]pyridine (300 mg, 0.587 mmol) in 1,4-dioxane (2 mL) and water (0.4 mL) was added tert-butyl 4-(4,4,5,5-tetramethyl-1,3,2-dioxaborolan-2-yl)-1H-pyrazole-1-carboxylate (207 mg, 0.704 mmol), potassium phosphate (249 mg, 1.173 mmol) and [dichloro[1,1'-bis(diphenylphosphino)ferrocene]palladium (II) dichloromethane adduct (47.9 mg, 0.059 mmol). The reaction was degassed with $N_2$ and stirred at 80° C. for 2 h. After this time it was cooled to r.t., and 2 mL of TFA was added. The reaction was stirred for additional 30 min before dilution with EtOAc. The organic solution was washed sequentially with water, sat. NaCl and dried over $Na_2SO_4$. The organic phases were filtered and concentrated to dryness. The residue was purified by Biotage Isolera to afford the desired product. LC-MS calculated for $C_{27}H_{26}N_5O_2$ (M+H)$^+$: m/z=452.2; found 452.2.

Step 5. N-((cis)-4-(4-(5-(2,3-Dihydro-1H-inden-4-yl)-6-methoxy-1H-pyrazolo[4,3-b]pyridin-3-yl)-1H-pyrazol-1-yl)cyclohexyl)acetamide In a vial N-((trans)-4-hydroxycyclohexyl)acetamide (13.93 mg, 0.089 mmol) and TEA (12.4 µl, 0.089 mmol) were dissolved in DCM (1 ml). Methanesulfonyl chloride (6.90 µl, 0.089 mmol) was added to the reaction mixture dropwise over 5 min at 0° C. After stirring at r.t. for 30 min, saturated $NaHCO_3$ solution was added to the reaction mixture followed by extraction with dichloromethane. The combined organic phases were dried over $Na_2SO_4$, filtered and concentrated. An acetonitrile (1 ml) solution of 5-(2,3-dihydro-1H-inden-4-yl)-6-methoxy-1-(4-methoxybenzyl)-3-(1H-pyrazol-4-yl)-1H-pyrazolo[4,3-b]pyridine (20 mg, 0.044 mmol) and $Cs_2CO_3$ (28.9 mg, 0.089 mmol) were added to the resultant material. The reaction mixture was heated to 100° C. After 5 h, triflic acid (0.5 ml) was added to the reaction mixture at r.t. After 10 min, the reaction mixture was diluted with MeOH then purified by prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{31}N_6O_2$ (M+H)+: m/z=471.2; found 471.2.

Example 54. 5-(2,3-Dihydro-1H-inden-4-yl)-3-(6-(2,4-dimethylpiperazin-1-yl)pyridin-3-yl)-6-methoxy-1H-pyrazolo[4,3-b]pyridine

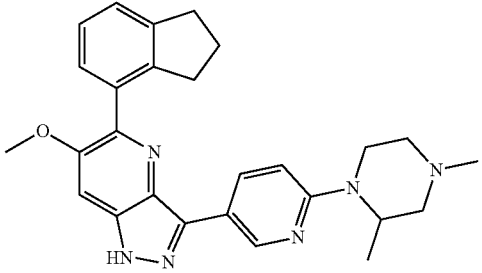

Step 1. 3-(6-Chloropyridin-3-yl)-5-(2,3-dihydro-1H-inden-4-yl)-6-methoxy-1-(4-methoxybenzyl)-1H-pyrazolo[4,3-b]pyridine

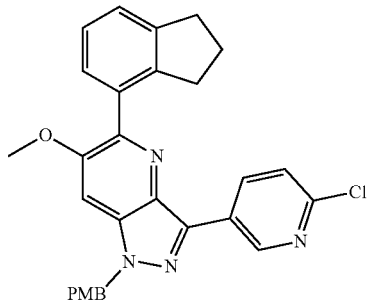

To a solution of 5-(2,3-dihydro-1H-inden-4-yl)-3-iodo-6-methoxy-1-(4-methoxybenzyl)-1H-pyrazolo[4,3-b]pyridine (Example 53, step 3; 500 mg, 0.98 mmol) in 1,4-dioxane (4 mL) and water (1 mL) was added (6-chloropyridin-3-yl) boronic acid (185 mg, 1.173 mmol), potassium phosphate (415 mg, 1.956 mmol), and [dichloro[1,1'-bis(diphenylphosphino)ferrocene]palladium (II) dichloromethane adduct (80 mg, 0.098 mmol). The reaction was degassed with $N_2$ and stirred at 80° C. for 8 h. After this time it was cooled to r.t. before dilution with EtOAc. The resultant solution was washed sequentially with water, sat. NaCl and dried over $Na_2SO_4$. The organic phases were filtered and concentrated to dryness. The residue was purified by silica gel chromatography to afford the desired product. LC-MS calculated for $C_{29}H_{26}ClN_4O_2$ (M+H)$^+$: m/z=497.2; found 497.2.

Step 2. 5-(2,3-Dihydro-1H-inden-4-yl)-3-(6-(2,4-dimethylpiperazin-1-yl)pyridin-3-yl)-6-methoxy-1H-pyrazolo[4,3-b]pyridine To a solution of 3-(6-chloropyridin-3-yl)-5-(2,3-dihydro-1H-inden-4-yl)-6-methoxy-1-(4-methoxybenzyl)-1H-pyrazolo[4,3-b]pyridine (20 mg, 0.040 mmol) in 1,4-dioxane (0.5 mL) was added 1,3-dimethylpiperazine (4.6 mg, 0.04 mmol), sodium tert-butoxide (7.7 mg, 0.080 mmol), and chloro(2-dicyclohexylphosphino-2',6'-diisopropoxy-1,1'-biphenyl)[2-(2'-amino-1,1'-biphenyl)]palladium(II) (3.29 mg, 4.02 µmol). The reaction was degassed with $N_2$ and stirred at 100° C. After 1 h, triflic acid (0.5 mL) was added to the reaction mixture at r.t. After 10 min, the reaction mixture was diluted with MeOH, then purified by prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{31}N_6O$ (M+H)+: m/z=455.3; found 455.3.

Example 55. 2-(3-(3-(6-(4-Acetylpiperazin-1-yl)pyridin-3-yl)-6-methoxy-1H-pyrazolo[4,3-b]pyridin-5-yl)-2-methylphenyl)acetonitrile

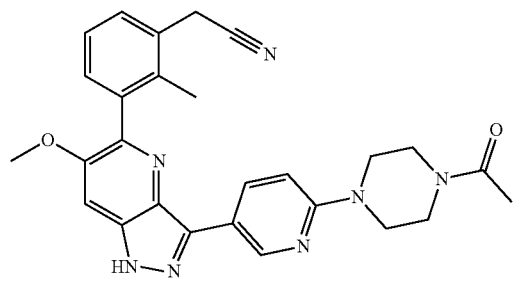 [SMILES: COc1cc2[nH]nc(-c3ccc(N4CCN(C(C)=O)CC4)nc3)c2nc1-c1cccc(CC#N)c1C]

Step 1. tert-Butyl 5-(3-(cyanomethyl)-2-methylphenyl)-3-iodo-6-methoxy-1H-pyrazolo[4,3-b]pyridine-1-carboxylate

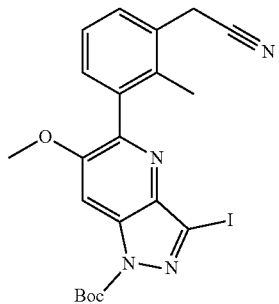 [SMILES: COc1cc2c(nc1-c1cccc(CC#N)c1C)c(I)nn2C(=O)OC(C)(C)C]

This compound was prepared according to the procedures described in Example 14, using 2-(2-methyl-3-(4,4,5,5-tetramethyl-1,3,2-dioxaborolan-2-yl)phenyl)acetonitrile (Intermediate 1) instead of 2-(2,3-dihydro-1H-inden-4-yl)-4,4,5,5-tetramethyl-1,3,2-dioxaborolane as starting material. LC-MS calculated for $C_{21}H_{22}IN_4O_3$ (M+H)$^+$: m/z=505.1; found 505.0.

Step 2. 2-(3-(3-(6-(4-acetylpiperazin-1-yl)pyridin-3-yl)-6-methoxy-1H-pyrazolo[4,3-b]pyridin-5-yl)-2-methylphenyl)acetonitrile To a solution of tert-butyl 5-(3-(cyano methyl)-2-methylphenyl)-3-iodo-6-methoxy-1H-pyrazolo[4,3-b]pyridine-1-carboxylate (20 mg, 0.040 mmol) in 1,4-dioxane (0.5 mL) and water (0.1 mL) was added 1-(4-(5-(4,4,5,5-tetramethyl-1,3,2-dioxaborolan-2-yl)pyri din-2-yl)piperazin-1-yl)ethan-1-one (16 mg, 0.048 mmol), potassium phosphate (16 mg, 0.079 mmol), and [dichloro[1,1'-bis(diphenylphosphino)ferrocene]palladium (II) dichloromethane adduct (3 mg, 4 mop. The reaction was degassed with $N_2$ and stirred at 80° C. for 2 h. After this time it was cooled to r.t., and 1 mL of TFA was added. The reaction was stirred for additional 30 min before it was diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{28}N_7O_2$ (M+H)+: m/z=482.2; found 482.3.

Example 56. 2-(3-(6-Methoxy-3-(6-morpholinopyridin-3-yl)-1H-pyrazolo[4,3-b]pyridin-5-yl)-2-methylphenyl)acetonitrile

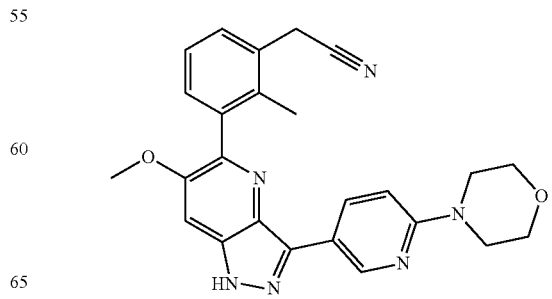

This compound was prepared according to the procedure described in Example 55, using 4-(5-(4,4,5,5-tetramethyl-1,3,2-dioxaborolan-2-yl)pyridin-2-yl)morpholine instead of 1-(4-(5-(4,4,5,5-tetramethyl-1,3,2-dioxaborolan-2-yl)pyridin-2-yl)piperazin-1-yl)ethan-1-one. The product was isolated as the TFA salt. LC-MS calculated for $C_{25}H_{25}N_6O_2$ $(M+H)^+$: m/z=441.2; found 441.2.

Example 57. 5-(2,3-Dihydro-1H-inden-4-yl)-6-methoxy-3-(6-(pyrrolidin-1-yl)pyridin-3-yl)-1H-pyrazolo[4,3-b]pyridine

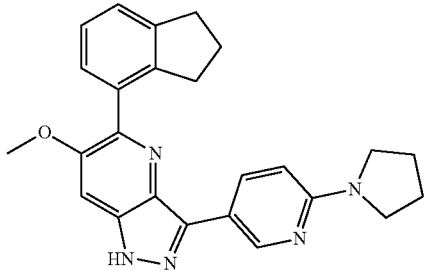 [SMILES: COc1cc2[nH]nc(-c3ccc(N4CCCC4)nc3)c2nc1-c1cccc2c1CCC2]

To a solution of 5-(2,3-dihydro-1H-inden-4-yl)-3-iodo-6-methoxy-1-(4-methoxybenzyl)-1H-pyrazolo[4,3-b]pyridine (Example 53, step 3; 20 mg, 0.04 mmol) in 1,4-dioxane (0.5 mL) and water (0.1 mL) was added 2-(pyrrolidin-1-yl)-5-(4,4,5,5-tetramethyl-1,3,2-dioxaborolan-2-yl)pyridine (13 mg, 0.047 mmol), potassium phosphate (17 mg, 0.078 mmol), and [dichloro[1,1'-bis(diphenylphosphino)ferrocene]palladium (II) dichloromethane adduct (3 mg, 4 μmol). The reaction was degassed with $N_2$ and stirred at 80° C. After 2 h, triflic acid (0.5 mL) was added to the reaction mixture at r.t. After 10 min, the reaction mixture was diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{25}H_{26}N_5O$ (M+H)+: m/z=412.2; found 412.2.

Example 58. 4-(5-(5-(2,3-Dihydro-1H-inden-4-yl)-6-methoxy-1H-pyrazolo[4,3-b]pyridin-3-yl)pyridin-2-yl)morpholine

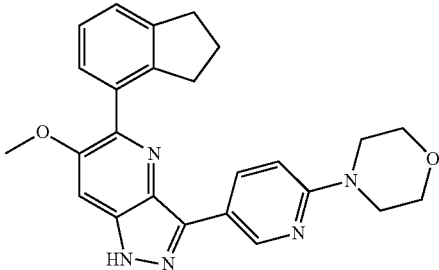 [SMILES: COc1cc2[nH]nc(-c3ccc(N4CCOCC4)nc3)c2nc1-c1cccc2c1CCC2]

This compound was prepared according to the procedure described in Example 57, using 4-(5-(4,4,5,5-tetramethyl-1,3,2-dioxaborolan-2-yl)pyridin-2-yl)morpholine instead of 2-(pyrrolidin-1-yl)-5-(4,4,5,5-tetramethyl-1,3,2-dioxaborolan-2-yl)pyridine. The product was isolated as the TFA salt. LC-MS calculated for $C_{25}H_{26}N_5O_2$ $(M+H)^+$: m/z=428.2; found 428.2. 1H NMR (600 MHz, DMSO-d6) δ 13.20 (s, 1H), 9.18 (d, J=2.2 Hz, 1H), 8.55 (dd, J=9.1, 2.4 Hz, 1H), 7.53 (s, 1H), 7.33-7.20 (m, 3H), 7.14 (s, 1H), 4.49 (bs, 3H), 3.85 (s, 3H), 3.75 (t, J=4.9 Hz, 4H), 2.93 (t, J=7.4 Hz, 2H), 2.79 (t, J=7.3 Hz, 2H), 2.48 (s, 1H), 1.98 (m, 2H) ppm.

Example 59. 4-(5-(5-(2,3-Dihydro-1H-inden-4-yl)-6-methoxy-1H-pyrazolo[4,3-b]pyridin-3-yl)pyridin-2-yl)-N-ethylpiperazine-1-carboxamide

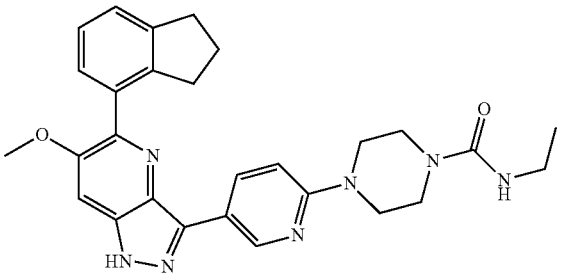 [SMILES: CCNC(=O)N1CCN(c2ccc(-c3n[nH]c4cc(OC)c(-c5cccc6c5CCC6)nc34)cn2)CC1]

Step 1. 5-(2,3-Dihydro-1H-inden-4-yl)-6-methoxy-1-(4-methoxybenzyl)-3-(6-(piperazin-1-yl)pyridin-3-yl)-1H-pyrazolo[4,3-b]pyridine

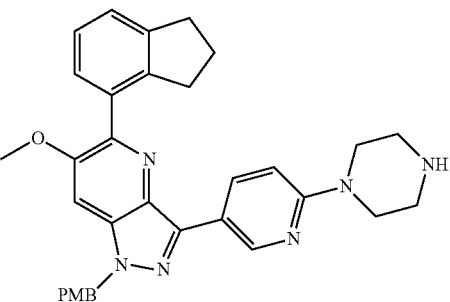

To a solution of 5-(2,3-dihydro-1H-inden-4-yl)-3-iodo-6-methoxy-1-(4-methoxybenzyl)-1H-pyrazolo[4,3-b]pyridine (Example 53, step 3; 200 mg, 0.4 mmol) in 1,4-dioxane (5 mL) and water (1 mL) were added tert-butyl 4-(5-(4,4,5,5-tetramethyl-1,3,2-dioxaborolan-2-yl)pyridin-2-yl)piperazine-1-carboxylate (183 mg, 0.469 mmol), potassium phosphate (166 mg, 0.78 mmol), and [dichloro[1,1'-bis(diphenylphosphino)ferrocene]palladium (II) dichloromethane adduct (32 mg, 0.039 mmol). The reaction was degassed with $N_2$ and stirred at 80° C. for 8 h. After this time it was cooled to r.t., and 2 ml of TFA was added. The reaction was stirred for an additional 30 min before dilution with EtOAc. The solution was washed sequentially with water, sat. NaCl and dried over $Na_2SO_4$. The organic phases were filtered and concentrated to dryness. The residue was purified by Biotage Isolera to afford the desired product. LC-MS calculated for $C_{33}H_{35}N_6O_2$ $(M+H)^+$: m/z=547.3; found 547.3.

Step 2. 4-(5-(5-(2,3-Dihydro-1H-inden-4-yl)-6-methoxy-1H-pyrazolo[4,3-b]pyridin-3-yl)pyridin-2-yl)-N-ethylpiperazine-1-carboxamide To a solution of 5-(2,3-dihydro-1H-inden-4-yl)-6-methoxy-1-(4-methoxybenzyl)-3-(6-(piperazin-1-yl)pyridin-3-yl)-1H-pyrazolo[4,3-b]pyridine (20 mg, 0.037 mmol) in DCM (1 ml) was added TEA (100, 0.073 mmol), and isocyanatoethane (3 mg, 0.040 mmol). The reaction was stirred at r.t. for 1 h before being concentrated to dryness. Triflic acid (0.5 ml) was added to the crude material and the reaction was stirred at r.t. for 10 min. The reaction was then diluted with water and MeOH, then purified by prep-LCMS (XBridge C18 column, eluting with a gradient of acetonitrile/water containing 0.1% TFA, at flow rate of 60 mL/min). The product was isolated as the TFA salt. LCMS calculated for $C_{28}H_{32}N_7O_2$ (M+H)$^+$: m/z=498.2; found 498.3.

Example 60. 4-(5-(5-(2,3-Dihydro-1H-inden-4-yl)-6-methoxy-1H-pyrazolo[4,3-b]pyridin-3-yl)pyridin-2-yl)piperazine-1-carboxamide

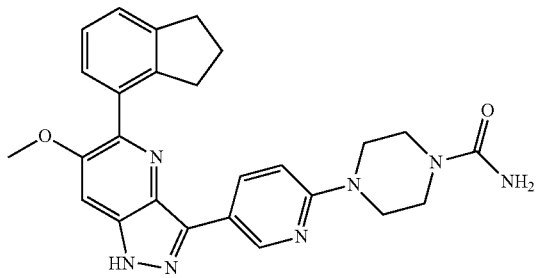 [SMILES: COc1cc2[nH]nc(-c3ccc(N4CCN(C(N)=O)CC4)nc3)c2nc1-c1cccc2c1CCC2]

This compound was prepared according to the procedure described in Example 59, using isocyanatotrimethylsilane instead of isocyanatoethane. The product was isolated as the TFA salt. LC-MS calculated for $C_{26}H_{28}N_7O_2$ (M+H)$^+$: m/z=470.2; found 470.2.

Example 61. 1-(4-(4-(5-(2,3-Dihydro-1H-inden-4-yl)-6-methoxy-1H-pyrazolo[4,3-b]pyridin-3-yl)phenyl)piperazin-1-yl)ethan-1-one

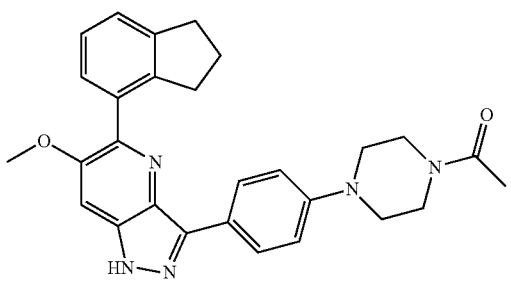 [SMILES: COc1cc2[nH]nc(-c3ccc(N4CCN(C(C)=O)CC4)cc3)c2nc1-c1cccc2c1CCC2]

This compound was prepared according to the procedure described in Example 57, using 1-(4-(4-(4,4,5,5-tetramethyl-1,3,2-dioxaborolan-2-yl)phenyl)piperazin-1-yl)ethan-1-one instead of 2-(pyrrolidin-1-yl)-5-(4,4,5,5-tetramethyl-1,3,2-dioxaborolan-2-yl)pyridine. The product was isolated as the TFA salt. LC-MS calculated for $C_{28}H_{30}N_5O_2$ (M+H)$^+$: m/z=468.2; found 468.2.

Example 62. 5-(2,3-Dihydro-1H-inden-4-yl)-3-(4-(4-isopropylpiperazin-1-yl)phenyl)-6-methoxy-1H-pyrazolo[4,3-b]pyridine

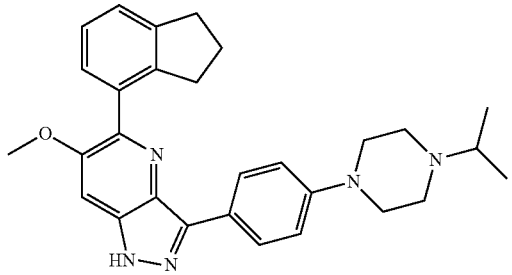 [SMILES: COc1cc2[nH]nc(-c3ccc(N4CCN(C(C)C)CC4)cc3)c2nc1-c1cccc2c1CCC2]

This compound was prepared according to the procedure described in Example 57, using 1-isopropyl-4-(4-(4,4,5,5-tetramethyl-1,3,2-dioxaborolan-2-yl)phenyl)piperazine instead of 2-(pyrrolidin-1-yl)-5-(4,4,5,5-tetramethyl-1,3,2-dioxaborolan-2-yl)pyridine. The product was isolated as the TFA salt. LC-MS calculated for $C_{29}H_{34}N_5O$ (M+H)$^+$: m/z=468.3; found 468.3.

Example 63. 5-(2,3-Dihydro-1H-inden-4-yl)-3-(4-(4-ethylpiperazin-1-yl)phenyl)-6-methoxy-1H-pyrazolo[4,3-b]pyridine

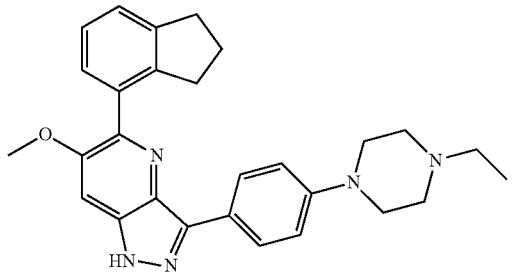 [SMILES: CCN1CCN(c2ccc(-c3n[nH]c4cc(OC)c(-c5cccc6c5CCC6)nc34)cc2)CC1]

This compound was prepared according to the procedure described in Example 57, using 1-ethyl-4-(4-(4,4,5,5-tetramethyl-1,3,2-dioxaborolan-2-yl)phenyl)piperazine instead of 2-(pyrrolidin-1-yl)-5-(4,4,5,5-tetramethyl-1,3,2-dioxaborolan-2-yl)pyridine. The product was isolated as the TFA salt. LC-MS calculated for $C_{28}H_{32}N_5O$ (M+H)$^+$: m/z=454.3; found 454.3.

Example 64. 1-(4-(5-(5-(2,3-Dihydro-1H-inden-4-yl)-6-methoxy-1H-pyrazolo[4,3-b]pyridin-3-yl)pyridin-2-yl)piperazin-1-yl)ethan-1-one

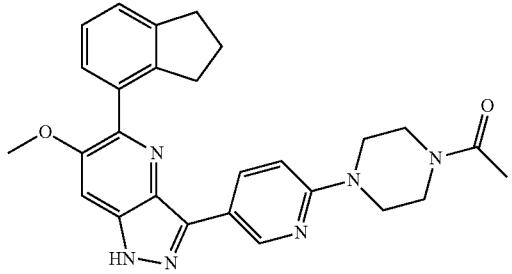 [SMILES: COc1cc2[nH]nc(-c3ccc(N4CCN(C(C)=O)CC4)nc3)c2nc1-c1cccc2c1CCC2]

This compound was prepared according to the procedure described in Example 57, using 1-(4-(5-(4,4,5,5-tetramethyl-1,3,2-dioxaborolan-2-yl)pyridin-2-yl)piperazin-1-yl)ethan-1-one instead of 2-(pyrrolidin-1-yl)-5-(4,4,5,5-tetramethyl-1,3,2-dioxaborolan-2-yl)pyridine. The product was isolated as the TFA salt. LC-MS calculated for $C_{27}H_{29}N_6O_2$ (M+H)$^+$: m/z=469.2; found 469.2.

Example 65. 8-(5-(5-(2,3-Dimethylphenyl)-6-methoxy-1H-pyrazolo[4,3-b]pyridin-3-yl)pyridin-2-yl)-1-oxa-3,8-diazaspiro[4.5]decan-2-one

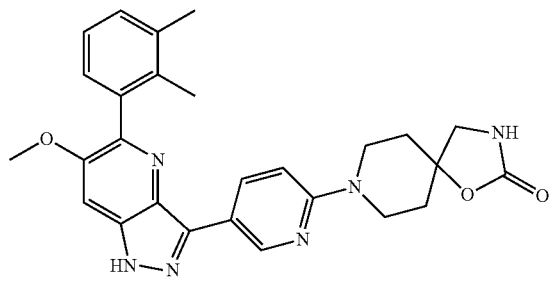 [SMILES: COc1cc2[nH]nc(-c3ccc(N4CCC5(CC4)CNC(=O)O5)nc3)c2nc1-c1cccc(C)c1C]

This compound was prepared according to the procedure described in Example 45, using 1-oxa-3,8-diazaspiro[4.5]decan-2-one hydrochloride instead of 1-methylpiperazin-2-one hydrochloride. The product was isolated as the TFA salt. LC-MS calculated for $C_{27}H_{29}N_6O_3$ (M+H)$^+$: m/z=485.2; found 485.2.

Example 66. 5-(2,3-Dimethylphenyl)-6-methoxy-3-(1-(pyridin-2-ylmethyl)-1H-pyrazol-4-yl)-1H-pyrazolo[4,3-b]pyridine

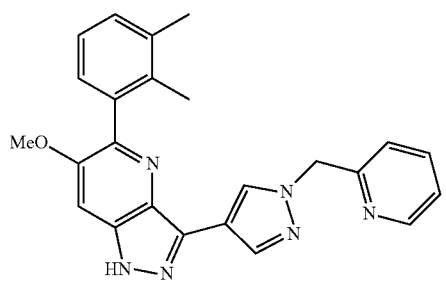 [SMILES: COc1cc2[nH]nc(-c3cnn(Cc4ccccn4)c3)c2nc1-c1cccc(C)c1C]

Step 1. 6-Bromo-1-(4-methoxybenzyl)-1H-pyrazolo[4,3-b]pyridine

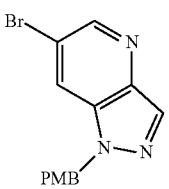

6-Bromo-1H-pyrazolo[4,3-b]pyridine (10 g, 50.5 mmol), 1-(chloromethyl)-4-methoxybenzene (8.7 g, 55.5 mmol), potassium carbonate (7.68 g, 55.5 mmol) were placed in a round bottom flask. After DMF (168 ml) was added, the reaction mixture was stirred at 80° C. for 4 h. After this time it was cooled to r.t., diluted with water and extracted with EtOAc 3 times. The combined organic phases were washed with sat. NaCl solution, dried over $Na_2SO_4$, filtered and concentrated to dryness. The residue was purified by silica gel chromatography to afford the desired product. LC-MS calculated for $C_{14}H_{13}BrN_3O$ (M+H)$^+$: m/z=318.2; found 318.2.

Step 2. 6-Methoxy-1-(4-methoxybenzyl)-1H-pyrazolo[4,3-b]pyridine

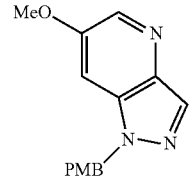

To a 250 mL round bottom flask was added $Cs_2CO_3$ (4.67 g, 14.3 mmol), t-butyl XPhos Pd G3 (0.47 g, 0.6 mmol), MeOH (10 ml), toluene (50 ml) and 6-bromo-1-(4-methoxybenzyl)-1H-pyrazolo[4,3-b]pyridine (3.8 g, 11.9 mmol). The mixture was evacuated and backfilled with $N_2$ three times and heated at 100° C. for 4 h. The resulting mixture was filtered and concentrated to dryness. The residue was purified by Biotage Isolera to afford the desired product. LC-MS calculated for $C_{15}H_{16}N_3O_2$ (M+H)$^+$: m/z=270.1; found 270.1.

Step 3. 6-Methoxy-1-(4-methoxybenzyl)-1H-pyrazolo[4,3-b]pyridine 4-oxide

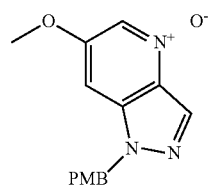

To a solution of 6-methoxy-1-(4-methoxybenzyl)-1H-pyrazolo[4,3-b]pyridine (13.3 g, 49.3 mmol) in DCM (100 ml) cooled in water bath was added 3-chlorobenzoperoxoic acid (16.6 g, 74 mmol). The reaction was stirred at r.t. for 2 h. The mixture was washed with $Na_2S_2O_3$ saturated solution, followed by $NaHCO_3$ saturated solution. The combined organic phases were washed with sat. NaCl, dried over $Na_2SO_4$, filtered and concentrated to dryness. The residue was purified by silica gel chromatography to afford the desired product. LC-MS calculated for $C_{15}H_{16}N_3O_3$ (M+H)$^+$: m/z=286.2; found 286.2.

Step 4. 5-Chloro-6-methoxy-1-(4-methoxybenzyl)-1H-pyrazolo[4,3-b]pyridine

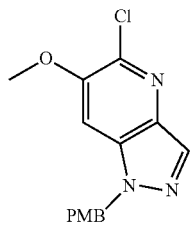

To a solution of 6-methoxy-1-(4-methoxybenzyl)-1H-pyrazolo[4,3-b]pyridine 4-oxide (12 g, 42.1 mmol) in DCM (90 ml) was added N,N-diisopropylethylamine (10.9 g, 84 mmol). The mixture was cooled in the ice bath and oxalyl chloride (8.01 g, 63.1 mmol) was added. The resulting mixture was stirred at 0° C. for 1 h before being quenched with saturated NaHCO$_3$ solution. The product was extracted with DCM, the combined organic phases were washed with sat. NaCl solution, dried over Na$_2$SO$_4$, filtered and concentrated to dryness. The residue was purified by Biotage Isolera to afford the desired product. LC-MS calculated for C$_{15}$H$_{15}$ClN$_3$O$_2$ (M+H)$^+$: m/z=304.1; found 304.1.

Step 5. 5-(2,3-Dimethylphenyl)-6-methoxy-1-(4-methoxybenzyl)-1H-pyrazolo[4,3-b]pyridine

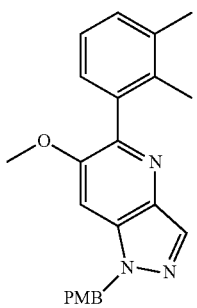

5-Chloro-6-methoxy-1-(4-methoxybenzyl)-1H-pyrazolo[4,3-b]pyridine (3.5 g, 11.52 mmol), (2,3-dimethylphenyl)boronic acid (2.07 g, 13.83 mmol), chloro(2-dicyclohexylphosphino-2',4',6'-triisopropyl-1,1'-biphenyl)[2-(2'-amino-1,1'-biphenyl)]palladium (0.90 g, 1.15 mmol) and cesium carbonate (7.51 g, 23.05 mmol) were placed in a round bottom flask and the flask was evacuated and backfilled with N$_2$ three times. After 1,4-dioxane (32 ml) and water (6.4 ml) were added, the reaction mixture was stirred at 100° C. for 1 h. After this time it was cooled to r.t., diluted with water and extracted with EtOAc 3 times. The combined organic phases were washed with sat. NaCl solution, dried over Na$_2$SO$_4$, filtered and concentrated to dryness. The residue was purified by Biotage Isolera to afford the desired product. LC-MS calculated for C$_{23}$H$_{24}$N$_3$O$_2$ (M+H)$^+$: m/z=374.2; found 374.2.

Step 6. 5-(2,3-Dimethylphenyl)-3-iodo-6-methoxy-1H-pyrazolo[4,3-b]pyridine

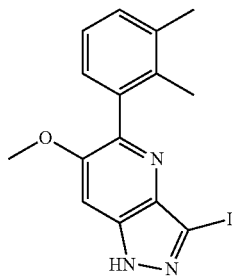 [SMILES: COc1cc2[nH]nc(I)c2nc1-c1cccc(C)c1C]

5-(2,3-Dimethylphenyl)-6-methoxy-1-(4-methoxybenzyl)-1H-pyrazolo[4,3-b]pyridine (3.87 g, 10.36 mmol) was dissolved in TFA (12 ml). The mixture was heated to 100° C. for 1 h before it was cooled to 0° C. and neutralized with 4N NaOH aqueous solution. The product was extracted with DCM (50 ml×3) and the combined organic phases were washed with sat. NaCl solution, dried over Na$_2$SO$_4$, filtered and concentrated to dryness. To the residue was added NIS (2.56 g, 11.4 mmol) and DMF (20 ml). The resulting mixture was heated to 80° C. for 2 h. After this time it was cooled to r.t., diluted with water and extracted with EtOAc 3 times. The combined organic phases were washed with sat. NaCl solution, dried over Na$_2$SO$_4$, filtered and concentrated to dryness. The residue was used directly in the next step without purification. LC-MS calculated for C$_{15}$H$_{15}$IN$_3$O (M+H)$^+$: m/z=380.2; found 380.2.

Step 7. tert-Butyl 5-(2,3-dimethylphenyl)-3-iodo-6-methoxy-1H-pyrazolo[4,3-b]pyridine-1-carboxylate

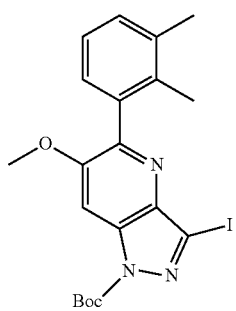 [SMILES: COc1cc2c(nc1-c1cccc(C)c1C)c(I)nn2C(=O)OC(C)(C)C]

To a solution of 5-(2,3-dimethylphenyl)-3-iodo-6-methoxy-1H-pyrazolo[4,3-b]pyridine (1.9 g, 5.01 mmol) in DMF (10 ml) was added di-tert-butyl dicarbonate (2.19 g, 10.02 mmol), triethylamine (1.27 g, 12.53 mmol) and 4-dimethylaminopyridine (6 mg, 0.05 mmol). The resulting mixture was stirred at r.t. for 2 h. After this time it was diluted with water and extracted with EtOAc 3 times. The combined organic phases were washed with sat. NaCl solution, dried over Na$_2$SO$_4$, filtered and concentrated to dryness. The residue was purified by Biotage Isolera to afford the desired product. LC-MS calculated for C$_{20}$H$_{23}$IN$_3$O$_3$ (M+H)$^+$: m/z=480.2; found 480.2.

Step 8. 5-(2,3-Dimethylphenyl)-6-methoxy-3-(1-(pyridin-2-ylmethyl)-1H-pyrazol-4-yl)-1H-pyrazolo[4,3-b]pyridine To a solution of tert-butyl 5-(2,3-dimethylphenyl)-3-iodo-6-methoxy-1H-pyrazolo[4,3-b]pyridine-1-carboxylate (15 mg, 0.031 mmol) in 1,4-dioxane (0.5 mL) and water (0.05 mL) were added 2-((4-(4,4,5,5-tetramethyl-1,3,2-dioxaborolan-2-yl)-1H-pyrazol-1-yl)methyl)pyridine (18 mg, 0.063 mmol), potassium phosphate (19.9 mg, 0.094 mmol), and chloro(2-dicyclohexylphosphino-2',4',6'-triisopropyl-1,1'-biphenyl)[2-(2'-amino-1,1'-biphenyl)]palladium (2.5 mg, 0.003 mmol). The reaction was degassed with N₂ and stirred at 80° C. for 3 h. After this time it was cooled to r.t., diluted with EtOAc, washed sequentially with water, sat. NaCl and dried over Na₂SO₄. The organic phases were combined, filtered and concentrated to dryness. The residue was dissolved in 4N HCl in dioxane (1 ml) and the resulting mixture was stirred at r.t. After 10 min, the reaction mixture was diluted with MeOH and was purified by prep-LCMS (XBridge C18 column, eluting with a gradient of acetonitrile/water containing 0.1% TFA, at flow rate of 60 mL/min). The product was isolated as the TFA salt. LC-MS calculated for $C_{24}H_{23}N_6O$ (M+H)+: m/z=411.2; found 411.2.

Example 67. 3-(1-Cyclopropyl-1H-pyrazol-4-yl)-5-(2,3-dimethylphenyl)-6-methoxy-1H-pyrazolo[4,3-b]pyridine

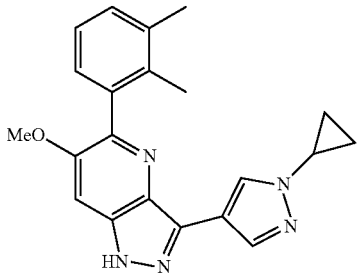 [SMILES: COc1cc2[nH]nc(-c3cnn(C4CC4)c3)c2nc1-c1cccc(C)c1C]

This compound was prepared according to the procedure described in Example 66, using 1-cyclopropyl-4-(4,4,5,5-tetramethyl-1,3,2-dioxaborolan-2-yl)-1H-pyrazole instead of 2-((4-(4,4,5,5-tetramethyl-1,3,2-dioxaborolan-2-yl)-1H-pyrazol-1-yl)methyl)pyridine as starting material. The product was isolated as the TFA salt. LC-MS calculated for $C_{21}H_{22}N_5O$ (M+H)⁺: m/z=360.2; found 360.2.

Example 68. 6-Methoxy-5-(2-methyl-3-(methyl-d3)phenyl)-3-(6-(4-methylpiperazin-1-yl)pyridin-3-yl)-1H-pyrazolo[4,3-b]pyridine

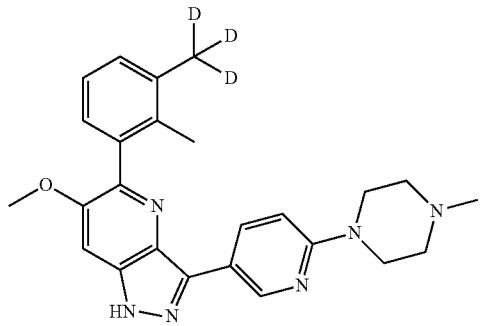

Step 1. 1-Bromo-2-methyl-3-(methyl-d3)benzene

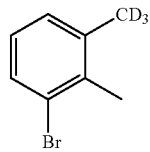

To a solution of 1-bromo-3-iodo-2-methylbenzene (300 mg, 1 mmol) in THF (3 mL) at −20° C. was slowly added isopropylmagnesium chloride solution 2.0 M in THF (0.76 ml, 1.5 mmol). The reaction mixture was stirred at 0° C. for 1 h before iodomethane-d3 was added. The mixture was stirred at r.t. overnight and then diluted with EtOAc. The mixture was washed sequentially with water and sat. NaCl solution and dried over Na₂SO₄. The organic phases were filtered and concentrated to dryness. The residue was purified by Biotage Isolera to afford the desired product.

Step 2. 4,4,5,5-Tetramethyl-2-(2-methyl-3-(methyl-d3)phenyl)-1,3,2-dioxaborolane

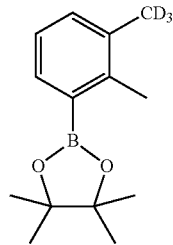 [SMILES: [2H]C([2H])([2H])c1cccc(B2OC(C)(C)C(C)(C)O2)c1C]

To a solution of 1-bromo-2-methyl-3-(methyl-d3)benzene (112 mg, 0.6 mmol) in 1,4-dioxane (4 ml) were added bis(pinacolato)diboron (302 mg, 1.19 mmol), potassium acetate (175 mg, 1.79 mmol), and [1,1'-bis(diphenylphosphino)ferrocene]dichloropalladium(II) (1:1) (49 mg, 0.06 mmol). The reaction was purged with N₂ and stirred at 90° C. for 12 h. After this time it was cooled to r.t. and diluted with EtOAc. It was then washed sequentially with water, sat. NaCl solution and dried over Na₂SO₄. The organic phases were filtered and concentrated to dryness. The residue was purified by Biotage Isolera to afford the desired product. LC-MS calculated for $C_{14}H_{19}D_3BO_2$ (M+H)+: m/z=236.2; found 236.2.

Step 3. 6-Methoxy-1-(4-methoxybenzyl)-5-(2-methyl-3-(methyl-d3)phenyl)-1H-pyrazolo[4,3-b]pyridine

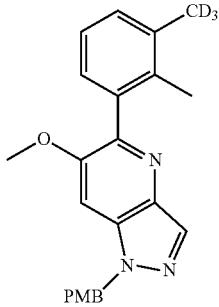

5-Chloro-6-methoxy-1-(4-methoxybenzyl)-1H-pyrazolo[4,3-b]pyridine (155 mg, 0.51 mmol), 4,4,5,5-tetramethyl-2-(2-methyl-3-(methyl-d3)phenyl)-1,3,2-dioxaborolane (100 mg, 0.43 mmol), chloro(2-dicyclohexylphosphino-2',4',6'-triisopropyl-1,1'-biphenyl)[2-(2'-amino-1,1'-biphenyl)]palladium (33 mg, 0.043 mmol) and cesium carbonate (277 mg, 0.85 mmol) were placed in a round bottom flask and the flask was evacuated and backfilled with $N_2$ three times. After 1,4-dioxane (2.5 ml) and water (0.5 ml) were added, the reaction mixture was stirred at 100° C. for 1 h. The reaction mixture was cooled to r.t., diluted with water and extracted with EtOAc 3 times. The combined organic phases were washed with sat. NaCl solution, dried over $Na_2SO_4$, filtered and concentrated to dryness. The residue was purified by Biotage Isolera to afford the desired product.

LC-MS calculated for $C_{23}H_{21}D_3N_3O_2$ $(M+H)^+$: m/z=377.2; found 377.2.

Step 4. 3-Iodo-6-methoxy-5-(2-methyl-3-(methyl-d3)phenyl)-1H-pyrazolo[4,3-b]pyridine

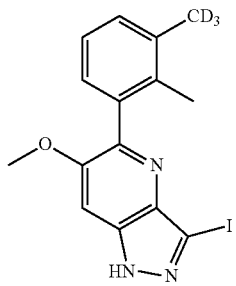 [SMILES: [2H]C([2H])([2H])c1cccc(-c2nc3c(I)n[nH]c3cc2OC)c1C]

6-Methoxy-1-(4-methoxybenzyl)-5-(2-methyl-3-(methyl-d3)phenyl)-1H-pyrazolo[4,3-b]pyridine (0.3 g, 0.8 mmol) was dissolved in TFA (1 ml). The mixture was heated to 100° C. for 1 h and then cooled to 0° C. and neutralized with 4N NaOH aqueous solution. The product was extracted with DCM (5 ml×3) and the combined organic phases were washed with sat. NaCl solution, dried over $Na_2SO_4$, filtered and concentrated to dryness.

To the residue was added MS (0.18 g, 0.8 mmol) and DMF (4 ml). The resulting mixture was heated to 80° C. for 2 h. After this time it was cooled to r.t., diluted with water and extracted with EtOAc 3 times. The combined organic phases were washed with sat. NaCl solution, dried over $Na_2SO_4$, filtered and concentrated to dryness. The residue was used directly in the next step without purification. LC-MS calculated for $C_{15}H_{12}D_3IN_3O$ $(M+H)^+$: m/z=383.2; found 383.2.

Step 5. 3-Iodo-6-methoxy-5-(2-methyl-3-(methyl-d3)phenyl)-1-((2-(trimethylsilyl)ethoxy)methyl)-1H-pyrazolo[4,3-b]pyridine

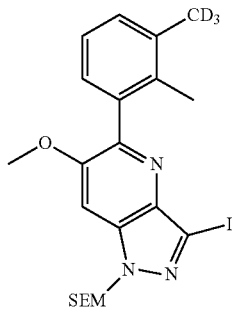 [SMILES: [2H]C([2H])([2H])c1cccc(-c2nc3c(I)nn(COCC[Si](C)(C)C)c3cc2OC)c1C]

To a solution of 3-iodo-6-methoxy-5-(2-methyl-3-(methyl-d3)phenyl)-1H-pyrazolo[4,3-b]pyridine (306 mg, 0.8 mmol) in DMF (4 ml) was added 2-(trimethylsilyl)ethoxymethyl chloride (0.2 g, 1.2 mmol) and cesium carbonate (0.52 g, 1.6 mmol). The resulting mixture was stirred at 80° C. for 1 h. After this time the mixture was diluted with water and extracted with EtOAc 3 times. The combined organic phases were washed with sat. NaCl solution, dried over $Na_2SO_4$, filtered and concentrated to dryness. The residue was used directly in the next step without purification. LC-MS calculated for $C_{21}H_{26}D_3IN_3O_2Si$ $(M+H)^+$: m/z=513.2; found 513.2.

Step 6. 6-Methoxy-5-(2-methyl-3-(methyl-d3)phenyl)-3-(6-(4-methylpiperazin-1-yl)pyridin-3-yl)-1H-pyrazolo[4,3-b]pyridine To a solution of 3-iodo-6-methoxy-5-(2-methyl-3-(methyl-d3)phenyl)-1-((2-(trimethylsilyl)-ethoxy)methyl)-1H-pyrazolo[4,3-b]pyridine (60 mg, 0.12 mmol) in 1,4-dioxane (1 mL) and water (0.1 mL) were added 1-methyl-4-(5-(4,4,5,5-tetramethyl-1,3,2-dioxaborolan-2-yl)pyridin-2-yl)piperazine (71 mg, 0.23 mmol), potassium phosphate (75 mg, 0.35 mmol), and [1,1'-bis(diphenylphosphino)ferrocene]dichloropalladium(II) (1:1) (10 mg, 0.012 mmol). The reaction was purged with $N_2$ and stirred at 80° C. for 2 h. The mixture was cooled to r.t. and diluted with EtOAc. It was then washed sequentially with water, sat. NaCl solution and dried over $Na_2SO_4$. The organic phases were filtered and concentrated to dryness. The residue was dissolved in TFA (0.5 ml) and stirred at r.t. for 1 h. The mixture was concentrated and ammonium hydroxide solution (0.5 ml) was added. The reaction mixture was stirred at r.t. for 1 h and then concentrated. The residue was dissolved in MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{25}H_{26}D_3N_6O$ $(M+H)^+$: m/z=432.2; found 432.2. $^1$H NMR (400 MHz, DMSO-d6) δ 9.23-9.18 (d, J=2.3 Hz, 1H), 8.53-8.46 (dd, J=8.9, 2.4 Hz, 1H), 7.54-7.49 (s, 1H), 7.26-7.21 (d, J=1.6 Hz, 1H), 7.20-7.14 (t, J=7.5 Hz, 1H), 7.12-7.06 (m, 2H), 4.50-4.42 (d, J=13.2 Hz, 2H), 3.87-3.82 (s, 3H), 3.22-3.05 (dt, J=24.7, 12.1 Hz, 4H), 2.88-2.82 (d, J=3.7 Hz, 3H), 2.00-1.95 (s, 3H) ppm.

Example 69. 1-(4-(4-(5-(2,3-Dimethylphenyl)-6-methoxy-1H-pyrazolo[4,3-b]pyridin-3-yl)-1H-pyrazol-1-yl)piperidin-1-yl)ethan-1-one

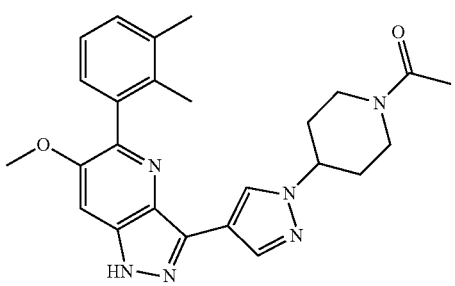 [SMILES: COc1cc2[nH]nc(-c3cnn(C4CCN(C(C)=O)CC4)c3)c2nc1-c1cccc(C)c1C]

Step 1. 5-(2,3-Dimethylphenyl)-3-iodo-6-methoxy-1-(4-methoxybenzyl)-1H-pyrazolo[4,3-b]pyridine

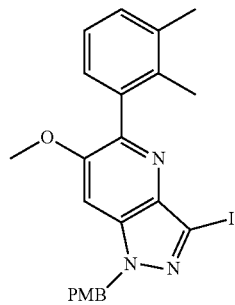

To a solution of 5-(2,3-dimethylphenyl)-3-iodo-6-methoxy-1H-pyrazolo[4,3-b]pyridine (Example 66, 1.9 g, 5.01 mmol) in DMF (10 ml) was added 1-(chloromethyl)-4-methoxybenzene (1.02 g, 6.51 mmol) and potassium carbonate (1.04 g, 7.52 mmol). The resulting mixture was stirred at 80° C. for 1 h. After this time it was diluted with water and the product was extracted with EtOAc 3 times. The combined organic phases were washed with sat. NaCl solution, dried over $Na_2SO_4$, filtered and concentrated to dryness. The residue was used directly in the next step without purification. LC-MS calculated for $C_{23}H_{23}IN_3O_2$ $(M+H)^+$: m/z=500.2; found 500.2.

Step 2. tert-butyl 4-(4-(5-(2,3-Dimethylphenyl)-6-methoxy-1-(4-methoxybenzyl)-1H-pyrazolo[4,3-b]pyridin-3-yl)-1H-pyrazol-1-yl)piperidine-1-carboxylate

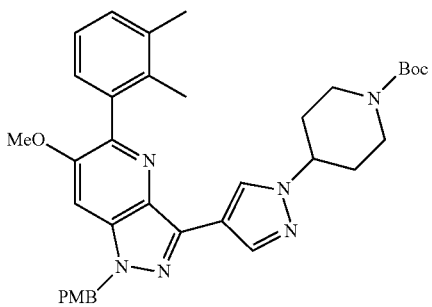

To a solution of 5-(2,3-dimethylphenyl)-3-iodo-6-methoxy-1-(4-methoxybenzyl)-1H-pyrazolo[4,3-b]pyridine (150 mg, 0.3 mmol) in 1,4-dioxane (3 mL) and water (0.3 mL) was added tert-butyl 4-(4-(4,4,5,5-tetramethyl-1,3,2-dioxaborolan-2-yl)-1H-pyrazol-1-yl)piperidine-1-carboxylate (227 mg, 0.6 mmol), potassium phosphate (191 mg, 0.9 mmol), and chloro(2-dicyclohexylphosphino-2',4',6'-triisopropyl-1,1'-biphenyl)[2-(2'-amino-1,1'-biphenyl)]palladium (24 mg, 0.03 mmol). The reaction was degassed with $N_2$ and stirred at 80° C. for 3 h. After this time it was cooled to r.t. and was diluted with EtOAc. The resultant solution was washed sequentially with water, sat. NaCl solution and dried over $Na_2SO_4$. The organic phases were filtered and concentrated to dryness. The residue was purified by Biotage Isolera to afford the desired product. LC-MS calculated for $C_{36}H_{43}N_6O_4$ (M+H)+: m/z=623.2; found 623.2.

Step 3. 5-(2,3-Dimethylphenyl)-6-methoxy-1-(4-methoxybenzyl)-3-(1-(piperidin-4-yl)-1H-pyrazol-4-yl)-1H-pyrazolo[4,3-b]pyridine

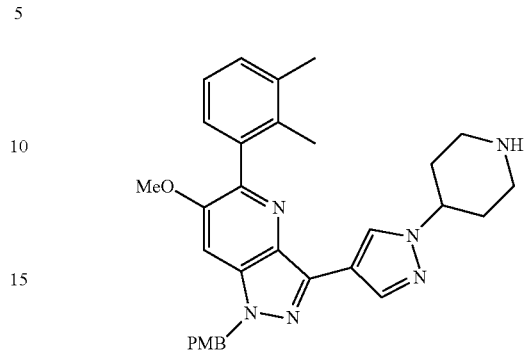

tert-Butyl 4-(4-(5-(2,3-dimethylphenyl)-6-methoxy-1-(4-methoxybenzyl)-1H-pyrazolo[4,3-b]pyridin-3-yl)-1H-pyrazol-1-yl)piperidine-1-carboxylate (156 mg, 0.3 mmol) was dissolved in 4N HCl in dioxane (3 ml) and the resulting mixture was stirred at r.t. After 10 min, the reaction mixture was concentrated to dryness and the crude was used directly for the next step. LC-MS calculated for $C_{31}H_{35}N_6O_2$ $(M+H)^+$: m/z=523.2; found 523.2.

Step 4. 1-(4-(4-(5-(2,3-Dimethylphenyl)-6-methoxy-1H-pyrazolo[4,3-b]pyridin-3-yl)-1H-pyrazol-1-yl)piperidin-1-yl)ethan-1-one To a solution of 5-(2,3-dimethylphenyl)-6-methoxy-1-(4-methoxybenzyl)-3-(1-(piperidin-4-yl)-1H-pyrazol-4-yl)-1H-pyrazolo[4,3-b]pyridine (10 mg, 0.019 mmol) in DCM (0.5 ml) was added N,N-diisopropylethylamine (24 mg, 0.19 mmol) and acetyl chloride (7.5 mg, 0.096 mmol). The reaction mixture was stirred at r.t. for 1 h. After this time it was diluted with EtOAc, washed sequentially with water, sat. NaCl solution and dried over $Na_2SO_4$. The organic phase was filtered and concentrated to dryness. The residue was dissolved in DCM (0.5 ml) and triflic acid (0.5 ml). After 30 min, the reaction mixture was diluted with MeOH then purified by prep-LCMS (XBridge C18 column, eluting with a gradient of acetonitrile/water containing 0.1% TFA, at flow rate of 60 mL/min). The product was isolated as the TFA salt. LC-MS calculated for $C_{25}H_{29}N_6O_2$ (M+H)+: m/z=445.2; found 445.2.

Example 70. Methyl 4-(4-(5-(2,3-dimethylphenyl)-6-methoxy-1H-pyrazolo[4,3-b]pyridin-3-yl)-1H-pyrazol-1-yl)piperidine-1-carboxylate

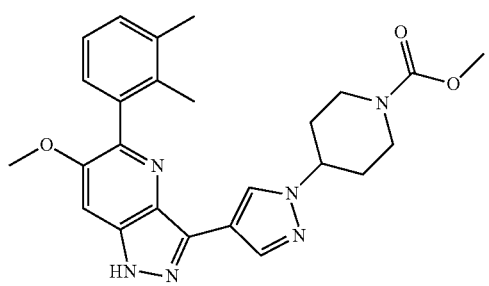

This compound was prepared according to the procedure described in Example 69, using methyl carbonochloridate instead of acetyl chloride as starting material. The product was isolated as the TFA salt. LC-MS calculated for $C_{25}H_{29}N_6O_3$ (M+H)$^+$: m/z=461.2; found 461.2.

Example 71. Methyl 3-(4-(5-(2,3-dimethylphenyl)-6-methoxy-1H-pyrazolo[4,3-b]pyridin-3-yl)-1H-pyrazol-1-yl)azetidine-1-carboxylate

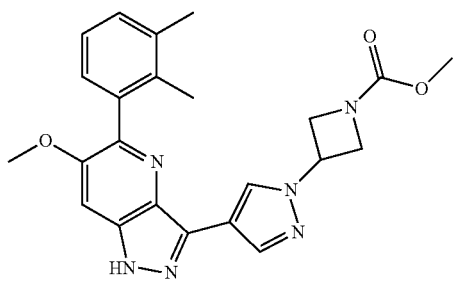

Step 1. tert-Butyl 3-(4-(5-(2,3-dimethylphenyl)-6-methoxy-1-(4-methoxybenzyl)-1H-pyrazolo[4,3-b]pyridin-3-yl)-1H-pyrazol-1-yl)azetidine-1-carboxylate

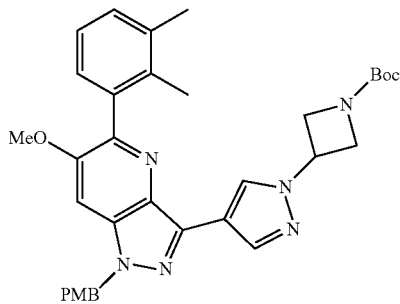

To a solution of 5-(2,3-dimethylphenyl)-3-iodo-6-methoxy-1-(4-methoxybenzyl)-1H-pyrazolo[4,3-b]pyridine (example 69, 150 mg, 0.3 mmol) in 1,4-dioxane (3 mL) and water (0.3 mL) were added tert-butyl 3-(4-(4,4,5,5-tetramethyl-1,3,2-dioxaborolan-2-yl)-1H-pyrazol-1-yl)azetidine-1-carboxylate (210 mg, 0.6 mmol), potassium phosphate (191 mg, 0.9 mmol), and chloro(2-dicyclohexylphosphino-2',4',6'-triisopropyl-1,1'-biphenyl)[2-(2'-amino-1,1'-biphenyl)]palladium (24 mg, 0.03 mmol). The reaction was degassed with $N_2$ and stirred at 80° C. for 3 h. After this time it was cooled to r.t. before being diluted with EtOAc. It was then washed sequentially with water, sat. NaCl solution and dried over $Na_2SO_4$. The organic phases were filtered and concentrated to dryness. The residue was purified by Biotage Isolera to afford the desired product. LC-MS calculated for $C_{34}H_{39}N_6O_4$ (M+H)+: m/z=595.2; found 595.2.

Step 2. 3-(1-(Azetidin-3-yl)-1H-pyrazol-4-yl)-5-(2,3-dimethylphenyl)-6-methoxy-1-(4-methoxybenzyl)-1H-pyrazolo[4,3-b]pyridine

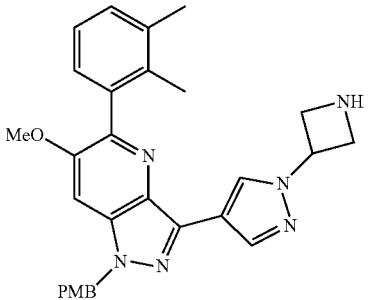

tert-Butyl 3-(4-(5-(2,3-dimethylphenyl)-6-methoxy-1-(4-methoxybenzyl)-1H-pyrazolo[4,3-b]pyridin-3-yl)-1H-pyrazol-1-yl)azetidine-1-carboxylate (178 mg, 0.3 mmol) was dissolved in 4N HCl in dioxane (3 ml) and the resulting mixture was stirred at r.t. After 10 min, the reaction mixture was concentrated to dryness and the crude was used directly in the next step. LC-MS calculated for $C_{29}H_{31}N_6O_2$ (M+H)$^+$: m/z=495.2; found 495.2.

Step 3. Methyl 3-(4-(5-(2,3-dimethylphenyl)-6-methoxy-1H-pyrazolo[4,3-b]pyridin-3-yl)-1H-pyrazol-1-yl)azetidine-1-carboxylate To a solution of 3-(1-(azetidin-3-yl)-1H-pyrazol-4-yl)-5-(2,3-dimethylphenyl)-6-methoxy-1-(4-methoxybenzyl)-1H-pyrazolo[4,3-b]pyridine (10 mg, 0.02 mmol) in DCM (0.5 ml) was added N,N-diisopropylethylamine (24 mg, 0.19 mmol) and methyl carbonochloridate (9 mg, 0.096 mmol). The mixture was stirred at r.t. for 1 h. After this time it was diluted with EtOAc, washed sequentially with water, sat. NaCl solution and dried over $Na_2SO_4$. The organic phases were filtered and concentrated to dryness. The residue was dissolved in DCM (0.5 ml) and triflic acid (0.5 ml). After 30 min, the reaction mixture was diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{23}H_{25}N_6O_3$ (M+H)$^+$: m/z=433.2; found 433.2.

Example 72. 3-(4-(5-(2,3-Dimethylphenyl)-6-methoxy-1H-pyrazolo[4,3-b]pyridin-3-yl)-1H-pyrazol-1-yl)-N,N-dimethylazetidine-1-carboxamide

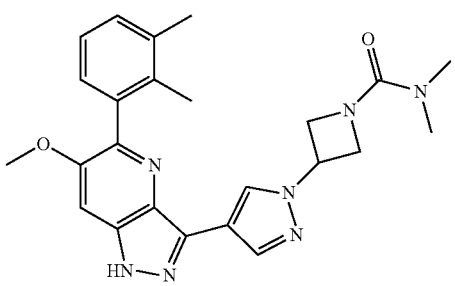

To a solution of 3-(1-(azetidin-3-yl)-1H-pyrazol-4-yl)-5-(2,3-dimethylphenyl)-6-methoxy-1-(4-methoxybenzyl)-1H-pyrazolo[4,3-b]pyridine (Example 71, 10 mg, 0.02 mmol) in DCM (0.5 ml) was added N,N-diisopropylethylamine (24 mg, 0.19 mmol) and dimethylcarbamic chloride (11 mg, 0.1 mmol). The mixture was stirred at r.t. for 1 h. After this time it was diluted with EtOAc, washed sequentially with water, sat. NaCl solution and dried over Na$_2$SO$_4$. The organic phases were filtered and concentrated to dryness. The residue was dissolved in DCM (0.5 ml) and triflic acid (0.5 ml). After 30 min, the reaction mixture was diluted with MeOH then purified by prep-LCMS (XBridge C18 column, eluting with a gradient of acetonitrile/water containing 0.1% TFA, at flow rate of 60 mL/min). The product was isolated as the TFA salt. LC-MS calculated for C$_{24}$H$_{28}$N$_7$O$_2$ (M+H)$^+$: m/z=446.2; found 446.2. $^1$H NMR (500 MHz, DMSO-d6) δ 8.53-8.31 (s, 1H), 8.26-8.10 (s, 1H), 7.55-7.40 (s, 1H), 7.24-7.19 (d, J=8.1 Hz, 1H), 7.19-7.13 (t, J=7.5 Hz, 1H), 7.11-7.07 (dd, J=7.4, 1.7 Hz, 1H), 5.47-5.24 (m, 1H), 4.32-4.26 (t, J=8.4 Hz, 2H), 4.26-4.20 (dd, J=8.7, 5.9 Hz, 2H), 3.91-3.70 (s, 3H), 2.82-2.76 (s, 6H), 2.36-2.27 (s, 3H), 2.01-1.92 (s, 3H) ppm.

Example 73. 4-(6-Methoxy-3-(6-((tetrahydrofuran-3-yl)oxy)pyridin-3-yl)-1H-pyrazolo[4,3-b]pyridin-5-yl)-2,3-dihydro-1H-inden-2-ol

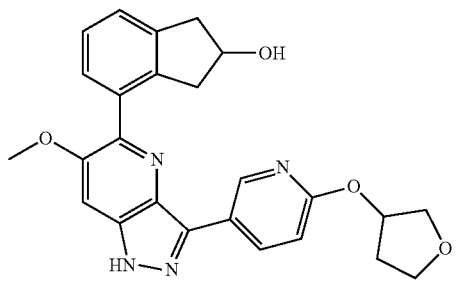 [SMILES: COc1cc2[nH]nc(-c3ccc(OC4CCOC4)nc3)c2nc1-c1cccc2c1CC(O)C2]

Step 1. tert-Butyl 5-(2-hydroxy-2,3-dihydro-1H-inden-4-yl)-6-methoxy-1H-pyrazolo[4,3-b]pyridine-1-carboxylate

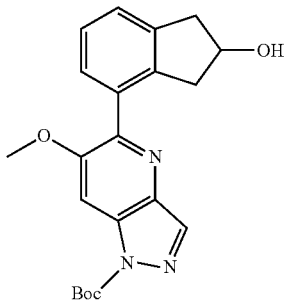 [SMILES: COc1cc2c(cnn2C(=O)OC(C)(C)C)nc1-c1cccc2c1CC(O)C2]

tert-Butyl 5-chloro-6-methoxy-1H-pyrazolo[4,3-b]pyridine-1-carboxylate (2.00 g, 7.05 mmol), 4-(4,4,5,5-tetramethyl-1,3,2-dioxaborolan-2-yl)-2,3-dihydro-1H-inden-2-ol (2.2 g, 8.46 mmol), chloro(2-dicyclohexylphosphino-2',4',6'-triisopropyl-1,1'-biphenyl)[2-(2'-amino-1,1'-biphenyl)]palladium (120 mg, 0.15 mmol) and potassium phosphate (4.6 g, 14.1 mmol) were placed in a flask and the flask was evacuated and backfilled with N$_2$ three times. After 1,4-dioxane (20 ml) and water (4 ml) were added, the reaction mixture was stirred at 80° C. for 2 hrs. After cooling to r.t., water was added and the desired product was extracted with EtOAc. The organic phase was washed with brine, dried over sodium sulfate and the solvent was evaporated in vacuo. Crude material was purified by Biotage Isolera to give a white solid (2.40 g, 89%). LCMS calculated for C$_{21}$H$_{24}$N$_3$O$_4$ (M+H)$^+$: m/z=382.2; found 382.2.

Step 2. 4-(6-Methoxy-1H-pyrazolo[4,3-b]pyridin-5-yl)-2,3-dihydro-1H-inden-2-ol

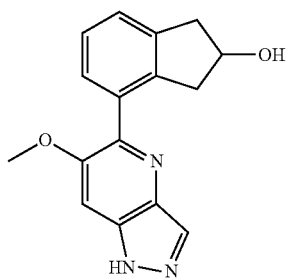 [SMILES: COc1cc2[nH]ncc2nc1-c1cccc2c1CC(O)C2]

tert-Butyl 5-(2-hydroxy-2,3-dihydro-1H-inden-4-yl)-6-methoxy-1H-pyrazolo[4,3-b]pyridine-1-carboxylate (2.40 g, 6.29 mmol) in a mixture of DCM (20 ml) and TFA (10 ml) was stirred at r.t. for 1 h. The reaction mixture was then concentrated in vacuo, dissolved in DCM and neutralized with NaHCO$_3$ solution. The organic phase was separated, dried over sodium sulfate and concentrated in vacuo. Crude material was used in the next step without further purification. LCMS calculated for C$_{16}$H$_{16}$N$_3$O$_2$ (M+H)$^+$: m/z=282.1; found 282.1.

Step 3. tert-Butyl 5-(2-hydroxy-2,3-dihydro-1H-inden-4-yl)-3-iodo-6-methoxy-1H-pyrazolo[4,3-b]pyridine-1-carboxylate

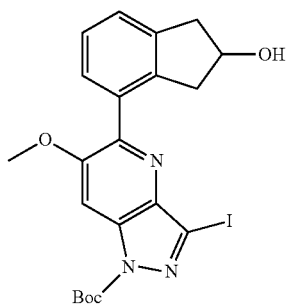 [SMILES: COc1cc2c(nc1-c1cccc3c1CC(O)C3)c(I)nn2C(=O)OC(C)(C)C]

NIS (2.1 g, 9.38 mmol) was added to a solution of 4-(6-methoxy-1H-pyrazolo[4,3-b]pyridin-5-yl)-2,3-dihydro-1H-inden-2-ol (2.40 g, 8.53 mmol) in DMF (20 ml). After stirring at 80° C. for 2 hrs, the reaction mixture was cooled to r.t., and triethylamine (1.50 ml, 10.5 mmol) and Boc-anhydride (2.30 g, 10.5 mmol) were added. After additional stirring at r.t. for 1 hr, water was added and the precipitated product was collected by filtration and air dried. The crude material was purified by Biotage Isolera to give a white solid. LCMS calculated for C$_{21}$H$_{23}$IN$_3$O$_4$ (M+H)$^+$: m/z=508.3; found 508.3.

The two enantiomers were separated with chiral prep-HPLC (Phenomenex LUX Amylose Sum 21.2×250 mm, eluting with 35% MeOH (containing 2 mM NH₃) in CO₂, at flow rate of 70 mL/min, $t_{R, peak\ 1}$=2.9 min, $t_{R, peak\ 2}$=3.6 min). Peak 2 was collected and the solvents were evaporated in vacuo.

Step 4. tert-Butyl 5-(2-hydroxy-2,3-dihydro-1H-inden-4-yl)-6-methoxy-3-(6-((tetrahydrofuran-3-yl)oxy)pyridin-3-yl)-1H-pyrazolo[4,3-b]pyridine-1-carboxylate

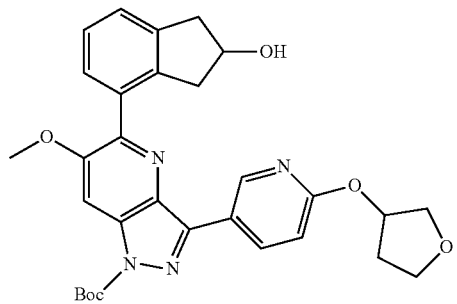 [SMILES: COc1cc2c(nc1-c1cccc3c1CC(O)C3)c(-c1ccc(OC3CCOC3)nc1)nn2C(=O)OC(C)(C)C]

tert-Butyl 5-(2-hydroxy-2,3-dihydro-1H-inden-4-yl)-3-iodo-6-methoxy-1H-pyrazolo[4,3-b]pyridine-1-carboxylate (100 mg, 0.197 mmol), 2-((tetrahydrofuran-3-yl)oxy)-5-(4,4,5,5-tetramethyl-1,3,2-dioxaborolan-2-yl)pyridine (68.9 mg, 0.237 mmol), chloro(2-dicyclohexylphosphino-2',4',6'-triisopropyl-1,1'-biphenyl)[2-(2'-amino-1,1'-biphenyl)]palladium (17 mg, 22 µmol) and potassium phosphate (85 mg, 0.40 mmol) were placed in a vial and the vial was evacuated and backfilled with N₂ three times. After 1,4-dioxane (5 ml) and water (1.0 ml) were added, the reaction mixture was stirred at 80° C. for 2 hrs. After cooling to r.t., water was added and the desired product was extracted with EtOAc. The organic phase was washed with brine, dried over sodium sulfate and the solvent was evaporated in vacuo. Crude material was purified by Biotage Isolera to give a white solid (90 mg, 84%). LCMS calculated for $C_{30}H_{33}N_4O_6$ (M+H)⁺: m/z=545.2; found 545.2.

Step 5. 4-(6-Methoxy-3-(6-((tetrahydrofuran-3-yl)oxy)pyridin-3-yl)-1H-pyrazolo[4,3-b]pyridin-5-yl)-2,3-dihydro-1H-inden-2-ol The two enantiomers of tert-butyl 5-(2-hydroxy-2,3-dihydro-1H-inden-4-yl)-6-methoxy-3-(6-((tetrahydrofuran-3-yl)oxy)pyridin-3-yl)-1H-pyrazolo[4,3-b]pyridine-1-carboxylate (90 mg, 0.197 mmol) were separated with chiral prep-HPLC (Phenomenex LUX i-Cellulose-5 5 um 21.2×250 mm, eluting with 35% MeOH (2 nM NH₃) in CO₂, at flow rate of 65 mL/min, $t_{R, peak\ 1}$=11.1 min $t_{R, peak\ 2}$=12.4 min). Peak 2 was collected and the solvents were evaporated in vacuo. The resultant material was dissolved in 1,4-dioxane (2 ml) and water (2 ml). After addition of cesium carbonate (31.3 mg, 0.096 mmol), the reaction mixture was heated at 100° C. for 2 hrs. After cooling to room temperature, the mixture was diluted with CH₃CN and purified by prep-LCMS (XBridge C18 column, eluting with a gradient of acetonitrile/water containing 0.1% TFA, at flow rate of 60 mL/min). The product was isolated as the TFA salt. LCMS calculated for $C_{25}H_{25}N_4O_4$ (M+H)⁺: m/z=445.2; Found: 445.2.

Example 74. 4-(6-Methoxy-3-(1-methyl-1H-pyrazol-4-yl)-1H-pyrazolo[4,3-b]pyridin-5-yl) 2,3-dihydro-1H-inden-2-d-2-ol

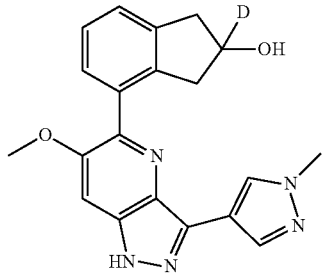

Step 1. 4-Bromo-2,3-dihydro-1H-inden-2-d-2-ol

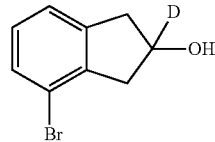 [SMILES: [2H]C1(O)Cc2cccc(Br)c2C1]

Sodium borodeuteride (0.397 g, 9.48 mmol) was added to a solution of 4-bromo-1,3-dihydro-2H-inden-2-one (1.00 g, 4.74 mmol) in THF (5 ml) and MeOH (5 ml). After the reaction mixture was stirred at r.t. for 1 h, water was added. The desired product was extracted with EtOAc, the organic phase was washed with brine, dried over sodium sulfate and the solvents were evaporated in vacuo. The resultant crude product was used in the next step without further purification.

Step 2. 4-(4,4,5,5-Tetramethyl-1,3,2-dioxaborolan-2-yl)-2,3-dihydro-1H-inden-2-d-2-ol

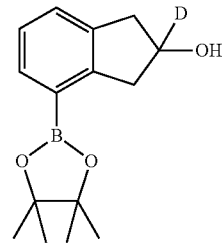 [SMILES: [2H]C1(O)Cc2cccc(B3OC(C)(C)C(C)(C)O3)c2C1]

This compound was prepared according to the procedures described in Intermediate 2, using 4-bromo-2,3-dihydro-1H-inden-2-d-2-ol instead of 4-bromo-2,3-dihydro-1H-inden-1-ol as starting material.

Step 3. 4-(6-Methoxy-3-(1-methyl-1H-pyrazol-4-yl)-1H-pyrazolo[4,3-b]pyridin-5-yl) 2,3-dihydro-JH-inden-2-d-2-ol tert-Butyl 5-chloro-6-methoxy-3-(1-methyl-1H-pyrazol-4-yl)-1H-pyrazolo[4,3-b]pyridine-1-carboxylate (1.05 g, 2.89 mmol), 4-(4,4,5,5-tetramethyl-1,3,2-dioxaborolan-2- yl)-2,3-dihydro-1H-inden-2-d-2-ol (0.904 g, 3.46 mmol), chloro(2-dicyclohexylphosphino-2',4',6'-triisopropyl-1,1'-biphenyl)[2-(2'-amino-1,1'-biphenyl)]palladium (150 mg, 0.20 mmol) and potassium phosphate (150 mg, 7.00 mmol) were placed in a vial and the vial was evacuated and backfilled with $N_2$ three times. After 1,4-dioxane (10.0 ml) and water (2.0 ml) were added, the reaction mixture was stirred at 100° C. for 1 h. After cooling to room temperature, the mixture was diluted with DCM and filtered. The filtrate was concentrated in vacuo and the resultant residue was purified by Biotage Isolera.

The two enantiomers were separated with chiral prep-HPLC (Phenomenex LUX Cellulose-1 5um 21.2×250 mm, eluting with 10% EtOH in $CO_2$, at flow rate of 65 mL/min, $t_{R, peak\ 1}$=19.5 min, $t_{R, peak\ 2}$=21.8 min). Peak 2 was collected and the solvents were evaporated in vacuo.

The resultant material was dissolved in 1,4-dioxane (2 ml) and water (2 ml). After addition of cesium carbonate (31.3 mg, 0.096 mmol) the reaction mixture was heated at 100° C. for 2 h. After cooling to room temperature, the mixture was diluted with $CH_3CN$ and purified by prep-LCMS (XBridge C18 column, eluting with a gradient of acetonitrile/water containing 0.1% TFA, at flow rate of 60 mL/min). The product was isolated as the TFA salt. LCMS calculated for $C_{20}DH_{19}N_5O_2$ (M+H)$^+$: m/z=363.2; Found: 363.2. $^1$H NMR (500 MHz, DMSO-d6) δ 8.35 (s, 1H), 8.08 (s, 1H), 7.50 (s, 1H), 7.34-7.28 (d, J=7.2 Hz, 1H), 7.29-7.20 (m, 2H), 3.90 (s, 3H), 3.84 (s, 3H), 3.16-3.11 (d, J=16.0, 1H), 3.08-3.00 (d, J=16.0, 1H), 2.88-2.80 (d, J=16.0, 1H), 2.70-2.64 (d, J=16.0, 1H) ppm.

Example 75. 4-(6-Methoxy-3-(6-(1-methyl-5-oxopyrrolidin-3-yl)pyridin-3-yl)-1H-pyrazolo[4,3-b]pyridin-5-yl)-2,3-dihydro-1H-indene-1-carbonitrile

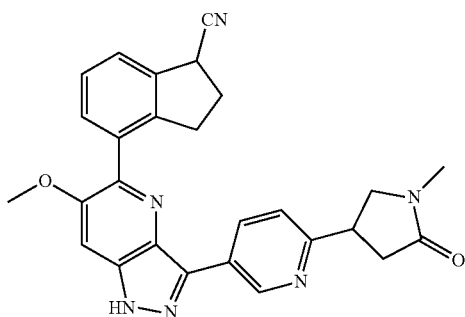 [SMILES: COc1cc2[nH]nc(-c3ccc(C4CC(=O)N(C)C4)nc3)c2nc1-c1cccc2c1CCC2C#N]

Step 1. tert-Butyl 4-(5-bromopyridin-2-yl)-2-oxopyrrolidine-1-carboxylate

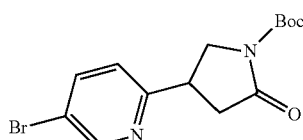

A 30-mL screw-top vial equipped with a stir bar was charged with diethyl 2,6-dimethyl-1,4-dihydropyridine-3,5-dicarboxylate (413 mg, 1.629 mmol), 5-bromo-2-iodopyridine (300 mg, 1.057 mmol), [Ir{dF(CF$_3$)ppy}$_2$(dtbbpy)]PF$_6$ (28.1 mg, 0.025 mmol), and tert-butyl 2-oxo-2,5-dihydro-1H-pyrrole-1-carboxylate (689 mg, 3.76 mmol). The vial was sealed and the atmosphere was exchanged by applying vacuum and backfilling with $N_2$. Under $N_2$ atmosphere, the tube was charged with degassed solvent (3:1 DMSO:$H_2O$, 15 mL) via syringe. The resulting suspension was stirred under irradiation with blue LEDs for 18 hours. The reaction mixture was then treated with saturated sodium bicarbonate solution (60 mL) and extracted with ethyl acetate (3×40 mL). The organic phases were combined, dried over magnesium sulfate, filtered, and concentrated under vacuum. The residue was purified by flash column chromatography to afford the desired product. LC-MS calculated for $C_{14}H_{18}BrN_2O_3$ (M+H)$^+$: m/z=341.0; found 341.0.

Step 2.
4-(5-Bromopyridin-2-yl)-1-methylpyrrolidin-2-one

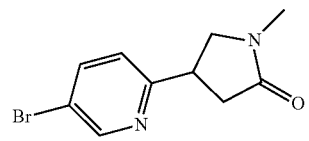

tert-Butyl 4-(5-bromopyridin-2-yl)-2-oxopyrrolidine-1-carboxylate (294 mg, 0.865 mmol) was dissolved in 1 mL of TFA and the resulting mixture was stirred at r.t. After 10 min, the reaction mixture was concentrated to dryness. The resultant residue was taken up in 2 mL of DMF and cooled to 0° C. with an ice bath. Sodium hydride (41.5 mg, 1.73 mmol) was added, and the resulting solution was stirred at 0° C. for 30 min. MeI (108 μl, 1.73 mmol) was then added, and the resulting mixture was warmed to r.t. and stirred for 2 hrs. The reaction was treated with saturated NH$_4$Cl solution and extracted with DCM. The organic phases were combined, dried over magnesium sulfate, filtered, and concentrated under vacuum. The residue was purified by flash column chromatography to afford the desired product. LC-MS calculated for $C_{10}H_{12}BrN_2O$ (M+H)+: m/z=255.0; found 255.0.

The two enantiomers were separated with chiral prep-HPLC (Phenomenex LUX Amylose-1 5um 21.2×250 mm, eluting with 35% MeOH in $CO_2$, at flow rate of 65 mL/min, $t_{R, peak\ 1}$=3.6 min, $t_{R, peak\ 2}$=4.7 min)

Step 3. 1-Methyl-4-(5-(4,4,5,5-tetramethyl-1,3,2-dioxaborolan-2-yl)pyridin-2-yl)pyrrolidin-2-one Peak 1

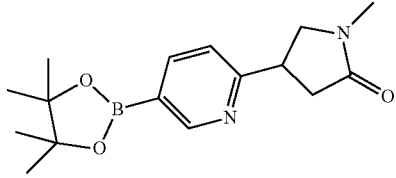

Peak 2

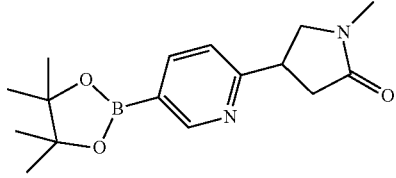

Two enantiomers of 4-(5-bromopyridin-2-yl)-1-methylpyrrolidin-2-one (60 mg, 0.235 mmol) were individually added to mixture of bis(pinacolato)diboron (65.7 mg, 0.259 mmol), potassium acetate (69.2 mg, 0.706 mmol), and PdCl$_2$(dppf)-CH$_2$Cl$_2$ adduct (19.21 mg, 0.024 mmol) in 1,4-dioxane (1 mL). The mixture was heated to 100° C. for 8 h. After this time, it was cooled to r.t. The crude product solution was used directly in the next step without further purification. LCMS calculated for C$_{16}$H$_{24}$BN$_2$O$_3$ (M+H)$^+$: m/z=303.2; found 303.2.

Step 4.
4-Bromo-2,3-dihydro-1H-indene-1-carbonitrile

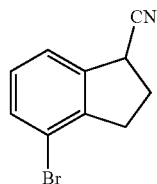 [SMILES: N#CC1CCc2c(Br)cccc21]

To a solution of 4-bromo-2,3-dihydro-1H-inden-1-one (10 g, 47.4 mmol) in DME (250 mL) and $^t$BuOH (40 mL) was added potassium tert-butoxide (10.63 g, 95 mmol) and tosylmethylisocyanide (11.10 g, 56.9 mmol) at 0° C. The mixture was stirred overnight before being treated with water and 1N HCl. The mixture was extracted with EtOAc, the organic phases were combined, dried over magnesium sulfate, filtered, and concentrated under vacuum. The residue was purified by flash column chromatography to afford the desired product. LC-MS calculated for C$_{10}$H$_9$BrN (M+H)$^+$: m/z=222.0; found 222.2.

Step 5. 4-(4,4,5,5-Tetramethyl-1,3,2-dioxaborolan-2-yl)-2,3-dihydro-1H-indene-1-carbonitrile

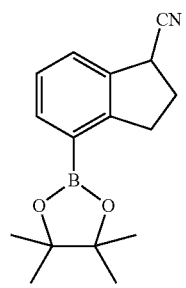 [SMILES: CC1(C)OB(c2cccc3c2CCC3C#N)OC1(C)C]

A mixture of 4-bromo-2,3-dihydro-1H-indene-1-carbonitrile (5.8 g, 26.5 mmol), potassium acetate (7.81 g, 80 mmol), bis(pinacolato)diboron (8.09 g, 31.8 mmol), PdCl$_2$(dppf)-CH$_2$Cl$_2$ adduct (1.083 g, 1.327 mmol) in 1,4-dioxane (100 mL) was heated to 100° C. for 8 h. After this time, it was cooled to r.t. The crude product solution was used directly in following step without further purification. LCMS calculated for C$_{16}$H$_{21}$BNO$_2$ (M+H)$^+$: m/z=270.2; found 270.2.

Step 6. 4-(6-Methoxy-1H-pyrazolo[4,3-b]pyridin-5-yl)-2,3-dihydro-1H-indene-1-carbonitrile

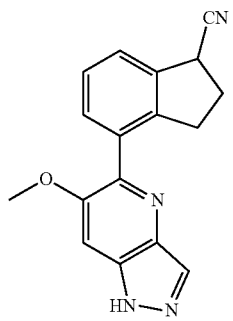 [SMILES: COc1cc2[nH]ncc2nc1-c1cccc2c1CCC2C#N]

5-Chloro-6-methoxy-1-trityl-1H-pyrazolo[4,3-b]pyridine (Example 1, step 4) (8.52 g, 20 mmol), 4-(4,4,5,5-tetramethyl-1,3,2-dioxaborolan-2-yl)-2,3-dihydro-1H-indene-1-carbonitrile (6.46 g, 24.00 mmol), chloro(2-dicyclohexylphosphino-2',4',6'-triisopropyl-1,1'-biphenyl)[2-(2'-amino-1,1'-biphenyl)]palladium (0.80 g, 1.0 mmol) and K$_3$PO$_4$ (8.48 g, 40.0 mmol) were placed in a round bottom flask and the flask was evacuated and backfilled with N$_2$ three times. After 1,4-dioxane (30 mL) and water (6 mL) were added, the reaction mixture was stirred at 100° C. for 1 h. After this time, it was cooled to r.t., diluted with water and extracted with EtOAc 3 times. The combined organic phases were washed with sat. NaCl solution, dried over Na$_2$SO$_4$, filtered and concentrated to dryness. To the residue was added 20 mL of TFA, the solution was cooled to 0° C. before triethylsilane (6.39 ml, 40.0 mmol) was added slowly. The resulting solution was stirred at rt. for 4 h, then concentrated to dryness, washed with sat. NaHCO$_3$ and extracted with EtOAc. The combined organic phases were washed with sat. NaCl solution, dried over Na$_2$SO$_4$, filtered and concentrated to dryness and purified by flash column chromatography to afford the desired product. LC-MS calculated for C$_{17}$H$_{15}$N$_4$O (M+H)$^+$: m/z=291.1; found 291.1.

Step 7. tert-Butyl 5-(1-cyano-2,3-dihydro-1H-inden-4-yl)-3-iodo-6-methoxy-1H-pyrazolo[4,3-b]pyridine-1-carboxylate

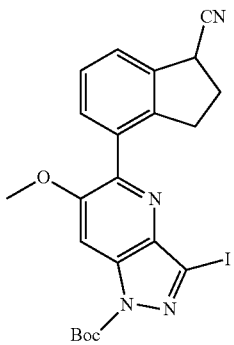 [SMILES: COc1cc2c(nc1-c1cccc3c1CCC3C#N)c(I)nn2C(=O)OC(C)(C)C]

NIS (4.26 g, 18.94 mmol) was added to a solution of 4-(6-methoxy-1H-pyrazolo[4,3-b]pyridin-5-yl)-2,3-dihydro-1H-indene-1-carbonitrile (5.0 g, 17.22 mmol) in DMF (60 ml). After stirring at 60° C. for 2 h, the reaction mixture was cooled to r.t., and DIEA (6.02 ml, 34.4 mmol) and Boc-anhydride (5.64 g, 25.8 mmol) were added. After additional stirring at r.t. for 1 h, water was added and the product was extracted with EtOAc. The combined organic phases were washed with sat. NaCl solution, dried over Na$_2$SO$_4$, filtered, concentrated to dryness and purified by flash column chromatography to afford the desired product. LC-MS calculated for C$_{22}$H$_{22}$IN$_4$O$_3$ (M+H)$^+$: m/z=517.1; found 517.1.

Step 8. 4-(6-Methoxy-3-(6-(1-methyl-5-oxopyrrolidin-3-yl)pyridin-3-yl)-1H-pyrazolo[4,3-b]pyridin-5-yl)-2,3-dihydro-1H-indene-1-carbonitrile tert-Butyl 5-(1-cyano-2,3-dihydro-1H-inden-4-yl)-3-iodo-6-methoxy-1H-pyrazolo[4,3-b]pyridine-1-carboxylate (50 mg, 0.097 mmol), 1-methyl-4-(5-(4,4,5,5-tetramethyl-1,3,2-dioxaborolan-2-yl)pyridin-2-yl)pyrrolidin-2-one (peak 1 from step 5, 35.1 mg, 0.116 mmol), PdCl$_2$(dppf)-CH$_2$Cl$_2$ adduct (7.91 mg, 9.68 µmol), and K$_3$PO$_4$ (41.1 mg, 0.194 mmol) were placed in a vial and the vial was evacuated and backfilled with N$_2$ three times. After 1,4-dioxane (1 ml) and water (100 µl) were added, the reaction mixture was stirred at 80° C. for 1 h. Then the reaction was filtered, and the solvents were evaporated in vacuo. DCM (1 ml) and TFA (0.5 ml) were added and the reaction mixture was stirred at r.t. for 30 min. The mixture was then diluted with CH$_3$CN and water and purified with prep-LCMS (XBridge C18 column, eluting with a gradient of acetonitrile/water containing 0.1% TFA, at flow rate of 60 mL/min). The product was isolated as the TFA salt.

The product was washed with sat. NaHCO$_3$ and further separated with chiral prep-HPLC (Phenomenex Lux 5 um Cellulose-2, 21.2×250 mm, eluting with 80% EtOH in hexane, at flow rate of 20 mL/min, t$_{R, peak 1}$=13 min, t$_{R, peak 2}$=16 min). Peak 1 is the desired product. LCMS calculated for C$_{27}$H$_{25}$N$_6$O$_2$ (M+H)$^+$: m/z=465.2; Found: 465.2. $^1$H NMR (500 MHz, DMSO-d6) δ 13.46 (s, 1H), 9.55 (d, J=2.1 Hz, 1H), 8.68 (dd, J=8.2, 2.2 Hz, 1H), 7.61 (s, 1H), 7.56-7.46 (m, 3H), 7.41 (t, J=7.5 Hz, 1H), 4.58 (t, J=8.1 Hz, 1H), 3.91 (s, 3H), 3.86-3.71 (m, 2H), 3.52 (dd, J=9.2, 6.4 Hz, 1H), 3.02-2.84 (m, 2H), 2.77 (s, 3H), 2.68-2.53 (m, 3H), 2.21 (dq, J=12.5, 8.3 Hz, 1H) ppm.

Example 76. 4-(6-Methoxy-3-(6-(1-methyl-5-oxopyrrolidin-3-yl)pyridin-3-yl)-1H-pyrazolo[4,3-b]pyridin-5-yl)-2,3-dihydro-1H-indene-1-carbonitrile

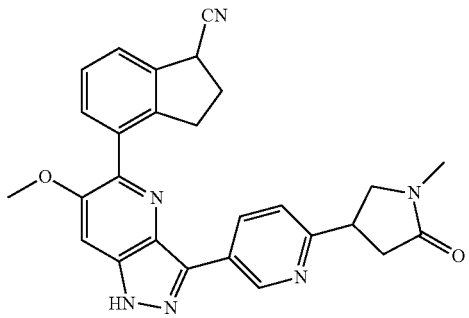 [SMILES: COc1cc2[nH]nc(-c3ccc(C4CC(=O)N(C)C4)nc3)c2nc1-c1cccc2c1CCC2C#N]

This compound was prepared according to the procedures described in Example 75, using 1-methyl-4-(5-(4,4,5,5-tetramethyl-1,3,2-dioxaborolan-2-yl)pyridin-2-yl)pyrrolidin-2-one enantiomer peak 2 instead of peak 1 from step 3. The product was isolated as the TFA salt.

The two enantiomers were separated with chiral prep-HPLC (Phenomenex LUX Amylose-1 Sum 21.2×250 mm, eluting with 45% EtOH in hexanes, at flow rate of 20 mL/min, t$_{R, peak 1}$=9.7 min, t$_{R, peak 2}$=12.7 min), in which peak 2 is the desired product. LCMS calculated for C$_{27}$H$_{25}$N$_6$O$_2$ (M+H)$^+$: m/z=465.2; Found: 465.2.

Example 77. (S)-1-(4-(5-(5-(2,3-Dimethylphenyl)-6-methoxy-1H-pyrazolo[4,3-b]pyridin-3-yl)pyridin-2-yl)piperidin-1-yl)-2-hydroxypropan-1-one

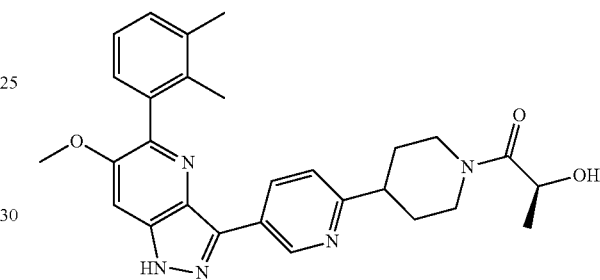

Step 1. 5-(2,3-Dimethylphenyl)-3-iodo-6-methoxy-1-((2-(trimethylsilyl)ethoxy)methyl)-1H-pyrazolo[4,3-b]pyridine

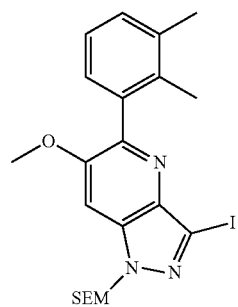

To a DMF (10 mL) solution of 5-(2,3-dimethylphenyl)-3-iodo-6-methoxy-1H-pyrazolo[4,3-b]pyridine (1.5 g, 3.90 mmol) was added DIEA (1.363 ml, 7.80 mmol) and SEM-Cl (1.04 ml, 5.85 mmol) at 0° C. After stirring overnight, the reaction was treated with water and the product was extracted with EtOAc. The combined organic phases were washed with sat. NaCl solution, dried over Na$_2$SO$_4$, filtered, concentrated to dryness and purified by flash column chromatography to afford the desired product. LC-MS calculated for C$_{21}$H$_{29}$IN$_3$O$_2$Si (M+H)$^+$: m/z=510.1; found 510.1.

Step 2. 3-(6-Chloropyridin-3-yl)-5-(2,3-dimethylphenyl)-6-methoxy-1-((2-(trimethylsilyl)ethoxy)methyl)-1H-pyrazolo[4,3-b]pyridine

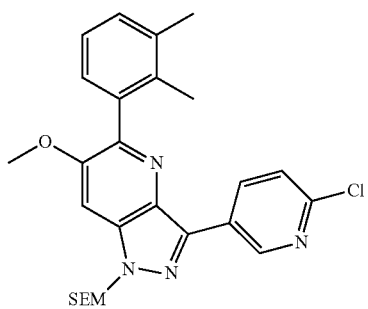 [SMILES: COc1cc2c(nc1-c1cccc(C)c1C)c(-c1ccc(Cl)nc1)nn2COCC[Si](C)(C)C]

To a solution of 5-(2,3-dimethylphenyl)-3-iodo-6-methoxy-1-((2-(trimethylsilyl)ethoxy)methyl)-1H-pyrazolo[4,3-b]pyridine (761 mg, 1.493 mmol) in 1,4-dioxane (5 mL) and water (1 mL) were added (6-chloropyridin-3-yl)boronic acid (282 mg, 1.792 mmol), $K_3PO_4$ (633 mg, 2.99 mmol), and $PdCl_2(dppf)$-$CH_2Cl_2$ adduct (119 mg, 0.149 mmol). The reaction was degassed with $N_2$ and stirred at 80° C. for 3 h. After this time, it was cooled to r.t., diluted with EtOAc, washed sequentially with water, sat. NaCl and dried over $Na_2SO_4$. The organic phases were combined, filtered, concentrated to dryness and purified by flash column chromatography to afford the desired product. LC-MS calculated for $C_{26}H_{32}ClN_4O_2Si$ $(M+H)^+$: m/z=495.2; found 495.2.

Step 3. tert-butyl 5-(5-(2,3-Dimethylphenyl)-6-methoxy-1-((2-(trimethylsilyl)ethoxy)methyl)-1H-pyrazolo[4,3-b]pyridin-3-yl)-3',6'-dihydro-[2,4'-bipyridine]-1'(2'H)-carboxylate

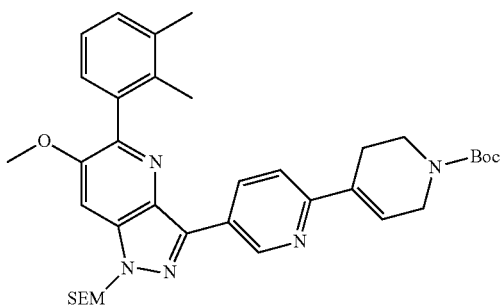 [SMILES: COc1cc2c(nc1-c1cccc(C)c1C)c(-c1ccc(C3=CCN(C(=O)OC(C)(C)C)CC3)nc1)nn2COCC[Si](C)(C)C]

To a solution of 3-(6-chloropyridin-3-yl)-5-(2,3-dimethylphenyl)-6-methoxy-1-((2-(trimethylsilyl)ethoxy)methyl)-1H-pyrazolo[4,3-b]pyridine (99 mg, 0.201 mmol) in 1,4-dioxane (2 mL) and water (0.4 mL) were added tert-butyl 4-(4,4,5,5-tetramethyl-1,3,2-dioxaborolan-2-yl)-3,6-dihydropyridine-1(2H)-carboxylate (124 mg, 0.402 mmol), $K_3PO_4$ (85 mg, 0.402 mmol) and chloro(2-dicyclohexylphosphino-2',4',6'-triisopropyl-1,1'-biphenyl)[2-(2'-amino-1,1'-biphenyl)]palladium (16 mg, 0.02 mmol). The reaction was degassed with $N_2$ and stirred at 100° C. for 3 h. After this time, it was cooled to r.t., diluted with EtOAc, washed sequentially with water, sat. NaCl and dried over $Na_2SO_4$. The organic phases were combined, filtered, concentrated to dryness and purified by flash column chromatography to afford the desired product. LC-MS calculated for $C_{36}H_{48}N_5O_4Si$ $(M+H)^+$: m/z=642.3; found 642.2.

Step 4. 5-(2,3-Dimethylphenyl)-6-methoxy-3-(6-(piperidin-4-yl)pyridin-3-yl)-1-((2-(trimethylsilyl)ethoxy)methyl)-1H-pyrazolo[4,3-b]pyridine

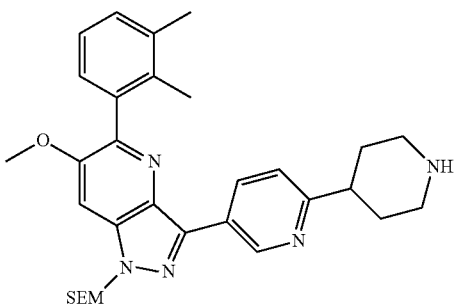 [SMILES: COc1cc2c(nc1-c1cccc(C)c1C)c(-c1ccc(C3CCNCC3)nc1)nn2COCC[Si](C)(C)C]

To a MeOH (5 mL) solution of tert-butyl 5-(5-(2,3-dimethylphenyl)-6-methoxy-1-((2-(trimethylsilyl)ethoxy)methyl)-1H-pyrazolo[4,3-b]pyridin-3-yl)-3',6'-dihydro-[2,4'-bipyridine]-1'(2'H)-carboxylate (100 mg, 0.156 mmol) was added Pd/C (16.58 mg, 0.016 mmol). The reaction was purged with $H_2$ and stirred at r.t. connected to a balloon filled with hydrogen for 4 hrs. After completion, the reaction was filtrated through a short Celite pipette and the reaction was concentrated. The crude product was dissolved in DCM (2 mL) and treated with TFA (0.5 mL) at r.t. The mixture was then concentrated to dryness and used in the next reaction without further purification. LC-MS calculated for $C_{31}H_{42}N_5O_2Si$ $(M+H)^+$: m/z=544.3; found 544.2.

Step 5. (S)-1-(4-(5-(5-(2,3-Dimethylphenyl)-6-methoxy-1H-pyrazolo[4,3-b]pyridin-3-yl)pyridin-2-yl)piperidin-1-yl)-2-hydroxypropan-1-one To a THF (1 mL) solution of 5-(2,3-dimethylphenyl)-6-methoxy-3-(6-(piperidin-4-yl)pyridin-3-yl)-1-((2-(trimethylsilyl)ethoxy)methyl)-1H-pyrazolo[4,3-b]pyridine (20 mg, 0.037 mmol) was added (S)-2-hydroxypropanoic acid (3.31 mg, 0.037 mmol), DIEA (6.42 μl, 0.037 mmol) and HATU (13.98 mg, 0.037 mmol). After stirring overnight, 1 mL of 4 N HCl was added to the reaction, which was then heated to 50° C. for 30 min. MeOH was added and the reaction was purified by prep-LCMS (XBridge C18 column, eluting with a gradient of acetonitrile/water containing 0.1% TFA, at flow rate of 60 mL/min). The product was isolated as the TFA salt. LC-MS calculated for $C_{28}H_{32}N_5O_3(M+H)^+$: m/z=486.2; found 486.2. $^1$H NMR (400 MHz, DMSO-d6) δ 13.41 (s, 1H), 9.49 (s, 1H), 8.67 (d, J=8.0 Hz, 1H), 7.57 (s, 1H), 7.49 (d, J=8.2 Hz, 1H), 7.17 (m, 3H), 4.47 (m, 2H), 4.11 (d, J=13.4 Hz, 1H), 3.86 (s, 3H), 3.14 (m, 1H), 3.08-3.00 (m, 1H), 2.72 (m, 1H), 2.32 (s, 3H), 1.98 (s, 3H), 1.91 (d, J=12.5 Hz, 2H), 1.80-1.54 (m, 2H), 1.20 m, 3H) ppm.

Example 78. 1-(4-(5-(5-(2,3-Dimethylphenyl)-6-methoxy-1H-pyrazolo[4,3-b]pyridin-3-yl)pyridin-2-yl)piperidin-1-yl)-2-hydroxyethan-1-one

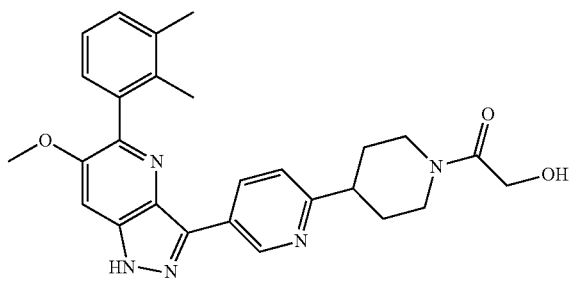 [SMILES: COc1cc2[nH]nc(-c3ccc(C4CCN(C(=O)CO)CC4)nc3)c2nc1-c1cccc(C)c1C]

This compound was prepared according to the procedure described in Example 77, using 2-hydroxyacetic acid instead of (S)-2-hydroxypropanoic acid. The product was isolated as the TFA salt. LC-MS calculated for $C_{27}H_{30}N_5O_3(M+H)^+$: m/z=472.2; found 472.2. 1H NMR (600 MHz, DMSO-d6) δ 13.77 (s, 1H), 9.67 (d, J=2.1 Hz, 1H), 9.07-8.97 (m, 1H), 7.84 (d, J=8.4 Hz, 1H), 7.73 (s, 1H), 7.41-7.21 (m, 3H), 4.64 (d, J=12.8 Hz, 1H), 4.28 (m, 1H), 3.99 (s, 3H), 3.98-3.92 (m, 2H), 3.29-3.20 (m, 2H), 2.87 (m, 1H), 2.44 (s, 3H), 2.10 (s, 3H), 2.06 (d, J=13.1 Hz, 2H), 1.82 (m, 2H) ppm.

Example 79. 4-(5-(5-(2,3-Dimethylphenyl)-6-methoxy-1H-pyrazolo[4,3-b]pyridin-3-yl)pyridin-2-yl)cyclohexane-1-carboxylic acid

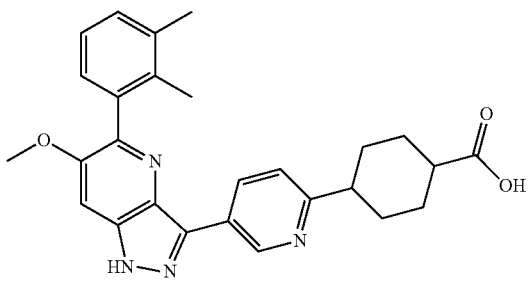 [SMILES: COc1cc2[nH]nc(-c3ccc(C4CCC(C(=O)O)CC4)nc3)c2nc1-c1cccc(C)c1C]

Step 1. 5-(2,3-Dimethylphenyl)-3-iodo-6-methoxy-1-((2-(trimethylsilyl)ethoxy)methyl)-1H-pyrazolo[4,3-b]pyridine

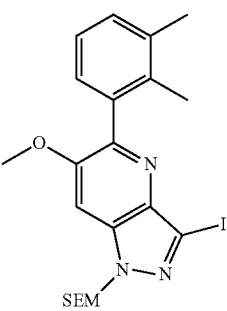 [SMILES: COc1cc2c(nc1-c1cccc(C)c1C)c(I)nn2COCC[Si](C)(C)C]

N-iodosuccinimide (0.586 g, 2.61 mmol) was added to a solution of 5-(2,3-dimethylphenyl)-3-iodo-6-methoxy-1H-pyrazolo[4,3-b]pyridine (0.82 g, 2.17 mmol) in DMF (6 ml) and the reaction was stirred at 60° C. for 1 hr. After cooling with the ice bath, the mixture was treated with DIPEA (0.455 ml, 2.61 mmol), followed by SEM-Cl (0.385 ml, 2.17 mmol). The reaction mixture was stirred at r.t. for 2 hrs, then treated with water and the product was extracted with EtOAc. The organic phase was washed with sat. $Na_2S_2O_3$, brine, dried over $Na_2SO_4$, filtered and concentrated. The residue was purified by Biotage Isolera to afford the desired product. LC-MS calculated for $C_{21}H_{29}IN_3O_2Si$ $(M+H)^+$: m/z=510.1; found 510.0.

Step 2. 3-(6-Chloropyridin-3-yl)-5-(2,3-dimethylphenyl)-6-methoxy-1-((2-(trimethylsilyl)ethoxy)methyl)-1H-pyrazolo[4,3-b]pyridine

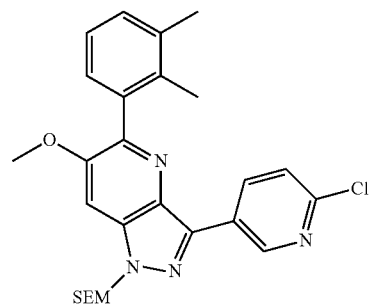 [SMILES: COc1cc2c(nc1-c1cccc(C)c1C)c(-c1ccc(Cl)nc1)nn2COCC[Si](C)(C)C]

5-(2,3-Dimethylphenyl)-3-iodo-6-methoxy-1-((2-(trimethylsilyl)ethoxy)methyl)-1H-pyrazolo[4,3-b]pyridine (0.500 g, 0.981 mmol), (6-chloropyridin-3-yl)boronic acid (0.232 g, 1.472 mmol), bis(diphenylphosphino)ferrocene]-dichloropalladium(II) (75 mg, 0.09 mmol) and $K_3PO_4$ (0.417 g, 1.96 mmol) were placed in a vial with septum. The vial was evacuated and backfilled with $N_2$ three times, 1,4-dioxane (5 mL) and water (0.5 mL) were added, and the reaction was stirred at 60° C. for 1 hr. The mixture was filtered. The filtrate was partitioned between water and EtOAc. The organic phase was separated, washed with brine, dried over $Na_2SO_4$, filtered and concentrated. The residue was purified by Biotage Isolera to afford the desired product. LC-MS calculated for $C_{26}H_{32}ClN_4O_2Si$ $(M+H)^+$: m/z=495.2; found 495.3.

Step 3. Ethyl 4-(5-(5-(2,3-dimethylphenyl)-6-methoxy-1-((2-(trimethylsilyl)ethoxy)methyl)-1H-pyrazolo[4,3-b]pyridin-3-yl)pyridin-2-yl)cyclohex-3-ene-1-carboxylate

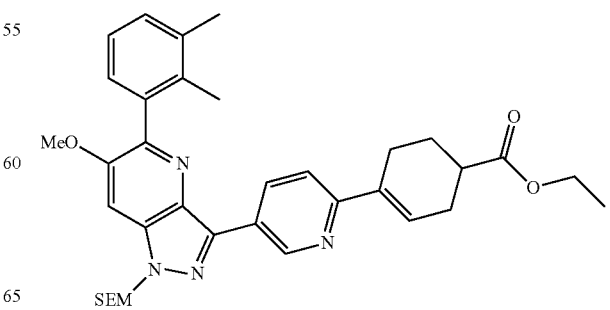

3-(6-Chloropyridin-3-yl)-5-(2,3-dimethylphenyl)-6-methoxy-1-((2-(trimethylsilyl)ethoxy)-methyl)-1H-pyrazolo[4,3-b]pyridine (430 mg, 0.869 mmol), 4-(4,4,5,5-tetramethyl-1,3,2-dioxaborolan-2-yl)cyclohex-3-ene-1-carboxylate (365 mg, 1.3 mmol), dicyclohexyl(2',4',6'-triisopropylbiphenyl-2-yl)phosphine-(2'-aminobiphenyl-2-yl)(chloro)palladium (68 mg, 0.087 mmol) and $K_3PO_4$ (221 mg, 1.042 mmol) were placed in a vial with septum. The vial was evacuated and backfilled with $N_2$ three times, 1,4-dioxane (5 mL) and water (1.0 mL) were added and the reaction mixture was stirred at 80° C. for 7 hrs. After cooling to r.t., the reaction was treated with water and the product was extracted with EtOAc. The organic phase was separated, washed with brine, dried and concentrated. The residue was purified by Biotage Isolera to afford the desired product. LC-MS calculated for $C_{35}H_{45}N_4O_4Si$ $(M+H)^+$: m/z=613.3; found 613.5.

Step 4. 4-(5-(5-(2,3-Dimethylphenyl)-6-methoxy-1-((2-(trimethylsilyl)ethoxy)methyl)-1H-pyrazolo[4,3-b]pyridin-3-yl)pyridin-2-yl)cyclohexane-1-carboxylic acid

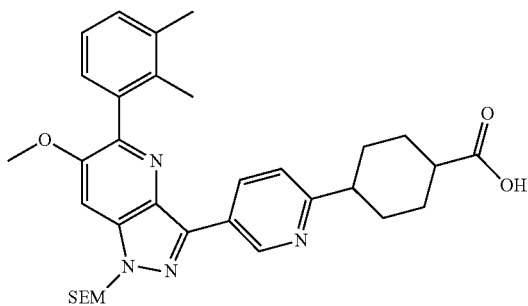 [SMILES: COc1cc2c(nc1-c1cccc(C)c1C)c(-c1ccc(C3CCC(C(=O)O)CC3)nc1)nn2COCC[Si](C)(C)C]

A mixture of ethyl 4-(5-(5-(2,3-dimethylphenyl)-6-methoxy-1-((2-(trimethylsilyl)ethoxy)-methyl)-1H-pyrazolo[4,3-b]pyridin-3-yl)pyridin-2-yl)cyclohexane-1-carboxylate (0.53 g, 0.865 mmol) and platinum(IV) oxide hydrate (0.068 g, 0.259 mmol) in ethyl acetate (10 ml) was stirred under a balloon of hydrogen at r.t. overnight. The reaction was then filtered through a pad of Celite and rinsed with EtOAc. After concentrating in vacuo, the residue was purified by Biotage Isolera to afford the ester intermediate. The ester was dissolved in a THF (2 ml), MeOH (2 ml), and water (2 ml) mixture. 1M solution of sodium hydroxide (4.32 ml, 4.32 mmol) was added to the resulted solution. The reaction mixture was stirred at r.t. for 1 h. The organic solvents were removed in vacuo, and pH of the resulting solution was adjusted to 4-5 with 1N HCl solution. The solids formed were collected by filtration, washed with water, and air dried to give the desired product. LC-MS calculated for $C_{33}H_{43}N_4O_4Si$ $(M+H)^+$: m/z=587.3; found 587.4.

Step 5. 4-(5-(5-(2,3-Dimethylphenyl)-6-methoxy-M-pyrazolo[4,3-b]pyridin-3-yl)pyridin-2-yl)cyclohexane-1-carboxylic acid TFA (0.5 ml, 2.60 mmol) was added to a solution of 4-(5-(5-(2,3-dimethylphenyl)-6-methoxy-1-((2-(trimethylsilyl)ethoxy)methyl)-1H-pyrazolo[4,3-b]pyridin-3-yl)pyridin-2-yl)cyclohexane-1-carboxylic acid (20 mg, 0.034 mmol) in DCM (0.5 ml) and the reaction mixture was stirred at r.t. for 1 h. After concentrating in vacuo, the residue was treated with ammonium hydroxide solution in water (28%) (0.5 ml) and MeOH (1 ml). The reaction mixture was stirred at r.t. for 1 h. The reaction was then diluted with water and MeOH and purified by prep-LCMS (XBridge C18 column, eluting with a gradient of acetonitrile/water containing 0.1% TFA, at flow rate of 60 mL/min). The product was isolated as the TFA salt. LCMS calculated for $C_{27}H_{29}N_4O_3$ $(M+H)^+$: m/z=457.2; found 457.2.

Example 80. (3S,4R)-1-(5-(5-(2,3-Dimethylphenyl)-6-methoxy-1H-pyrazolo[4,3-b]pyridin-3-yl)pyridin-2-yl)-4-fluoropyrrolidin-3-amine

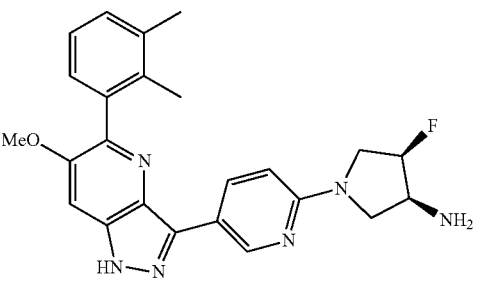 [SMILES: COc1cc2[nH]nc(-c3ccc(N4C[C@@H](F)[C@@H](N)C4)nc3)c2nc1-c1cccc(C)c1C]

Step 1. 5-(2,3-Dimethylphenyl)-3-(6-fluoropyridin-3-yl)-6-methoxy-1-((2-(trimethylsilyl)ethoxy)methyl)-1H-pyrazolo[4,3-b]pyridine

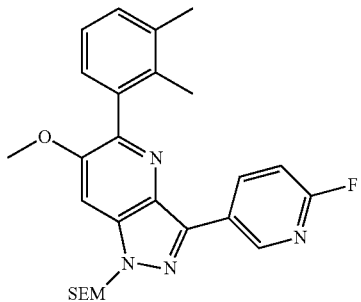 [SMILES: COc1cc2c(nc1-c1cccc(C)c1C)c(-c1ccc(F)nc1)nn2COCC[Si](C)(C)C]

5-(2,3-Dimethylphenyl)-3-iodo-6-methoxy-1-((2-(trimethylsilyl)ethoxy)methyl)-1H-pyrazolo[4,3-b]pyridine (0.830 g, 1.629 mmol), (6-fluoropyridin-3-yl)boronic acid (0.344 g, 2.444 mmol), dicyclohexyl(2',4',6'-triisopropylbiphenyl-2-yl)phosphine-(2'-aminobiphenyl-2-yl)(chloro)palladium (0.128 g, 0.163 mmol) and $K_3PO_4$ (0.69 g, 3.26 mmol) were placed in a vial with septum. The vial was evacuated and backfilled with $N_2$ three times, 1,4-dioxane (10 mL) and water (2 mL) were added, and the reaction mixture was stirred at 60° C. for 1 h. The mixture was filtered. The filtrate was partitioned between water and EtOAc. The organic phase was separated, washed with brine, dried over $Na_2SO_4$, filtered and concentrated. The residue was purified by Biotage Isolera to afford the desired product. LC-MS calculated for $C_{26}H_{32}FN_4O_2Si$ $(M+H)^+$: m/z=479.2; found 479.1.

Step 2. (3S,4R)-1-(5-(5-(2,3-Dimethylphenyl)-6-methoxy-1H-pyrazolo[4,3-b]pyridin-3-yl)pyridin-2-yl)-4-fluoropyrrolidin-3-amine A mixture of 5-(2,3-dimethylphenyl)-3-(6-fluoropyridin-3-yl)-6-methoxy-1-((2-(trimethylsilyl)-ethoxy)methyl)-1H- pyrazolo[4,3-b]pyridine (20 mg, 0.042 mmol), tert-butyl ((3S,4R)-4-fluoropyrrolidin-3-yl)carbamate (8.53 mg, 0.042 mmol) and DIPEA (21.89 µl, 0.125 mmol) in DMSO (0.2 ml) was stirred at 110° C. overnight. After cooling to r.t., the mixture was partitioned between water and EtOAc. The organic phase was separated, washed with brine, dried and concentrated. The residue was dissolved in DCM (0.5 ml), treated with TFA (0.5 ml, 2.60 mmol) and stirred at r.t. for 1 h. After concentrating in vacuo, the residue was treated with ammonium hydroxide solution in water (28%) (0.5 ml) and MeOH (1 ml). The reaction mixture was stirred at r.t for 1 h. The reaction was then diluted with water and MeOH and purified by prep-LCMS (XBridge C18 column, eluting with a gradient of acetonitrile/water containing 0.1% TFA, at flow rate of 60 mL/min). The product was isolated as the TFA salt. LCMS calculated for $C_{24}H_{26}FN_6O$ $(M+H)^+$: m/z=433.2; found 433.2. $^1$H NMR (600 MHz, DMSO-d6) δ 9.18 (s, 1H), 8.66 (s, 2H), 8.53 (dd, J=8.9, 2.3 Hz, 1H), 7.53 (s, 1H), 7.25-7.21 (m, 1H), 7.17 (t, J=7.5 Hz, 1H), 7.12 (d, J=9.0 Hz, 1H), 6.80 (d, J=9.0 Hz, 1H), 5.50 (dt, J=53.9, 3.5 Hz, 1H), 4.25-4.08 (m, 1H), 4.05-3.98 (m, 1H), 3.95-3.86 (m, 1H), 3.85 (s, 3H), 3.78 (dd, J=13.2, 3.5 Hz, 1H), 3.48 (t, J=9.7 Hz, 1H), 2.32 (s, 3H), 1.98 (s, 3H) ppm.

Example 81. (2S)-1-(4-(5-(5-(2-Fluoro-2,3-dihydro-1H-inden-4-yl)-6-methoxy-1H-pyrazolo[4,3-b]pyridin-3-yl)pyridin-2-yl)piperidin-1-yl)-2-hydroxypropan-1-one

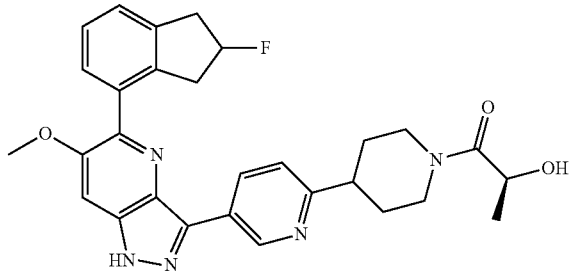 [SMILES: COc1cc2[nH]nc(-c3ccc(C4CCN(C(=O)[C@H](C)O)CC4)nc3)c2nc1-c1cccc2c1CC(F)C2]

Step 1. Chiral Separation of 4-bromo-2,3-dihydro-1H-inden-2-ol

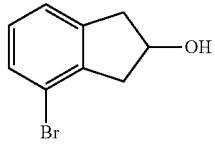

peak 2

Two enantiomers of the commercially available 4-bromo-2,3-dihydro-1H-inden-2-ol were separated by chiral prep-SFC (ChiralTech IG Sum 21×250 mm, eluting with 15% EtOH (containing 2 mM ammonia), at flow rate of 70 mL/min, $t_{R, peak\ 1}$=3.2 min, $t_{R, peak\ 2}$=3.9 min). Peak 2 was collected and the solvents were evaporated in vacuo.

Step 2. 4-Bromo-2-fluoro-2,3-dihydro-1H-indene

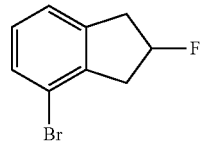 [SMILES: FC1Cc2cccc(Br)c2C1]

A solution of 4-bromo-2,3-dihydro-1H-inden-2-ol (0.50 g, 2.3 mmol) (Peak 2 from chiral separation in Step 1) in DCM (5 mL) was cooled in dry ice/acetone bath before DAST (0.4 mL, 3.03 mmol) was slowly added. After 30 min the mixture was allowed to warm to r.t. The reaction was treated with ice and the product was extracted with DCM. The organic phase was separated, washed with brine, dried over sodium sulfate and the solvent was removed in vacuo. The obtained crude material was purified by Biotage Isolera.

Step 3. 2-(2-Fluoro-2,3-dihydro-1H-inden-4-yl)-4,4,5,5-tetramethyl-1,3,2-dioxaborolane

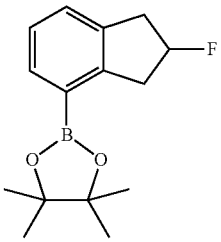 [SMILES: CC1(C)OB(c2cccc3c2CC(F)C3)OC1(C)C]

A mixture of 4-bromo-2-fluoro-2,3-dihydro-1H-indene (0.20 g, 0.930 mmol), 4,4,4',4',5,5,5',5'-octamethyl-2,2'-bi(1,3,2-dioxaborolane) (0.472 g, 1.9 mmol), [1,1'-bis(diphenylphosphino)-ferrocene]-dichloropalladium(II) (25 mg, 0.03 mmol) and potassium acetate (0.5 g) in dioxane (5 mL) was stirred at 80° C. overnight. After cooling to r.t., the reaction mixture was filtered, the solvent was evaporated in vacuo and the crude material was purified by Biotage Isolera.

Step 4. 5-(2-Fluoro-2,3-dihydro-1H-inden-4-yl)-6-methoxy-1H-pyrazolo[4,3-b]pyridine

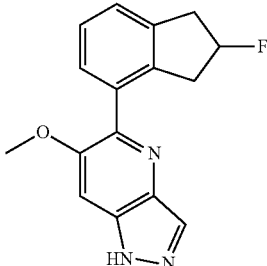

A mixture of 2-(2-fluoro-2,3-dihydro-1H-inden-4-yl)-4,4,5,5-tetramethyl-1,3,2-dioxaborolane (0.25 g, 0.95 mmol), tert-butyl 5-chloro-6-methoxy-1H-pyrazolo[4,3-b]pyridine-1-carboxylate (0.27 g, 0.954 mmol), chloro(2-dicyclohexylphosphino-2',4',6'-triisopropyl-1,1'-biphenyl)[2-(2'-amino-1,1'-biphenyl)]palladium (25 mg, 33 mmol) and K₃PO₄ (300 mg) in dioxane (4 mL) and water (0.4 mL) was stirred at 80° C. under nitrogen overnight. After cooling to r.t., the reaction mixture was filtered, the solvent was evaporated in vacuo and the crude material was purified by Biotage Isolera.

4N HCl in dioxane (2 mL) was then added to the desired product and the reaction mixture was stirred at r.t. for 2 hrs. It was diluted with ethyl acetate and neutralized with NaHCO₃ solution. The organic phase was separated, washed with brine, dried over sodium sulfate, filtered and the solvents were removed in vacuo. LC-MS calculated for $C_{16}H_{15}FN_3O$ (M+H)⁺: m/z=284.1; found 284.2.

Step 5. tert-Butyl 5-(2-fluoro-2,3-dihydro-1H-inden-4-yl)-3-iodo-6-methoxy-1H-pyrazolo[4,3-b]pyridine-1-carboxylate

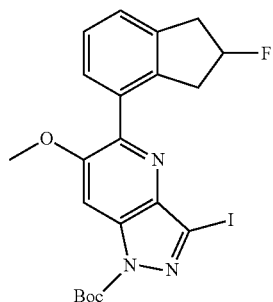 [SMILES: COc1cc2c(nc1-c1cccc3c1CC(F)C3)c(I)nn2C(=O)OC(C)(C)C]

NIS (0.206 g, 0.918 mmol) was added to a solution of 5-(2-fluoro-2,3-dihydro-1H-inden-4-yl)-6-methoxy-1H-pyrazolo[4,3-b]pyridine (0.26 g, 0.918 mmol) in DMF (5 ml). After stirring at 60° C. for 2 h, the reaction mixture was cooled to r.t., and triethylamine (0.23 ml, 1.64 mmol) and Boc-anhydride (0.30 g, 1.37 mmol) were added. After additional stirring at r.t. for 1 h, water was added and precipitated product was collected by filtration, air dried and used in the next step without further purification. LC-MS calculated for $C_{21}H_{22}FIN_3O_3$ (M+H)⁺: m/z=510.1; found 510.1.

Step 6. tert-Butyl 5-bromo-3',6'-dihydro-[2,4'-bipyridine]-1'(2'H)-carboxylate

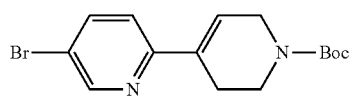

A mixture of tert-butyl 4-(4,4,5,5-tetramethyl-1,3,2-dioxaborolan-2-yl)-3,6-dihydropyridine-1(2H)-carboxylate (1.85 g, 5.98 mmol), chloro(2-dicyclohexylphosphino-2',4',6'-triisopropyl-1,1'-biphenyl)[2-(2'-amino-1,1'-biphenyl)]palladium (250 mg, 0.330 mmol), K₃PO₄ (1.0 g) in dioxane (10 mL) and water (2 mL) was stirred at 80° C. overnight. The reaction mixture was then cooled to r.t., filtered, and the solvent was evaporated in vacuo. The obtained crude material was purified by Biotage Isolera twice to give 0.23 g of white solid. LC-MS calculated for $C_{11}H_{11}BrN_2O_2$ (M-tBu+H)⁺: m/z=282.1, 284.1; found 282.1, 284.1.

Step 7. tert-Butyl 5-(4,4,5,5-tetramethyl-1,3,2-dioxaborolan-2-yl)-3',6'-dihydro-[2,4'-bipyridine]-1'(2'H)-carboxylate

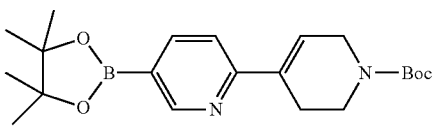 [SMILES: CC(C)(C)OC(=O)N1CC=C(c2ccc(B3OC(C)(C)C(C)(C)O3)cn2)CC1]

A mixture of 4,4,4',4',5,5,5',5'-octamethyl-2,2'-bi(1,3,2-dioxaborolane) (0.275 g, 1.085 mmol), tert-butyl 5-bromo-3',6'-dihydro-[2,4'-bipyridine]-1'(2'H)-carboxylate (0.23 g, 0.678 mmol), potassium acetate (0.2 g) and [1,1'-bis(diphenylphosphino)ferrocene]-dichloropalladium(II) (50 mg, 0.06 mmol) in dioxane (3 mL) was stirred at 80° C. overnight. After cooling to r.t., the reaction mixture was filtered, the solvent was evaporated in vacuo and the crude material was purified by Biotage Isolera. LC-MS calculated for $C_{21}H_{32}BN_2O_4$ (M+H)⁺: m/z=387.2; found 387.2.

Step 8. tert-Butyl 3-(1'-(tert-butoxycarbonyl)-1',2',3',6'-tetrahydro-[2,4'-bipyridin]-5-yl)-5-(2-fluoro-2,3-dihydro-1H-inden-4-yl)-6-methoxy-1H-pyrazolo[4,3-b]pyridine-1-carboxylate

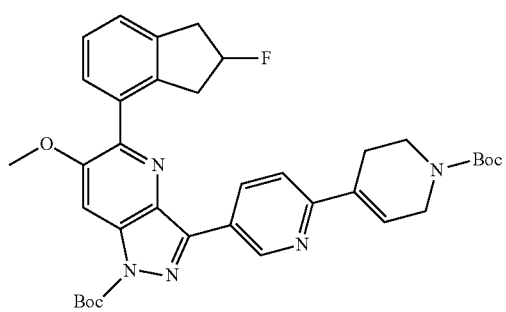 [SMILES: COc1cc2c(nc1-c1cccc3c1CC(F)C3)c(-c1ccc(C3=CCN(C(=O)OC(C)(C)C)CC3)nc1)nn2C(=O)OC(C)(C)C]

A mixture of tert-butyl 5-(4,4,5,5-tetramethyl-1,3,2-dioxaborolan-2-yl)-3',6'-dihydro-[2,4'-bipyridine]-1'(2'H)-carboxylate (0.050 g, 0.130 mmol), tert-butyl 5-(2-fluoro-2,3-dihydro-1H-inden-4-yl)-3-iodo-6-methoxy-1H-pyrazolo[4,3-b]pyridine-1-carboxylate (0.066 g, 0.130 mmol) chloro(2-dicyclohexylphosphino-2',4',6'-triisopropyl-1,1'-biphenyl)[2-(2'-amino-1,1'-biphenyl)]palladium (8 mg, 11 μmol) and K₃PO₄ (0.050 g) in dioxane (3 mL) and water (0.3 mL) was stirred at 80° C. overnight. After cooling to r.t., the reaction mixture was filtered and the solvent was evaporated in vacuo. The crude material was dissolved in methanol and purified by prep-LCMS (XBridge C18 column, eluting with a gradient of acetonitrile/water containing 0.1% TFA, at flow rate of 60 mL/min). LC-MS calculated for $C_{36}H_{41}FN_5O_5$ (M+H)⁺: m/z=642.3, found 642.3.

Step 9. 5-(2-Fluoro-2,3-dihydro-1H-inden-4-yl)-6-methoxy-3-(6-(piperidin-4-yl)pyridin-3-yl)-1H-pyrazolo[4,3-b]pyridine

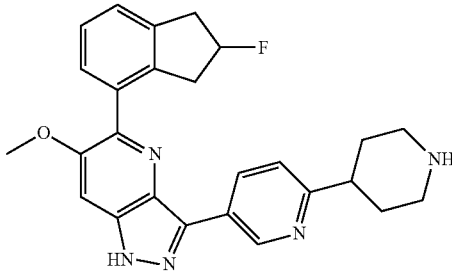 [SMILES: COc1cc2[nH]nc(-c3ccc(C4CCNCC4)nc3)c2nc1-c1cccc2c1CC(F)C2]

A mixture of tert-butyl 3-(1'-(tert-butoxycarbonyl)-1',2',3',6'-tetrahydro-[2,4'-bipyridin]-5-yl)-5-(2-fluoro-2,3-dihydro-1H-inden-4-yl)-6-methoxy-1H-pyrazolo[4,3-b]pyridine-1-carboxylate (0.010 g, 0.016 mmol) and palladium on carbon (5 mg, 10%) in methanol (5 mL) was connected to a balloon filled with hydrogen and the reaction mixture was stirred at r.t. for 3 hrs. The reaction mixture was then filtered and concentrated in vacuo. 4N HCl solution in dioxane was then added and the reaction was stirred at r.t. for 30 min. It was then diluted with methanol and purified by prep-LCMS (XBridge C18 column, eluting with a gradient of acetonitrile/water containing 0.1% TFA, at flow rate of 60 mL/min). LC-MS calculated for $C_{26}H_{27}FN_5O$ (M+H)$^+$: m/z=444.1, found 444.1.

Step 10. (2S)-1-(4-(5-(5-(2-Fluoro-2,3-dihydro-1H-inden-4-yl)-6-methoxy-1H-pyrazolo[4,3-b]pyridin-3-yl)pyridin-2-yl)piperidin-1-yl)-2-hydroxypropan-1-one HATU (35 mg, 0.09 mmol) was added to a solution of (S)-2-hydroxypropanoic acid (32 mg, 0.355 mmol), 5-(2-fluoro-2,3-dihydro-1H-inden-4-yl)-6-methoxy-3-(6-(piperidin-4-yl)pyridin-3-yl)-1H-pyrazolo[4,3-b]pyridine (5 mg, 10.15 μmol) and DIPEA (0.05 mL) in DMF (1 mL). After stirring at r.t. for 1 h, the reaction mixture was diluted with methanol, filtered and purified with prep-LCMS (XBridge C18 column, eluting with a gradient of acetonitrile/water containing 0.1% TFA, at flow rate of 60 mL/min). The product was isolated as the TFA salt. LC-MS calculated for $C_{29}H_{31}FN_5O_3$ (M+H)$^+$: m/z=516.3, found 516.3.

Example 82. 1-(4-(5-(5-(2-Fluoro-2,3-dihydro-1H-inden-4-yl)-6-methoxy-1H-pyrazolo[4,3-b]pyridin-3-yl)pyridin-2-yl)piperidin-1-yl)-2-hydroxyethan-1-one

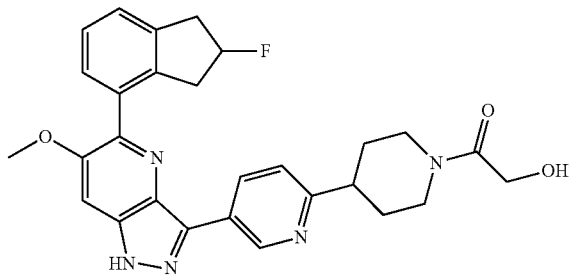 [SMILES: COc1cc2[nH]nc(-c3ccc(C4CCN(C(=O)CO)CC4)nc3)c2nc1-c1cccc2c1CC(F)C2]

This compound was prepared according to the procedures described in Example 81, using 2-hydroxyacetic acid instead of (S)-2-hydroxypropanoic acid as starting material. The product was isolated as the TFA salt. LC-MS calculated for $C_{28}H_{29}FN_5O_3$ (M+H)$^+$: m/z=502.2, found 502.2.

Example 83. (7R,8aS)-2-(5-(5-(2-Fluoro-2,3-dihydro-1H-inden-4-yl)-6-methoxy-1H-pyrazolo[4,3-b]pyridin-3-yl)pyridin-2-yl)octahydropyrrolo[1,2-a]pyrazin-7-ol

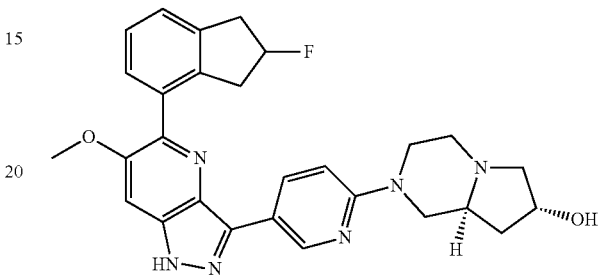

Step 1. (7R,8aS)-2-(5-Bromopyridin-2-yl)octahydropyrrolo[1,2-a]pyrazin-7-ol

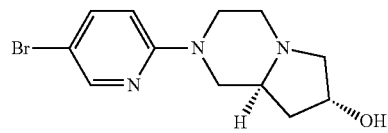 [SMILES: O[C@@H]1C[C@H]2CN(c3ccc(Br)cn3)CCN2C1]

A mixture of (7R,8aS)-octahydropyrrolo[1,2-c]pyrazin-7-ol (0.045 g, 0.316 mmol), 5-bromo-2-fluoropyridine (0.056 g, 0.316 mmol) and $Cs_2CO_3$ (120 mg, 0.369 mmol) in DMF (1 mL) was stirred at 80° C. for 4 h. The solvent was then evaporated in vacuo and the residue was purified by Biotage Isolera. LC-MS calculated for $C_{12}H_{17}BrN_3O$ (M+H)$^+$: m/z=298.1, 300.1, found 297.9, 299.9.

Step 2. (7R,8aS)-2-(5-(4,4,5,5-Tetramethyl-1,3,2-dioxaborolan-2-yl)pyridin-2-yl)octahydropyrrolo[1,2-a]pyrazin-7-ol

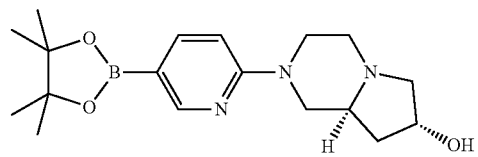 [SMILES: CC1(C)OB(c2ccc(N3CCN4C[C@H](O)C[C@H]4C3)nc2)OC1(C)C]

A mixture of 4,4,4',4',5,5,5',5'-octamethyl-2,2'-bi(1,3,2-dioxaborolane) (0.061 g, 0.241 mmol), (7R,8aS)-2-(5-bromopyridin-2-yl)octahydropyrrolo[1,2-a]pyrazin-7-ol (0.045 g, 0.151 mmol), potassium acetate (0.050 g) and [1,1'-bis(diphenylphosphino)ferrocene]-dichloropalladium(II) (16 mg, 0.02 mmol) in dioxane (2 mL) was stirred at 80° C. overnight. After cooling to r.t., the reaction mixture was filtered, the solvent was evaporated in vacuo and the crude material was purified by prep-LCMS (XBridge C18 column, eluting with a gradient of acetonitrile/water containing 0.1% TFA, at flow rate of 60 mL/min). LC-MS calculated for $C_{18}H_{29}BN_3O_3$ (M+H)+: m/z=346.2, found 346.2.

Step 3. (7R,8aS)-2-(5-(5-(2-Fluoro-2,3-dihydro-1H-inden-4-yl)-6-methoxy-1H-pyrazolo[4,3-b]pyridin-3-yl)pyridin-2-yl)octahydropyrrolo[1,2-a]pyrazin-7-ol A mixture of (7R,8aS)-2-(5-(4,4,5,5-tetramethyl-1,3,2-dioxaborolan-2-yl)pyridin-2-yl)octahydropyrrolo[1,2-c]pyrazin-7-ol (0.027 g, 0.079 mmol), tert-butyl 5-(2-fluoro-2,3-dihydro-1H-inden-4-yl)-3-iodo-6-methoxy-1H-pyrazolo[4,3-b]pyridine-1-carboxylate (0.020 g, 0.039 mmol), chloro(2-dicyclohexylphosphino-2',4',6'-triisopropyl-1,1'-biphenyl)[2-(2'-amino-1,1'-biphenyl)]palladium (8 mg, 10 μmol) and $K_3PO_4$ (10 mg) in dioxane (1 mL) and water (0.1 mL) was stirred at 80° C. overnight. The mixture was concentrated in vacuo. After methanol (1 mL) and 4N HCl in dioxane (1 mL) were added, the obtained reaction mixture was stirred at r.t. for 1 h. It was then diluted with methanol, filtered and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{28}H_{30}FN_6O_2$ (M+H)+: m/z=501.3, found 501.2. 1H NMR (500 MHz, DMSO-$d_6$) δ 9.30-9.19 (m, 1H), 8.52 (dd, J=8.8, 2.3 Hz, 1H), 7.55 (s, 1H), 7.43-7.35 (m, 2H), 7.32 (t, J=7.5 Hz, 1H), 6.91 (d, J=8.9 Hz, 1H), 5.49 (dt, J=53.5, 4.8 Hz, 1H), 4.71 (dd, J=102.1, 13.9 Hz, 1H), 4.47 (d, J=4.0 Hz, 1H), 4.30 (dd, J=14.5, 4.5 Hz, 1H), 4.18-4.04 (m, 1H), 3.90 (s, 3H), 3.85-3.75 (m, 1H), 3.73-3.59 (m, 2H), 3.56-3.11 (m, 6H), 2.96 (dd, J=25.8, 17.8 Hz, 1H), 2.15-1.94 (m, 2H) ppm.

Example 84. 5-(2-Fluoro-2,3-dihydro-1H-inden-4-yl)-6-methoxy-3-(1-methyl-1H-pyrazol-4-yl)-1H-pyrazolo[4,3-b]pyridine

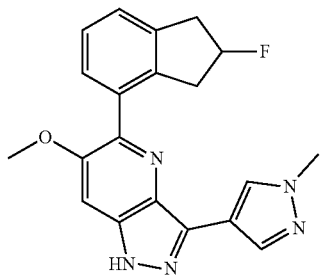

This compound was prepared according to the procedures described in Example 83, using 1-methyl-4-(4,4,5,5-tetramethyl-1,3,2-dioxaborolan-2-yl)-1H-pyrazole instead of (7R,8aS)-2-(5-(4,4,5,5-tetramethyl-1,3,2-dioxaborolan-2-yl)pyridin-2-yl)octahydropyrrolo[1,2-c]pyrazin-7-ol as starting material. The product was isolated as the TFA salt. LC-MS calculated for $C_{20}H_{19}FN_5O$ (M+H)+: m/z=364.1, found 364.1. 1H NMR (600 MHz, DMSO-d6) δ 8.29 (s, 1H), 8.06 (s, 1H), 7.49 (s, 1H), 7.40 (d, J=7.6 Hz, 1H), 7.38-7.34 (m, 1H), 7.33-7.29 (m, 1H), 5.62-5.36 (m, 1H), 3.91 (s, 3H), 3.89 (s, 3H), 3.45-3.13 (m, 3H), 3.01 (dd, J=25.9, 17.8 Hz, 1H) ppm.

Example 85. (7S,8aR)-2-(5-(5-(2,3-Dimethylphenyl)-6-methoxy-1H-pyrazolo[4,3-b]pyridin-3-yl)pyridin-2-yl)octahydropyrrolo[1,2-a]pyrazin-7-ol

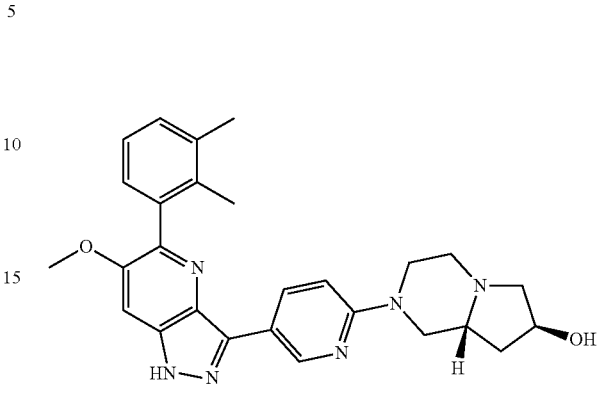

Step 1. tert-Butyl 5-(2,3-dimethylphenyl)-3-(6-fluoropyridin-3-yl)-6-methoxy-1H-pyrazolo[4,3-b]pyridine-1-carboxylate

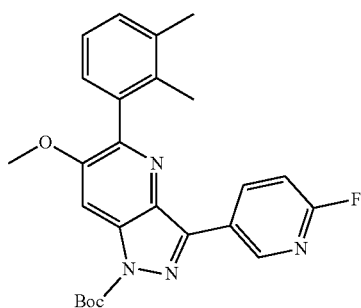 [SMILES: COc1cc2c(nc1-c1cccc(C)c1C)c(-c1ccc(F)nc1)nn2C(=O)OC(C)(C)C]

A mixture of tert-butyl 5-(2,3-dimethylphenyl)-3-iodo-6-methoxy-1H-pyrazolo[4,3-b]pyridine-1-carboxylate (200 mg, 0.417 mmol), 2-fluoro-5-(4,4,5,5-tetramethyl-1,3,2-dioxaborolan-2-yl)pyridine (186 mg, 0.835 mmol), XphosPd G2 (32.8 mg, 0.042 mmol), and potassium phosphate (354 mg, 1.669 mmol) in dioxane (5 ml) and water (0.5 ml) was heated to 80° C. for 2 hrs. After this time the solution was cooled to r.t., diluted with water and extracted with EtOAc. The combined organic phases were washed with sat. aq. NaCl and dried over $Na_2SO_4$, then filtered and concentrated to dryness. The residue was purified by Biotage Isolera to afford the desired product. LCMS calculated for $C_{25}H_{26}FN_4O_3$ (M+H)+: m/z=449.2; found 449.2.

Step 2. (7S,8aR)-2-(5-(5-(2,3-Dimethylphenyl)-6-methoxy-1H-pyrazolo[4,3-b]pyridin-3-yl)pyridin-2-yl)octahydropyrrolo[1,2-a]pyrazin-7-ol A solution of tert-butyl 5-(2,3-dimethylphenyl)-3-(6-fluoropyridin-3-yl)-6-methoxy-1H-pyrazolo[4,3-b]pyridine-1-carboxylate (20 mg, 0.045 mmol), (7S,8aR)-octahydropyrrolo[1,2-a]pyrazin-7-ol dihydrochloride (28.8 mg, 0.134 mmol), and N,N-diisopropylethylamine (78 μl, 0.45 mmol) in DMSO (1 ml) was heated at 100° C. for 20 hrs. After this time the solution was cooled to r.t., diluted with water and extracted with EtOAc. The combined organic phases were washed with sat. aq. NaCl and dried over $Na_2SO_4$, then filtered and concentrated to dryness. The residue was then dissolved in DCM (1 mL) and TFA (1 mL) was added. The mixture was stirred at r.t. for 1 hr and purified by prep-LCMS (XBridge C18 column, eluting with a gradient of acetonitrile/water containing 0.1% TFA, at flow rate of 60 mL/min). The product was isolated as the TFA salt. LCMS calculated for $C_{27}H_{31}N_6O_2$ $(M+H)^+$: m/z=471.2; found 471.5.

Example 86. 4-(5-(5-(2,3-Dimethylphenyl)-6-methoxy-1H-pyrazolo[4,3-b]pyridin-3-yl)pyridin-2-yl)-1-imino-1λ⁶-thiomorpholine 1-oxide

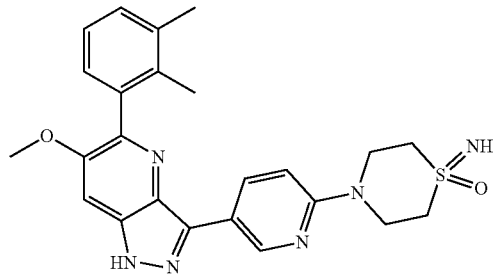 [SMILES: COc1cc2[nH]nc(-c3ccc(N4CCS(=N)(=O)CC4)nc3)c2nc1-c1cccc(C)c1C]

This compound was prepared according to the procedure described in Example 85, using 1-imino-1κ⁶-thiomorpholine 1-oxide hydrochloride instead of (7S,8aR)-octahydropyrrolo[1,2-c]pyrazin-7-ol dihydrochloride as starting material. The product was isolated as the TFA salt. LC-MS calculated for $C_{24}H_{27}N_6O_2S$ $(M+H)^+$: m/z=463.2; found 463.2. ¹H NMR (500 MHz, DMSO-d6) δ 9.23 (d, J=2.3 Hz, 1H), 8.52 (dd, J=8.9, 2.3 Hz, 1H), 7.52 (s, 1H), 7.25-7.14 (m, 3H), 7.11 (dd, J=7.6, 1.5 Hz, 1H), 4.59 (dt, J=15.1, 4.1 Hz, 2H), 3.85 (s, 3H), 3.81-3.72 (m, 2H), 3.72-3.64 (m, 2H), 3.60-3.52 (m, 2H), 2.32 (s, 3H), 1.98 (s, 3H) ppm.

Example 87. (7R,8aS)-2-(5-(5-(2,3-Dimethylphenyl)-6-methoxy-1H-pyrazolo[4,3-b]pyridin-3-yl)pyridin-2-yl)octahydropyrrolo[1,2-a]pyrazin-7-ol

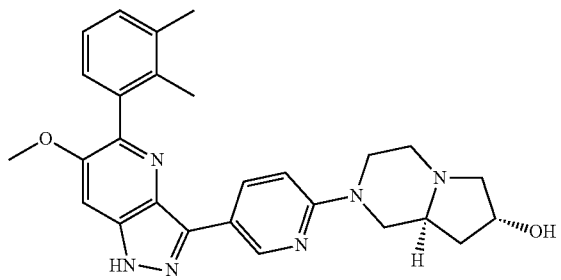 [SMILES: COc1cc2[nH]nc(-c3ccc(N4CCN5C[C@H](O)C[C@H]5C4)nc3)c2nc1-c1cccc(C)c1C]

Step 1. tert-Butyl 5-(2,3-dimethylphenyl)-3-(6-fluoropyridin-3-yl)-6-methoxy-1H-pyrazolo[4,3-b]pyridine-1-carboxylate

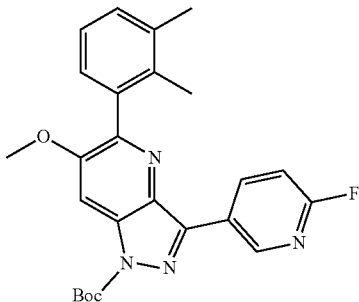 [SMILES: COc1cc2c(nc1-c1cccc(C)c1C)c(-c1ccc(F)nc1)nn2C(=O)OC(C)(C)C]

A mixture of tert-butyl 5-(2,3-dimethylphenyl)-3-iodo-6-methoxy-1H-pyrazolo[4,3-b]pyridine-1-carboxylate (200 mg, 0.417 mmol) (Example 41, Step 7), 2-fluoro-5-(4,4,5,5-tetramethyl-1,3,2-dioxaborolan-2-yl)pyridine (186 mg, 0.835 mmol), XphosPd G2 (32.8 mg, 0.042 mmol), and potassium phosphate (354 mg, 1.669 mmol) in dioxane (5 ml) and water (0.5 ml) was heated to 80° C. for 2 hrs. After this time the solution was cooled to r.t., diluted with water and extracted with EtOAc. The combined organic phases were washed with sat. aq. NaCl and dried over $Na_2SO_4$, then filtered and concentrated to dryness. The residue was then purified by silica gel chromatography to afford the desired product. LCMS calculated for $C_{25}H_{26}FN_4O_3$ $(M+H)^+$: m/z=449.2; found 449.2.

Step 2. (7R,8aS)-2-(5-(5-(2,3-Dimethylphenyl)-6-methoxy-1H-pyrazolo[4,3-b]pyridin-3-yl)pyridin-2-yl)octahydropyrrolo[1,2-a]pyrazin-7-ol A solution of tert-butyl 5-(2,3-dimethylphenyl)-3-(6-fluoropyridin-3-yl)-6-methoxy-1H-pyrazolo[4,3-b]pyridine-1-carboxylate (20 mg, 0.045 mmol), (7R,8aS)-octahydropyrrolo[1,2-c]pyrazin-7-ol (19.0 mg, 0.134 mmol), and N,N-diisopropylethylamine (38.9 µl, 0.223 mmol) in DMSO (1 ml) was heated at 100° C. for 20 hrs. After this time the solution was cooled to r.t., diluted with water and extracted with EtOAc. The combined organic phases were washed with sat. aq. NaCl and dried over $Na_2SO_4$, then filtered and concentrated to dryness. The residue was then dissolved in DCM (1 mL) and TFA (1 mL) was added. The mixture was stirred at r.t. for 1 hr and purified by prep-LCMS (XBridge C18 column, eluting with a gradient of acetonitrile/water containing 0.1% TFA, at flow rate of 60 mL/min). The product was isolated as the TFA salt. LCMS calculated for $C_{27}H_{31}N_6O_2$ $(M+H)^+$: m/z=471.2; found 471.5. ¹H NMR (500 MHz, DMSO-d6, for the free base version) δ 9.15 (d, J=2.3 Hz, 1H), 8.41 (dd, J=9.1, 2.4 Hz, 1H), 7.54 (s, 1H), 7.22 (d, J=7.4 Hz, 1H), 7.16 (t, J=7.5 Hz, 1H), 7.11 (d, J=7.5 Hz, 1H), 6.94 (d, J=9.0 Hz, 1H), 4.46-4.35 (m, 1H), 4.29-4.20 (m, 2H), 3.83 (s, 3H), 3.45-3.18 (m, 2H), 3.00-2.92 (m, 1H), 2.84 (td, J=12.2, 3.4 Hz, 1H), 2.47 (t, J=11.1 Hz, 1H), 2.32 (s, 3H), 2.30-2.14 (m, 2H), 1.99-1.94 (m, 4H), 1.69-1.58 (m, 2H).

Example 88. (S)—N-(1-(5-(5-(2,3-Dimethylphenyl)-6-methoxy-1H-pyrazolo[4,3-b]pyridin-3-yl)pyridin-2-yl)pyrrolidin-3-yl)-2-hydroxy-N-methylacetamide

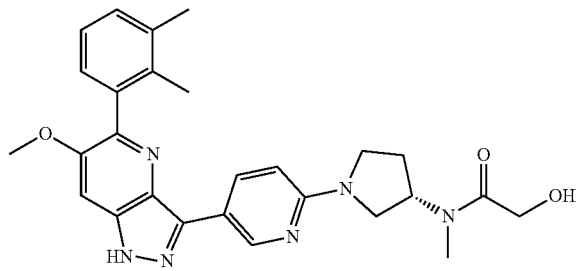 [SMILES: COc1cc2[nH]nc(-c3ccc(N4CC[C@H](N(C)C(=O)CO)C4)nc3)c2nc1-c1cccc(C)c1C]

Step 1. tert-Butyl (S)-methyl(1-(5-(4,4,5,5-tetramethyl-1,3,2-dioxaborolan-2-yl)pyridin-2-yl)pyrrolidin-3-yl)carbamate

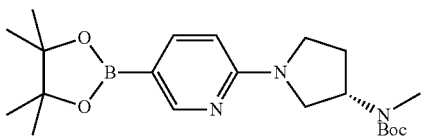

This compound was prepared according to the procedure described in Example 83, Step 1-2, using tert-butyl (S)-methyl(pyrrolidin-3-yl)carbamate instead of (7R,8aS)-octahydropyrrolo[1,2-a]pyrazin-7-ol as starting material. LC-MS calculated for $C_{21}H_{35}BN_3O_4$ (M+H)$^+$: m/z=404.3, found 404.2.

Step 2. (S)-1-(5-(5-(2,3-Dimethylphenyl)-6-methoxy-1H-pyrazolo[4,3-b]pyridin-3-yl)pyridin-2-yl)-N-methylpyrrolidin-3-amine

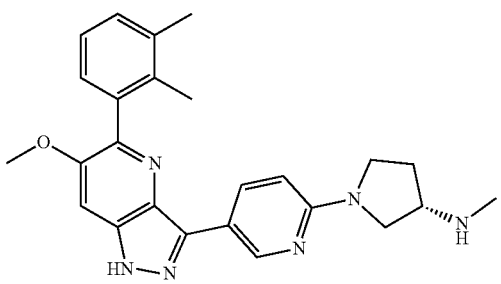

A mixture of tert-butyl 5-(2,3-dimethylphenyl)-3-iodo-6-methoxy-1H-pyrazolo[4,3-b]pyridine-1-carboxylate (0.20 g, 0.42 mmol), tert-butyl (S)-methyl(1-(5-(4,4,5,5-tetramethyl-1,3,2-dioxaborolan-2-yl)pyridin-2-yl)pyrrolidin-3-yl)carbamate (0.26 g, 0.81 mmol), XPhosPd G2 (20 mg, 25 μmol) and $K_3PO_4$ (0.050 g, 0.24 mmol) in dioxane (5 mL) water (0.5 mL) was stirred at 80° C. overnight. After cooling to r.t., the reaction was filtered, the solvent evaporated in vacuo and the residue was purified by Biotage Isolera. The fractions containing the desired product were combined and concentrated in vacuo. 4N HCl in dioxane (2 mL) was added to the obtained material and the reaction mixture was stirred at r.t. for 1 hr. It was then concentrated in vacuo and was directly used in the next step without further purification. LC-MS calculated for $C_{25}H_{29}N_6O$ (M+H)$^+$: m/z=429.2, found 429.1.

Step 3. (S)—N-(1-(5-(5-(2,3-Dimethylphenyl)-6-methoxy-1H-pyrazolo[4,3-b]pyridin-3-yl)pyridin-2-yl)pyrrolidin-3-yl)-2-hydroxy-N-methylacetamide HATU (100 mg, 0.263 mmol) was added to a solution of (S)-1-(5-(5-(2,3-dimethylphenyl)-6-methoxy-1H-pyrazolo[4,3-b]pyridin-3-yl)pyridin-2-yl)-N-methylpyrrolidin-3-amine (0.078 g, 0.18 mmol), 2-hydroxyacetic acid (0.100 g, 1.32 mmol) and DIPEA (0.05 mL, 0.29 mmol) in DMF (2 mL). After stirring at r.t. for 1 hr, the reaction mixture was diluted with methanol, filtered and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{31}N_6O_3$ (M+H)$^+$: m/z=487.3, found 487.2.

Example 89. 2-(3-(3-(6-(4-(2-Hydroxyethyl)piperazin-1-yl)pyridin-3-yl)-6-methoxy-1H-pyrazolo[4,3-b]pyridin-5-yl)-2-methylphenyl)acetonitrile

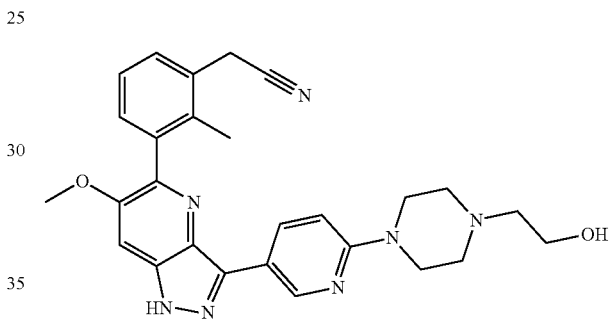

Step 1. 2-(4-(5-(4,4,5,5-Tetramethyl-1,3,2-dioxaborolan-2-yl)pyridin-2-yl)piperazin-1-yl)ethan-1-ol

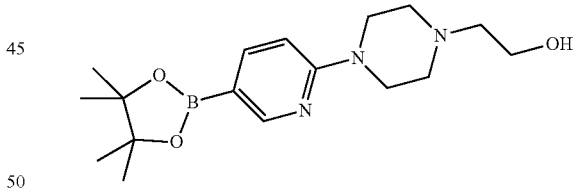

To a solution of 1-(5-(4,4,5,5-tetramethyl-1,3,2-dioxaborolan-2-yl)pyridin-2-yl)piperazine (25 mg, 0.086 mmol) and cesium carbonate (85 mg, 0.26 mmol) in 1,4-dioxane (0.62 mL) was added 2-bromoethan-1-ol (12 μL, 0.18 mmol). The reaction was stirred at 50° C. for 3 hrs. After cooling to r.t., the reaction mixture was filtered, the solvent evaporated in vacuo and crude material was used in next step without further purification. LCMS calculated for $C_{11}H_{19}BN_3O_3$ (Boronic acid, M+H)$^+$: m/z=252.2, found: 252.3.

Step 2. 2-(3-(3-(6-(4-(2-Hydroxyethyl)piperazin-1-yl)pyridin-3-yl)-6-methoxy-1H-pyrazolo[4,3-b]pyridin-5-yl)-2-methylphenyl)acetonitrile To a solution of tert-butyl 5-(3-(cyanomethyl)-2-methylphenyl)-3-iodo-6-methoxy-1H-pyrazolo[4,3-b]pyridine- 1-carboxylate (Example 55, step 1; 30 mg, 0.059 mmol) in 1,4-dioxane (0.27 mL) and water (27 µL) was added 2-(4-(5-(4,4,5,5-tetramethyl-1,3,2-dioxaborolan-2-yl)pyridin-2-yl)piperazin-1-yl)ethan-1-ol (25 mg, 0.074 mmol), potassium phosphate (19 mg, 0.089 mmol), and XphosPd G2 (9 mg, 0.01 mmol). The reaction was degassed with $N_2$ and stirred at 80° C. for 1 hr. After this time it was cooled to r.t., and 1 mL of TFA was added. The reaction was stirred for additional 30 min before it was diluted with MeOH and purified by prep-LCMS (XBridge C18 column, eluting with a gradient of acetonitrile/water containing 0.1% TFA, at flow rate of 60 mL/min followed by a second C18 column, eluting with a gradient of acetonitrile/water containing 0.15% $NH_4OH$, at flow rate of 60 mL/min). The product was isolated as the TFA salt. LC-MS calculated for $C_{27}H_{30}N_7O_2$ $(M+H)^+$: m/z=484.3, found 484.4. $^1H$ NMR (600 MHz, DMSO-d6) δ 13.30-13.10 (s, 1H), 9.74-9.64 (s, 1H), 9.19 (d, J=2.3 Hz, 1H), 8.47 (dd, J=8.9, 2.3 Hz, 1H), 7.54 (s, 1H), 7.44 (dd, J=7.6, 1.4 Hz, 1H), 7.33 (t, J=7.6 Hz, 1H), 7.28 (dd, J=7.7, 1.5 Hz, 1H), 7.08 (d, J=8.9 Hz, 1H), 4.42 (d, J=13.9 Hz, 2H), 4.09 (s, 2H), 3.84 (s, 3H), 3.76 (dd, J=6.1, 4.3 Hz, 2H), 3.58 (d, J=12.1 Hz, 2H), 3.33-3.18 (m, 4H), 3.17-3.08 (m, 2H), 2.05 (s, 3H) ppm.

Example 90. (7R,8aS)-2-(5-(6-Methoxy-5-(3-methoxy-2-methylphenyl)-1H-pyrazolo[4,3-b]pyridin-3-yl)pyridin-2-yl)octahydropyrrolo[1,2-a]pyrazin-7-ol

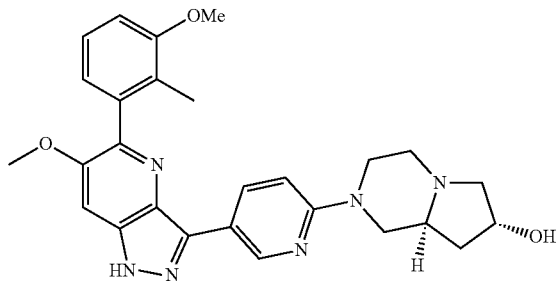 [SMILES: COc1cc2[nH]nc(-c3ccc(N4CCN5C[C@H](O)C[C@H]5C4)nc3)c2nc1-c1cccc(OC)c1C]

Step 1. tert-Butyl 5-chloro-3-(6-((7R,8aS)-7-hydroxyhexahydropyrrolo[1,2-a]pyrazin-2(1H)-yl)pyridin-3-yl)-6-methoxy-1H-pyrazolo[4,3-b]pyridine-1-carboxylate

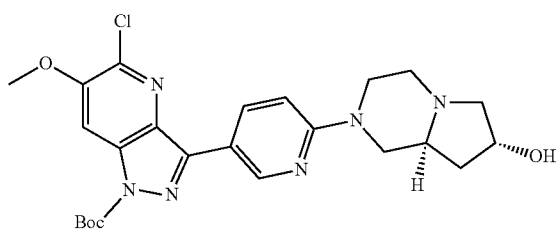 [SMILES: COc1cc2c(nc1Cl)c(-c1ccc(N3CCN4C[C@H](O)C[C@H]4C3)nc1)nn2C(=O)OC(C)(C)C]

This compound was prepared according to the procedures described in Example 1, Steps 1-7, using (7R,8aS)-2-(5-(4,4,5,5-tetramethyl-1,3,2-dioxaborolan-2-yl)pyridin-2-yl)octahydropyrrolo[1,2-c]pyrazin-7-ol (Example 83, Steps 1-2) instead of 1-methyl-4-(4,4,5,5-tetramethyl-1,3,2-dioxaborolan-2-yl)-1H-pyrazole as starting material. LCMS calculated for $C_{24}H_{30}ClN_6O_4$ $(M+H)^+$: m/z=501.2, found: 501.2.

Step 2. (7R,8aS)-2-(5-(6-Methoxy-5-(3-methoxy-2-methylphenyl)-1H-pyrazolo[4,3-b]pyridin-3-yl)pyridin-2-yl)octahydropyrrolo[1,2-a]pyrazin-7-ol tert-Butyl 5-chloro-3-(6-((7R,8aS)-7-hydroxyhexahydropyrrolo[1,2-a]pyrazin-2(1H)-yl)pyridin-3-yl)-6-methoxy-1H-pyrazolo[4,3-b]pyridine-1-carboxylate (8 mg, 0.02 mmol), (3-methoxy-2-methylphenyl)boronic acid (5.30 mg, 0.032 mmol), XphosPd G2 (1.9 mg, 2.4 µmol) and potassium phosphate (5.1 mg, 0.024 mmol) were placed in a vial and the vial was evacuated and backfilled with $N_2$ three times. After 1,4-dioxane (1 ml) and water (100 µl) were added, the reaction mixture was stirred at 100° C. for 1 hr. Then the reaction was filtered, and the solvents were evaporated in vacuo. DCM (1 ml) and TFA (0.5 ml) were added and the reaction mixture was stirred at r.t. for 30 min. It was then diluted with $CH_3CN$ and water and purified with prep-LCMS (XBridge C18 column, eluting with a gradient of acetonitrile/water containing 0.1% TFA, at flow rate of 60 mL/min). The product was isolated as the TFA salt. LCMS calculated for $C_{27}H_{31}N_6O_3$ $(M+H)^+$: m/z=487.3, found: 487.3. $^1H$ NMR (500 MHz, DMSO-d6) δ 9.23-9.16 (m, 1H), 8.51 (dd, J=8.9, 2.3 Hz, 1H), 7.52 (s, 1H), 7.25 (t, J=7.9 Hz, 1H), 7.03 (dd, J=8.4, 1.2 Hz, 1H), 6.94 (d, J=9.0 Hz, 1H), 6.90 (dd, J=7.6, 1.1 Hz, 1H), 4.52-4.43 (m, 1H), 4.35-4.23 (m, 1H), 4.16-4.00 (m, 1H), 3.89-3.83 (m, 6H), 3.82-3.75 (m, 1H), 3.73-3.60 (m, 3H), 3.56-3.47 (m, 1H), 3.47-3.40 (m, 2H), 2.19-1.95 (m, 2H), 1.92 (s, 3H) ppm.

Example 91. (7R,8aS)-2-(5-(5-(2,3-Dihydrobenzo[b][1,4]dioxin-5-yl)-6-methoxy-1H-pyrazolo[4,3-b]pyridin-3-yl)pyridin-2-yl)octahydropyrrolo[1,2-a]pyrazin-7-ol

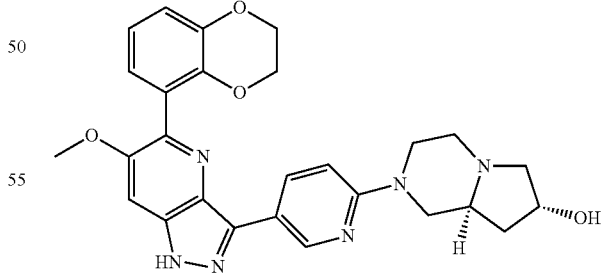

This compound was prepared according to the procedures described in Example 90, using 2-(2,3-dihydrobenzo[b][1,4]dioxin-5-yl)-4,4,5,5-tetramethyl-1,3,2-dioxaborolane instead of (3-methoxy-2-methylphenyl)boronic acid as starting material. The product was isolated as the TFA salt. LCMS calculated for $C_{27}H_{29}N_6O_4$ $(M+H)^+$: m/z=501.2; Found: 501.2.

Example 92. (7R,8aS)-2-(5-(5-(2-Cyclopropylphenyl)-6-methoxy-1H-pyrazolo[4,3-b]pyridin-3-yl)pyridin-2-yl)octahydropyrrolo[1,2-a]pyrazin-7-ol

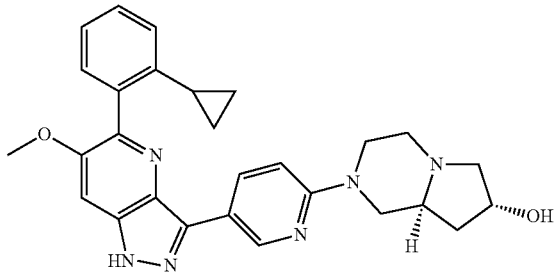 [SMILES: COc1cc2[nH]nc(-c3ccc(N4CCN5C[C@H](O)C[C@H]5C4)nc3)c2nc1-c1ccccc1C1CC1]

This compound was prepared according to the procedures described in Example 90, using (2-cyclopropylphenyl)boronic acid instead of (3-methoxy-2-methylphenyl)boronic acid as starting material. The product was isolated as the TFA salt. LCMS calculated for $C_{28}H_{31}N_6O_2$ (M+H)$^+$: m/z=483.2; Found: 483.3.

Example 93. (7R,8aS)-2-(5-(5-(Chroman-5-yl)-6-methoxy-1H-pyrazolo[4,3-b]pyridin-3-yl)pyridin-2-yl)octahydropyrrolo[1,2-a]pyrazin-7-ol

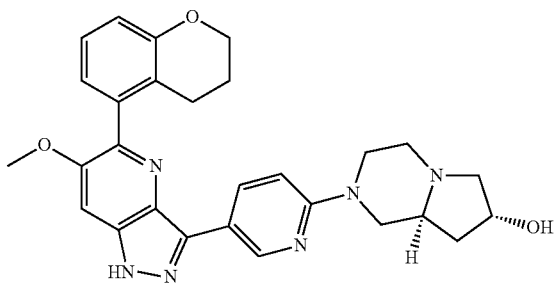 [SMILES: COc1cc2[nH]nc(-c3ccc(N4CCN5C[C@H](O)C[C@H]5C4)nc3)c2nc1-c1cccc2c1CCCO2]

This compound was prepared according to the procedures described in Example 90, using 2-(chroman-5-yl)-4,4,5,5-tetramethyl-1,3,2-dioxaborolane acid instead of (3-methoxy-2-methylphenyl)boronic acid as starting material. The product was isolated as the TFA salt. LCMS calculated for $C_{28}H_{31}N_6O_3$ (M+H)$^+$: m/z=499.3; Found: 499.2.

Example 94. (7R,8aS)-2-(5-(5-(2-Fluoro-3-methylphenyl)-6-methoxy-1H-pyrazolo[4,3-b]pyridin-3-yl)pyridin-2-yl)octahydropyrrolo[1,2-a]pyrazin-7-ol

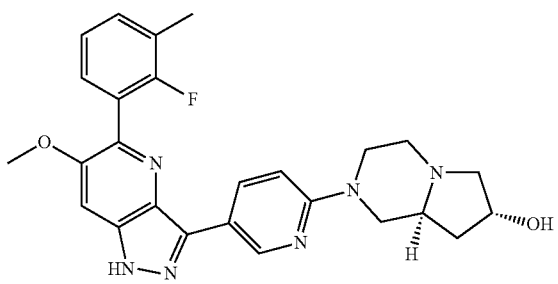 [SMILES: COc1cc2[nH]nc(-c3ccc(N4CCN5C[C@H](O)C[C@H]5C4)nc3)c2nc1-c1cccc(C)c1F]

This compound was prepared according to the procedures described in Example 90, using (2-fluoro-3-methylphenyl)boronic acid instead of (3-methoxy-2-methylphenyl)boronic acid as starting material. The product was isolated as the TFA salt. LCMS calculated for $C_{26}H_{28}FN_6O_2$ (M+H)$^+$: m/z=475.2; Found: 475.2. $^1$H NMR (500 MHz, DMSO-d$_6$) δ 9.25-9.18 (m, 1H), 8.50 (dd, J=8.9, 2.3 Hz, 1H), 7.55 (s, 1H), 7.37 (t, J=7.4 Hz, 1H), 7.35-7.31 (m, 1H), 7.21 (t, J=7.5 Hz, 1H), 6.94 (d, J=9.0 Hz, 1H), 4.47 (s, 1H), 4.30 (dd, J=14.0, 4.3 Hz, 1H), 4.16-4.06 (m, 1H), 3.88 (s, 3H), 3.84-3.76 (m, 1H), 3.73-3.60 (m, 3H), 3.58-3.46 (m, 1H), 3.46-3.39 (m, 2H), 2.31 (s, 3H), 2.17-1.91 (m, 2H) ppm.

Example 95. 4-(6-Methoxy-3-(6-(2-methoxyethoxy)pyridin-3-yl)-1H-pyrazolo[4,3-b]pyridin-5-yl)-2,3-dihydro-1H-inden-2-ol

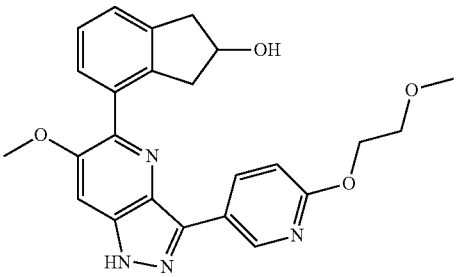

Step 1. 2-(2-Methoxyethoxy)-5-(4,4,5,5-tetramethyl-1,3,2-dioxaborolan-2-yl)pyridine

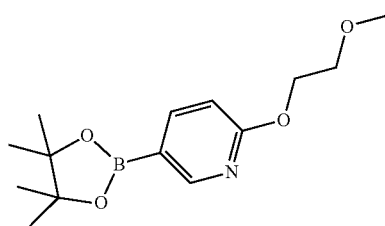

A mixture of 5-bromo-2-(2-methoxyethoxy)pyridine (250 mg, 1.08 mmol), 4,4,4',4',5,5,5',5'-octamethyl-2,2'-bi(1,3,2-dioxaborolane) (356 mg, 1.4 mmol), [1,1'-bis(diphenylphosphino)-ferrocene]-dichloropalladium(II) (88 mg, 0.11 mmol) and potassium acetate (159 mg, 1.62 mmol) in dioxane (5 mL) was stirred at 80° C. overnight. After cooling to r.t., the reaction mixture was filtered, the solvent was evaporated in vacuo and the crude material was purified by Biotage Isolera. LCMS calculated for $C_{14}H_{23}BNO_4$ (M+H)$^+$: m/z=280.2; Found: 280.2.

Step 2. 4-(6-Methoxy-3-(6-(2-methoxyethoxy)pyridin-3-yl)-1H-pyrazolo[4,3-b]pyridin-5-yl)-2,3-dihydro-1H-inden-2-ol This compound was prepared according to the procedures described in Example 73, using 2-(2-methoxyethoxy)-5-(4,4,5,5-tetramethyl-1,3,2-dioxaborolan-2-yl)pyridine instead of 2-((tetrahydrofuran-3-yl)oxy)-5-(4,4,5,5-tetramethyl-1,3,2-dioxaborolan-2-yl)pyridine as starting material. The product was isolated as the TFA salt. LCMS calculated for C$_{24}$H$_{25}$N$_4$O$_4$ (M+H)$^+$: m/z=433.2; Found: 433.2. $^1$H NMR (600 MHz, DMSO-d$_6$) δ 9.23 (d, J=2.3 Hz, 1H), 8.62 (dd, J=8.6, 2.3 Hz, 1H), 7.55 (s, 1H), 7.32 (d, J=7.3 Hz, 1H), 7.28 (d, J=6.1 Hz, 1H), 7.25 (t, J=7.4 Hz, 1H), 6.97 (d, J=8.7 Hz, 1H), 4.52-4.45 (m, 1H), 4.45-4.41 (m, 2H), 3.89 (s, 3H), 3.71-3.64 (m, 2H), 3.31 (s, 3H), 3.16 (dd, J=16.0, 6.0 Hz, 1H), 3.03 (dd, J=16.4, 6.0 Hz, 1H), 2.84 (dd, J=15.9, 3.8 Hz, 1H), 2.65 (dd, J=16.4, 3.9 Hz, 1H) ppm.

Example 96. 4-(6-Methoxy-3-(6-((tetrahydro-2H-pyran-4-yl)oxy)pyridin-3-yl)-1H-pyrazolo[4,3-b]pyridin-5-yl)-2,3-dihydro-1H-inden-2-ol

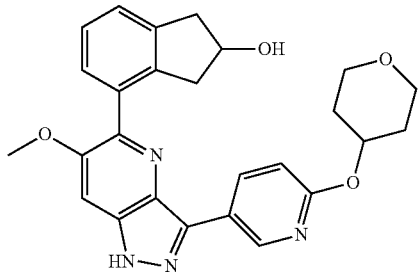 [SMILES: COc1cc2[nH]nc(-c3ccc(OC4CCOCC4)nc3)c2nc1-c1cccc2c1CC(O)C2]

This compound was prepared according to the procedures described in Example 95, using 5-bromo-2-((tetrahydro-2H-pyran-4-yl)oxy)pyridine instead of 5-bromo-2-(2-methoxyethoxy)pyridine as starting material. The product was isolated as the TFA salt. LCMS calculated for C$_{26}$H$_{27}$N$_4$O$_4$ (M+H)$^+$: m/z=459.2; Found: 459.2. $^1$H NMR (600 MHz, DMSO-d6) δ 9.22 (d, J=2.4 Hz, 1H), 8.61 (dd, J=8.6, 2.3 Hz, 1H), 7.55 (s, 1H), 7.32 (d, J=5.9 Hz, 1H), 7.28 (d, J=6.1 Hz, 1H), 7.25 (t, J=7.4 Hz, 1H), 6.94 (d, J=8.6 Hz, 1H), 5.24 (tt, J=8.9, 4.2 Hz, 1H), 4.53-4.43 (m, 1H), 3.89 (s, 3H), 3.88-3.83 (m, 2H), 3.57-3.45 (m, 2H), 3.16 (dd, J=16.0, 6.1 Hz, 1H), 3.01 (dd, J=16.4, 6.0 Hz, 1H), 2.84 (dd, J=15.9, 3.8 Hz, 1H), 2.64 (dd, J=16.4, 3.8 Hz, 1H), 2.09-2.01 (m, 2H), 1.75-1.60 (m, 2H) ppm.

Example 97. 4-(3-(6-Cyclopropylpyridin-3-yl)-6-methoxy-1H-pyrazolo[4,3-b]pyridin-5-yl)-2,3-dihydro-1H-inden-2-ol

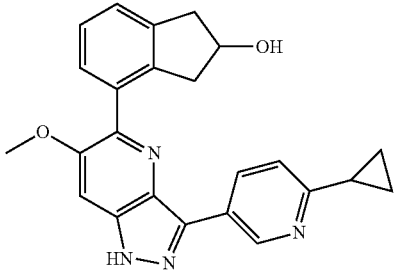 [SMILES: COc1cc2[nH]nc(-c3ccc(C4CC4)nc3)c2nc1-c1cccc2c1CC(O)C2]

This compound was prepared according to the procedures described in Example 73, using (6-cyclopropylpyridin-3-yl) boronic acid instead of 2-((tetrahydrofuran-3-yl)oxy)-5-(4,4,5,5-tetramethyl-1,3,2-dioxaborolan-2-yl)pyridine as starting material. The product was isolated as the TFA salt. LCMS calculated for C$_{24}$H$_{23}$N$_4$O$_2$ (M+H)$^+$: m/z=399.2; Found: 399.2. $^1$H NMR (500 MHz, DMSO-d$_6$) δ 9.47 (d, J=2.2 Hz, 1H), 8.74 (d, J=8.3 Hz, 1H), 7.59 (s, 1H), 7.52 (d, J=8.4 Hz, 1H), 7.36-7.31 (m, 1H), 7.29 (d, J=7.1 Hz, 1H), 7.25 (t, J=7.4 Hz, 1H), 4.55-4.44 (m, 1H), 3.90 (s, 3H), 3.16 (dd, J=16.0, 6.0 Hz, 1H), 3.04 (dd, J=16.4, 5.9 Hz, 1H), 2.84 (dd, J=16.1, 3.8 Hz, 1H), 2.64 (dd, J=16.3, 3.8 Hz, 1H), 2.29-2.17 (m, 1H), 1.15-0.94 (m, 4H) ppm.

Example 98. N-(1-(5-(5-(2,3-Dimethylphenyl)-6-methoxy-1H-pyrazolo[4,3-b]pyridin-3-yl)pyridin-2-yl)azetidin-3-yl)-2-hydroxy-N-methylacetamide

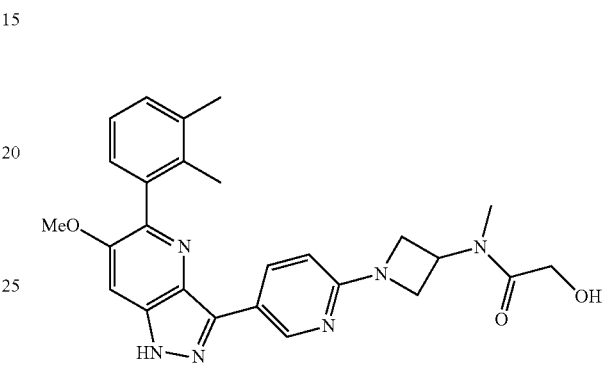

Step 1. 5-(2,3-Dimethylphenyl)-3-(6-fluoropyridin-3-yl)-6-methoxy-1-(4-methoxybenzyl)-1H-pyrazolo[4,3-b]pyridine

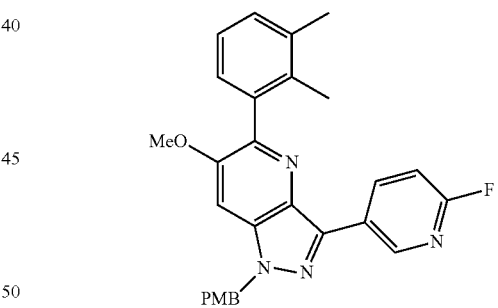

To a solution of 5-(2,3-dimethylphenyl)-3-iodo-6-methoxy-1-(4-methoxybenzyl)-1H-pyrazolo[4,3-b]pyridine (Example 69, Step 1, 255 mg, 0.511 mmol) in 1,4-dioxane (5 mL) and water (0.5 mL) was added 2-fluoro-5-(4,4,5,5-tetramethyl-1,3,2-dioxaborolan-2-yl)pyridine (219 mg, 0.940 mmol), potassium phosphate (312 mg, 1.47 mmol), and [1,1'-bis(diphenylphosphino)-ferrocene]dichloropalladium(II) (40 mg, 0.049 mmol). The reaction was degassed with N$_2$ and stirred at 80° C. for 3 hrs. After this time, it was cooled to r.t. and diluted with EtOAc. The resultant solution was washed sequentially with water, sat. aq. NaCl solution, and dried over Na$_2$SO$_4$. The organic phases were filtered and concentrated to dryness. The residue was purified by Biotage Isolera to afford the desired product. LC-MS calculated for C$_{28}$H$_{26}$FN$_4$O$_2$ (M+H)$^+$: m/z=469.2; found 469.2.

Step 2. tert-Butyl (1-(5-(5-(2,3-dimethylphenyl)-6-methoxy-1-(4-methoxybenzyl)-1H-pyrazolo[4,3-b]pyridin-3-yl)pyridin-2-yl)azetidin-3-yl)(methyl)carbamate

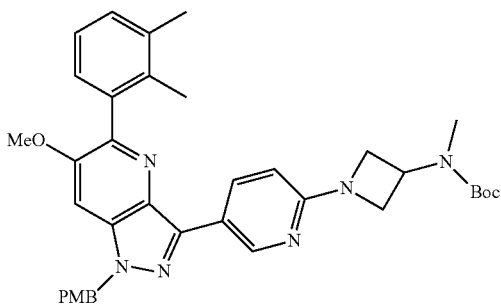

To a solution of 5-(2,3-dimethylphenyl)-3-(6-fluoropyridin-3-yl)-6-methoxy-1-(4-methoxybenzyl)-1H-pyrazolo[4,3-b]pyridine (120 mg, 0.256 mmol) in DMSO (2.5 mL) was added tert-butyl azetidin-3-yl(methyl)carbamate (114 mg, 0.512 mmol) and cesium carbonate (417 mg, 1.22 mmol). The reaction was degassed with $N_2$ and stirred at 100° C. for 5 hrs. After this time, it was cooled to r.t. and diluted with EtOAc. The resultant solution was washed sequentially with water, sat. aq. NaCl solution, and dried over $Na_2SO_4$. The organic phases were filtered and concentrated to dryness. The residue was purified by Biotage Isolera to afford the desired product. LC-MS calculated for $C_{37}H_{43}N_6O_4$ $(M+H)^+$: m/z=635.2; found 635.2.

Step 3. 1-(5-(5-(2,3-Dimethylphenyl)-6-methoxy-1-(4-methoxybenzyl)-1H-pyrazolo[4,3-b]pyridin-3-yl)pyridin-2-yl)-N-methylazetidin-3-amine

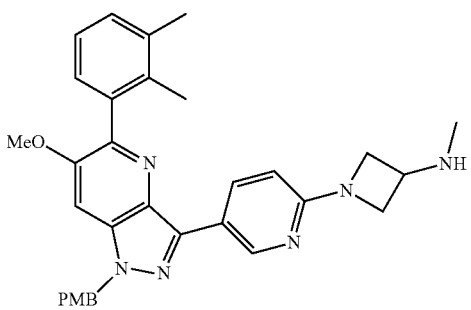

To a solution of tert-butyl (1-(5-(5-(2,3-dimethylphenyl)-6-methoxy-1-(4-methoxybenzyl)-1H-pyrazolo[4,3-b]pyridin-3-yl)pyridin-2-yl)azetidin-3-yl)(methyl)carbamate (163 mg, 0.256 mmol) in dichloromethane (0.5 mL) was added trifluoroacetic acid (0.5 mL). The reaction was stirred at r.t. for 1 hr. After this time, it was diluted with dichloromethane. The resultant solution was washed sequentially with water, sat. aq. NaCl solution and dried over $Na_2SO_4$. The organic phases were filtered and concentrated to dryness. The residue was used directly in the next step without purification. LC-MS calculated for $C_{32}H_{35}N_6O_2$ $(M+H)^+$: m/z=535.3; found 535.2.

Step 4. N-(1-(5-(5-(2,3-Dimethylphenyl)-6-methoxy-1H-pyrazolo[4,3-b]pyridin-3-yl)pyridin-2-yl)azetidin-3-yl)-2-hydroxy-N-methylacetamide To a solution of 1-(5-(5-(2,3-dimethylphenyl)-6-methoxy-1-(4-methoxybenzyl)-1H-pyrazolo[4,3-b]pyridin-3-yl)pyridin-2-yl)-N-methylazetidin-3-amine (10 mg, 0.019 mmol) in dichloromethane (0.5 mL) was added 2-hydroxyacetic acid (7 mg, 0.09 mmol), trimethylamine (22 mg, 0.17 mmol) and HATU (11 mg, 0.028 mmol). The reaction was stirred at r.t. for 1 hr. After this time, it was diluted with dichloromethane. The resultant solution was washed sequentially with water, sat. aq. NaCl solution, and dried over $Na_2SO_4$. The organic phases were filtered and concentrated to dryness. The residue was dissolved in dichloromethane (0.5 mL) and trifluoromethanesulfonic acid (0.2 mL). The reaction was stirred at r.t. After 30 min, the reaction mixture was diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{26}H_{29}N_6O_3$ $(M+H)^+$: m/z=473.2; found 473.2. $^1$H NMR (600 MHz, DMSO-$d_6$) δ 13.41 (s, 1H), 9.07 (d, J=2.0 Hz, 1H), 8.66 (d, J=9.2 Hz, 1H), 7.57 (s, 1H), 7.24 (dd, J=7.6, 1.4 Hz, 1H), 7.18 (t, J=7.5 Hz, 1H), 7.12 (dd, J=7.6, 1.5 Hz, 1H), 6.98 (t, J=9.9 Hz, 1H), 5.30 (td, J=8.1, 3.8 Hz, 1H), 4.44 (t, J=9.0 Hz, 2H), 4.35-4.29 (m, 2H), 4.17 (s, 1H), 4.12 (s, 1H), 3.86 (s, 3H), 2.99 (s, 3H), 2.32 (s, 3H), 1.98 (s, 3H) ppm.

Example 99. 1-(4-(5-(5-(2,3-Dihydro-1H-inden-4-yl)-6-methoxy-1H-pyrazolo[4,3-b]pyridin-3-yl)pyridin-2-yl)piperidin-1-yl)ethan-1-one

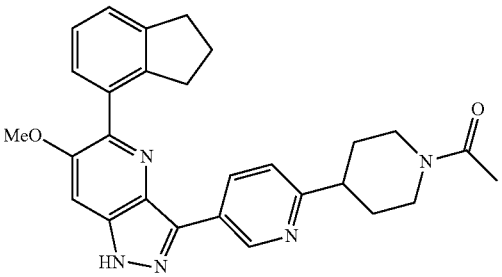 [SMILES: COc1cc2[nH]nc(-c3ccc(C4CCN(C(C)=O)CC4)nc3)c2nc1-c1cccc2c1CCC2]

Step 1. tert-butyl 5-(2,3-Dihydro-1H-inden-4-yl)-6-methoxy-1H-pyrazolo[4,3-b]pyridine-1-carboxylate

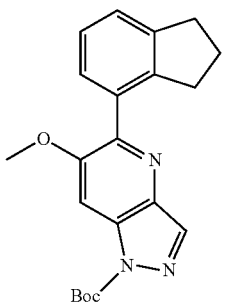 [SMILES: COc1cc2c(cnn2C(=O)OC(C)(C)C)nc1-c1cccc2c1CCC2]

tert-Butyl 5-chloro-6-methoxy-1H-pyrazolo[4,3-b]pyridine-1-carboxylate (6.4 g, 22.5 mmol), 2-(2,3-dihydro-1H-inden-4-yl)-4,4,5,5-tetramethyl-1,3,2-dioxaborolane (6.0 g, 24.7 mmol), chloro(2-dicyclohexylphosphino-2',4',6'-tri-i-propyl-1,1'-biphenyl)(2'-amino-1,1'-biphenyl-2-yl) palladium(II) (0.89 g, 1.124 mmol) and $Cs_2CO_3$ (14.65 g, 45.0 mmol) were placed in a 250 ml round-bottom flask and the flask was evacuated and backfilled with $N_2$ three times. Dioxane (80 ml) and water (20 ml) were added to the mixture and the reaction mixture was stirred at 70° C. overnight. After cooling to r.t., water was added and the desired product was extracted with EtOAc. The organic phase was washed with brine, dried over sodium sulfate and the solvent was evaporated in vacuo. Crude material was purified by Biotage Isolera to give a white solid (7.20 g, 88%). LCMS calculated for $C_{21}H_{24}N_3O_3$ $(M+H)^+$: m/z=366.2; found 366.2.

Step 2. 5-(2,3-Dihydro-1H-inden-4-yl)-6-methoxy-1H-pyrazolo[4,3-b]pyridine

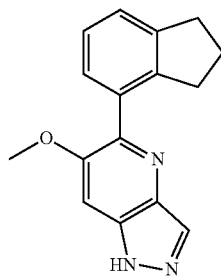

tert-Butyl 5-(2,3-dihydro-1H-inden-4-yl)-6-methoxy-1H-pyrazolo[4,3-b]pyridine-1-carboxylate (7.20 g, 19.7 mmol) in a mixture of DCM (30 ml) and TFA (15.0 ml) was stirred at r.t. for 1 h. The reaction was then concentrated in vacuo, the residue was dissolved in DCM and neutralized with $NaHCO_3$ solution. The organic phase was separated, dried over sodium sulfate and concentrated in vacuo. The obtained crude material was used for next step without further purification. LCMS calculated for $C_{16}H_{16}N_3O$ $(M+H)^+$: m/z=266.1; found 266.1.

Step 3. 5-(2,3-Dihydro-1H-inden-4-yl)-3-iodo-6-methoxy-1-(4-methoxybenzyl)-1H-pyrazolo[4,3-b]pyridine

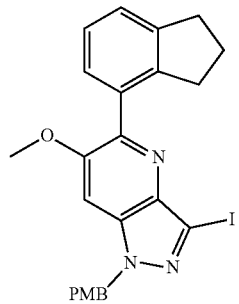

1-Iodopyrrolidine-2,5-dione (6.11 g, 27.1 mmol) was added to a solution of 5-(2,3-dihydro-1H-inden-4-yl)-6-methoxy-1H-pyrazolo[4,3-b]pyridine (6.00 g, 22.61 mmol) in DMF (60 ml). After stirring at 60° C. for 1 h, the mixture was cooled down to r.t., followed by the addition of cesium carbonate (14.74 g, 45.2 mmol) and 1-(chloromethyl)-4-methoxybenzene (3.66 ml, 27.1 mmol). The reaction mixture was stirred at 80° C. for 1 h. The reaction mixture was cooled down to r.t., water was added, and the product was extracted with EtOAc. The organic phase was separated, washed with brine, dried over $Na_2SO_4$ and concentrated in vacuo. The residue was purified by Biotage Isolera to give a yellow solid. LCMS calculated for $C_{24}H_{23}IN_3O_2$ $(M+H)^+$: m/z 512.2; found 512.2.

Step 4. 3-(6-Chloropyridin-3-yl)-5-(2,3-dihydro-1H-inden-4-yl)-6-methoxy-1-(4-methoxybenzyl)-1H-pyrazolo[4,3-b]pyridine

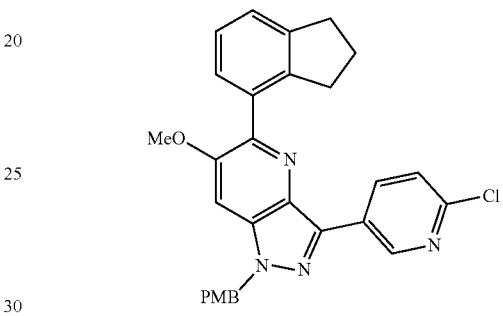

5-(2,3-Dihydro-1H-inden-4-yl)-3-iodo-6-methoxy-1-(4-methoxybenzyl)-1H-pyrazolo[4,3-b]pyridine (6.0 g, 11.73 mmol), (6-chloropyridin-3-yl)boronic acid (2.2 g, 14.08 mmol), $PdCl_2(dppf)\cdot CH_2Cl_2$ adduct (0.96 g, 1.173 mmol) and potassium phosphate (3.24 g, 15.25 mmol) were placed in a 250 ml round-bottom flask and the flask was evacuated and backfilled with $N_2$ three times. Dioxane (80 ml) and water (20 ml) were transferred to the flask, and the reaction mixture was stirred at 70° C. for 2 hrs. After cooling to r.t., water was added and the desired product was extracted with EtOAc. The organic phase was washed with brine, dried over sodium sulfate and the solvent was evaporated in vacuo. Crude material was purified by Biotage Isolera to give a yellow solid (5.0 g, 86%). LCMS calculated for $C_{29}H_{26}ClN_4O_2$ $(M+H)^+$: m/z=497.2; found 497.2.

Step 5. tert-Butyl-5-(5-(2,3-dihydro-1H-inden-4-yl)-6-methoxy-1-(4-methoxybenzyl)-1H-pyrazolo[4,3-b]pyridin-3-yl)-3',6'-dihydro-[2,4'-bipyridine]-1'(2'H)-carboxylate

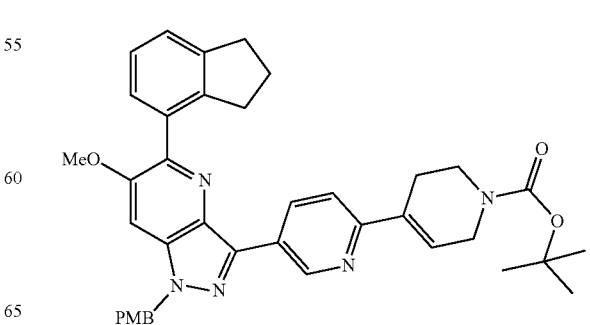

3-(6-Chloropyridin-3-yl)-5-(2,3-dihydro-1H-inden-4-yl)-6-methoxy-1-(4-methoxybenzyl)-1H-pyrazolo[4,3-b]pyridine (3.75 g, 7.55 mmol), XPhos Pd G2 (0.6 g, 0.76 mmol), tert-butyl 4-(4,4,5,5-tetramethyl-1,3,2-dioxaborolan-2-yl)-3,6-dihydropyridine-1(2H)-carboxylate (3.03 g, 9.81 mmol) and $Cs_2CO_3$ (4.92 g, 15.09 mmol) were placed in a 250 ml round-bottom flask with septum. After the flask was evacuated and backfilled with $N_2$ three times, dioxane (80 ml) and water (20 ml) were transferred to the flask. The reaction mixture was stirred at 70° C. for 2 hrs. After cooling to r.t., water was added and the desired product was extracted with EtOAc. The organic phase was washed with brine, dried over sodium sulfate and the solvent was evaporated in vacuo. Crude material was purified by Biotage Isolera to give an oil (4.0 g, 82%). LCMS calculated for $C_{39}H_{42}N_5O_4$ (M+H)$^+$: m/z=644.2; found 644.2.

Step 6. tert-Butyl 4-(5-(5-(2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate

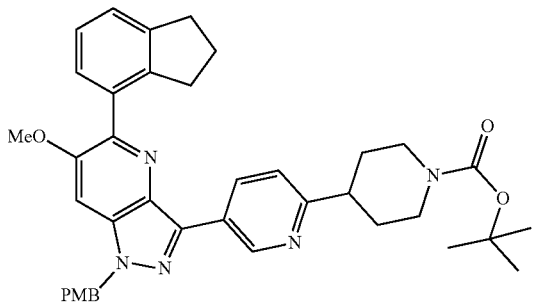

A mixture of tert-butyl 5-(5-(2,3-dihydro-1H-inden-4-yl)-6-methoxy-1-(4-methoxybenzyl)-1H-pyrazolo[4,3-b]pyridin-3-yl)-3',6'-dihydro-[2,4'-bipyridine]-1'(2'H)-carboxylate (0.80 g, 1.2 mmol) and Pd—C (0.132 g, 0.124 mmol) in MeOH (10 ml) and ethyl acetate (10 ml) was stirred in a Parr-Shaker under 30 psi of $H_2$ overnight. Then the reaction mixture was filtered, and the filtrate was concentrated in vacuo to give the desired product as colorless oil (0.80 g, 99%). LCMS calculated for $C_{39}H_{44}N_5O_4$ (M+H)$^+$: m/z=646.2; found 646.2.

Step 7. 5-(2,3-Dihydro-1H-inden-4-yl)-6-methoxy-1-(4-methoxybenzyl)-3-(6-(piperidin-4-yl)pyridin-3-yl)-1H-pyrazolo[4,3-b]pyridine

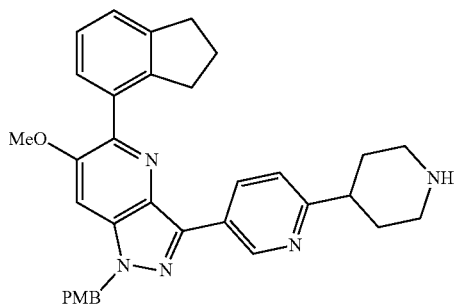

4N Solution of HCl in dioxane (10 ml) was added to a solution of tert-butyl 4-(5-(5-(2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate (0.80 g, 1.24 mmol) in a mixture of EtOAc (5 ml) and methanol (5 ml). The reaction mixture was stirred at r.t for 1 hr, then concentrated to dryness in vacuo to give the product as HCl salt (0.80 g, >98%). LCMS calculated for $C_{34}H_{36}N_5O_2$ (M+H)$^+$: m/z=546.2; found 546.2.

Step 8. 1-(4-(5-(5-(2,3-Dihydro-1H-inden-4-yl)-6-methoxy-1H-pyrazolo[4,3-b]pyridin-3-yl)pyridin-2-yl)piperidin-1-yl)ethan-1-one A solution of 5-(2,3-dihydro-1H-inden-4-yl)-6-methoxy-1-(4-methoxybenzyl)-3-(6-(piperidin-4-yl)pyridin-3-yl)-1H-pyrazolo[4,3-b]pyridine (0.80 g, 1.466 mmol) and triethylamine (0.511 ml, 3.67 mmol) in DCM (5 ml) was cooled to 0° C. and acetyl chloride (2.2 ml, 2.2 mmol) was added dropwise through a syringe. The reaction mixture was stirred at r.t. for 1 h, before being quenched with water. The desired product was extracted with DCM. The organic phase was washed with brine, dried over $Na_2SO_4$ and the solvent was removed in vacuo.

The residue was dissolved in DCM (2 ml), and trifluoromethanesulfonic acid (0.66 g, 4.4 mmol) was added. The reaction mixture was stirred at r.t for 1 h. Then the mixture was neutralized with saturated $NaHCO_3$ solution and the product was extracted with DCM. The organic phase was washed with brine, dried over sodium sulfate and concentrated in vacuo. The mixture was diluted with $CH_3CN$ and purified by prep-LCMS (XBridge C18 column, eluting with a gradient of acetonitrile/water containing 0.1% TFA, at flow rate of 60 mL/min). The product was isolated as the TFA salt. LCMS calculated for $C_{28}H_{30}N_5O_2$ (M+H)$^+$: m/z=468.2; Found: 468.2. $^1$H NMR (500 MHz, DMSO-$d_6$) δ 13.49 (s, 1H), 9.56 (d, J=2.1 Hz, 1H), 8.80 (d, J=8.3 Hz, 1H), 7.65 (d, J=8.3 Hz, 1H), 7.59 (s, 1H), 7.30 (t, J=7.3 Hz, 2H), 7.24 (t, J=7.4 Hz, 1H), 4.55 (d, J=13.2 Hz, 1H), 4.53 (d, J=13.2 Hz, 1H), 3.89 (s, 3H), 3.17 (td, J=13.1, 2.7 Hz, 1H), 3.12 (m, 1H), 2.96 (t, J=7.4 Hz, 2H), 2.80 (t, J=7.4 Hz, 2H), 2.65 (td, J=12.8, 2.8 Hz, 1H), 2.04 (s, 3H), 2.02-1.86 (m, 4H), 1.74 (qd, J=12.6, 4.2 Hz, 1H), 1.59 (qd, J=12.6, 4.3 Hz, 1H) ppm.

Example 100. 1-(4-(5-(5-(2,3-Dihydro-1H-inden-4-yl)-6-methoxy-1H-pyrazolo[4,3-b]pyridin-3-yl)pyridin-2-yl)piperidin-1-yl)-2-hydroxyethan-1-one

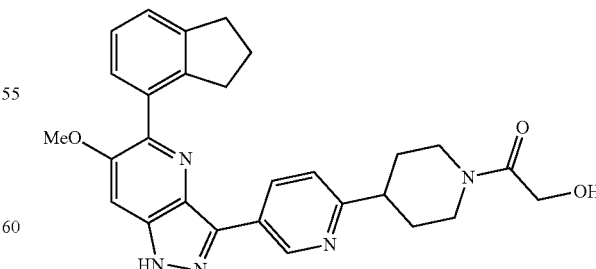

A solution of 5-(2,3-dihydro-1H-inden-4-yl)-6-methoxy-1-(4-methoxybenzyl)-3-(6-(piperidin-4-yl)pyridin-3-yl)-1H-pyrazolo[4,3-b]pyridine (1.0 g, 1.83 mmol) (from Example 99, Step 7), 2-hydroxyacetic acid (0.14 g, 1.8 mmol), HATU (1.22 g, 2.75 mmol) and DIPEA (0.960 ml, 5.50 mmol) in DMF (10 ml) was stirred at r.t. for 2 hrs. Then water was added and the product was extracted with DCM. The organic phase was washed with brine and dried over $Na_2SO_4$. The solution was concentrated in vacuo.

The residue was dissolved in DCM (2 ml), and trifluoromethanesulfonic acid (0.660 g, 4.40 mmol) was added. The reaction mixture was stirred at r.t for 1 h. Then the mixture was neutralized with saturated $NaHCO_3$ solution, and the desired product was extracted with DCM.

The organic phase was washed with brine, dried over sodium sulfate and concentrated in vacuo. The residue was redissolved in $CH_3CN$ and purified by prep-LCMS (XBridge C18 column, eluting with a gradient of acetonitrile/water containing 0.1% TFA, at flow rate of 60 mL/min). The product was isolated as the TFA salt. LCMS calculated for $C_{28}H_{30}N_5O_3$ $(M+H)^+$: m/z=484.2; Found: 484.2. $^1$H NMR (500 MHz, DMSO-$d_6$) δ 13.49 (s, 1H), 9.56 (d, J=2.1 Hz, 1H), 8.82 (dd, J=8.1, 2.1 Hz, 1H), 7.63 (d, J=8.3 Hz, 1H), 7.59 (s, 1H), 7.30 (t, J=7.3 Hz, 2H), 7.24 (t, J=7.4 Hz, 1H), 4.51 (d, J=13.1 Hz, 1H), 4.14 (t, J=7.4 Hz, 2H), 4.05 (s, 3H), 3.90 (t, J=7.4 Hz, 1H), 3.15-2.80 (m, 4H), 2.96 (t, J=7.4 Hz, 1H), 2.83-2.71 (m, 3H), 2.03-1.90 (m, 4H), 1.80-1.69 (m, 1H), 1.69-1.58 (m, 1H) ppm.

Example 101. 1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)-2-hydroxyethan-1-one (Peak 1)

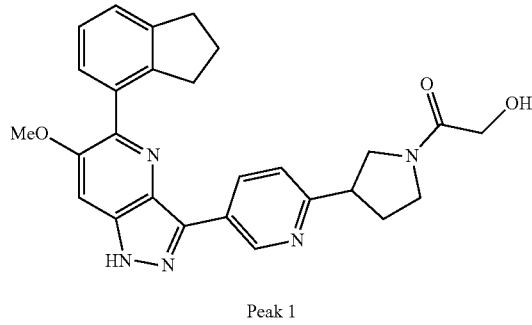 [SMILES: COc1cc2[nH]nc(-c3ccc(C4CCN(C(=O)CO)C4)nc3)c2nc1-c1cccc2c1CCC2]

Peak 1

Step 1. tert-Butyl 3-(5-(5-(2,3-dihydro-1H-inden-4-yl)-6-methoxy-1-(4-methoxybenzyl)-1H-pyrazolo[4,3-b]pyridin-3-yl)pyridin-2-yl)-2,5-dihydro-1H-pyrrole-1-carboxylate

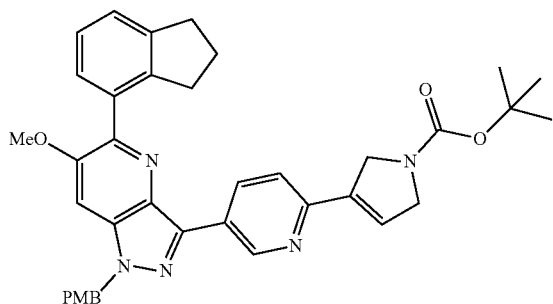

This compound was prepared according to the procedure described in Example 99, step 5, using tert-butyl 3-(4,4,5,5-tetramethyl-1,3,2-dioxaborolan-2-yl)-2,5-dihydro-1H-pyrrole-1-carboxylate instead of tert-butyl 4-(4,4,5,5-tetramethyl-1,3,2-dioxaborolan-2-yl)-3,6-dihydropyridine-1(2H)-carboxylate. LC-MS calculated for $C_{38}H_{40}N_5O_4$ $(M+H)^+$: m/z=630.3; found 630.2.

Step 2. tert-Butyl 3-(5-(5-(2,3-dihydro-1H-inden-4-yl)-6-methoxy-1-(4-methoxybenzyl)-1H-pyrazolo[4,3-b]pyridin-3-yl)pyridin-2-yl)pyrrolidine-1-carboxylate (Peak 1 and Peak 2)

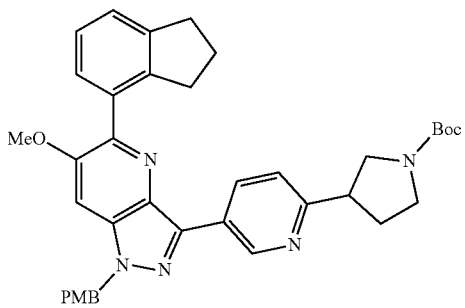

Peak 1

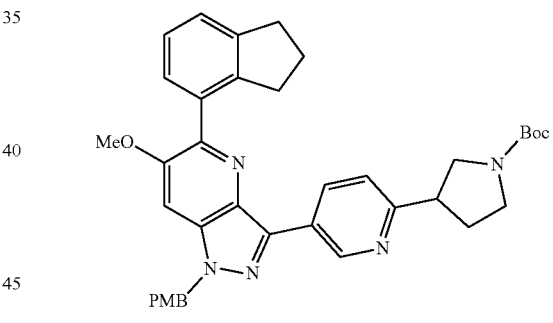

Peak 2

Racemic mixture of this compound was prepared according to the procedure described in Example 99, step 6, using tert-butyl 3-(5-(5-(2,3-dihydro-1H-inden-4-yl)-6-methoxy-1-(4-methoxybenzyl)-1H-pyrazolo[4,3-b]pyridin-3-yl)pyridin-2-yl)-2,5-dihydro-1H-pyrrole-1-carboxylate instead of tert-butyl-5-(5-(2,3-dihydro-1H-inden-4-yl)-6-methoxy-1-(4-methoxybenzyl)-1H-pyrazolo[4,3-b]pyridin-3-yl)-3',6'-dihydro-[2,4'-bipyridine]-1'(2'H)-carboxylate as starting material. LC-MS calculated for $C_{38}H_{42}N_5O_4$ $(M+H)^+$: m/z=632.3; found 632.2.

The two enantiomers were separated with chiral prep-SFC (Phenomenex Cellulose-5 5 um 21.2×250 mm, eluting with 15% MeOH in $CO_2$, at flow rate of 90 mL/min, $t_{R, peak\ 1}$=4.9 min, $t_{R, peak\ 2}$=5.6 min). Peak 1 and Peak 2 were collected and the solvents were evaporated in vacuo. LCMS calculated for $C_{38}H_{42}N_5O_4$ $(M+H)^+$: m/z=632.3; Found: 632.2.

Step 3. 5-(2,3-Dihydro-1H-inden-4-yl)-6-methoxy-1-(4-methoxybenzyl)-3-(6-(pyrrolidin-3-yl)pyridin-3-yl)-1H-pyrazolo[4,3-b]pyridine (Peak 1 and Peak 2)

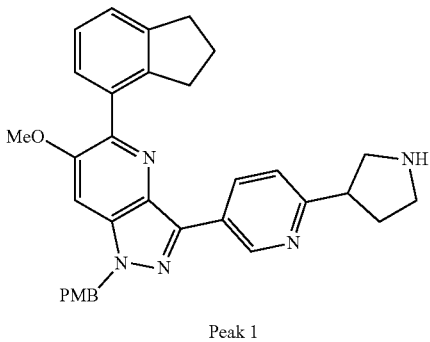

Peak 1

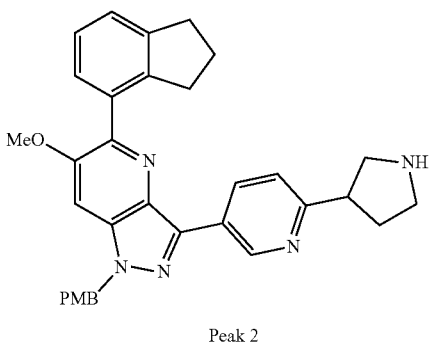

Peak 2

These compounds were prepared according to the procedure described in Example 99, step 7, using tert-butyl 3-(5-(5-(2,3-dihydro-1H-inden-4-yl)-6-methoxy-1-(4-methoxybenzyl)-1H-pyrazolo[4,3-b]pyridin-3-yl)pyridin-2-yl)pyrrolidine-1-carboxylate instead of tert-butyl 4-(5-(5-(2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate. LC-MS calculated for $C_{33}H_{34}N_5O_2$ $(M+H)^+$: m/z=532.3; found 532.2.

Step 4. 1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)-2-hydroxyethan-1-one (Peak 1)

This compound was prepared according to the procedure described in Example 100, using 5-(2,3-dihydro-1H-inden-4-yl)-6-methoxy-1-(4-methoxybenzyl)-3-(6-(pyrrolidin-3-yl)pyridin-3-yl)-1H-pyrazolo[4,3-b]pyridine (Peak 1) instead of 5-(2,3-dihydro-1H-inden-4-yl)-6-methoxy-1-(4-methoxybenzyl)-3-(6-(piperidin-4-yl)pyridin-3-yl)-1H-pyrazolo[4,3-b]pyridine as starting material. LC-MS calculated for $C_{27}H_{28}N_5O_3$ $(M+H)^+$: m/z=470.2; found 470.2. $^1H$ NMR (500 MHz, DMSO-$d_6$) δ 13.43 (s, 1H), 9.56 (d, J=2.1 Hz, 1H), 8.73 (td, J=8.1, 7.5, 2.2 Hz, 1H), 7.57 (d, J=15.1 Hz, 2H), 7.30 (t, J=7.0 Hz, 2H), 7.24 (t, J=7.4 Hz, 1H), 4.10-3.98 (m, 2H), 3.90 (s, 3H), 3.90-3.81 (m, 1H), 3.73-3.60 (m, 3H), 3.51-3.36 (m, 1H), 2.96 (t, J=7.4 Hz, 2H), 2.80 (t, J=7.4 Hz, 2H), 2.40-2.13 (m, 2H), 1.98 (p, J=7.4 Hz, 2H) ppm.

Example 102. 1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)-2-hydroxyethan-1-one (Peak 2)

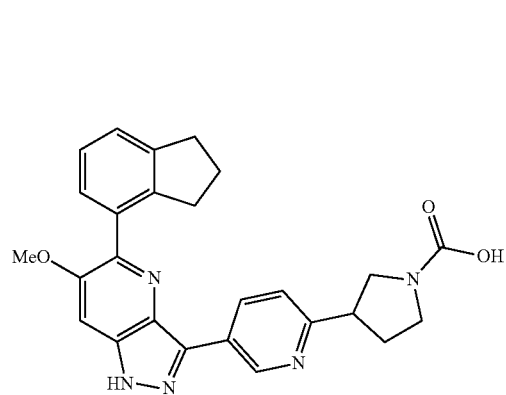

Peak 2

This compound was prepared according to the procedure described in Example 100, using 5-(2,3-dihydro-1H-inden-4-yl)-6-methoxy-1-(4-methoxybenzyl)-3-(6-(pyrrolidin-3-yl)pyridin-3-yl)-1H-pyrazolo[4,3-b]pyridine (Peak 2) instead of 5-(2,3-dihydro-1H-inden-4-yl)-6-methoxy-1-(4-methoxybenzyl)-3-(6-(piperidin-4-yl)pyridin-3-yl)-1H-pyrazolo[4,3-b]pyridine. LC-MS calculated for $C_{27}H_{28}N_5O_3(M+H)^+$: m/z=470.2; found 470.2.

Example 103. 1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)ethan-1-one (Peak 1)

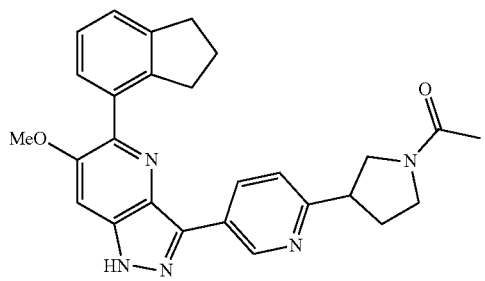

Peak 1

This compound was prepared according to the procedure described in Example 99, step 8, using 5-(2,3-dihydro-1H-inden-4-yl)-6-methoxy-1-(4-methoxybenzyl)-3-(6-(pyrrolidin-3-yl)pyridin-3-yl)-1H-pyrazolo[4,3-b]pyridine (Peak 1) instead of 5-(2,3-dihydro-1H-inden-4-yl)-6-methoxy-1-(4-methoxybenzyl)-3-(6-(piperidin-4-yl)pyridin-3-yl)-1H-pyrazolo[4,3-b]pyridine. LC-MS calculated for $C_{27}H_{28}N_5O_2(M+H)^+$: m/z=454.2; found 454.2.

Example 104. 1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)ethan-1-one (Peak 2)

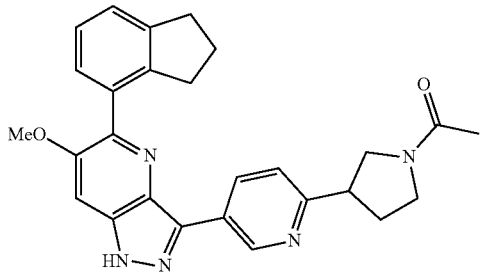

Peak 2

This compound was prepared according to the procedure described in Example 99, step 8, using 5-(2,3-dihydro-1H-inden-4-yl)-6-methoxy-1-(4-methoxybenzyl)-3-(6-(pyrrolidin-3-yl)pyridin-3-yl)-1H-pyrazolo[4,3-b]pyridine (Peak 2) instead of 5-(2,3-dihydro-1H-inden-4-yl)-LC-MS calculated for $C_{27}H_{28}N_5O_2(M+H)^+$: m/z=454.2; found 454.2. $^1$H NMR (500 MHz, DMSO-$d_6$) δ 13.45 (s, 1H), 9.57 (t, J=2.1 Hz, 1H), 8.76 (ddd, J=10.2, 8.1, 2.2 Hz, 1H), 7.62-7.56 (m, 2H), 7.30 (t, J=7.1 Hz, 2H), 7.24 (t, J=7.4 Hz, 1H), 3.95-3.83 (m, 4H), 3.74-3.50 (m, 3H), 3.46 (dd, J=11.5, 8.3 Hz, 1H), 3.34 (ddd, J=11.6, 9.3, 7.0 Hz, 1H), 2.96 (d, J=14.7 Hz, 2H), 2.80 (t, J=7.3 Hz, 2H), 2.38-2.15 (m, 2H), 2.14-1.94 (m, 4H) ppm.

Example 105. 3-(5-(5-(2,3-Dihydro-1H-inden-4-yl)-6-methoxy-1H-pyrazolo[4,3-b]pyridin-3-yl)pyridin-2-yl)-[1,3'-bipyrrolidin]-2'-one (Peak 1)

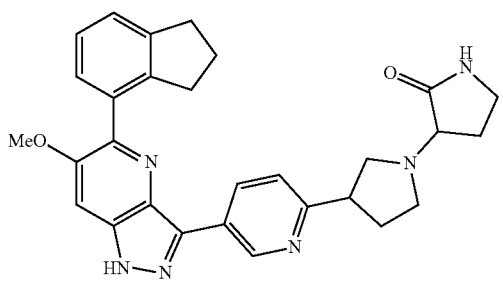

Peak 1

A mixture of 5-(2,3-dihydro-1H-inden-4-yl)-6-methoxy-1-(4-methoxybenzyl)-3-(6-(pyrrolidin-3-yl)pyridin-3-yl)-1H-pyrazolo[4,3-b]pyridine (Peak 1) (15 mg, 0.028 mmol), 3-bromopyrrolidin-2-one (7 mg, 0.042 mmol) and cesium carbonate (18 mg, 0.056 mmol) in 1,4-dioxane (1 ml) and DMF (0.2 ml) was stirred at 70° C. for 2 h. The mixture was cooled to r.t., quenched with NaHCO$_3$ solution, and the product was extracted with DCM. The organic phase was washed with brine and dried over Na$_2$SO$_4$. The solution was concentrated in vacuo.

The residue was dissolved in DCM (0.5 ml), and trifluoromethanesulfonic acid (00.16 g, 1.0 mmol) was added. The reaction mixture was stirred at r.t for 1 h. Then the mixture was neutralized with saturated NaHCO$_3$ solution and the product was extracted with DCM. The organic phase was washed with brine, dried over sodium sulfate and concentrated in vacuo. The mixture was diluted with CH$_3$CN and purified by prep-LCMS (XBridge C18 column, eluting with a gradient of acetonitrile/water containing 0.1% TFA, at flow rate of 60 mL/min). The product was isolated as the TFA salt. LCMS calculated for $C_{29}H_{31}N_6O_2$ (M+H)$^+$: m/z=495.2; Found: 495.2.

Example 106. 3-(5-(5-(2,3-Dihydro-1H-inden-4-yl)-6-methoxy-1H-pyrazolo[4,3-b]pyridin-3-yl)pyridin-2-yl)-1'-methyl-[1,3'-bipyrrolidin]-2'-one (Peak 1)

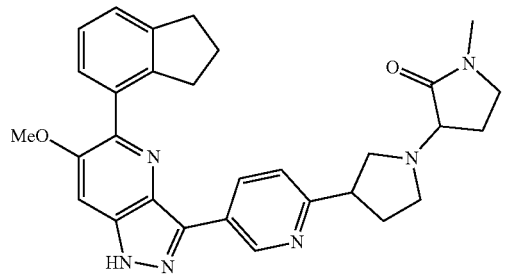

Peak 1

This compound was prepared according to the procedure described in Example 105, using 3-bromo-1-methylpyrrolidin-2-one instead of 3-bromopyrrolidin-2-one. LC-MS calculated for $C_{30}H_{33}N_6O_2$ (M+H)$^+$: m/z=509.3; found 509.2.

Example 107. 2-(3-(5-(5-(2,3-Dihydro-1H-inden-4-yl)-6-methoxy-1H-pyrazolo[4,3-b]pyridin-3-yl)pyridin-2-yl)pyrrolidin-1-yl)propanamide (Peak 1)

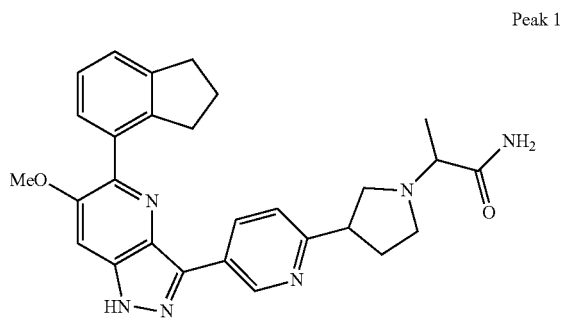 [SMILES: COc1cc2[nH]nc(-c3ccc(C4CCN(C(C)C(N)=O)C4)nc3)c2nc1-c1cccc2c1CCC2]

Peak 1

This compound was prepared according to the procedure described in Example 105, using 2-bromopropanamide instead of 3-bromopyrrolidin-2-one. LC-MS calculated for $C_{28}H_{31}N_6O_2(M+H)^+$: m/z=483.2; found 483.2.

Example 108. 5-(2,3-Dihydro-1H-inden-4-yl)-6-methoxy-3-(6-(1-(methyl-L-prolyl)piperidin-4-yl)pyridin-3-yl)-1H-pyrazolo[4,3-b]pyridine

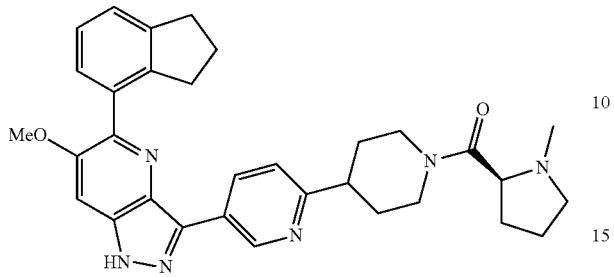

This compound was prepared according to the procedure described in Example 100, using methyl-L-proline instead of 2-hydroxyacetic acid. LC-MS calculated for $C_{32}H_{37}N_6O_2$ (M+H)⁺: m/z=537.3; found 537.3.

Example 109. (3-(5-(5-(2,3-Dihydro-1H-inden-4-yl)-6-methoxy-1H-pyrazolo[4,3-b]pyridin-3-yl)pyridin-2-yl)pyrrolidin-1-yl)((R)-4-methylmorpholin-3-yl)methanone (Peak 2)

Peak 2

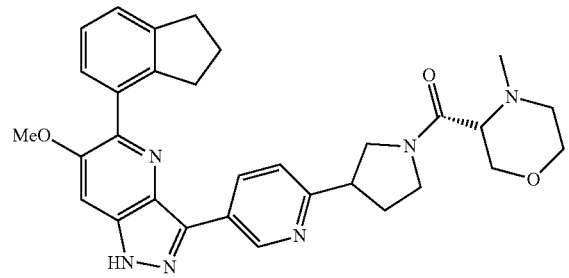

This compound was prepared according to the procedure described in Example 102, using (R)-4-methylmorpholine-3-carboxylic acid instead of 2-hydroxyacetic acid. LC-MS calculated for $C_{31}H_{35}N_6O_3$(M+H)⁺: m/z=539.3; found 539.3.

Example 110. 4-(6-Methoxy-3-(6-(4-methylpiperazin-1-yl)pyridin-3-yl)-1H-pyrazolo[4,3-b]pyridin-5-yl)-2,3-dihydro-1H-indene-1-carbonitrile

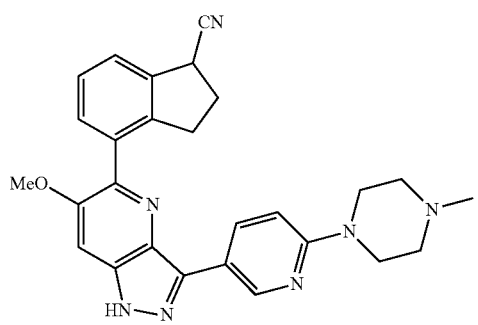 [SMILES: COc1cc2[nH]nc(-c3ccc(N4CCN(C)CC4)nc3)c2nc1-c1cccc2c1CCC2C#N]

Step 1. 4-(3-Iodo-6-methoxy-1-((2-(trimethylsilyl)ethoxy)methyl)-1H-pyrazolo[4,3-b]pyridin-5-yl)-2,3-dihydro-JH-indene-1-carbonitrile

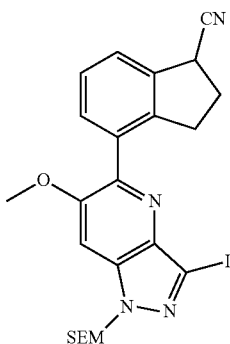 [SMILES: COc1cc2c(nc1-c1cccc3c1CCC3C#N)c(I)nn2COCC[Si](C)(C)C]

NIS (2.01 g, 8.96 mmol) was added to a solution of 4-(6-methoxy-1H-pyrazolo[4,3-b]pyridin-5-yl)-2,3-dihydro-1H-indene-1-carbonitrile (2.6 g, 8.96 mmol) in DMF (60 ml). After stirring at 60° C. for 2 h, the reaction mixture was cooled to r.t., and DIEA (3.13 ml, 17.91 mmol) and SEM-Cl (2.4 ml, 13.43 mmol) were added. After additional stirring at r.t. for 12 hrs, water was added and the product was extracted with EtOAc. The combined organic phases were washed with sat. NaCl solution, dried over Na₂SO₄, filtered, concentrated to dryness and purified by flash column chromatography to afford the desired product. LC-MS calculated for $C_{23}H_{28}IN_4O_2Si$ (M+H)⁺: m/z=547.1; found 547.1.

Step 2. 4-(6-Methoxy-3-(6-(4-methylpiperazin-1-yl)pyridin-3-yl)-1H-pyrazolo[4,3-b]pyridin-5-yl)-2,3-dihydro-1H-indene-1-carbonitrile 4-(3-Iodo-6-methoxy-1-((2-(trimethylsilyl)ethoxy)methyl)-1H-pyrazolo[4,3-b]pyridin-5-yl)-2,3-dihydro-1H-indene-1-carbonitrile (50 mg, 0.091 mmol), 1-methyl-4-(5-(4,4,5,5-tetramethyl-1,3,2-dioxaborolan-2-yl)pyridin-2-yl)piperazine (42 mg, 0.137 mmol), PdCl₂(dppf)-CH₂Cl₂ adduct (8 mg, 9.68 μmol), and Na₂CO₃ (20 mg, 0.183 mmol) were placed in a vial and the vial was evacuated and backfilled with N₂ three times. After 1,4-dioxane (1 ml) and water (100 μl) were added, the reaction mixture was stirred at 80° C. for 1 h. Then the reaction was filtered, and the solvents were evaporated in vacuo. DCM (1 ml) and TFA (0.5 ml) were added and the reaction mixture was stirred at r.t. for 30 min. The reaction was then concentrated and 1 mL of MeOH and ammonium hydroxide solution were added, the mixture was stirred for 10 min and then diluted with CH₃CN and water and purified with prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{28}N_7O$ (M+H)⁺: m/z=466.2; found 466.2.

Example 111. 4-(3-(1-(3-Cyanocyclobutyl)-1H-pyrazol-4-yl)-6-methoxy-1H-pyrazolo[4,3-b]pyridin-5-yl)-2,3-dihydro-1H-indene-1-carbonitrile

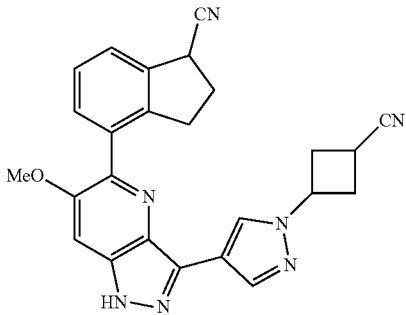 [SMILES: COc1cc2[nH]nc(-c3cnn(C4CC(C#N)C4)c3)c2nc1-c1cccc2c1CCC2C#N]

This compound was prepared according to the procedures described in Example 110, using 3-(4-(4,4,5,5-tetramethyl-1,3,2-dioxaborolan-2-yl)-1H-pyrazol-1-yl)cyclobutane-1-carbonitrile instead of 1-methyl-4-(5-(4,4,5,5-tetramethyl-1,3,2-dioxaborolan-2-yl)pyridin-2-yl)piperazine in step 2. The product was isolated as the TFA salt. LCMS calculated for $C_{25}H_{22}N_7O$ (M+H)$^+$: m/z=436.2; Found: 436.2.

Example 112. 4-(3-(1-(1-Acetylpiperidin-4-yl)-1H-pyrazol-4-yl)-6-methoxy-1H-pyrazolo[4,3-b]pyridin-5-yl)-2,3-dihydro-1H-indene-1-carbonitrile

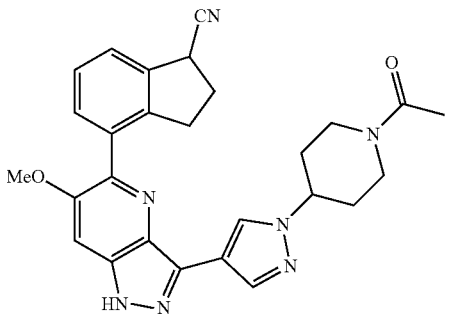 [SMILES: COc1cc2[nH]nc(-c3cnn(C4CCN(C(C)=O)CC4)c3)c2nc1-c1cccc2c1CCC2C#N]

This compound was prepared according to the procedures described in Example 110, using 1-(4-(4-(4,4,5,5-tetramethyl-1,3,2-dioxaborolan-2-yl)-1H-pyrazol-1-yl)piperidin-1-yl)ethan-1-one instead of 1-methyl-4-(5-(4,4,5,5-tetramethyl-1,3,2-dioxaborolan-2-yl)pyridin-2-yl)piperazine in step 2. The product was isolated as the TFA salt. LCMS calculated for $C_{27}H_{28}N_7O_2$ (M+H)$^+$: m/z=482.2; Found: 482.2.

Example 113. 4-(3-(6-(4-Hydroxycyclohexyl)pyridin-3-yl)-6-methoxy-1H-pyrazolo[4,3-b]pyridin-5-yl)-2,3-dihydro-1H-indene-1-carbonitrile

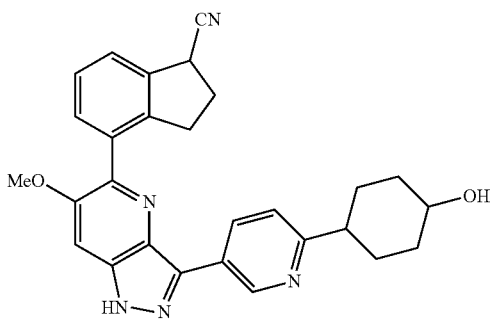 [SMILES: COc1cc2[nH]nc(-c3ccc(C4CCC(O)CC4)nc3)c2nc1-c1cccc2c1CCC2C#N]

Step 1. 4-(3-(6-Chloropyridin-3-yl)-6-methoxy-1-((2-(trimethylsilyl)ethoxy)methyl)-1H-pyrazolo[4,3-b]pyridin-5-yl)-2,3-dihydro-1H-indene-1-carbonitrile

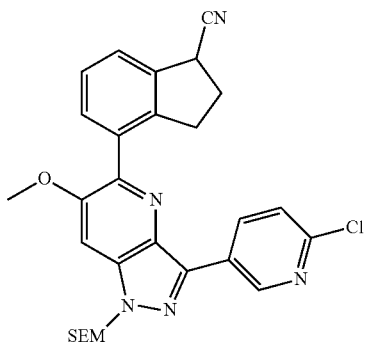 [SMILES: COc1cc2c(nc1-c1cccc3c1CCC3C#N)c(-c1ccc(Cl)nc1)nn2COCC[Si](C)(C)C]

4-(3-Iodo-6-methoxy-1-((2-(trimethylsilyl)ethoxy)methyl)-1H-pyrazolo[4,3-b]pyridin-5-yl)-2,3-dihydro-1H-indene-1-carbonitrile (400 mg, 0.732 mmol), (6-chloropyridin-3-yl)boronic acid (127 mg, 0.805 mmol), PdCl$_2$(dppf)-CH$_2$Cl$_2$ adduct (60 mg, 0.073 mmol) and K$_3$PO$_4$ (310 mg, 1.46 mmol) were placed in a vial with septum. The vial was evacuated and backfilled with N$_2$ three times, 1,4-dioxane (10 mL) and water (2 mL) were added, and the reaction mixture was stirred at 80° C. for 1 h. The mixture was filtered. The filtrate was partitioned between water and EtOAc. The organic phase was separated, washed with brine, dried over Na$_2$SO$_4$, filtered and concentrated. The residue was purified by Biotage Isolera to afford the desired product. LC-MS calculated for $C_{28}H_{31}ClN_5O_2Si$ (M+H)$^+$: m/z=532.2; found 532.1.

Step 2. 4-(3-(6-(4-Hydroxycyclohex-1-en-1-yl)pyridin-3-yl)-6-methoxy-1-((2-(trimethylsilyl)ethoxy)methyl)-1H-pyrazolo[4,3-b]pyridin-5-yl)-2,3-dihydro-1H-indene-1-carbonitrile

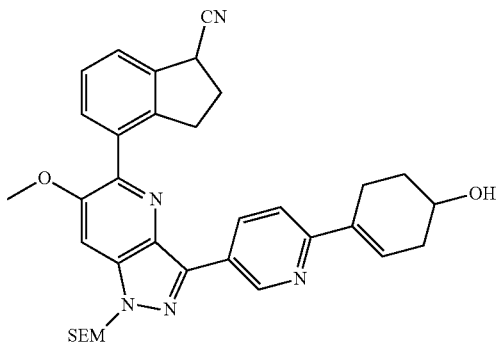 [SMILES: COc1cc2c(nc1-c1cccc3c1CCC3C#N)c(-c1ccc(C3=CCC(O)CC3)nc1)nn2COCC[Si](C)(C)C]

4-(3-(6-Chloropyridin-3-yl)-6-methoxy-1-((2-(trimethylsilyl)ethoxy)methyl)-1H-pyrazolo[4,3-b]pyridin-5-yl)-2,3-dihydro-1H-indene-1-carbonitrile (50 mg, 0.094 mmol), 4-(4,4,5,5-tetramethyl-1,3,2-dioxaborolan-2-yl)cyclohex-3-en-1-ol (32 mg, 0.141 mmol), Xphos-PdG2 (8 mg, 9.40 µmol) and K$_3$PO$_4$ (40 mg, 0.188 mmol) were placed in a vial with septum. The vial was evacuated and backfilled with N$_2$ three times, 1,4-dioxane (1 mL) and water (0.2 mL) were added, and the reaction mixture was stirred at 100° C. for 1 h. The mixture was filtered.

The filtrate was partitioned between water and EtOAc. The organic phase was separated, washed with brine, dried over Na$_2$SO$_4$, filtered and concentrated. The residue was purified by Biotage Isolera to afford the desired product. LC-MS calculated for C$_{34}$H$_{40}$N$_5$O$_3$Si (M+H)$^+$: m/z=594.3; found 594.3.

Step 3. 4-(3-(6-(4-Hydroxycyclohexyl)pyridin-3-yl)-6-methoxy-1H-pyrazolo[4,3-b]pyridin-5-yl)-2,3-dihydro-1H-indene-1-carbonitrile A mixture of 4-(3-(6-(4-hydroxycyclohex-1-en-1-yl)pyridin-3-yl)-6-methoxy-1-((2-(trimethylsilyl)ethoxy)methyl)-1H-pyrazolo[4,3-b]pyridin-5-yl)-2,3-dihydro-1H-indene-1-carbonitrile (35 mg, 0.059 mmol) and palladium on carbon (6 mg, 10%) in methanol (5 mL) was connected to a balloon filled with hydrogen and the reaction mixture was stirred at r.t. for 3 hrs. The reaction mixture was then filtered and concentrated in vacuo. 4N HCl solution in dioxane was then added and the reaction was stirred at r.t. for 30 min. It was then diluted with methanol and purified by prep-LCMS (XBridge C18 column, eluting with a gradient of acetonitrile/water containing 0.1% TFA, at flow rate of 60 mL/min). LC-MS calculated for C$_{28}$H$_{28}$N$_5$O$_2$ (M+H)$^+$: m/z=466.2, found 466.2.

Example 114. 4-(3-(6-(4-(2-Hydroxyethyl)piperazin-1-yl)pyridin-3-yl)-6-methoxy-1H-pyrazolo[4,3-b]pyridin-5-yl)-2,3-dihydro-1H-indene-1-carbonitrile

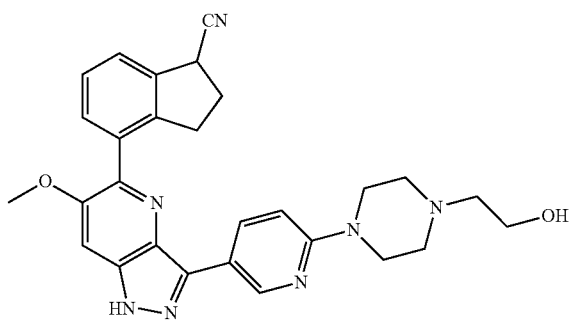 [SMILES: COc1cc2[nH]nc(-c3ccc(N4CCN(CCO)CC4)nc3)c2nc1-c1cccc2c1CCC2C#N]

This compound was prepared according to the procedures described in Example 110, using 2-(4-(5-(4,4,5,5-tetramethyl-1,3,2-dioxaborolan-2-yl)pyridin-2-yl)piperazin-1-yl)ethan-1-ol instead of 1-methyl-4-(5-(4,4,5,5-tetramethyl-1,3,2-dioxaborolan-2-yl)pyridin-2-yl)piperazine in step 2. The product was isolated as the TFA salt. LCMS calculated for C$_{28}$H$_{30}$N$_7$O$_2$ (M+H)$^+$: m/z=496.2; Found: 496.2. $^1$H NMR (500 MHz, DMSO-d$_6$) δ 13.2 (1H, s), 9.22 (d, J=1.6 Hz, 1H), 8.52 (dd, J=8.9, 1.9 Hz, 1H), 7.56 (s, 1H), 7.49 (d, J=7.6 Hz, 2H), 7.41 (t, J=7.5 Hz, 1H), 7.11 (d, J=8.9 Hz, 1H), 4.57 (t, J=8.0 Hz, 1H), 4.44 (d, J=13.6 Hz, 2H), 3.90 (s, 3H), 3.81-3.75 (m, 2H), 3.60 (d, J=11.6 Hz, 2H), 3.31 (m, 4H), 3.17-3.12 (m, 2H), 2.90 (m, 2H), 2.56 (m, 1H), 2.21 (m, 1H) ppm.

Example 115. 4-(3-(6-(1-(2-Hydroxyacetyl)piperidin-4-yl)pyridin-3-yl)-6-methoxy-1H-pyrazolo[4,3-b]pyridin-5-yl)-2,3-dihydro-1H-indene-1-carbonitrile

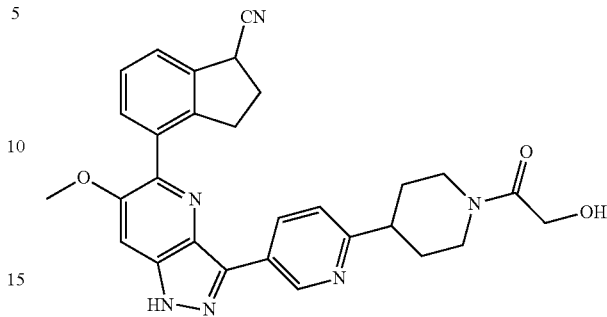

Step 1. tert-butyl 5-(5-(1-Cyano-2,3-dihydro-1H-inden-4-yl)-6-methoxy-1-((2-(trimethylsilyl)ethoxy)methyl)-1H-pyrazolo[4,3-b]pyridin-3-yl)-3',6'-dihydro-[2,4'-bipyridine]-1'(2'H)-carboxylate

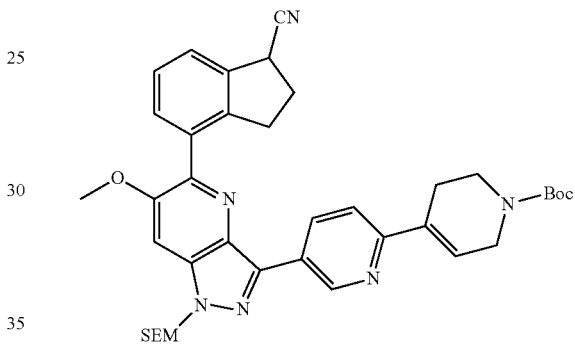

A mixture of 4-(3-iodo-6-methoxy-1-((2-(trimethylsilyl)ethoxy)methyl)-1H-pyrazolo[4,3-b]pyridin-5-yl)-2,3-dihydro-1H-indene-1-carbonitrile (600 mg, 1.098 mmol), tert-butyl 5-(4,4,5,5-tetramethyl-1,3,2-dioxaborolan-2-yl)-3',6'-dihydro-[2,4'-bipyridine]-1'(2'H)-carboxylate (467 mg, 1.208 mmol), PdCl$_2$(dppf)-CH$_2$Cl$_2$ adduct (90 mg, 0.110 mmol) and K$_3$PO$_4$ (466 mg, 2.2 mmol) in 1,4-dioxane (6 mL) and water (0.6 mL) was stirred at 80° C. overnight. After cooling to r.t., the reaction mixture was filtered and the solvent was evaporated in vacuo. The crude material was dissolved in methanol and purified by Biotage Isolera to afford the desired product. LC-MS calculated for C$_{38}$H$_{47}$N$_6$O$_4$Si (M+H)$^+$: m/z=679.3; found 679.3.

Step 2. 4-(6-Methoxy-3-(6-(piperidin-4-yl)pyridin-3-yl)-1H-pyrazolo[4,3-b]pyridin-5-yl)-2,3-dihydro-1H-indene-1-carbonitrile

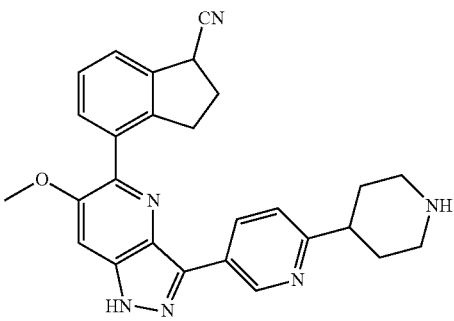 [SMILES: COc1cc2[nH]nc(-c3ccc(C4CCNCC4)nc3)c2nc1-c1cccc2c1CCC2C#N]

A mixture of tert-butyl 5-(5-(1-cyano-2,3-dihydro-1H-inden-4-yl)-6-methoxy-1-((2-(trimethylsilyl)ethoxy)methyl)-1H-pyrazolo[4,3-b]pyridin-3-yl)-3',6'-dihydro-[2,4'-bipyridine]-1'(2'H)-carboxylate (150 mg, 0.221 mmol) and palladium on carbon (23 mg, 10%) in methanol (5 mL) was connected to a balloon filled with hydrogen and the reaction mixture was stirred at r.t. for 3 hrs. The reaction mixture was then filtered and concentrated in vacuo. 4N HCl solution in dioxane was then added and the reaction was stirred at r.t. for 30 min. It was then diluted with methanol and purified by prep-LCMS (XBridge C18 column, eluting with a gradient of acetonitrile/water containing 0.1% TFA, at flow rate of 60 mL/min). LC-MS calculated for $C_{27}H_{27}N_6O$ (M+H)$^+$: m/z=451.2, found 451.2.

Step 3. 4-(3-(6-(1-(2-Hydroxyacetyl)piperidin-4-yl)pyridin-3-yl)-6-methoxy-M-pyrazolo[4,3-b]pyridin-5-yl)-2,3-dihydro-M-indene-1-carbonitrile HATU (63 mg, 0.166 mmol) was added to a solution of 2-hydroxyacetic acid (13 mg, 0.166 mmol), 4-(6-methoxy-3-(6-(piperidin-4-yl)pyridin-3-yl)-1H-pyrazolo[4,3-b]pyridin-5-yl)-2,3-dihydro-1H-indene-1-carbonitrile (50 mg, 0.111 mmol) and DIEA (39 µl, 0.222 mmol) in DMF (1 mL). After stirring at r.t. for 1 h, the reaction mixture was diluted with methanol, filtered and purified with prep-LCMS (XBridge C18 column, eluting with a gradient of acetonitrile/water containing 0.1% TFA, at flow rate of 60 mL/min). The product was isolated as the TFA salt. LC-MS calculated for $C_{29}H_{29}N_6O_3$ (M+H)$^+$: m/z=509.2, found 509.3. $^1$H NMR (500 MHz, DMSO-d$_6$) δ 13.5 (s, 1H), 9.53 (s, 1H), 8.76 (d, J=7.9 Hz, 1H), 7.62 (s, 1H), 7.57 (d, J=8.0 Hz, 1H), 7.50 (d, J=7.6 Hz, 2H), 7.41 (t, J=7.5 Hz, 1H), 4.57 (t, J=8.0 Hz, 1H), 4.51 (d, J=11.9 Hz, 1H), 4.13 (q, J=14.8 Hz, 2H), 3.91 (s, 3H), 3.82 (d, J=12.6 Hz, 1H), 3.13-3.03 (m, 2H), 2.93 (m, 2H), 2.75 (t, J=12.4 Hz, 1H), 2.56 (m, 1H), 2.22 (dd, J=12.5, 8.2 Hz, 1H), 1.93 (d, J=12.3 Hz, 2H), 1.62 (m, 2H) ppm.

Example 116. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxyethan-1-one

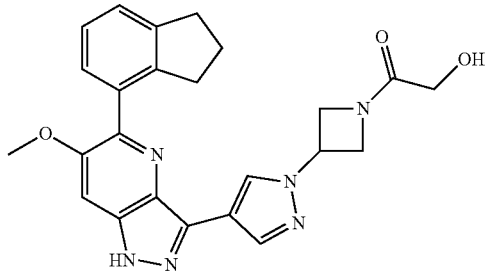 [SMILES: COc1cc2[nH]nc(-c3cnn(C4CN(C(=O)CO)C4)c3)c2nc1-c1cccc2c1CCC2]

Step 1. 3-(1-(Azetidin-3-yl)-1H-pyrazol-4-yl)-5-(2,3-dihydro-1H-inden-4-yl)-6-methoxy-1H-pyrazolo[4,3-b]pyridine

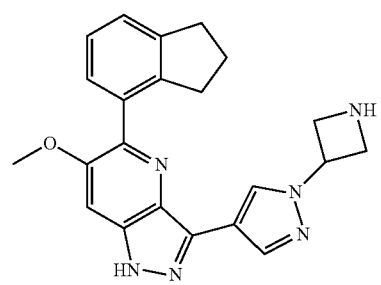 [SMILES: COc1cc2[nH]nc(-c3cnn(C4CNC4)c3)c2nc1-c1cccc2c1CCC2]

This compound was prepared according to the procedures described in Example 129, using tert-butyl 3-(4-(4,4,5,5-tetramethyl-1,3,2-dioxaborolan-2-yl)-1H-pyrazol-1-yl)azetidine-1-carboxylate instead of tert-butyl (S)-3-(4-(4,4,5,5-tetramethyl-1,3,2-dioxaborolan-2-yl)-1H-pyrazol-1-yl)pyrrolidine-1-carboxylate as starting material. LC-MS calculated for $C_{22}H_{23}N_6O$ (M+H)$^+$: m/z=387.2; found 387.2.

Step 2. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxyethan-1-one A solution of 3-(1-(azetidin-3-yl)-1H-pyrazol-4-yl)-5-(2,3-dihydro-1H-inden-4-yl)-6-methoxy-1H-pyrazolo[4,3-b]pyridine (10 mg, 0.026 mmol), 2-hydroxyacetic acid (2 mg, 0.026 mmol), BOP reagent (17 mg, 0.04 mmol) and DIPEA (14 µl. 0.078 mmol) in DMF (0.4 ml) was stirred at r.t. for 1 hour. Then to the mixture was added 0.1 ml of 1N NaOH solution. The reaction mixture was stirred at 40° C. for 1 h. The reaction mixture was then diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{24}H_{25}N_6O_3$ (M+H)$^+$: m/z=445.2; found 445.1. $^1$H NMR (500 MHz, DMSO-d$_6$) δ 8.47 (d, J=1.8 Hz, 1H), 8.22 (d, J=1.8 Hz, 1H), 7.48 (d, J=1.9 Hz, 1H), 7.28 (t, J=7.7 Hz, 2H), 7.25-7.19 (m, 1H), 5.44 (ddd, J=12.7, 7.7, 4.9 Hz, 1H), 4.65 (t, J=8.8 Hz, 1H), 4.51 (dd, J=9.7, 5.3 Hz, 1H), 4.36 (t, J=9.2 Hz, 1H), 4.20 (dd, J=10.3, 5.3 Hz, 1H), 3.97 (d, J=1.8 Hz, 2H), 3.87 (d, J=1.8 Hz, 3H), 2.95 (t, J=7.5 Hz, 2H), 2.80 (t, J=7.4 Hz, 2H), 1.98 (p, J=7.3 Hz, 2H) ppm.

Example 117. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-3-(dimethylamino)propan-1-one

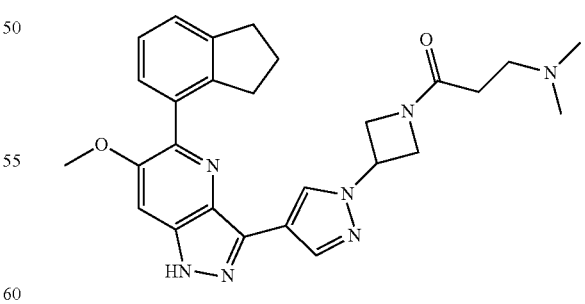

This compound was prepared according to the procedures described in Example 116, using 3-(dimethylamino)propanoic acid instead of 2-hydroxyacetic acid as starting material. The product was isolated as the TFA salt. LC-MS calculated for $C_{27}H_{32}N_7O_2$ (M+H)$^+$: m/z=486.2; found 486.3.

Example 118. (S)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(dimethylamino)propan-1-one

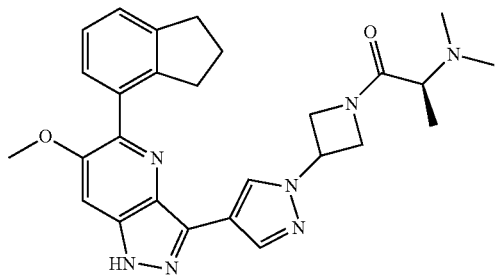

This compound was prepared according to the procedures described in Example 116, using dimethyl-L-alanine instead of 2-hydroxyacetic acid as starting material. The product was isolated as the TFA salt. LC-MS calculated for $C_{27}H_{32}N_7O_2$ $(M+H)^+$: m/z=486.2; found 486.3. $^1$H NMR (500 MHz, DMSO-$d_6$) δ 9.81 (s, 1H), 8.52 (dd, J=8.3, 1.8 Hz, 1H), 8.25 (d, J=1.8 Hz, 1H), 7.49 (d, J=1.9 Hz, 1H), 7.28 (dd, J=12.5, 7.4 Hz, 2H), 7.22 (t, J=7.4 Hz, 1H), 5.48 (m, 1H), 4.80 (t, J=8.9 Hz, 1H), 4.74-4.63 (m, 1H), 4.58-4.41 (m, 1H), 4.29 (m, 1H), 4.13 (q, J=6.8 Hz, 1H), 3.87 (d, J=1.7 Hz, 3H), 2.95 (t, J=7.4 Hz, 2H), 2.80 (d, J=4.0 Hz, 6H), 1.98 (p, J=7.4 Hz, 2H), 1.44 (dd, J=7.0, 1.8 Hz, 3H) ppm.

Example 119. (S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-methylazetidin-2-yl)methanone

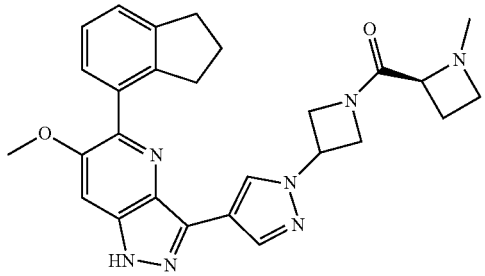 [SMILES: COc1cc2[nH]nc(-c3cnn(C4CN(C(=O)[C@@H]5CCN5C)C4)c3)c2nc1-c1cccc2c1CCC2]

This compound was prepared according to the procedures described in Example 116, using (S)-1-methylazetidine-2-carboxylic acid instead of 2-hydroxyacetic acid as starting material. The product was isolated as the TFA salt. LC-MS calculated for $C_{27}H_{30}N_7O_2$ $(M+H)^+$: m/z=484.2; found 484.2.

Example 120. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(4-methylpiperazin-1-yl)ethan-1-one

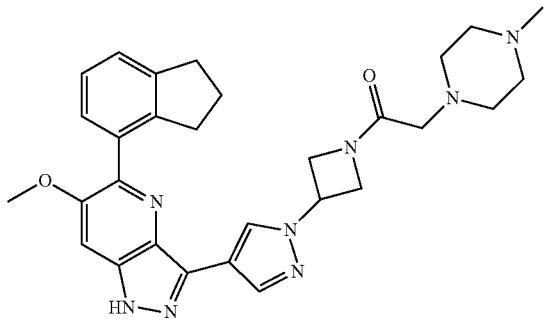

This compound was prepared according to the procedures described in Example 116, using 2-(4-methylpiperazin-1-yl) acetic acid instead of 2-hydroxyacetic acid as starting material. The product was isolated as the TFA salt. LC-MS calculated for $C_{29}H_{35}N_8O_2$ $(M+H)^+$: m/z=527.3; found 527.3.

Example 121. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(4-hydroxypiperidin-1-yl)ethan-1-one

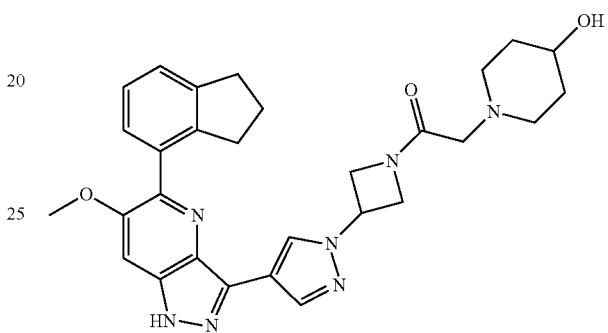

This compound was prepared according to the procedures described in Example 116, using 2-(4-hydroxypiperidin-1-yl)acetic acid instead of 2-hydroxyacetic acid as starting material. The product was isolated as the TFA salt. LC-MS calculated for $C_{27}H_{34}N_7O_3$ $(M+H)^+$: m/z=528.3; found 528.2.

Example 122. (R)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-methylazetidin-2-yl)methanone

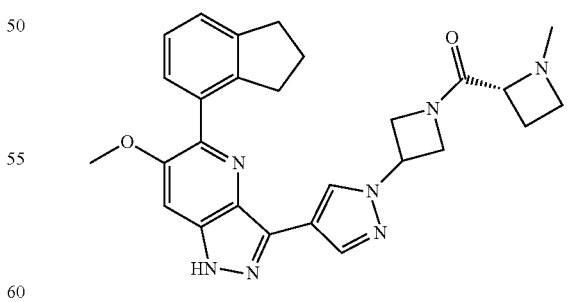

This compound was prepared according to the procedures described in Example 116, using (R)-1-methylazetidine-2-carboxylic acid instead of 2-hydroxyacetic acid as starting material. The product was isolated as the TFA salt. LC-MS calculated for $C_{27}H_{30}N_7O_2$ $(M+H)^+$: m/z=484.2; found 484.2.

Example 123. (R)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxypropan-1-one

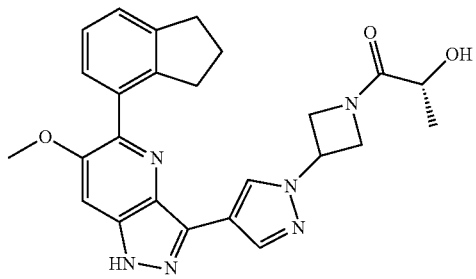 [SMILES: COc1cc2[nH]nc(-c3cnn(C4CN(C(=O)[C@@H](C)O)C4)c3)c2nc1-c1cccc2c1CCC2]

This compound was prepared according to the procedures described in Example 116, using (R)-2-hydroxypropanoic acid instead of 2-hydroxyacetic acid as starting material. The product was isolated as the TFA salt. LC-MS calculated for $C_{25}H_{27}N_6O_3$ (M+H)$^+$: m/z=459.2; found 459.2 $^1$H NMR (500 MHz, DMSO-d$_6$) δ 8.47 (s, 1H), 8.22 (d, J=1.6 Hz, 1H), 7.48 (d, J=1.7 Hz, 1H), 7.28 (t, J=7.9 Hz, 2H), 7.22 (t, J=7.1 Hz, 1H), 5.43 (m, 1H), 4.72 (m, 1H), 4.62-4.53 (m, 1H), 4.33 (dt, J=17.0, 9.2 Hz, 1H), 4.23-4.12 (m, 2H), 3.87 (d, J=1.7 Hz, 3H), 2.95 (t, J=7.4 Hz, 2H), 2.80 (t, J=7.4 Hz, 2H), 1.98 (p, J=7.3 Hz, 2H), 1.21 (dd, J=6.7, 1.7 Hz, 3H).

Example 124. (S)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxypropan-1-one

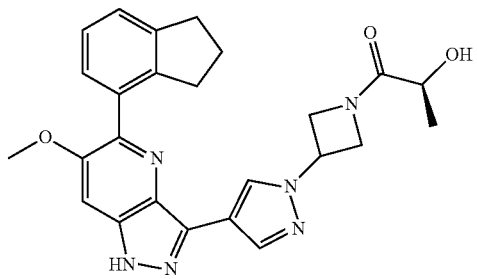 [SMILES: COc1cc2[nH]nc(-c3cnn(C4CN(C(=O)[C@H](C)O)C4)c3)c2nc1-c1cccc2c1CCC2]

This compound was prepared according to the procedures described in Example 116, using (S)-2-hydroxypropanoic acid instead of 2-hydroxyacetic acid as starting material. The product was isolated as the TFA salt. LC-MS calculated for $C_{25}H_{27}N_6O_3$ (M+H)$^+$: m/z=459.2; found 459.2.

Example 125. (3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((trans)-3-hydroxycyclobutyl)methanone

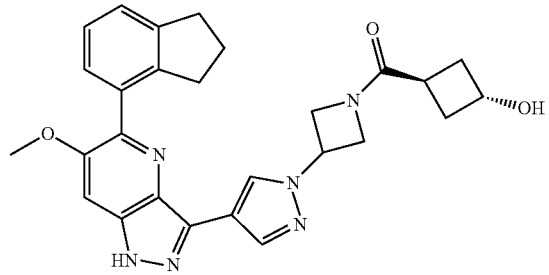 [SMILES: COc1cc2[nH]nc(-c3cnn(C4CN(C(=O)[C@H]5C[C@H](O)C5)C4)c3)c2nc1-c1cccc2c1CCC2]

This compound was prepared according to the procedures described in Example 116, using (trans)-3-hydroxycyclobutane-1-carboxylic acid instead of 2-hydroxyacetic acid as starting material. The product was isolated as the TFA salt. LC-MS calculated for $C_{27}H_{28}N_6O_3$ (M+H)$^+$: m/z=485.2; found 485.2.

Example 126. (3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((cis)-3-hydroxycyclobutyl)methanone

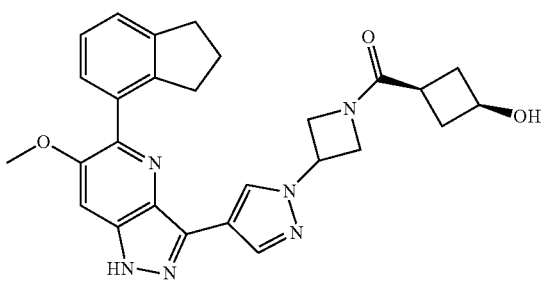 [SMILES: COc1cc2[nH]nc(-c3cnn(C4CN(C(=O)[C@H]5C[C@@H](O)C5)C4)c3)c2nc1-c1cccc2c1CCC2]

This compound was prepared according to the procedures described in Example 116, using (cis)-3-hydroxycyclobutane-1-carboxylic acid instead of 2-hydroxyacetic acid as starting material. LC-MS calculated for $C_{27}H_{29}N_6O_3$ (M+H)$^+$: m/z=485.2; found 485.2. $^1$H NMR (600 MHz, DMSO-d$_6$) δ 8.47 (s, 1H), 8.21 (s, 1H), 7.48 (s, 1H), 7.28 (t, J=8.2 Hz, 2H), 7.22 (t, J=7.4 Hz, 1H), 5.41 (m, 1H), 4.52 (t, J=8.5 Hz, 1H), 4.38 (dd, J=9.1, 5.3 Hz, 1H), 4.29 (dd, J=9.9, 8.2 Hz, 1H), 4.14 (dd, J=10.1, 5.3 Hz, 1H), 3.95 (m, 1H), 3.87 (s, 3H), 2.95 (t, J=7.4 Hz, 2H), 2.80 (t, J=7.4 Hz, 2H), 2.56-2.46 (m, 1H), 2.31 (m, 2H), 2.02-1.90 (m, 4H).

Example 127. (R)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(4-methylmorpholin-3-yl)methanone

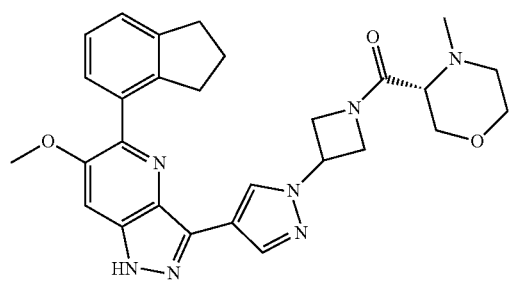 [SMILES: COc1cc2[nH]nc(-c3cnn(C4CN(C(=O)[C@H]5COCCN5C)C4)c3)c2nc1-c1cccc2c1CCC2]

This compound was prepared according to the procedures described in Example 116, using (R)-4-methylmorpholine-3-carboxylic acid instead of 2-hydroxyacetic acid as starting material. The product was isolated as the TFA salt. LC-MS calculated for $C_{28}H_{32}N_7O_3$ (M+H)$^+$: m/z=514.2; found 514.2.

Example 128. (S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(4-methylmorpholin-3-yl)methanone

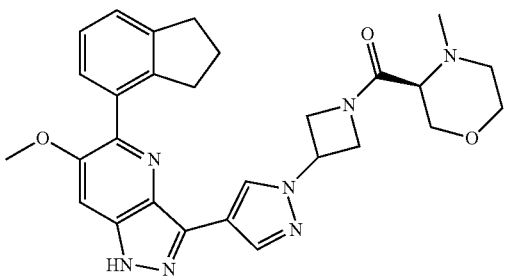 [SMILES: COc1cc2[nH]nc(-c3cnn(C4CN(C(=O)[C@@H]5COCCN5C)C4)c3)c2nc1-c1cccc2c1CCC2]

This compound was prepared according to the procedures described in Example 116, using (S)-4-methylmorpholine-3-carboxylic acid instead of 2-hydroxyacetic acid as starting material. The product was isolated as the TFA salt. LC-MS calculated for $C_{28}H_{32}N_7O_3$ (M+H)$^+$: m/z=514.2; found 514.2.

Example 129. (S)-1-(3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxyethan-1-one

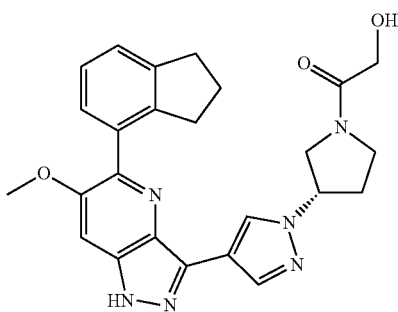 [SMILES: COc1cc2[nH]nc(-c3cnn([C@H]4CCN(C(=O)CO)C4)c3)c2nc1-c1cccc2c1CCC2]

Step 1. 5-(2,3-Dihydro-1H-inden-4-yl)-3-iodo-6-methoxy-1-((2-(trimethylsilyl)ethoxy)methyl)-1H-pyrazolo[4,3-b]pyridine

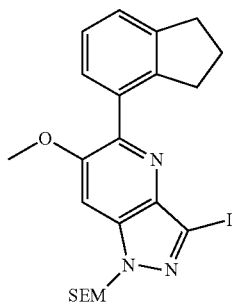 [SMILES: COc1cc2c(nc1-c1cccc3c1CCC3)c(I)nn2COCC[Si](C)(C)C]

To a solution of 5-(2,3-dihydro-1H-inden-4-yl)-6-methoxy-1H-pyrazolo[4,3-b]pyridine (2.20 g, 8.29 mmol) in DMF (26 ml) was added N-iodosuccinimide (2.80 g, 12.44 mmol), and the reaction mixture was stirred at 60° C. for 1 h. After being cooled down with the ice bath, to the reaction mixture was added DIPEA (1.7 ml, 9.95 mmol), followed by SEM-Cl (1.62 ml, 9.12 mmol). The reaction mixture was stirred at r.t. for 2 h. Then it was quenched with water, and the desired product was extracted with EtOAc. The organic phase was washed with sat. $Na_2S_2O_3$ solution, dried over $Na_2SO_4$, concentrated in vacuo, and the residue was purified by Biotage Isolera. The purification gave the desired product as oil. LC-MS calculated for $C_{22}H_{29}IN_3O_2Si$ (M+H)$^+$: m/z=522.1; found 522.1.

Step 2. (S)-5-(2,3-Dihydro-1H-inden-4-yl)-6-methoxy-3-(1-(pyrrolidin-3-yl)-1H-pyrazol-4-yl)-1H-pyrazolo[4,3-b]pyridine

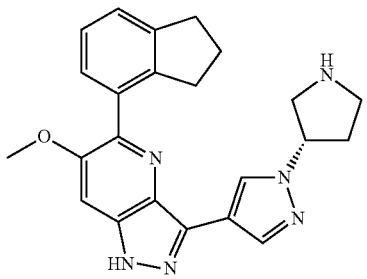 [SMILES: COc1cc2[nH]nc(-c3cnn([C@H]4CCNC4)c3)c2nc1-c1cccc2c1CCC2]

5-(2,3-Dihydro-1H-inden-4-yl)-3-iodo-6-methoxy-1-((2-(trimethylsilyl)ethoxy)methyl)-1H-pyrazolo[4,3-b]pyridine (440 mg, 0.844 mmol), tert-butyl (S)-3-(4-(4,4,5,5-tetramethyl-1,3,2-dioxaborolan-2-yl)-1H-pyrazol-1-yl)pyrrolidine-1-carboxylate (400 mg, 1.1 mmol), dicyclohexyl(2',4',6'-triisopropylbiphenyl-2-yl)phosphine-(2'-aminobiphenyl-2-yl)(chloro)palladium (1:1) (66 mg, 0.084 mmol) and $K_3PO_4$ (358 mg, 1.688 mmol) were placed in a vial with septum. After 3 times vacuum/$N_2$, 1,4-dioxane (6 mL) and water (1 mL) were added, and the reaction mixture was stirred at 60° C. for 1 h. Then it was cooled to r.t. and diluted with EtOAc/water. The organic phase was washed with brine, dried over $Na_2SO_4$, concentrated in vacuo, and the residue was purified by Biotage Isolera.

TFA (5 ml) and DCM (5 ml) were added to the obtained material and the reaction was stirred at r.t. for 1 h. Then it was concentrated in vacuo and redissolved in MeOH (5 ml). The concentrated water ammonia solution (1 ml) was added and the reaction was stirred at r.t. for 1 h. Then water was added, and the product was extracted with DCM. The organic phase was washed with brine, dried over $Na_2SO_4$ and concentrated to give the desired product. LC-MS calculated for $C_{23}H_{25}N_6O$ (M+H)$^+$: m/z=401.2; found 401.2.

Step 3. (S)-1-(3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxyethan-1-one This compound was prepared according to the procedures described in Example 116, using (S)-5-(2,3-dihydro-1H-inden-4-yl)-6-methoxy-3-(1-(pyrrolidin-3-yl)-1H-pyrazol- 4-yl)-1H-pyrazolo[4,3-b]pyridine instead of 3-(1-(azetidin-3-yl)-1H-pyrazol-4-yl)-5-(2,3-dihydro-1H-inden-4-yl)-6-methoxy-1H-pyrazolo[4,3-b]pyridine as starting material. The product was isolated as the TFA. LC-MS calculated for $C_{25}H_{27}N_6O_3$ (M+H)$^+$: m/z=459.2; found 459.2. $^1$H NMR (500 MHz, DMSO-d$_6$) δ 8.41 (m, 1H), 8.14 (m, 1H), 7.48 (d, J=1.9 Hz, 1H), 7.29 (d, J=7.4 Hz, 2H), 7.26-7.19 (m, 1H), 5.18-5.12 (m, 1H), 4.04 (s, 1H), 4.00 (s, 1H), 3.90 (t, J=5.6 Hz, 2H), 3.87 (s, 3H), 3.78-3.61 (m, 2H), 3.57-3.52 (m, 1H), 3.52-3.46 (m, 1H), 2.95 (t, J=7.4 Hz, 2H), 2.81 (t, J=7.4 Hz, 2H), 2.46-2.24 (m, 2H), 1.98 (p, J=7.4 Hz, 2H).

Example 130. (S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(tetrahydrofuran-2-yl)methanone

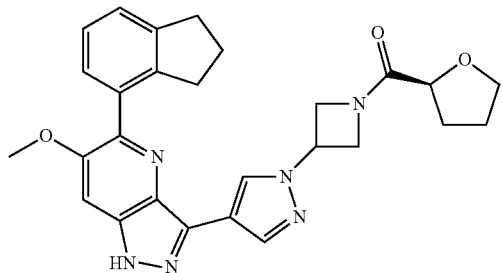 [SMILES: COc1cc2[nH]nc(-c3cnn(C4CN(C(=O)[C@@H]5CCCO5)C4)c3)c2nc1-c1cccc2c1CCC2]

This compound was prepared according to the procedures described in Example 116, using (S)-tetrahydrofuran-2-carboxylic acid instead of 2-hydroxyacetic acid as starting material. The product was isolated as the TFA salt. LC-MS calculated for $C_{27}H_{29}N_6O_3$ (M+H)$^+$: m/z=485.2; found 485.4.

Example 131. (S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(tetrahydrofuran-3-yl)methanone

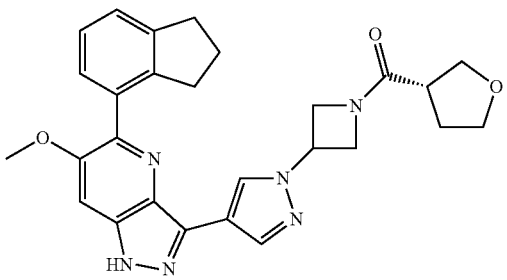 [SMILES: COc1cc2[nH]nc(-c3cnn(C4CN(C(=O)[C@H]5CCOC5)C4)c3)c2nc1-c1cccc2c1CCC2]

This compound was prepared according to the procedures described in Example 116, using (S)-tetrahydrofuran-3-carboxylic acid instead of 2-hydroxyacetic acid as starting material. The product was isolated as the TFA salt. LC-MS calculated for $C_{27}H_{29}N_6O_3$ (M+H)$^+$: m/z=485.2; found 485.4.

Example 132. (R)-1-((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxypropan-1-one

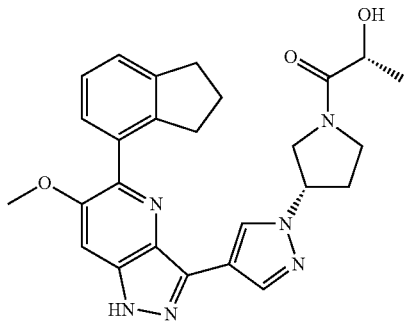 [SMILES: COc1cc2[nH]nc(-c3cnn([C@H]4CCN(C(=O)[C@@H](C)O)C4)c3)c2nc1-c1cccc2c1CCC2]

This compound was prepared according to the procedures described in Example 129, using (R)-2-hydroxypropanoic acid instead of 2-hydroxyacetic acid as starting material. The product was isolated as the TFA salt. LC-MS calculated for $C_{26}H_{29}N_6O_3$ (M+H)$^+$: m/z=473.2; found 473.2.

Example 133. (S)-1-((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxypropan-1-one

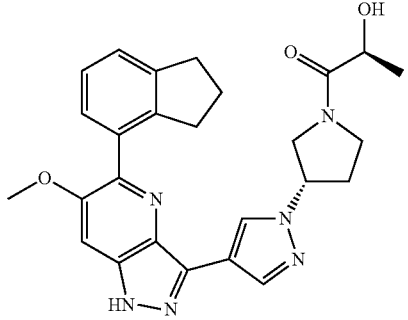 [SMILES: COc1cc2[nH]nc(-c3cnn([C@H]4CCN(C(=O)[C@H](C)O)C4)c3)c2nc1-c1cccc2c1CCC2]

This compound was prepared according to the procedures described in Example 129, using (S)-2-hydroxypropanoic acid instead of 2-hydroxyacetic acid as starting material. The product was isolated as the TFA salt. LC-MS calculated for $C_{26}H_{29}N_6O_3$ (M+H)$^+$: m/z=473.2; found 473.2.

Example 134. (R)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-3-hydroxybutan-1-one

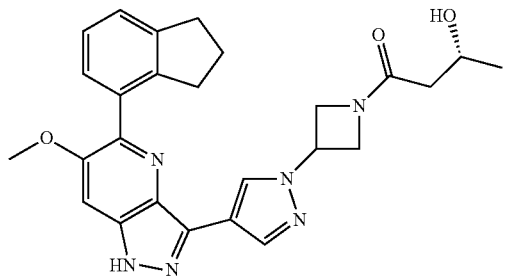 [SMILES: COc1cc2[nH]nc(-c3cnn(C4CN(C(=O)C[C@@H](C)O)C4)c3)c2nc1-c1cccc2c1CCC2]

This compound was prepared according to the procedures described in Example 116, using (R)-3-hydroxybutanoic acid instead of 2-hydroxyacetic acid as starting material. The product was isolated as the TFA salt. LC-MS calculated for $C_{26}H_{29}N_6O_3$ (M+H)$^+$: m/z=473.2; found 473.2.

Example 135. (3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1r,3r)-3-hydroxy-3-methylcyclobutyl)methanone

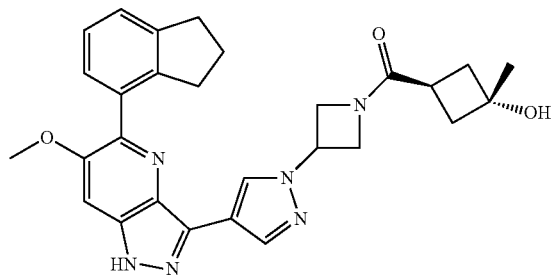 [SMILES: COc1cc2[nH]nc(-c3cnn(C4CN(C(=O)[C@H]5C[C@](C)(O)C5)C4)c3)c2nc1-c1cccc2c1CCC2]

This compound was prepared according to the procedures described in Example 116, using (1r,3r)-3-hydroxy-3-methylcyclobutane-1-carboxylic acid as starting material. LC-MS calculated for $C_{28}H_{31}N_6O_3$ (M+H)$^+$: m/z=499.2; found 499.2.

Example 136. (3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1s,3s)-3-hydroxy-3-methylcyclobutyl)methanone

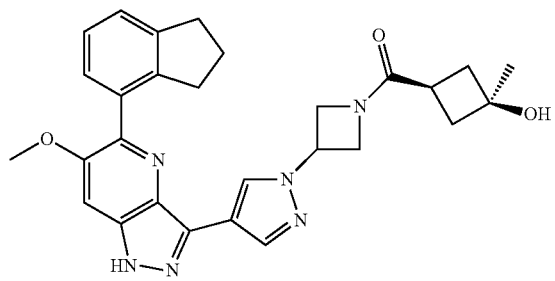 [SMILES: COc1cc2[nH]nc(-c3cnn(C4CN(C(=O)[C@H]5C[C@@](C)(O)C5)C4)c3)c2nc1-c1cccc2c1CCC2]

This compound was prepared according to the procedures described in Example 116, using (1s,3s)-3-hydroxy-3-methylcyclobutane-1-carboxylic acid instead of 2-hydroxyacetic acid as starting material. The product was isolated as the TFA salt. LC-MS calculated for $C_{28}H_{31}N_6O_3$ (M+H)$^+$: m/z=499.2; found 499.2. $^1$H NMR (600 MHz, DMSO-d$_6$) δ 8.47 (s, 1H), 8.22 (s, 1H), 7.48 (s, 1H), 7.28 (t, J=7.5 Hz, 2H), 7.22 (t, J=7.4 Hz, 1H), 5.41 (m, 1H), 4.52 (t, J=8.6 Hz, 1H), 4.39 (dd, J=9.1, 5.2 Hz, 1H), 4.30 (dd, J=10.0, 8.1 Hz, 1H), 4.14 (dd, J=10.1, 5.3 Hz, 1H), 3.87 (s, 3H), 2.95 (t, J=7.4 Hz, 2H), 2.80 (t, J=7.3 Hz, 2H), 2.67-2.58 (m, 1H), 2.15 (m, 2H), 2.04 (m, 2H), 1.98 (p, J=7.4 Hz, 2H), 1.25 (s, 3H).

Example 137. ((R)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((S)-4-methylmorpholin-3-yl)methanone

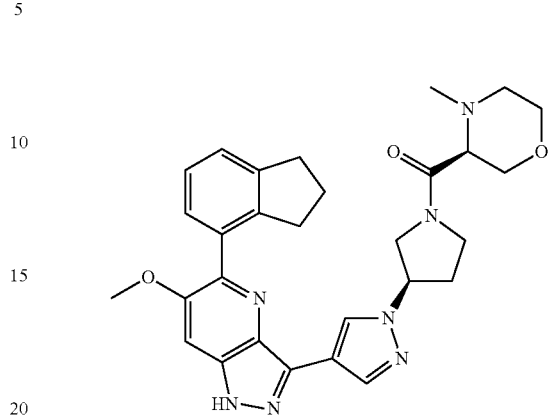

Step 1. (R)-5-(2,3-Dihydro-1H-inden-4-yl)-6-methoxy-3-(1-(pyrrolidin-3-yl)-1H-pyrazol-4-yl)-1H-pyrazolo[4,3-b]pyridine

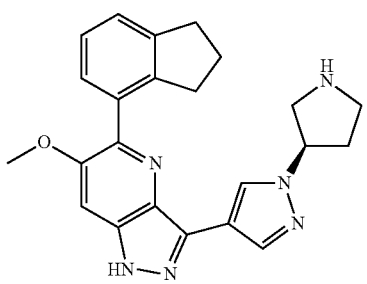 [SMILES: COc1cc2[nH]nc(-c3cnn([C@@H]4CCNC4)c3)c2nc1-c1cccc2c1CCC2]

This compound was prepared according to the procedures described in Example 129 (step 2) using (R)-3-(4-(4,4,5,5-tetramethyl-1,3,2-dioxaborolan-2-yl)-1H-pyrazol-1-yl)pyrrolidine-1-carboxylate instead of (S)-3-(4-(4,4,5,5-tetramethyl-1,3,2-dioxaborolan-2-yl)-1H-pyrazol-1-yl)pyrrolidine-1-carboxylate as starting material. LC-MS calculated for $C_{23}H_{25}N_6O$ (M+H)$^+$: m/z=401.2; found 401.2.

Step 2. ((R)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((S)-4-methylmorpholin-3-yl)methanone This compound was prepared according to the procedures described in Example 116, using (R)-5-(2,3-dihydro-1H-inden-4-yl)-6-methoxy-3-(1-(pyrrolidin-3-yl)-1H-pyrazol-4-yl)-1H-pyrazolo[4,3-b]pyridine instead of 3-(1-(azetidin-3-yl)-1H-pyrazol-4-yl)-5-(2,3-dihydro-1H-inden-4-yl)-6-methoxy-1H-pyrazolo[4,3-b]pyridine and (S)-4-methylmorpholine-3-carboxylic acid instead of 2-hydroxyacetic acid as starting material. The product was isolated as the TFA. LC-MS calculated for $C_{29}H_{34}N_7O_3$ (M+H)$^+$: m/z=528.3; found 528.3.

Example 138. ((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((R)-4-methylmorpholin-3-yl)methanone

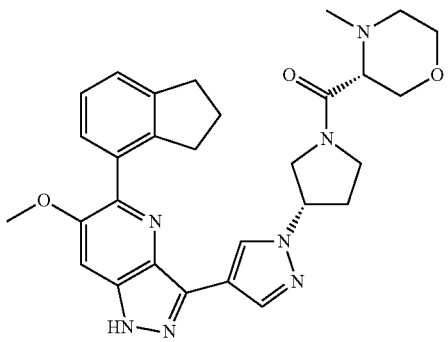 [SMILES: COc1cc2[nH]nc(-c3cnn([C@H]4CCN(C(=O)[C@H]5COCCN5C)C4)c3)c2nc1-c1cccc2c1CCC2]

This compound was prepared according to the procedures described in Example 129, using (R)-4-methylmorpholine-3-carboxylic acid instead of 2-hydroxyacetic acid as starting material. The product was isolated as the TFA salt. LC-MS calculated for $C_{29}H_{34}N_7O_3$ $(M+H)^+$: m/z=528.3; found 528.3.

Example 139. (3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-(hydroxymethyl)cyclobutyl)methanone

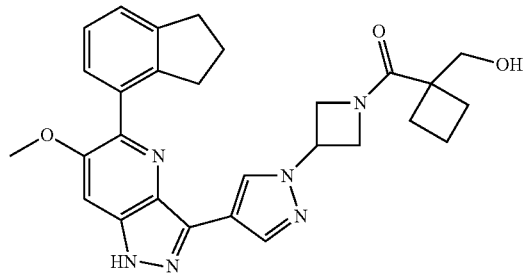 [SMILES: COc1cc2[nH]nc(-c3cnn(C4CN(C(=O)C5(CO)CCC5)C4)c3)c2nc1-c1cccc2c1CCC2]

This compound was prepared according to the procedures described in Example 116, using 1-(hydroxymethyl)cyclobutane-1-carboxylic acid instead of 2-hydroxyacetic acid as starting material. The product was isolated as the TFA salt. LC-MS calculated for $C_{28}H_{31}N_6O_3$ $(M+H)^+$: m/z=499.2; found 499.3.

Example 140. (S)-(3-(4-(5-(2,3-dihydro-1H-inden-4-yl)-6-methoxy-1H-pyrazolo[4,3-b]pyridin-3-yl)-1H-pyrazol-1-yl)azetidin-1-yl)(1-ethylazetidin-2-yl)methanone

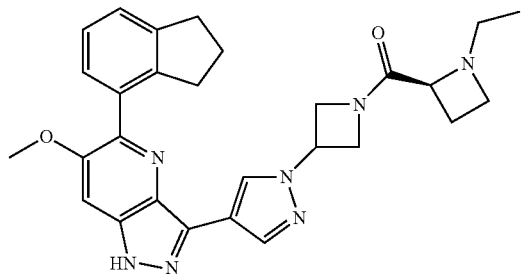 [SMILES: CCN1CC[C@H]1C(=O)N1CC(n2cc(-c3n[nH]c4cc(OC)c(-c5cccc6c5CCC6)nc34)cn2)C1]

This compound was prepared according to the procedures described in Example 116, using (S)-1-ethylazetidine-2-carboxylic acid instead of 2-hydroxyacetic acid as starting material. The product was isolated as the TFA salt. LC-MS calculated for $C_{28}H_{32}N_7O_2$ $(M+H)^+$: m/z=498.2; found 498.2.

Example 141. (S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-(2-fluoroethyl)azetidin-2-yl)methanone

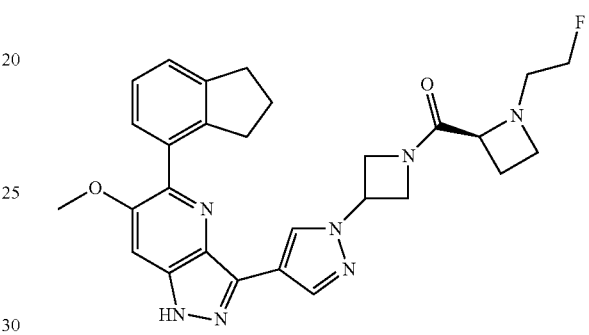

This compound was prepared according to the procedures described in Example 116, using (S)-1-(2-fluoroethyl)azetidine-2-carboxylic acid instead of 2-hydroxyacetic acid as starting material. The product was isolated as the TFA salt. LC-MS calculated for $C_{28}H_{31}FN_7O_2$ $(M+H)^+$: m/z=516.2; found 516.2.

Example 142. (S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-isopropylazetidin-2-yl)methanone

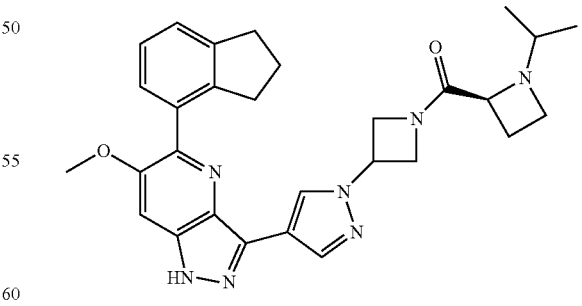

This compound was prepared according to the procedures described in Example 116, using (S)-1-isopropylazetidine-2-carboxylic acid instead of 2-hydroxyacetic acid as starting material. The product was isolated as the TFA salt. LC-MS calculated for $C_{29}H_{34}N_7O_2$ $(M+H)^+$: m/z=512.3; found 512.3.

Example 143. ((S)-3-(4-(5-(2,3-dihydro-1H-inden-4-yl)-6-methoxy-1H-pyrazolo[4,3-b]pyridin-3-yl)-1H-pyrazol-1-yl)pyrrolidin-1-yl)((S)-1-(2-fluoroethyl)azetidin-2-yl)methanone

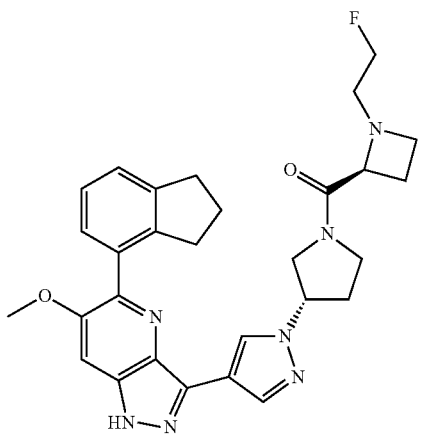 [SMILES: COc1cc2[nH]nc(-c3cnn([C@H]4CCN(C(=O)[C@@H]5CCN5CCF)C4)c3)c2nc1-c1cccc2c1CCC2]

This compound was prepared according to the procedures described in Example 129, using (S)-1-(2-fluoroethyl)azetidine-2-carboxylic acid instead of 2-hydroxyacetic acid as starting material. The product was isolated as the TFA salt. LC-MS calculated for $C_{29}H_{33}FN_7O_2(M+H)^+$: m/z=530.3; found 530.3.

Example 144. ((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((trans)-3-hydroxycyclobutyl)methanone

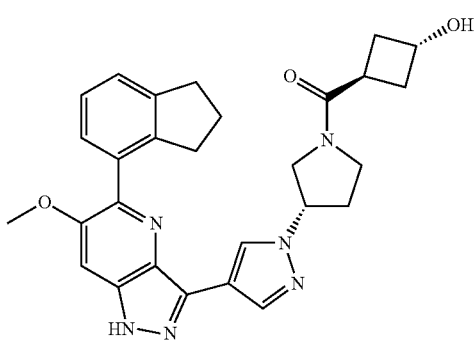 [SMILES: COc1cc2[nH]nc(-c3cnn([C@H]4CCN(C(=O)[C@H]5C[C@H](O)C5)C4)c3)c2nc1-c1cccc2c1CCC2]

This compound was prepared according to the procedures described in Example 129, using (trans)-3-hydroxycyclobutane-1-carboxylic acid instead of 2-hydroxyacetic acid as starting material. The product was isolated as the TFA salt. LC-MS calculated for $C_{28}H_{31}N_6O_3(M+H)^+$: m/z=499.2; found 499.3.

Example 145. ((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((cis)-3-hydroxycyclobutyl)methanone

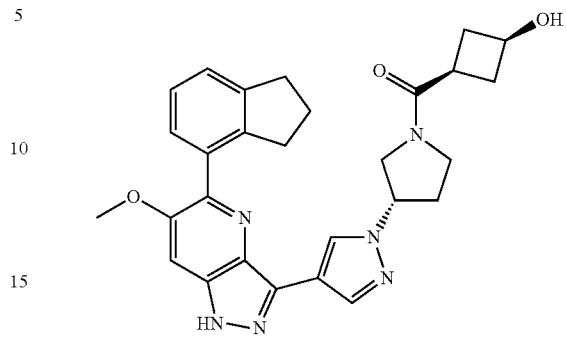

This compound was prepared according to the procedures described in Example 129, using (cis)-3-hydroxycyclobutane-1-carboxylic acid instead of 2-hydroxyacetic acid as starting material. The product was isolated as the TFA salt. LC-MS calculated for $C_{28}H_{31}N_6O_3(M+H)^+$: m/z=499.2; found 499.2.

Example 146. ((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((1s,3r)-3-hydroxy-3-methylcyclobutyl)methanone

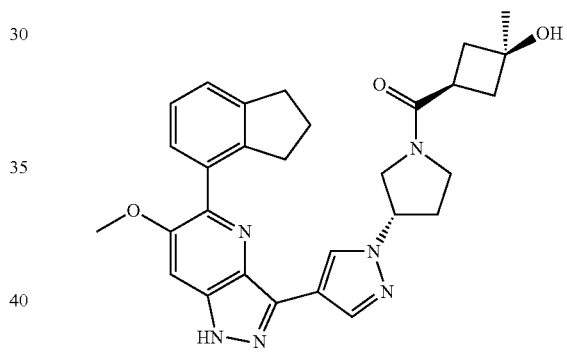

This compound was prepared according to the procedures described in Example 129, using, (1s,3s)-3-hydroxy-3-methylcyclobutane-1-carboxylic acid instead of 2-hydroxyacetic acid as starting material. The product was isolated as the TFA salt. LC-MS calculated for $C_{29}H_{33}N_6O_3(M+H)^+$: m/z=513.2; found 513.2.

Example 147. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-methoxyethan-1-one

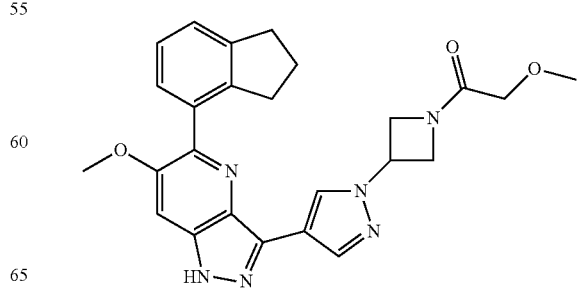

This compound was prepared according to the procedures described in Example 116, using 2-methoxyacetic acid instead of 2-hydroxyacetic acid as starting material. The product was isolated as the TFA salt. LC-MS calculated for $C_{25}H_{27}N_6O_3(M+H)^+$: m/z=459.2; found 459.2.

Example 148. 1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(dimethylamino)-2-methylpropan-1-one

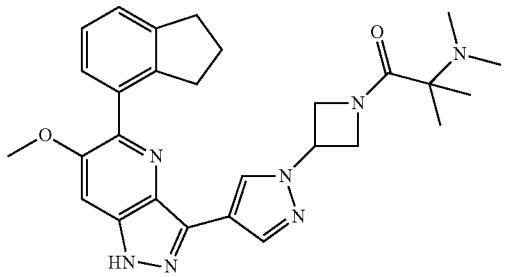

This compound was prepared according to the procedures described in Example 116, using 2-(dimethylamino)-2-methylpropanoic acid instead of 2-hydroxyacetic acid as starting material. The product was isolated as the TFA salt. LC-MS calculated for $C_{28}H_{34}N_7O_2$ $(M+H)^+$: m/z=500.2; found 500.2.

Example 149. 1-(3-(4-(5-(2,3-Dihydro-1H-inden-4-yl)-6-methoxy-1H-pyrazolo[4,3-b]pyridin-3-yl)-1H-pyrazol-1-yl)azetidine-1-carbonyl)cyclopropane-1-carbonitrile

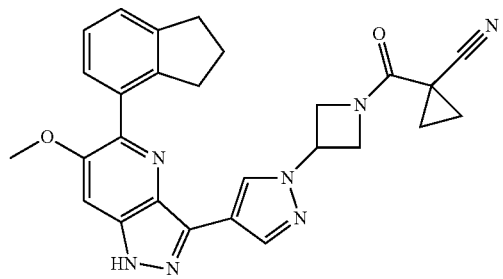 [SMILES: COc1cc2[nH]nc(-c3cnn(C4CN(C(=O)C5(C#N)CC5)C4)c3)c2nc1-c1cccc2c1CCC2]

This compound was prepared according to the procedures described in Example 116, using 1-cyanocyclopropane-1-carboxylic acid instead of 2-hydroxyacetic acid as starting material. The product was isolated as the TFA salt. LC-MS calculated for $C_{27}H_{26}N_7O_2(M+H)^+$: m/z=480.2; found 480.2.

Example 150. 2-((3-(4-(5-(2,3-Dihydro-1H-inden-4-yl)-6-methoxy-1H-pyrazolo[4,3-b]pyridin-3-yl)-1H-pyrazol-1-yl)azetidin-1-yl)sulfonyl)ethan-1-ol

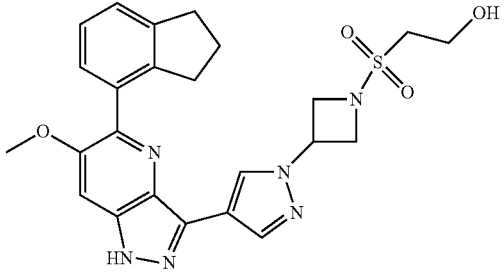 [SMILES: COc1cc2[nH]nc(-c3cnn(C4CN(S(=O)(=O)CCO)C4)c3)c2nc1-c1cccc2c1CCC2]

Step 1. 3-(1-(Azetidin-3-yl)-1H-pyrazol-4-yl)-5-(2,3-dihydro-1H-inden-4-yl)-6-methoxy-1-(4-methoxybenzyl)-1H-pyrazolo[4,3-b]pyridine

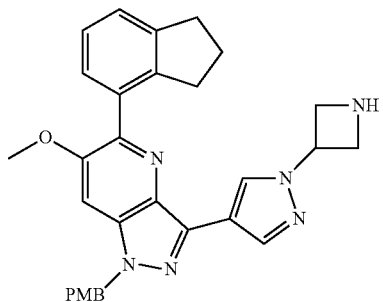

5-(2,3-Dihydro-1H-inden-4-yl)-3-iodo-6-methoxy-1-(4-methoxybenzyl)-1H-pyrazolo[4,3-b]pyridine (0.8 g, 1.56 mmol), tert-butyl 3-(4-(4,4,5,5-tetramethyl-1,3,2-dioxaborolan-2-yl)-1H-pyrazol-1-yl)azetidine-1-carboxylate (0.71 g, 2.03 mmol), dicyclohexyl(2',4',6'-triisopropylbiphenyl-2-yl)phosphine-(2'-aminobiphenyl-2-yl)(chloro)palladium (1:1) (0.12 g, 0.156 mmol) and cesium carbonate (0.66 g, 2.03 mmol) were placed in a vial with septum. After 3 times vacuum/$N_2$1,4-dioxane (10 mL) and water (2 mL) were added, and the reaction mixture was stirred at 60° C. for 1 h. Then it was cooled to r.t. and diluted with EtOAc/water. The organic phase separated, washed with brine, dried over $Na_2SO_4$, concentrated in vacuo, and the residue was purified by Biotage Isolera.

TFA (5 ml) and DCM (5 ml) were added to the obtained intermediate, and the reaction mixture was stirred at r.t. for 1 h. Then it was concentrated in vacuo, and the reaction was neutralized with the saturated $NaHCO_3$ solution. The product was extracted with DCM. The organic phase was washed with brine, dried over $Na_2SO_4$ and concentrated to give the desired product. LC-MS calculated for $C_{30}H_{31}N_6O_2$ $(M+H)^+$: m/z=507.2; found 507.2.

Step 2. 2-((3-(4-(5-(2,3-Dihydro-1H-inden-4-yl)-6-methoxy-1H-pyrazolo[4,3-b]pyridin-3-yl)-1H-pyrazol-1-yl)azetidin-1-yl)sulfonyl)ethan-1-ol To a solution of 3-(1-(azetidin-3-yl)-1H-pyrazol-4-yl)-5-(2,3-dihydro-1H-inden-4-yl)-6-methoxy-1-(4-methoxybenzyl)-1H-pyrazolo[4,3-b]pyridine (10 mg, 0.020 mmol) and TEA (6 µl, 0.04 mmol) in DCM (1 ml) at 0° C. was added 2-hydroxyethane-1-sulfonyl chloride (3 mg, 0.020 mmol). The reaction mixture was stirred at r.t. for 1 h. Then it was quenched with brine, and the product was extracted with DCM. The organic phase was dried over sodium sulfate and concentrated in vacuo.

The residue was dissolved in DCM (0.5 ml), and trifluoromethanesulfonic acid (0.2 ml) was added. The reaction mixture was stirred at r.t for 1 h. Then the mixture was neutralized with saturated NaHCO$_3$ solution and the product was extracted with DCM. The organic phase was washed with brine, dried over sodium sulfate and concentrated in vacuo. The mixture was diluted with CH$_3$CN and purified by prep-LCMS (XBridge C18 column, eluting with a gradient of acetonitrile/water containing 0.1% TFA, at flow rate of 60 mL/min). The product was isolated as the TFA salt. LC-MS calculated for C$_{24}$H$_{27}$N$_6$O$_4$S (M+H)$^+$: m/z=495.2; found 495.1.

Example 151. 2-((3-(4-(5-(2,3-Dihydro-1H-inden-4-yl)-6-methoxy-1H-pyrazolo[4,3-b]pyridin-3-yl)-1H-pyrazol-1-yl)azetidin-1-yl)sulfonyl)-N,N-dimethylethan-1-amine

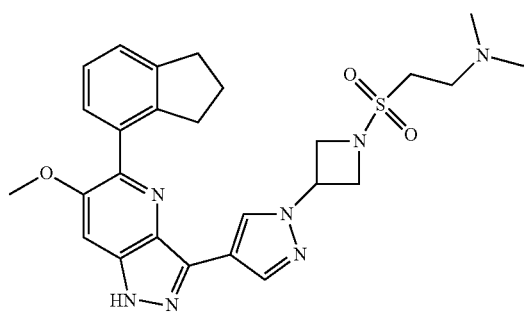

This compound was prepared according to the procedures described in Example 150, using 2-(dimethylamino)ethane-1-sulfonyl chloride instead of 2-hydroxyethane-1-sulfonyl chloride as starting material. The product was isolated as the TFA salt. LC-MS calculated for C$_{26}$H$_{32}$N$_7$O$_3$S (M+H)$^+$: m/z=522.2; found 522.2.

Example 152. 2-Methoxyethyl 3-(4-(5-(2,3-dihydro-1H-inden-4-yl)-6-methoxy-1H-pyrazolo[4,3-b]pyridin-3-yl)-1H-pyrazol-1-yl)azetidine-1-carboxylate

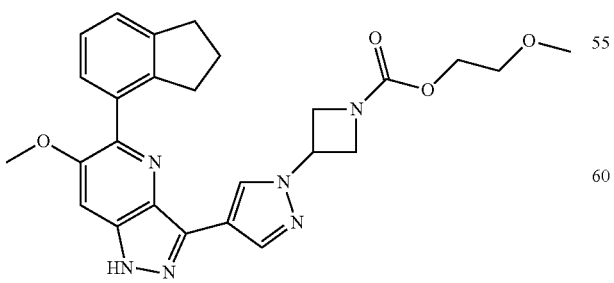

This compound was prepared according to the procedures described in Example 150, using 2-methoxyethyl carbono-chloridate instead of 2-hydroxyethane-1-sulfonyl chloride as starting material. The product was isolated as the TFA salt. LC-MS calculated for C$_{26}$H$_{29}$N$_6$O$_4$ (M+H)$^+$: m/z=489.2; found 489.2.

Example 153. (3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1s,3s)-3-methoxycyclobutyl)methanone

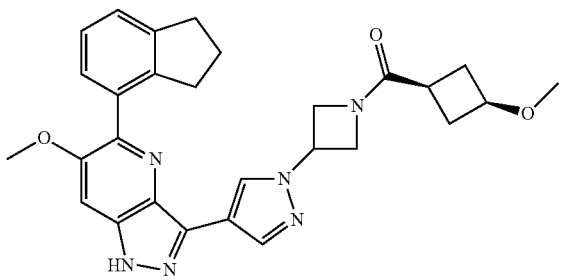

This compound was prepared according to the procedures described in Example 116, using (1s, 3 s)-3-methoxycyclobutane-1-carboxylic acid instead of 2-hydroxyacetic acid as starting material. The product was isolated as the TFA salt. LC-MS calculated for C$_{28}$H$_{31}$N$_6$O$_3$ (M+H)$^+$: m/z=499.2; found 499.2.

Example 154. N-(3-(5-(5-(2,3-Dihydro-1H-inden-4-yl)-6-methoxy-1H-pyrazolo[4,3-b]pyridin-3-yl)pyridin-2-yl)cyclopentyl)-N-methylmethanesulfonamide

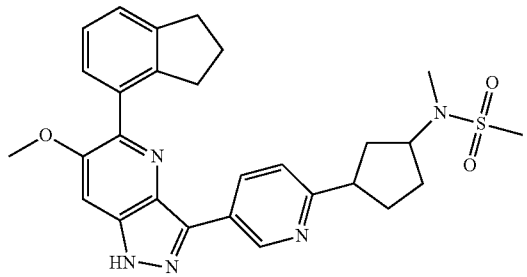

Step 1. 3-(6-Bromopyridin-3-yl)-5-(2,3-dihydro-1H-inden-4-yl)-6-methoxy-1-(4-methoxybenzyl)-1H-pyrazolo[4,3-b]pyridine

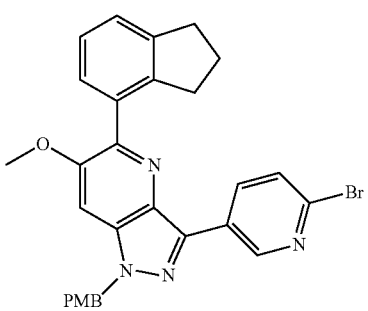

5-(2,3-Dihydro-1H-inden-4-yl)-3-iodo-6-methoxy-1-(4-methoxybenzyl)-1H-pyrazolo[4,3-b]pyridine (3.5 g, 6.84 mmol), (6-bromopyridin-3-yl)boronic acid (2.5 g, 12.32 mmol), Pd(dppf)$_2$Cl$_2$ (1.5 g) and Cs$_2$CO$_3$ (3.5 g) in dioxane (35 mL) and water (8 mL) were mixed together. The reaction mixture was purged with nitrogen and heated at 70° C. for 4 hrs. The resulting solution was filtered, and the solids were washed with DCM. The filtrate fractions were combined, concentrated in vacuo, and the product was purified by Biotage Isolera. LCMS calculated for C$_{29}$H$_{26}$BrN$_4$O$_2$ (M+H)$^+$: m/z=541.3; Found: 541.3.

Step 2. tert-Butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclopent-3-en-1-yl)carbamate

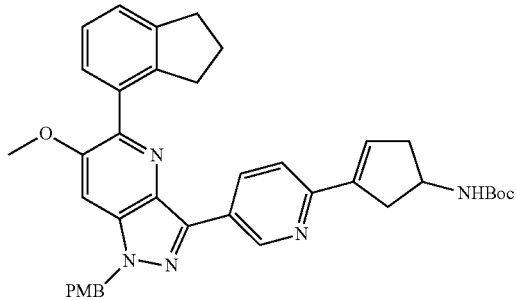

3-(6-Bromopyridin-3-yl)-5-(2,3-dihydro-1H-inden-4-yl)-6-methoxy-1-(4-methoxybenzyl)-1H-pyrazolo[4,3-b]pyridine (1.06 g, 2.0 mmol), tert-butyl (3-(4,4,5,5-tetramethyl-1,3,2-dioxaborolan-2-yl)cyclopent-3-en-1-yl)carbamate (0.73 g, 2.35 mmol), Cs$_2$CO$_3$ (1.0 g) and X-Phos Pd G2 (250 mg) in 1,4-dioxanes (20 mL) and water (2 mL) were mixed together and flushed with nitrogen. The mixture was sealed and heated at 80° C. for 3 hr. The reaction was filtered and the filtrate was concentrated in vacuo. The crude material was purified with Biotage Isolera to give the desired product. LCMS calculated for C$_{39}$H$_{42}$N$_5$O$_4$ (M+H)$^+$: m/z=644.3; Found: 644.4.

Step 3. tert-Butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclopentyl)carbamate

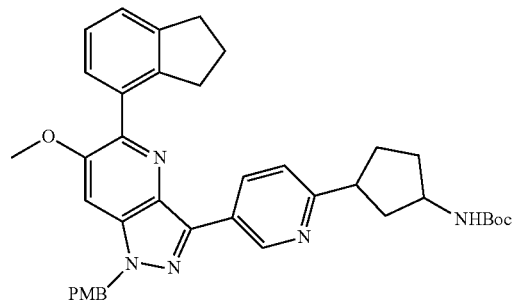

A mixture of tert-butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclopent-3-en-1-yl)carbamate (1.2 g, 1.86 mmol) and Pd/C (0.30 g) in a solution of methanol (20 mL) and 1,4-dioxanes (20 mL) was stirred under 50 psi of hydrogen overnight. It was then filtered and concentrated in vacuo. The crude material was purified with Biotage Isolera to give the desired product. LCMS calculated for C$_{39}$H$_{44}$N$_5$O$_4$ (M+H)$^+$: m/z=646.3; Found: 646.4.

Step 4. 3-(5-(5-(2,3-Dihydro-1H-inden-4-yl)-6-methoxy-1-(4-methoxybenzyl)-1H-pyrazolo[4,3-b]pyridin-3-yl)pyridin-2-yl)-N-methylcyclopentan-1-amine

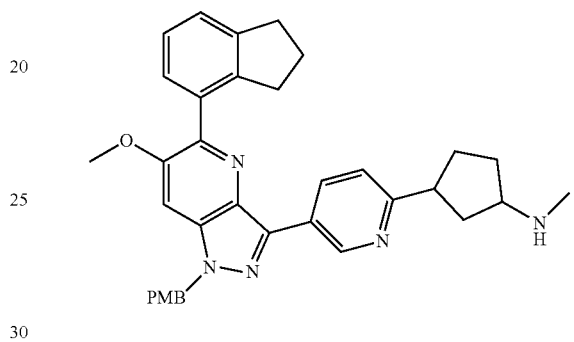

2 M solution of LAH in THF (2 ml) was slowly added to a solution of tert-butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclopentyl)carbamate (0.70 g, 1.084 mmol) in THF (5 ml) upon cooling in the dry ice-hexane bath. The reaction mixture was allowed to warm to r.t. and stirred overnight. The reaction was carefully quenched with ice. To it was added 20 mL of 1N NaOH solution. The product was extracted with DCM 2×20 mL. Organic phase was separated, filtered through Celite, dried over Na$_2$SO$_4$ and concentrated in vacuo. The resulting material was used for next step without further purification. LCMS calculated for C$_{35}$H$_{38}$N$_5$O$_2$ (M+H)$^+$: m/z=560.3; Found: 560.4.

Step 5. N-(3-(5-(5-(2,3-Dihydro-1H-inden-4-yl)-6-methoxy-1H-pyrazolo[4,3-b]pyridin-3-yl)pyridin-2-yl)cyclopentyl)-N-methylmethanesulfonamide Methanesulfonyl chloride (8 mg, 0.071 mmol) was added to a solution of 3-(5-(5-(2,3-dihydro-1H-inden-4-yl)-6-methoxy-1-(4-methoxybenzyl)-1H-pyrazolo[4,3-b]pyridin-3-yl)pyridin-2-yl)-N-methylcyclopentan-1-amine (4 mg, 7.2 µmol) and DIPEA (50 mg) in THF (0.5 mL), and the reaction mixture was stirred at r.t. for 1 h. To this solution 0.5 ml of triflic acid/DCM (1:1) mixture was added and the reaction was stirred at r.t. for additional 1 h. Then the mixture was neutralized with saturated NaHCO$_3$ solution and the product was extracted with DCM. The organic phase was washed with brine, dried over sodium sulfate and concentrated in vacuo. The mixture was diluted with CH$_3$CN and purified by prep-LCMS (XBridge C18 column, eluting with a gradient of acetonitrile/water containing 0.1% TFA, at flow rate of 60 mL/min). LCMS calculated for C$_{28}$H$_{32}$N$_5$O$_3$S (M+H)$^+$: m/z=518.2; Found: 518.3.

Example 155. N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxy-N-methylacetamide (Peak 1)

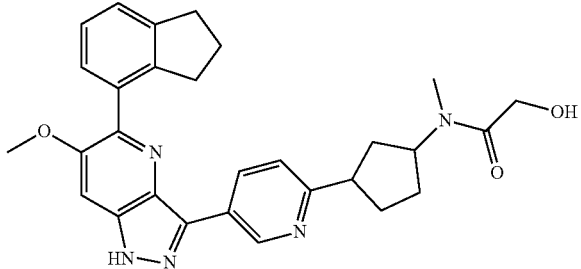 [SMILES: COc1cc2[nH]nc(-c3ccc(C4CCC(N(C)C(=O)CO)C4)nc3)c2nc1-c1cccc2c1CCC2]

Step 1. tert-Butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclopentyl)(methyl)carbamate

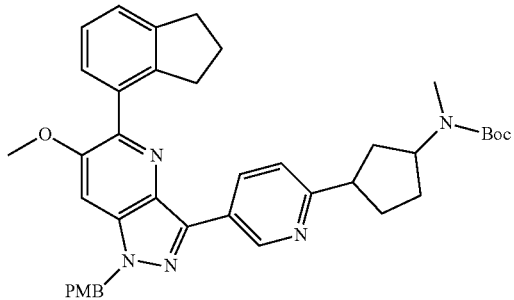

Boc-anhydride (0.20 g) was added to a solution of 3-(5-(5-(2,3-dihydro-1H-inden-4-yl)-6-methoxy-1-(4-methoxybenzyl)-1H-pyrazolo[4,3-b]pyridin-3-yl)pyridin-2-yl)-N-methylcyclopentan-1-amine (0.10 g, 0.18 mmol) and triethylamine (0.5 mL) in dichloromethane (5 mL), and the reaction mixture was stirred at r.t. overnight. Water was added to the reaction mixture, and the desired product was extracted with DCM. Organic phases were combined, dried over sodium sulfate, concentrated in vacuo, and purified by Biotage Isolera. LCMS calculated for $C_{40}H_{46}N_5O_4$ (M+H)$^+$: m/z=660.3; Found: 660.4.

The two enantiomers were separated on chiral prep-SFC with chiral column Phenomenex Lux 5um i-Amylose-1 (21.2×250 mm), eluting with 25% methanol in $CO_2$ (65 ml/min).

Step 2. 3-(5-(5-(2,3-Dihydro-1H-inden-4-yl)-6-methoxy-1-(4-methoxybenzyl)-1H-pyrazolo[4,3-b]pyridin-3-yl)pyridin-2-yl)-N-methylcyclopentan-1-amine (Peak 1)

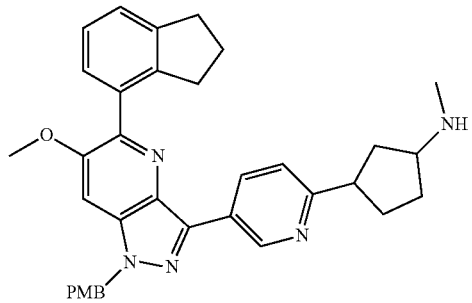

2 mL of 4N HCl solution in dioxane was added to a solution of tert-butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclopentyl)(methyl)carbamate (10 mg, 0.015 mmol) (Peak 1 from chiral separation) in 0.5 mL of methanol. After the reaction mixture was stirred at r.t. overnight, the solvent was removed in vacuo, and obtained HCl salt of the desired product was used in the next step without further purification. LCMS calculated for $C_{35}H_{38}N_5O_2$ (M+H)$^+$: m/z=560.3; Found: 560.4.

Step 3. N-(3-(5-(5-(2,3-dihydro-1H-inden-4-yl)-6-methoxy-1H-pyrazolo[4,3-b]pyridin-3-yl)pyridin-2-yl)cyclopentyl)-2-hydroxy-N-methylacetamide (Peak 1)

HATU (10 mg) was added to a solution of 3-(5-(5-(2,3-dihydro-1H-inden-4-yl)-6-methoxy-1-(4-methoxybenzyl)-1H-pyrazolo[4,3-b]pyridin-3-yl)pyridin-2-yl)-N-methylcyclopentan-1-amine (5 mg, 8.93 μmol, Peak 1), 2-hydroxyacetic acid (7 mg, 0.089 mmol) and DIPEA (50 mg) DMF (0.5 mL). The reaction mixture was stirred at r.t. for 1 h before water was added, and the desired product was extracted with DCM. The organic fractions were combined, dried over sodium sulfate and concentrated in vacuo.

The residue was dissolved in DCM (2 ml), and trifluoromethanesulfonic acid (0.66 g, 4.4 mmol) was added. The reaction mixture was stirred at r.t for 1 h. Then the mixture was neutralized with saturated $NaHCO_3$ solution and the product was extracted with DCM. The organic phase was washed with brine, dried over sodium sulfate and concentrated in vacuo. The mixture was diluted with $CH_3CN$ and purified by prep-LCMS (XBridge C18 column, eluting with a gradient of acetonitrile/water containing 0.1% TFA, at flow rate of 60 mL/min). LCMS calculated for $C_{29}H_{32}N_5O_3$ (M+H)$^+$: m/z=498.2; Found: 498.3.

Example 156. (2S)—N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxypropanamid

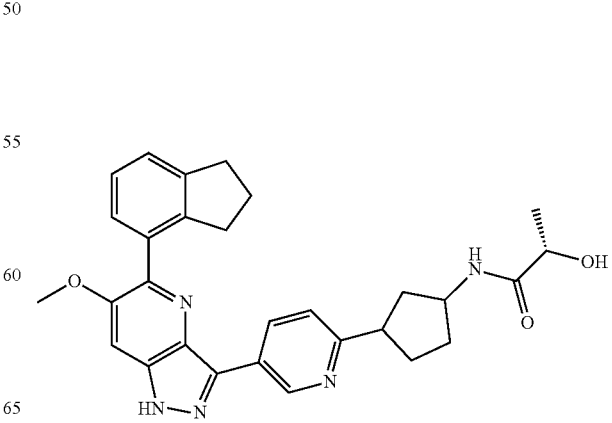

Step 1. 3-(5-(5-(2,3-Dihydro-1H-inden-4-yl)-6-methoxy-1H-pyrazolo[4,3-b]pyridin-3-yl)pyridin-2-yl)cyclopentan-1-amine

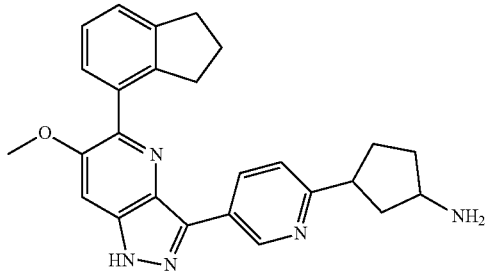 [SMILES: COc1cc2[nH]nc(-c3ccc(C4CCC(N)C4)nc3)c2nc1-c1cccc2c1CCC2]

tert-Butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclopentyl)carbamate (0.10 g, 0.155 mmol) was dissolved in DCM (2 ml), and trifluoromethanesulfonic acid (0.66 g, 4.4 mmol) was added. The reaction mixture was stirred at r.t for 1 h. Then the mixture was neutralized with saturated NaHCO$_3$ solution and the product was extracted with DCM. The organic phase was washed with brine, dried over sodium sulfate and concentrated in vacuo. LCMS calculated for $C_{26}H_{28}N_5O$ (M+H)$^+$: m/z=426.3; Found: 426.4.

Step 2. (2S)—N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxypropanamid HATU (10 mg) was added to a solution of 3-(5-(5-(2,3-dihydro-1H-inden-4-yl)-6-methoxy-1H-pyrazolo[4,3-b]pyridin-3-yl)pyridin-2-yl)cyclopentan-1-amine (0.005 g, 11.7 mop, (S)-2-hydroxypropanoic acid (8.25 mg, 0.092 mmol) and DIPEA (50 mg) in DMF (0.5 mL), and the reaction mixture was stirred at r.t. for 1 h. The reaction mixture was then diluted with 4.5 mL of methanol, filtered and purified by prep-LCMS (XBridge C18 column, eluting with a gradient of acetonitrile/water containing 0.1% TFA, at flow rate of 60 mL/min). LCMS calculated for $C_{29}H_{32}N_5O_3$ (M+H)$^+$: m/z=498.2; Found: 498.3.

Example 157. N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxyacetamide

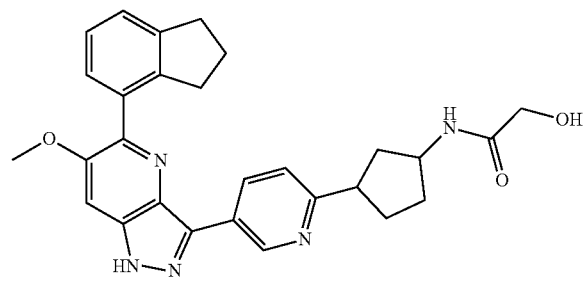 [SMILES: COc1cc2[nH]nc(-c3ccc(C4CCC(NC(=O)CO)C4)nc3)c2nc1-c1cccc2c1CCC2]

HATU (10 mg) was added to a solution of 3-(5-(5-(2,3-dihydro-1H-inden-4-yl)-6-methoxy-1H-pyrazolo[4,3-b]pyridin-3-yl)pyridin-2-yl)cyclopentan-1-amine (5 mg, 11.7 μmol), 2-hydroxyacetic acid (7 mg, 0.092 mmol) and DIPEA (50 mg) in DMF (0.5 mL), and the reaction mixture was stirred at r.t. for 1 h. The reaction mixture was then diluted with 4.5 mL of methanol, filtered and purified by prep-LCMS (XBridge C18 column, eluting with a gradient of acetonitrile/water containing 0.1% TFA, at flow rate of 60 mL/min). LCMS calculated for $C_{28}H_{30}N_5O_3$ (M+H)$^+$: m/z=484.2; Found: 484.4.

Example 158. 2-(1-(4-(5-(2,3-Dihydro-1H-inden-4-yl)-6-methoxy-1H-pyrazolo[4,3-b]pyridin-3-yl)phenyl)-3-azabicyclo[3.1.0]hexan-3-yl)ethan-1-ol

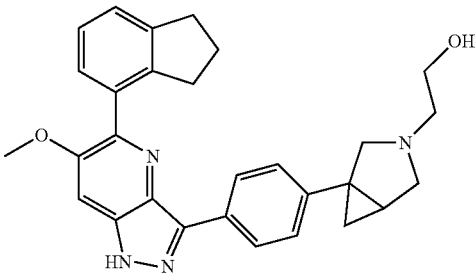 [SMILES: COc1cc2[nH]nc(-c3ccc(C45CC4CN(CCO)C5)cc3)c2nc1-c1cccc2c1CCC2]

Step 1. 1-(4-Bromophenyl)-3-(2-((tert-butyldimethylsilyl)oxy)ethyl)-3-azabicyclo[3.1.0]hexane

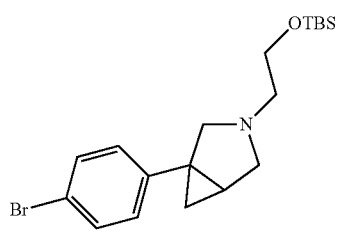 [SMILES: CC(C)(C)[Si](C)(C)OCCN1CC2CC2(c2ccc(Br)cc2)C1]

To a solution of 1-(4-bromophenyl)-3-azabicyclo[3.1.0]hexane (1.0 g, 4.20 mmol) and 2-((tert-butyldimethylsilyl)oxy)acetaldehyde (3.66 g, 21.00 mmol) in DCM (42.0 ml) was added sodium triacetoxyhydroborate (2.67 g, 12.60 mmol), and the resulting mixture was stirred at r.t. for 20 hrs. After this time, the solution was diluted with water and the product was extracted with DCM. The combined organic phases were washed with sat. aq. NaCl and dried with Na$_2$SO$_4$, then filtered and concentrated to dryness. The residue was then purified by silica gel chromatography to afford the desired product. LC-MS calculated for $C_{19}H_{31}BrNOSi$ (M+H)$^+$: m/z=396.1; found 396.3.

Step 2. 3-(2-((tert-Butyldimethylsilyl)oxy)ethyl)-1-(4-(4,4,5,5-tetramethyl-1,3,2-dioxaborolan-2-yl)phenyl)-3-azabicyclo[3.1.0]hexane

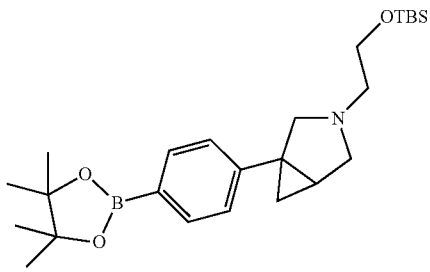 [SMILES: CC1(C)OB(c2ccc(C34CC3CN(CCO[Si](C)(C)C(C)(C)C)C4)cc2)OC1(C)C]

A mixture of 1-(4-bromophenyl)-3-(2-((tert-butyldimethylsilyl)oxy)ethyl)-3-azabicyclo[3.1.0]hexane (1.62 g, 4.09 mmol), bis(pinacolato)diboron (1.45 g, 5.72 mmol), PdCl$_2$dppf*DCM (0.501 g, 0.613 mmol) and potassium acetate (1.2 g, 12.26 mmol) in dioxane (30 ml) was heated to 85° C. for 20 hrs. The reaction mixture was then filtered through Celite, washed with EtOAc, and concentrated. The residue was then purified by silica gel chromatography to afford the desired product. LCMS calculated for C$_{25}$H$_{43}$BNO$_3$Si (M+H)$^+$: m/z=444.3; Found: 444.5.

Step 3. 2-(1-(4-(5-(2,3-Dihydro-1H-inden-4-yl)-6-methoxy-1H-pyrazolo[4,3-b]pyridin-3-yl)phenyl)-3-azabicyclo[3.1.0]hexan-3-yl)ethan-1-ol A mixture of tert-butyl 5-(2,3-dihydro-1H-inden-4-yl)-3-iodo-6-methoxy-1H-pyrazolo[4,3-b]pyridine-1-carboxylate (30 mg, 0.061 mmol), 3-(2-((tert-butyldimethylsilyl)oxy)ethyl)-1-(4-(4,4,5,5-tetramethyl-1,3,2-dioxaborolan-2-yl)phenyl)-3-azabicyclo[3.1.0]hexane (54 mg, 0.122 mmol), Xphos Pd G2 (10 mg, 0.012 mmol), and potassium phosphate (39 mg, 0.183 mmol) in dioxane (1 ml) and water (0.1 ml) was heated to 80° C. for 20 hrs. After this time, the solution was cooled to r.t., diluted with water and extracted with EtOAc. The combined organic phases were washed with sat. aq. NaCl and dried over Na$_2$SO$_4$, then filtered and concentrated to dryness. The residue was then dissolved in DCM (1 mL) and TFA (1 mL) was added. The mixture was stirred at r.t. for 1 h and purified by prep-LCMS (XBridge C18 column, eluting with a gradient of acetonitrile/water containing 0.1% TFA, at flow rate of 60 mL/min). LCMS calculated for C$_{29}$H$_{31}$N$_4$O$_2$ (M+H)$^+$: m/z=467.2; found 467.3.

Example 159. 4-(3-(4-((1R,5S)-3-(2-Hydroxyethyl)-3-azabicyclo[3.1.0]hexan-1-yl)phenyl)-6-methoxy-1H-pyrazolo[4,3-b]pyridin-5-yl)-2,3-dihydro-1H-indene-1-carbonitrile

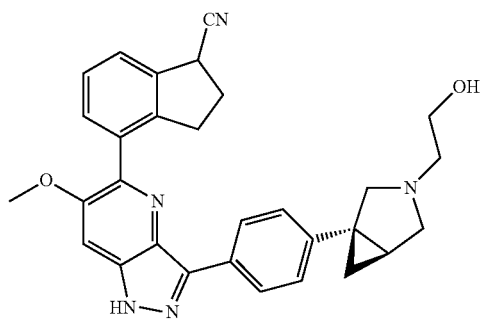 [SMILES: COc1cc2[nH]nc(-c3ccc([C@@]45C[C@@H]4CN(CCO)C5)cc3)c2nc1-c1cccc2c1CCC2C#N]

Step 1. (1R,5S)-3-(2-((tert-Butyldimethylsilyl)oxy)ethyl)-1-(4-(4,4,5,5-tetramethyl-1,3,2-dioxaborolan-2-yl)phenyl)-3-azabicyclo[3.1.0]hexane

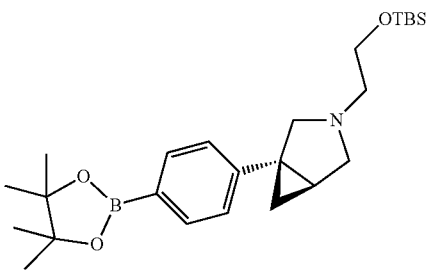 [SMILES: CC1(C)OB(c2ccc([C@@]34C[C@@H]3CN(CCO[Si](C)(C)C(C)(C)C)C4)cc2)OC1(C)C]

This compound was prepared according to the procedure described in Example 158, using (1R,5S)-1-(4-bromophenyl)-3-azabicyclo[3.1.0]hexane instead of 1-(4-bromophenyl)-3-azabicyclo[3.1.0]hexane. LCMS calculated for C$_{25}$H$_{43}$BNO$_3$Si (M+H)$^+$: m/z=444.3; Found: 444.5.

Step 2. 4-(3-(4-((1R,5S)-3-(2-Hydroxyethyl)-3-azabicyclo[3.1.0]hexan-1-yl)phenyl)-6-methoxy-1H-pyrazolo[4,3-b]pyridin-5-yl)-2,3-dihydro-1H-indene-1-carbonitrile This compound was prepared according to the procedure described in Example 158, using 4-(3-iodo-6-methoxy-1-((2-(trimethyl silyl)ethoxy)methyl)-1H-pyrazolo[4,3-b]pyridin-5-yl)-2,3-dihydro-1H-indene-1-carbonitrile and (1R,5S)-3-(2-((tert-butyldimethylsilyl)oxy)ethyl)-1-(4-(4,4,5,5-tetramethyl-1,3,2-dioxaborolan-2-yl)phenyl)-3-azabicyclo[3.1.0]hexane instead of tert-butyl 5-(2,3-dihydro-1H-inden-4-yl)-3-iodo-6-methoxy-1H-pyrazolo[4,3-b]pyridine-1-carboxylate and 3-(2-((tert-butyldimethyl silyl)oxy)ethyl)-1-(4-(4,4,5,5-tetramethyl-1,3,2-dioxaborolan-2-yl)phenyl)-3-azabicyclo[3.1.0]hexane as starting materials. LCMS calculated for C$_{30}$H$_{30}$N$_5$O$_2$ (M+H)$^+$: m/z=492.2; Found: 492.4.

Example 160. 1-((5-(5-(2,3-Dihydro-1H-inden-4-yl)-6-methoxy-1H-pyrazolo[4,3-b]pyridin-3-yl)pyridin-2-yl)methyl)piperidin-4-ol

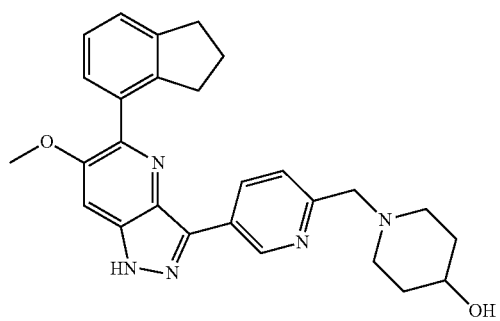 [SMILES: COc1cc2[nH]nc(-c3ccc(CN4CCC(O)CC4)nc3)c2nc1-c1cccc2c1CCC2]

Step 1. tert-Butyl 5-(2,3-dihydro-1H-inden-4-yl)-3-(6-(hydroxymethyl)pyridin-3-yl)-6-methoxy-1H-pyrazolo[4,3-b]pyridine-1-carboxylate

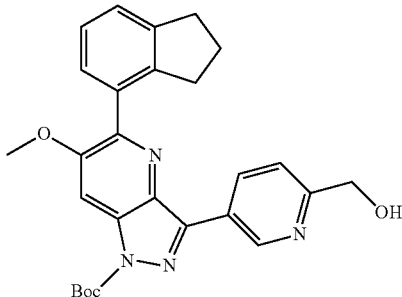 [SMILES: COc1cc2c(nc1-c1cccc3c1CCC3)c(-c1ccc(CO)nc1)nn2C(=O)OC(C)(C)C]

A mixture of tert-butyl 5-(2,3-dihydro-1H-inden-4-yl)-3-iodo-6-methoxy-1H-pyrazolo[4,3-b]pyridine-1-carboxylate (1.5 g, 3.05 mmol), (5-(4,4,5,5-tetramethyl-1,3,2-dioxaborolan-2-yl)pyridin-2-yl)methanol (1.8 g, 7.63 mmol), XPhos Pd G2 (0.48 g, 0.61 mmol), and potassium phosphate (2.59 g, 12.21 mmol) in dioxane (20 ml) and water (2.0 ml) was heated to 80° C. for 20 hrs. After this time, the solution was cooled to r.t., diluted with water and the product was extracted with EtOAc. The combined organic phases were washed with sat. aq. NaCl and dried with $Na_2SO_4$, then filtered and concentrated to dryness. The residue was then purified by silica gel chromatography to afford the desired product. LCMS calculated for $C_{27}H_{29}N_4O_4$ (M+H)$^+$: m/z=473.2; Found: 473.1.

Step 2. tert-Butyl 5-(2,3-dihydro-1H-inden-4-yl)-6-methoxy-3-(6-(((methylsulfonyl)oxy)methyl)pyridin-3-yl)-1H-pyrazolo[4,3-b]pyridine-1-carboxylate

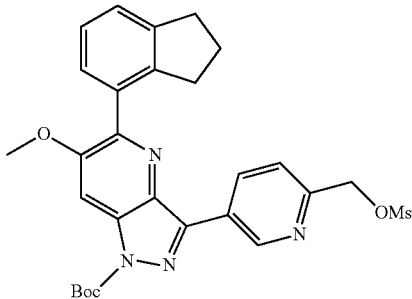 [SMILES: COc1cc2c(nc1-c1cccc3c1CCC3)c(-c1ccc(COS(C)(=O)=O)nc1)nn2C(=O)OC(C)(C)C]

To a solution of tert-butyl 5-(2,3-dihydro-1H-inden-4-yl)-3-(6-(hydroxymethyl)pyridin-3-yl)-6-methoxy-1H-pyrazolo[4,3-b]pyridine-1-carboxylate (400 mg, 0.846 mmol) and N,N-diisopropylethylamine (591 µl, 3.39 mmol) in DCM (10 ml) was added methanesulfonyl chloride (200 µl, 2.54 mmol). The resulting solution was stirred at r.t. for 1.5 hrs. The reaction was then quenched with sat. aq. NaHCO$_3$, extracted with DCM, dried over Na$_2$SO$_4$ and concentrated. The crude product was used directly in the next step. LCMS calculated for $C_{28}H_{31}N_4O_6S$ (M+H)$^+$: m/z=551.2; Found: 551.0.

Step 3. 1-((5-(5-(2,3-Dihydro-1H-inden-4-yl)-6-methoxy-1H-pyrazolo[4,3-b]pyridin-3-yl)pyridin-2-yl)methyl)piperidin-4-ol A mixture of tert-butyl 5-(2,3-dihydro-1H-inden-4-yl)-6-methoxy-3-(6-(((methylsulfonyl)oxy)methyl)pyridin-3-yl)-1H-pyrazolo[4,3-b]pyridine-1-carboxylate (30 mg, 0.054 mmol), piperidin-4-ol (11 mg, 0.109 mmol), and potassium carbonate (23 mg, 0.163 mmol) in DMF (0.5 ml) was heated to 50° C. for 2 hrs. After this time, the solution was cooled to r.t., diluted with water and extracted with DCM. The combined organic phases were washed with sat. aq. NaCl and dried with Na$_2$SO$_4$, then filtered and concentrated to dryness. The residue was then dissolved in DCM (1 mL), and TFA (1 mL) was added. The mixture was stirred at r.t. for 1 h and purified by prep-LCMS (XBridge C18 column, eluting with a gradient of acetonitrile/water containing 0.1% TFA, at flow rate of 60 mL/min). LCMS calculated for $C_{27}H_{30}N_5O_2$ (M+H)$^+$: m/z=456.2; found 456.2.

Example 161. 5-((5-(5-(2,3-Dihydro-1H-inden-4-yl)-6-methoxy-1H-pyrazolo[4,3-b]pyridin-3-yl)pyridin-2-yl)methyl)-2-oxa-5-azabicyclo[2.2.1]heptane

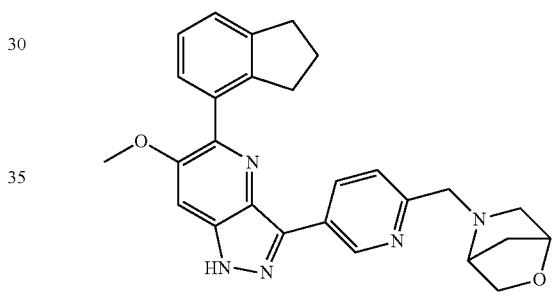

This compound was prepared according to the procedure described in Example 160, using 2-oxa-5-azabicyclo[2.2.1]heptane hydrochloride instead of piperidin-4-ol. LC-MS calculated for $C_{27}H_{28}N_5O_2$ (M+H)$^+$: m/z=454.2; found 454.1.

Example 162. 4-(1-(5-(5-(2,3-Dihydro-1H-inden-4-yl)-6-methoxy-1H-pyrazolo[4,3-b]pyridin-3-yl)pyridin-2-yl)ethyl)morpholine

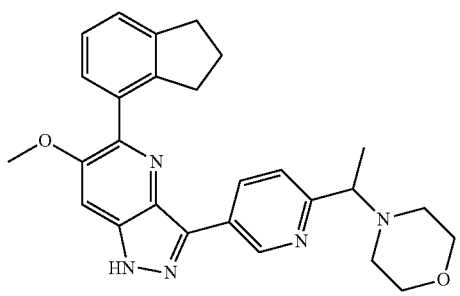 [SMILES: COc1cc2[nH]nc(-c3ccc(C(C)N4CCOCC4)nc3)c2nc1-c1cccc2c1CCC2]

Step 1. tert-Butyl 3-(6-acetylpyridin-3-yl)-5-(2,3-dihydro-1H-inden-4-yl)-6-methoxy-1H-pyrazolo[4,3-b]pyridine-1-carboxylate

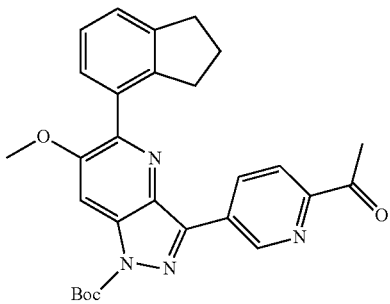 [SMILES: COc1cc2c(nc1-c1cccc3c1CCC3)c(-c1ccc(C(C)=O)nc1)nn2C(=O)OC(C)(C)C]

A mixture of tert-butyl 5-(2,3-dihydro-1H-inden-4-yl)-3-iodo-6-methoxy-1H-pyrazolo[4,3-b]pyridine-1-carboxylate (0.30 g, 0.611 mmol), 1-(5-(4,4,5,5-tetramethyl-1,3,2-dioxaborolan-2-yl)pyridin-2-yl)ethan-1-one (0.27 g, 1.093 mmol), SPhos Pd G3 (0.095 g, 0.122 mmol), and cesium carbonate (0.6 g, 1.832 mmol) in dioxane (4 ml) and water (0.4 ml) was heated at 80° C. for 2 hrs. After this time, the solution was cooled to r.t., diluted with water and extracted with EtOAc. The combined organic phases were washed with sat. aq. NaCl and dried with Na$_2$SO$_4$, then filtered and concentrated to dryness. The residue was then purified by silica gel chromatography to afford the desired product. LCMS calculated for C$_{28}$H$_{29}$N$_4$O$_4$ (M+H)$^+$: m/z=485.2; Found: 485.0.

Step 2. 4-(1-(5-(5-(2,3-Dihydro-1H-inden-4-yl)-6-methoxy-1H-pyrazolo[4,3-b]pyridin-3-yl)pyridin-2-yl)ethyl)morpholine A mixture of tert-butyl 3-(6-acetylpyridin-3-yl)-5-(2,3-dihydro-1H-inden-4-yl)-6-methoxy-1H-pyrazolo[4,3-b]pyridine-1-carboxylate (30 mg, 0.062 mmol), morpholine (11 mg, 0.124 mmol), and sodium triacetoxyhydroborate (26 mg, 0.124 mmol) in DCM (1 ml) was stirred at r.t. for 20 hrs. After this time, the solution was diluted with water and extracted with DCM. The combined organic phases were washed with sat. aq. NaCl and dried with Na$_2$SO$_4$, then filtered and concentrated to dryness. The residue was then dissolved in DCM (1 mL), and TFA (1 mL) was added. The mixture was stirred at r.t. for 1 h and purified by prep-LCMS (XBridge C18 column, eluting with a gradient of acetonitrile/water containing 0.1% TFA, at flow rate of 60 mL/min). LCMS calculated for C$_{27}$H$_{30}$N$_5$O$_2$ (M+H)$^+$: m/z=456.2; found 456.2.

Example 163. 7-((5-(5-(2,3-Dihydro-1H-inden-4-yl)-6-methoxy-1H-pyrazolo[4,3-b]pyridin-3-yl)pyridin-2-yl)methyl)-5,6,7,8-tetrahydro-[1,2,4]triazolo[1,5-a]pyrazine

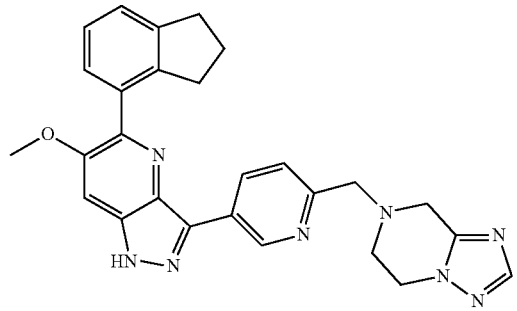 [SMILES: COc1cc2[nH]nc(-c3ccc(CN4CCn5ncnc5C4)nc3)c2nc1-c1cccc2c1CCC2]

This compound was prepared according to the procedure described in Example 160, using 5,6,7,8-tetrahydro-[1,2,4]triazolo[1,5-a]pyrazine instead of piperidin-4-ol. LC-MS calculated for C$_{27}$H$_{27}$N$_8$O (M+H)$^+$: m/z=479.2; found 479.0.

Example 164. 4-(5-(5-(2,3-Dihydro-1H-inden-4-yl)-6-methoxy-1H-pyrazolo[4,3-b]pyridin-3-yl)pyridin-2-yl)-1-(2-hydroxyethyl)piperidine-4-carbonitrile

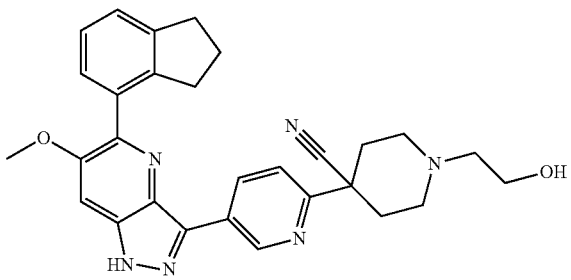 [SMILES: COc1cc2[nH]nc(-c3ccc(C4(C#N)CCN(CCO)CC4)nc3)c2nc1-c1cccc2c1CCC2]

Step 1. tert-Butyl 4-(5-bromopyridin-2-yl)-4-cyanopiperidine-1-carboxylate

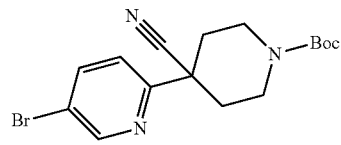 [SMILES: CC(C)(C)OC(=O)N1CCC(C#N)(c2ccc(Br)cn2)CC1]

To a solution of tert-butyl 4-cyanopiperidine-1-carboxylate (2.0 g, 9.51 mmol) in THF (48 ml) at 0° C. was added a solution of sodium bis(trimethylsilyl)amide in THF (1.0 M, 12.4 mL, 12.4 mmol) dropwise. The resulting solution was stirred at r.t. After 1 hr, 5-bromo-2-fluoropyridine (2.5 g, 14.27 mmol) was added dropwise and the resulting solution was stirred at r.t. for 20 hrs. After this time, the solution was quenched with water and extracted with DCM. The combined organic phases were washed with sat. aq. NaCl and dried with Na$_2$SO$_4$, then filtered and concentrated to dryness. The residue was then purified by silica gel chromatography to afford the desired product. LCMS calculated for C$_{12}$H$_{13}$BrN$_3$O$_2$ (M-C4H$_7$)$^+$: m/z=310.0; Found: 309.9.

Step 2. tert-Butyl 4-cyano-4-(5-(4,4,5,5-tetramethyl-1,3,2-dioxaborolan-2-yl)pyridin-2-yl)piperidine-1-carboxylate

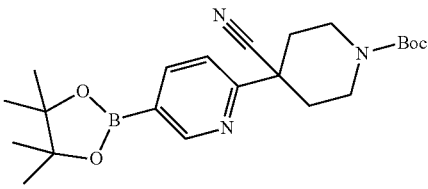 [SMILES: CC(C)(C)OC(=O)N1CCC(C#N)(c2ccc(B3OC(C)(C)C(C)(C)O3)cn2)CC1]

A mixture of tert-butyl 4-(5-bromopyridin-2-yl)-4-cyanopiperidine-1-carboxylate (2.50 g, 6.83 mmol), 4,4,4',4',5,5,5',5'-octamethyl-2,2'-bi(1,3,2-dioxaborolane) (2.4 g, 9.6 mmol), PdCl$_2$dppf.DCM (0.836 g, 1.02 mmol), and potassium acetate (2.01 g, 20.5 mmol) in dioxane (50 ml) was heated at 85° C. for 20 hrs. The reaction mixture was then filtered through celite, washed with EtOAc, and concentrated. The residue was then purified by silica gel chromatography to afford the desired product. LCMS calculated for C$_{18}$H$_{25}$BN$_3$O$_4$ (M-C4H$_7$)$^+$: m/z=358.2; Found: 358.1.

Step 3. 4-(5-(5-(2,3-Dihydro-1H-inden-4-yl)-6-methoxy-1H-pyrazolo[4,3-b]pyridin-3-yl)pyridin-2-yl)piperidine-4-carbonitrile

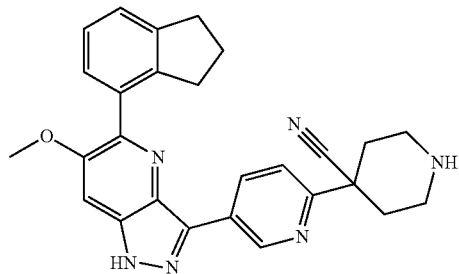 [SMILES: COc1cc2[nH]nc(-c3ccc(C4(C#N)CCNCC4)nc3)c2nc1-c1cccc2c1CCC2]

A mixture of tert-butyl 5-(2,3-dihydro-1H-inden-4-yl)-3-iodo-6-methoxy-1H-pyrazolo[4,3-b]pyridine-1-carboxylate (265 mg, 0.539 mmol), tert-butyl 4-cyano-4-(5-(4,4,5,5-tetramethyl-1,3,2-dioxaborolan-2-yl)pyridin-2-yl)piperidine-1-carboxylate (446 mg, 1.08 mmol), SPhos Pd G3 (84 mg, 0.108 mmol), and cesium carbonate (527 mg, 1.618 mmol) in dioxane (3 ml) and water (0.3 ml) was heated to 80° C. for 20 hrs. After this time, the solution was cooled to r.t., diluted with water and extracted with EtOAc. The combined organic phases were washed with sat. aq. NaCl and dried with Na$_2$SO$_4$, then filtered and concentrated to dryness. The residue was then dissolved in DCM (3 mL), and TFA (2 mL) was added. The solution was stirred at r.t. for 1 h. The solvent was then removed and the residue was purified by silica gel chromatography to afford the desired product. LCMS calculated for C$_{27}$H$_{27}$N$_6$O (M+H)$^+$: m/z=451.2; Found: 451.2.

Step 4. 4-(5-(5-(2,3-Dihydro-1H-inden-4-yl)-6-methoxy-1H-pyrazolo[4,3-b]pyridin-3-yl)pyridin-2-yl)-1-(2-hydroxyethyl)piperidine-4-carbonitrile A mixture of 4-(5-(5-(2,3-dihydro-1H-inden-4-yl)-6-methoxy-1H-pyrazolo[4,3-b]pyridin-3-yl)pyridin-2-yl)piperidine-4-carbonitrile (30 mg, 0.067 mmol), 2-((tert-butyldimethylsilyl)oxy)acetaldehyde (35 mg, 0.200 mmol), and sodium triacetoxyhydroborate (28 mg, 0.133 mmol) in DCM (1 ml) was stirred at r.t. for 20 hrs. After this time, the solution was diluted with water and extracted with DCM. The combined organic phases were washed with sat. aq. NaCl and dried with Na$_2$SO$_4$, then filtered and concentrated to dryness. The residue was then dissolved in DCM (1 mL), and TFA (1 mL) was added. The mixture was stirred at r.t. for 1 h and purified by prep-LCMS (XBridge C18 column, eluting with a gradient of acetonitrile/water containing 0.1% TFA, at flow rate of 60 mL/min). LCMS calculated for C$_{29}$H$_{31}$N$_6$O$_2$ (M+H)$^+$: m/z=495.2; found 495.0.

Example 165. 4-(5-(5-(2,3-Dihydro-1H-inden-4-yl)-6-methoxy-1H-pyrazolo[4,3-b]pyridin-3-yl)pyridin-2-yl)-1-(2-hydroxyacetyl)piperidine-4-carbonitrile

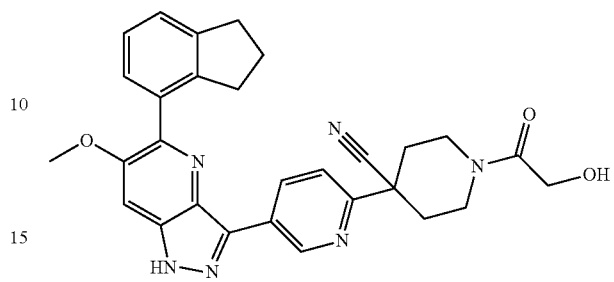

A mixture of 4-(5-(5-(2,3-dihydro-1H-inden-4-yl)-6-methoxy-1H-pyrazolo[4,3-b]pyridin-3-yl)pyridin-2-yl)piperidine-4-carbonitrile (30 mg, 0.067 mmol), 2-hydroxyacetic acid (5 mg, 0.067 mmol), HATU (38 mg, 0.10 mmol), and N,N-diisopropylethylamine (23 µl, 0.133 mmol) in DMF (0.5 ml) was stirred at r.t. for 1 hr. The mixture was then diluted with MeCN and purified by prep-LCMS (XBridge C18 column, eluting with a gradient of acetonitrile/water containing 0.1% TFA, at flow rate of 60 mL/min). LCMS calculated for C$_{29}$H$_{29}$N$_6$O$_3$ (M+H)$^+$: m/z=509.2; found 509.0.

Example 166. 2-(3-(6-Methoxy-3-(6-(4-(2-methoxyethyl)piperazin-1-yl)pyridin-3-yl)-1H-pyrazolo[4,3-b]pyridin-5-yl)-2-methylphenyl)acetonitrile

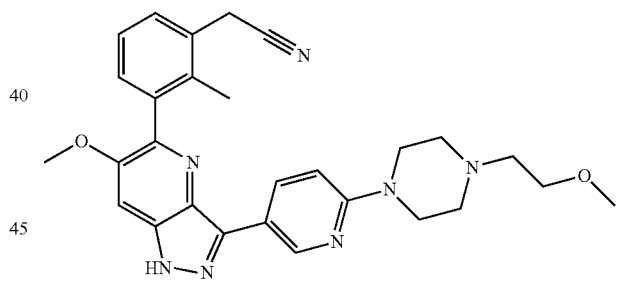

Step 1. 1-(2-Methoxyethyl)-4-(5-(4,4,5,5-tetramethyl-1,3,2-dioxaborolan-2-yl)pyridin-2-yl)piperazine

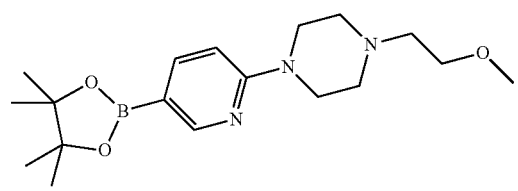

This compound was prepared according to the procedures described in Example 89, step 1, using 1-bromo-2-methoxyethane instead of 2-bromoethan-1-ol as starting material.

The product was isolated as the TFA salt. LCMS calculated for $C_{12}H_{21}BN_3O_3$ (Boronic acid, M+H)⁺: m/z=266.2, found: 266.3.

Step 2. 2-(3-(6-Methoxy-3-(6-(4-(2-methoxyethyl) piperazin-1-yl)pyridin-3-yl)-1H-pyrazolo[4,3-b]pyridin-5-yl)-2-methylphenyl)acetonitrile This compound was prepared according to the procedures described in Example 89, step 2, using 1-(2-methoxyethyl)-4-(5-(4,4,5,5-tetramethyl-1,3,2-dioxaborolan-2-yl)pyridin-2-yl)piperazine instead of 2-(4-(5-(4,4,5,5-tetramethyl-1,3,2-dioxaborolan-2-yl)pyridin-2-yl)piperazin-1-yl)ethan-1-ol as starting material. The mixture was purified by prep-LCMS (XBridge C18 column, eluting with a gradient of acetonitrile/water containing 0.1% TFA, at flow rate of 60 mL/min). The product was isolated as the TFA salt. LC-MS calculated for $C_{28}H_{32}N_7O_2$ (M+H)⁺: m/z=498.3, found 498.4. ¹H NMR (500 MHz, DMSO-d6) δ 13.40-12.90 (s, 1H), 9.89-9.71 (s, 1H), 8.48 (d, J=9.0 Hz, 1H), 7.54 (s, 1H), 7.45 (d, J=7.5 Hz, 1H), 7.35-7.30 (m, 1H), 7.28 (d, J=7.6 Hz, 1H), 7.08 (d, J=8.9 Hz, 1H), 4.42 (d, J=14.0 Hz, 2H), 4.09 (s, 2H), 3.84 (s, 3H), 3.69 (t, J=4.9 Hz, 2H), 3.57 (d, J=12.1 Hz, 2H), 3.39-3.32 (m, 5H), 3.25 (t, J=13.0 Hz, 2H), 3.17-3.07 (m, 2H), 2.05 (s, 3H) ppm.

Example 167. 4-(6-Methoxy-3-(1-(1-(tetrahydro-2H-pyran-4-carbonyl)piperidin-4-yl-4-d)-1H-pyrazol-4-yl)-1H-pyrazolo[4,3-b]pyridin-5-yl)-2,3-dihydro-1H-indene-1-carbonitrile

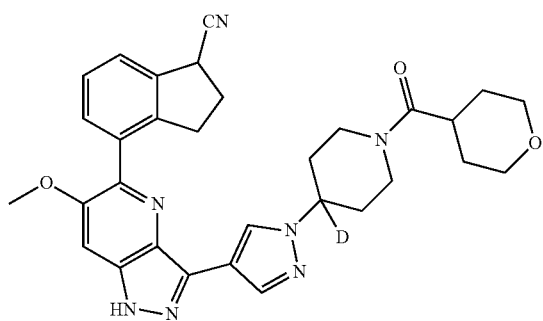 [SMILES: [2H]C1(n2cc(-c3n[nH]c4cc(OC)c(-c5cccc6c5CCC6C#N)nc34)cn2)CCN(C(=O)C2CCOCC2)CC1]

Step 1. tert-Butyl 4-hydroxypiperidine-1-carboxylate-4-d

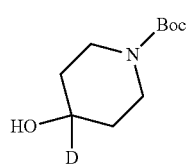 [SMILES: [2H]C1(O)CCN(C(=O)OC(C)(C)C)CC1]

To a solution of tert-butyl 4-oxopiperidine-1-carboxylate (2.0 g, 10 mmol) in methanol (20 mL) at 0° C. was added sodium borodeuteride (0.84 g, 20 mmol) portionwise. After addition was completed, the reaction mixture was stirred under nitrogen at 0° C. for 2 hrs. The reaction mixture was then allowed to warm to room temperature for 45 minutes, before quenching with brine. The aqueous solution was extracted 3 times with ethyl acetate. The pooled organic extracts were dried over sodium sulfate, filtered, and the solvent was removed in vacuo. The resultant product was used in the next step without further purification. LCMS calculated for $C_6H_{11}DNO_3$ (M-tBu+H)⁺: m/z=147.1, found: 147.1.

Step 2. tert-Butyl 4-((methylsulfonyl)oxy)piperidine-1-carboxylate-4-d

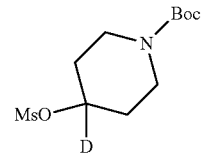

To a solution of tert-butyl 4-hydroxypiperidine-1-carboxylate-4-d (2.1 g, 10 mmol) in anhydrous dichloromethane (103 mL) at 0° C. was added triethylamine (2.2 g, 15 mmol) by syringe. Dropwise by syringe, methanesulfonyl chloride (0.97 mL, 12 mmol) was added to the stirred reaction mixture. The reaction was allowed to warm to room temperature for 1 hr before the solvent was removed in vacuo. The resultant residue was dissolved in 100 mL of diethyl ether. The ether solution was sequentially washed with 15 mL 1 M aqueous hydrochloric acid, 15 mL water, and 15 mL saturated aqueous sodium bicarbonate. The organic phase was then dried over sodium sulfate, filtered, and the solvent was removed in vacuo. The resultant product was used in the next step without further purification. LCMS calculated for $C_7H_{13}DNO_5S$ (M-tBu+H)⁺: m/z=225.1, found: 225.0.

Step 3. tert-Butyl 4-(4-iodo-1H-pyrazol-1-yl)piperidine-1-carboxylate-4-d

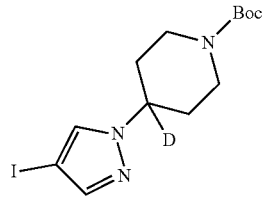 [SMILES: [2H]C1(n2cc(I)cn2)CCN(C(=O)OC(C)(C)C)CC1]

To a solution of 4-iodo-1H-pyrazole (1.46 g, 7.54 mmol) in DMF (26 mL) at 0° C. was added sodium hydride (0.362 g, 60 wt %, 9.04 mmol) portionwise. After addition was completed, the reaction mixture was stirred under nitrogen at 0° C. for 1 hr. Then, to this solution was added tert-butyl 4-((methylsulfonyl)oxy)piperidine-1-carboxylate-4-d (2.32 g, 8.29 mmol) in DMF (3 mL). The reaction mixture was then heated to 100° C. for 3 hrs, after which it was cooled back to room temperature and quenched with 50 mL water. The aqueous solution was extracted 4 times with 50 mL ethyl acetate. The pooled organic phases were then dried over sodium sulfate, filtered, and the solvent was removed in vacuo. The residue was purified by silica gel chromatography to afford the desired product. LCMS calculated for $C_9H_{12}DIN_3O_2$ (M-tBu+H)⁺: m/z=323.0, found: 323.0.

Step 4. tert-Butyl 4-(4-(4,4,5,5-tetramethyl-1,3,2-dioxaborolan-2-yl)-1H-pyrazol-1-yl)piperidine-1-carboxylate-4-d

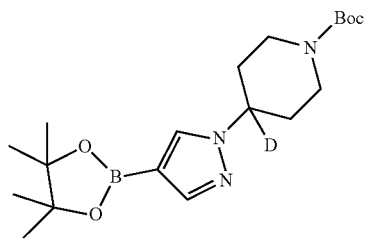 [SMILES: [2H]C1(n2cc(B3OC(C)(C)C(C)(C)O3)cn2)CCN(C(=O)OC(C)(C)C)CC1]

To a solution of tert-butyl 4-(4-iodo-1H-pyrazol-1-yl)piperidine-1-carboxylate-4-d (1.95 g, 5.15 mmol) in DMSO (22 ml) were added bis(pinacolato)diboron (1.83 g, 7.21 mmol), potassium acetate (2.02 g, 20.6 mmol), and tetrakis(triphenylphosphine)palladium(0) (595 mg, 0.515 mmol). The reaction was purged with $N_2$ and stirred at 80° C. for 2 hrs. After this time it was cooled to room temperature and filtered through a pad of Celite, rinsing with ethyl acetate. The organic solution was then washed twice with brine, dried over sodium sulfate, filtered, and concentrated in vacuo. The residue was purified by silica gel chromatography to afford the desired product. LCMS calculated for $C_{19}H_{32}DBN_3O_4$ (M+H)$^+$: m/z=379.3, found: 379.3.

Step 5. tert-Butyl 3-(1-(1-(tert-butoxycarbonyl)piperidin-4-yl-4-d)-1H-pyrazol-4-yl)-5-(1-cyano-2,3-dihydro-1H-inden-4-yl)-6-methoxy-1H-pyrazolo[4,3-b]pyridine-1-carboxylate

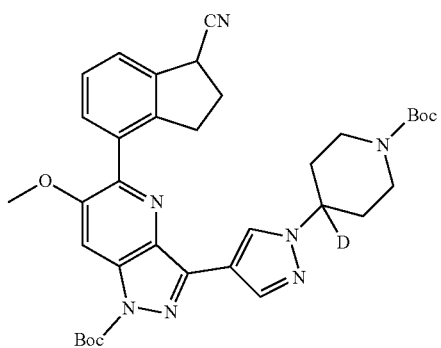 [SMILES: [2H]C1(n2cc(-c3nn(C(=O)OC(C)(C)C)c4cc(OC)c(-c5cccc6c5CCC6C#N)nc34)cn2)CCN(C(=O)OC(C)(C)C)CC1]

To a solution of tert-butyl 5-(1-cyano-2,3-dihydro-1H-inden-4-yl)-3-iodo-6-methoxy-1H-pyrazolo[4,3-b]pyridine-1-carboxylate (Example 75, step 7; 287 mg, 0.555 mmol) in 1,4-dioxane (4.6 mL) and water (0.93 mL) was added tert-butyl 4-(4-(4,4,5,5-tetramethyl-1,3,2-dioxaborolan-2-yl)-1H-pyrazol-1-yl)piperidine-1-carboxylate-4-d (252 mg, 0.666 mmol), potassium phosphate (236 mg, 1.11 mmol), and XphosPd G2 (44 mg, 0.055 mmol). The reaction was degassed with $N_2$ and stirred at 60° C. for 2 hr. After this time it was cooled to room temperature and filtered through a pad of Celite, rinsing with ethyl acetate. The residue was purified by silica gel chromatography to afford the desired product. LCMS calculated for $C_{35}H_{41}DN_7O_5$ (M+H)$^+$: m/z=641.3, found: 641.4.

Step 6. 4-(6-Methoxy-3-(1-(piperidin-4-yl-4-d)-1H-pyrazol-4-yl)-1H-pyrazolo[4,3-b]pyridin-5-yl)-2,3-dihydro-1H-indene-1-carbonitrile

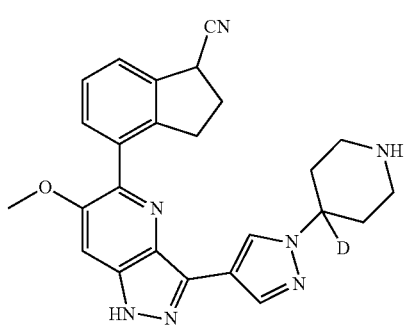 [SMILES: [2H]C1(n2cc(-c3n[nH]c4cc(OC)c(-c5cccc6c5CCC6C#N)nc34)cn2)CCNCC1]

To a solution of tert-butyl 3-(1-(1-(tert-butoxycarbonyl)piperidin-4-yl-4-d)-1H-pyrazol-4-yl)-5-(1-cyano-2,3-dihydro-1H-inden-4-yl)-6-methoxy-1H-pyrazolo[4,3-b]pyridine-1-carboxylate (15 mg, 0.023 mmol) in dichloromethane (82 µL) was added TFA (82 µL, 1.1 mmol) at room temperature. The reaction mixture was stirred for 30 min, then concentrated in vacuo.

The residue was adjusted to pH 7 by addition of saturated aqueous sodium bicarbonate, then extracted twice with 10% methanol/dichloromethane. The pooled organic extracts were dried over sodium sulfate, filtered, and concentrated in vacuo. The resultant product was used in next step without further purification. LCMS calculated for $C_{25}H_{25}DN_7O$ (M+H)$^+$: m/z=441.2, found: 441.2.

Step 7. 4-(6-Methoxy-3-(1-(1-(tetrahydro-2H-pyran-4-carbonyl)piperidin-4-yl-4-d)-1H-pyrazol-4-yl)-1H-pyrazolo[4,3-b]pyridin-5-yl)-2,3-dihydro-1H-indene-1-carbonitrile To a solution of 4-(6-methoxy-3-(1-(piperidin-4-yl-4-d)-1H-pyrazol-4-yl)-1H-pyrazolo[4,3-b]pyridin-5-yl)-2,3-dihydro-1H-indene-1-carbonitrile (10 mg, 0.023 mmol), tetrahydro-2H-pyran-4-carboxylic acid (3.0 mg, 0.023 mmol), and BOP (15 mg, 0.035 mmol) in DMF (0.36 mL) was added diisopropylethylamine (10 µL, 0.058 mmol) with stirring at room temperature. Stirring of the reaction mixture was continued for 80 min, then it was diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{31}H_{33}DN_7O_3$ (M+H)$^+$: m/z=553.3, found 553.3.

Example 168. 4-(6-Methoxy-3-(1-((S)-1-(2-methoxyacetyl)pyrrolidin-3-yl)-1H-pyrazol-4-yl)-1H-pyrazolo[4,3-b]pyridin-5-yl)-2,3-dihydro-1H-indene-1-carbonitrile

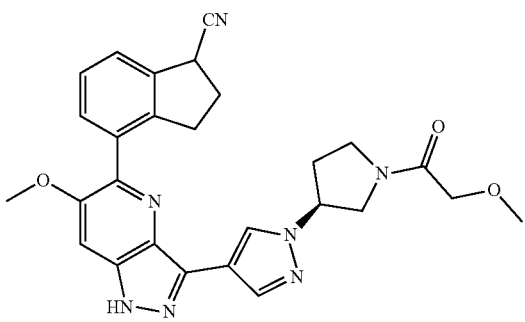

Step 1. tert-Butyl 3-(1-((S)-1-(tert-butoxycarbonyl)pyrrolidin-3-yl)-1H-pyrazol-4-yl)-5-(1-cyano-2,3-dihydro-1H-inden-4-yl)-6-methoxy-1H-pyrazolo[4,3-b]pyridine-1-carboxylate

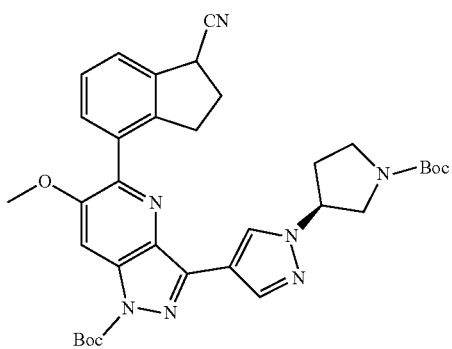 [SMILES: COc1cc2c(nc1-c1cccc3c1CCC3C#N)c(-c1cnn([C@H]3CCN(C(=O)OC(C)(C)C)C3)c1)nn2C(=O)OC(C)(C)C]

This compound was prepared according to the procedures described in Example 167, step 5, using tert-butyl (S)-3-(4-(4,4,5,5-tetramethyl-1,3,2-dioxaborolan-2-yl)-1H-pyrazol-1-yl)pyrrolidine-1-carboxylate instead of tert-butyl 4-(4-(4,4,5,5-tetramethyl-1,3,2-dioxaborolan-2-yl)-1H-pyrazol-1-yl)piperidine-1-carboxylate-4-d as starting material. The residue was purified by silica gel chromatography to afford the desired product. Separation of diastereomers was achieved by chiral prep-SFC (ChiralPak IH 5um 21.2×250 mm, eluting with 15% EtOH (containing 2 mM ammonia), at 40° C., at a flow rate of 70 mL/min, $t_{R,\ peak\ 1}$=4.6 min $t_{R,\ peak\ 2}$=5.8 min). Peak 2 was collected and the solvents were evaporated in vacuo. LCMS calculated for $C_{30}H_{32}N_7O_5$ (M-tBu+H)$^+$: m/z=570.3, found: 570.3.

Step 2. 4-(6-Methoxy-3-(1-((S)-pyrrolidin-3-yl)-1H-pyrazol-4-yl)-1H-pyrazolo[4,3-b]pyridin-5-yl)-2,3-dihydro-1H-indene-1-carbonitrile

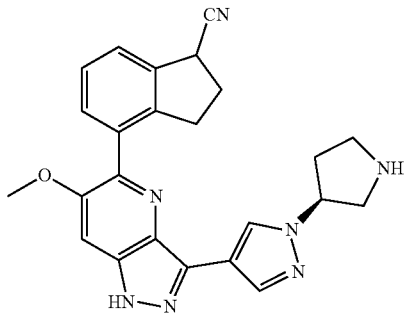 [SMILES: COc1cc2[nH]nc(-c3cnn([C@H]4CCNC4)c3)c2nc1-c1cccc2c1CCC2C#N]

This compound was prepared according to the procedures described in Example 167, step 6, using tert-butyl 3-(1-((S)-1-(tert-butoxycarbonyl)pyrrolidin-3-yl)-1H-pyrazol-4-yl)-5-(1-cyano-2,3-dihydro-1H-inden-4-yl)-6-methoxy-1H-pyrazolo[4,3-b]pyridine-1-carboxylate instead of tert-butyl 3-(1-(1-(tert-butoxycarbonyl)piperidin-4-yl-4-d)-1H-pyrazol-4-yl)-5-(1-cyano-2,3-dihydro-1H-inden-4-yl)-6-methoxy-1H-pyrazolo[4,3-b]pyridine-1-carboxylate as starting material. LCMS calculated for $C_{24}H_{24}N_7O$ (M+H)$^+$: m/z=426.2, found: 426.2.

Step 3. 4-(6-Methoxy-3-(1-((S)-1-(2-methoxyacetyl)pyrrolidin-3-yl)-1H-pyrazol-4-yl)-1H-pyrazolo[4,3-b]pyridin-5-yl)-2,3-dihydro-1H-indene-1-carbonitrile This compound was prepared according to the procedures described in Example 167, step 7, using 4-(6-methoxy-3-(1-((S)-pyrrolidin-3-yl)-1H-pyrazol-4-yl)-1H-pyrazolo[4,3-b]pyridin-5-yl)-2,3-dihydro-1H-indene-1-carbonitrile instead of 4-(6-methoxy-3-(1-(piperidin-4-yl-4-d)-1H-pyrazol-4-yl)-1H-pyrazolo[4,3-b]pyridin-5-yl)-2,3-dihydro-1H-indene-1-carbonitrile and using 2-methoxyacetic acid instead of tetrahydro-2H-pyran-4-carboxylic acid as starting materials. LCMS calculated for $C_{27}H_{28}N_7O_3$ (M+H)$^+$: m/z=498.2, found: 498.2.

Example 169. 4-(6-Methoxy-3-(1-((S)-1-((S)-tetrahydrofuran-2-carbonyl)pyrrolidin-3-yl)-1H-pyrazol-4-yl)-1H-pyrazolo[4,3-b]pyridin-5-yl)-2,3-dihydro-1H-indene-1-carbonitrile

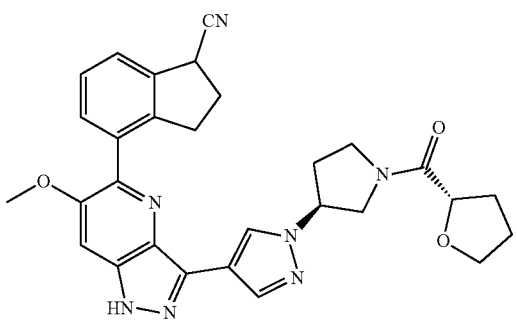 [SMILES: COc1cc2[nH]nc(-c3cnn([C@H]4CCN(C(=O)[C@@H]5CCCO5)C4)c3)c2nc1-c1cccc2c1CCC2C#N]

This compound was prepared according to the procedures described in Example 167, step 7, using 4-(6-methoxy-3-(1-((S)-pyrrolidin-3-yl)-1H-pyrazol-4-yl)-1H-pyrazolo[4,3-b]pyridin-5-yl)-2,3-dihydro-1H-indene-1-carbonitrile instead of 4-(6-methoxy-3-(1-(piperidin-4-yl-4-d)-1H-pyrazol-4-yl)-1H-pyrazolo[4,3-b]pyridin-5-yl)-2,3-dihydro-1H-indene-1-carbonitrile and using (S)-tetrahydrofuran-2-carboxylic acid instead of tetrahydro-2H-pyran-4-carboxylic acid as starting materials. LCMS calculated for $C_{29}H_{30}N_7O_3$ (M+H)$^+$: m/z=524.2, found: 524.2.

Example 170. (7R,8aS)-2-(5-(5-(2,3-Dihydro-1H-inden-4-yl)-6-methoxy-1H-pyrazolo[4,3-b]pyridin-3-yl)pyridin-2-yl)octahydropyrrolo[1,2-a]pyrazin-7-ol

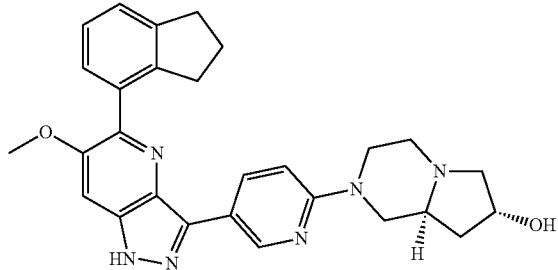 [SMILES: COc1cc2[nH]nc(-c3ccc(N4CCN5C[C@H](O)C[C@H]5C4)nc3)c2nc1-c1cccc2c1CCC2]

This compound was prepared according to the procedures described in Example 90, using 2-(2,3-dihydro-1H-inden-4-yl)-4,4,5,5-tetramethyl-1,3,2-dioxaborolane instead of (3-methoxy-2-methylphenyl)boronic acid as starting material. The product was isolated as the TFA salt. LCMS calculated for $C_{28}H_{31}N_6O_2$ (M+H)$^+$: m/z=483.3; Found: 483.3.

Example 171. N-(1-(5-(5-(2,3-Dihydro-1H-inden-4-yl)-6-methoxy-1H-pyrazolo[4,3-b]pyridin-3-yl)pyridin-2-yl)azetidin-3-yl)-2-hydroxy-N-methylacetamide

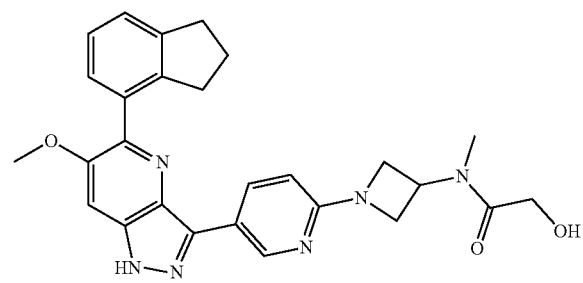 [SMILES: COc1cc2[nH]nc(-c3ccc(N4CC(N(C)C(=O)CO)C4)nc3)c2nc1-c1cccc2c1CCC2]

Step 1. tert-Butyl (1-(5-bromopyridin-2-yl)azetidin-3-yl)(methyl)carbamate

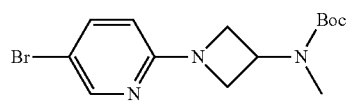 [SMILES: CN(C(=O)OC(C)(C)C)C1CN(c2ccc(Br)cn2)C1]

To a solution of 5-bromo-2-fluoropyridine (2 g, 11.36 mmol) in DMSO (10 mL) was added tert-butyl azetidin-3-yl(methyl)carbamate (2.18 g, 11.36 mmol) and cesium carbonate (7.4 g, 22.73 mmol). The reaction was degassed with $N_2$ and stirred at 100° C. for 2 hrs. After this time, it was cooled to r.t. and diluted with EtOAc. The resultant solution was washed sequentially with water, sat. aq. NaCl solution, and dried over $Na_2SO_4$. The organic phases were filtered and concentrated to dryness. The residue was purified by Biotage Isolera to afford the desired product. LC-MS calculated for $C_{14}H_{21}BrN_3O_2$ (M+H)$^+$: m/z=342.1; found 342.1.

Step 2. tert-Butyl methyl(1-(5-(4,4,5,5-tetramethyl-1,3,2-dioxaborolan-2-yl)pyridin-2-yl)azetidin-3-yl)carbamate

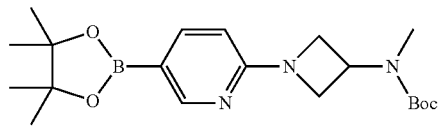 [SMILES: CN(C(=O)OC(C)(C)C)C1CN(c2ccc(B3OC(C)(C)C(C)(C)O3)cn2)C1]

A mixture of tert-butyl (1-(5-bromopyridin-2-yl)azetidin-3-yl)(methyl)carbamate (2.96 g, 8.65 mmol), 4,4,4',4',5,5,5',5'-octamethyl-2,2'-bi(1,3,2-dioxaborolane) (3.3 g, 12.97 mmol), [1,1'-bis(diphenylphosphino)-ferrocene]-dichloropalladium(II) (706 mg, 0.865 mmol) and potassium acetate (1.66 g, 17.3 mmol) in dioxane (20 mL) was stirred at 100° C. for 90 minutes. After cooling to r.t., the reaction mixture was filtered, the solvent was evaporated in vacuo and the crude material was purified by Biotage Isolera. LCMS calculated for $C_{20}H_{33}BN_3O_4$ (M+H)$^+$: m/z=390.2; Found: 390.2.

Step 3. tert-Butyl (1-(5-(5-(2,3-dihydro-1H-inden-4-yl)-6-methoxy-1-(4-methoxybenzyl)-1H-pyrazolo[4,3-b]pyridin-3-yl)pyridin-2-yl)azetidin-3-yl)(methyl)carbamate

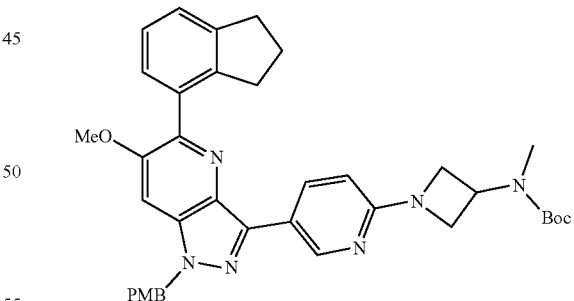

To a solution of 5-(2,3-dihydro-1H-inden-4-yl)-3-iodo-6-methoxy-1-(4-methoxybenzyl)-1H-pyrazolo[4,3-b]pyridine (Example 53, step 3; 1 g, 1.96 mmol) in 1,4-dioxane (6 mL) and water (1.2 mL) was added tert-butyl methyl(1-(5-(4,4,5,5-tetramethyl-1,3,2-dioxaborolan-2-yl)pyridin-2-yl)azetidin-3-yl)carbamate (1.14 g, 2.93 mmol), potassium phosphate (1.25 g, 5.87 mmol), and [1,1'-bis(diphenylphosphino)-ferrocene]dichloropalladium(II) (160 mg, 0.196 mmol). The reaction was degassed with $N_2$ and stirred at 80° C. for 2 hrs. After this time, it was cooled to r.t. and diluted with EtOAc. The resultant solution was washed sequentially with water, sat. aq. NaCl solution, and dried over Na$_2$SO$_4$. The organic phases were filtered and concentrated to dryness. The residue was purified by Biotage Isolera to afford the desired product. LC-MS calculated for C$_{38}$H$_{43}$N$_6$O$_4$ (M+H)$^+$: m/z=647.3; found 647.3.

Step 4. 1-(5-(5-(2,3-Dihydro-1H-inden-4-yl)-6-methoxy-1-(4-methoxybenzyl)-1H-pyrazolo[4,3-b]pyridin-3-yl)pyridin-2-yl)-N-methylazetidin-3-amine

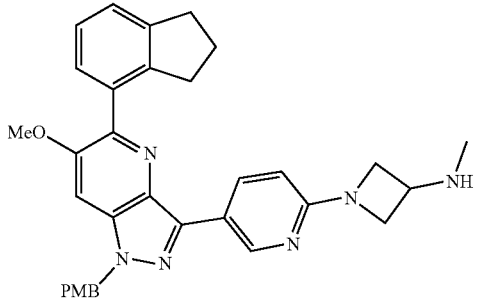

To a solution of tert-butyl (1-(5-(5-(2,3-dihydro-1H-inden-4-yl)-6-methoxy-1-(4-methoxybenzyl)-1H-pyrazolo[4,3-b]pyridin-3-yl)pyridin-2-yl)azetidin-3-yl)(methyl)carbamate (1.01 g, 1.56 mmol) in dichloromethane (3 mL) was added trifluoroacetic acid (4 mL). The reaction was stirred at r.t. for 1 hr. After this time, it was diluted with dichloromethane. The resultant solution was washed sequentially with water, sat. aq. NaCl solution and dried over Na$_2$SO$_4$. The organic phases were filtered and concentrated to dryness. The residue was used directly in the next step without purification. LC-MS calculated for C$_{33}$H$_{35}$N$_6$O$_2$ (M+H)$^+$: m/z=547.3; found 547.3.

Step 5. N-(1-(5-(5-(2,3-Dihydro-1H-inden-4-yl)-6-methoxy-1H-pyrazolo[4,3-b]pyridin-3-yl)pyridin-2-yl)azetidin-3-yl)-2-hydroxy-N-methylacetamide To a solution of 1-(5-(5-(2,3-dihydro-1H-inden-4-yl)-6-methoxy-1-(4-methoxybenzyl)-1H-pyrazolo[4,3-b]pyridin-3-yl)pyridin-2-yl)-N-methylazetidin-3-amine (200 mg, 0.37 mmol) in dichloromethane (4 mL) was added 2-hydroxyacetic acid (42 mg, 0.55 mmol), trimethylamine (95 mg, 0.73 mmol) and HATU (181 mg, 0.48 mmol). The reaction was stirred at r.t. for 1 hr. After this time, it was diluted with dichloromethane. The resultant solution was washed sequentially with water, sat. aq. NaCl solution, and dried over Na$_2$SO$_4$. The organic phases were filtered and concentrated to dryness. The residue was dissolved in dichloromethane (3 mL) and trifluoromethanesulfonic acid (1.5 mL). The reaction was stirred at r.t. After 30 min, the reaction mixture was quenched with 4N NaOH aq. solution and diluted with dichloromethane. The resultant mixture was washed sequentially with water, sat. aq. NaCl solution and dried over Na$_2$SO$_4$. The organic phases were filtered and concentrated to dryness. The residue was diluted with MeOH and was purified by prep-LCMS (XBridge C18 column, eluting with a gradient of acetonitrile/water containing 0.1% TFA, at flow rate of 60 mL/min). The product was isolated as the TFA salt. LC-MS calculated for C$_{27}$H$_{29}$N$_6$O$_3$ (M+H)$^+$: m/z=485.2; found 485.2.

Example 172. (3-(5-(5-(2,3-Dihydro-1H-inden-4-yl)-6-methoxy-1H-pyrazolo[4,3-b]pyridin-3-yl)pyridin-2-yl)azetidin-1-yl)(tetrahydrofuran-2-yl)methanone

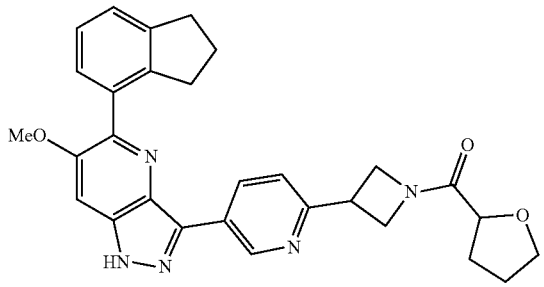 [SMILES: COc1cc2[nH]nc(-c3ccc(C4CN(C(=O)C5CCCO5)C4)nc3)c2nc1-c1cccc2c1CCC2]

Step 1. tert-Butyl 3-(5-bromopyridin-2-yl)azetidine-1-carboxylate

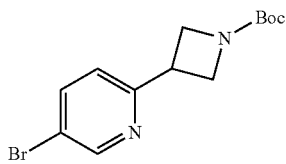 [SMILES: CC(C)(C)OC(=O)N1CC(c2ccc(Br)cn2)C1]

To a solution of zinc dust (1.73 g, 26.5 mmol) in THF (30 mL) was added 1,2-dibromoethane (332 mg, 1.77 mmol) and chlorotrimethylsilane (192 mg, 1.77 mmol). The reaction was degassed with N$_2$ and stirred at 60° C. for 15 minutes before tert-butyl 3-iodoazetidine-1-carboxylate (5 g, 17.7 mmol) in DMA (30 mL) was added. The mixture was heated to 60° C. and stirred for 15 minutes before cooled down to r.t. To the cooled mixture was added 2,5-dibromopyridine (4.6 g, 19.4 mmol), [1,1'-bis(diphenylphosphino)ferrocene]-dichloropalladium(II) (1:1) (721 mg, 0.88 mmol) and copper iodide (168 mg, 0.88 mmol). The mixture was heated to 80° C. for 2 hrs. After this time, it was cooled to r.t. and diluted with EtOAc. The resultant solution was washed sequentially with water, sat. aq. NaCl solution, and dried over Na$_2$SO$_4$. The organic phases were filtered and concentrated to dryness. The residue was purified by Biotage Isolera to afford the desired product. LC-MS calculated for C$_{13}$H$_{18}$BrN$_2$O$_2$ (M+H)$^+$: m/z=313.0; found 313.0.

Step 2. tert-Butyl methyl(1-(5-(4,4,5,5-tetramethyl-1,3,2-dioxaborolan-2-yl)pyridin-2-yl)azetidin-3-yl)carbamate

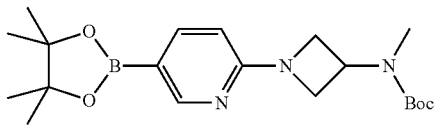 [SMILES: CN(C(=O)OC(C)(C)C)C1CN(c2ccc(B3OC(C)(C)C(C)(C)O3)cn2)C1]

A mixture of tert-butyl (1-(5-bromopyridin-2-yl)azetidin-3-yl)(methyl)carbamate (2.96 g, 8.65 mmol), 4,4,4',4',5,5,5',5'-octamethyl-2,2'-bi(1,3,2-dioxaborolane) (3.3 g, 12.97 mmol), [1,1'-bis(diphenylphosphino)-ferrocene]-dichloropalladium(II) (706 mg, 0.865 mmol) and potassium acetate (1.66 g, 17.3 mmol) in dioxane (20 mL) was stirred at 100° C. for 90 minutes. After cooling to r.t., the reaction mixture was filtered, the solvent was evaporated in vacuo and the crude material was purified by Biotage Isolera. LCMS calculated for $C_{20}H_{33}BN_3O_4$ (M+H)$^+$: m/z=390.2; Found: 390.2.

Step 3. tert-Butyl 3-(5-(5-(2,3-dihydro-1H-inden-4-yl)-6-methoxy-1-(4-methoxybenzyl)-1H-pyrazolo[4,3-b]pyridin-3-yl)pyridin-2-yl)azetidine-1-carboxylate

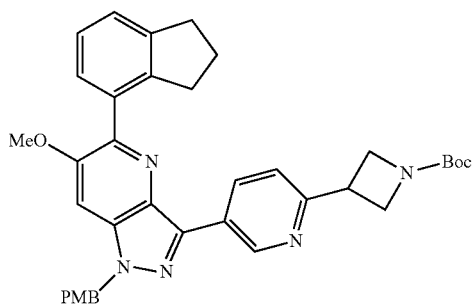

To a solution of 5-(2,3-dihydro-1H-inden-4-yl)-3-iodo-6-methoxy-1-(4-methoxybenzyl)-1H-pyrazolo[4,3-b]pyridine (Example 53, step 3; 545 mg, 1.07 mmol) in 1,4-dioxane (5 mL) and water (1 mL) was added tert-butyl 3-(5-(4,4,5,5-tetramethyl-1,3,2-dioxaborolan-2-yl)pyridin-2-yl)azetidine-1-carboxylate (499 mg, 1.39 mmol), potassium phosphate (521 mg, 1.60 mmol), and (2-dicyclohexylphosphino-2',6'-dimethoxybiphenyl) [2-(2'-amino-1,1'-biphenyl)]palladium(II) methanesulfonate (83 mg, 0.11 mmol). The reaction was degassed with N$_2$ and stirred at 80° C. for 2 hrs. After this time, it was cooled to r.t. and diluted with EtOAc. The resultant solution was washed sequentially with water, sat. aq. NaCl solution, and dried over Na$_2$SO$_4$. The organic phases were filtered and concentrated to dryness. The residue was purified by Biotage Isolera to afford the desired product. LC-MS calculated for $C_{37}H_{40}N_5O_4$ (M+H)$^+$: m/z=618.3; found 618.3.

Step 4. 3-(6-(Azetidin-3-yl)pyridin-3-yl)-5-(2,3-dihydro-1H-inden-4-yl)-6-methoxy-1-(4-methoxybenzyl)-1H-pyrazolo[4,3-b]pyridine

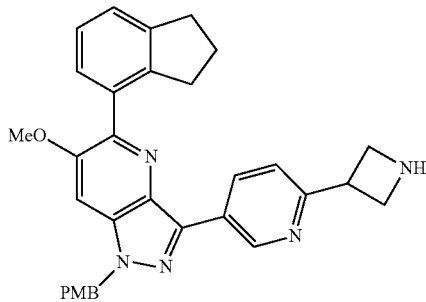

To a solution of tert-butyl 3-(5-(5-(2,3-dihydro-1H-inden-4-yl)-6-methoxy-1-(4-methoxybenzyl)-1H-pyrazolo[4,3-b]pyridin-3-yl)pyridin-2-yl)azetidine-1-carboxylate (527 mg, 0.85 mmol) in dichloromethane (2 mL) was added trifluoroacetic acid (2 mL). The reaction was stirred at r.t. for 1 hr. After this time, it was diluted with dichloromethane. The resultant solution was washed sequentially with water, sat. aq. NaCl solution and dried over Na$_2$SO$_4$. The organic phases were filtered and concentrated to dryness. The residue was used directly in the next step without purification. LC-MS calculated for $C_{32}H_{32}N_5O_2$ (M+H)$^+$: m/z=518.2; found 518.2.

Step 5. (3-(5-(5-(2,3-Dihydro-1H-inden-4-yl)-6-methoxy-1H-pyrazolo[4,3-b]pyridin-3-yl)pyridin-2-yl)azetidin-1-yl)(tetrahydrofuran-2-yl)methanone To a solution of 3-(6-(azetidin-3-yl)pyridin-3-yl)-5-(2,3-dihydro-1H-inden-4-yl)-6-methoxy-1-(4-methoxybenzyl)-1H-pyrazolo[4,3-b]pyridine (20 mg, 0.039 mmol) in dichloromethane (0.5 mL) was added tetrahydrofuran-2-carboxylic acid (9 mg, 0.077 mmol), triethylamine (10 mg, 0.077 mmol) and HATU (22 mg, 0.058 mmol). The reaction was stirred at r.t. for 1 hr. After this time, it was diluted with dichloromethane. The resultant solution was washed sequentially with water, sat. aq. NaCl solution, and dried over Na$_2$SO$_4$. The organic phases were filtered and concentrated to dryness. The residue was dissolved in dichloromethane (0.5 mL) and trifluoromethanesulfonic acid (0.1 mL). The reaction was stirred at r.t. After 30 min, the reaction mixture was quenched with 4N NaOH aq. solution and diluted with dichloromethane. The resultant mixture was washed sequentially with water, sat. aq. NaCl solution and dried over Na$_2$SO$_4$. The organic phases were filtered and concentrated to dryness. The residue was diluted with MeOH and was purified by prep-LCMS (XBridge C18 column, eluting with a gradient of acetonitrile/water containing 0.1% TFA, at flow rate of 60 mL/min). The product was isolated as the TFA salt. LC-MS calculated for $C_{29}H_{30}N_5O_3$ (M+H)$^+$: m/z=496.2; found 496.2.

Example 173. (S)-(3-(5-(5-(2,3-Dihydro-1H-inden-4-yl)-6-methoxy-1H-pyrazolo[4,3-b]pyridin-3-yl)pyridin-2-yl)azetidin-1-yl)(1-methylpiperidin-2-yl)methanone

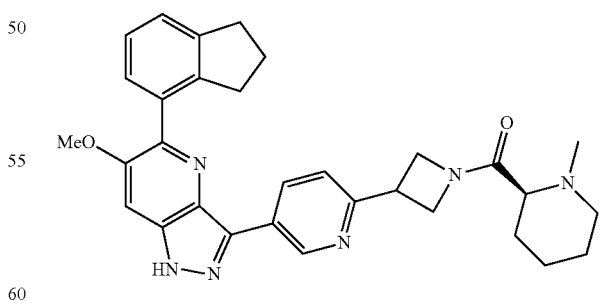

This compound was prepared according to the procedures described in Example 172, step 5, using (S)-1-methylpiperidine-2-carboxylic acid instead of tetrahydrofuran-2-carboxylic acid as starting material. The product was isolated as the TFA salt. LCMS calculated for $C_{31}H_{35}N_6O_2$ (M+H)$^+$: m/z=523.3; Found: 523.3.

Example 174. 1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-(dimethylamino)ethan-1-one

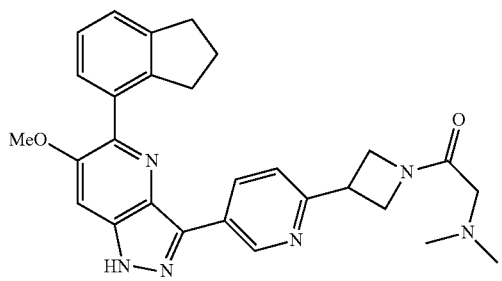 [SMILES: COc1cc2[nH]nc(-c3ccc(C4CN(C(=O)CN(C)C)C4)nc3)c2nc1-c1cccc2c1CCC2]

This compound was prepared according to the procedures described in Example 172, step 5, using dimethylglycine instead of tetrahydrofuran-2-carboxylic acid as starting material. The product was isolated as the TFA salt. LCMS calculated for $C_{28}H_{31}N_6O_2$ (M+H)$^+$: m/z=483.2; Found: 483.2.

Example 175. 1-(3-(5-(5-(2,3-Dihydro-1H-inden-4-yl)-6-methoxy-1H-pyrazolo[4,3-b]pyridin-3-yl)pyridin-2-yl)azetidin-1-yl)-3-hydroxypropan-1-one

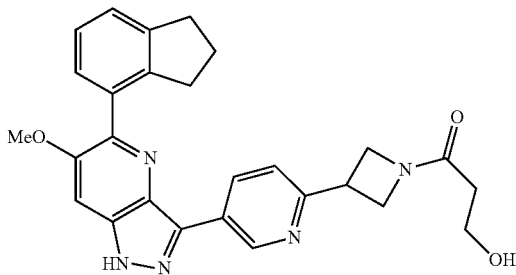

This compound was prepared according to the procedures described in Example 172, step 5, using 3-hydroxypropanoic acid instead of tetrahydrofuran-2-carboxylic acid as starting material. The product was isolated as the TFA salt. LCMS calculated for $C_{27}H_{28}N_5O_3$ (M+H)$^+$: m/z=470.2; Found: 470.2.

Example 176. 1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-hydroxyethan-1-one

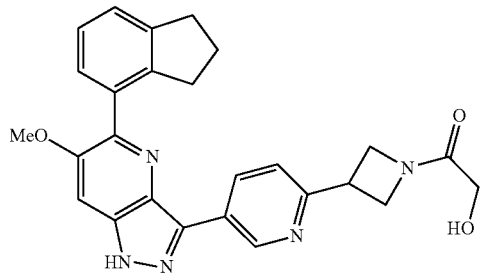 [SMILES: COc1cc2[nH]nc(-c3ccc(C4CN(C(=O)CO)C4)nc3)c2nc1-c1cccc2c1CCC2]

This compound was prepared according to the procedures described in Example 172, step 5, using 2-hydroxyacetic acid instead of tetrahydrofuran-2-carboxylic acid as starting material. The product was isolated as the TFA salt. LCMS calculated for $C_{26}H_{26}N_5O_3$ (M+H)$^+$: m/z=456.2; Found: 456.2.

Example 177. (S)-1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-hydroxypropan-1-one

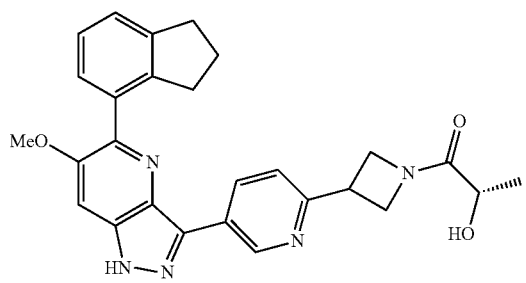 [SMILES: COc1cc2[nH]nc(-c3ccc(C4CN(C(=O)[C@H](C)O)C4)nc3)c2nc1-c1cccc2c1CCC2]

This compound was prepared according to the procedures described in Example 172, step 5, using (S)-2-hydroxypropanoic acid instead of tetrahydrofuran-2-carboxylic acid as starting material. The product was isolated as the TFA salt. LCMS calculated for $C_{27}H_{28}N_5O_3$ (M+H)$^+$: m/z=470.2; Found: 470.2.

Example 178. N-(3-(5-(5-(2,3-Dihydro-1H-inden-4-yl)-6-methoxy-1H-pyrazolo[4,3-b]pyridin-3-yl)pyridin-2-yl)cyclobutyl)-2-hydroxy-N-methylacetamide

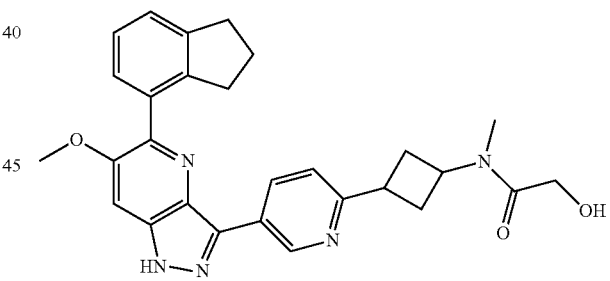

Step 1. tert-Butyl (3-(5-bromopyridin-2-yl)cyclobutyl)(methyl)carbamate

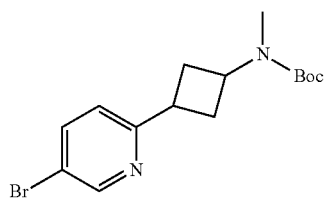 [SMILES: CN(C(=O)OC(C)(C)C)C1CC(c2ccc(Br)cn2)C1]

To a solution of zinc dust (892 mg, 13.64 mmol) in THF (20 mL) was added 1,2-dibromoethane (171 mg, 0.91 mmol)

and chlorotrimethylsilane (99 mg, 0.91 mmol). The reaction was degassed with N₂ and stirred at 60° C. for 15 minutes before tert-butyl (3-iodocyclobutyl)(methyl)carbamate (2.83 g, 9.09 mmol) in DMA (20 mL) was added. The mixture was heated to 60° C. and stirred for 15 minutes before cooled down to r.t. To the cooled mixture was added 2,5-dibromopyridine (2.37 g, 10 mmol), [1,1'-bis(diphenylphosphino)ferrocene]-dichloropalladium(II) (1:1) (371 mg, 0.46 mmol) and copper iodide (87 mg, 0.049 mmol). The mixture was heated to 80° C. for 2 hrs. After this time, it was cooled to r.t. and diluted with EtOAc. The resultant solution was washed sequentially with water, sat. aq. NaCl solution, and dried over Na₂SO₄. The organic phases were filtered and concentrated to dryness. The residue was purified by Biotage Isolera to afford the desired product. LC-MS calculated for $C_{15}H_{22}BrN_2O_2$ (M+H)⁺: m/z=341.1; found 341.1.

Step 2. tert-Butyl methyl(3-(5-(4,4,5,5-tetramethyl-1,3,2-dioxaborolan-2-yl)pyridin-2-yl)cyclobutyl) carbamate

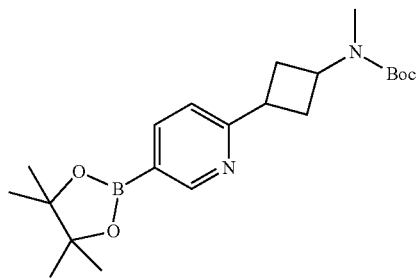 [SMILES: CN(C(=O)OC(C)(C)C)C1CC(c2ccc(B3OC(C)(C)C(C)(C)O3)cn2)C1]

A mixture of tert-butyl (3-(5-bromopyridin-2-yl)cyclobutyl)(methyl)carbamate (1.34 g, 3.93 mmol), 4,4,4',4',5,5,5',5'-octamethyl-2,2'-bi(1,3,2-dioxaborolane) (1.5 g, 5.89 mmol), [1,1'-bis(diphenylphosphino)-ferrocene]-dichloropalladium(II) (320 mg, 0.393 mmol) and potassium acetate (754 mg, 7.85 mmol) in dioxane (14 mL) was stirred at 80° C. for 2 hrs. After cooling to r.t., the reaction mixture was filtered, the solvent was evaporated in vacuo, and the crude material was purified by Biotage Isolera. LCMS calculated for $C_{21}H_{34}BN_2O_4$ (M+H)⁺: m/z=389.3; Found: 389.3.

Step 3. tert-Butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclobutyl)(methyl) carbamate

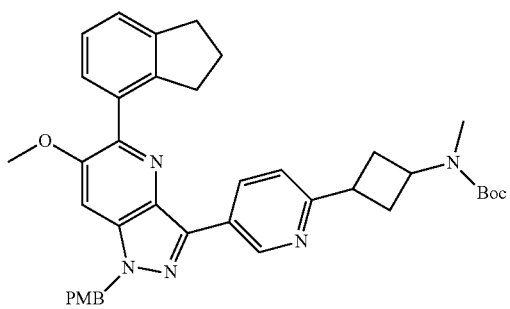

To a solution of 5-(2,3-dihydro-1H-inden-4-yl)-3-iodo-6-methoxy-1-(4-methoxybenzyl)-1H-pyrazolo[4,3-b]pyridine (Example 53, step 3; 456 mg, 0.89 mmol) in 1,4-dioxane (5 mL) and water (1 mL) was added tert-butyl methyl(3-(5-(4,4,5,5-tetramethyl-1,3,2-dioxaborolan-2-yl)pyridin-2-yl)cyclobutyl)carbamate (450 mg, 1.16 mmol), cesium carbonate (436 mg, 1.34 mmol), and (2-dicyclohexylphosphino-2',6'-dimethoxybiphenyl) [2-(2'-amino-1,1'-biphenyl)]palladium(II) methanesulfonate (70 mg, 0.089 mmol). The reaction was degassed with N₂ and stirred at 80° C. for 2 hrs. After this time, it was cooled to r.t. and diluted with EtOAc. The resultant solution was washed sequentially with water, sat. aq. NaCl solution, and dried over Na₂SO₄. The organic phases were filtered and concentrated to dryness. The residue was purified by Biotage Isolera to afford the desired product. LC-MS calculated for $C_{39}H_{44}N_5O_4$ (M+H)⁺: m/z=646.3; found 646.3.

Step 4. 3-(5-(5-(2,3-Dihydro-1H-inden-4-yl)-6-methoxy-1-(4-methoxybenzyl)-1H-pyrazolo[4,3-b]pyridin-3-yl)pyridin-2-yl)-N-methylcyclobutan-1-amine

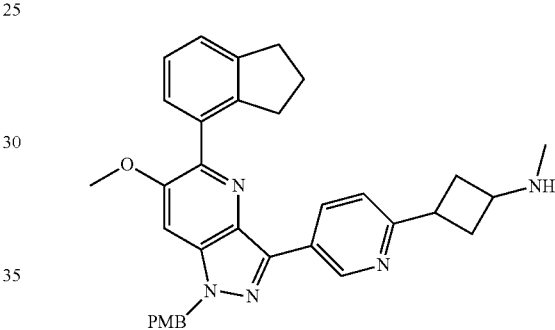

To a solution of tert-butyl (3-(5-(5-(2,3-dihydro-1H-inden-4-yl)-6-methoxy-1-(4-methoxybenzyl)-1H-pyrazolo[4,3-b]pyridin-3-yl)pyridin-2-yl)cyclobutyl)(methyl)carbamate (461 mg, 0.71 mmol) in dichloromethane (2 mL) was added trifluoroacetic acid (2 mL). The reaction was stirred at r.t. for 1 hr. After this time, it was diluted with dichloromethane. The resultant solution was washed sequentially with water, sat. aq. NaCl solution and dried over Na₂SO₄. The organic phases were filtered and concentrated to dryness. The residue was used directly in the next step without purification. LC-MS calculated for $C_{34}H_{36}N_5O_2$ (M+H)⁺: m/z=546.3; found 546.3.

Step 5. N-(3-(5-(5-(2,3-Dihydro-1H-inden-4-yl)-6-methoxy-1H-pyrazolo[4,3-b]pyridin-3-yl)pyridin-2-yl)cyclobutyl)-2-hydroxy-N-methylacetamide To a solution of 3-(5-(5-(2,3-dihydro-1H-inden-4-yl)-6-methoxy-1-(4-methoxybenzyl)-1H-pyrazolo[4,3-b]pyridin-3-yl)pyridin-2-yl)-N-methylcyclobutan-1-amine (20 mg, 0.037 mmol) in dichloromethane (0.5 mL) was added 2-hydroxyacetic acid (6 mg, 0.073 mmol), trimethylamine (9 mg, 0.073 mmol) and HATU (21 mg, 0.055 mmol). The reaction was stirred at r.t. for 1 hr. After this time, it was diluted with dichloromethane. The resultant solution was washed sequentially with water, sat. aq. NaCl solution, and dried over Na₂SO₄. The organic phases were filtered and concentrated to dryness. The residue was dissolved in dichloromethane (0.5 mL) and trifluoromethanesulfonic acid (0.1 mL). The reaction was stirred at r.t. After 30 min, the reaction mixture was quenched with 4N NaOH aq. solution and diluted with dichloromethane. The resultant mixture was washed sequentially with water, sat. aq. NaCl solution and dried over Na$_2$SO$_4$. The organic phases were filtered and concentrated to dryness. The residue was diluted with MeOH and was purified by prep-LCMS (XBridge C18 column, eluting with a gradient of acetonitrile/water containing 0.1% TFA, at flow rate of 60 mL/min). The product was isolated as the TFA salt. LC-MS calculated for C$_{28}$H$_{30}$N$_5$O$_3$ (M+H)$^+$: m/z=484.2; found 484.2.

Example 179. 1-(3-(5-(5-(2,3-Dihydro-1H-inden-4-yl)-6-methoxy-1H-pyrazolo[4,3-b]pyridin-3-yl)pyridin-2-yl)azetidin-1-yl-3-d)-2-hydroxyethan-1-one

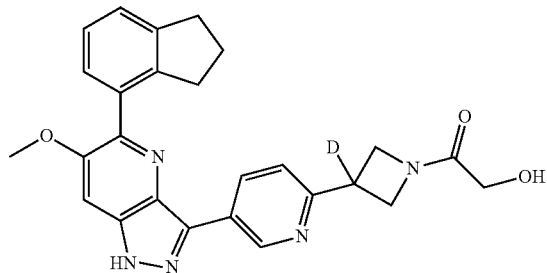 [SMILES: [2H]C1(c2ccc(-c3n[nH]c4cc(OC)c(-c5cccc6c5CCC6)nc34)cn2)CN(C(=O)CO)C1]

Step 1. tert-Butyl 3-hydroxyazetidine-1-carboxylate-3-d

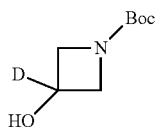

To a solution of tert-butyl 3-oxoazetidine-1-carboxylate (420 mg, 2.45 mmol) in MeOH (5 mL) at 0° C. was added sodium borodeuteride (124 mg, 2.94 mmol) portionwise. The mixture was warmed to r.t. and stirred for 30 minutes. After this time, the resultant solution was concentrated to dryness. The residue was purified by Biotage Isolera to afford the desired product. LC-MS calculated for C$_8$H$_{15}$DNO$_3$ (M+H)$^+$: m/z=175.1; found 175.1.

Step 2. tert-Butyl 3-iodoazetidine-1-carboxylate-3-d

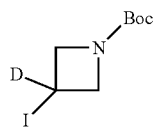

To a solution of tert-butyl 3-hydroxyazetidine-1-carboxylate-3-d (180 mg, 1.03 mmol) in THF (4 mL) was added imidazole (141 mg, 2.07 mmol), triphenylphosphine (677 mg, 2.58 mmol) and iodine (394 mg, 1.55 mmol). The mixture was heated to 50° C. and stirred overnight. After this time, the resultant solution was concentrated to dryness. The residue was purified by Biotage Isolera to afford the desired product. LC-MS calculated for C$_8$H$_{14}$DINO$_2$ (M+H)$^+$: m/z=285.0; found 285.0.

Step 3. tert-Butyl 3-(5-bromopyridin-2-yl)azetidine-1-carboxylate-3-d

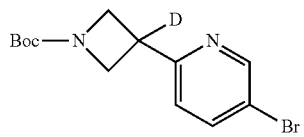 [SMILES: [2H]C1(c2ccc(Br)cn2)CN(C(=O)OC(C)(C)C)C1]

To a solution of zinc dust (97 mg, 1.48 mmol) in THF (3 mL) was added 1,2-dibromoethane (19 mg, 0.1 mmol) and chlorotrimethylsilane (11 mg, 0.1 mmol). The reaction was degassed with N$_2$ and stirred at 60° C. for 15 minutes before tert-butyl 3-iodoazetidine-1-carboxylate-3-d (280 mg, 0.99 mmol) in DMA (3 mL) was added. The mixture was heated to 60° C. and stirred for 15 minutes before cooled down to r.t. To the cooled mixture was added 2,5-dibromopyridine (257 mg, 1.08 mmol), [1,1'-bis(diphenylphosphino)ferrocene]dichloropalladium(II) (1:1) (40 mg, 0.049 mmol) and copper iodide (9 mg, 0.049 mmol). The mixture was heated to 80° C. for 2 hrs. After this time, it was cooled to r.t. and diluted with EtOAc. The resultant solution was washed sequentially with water, sat. aq. NaCl solution, and dried over Na$_2$SO$_4$. The organic phases were filtered and concentrated to dryness. The residue was purified by Biotage Isolera to afford the desired product. LC-MS calculated for C$_{13}$H$_{17}$DBrN$_2$O$_2$ (M+H)$^+$: m/z=314.1; found 314.1.

Step 4. tert-Butyl 3-(5-(4,4,5,5-tetramethyl-1,3,2-dioxaborolan-2-yl)pyridin-2-yl)azetidine-1-carboxylate-3-d

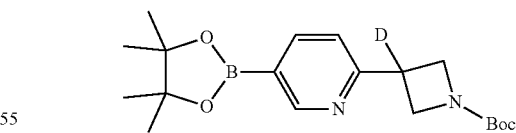

A mixture of tert-butyl 3-(5-bromopyridin-2-yl)azetidine-1-carboxylate-3-d (206 mg, 0.66 mmol), 4,4,4',4',5,5,5',5'-octamethyl-2,2'-bi(1,3,2-dioxaborolane) (250 mg, 0.98 mmol), [1,1'-bis(diphenylphosphino)-ferrocene]-dichloropalladium(II) (54 mg, 0.066 mmol) and potassium acetate (126 mg, 1.31 mmol) in dioxane (3 mL) was stirred at 80° C. for 2 hrs. After cooling to r.t., the reaction mixture was filtered, the solvent was evaporated in vacuo and the crude material was purified by Biotage Isolera. LCMS calculated for C$_{19}$H$_{29}$DBN$_2$O$_4$ (M+H)$^+$: m/z=362.2; Found: 362.2.

Step 5. 5-(2,3-Dihydro-1H-inden-4-yl)-3-iodo-6-methoxy-1-((2-(trimethylsilyl)ethoxy)-methyl)-1H-pyrazolo[4,3-b]pyridine

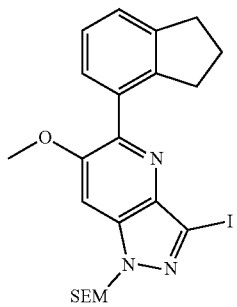 [SMILES: COc1cc2c(nc1-c1cccc3c1CCC3)c(I)nn2COCC[Si](C)(C)C]

To a solution of 5-(2,3-dihydro-1H-inden-4-yl)-6-methoxy-1H-pyrazolo[4,3-b]pyridine (Example 53, step 2; 2.5 g, 6.39 mmol) in DMF (5 mL) was added N-iodosuccinimide (2.87 g, 12.78 mmol). The resulting mixture was stirred at 60° C. for 1 h. The mixture was cooled to r.t., and 2-(trimethylsilyl)ethoxymethyl chloride (1.39 g, 8.31 mmol) and Cs₂CO₃ (3.12 g, 9.59 mmol) were added. The reaction mixture was stirred at 80° C. for 1 h. After this time, it was cooled to r.t., diluted with water and extracted with EtOAc three times. The combined organic phases were washed with sat. NaCl, dried with Na₂SO₄, filtered and concentrated to dryness. The residue was purified by Biotage Isolera to afford the desired product. LC-MS calculated for $C_{22}H_{29}IN_3O_2Si$ (M+H)+: m/z=522.1; found 522.1.

Step 6. tert-Butyl 3-(5-(5-(2,3-dihydro-1H-inden-4-yl)-6-methoxy-1-((2-(trimethylsilyl)ethoxy)methyl)-1H-pyrazolo[4,3-b]pyridin-3-yl)pyridin-2-yl)azetidine-1-carboxylate-3-d

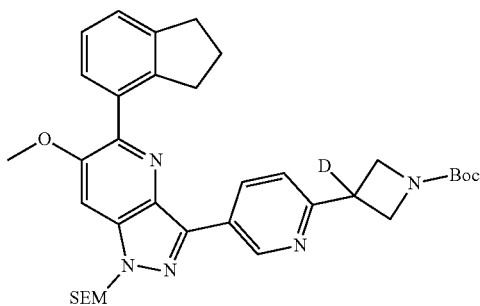 [SMILES: [2H]C1(c2ccc(-c3nn(COCC[Si](C)(C)C)c4cc(OC)c(-c5cccc6c5CCC6)nc34)cn2)CN(C(=O)OC(C)(C)C)C1]

To a solution of 5-(2,3-dihydro-1H-inden-4-yl)-3-iodo-6-methoxy-1-((2-(trimethylsilyl)ethoxy)-methyl)-1H-pyrazolo[4,3-b]pyridine (70 mg, 0.13 mmol) in 1,4-dioxane (1 mL) and water (0.2 mL) was added tert-butyl 3-(5-(4,4,5,5-tetramethyl-1,3,2-dioxaborolan-2-yl)pyridin-2-yl)azetidine-1-carboxylate-3-d (63 mg, 0.17 mmol), cesium carbonate (66 mg, 0.20 mmol) and (2-dicyclohexylphosphino-2',6'-dimethoxybiphenyl) [2-(2'-amino-1,1'-biphenyl)]palladium(II) methanesulfonate (10 mg, 0.013 mmol). The reaction was degassed with N₂ and stirred at 80° C. for 1 hr. After this time, it was cooled to r.t. and diluted with EtOAc. The resultant solution was washed sequentially with water, sat. aq. NaCl solution, and dried over Na₂SO₄. The organic phases were filtered and concentrated to dryness. The residue was purified by Biotage Isolera to afford the desired product. LC-MS calculated for $C_{35}H_{45}DN_5O_4Si$ (M+H)+: m/z=629.3; found 629.3.

Step 7. 3-(6-(Azetidin-3-yl-3-d)pyridin-3-yl)-5-(2,3-dihydro-1H-inden-4-yl)-6-methoxy-1H-pyrazolo[4,3-b]pyridine

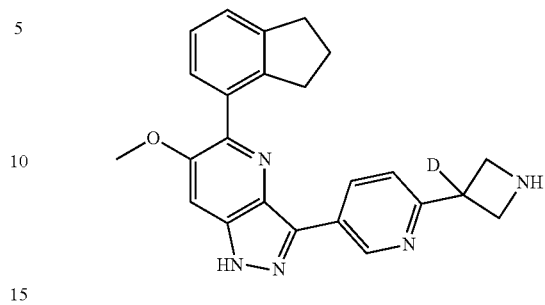

To a solution of tert-butyl 3-(5-(5-(2,3-dihydro-1H-inden-4-yl)-6-methoxy-1-((2-(trimethylsilyl)ethoxy)methyl)-1H-pyrazolo[4,3-b]pyridin-3-yl)pyridin-2-yl)azetidine-1-carboxylate-3-d (84 mg, 0.134 mmol) in dichloromethane (1 mL) was added trifluoroacetic acid (1 mL). The reaction was stirred at r.t. for 1 hr. After this time, it was diluted with dichloromethane. The resultant solution was washed sequentially with water, sat. aq. NaCl solution and dried over Na₂SO₄. The organic phases were filtered and concentrated to dryness. The residue was used directly in the next step without purification. LC-MS calculated for $C_{24}H_{23}DN_5O$ (M+H)+: m/z=399.2; found 399.2.

Step 8. 1-(3-(5-(5-(2,3-Dihydro-1H-inden-4-yl)-6-methoxy-1H-pyrazolo[4,3-b]pyridin-3-yl)pyridin-2-yl)azetidin-1-yl-3-d)-2-hydroxyethan-1-one To a solution of 3-(6-(azetidin-3-yl-3-d)pyridin-3-yl)-5-(2,3-dihydro-1H-inden-4-yl)-6-methoxy-1H-pyrazolo[4,3-b]pyridine (20 mg, 0.05 mmol) in dichloromethane (0.5 mL) was added 2-hydroxyacetic acid (4 mg, 0.05 mmol), trimethylamine (14 mg, 0.106 mmol) and BOP (21 mg, 0.048 mmol). The reaction was stirred at r.t. for 1 hr. After this time, it was diluted with MeOH and was purified by prep-LCMS (XBridge C18 column, eluting with a gradient of acetonitrile/water containing 0.1% TFA, at flow rate of 60 mL/min). The product was isolated as the TFA salt. LC-MS calculated for $C_{26}H_{25}DN_5O_3$ (M+H)+: m/z=457.2; found 457.2.

Example 180. Methyl 4-(5-(5-(1-Cyano-2,3-dihydro-1H-inden-4-yl)-6-methoxy-1H-pyrazolo[4,3-b]pyridin-3-yl)pyridin-2-yl)piperidine-1-carboxylate

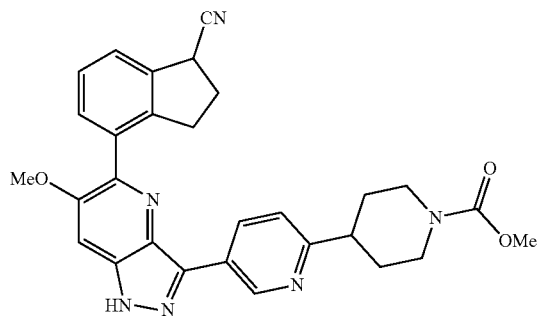 [SMILES: COC(=O)N1CCC(c2ccc(-c3n[nH]c4cc(OC)c(-c5cccc6c5CCC6C#N)nc34)cn2)CC1]

Step 1. tert-Butyl 5-chloro-3',6'-dihydro-[2,4'-bi-pyridine]-1'(2'H)-carboxylate

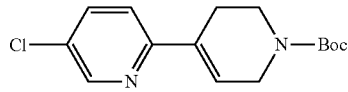 [SMILES: CC(C)(C)OC(=O)N1CC=C(c2ccc(Cl)cn2)CC1]

A mixture of 2-bromo-5-chloropyridine (2 g, 10.39 mmol), tert-butyl 4-(4,4,5,5-tetramethyl-1,3,2-dioxaborolan-2-yl)-3,6-dihydropyridine-1(2H)-carboxylate (3.21 g, 10.39 mmol), [1,1'-bis(diphenylphosphino)ferrocene]-dichloropalladium(II) (0.85 g, 1.04 mmol), and $K_3PO_4$ (4.41 g, 20.79 mmol) in dioxane (20 ml) and water (4.00 ml) was sparged with $N_2$ and heated to 80° C. for 2 h. The reaction mixture was diluted with EtOAc/MeOH, filtered through celite, and the residue was purified by ISCO NextGen. LC-MS calculated for $C_{11}H_{12}ClN_2O_2$ (M-$C_4H_9$+H)$^+$: m/z=239.1; found 239.0.

Step 2. tert-Butyl 4-(5-chloropyridin-2-yl)piperidine-1-carboxylate

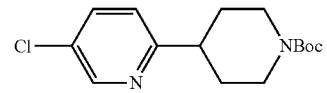 [SMILES: CC(C)(C)OC(=O)N1CCC(c2ccc(Cl)cn2)CC1]

5% Rh/C (0.5 g, 4.86 mmol) was added to a solution of tert-butyl 5-chloro-3',6'-dihydro-[2,4'-bipyridine]-1'(2'H)-carboxylate (1.5 g, 5.09 mmol) in EtOH (10 mL) and EtOAc (10 mL). The reaction was purged with $H_2$ and stirred at r.t. connected to a balloon filled with hydrogen for 16 hrs. After completion, the reaction was filtrated through Celite using EtOAc. The filtrate was then concentrated to dryness and used in the next reaction without further purification. LC-MS calculated for $C_{11}H_{14}ClN_2O_2$ (M-$C_4H_9$+H)$^+$: m/z=241.1; found 241.2.

Step 3. tert-Butyl 4-(5-(4,4,5,5-tetramethyl-1,3,2-dioxaborolan-2-yl)pyridin-2-yl)piperidine-1-carboxylate

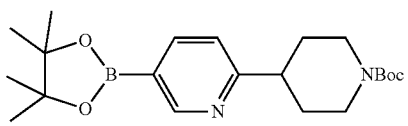 [SMILES: CC(C)(C)OC(=O)N1CCC(c2ccc(B3OC(C)(C)C(C)(C)O3)cn2)CC1]

A mixture of tert-butyl 4-(5-chloropyridin-2-yl)piperidine-1-carboxylate (0.75 g, 2.53 mmol), 4,4,4',4',5,5,5',5'-octamethyl-2,2'-bi(1,3,2-dioxaborolane) (0.96 g, 3.79 mmol), potassium acetate (0.74 g, 7.58 mmol), XPhos (0.18 g, 0.379 mmol) and palladium(II) acetate (0.085 g, 0.379 mmol) in 1,4-dioxane (8 mL) was sparged with $N_2$ and heated to 80° C. for 1 h. After cooling to r.t., the reaction mixture was filtered using EtOAc/MeOH and the solvent was evaporated in vacuo. The crude material was used in the next reaction without further purification. LC-MS calculated for corresponding boronic acid $C_{15}H_{24}BN_2O_4$ (M-$C_6H_{10}$+H)$^+$: m/z=307.2; found 307.2.

Step 4. 4-(3-Iodo-6-methoxy-1-(4-methoxybenzyl)-1H-pyrazolo[4,3-b]pyridin-5-yl)-2,3-dihydro-1H-indene-1-carbonitrile

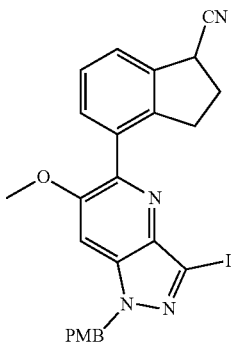

This compound was prepared according to the procedures described in Example 53, step 3, using 4-(6-methoxy-1H-pyrazolo[4,3-b]pyridin-5-yl)-2,3-dihydro-1H-indene-1-carbonitrile (Example 75, step 6) instead of 5-(2,3-dihydro-1H-inden-4-yl)-6-methoxy-1H-pyrazolo[4,3-b]pyridine as starting material. LC-MS calculated for $C_{25}H_{22}IN_4O_2$ (M+H)$^+$: m/z=537.1; found 537.1.

Step 5. tert-Butyl 4-(5-(5-(1-cyano-2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate

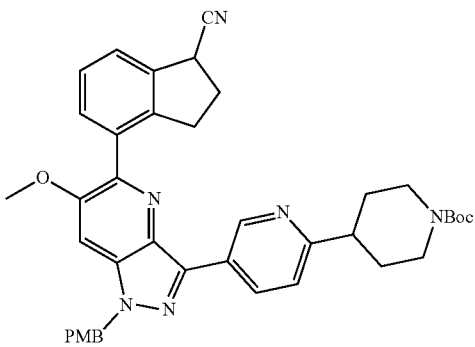

A mixture of 4-(3-iodo-6-methoxy-1-(4-methoxybenzyl)-1H-pyrazolo[4,3-b]pyridin-5-yl)-2,3-dihydro-1H-indene-1-carbonitrile (1.2 g, 2.237 mmol), tert-butyl 4-(5-(4,4,5,5-tetramethyl-1,3,2-dioxaborolan-2-yl)pyridin-2-yl) piperidine-1-carboxylate (0.96 g, 2.46 mmol), [1,1'-bis(diphenylphosphino)ferrocene]-dichloropalladium(II) (0.183 g, 0.224 mmol) and $K_3PO_4$ (1.43 g, 6.71 mmol) in 1,4-dioxane (10 mL) and water (2 mL) was sparged with $N_2$ and heated to 80° C. for 2 h. The reaction mixture was diluted with EtOAc/MeOH, filtered through celite and the residue was purified by ISCO NextGen. LC-MS calculated for $C_{40}H_{43}N_6O_4$ (M+H)$^+$: m/z=671.3; found 671.3.

Step 6. 4-(6-Methoxy-1-(4-methoxybenzyl)-3-(6-(piperidin-4-yl)pyridin-3-yl)-1H-pyrazolo[4,3-b]pyridin-5-yl)-2,3-dihydro-M-indene-1-carbonitrile

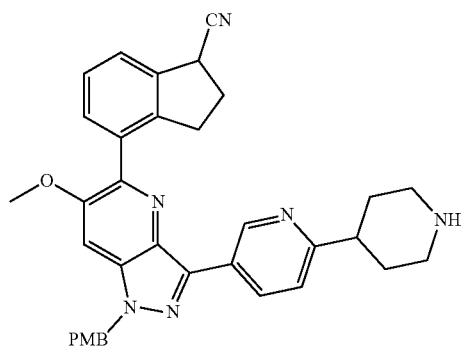

To tert-butyl 4-(5-(5-(1-cyano-2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate (69 mg, 0.103 mmol) was added DCM (0.5 mL) and TFA (1 mL) and the mixture was stirred at r.t. for 30 min. The excess TFA was evaporated in vacuo, the residue was diluted with DCM and then neutralized using saturated NaHCO$_3$ solution. The organic phase was dried over sodium sulfate, filtered, and the solvent was evaporated in vacuo. The crude material was used in the next reaction without further purification. LC-MS calculated for $C_{35}H_{35}N_6O_2$ (M+H)$^+$: m/z=571.3; found 571.3.

Step 7. Methyl 4-(5-(5-(1-cyano-2,3-dihydro-1H-inden-4-yl)-6-methoxy-1H-pyrazolo[4,3-b]pyridin-3-yl)pyridin-2-yl)piperidine-1-carboxylate To a solution of 4-(6-methoxy-1-(4-methoxybenzyl)-3-(6-(piperidin-4-yl)pyridin-3-yl)-1H-pyrazolo[4,3-b]pyridin-5-yl)-2,3-dihydro-1H-indene-1-carbonitrile (12 mg, 0.021 mmol) and trienthylamine (18 µl, 0.126 mmol) in dioxane (1 ml) was added methyl carbonochloridate (8 µl, 0.105 mmol). The mixture was stirred at r.t for 1 h. The reaction was quenched with water, extracted with DCM. The organic phase was dried over Na$_2$SO$_4$, filtered and concentrated. The residue was dissolved in DCM (1 mL) and added triflic acid (0.1 mL). The mixture was stirred at r.t. for 30 min then quenched with MeOH and excess DCM was evaporated in vacuo. The residue was diluted with CH$_3$CN and filtered through SiliPrep Thiol cartridge and purified by prep-LCMS (Waters SunFire C18 column, 5 um particle size, 30×100 mm) eluting with a gradient of acetonitrile/water containing 0.1% TFA, at flow rate of 60 mL/min). The product was isolated as the TFA salt. LCMS calculated for $C_{29}H_{29}N_6O_3$ (M+H)+: m/z=509.2; found 509.2.

Example 181. 4-(6-Methoxy-3-(6-(1-(morpholine-4-carbonyl)piperidin-4-yl)pyridin-3-yl)-1H-pyrazolo[4,3-b]pyridin-5-yl)-2,3-dihydro-1H-indene-1-carbonitrile, Peak 2

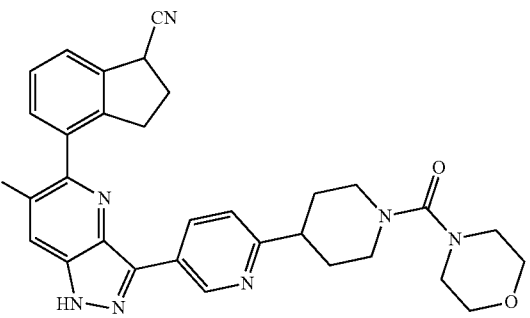

Step 1. tert-Butyl 4-(5-(5-(1-cyano-2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate (Peak 1 and Peak 2)

Peak 1

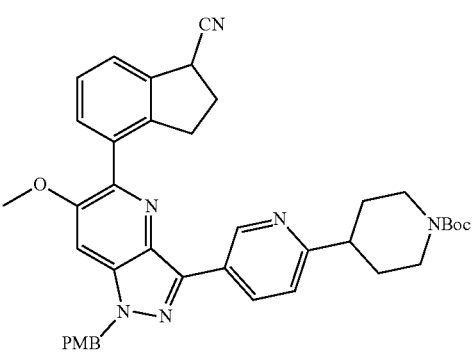

Peak 2

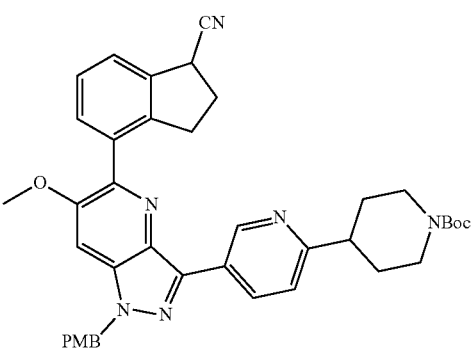

The racemic mixture was prepared according to the procedures described in Example 180, step 5. LC-MS calculated for $C_{40}H_{43}N_6O_4$ (M+H)$^+$: m/z=671.3; found 671.3. Then, two enantiomers were separated with prep FSC (ChriaIPAK IH, 21×250 mm, eluting with 30% MeOH in CO$_2$, at flow rate of 65 mL/min, $t_{R,peak\ 1}$=3.7 min, $t_{R,peak\ 2}$=4.1 min). Peak 2 was collected and the solvents were evaporated in vacuo and the residue was used directly in the next step without further purification.

Step 2. 4-(6-Methoxy-1-(4-methoxybenzyl)-3-(6-(piperidin-4-yl)pyridin-3-yl)-1H-pyrazolo[4,3-b]pyridin-5-yl)-2,3-dihydro-1H-indene-1-carbonitrile (Peak 2)

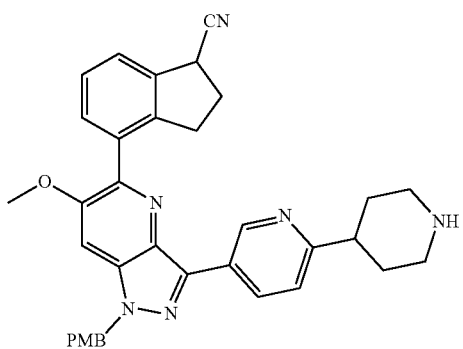

This compound was prepared according to the procedure described in Example 180, step 6, using tert-butyl 4-(5-(5-(1-cyano-2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate Peak 2 as starting material instead of the racemic material (Example 180, step 5). LC-MS calculated for $C_{35}H_{35}N_6O_2$ (M+H)$^+$: m/z=571.3; found 571.3.

Step 3. 4-(6-Methoxy-3-(6-(1-(morpholine-4-carbonyl)piperidin-4-yl)pyridin-3-yl)-1H-pyrazolo[4,3-b]pyridin-5-yl)-2,3-dihydro-1H-indene-1-carbonitrile (Peak 2)

This compound was prepared according to the procedure described in Example 180, step 7 using 4-(6-methoxy-1-(4-methoxybenzyl)-3-(6-(piperidin-4-yl)pyridin-3-yl)-1H-pyrazolo[4,3-b]pyridin-5-yl)-2,3-dihydro-1H-indene-1-carbonitrile Peak 2 and morpholine-4-carbonyl chloride as the starting materials. The product was isolated as the TFA salt. LC-MS calculated for $C_{32}H_{34}N_7O_3$(M+H)$^+$: m/z=564.3; found 564.2.

Example 182. 4-(3-(6-(1-Acetylpiperidin-4-yl)pyridin-3-yl)-6-methoxy-1H-pyrazolo[4,3-b]pyridin-5-yl)-2,3-dihydro-1H-indene-1-carbonitrile, Peak 2

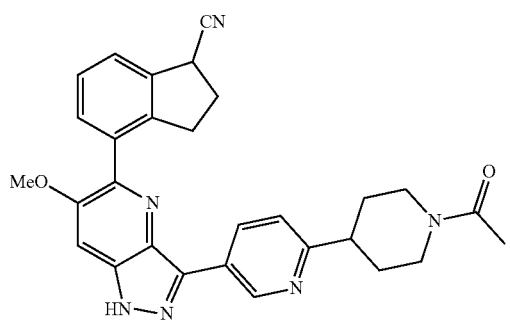 [SMILES: COc1cc2[nH]nc(-c3ccc(C4CCN(C(C)=O)CC4)nc3)c2nc1-c1cccc2c1CCC2C#N]

This compound was prepared according to the procedure described in Example 180 and 181, step 7, using 4-(6-methoxy-1-(4-methoxybenzyl)-3-(6-(piperidin-4-yl)pyridin-3-yl)-1H-pyrazolo[4,3-b]pyridin-5-yl)-2,3-dihydro-1H-indene-1-carbonitrile (Example 181, step 2, Peak 2) and acetyl chloride as the starting materials. The product was isolated as the TFA salt. LC-MS calculated for $C_{29}H_{29}N_6O_2$ (M+H)$^+$: m/z=493.2; found 493.2.

Example 183: 4-(3-(6-(1-Acetylpyrrolidin-3-yl)pyridin-3-yl)-6-methoxy-1H-pyrazolo[4,3-b]pyridin-5-yl)-2,3-dihydro-1H-indene-1-carbonitrile

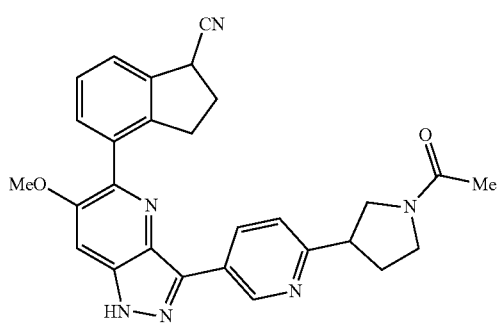 [SMILES: COc1cc2[nH]nc(-c3ccc(C4CCN(C(C)=O)C4)nc3)c2nc1-c1cccc2c1CCC2C#N]

Step 1. tert-Butyl 3-(5-chloropyridin-2-yl)-2,5-dihydro-1H-pyrrole-1-carboxylate

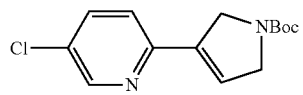 [SMILES: CC(C)(C)OC(=O)N1CC=C(c2ccc(Cl)cn2)C1]

This compound was prepared according to the procedure described in Example 180, step 1, using tert-butyl 3-(4,4,5,5-tetramethyl-1,3,2-dioxaborolan-2-yl)-2,5-dihydro-1H-pyrrole-1-carboxylate instead of tert-butyl 4-(4,4,5,5-tetramethyl-1,3,2-dioxaborolan-2-yl)-3,6-dihydropyridine-1(21H)-carboxylate as the starting material. LC-MS calculated for $C_{10}H_{10}ClN_2O_2$ (M-C$_4$H$_9$+H)$^+$: m/z=225.0; found 225.0.

Step 2. tert-Butyl 3-(5-chloropyridin-2-yl)pyrrolidine-1-carboxylate, Peak 1 and Peak 2

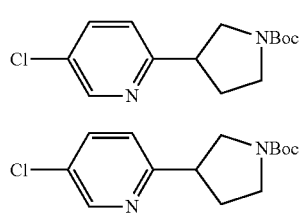

Peak 1

Peak 2

5% Rh/C (0.58 g, 5.64 mmol) was added to a solution of tert-butyl 3-(5-chloropyridin-2-yl)-2,5-dihydro-1H-pyrrole-1-carboxylate (1.9 g, 6.77 mmol) in THF (10 mL), EtOH (10 mL) and EtOAc (20.00 mL). The reaction was purged with H$_2$ and stirred at r.t. connected to a balloon filled with hydrogen for 20 hrs. After completion, the reaction was filtrated through Celite using EtOAc. The filtrate was then concentrated to dryness to afford the racemic mixture. LC-MS calculated for $C_{10}H_{12}ClN_2O_2$ (M-C4H9+H)+: m/z=227.1; found 227.1. The two enantiomers were separated with prep FSC (Phenomenex Lux Sum Amylose-1, 21.2×250 mm, eluting with 20% MeOH in $CO_2$, at flow rate of 70 mL/min, $t_{R, peak 1}$=2.9 min, $t_{R, peak 2}$=3.4 min). Peak 2 was collected and the solvents were evaporated in vacuo and the residue was used directly to the next step without further purification.

Step 3. tert-Butyl 3-(5-(4,4,5,5-tetramethyl-1,3,2-dioxaborolan-2-yl)pyridin-2-yl)pyrrolidine-1-carboxylate, Peak 2

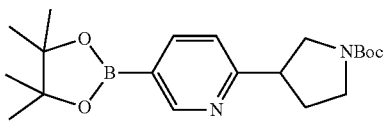 [SMILES: CC(C)(C)OC(=O)N1CCC(c2ccc(B3OC(C)(C)C(C)(C)O3)cn2)C1]

This compound was prepared according to the procedure described in Example 180, step 3, using tert-butyl 3-(5-chloropyridin-2-yl)pyrrolidine-1-carboxylate Peak 2 instead of tert-butyl 4-(5-chloropyridin-2-yl)piperidine-1-carboxylate as the starting material. LC-MS calculated for corresponding boronic acid $C_{14}H_{22}BN_2O_4$ (M-C6H10+H)+: m/z=293.2; found 293.1.

Step 4. tert-Butyl 3-(5-(5-(1-cyano-2,3-dihydro-1H-inden-4-yl)-6-methoxy-1-(4-methoxybenzyl)-1H-pyrazolo[4,3-b]pyridin-3-yl)pyridin-2-yl)pyrrolidine-1-carboxylate Peak A and Peak B peak A

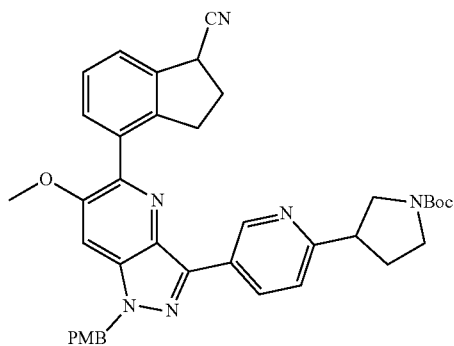

peak B

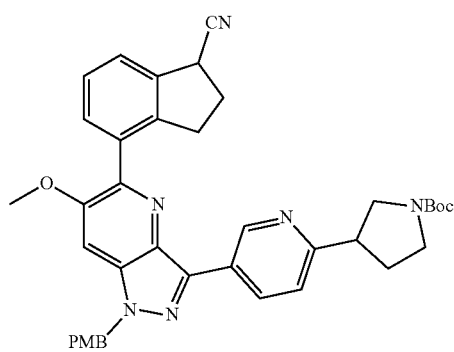

The diastereomeric mixture was prepared according to the procedures described in Example 180, step 5 using tert-butyl 3-(5-(4,4,5,5-tetramethyl-1,3,2-dioxaborolan-2-yl)pyridin-2-yl)pyrrolidine-1-carboxylate (Peak 2) instead of tert-butyl 4-(5-(4,4,5,5-tetramethyl-1,3,2-dioxaborolan-2-yl)pyridin-2-yl)piperidine-1-carboxylate as the starting material. LC-MS calculated for $C_{39}H_{41}N_6O_4$ (M+H)+: m/z=657.3; found 657.2. Then, the two diastereomers were separated with prep FSC (Phenomenex Cellulose-1 Sum 21.2×250 mm, eluting with 45% MeOH in $CO_2$, at flow rate of 100 mL/min, $t_{R, peak A}$=5.7 min, $t_{R, peak B}$=6.1 min). Peak A was collected and the solvents were evaporated in vacuo. The residue was used directly to the next step without further purification.

Step 5. 4-(6-Methoxy-1-(4-methoxybenzyl)-3-(6-(pyrrolidin-3-yl)pyridin-3-yl)-1H-pyrazolo[4,3-b]pyridin-5-yl)-2,3-dihydro-JH-indene-1-carbonitrile, Peak A

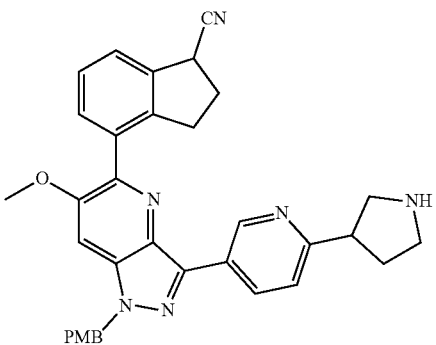

This compound was prepared according to procedure described in Example 180, step 6, using tert-butyl 3-(5-(5-(1-cyano-2,3-dihydro-1H-inden-4-yl)-6-methoxy-1-(4-methoxybenzyl)-1H-pyrazolo[4,3-b]pyridin-3-yl)pyridin-2-yl)pyrrolidine-1-carboxylate, Peak A as starting material instead of tert-butyl 4-(5-(5-(1-cyano-2,3-dihydro-1H-inden-4-yl)-6-methoxy-1-(4-methoxybenzyl)-1H-pyrazolo[4,3-b]pyridin-3-yl)pyridin-2-yl)piperidine-1-carboxylate. LC-MS calculated for $C_{34}H_{33}N_6O_2$ (M+H)+: m/z=557.3; found 557.2.

Step 6. 4-(3-(6-(1-Acetylpyrrolidin-3-yl)pyridin-3-yl)-6-methoxy-1H-pyrazolo[4,3-b]pyridin-5-yl)-2,3-dihydro-1H-indene-1-carbonitrile, Peak A This compound was prepared according to the procedure described in Example 180, step 7, using 4-(6-methoxy-1-(4-methoxybenzyl)-3-(6-(pyrrolidin-3-yl)pyridin-3-yl)-1H-pyrazolo[4,3-b]pyridin-5-yl)-2,3-dihydro-1H-indene-1-carbonitrile, Peak A and acetyl chloride as the starting materials. The product was isolated as the TFA salt. LC-MS calculated for $C_{28}H_{27}N_6O_2$ (M+H)+: m/z=479.2; found 479.2.

Example 184. 4-(6-Methoxy-3-(6-(1-(morpholine-4-carbonyl)pyrrolidin-3-yl)pyridin-3-yl)-1H-pyrazolo[4,3-b]pyridin-5-yl)-2,3-dihydro-1H-indene-1-carbonitrile

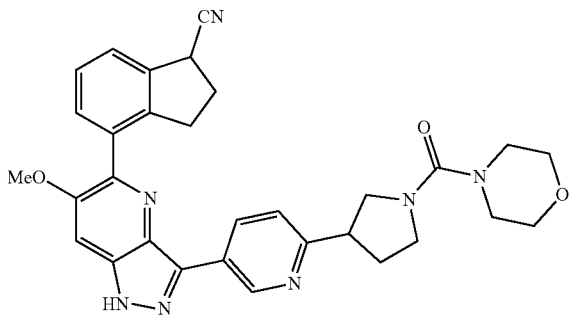 [SMILES: COc1cc2[nH]nc(-c3ccc(C4CCN(C(=O)N5CCOCC5)C4)nc3)c2nc1-c1cccc2c1CCC2C#N]

This compound was prepared according to the procedure described in Example 180, step 7, using 4-(6-methoxy-1-(4-methoxybenzyl)-3-(6-(piperidin-4-yl)pyridin-3-yl)-1H-pyrazolo[4,3-b]pyridin-5-yl)-2,3-dihydro-1H-indene-1-carbonitrile, Peak A and morpholine-4-carbonyl chloride as the starting material. The product was isolated as the TFA salt. LC-MS calculated for $C_{31}H_{32}N_7O_3$ (M+H)$^+$: m/z=550.3; found 550.2.

Example 185. 4-(3-(1-(Cyanomethyl)-1H-pyrazol-4-yl)-6-methoxy-1H-pyrazolo[4,3-b]pyridin-5-yl)-2,3-dihydro-1H-indene-1-carbonitrile

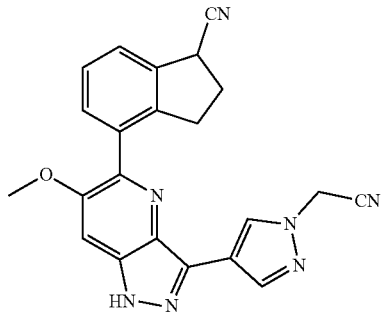 [SMILES: COc1cc2[nH]nc(-c3cnn(CC#N)c3)c2nc1-c1cccc2c1CCC2C#N]

Step 1. tert-Butyl 5-(1-cyano-2,3-dihydro-1H-inden-4-yl)-3-(1-(cyanomethyl)-1H-pyrazol-4-yl)-6-methoxy-1H-pyrazolo[4,3-b]pyridine-1-carboxylate

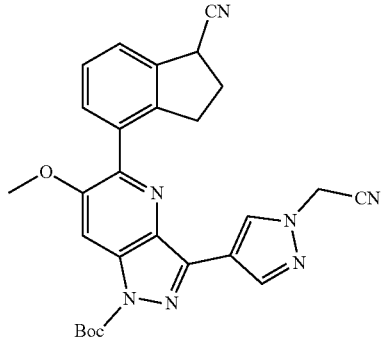 [SMILES: COc1cc2c(nc1-c1cccc3c1CCC3C#N)c(-c1cnn(CC#N)c1)nn2C(=O)OC(C)(C)C]

To a solution of tert-butyl 5-(1-cyano-2,3-dihydro-1H-inden-4-yl)-3-iodo-6-methoxy-1H-pyrazolo[4,3-b]pyridine-1-carboxylate (Example 75, step 7; 150 mg, 0.291 mmol) in 1,4-dioxane (1.2 mL) and water (0.24 mL) was added 2-(4-(4,4,5,5-tetramethyl-1,3,2-dioxaborolan-2-yl)-1H-pyrazol-1-yl)acetonitrile (81 mg, 0.35 mmol), potassium phosphate (123 mg, 0.581 mmol), and XphosPd G2 (23 mg, 0.029 mmol). The reaction was degassed with $N_2$ and stirred at 60° C. for 1 hr. After this time, it was cooled to room temperature and filtered through a pad of Celite, rinsing with ethyl acetate. The residue was purified by silica gel chromatography to afford the desired product. Separation of enantiomers was achieved by chiral prep-SFC (ChiralPak IB-N Sum 20×250 mm, eluting with 20% MeOH, at 40° C., at a flow rate of 70 mL/min, $t_{R, peak\ 1}$=7.1 min, $t_{R, peak\ 2}$=7.7 min). Peak 1 was collected and the solvents were evaporated in vacuo. LCMS calculated for $C_{27}H_{26}N_7O_3$ (M+H)$^+$: m/z=496.2, found: 496.2.

Step 2. 4-(3-(1-(Cyanomethyl)-1H-pyrazol-4-yl)-6-methoxy-1H-pyrazolo[4,3-b]pyridin-5-yl)-2,3-dihydro-1H-indene-1-carbonitrile To a solution of tert-butyl 5-(1-cyano-2,3-dihydro-1H-inden-4-yl)-3-(1-(cyanomethyl)-1H-pyrazol-4-yl)-6-methoxy-1H-pyrazolo[4,3-b]pyridine-1-carboxylate (36 mg, 0.073 mmol) in dichloromethane (50 μL) was added TFA (50 μL, 6.5 mmol) at room temperature. The reaction mixture was stirred for 30 min, then concentrated in vacuo. The residue was diluted with MeOH and purified by prep-LCMS (XBridge C18 column, eluting with a gradient of acetonitrile/water containing 0.1% TFA, at flow rate of 60 mL/min). The product was isolated as the TFA salt. LC-MS calculated for $C_{22}H_{18}N_7O$ (M+H)$^+$: m/z=396.2, found 396.2.

Example 186. 4-(6-Methoxy-3-(6-(4-methylpiperazin-1-yl)pyridin-3-yl)-1H-pyrazolo[4,3-b]pyridin-5-yl)-2,3-dihydro-1H-indene-1-carbonitrile

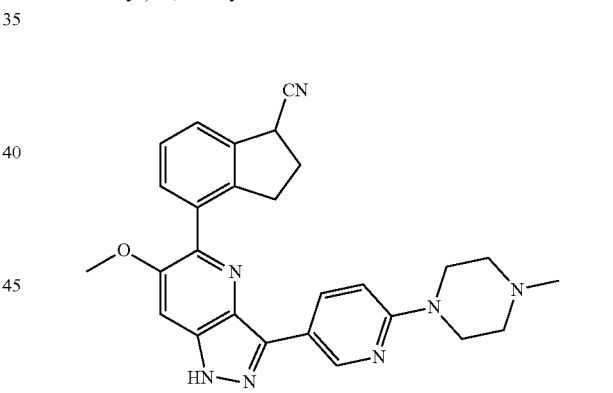

tert-Butyl 5-(1-cyano-2,3-dihydro-1H-inden-4-yl)-3-iodo-6-methoxy-1H-pyrazolo[4,3-b]pyridine-1-carboxylate (Peak 1, 50 mg, 0.097 mmol) (single enantiomer was obtained by chiral separation on chiral prep-HPLC Phenomenex Lux Sum Amylose-1, 21.2×250 mm, eluting with 15% EtOH in hexanes, at flow rate of 20 mL/min, $t_{R, peak\ 1}$=17.5 min, $t_{R, peak\ 2}$=23.3 min, 50 mg, 0.097 mmol), (6-(4-methylpiperazin-1-yl)pyridin-3-yl)boronic acid (25.1 mg, 0.116 mmol), Xphos-PdG2 (7.6 mg, 9.68 μmol), and NaHCO$_3$ (16 mg, 0.194 mmol) were placed in a vial and the vial was evacuated and backfilled with $N_2$ three times. After 1,4-dioxane (1 ml) and water (100 μl) were added, the reaction mixture was stirred at 70° C. for 1 h. Then the reaction was filtered, and the solvents were evaporated in vacuo. DCM (1 ml) and TFA (0.5 ml) were added and the reaction mixture was stirred at r.t. for 30 min. The mixture was then diluted with CH$_3$CN and water and purified with prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{28}N_7O$ (M+H)$^+$: m/z=466.2; found 466.2.

Example 187. 3-(3-(5-(5-(2,3-Dihydro-1H-inden-4-yl)-6-methoxy-1H-pyrazolo[4,3-b]pyridin-3-yl)pyridin-2-yl)azetidin-1-yl)propanenitrile

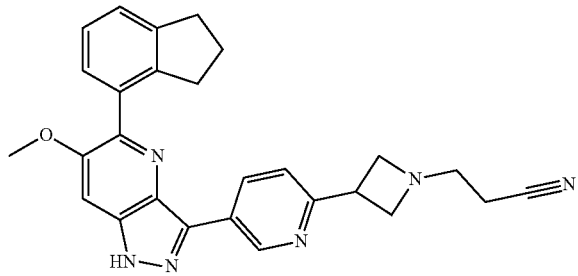 [SMILES: COc1cc2[nH]nc(-c3ccc(C4CN(CCC#N)C4)nc3)c2nc1-c1cccc2c1CCC2]

To a solution of 3-(6-(azetidin-3-yl)pyridin-3-yl)-5-(2,3-dihydro-1H-inden-4-yl)-6-methoxy-1-(4-methoxybenzyl)-1H-pyrazolo[4,3-b]pyridine (20 mg, 0.039 mmol, Example 172) in MeCN (1 mL) was added 3-bromopropanenitrile (15 mg, 0.12 mmol) and cesium carbonate (63 mg, 0.19 mmol). The reaction was heated at 50° C. for 2 hr. After this time, it was diluted with dichloromethane. The resultant solution was washed sequentially with water, sat. aq. NaCl solution, and dried over Na$_2$SO$_4$. The organic phases were filtered and concentrated to dryness. The residue was dissolved in dichloromethane (0.5 mL) and trifluoromethanesulfonic acid (0.1 mL). The reaction was stirred at r.t. After 30 min, the reaction mixture was quenched with 4N NaOH aq. solution and diluted with dichloromethane. The resultant mixture was washed sequentially with water, sat. aq. NaCl solution and dried over Na$_2$SO$_4$. The organic phases were filtered and concentrated to dryness. The residue was acidified with TFA and MeOH and was purified by prep-LCMS (XBridge C18 column, eluting with a gradient of acetonitrile/water containing 0.1% TFA, at flow rate of 60 mL/min). The product was isolated as the TFA salt. LC-MS calculated for $C_{27}H_{27}N_6O$ (M+H)$^+$: m/z=451.2; found 451.2.

Example 188. N-(3-(5-(5-(2,3-Dihydro-1H-inden-4-yl)-6-methoxy-1H-pyrazolo[4,3-b]pyridin-3-yl)pyridin-2-yl)cyclobutyl)-2-methoxy-N-methylacetamide

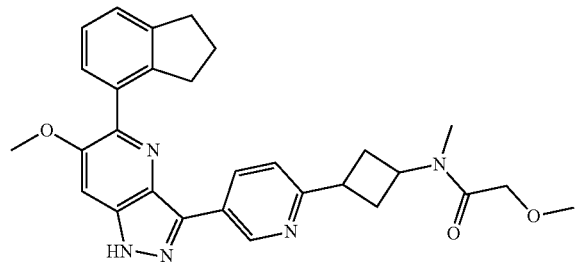

This compound was prepared according to the procedures described in Example 178, using 2-methoxyacetic acid instead of 2-hydroxyacetic acid as starting material. The product was isolated as the TFA salt. LCMS calculated for $C_{29}H_{32}N_5O_3$ (M+H)$^+$: m/z=498.2; Found: 498.2.

Example 189. N-(3-(5-(5-(2,3-Dihydro-1H-inden-4-yl)-6-methoxy-1H-pyrazolo[4,3-b]pyridin-3-yl)pyridin-2-yl)cyclobutyl)-3-hydroxy-N-methylpropanamide

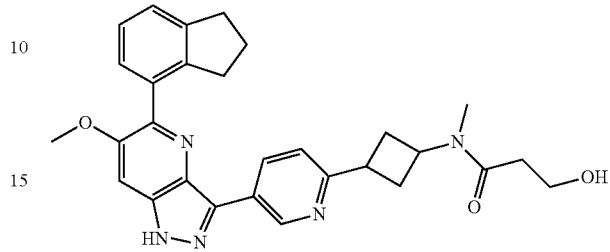

This compound was prepared according to the procedures described in Example 178, using 3-hydroxypropanoic acid instead of 2-hydroxyacetic acid as starting material. The product was isolated as the TFA salt. LCMS calculated for $C_{29}H_{32}N_5O_3$ (M+H)$^+$: m/z=498.2; Found: 498.2.

Example 190. (S)—N-(3-(5-(5-(2,3-Dihydro-1H-inden-4-yl)-6-methoxy-1H-pyrazolo[4,3-b]pyridin-3-yl)pyridin-2-yl)cyclobutyl)-2-hydroxy-N-methylpropanamide

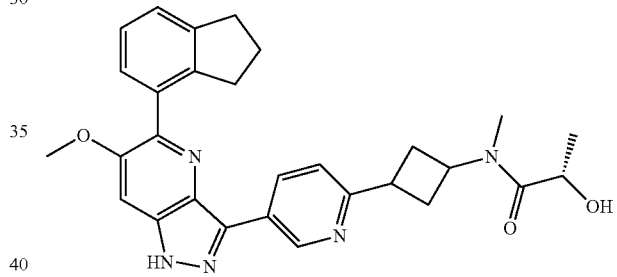

This compound was prepared according to the procedures described in Example 178, using (S)-2-hydroxypropanoic acid instead of 2-hydroxyacetic acid as starting material. The product was isolated as the TFA salt. LCMS calculated for $C_{29}H_{32}N_5O_3$ (M+H)$^+$: m/z=498.2; Found: 498.2.

Example 191A. 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one

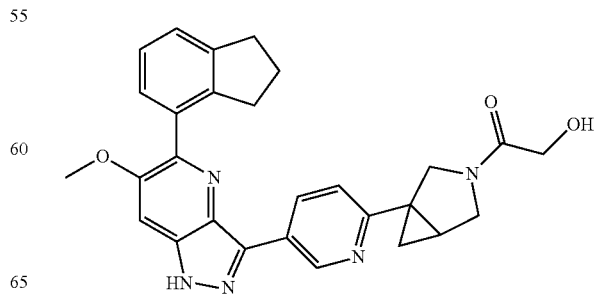

Step 1. tert-Butyl 5-(2,3-dihydro-1H-inden-4-yl)-3-iodo-6-methoxy-1H-pyrazolo[4,3-b]pyridine-1-carboxylate

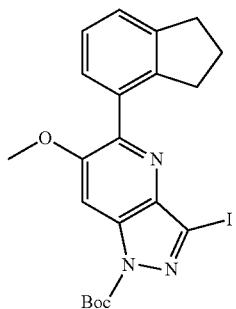 [SMILES: COc1cc2c(nc1-c1cccc3c1CCC3)c(I)nn2C(=O)OC(C)(C)C]

NIS (0.220 g, 0.978 mmol) was added to a solution of 5-(2,3-dihydro-1H-inden-4-yl)-6-methoxy-1H-pyrazolo[4,3-b]pyridine (0.20 g, 0.754 mmol) in DMF (10 ml). After stirring at 80° C. for 2 h, the reaction mixture was cooled to r.t., and triethylamine (0.3 ml, 2.2 mmol) and Boc-anhydride (0.411 g, 1.89 mmol) were added. After additional stirring at r.t. for 1 h, water was added and the precipitated product was collected by filtration and air dried. Crude material was purified by Biotage Isolera to give a white solid (0.29 g, 78%). LCMS calculated for $C_{21}H_{23}IN_3O_3$ $(M+H)^+$: m/z=492.1; found 492.1.

Step 2. tert-Butyl 1-(5-bromopyridin-2-yl)-3-azabicyclo[3.1.0]hexane-3-carboxylate

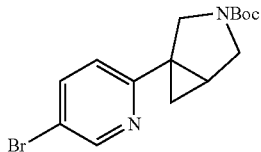 [SMILES: CC(C)(C)OC(=O)N1CC2CC2(c2ccc(Br)cn2)C1]

A mixture of 2,5-dibromopyridine (0.49 g, 2.075 mmol), tert-butyl 1-(trifluoro-14-boraneyl)-3-azabicyclo[3.1.0]hexane-3-carboxylate, potassium salt (0.30 g, 1.04 mmol), cesium carbonate (1.01 g, 3.11 mmol), and cataCXium® A Pd G3 (0.076 g, 0.104 mmol) in toluene (20 ml) and water (2 ml) was heated to 80° C. for 40 hrs. After this time, the solution was diluted with water and product was extracted with EtOAc. The combined organic layers were washed with sat. aq. NaCl and dried with $Na_2SO_4$, then filtered and concentrated to dryness. The residue was then purified by silica gel chromatography to afford the desired product. LCMS calculated for $C_{11}H_{12}BrN_2O_2$ $(M-C4H_7)^+$: m/z=283.0; Found: 283.1.

Step 3. tert-Butyl 1-(5-(4,4,5,5-tetramethyl-1,3,2-dioxaborolan-2-yl)pyridin-2-yl)-3-azabicyclo[3.1.0]hexane-3-carboxylate

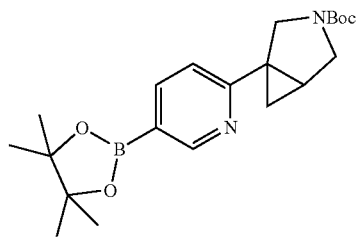 [SMILES: CC(C)(C)OC(=O)N1CC2CC2(c2ccc(B3OC(C)(C)C(C)(C)O3)cn2)C1]

A mixture of tert-butyl 1-(5-bromopyridin-2-yl)-3-azabicyclo[3.1.0]hexane-3-carboxylate (85 mg, 0.25 mmol), 4,4,4',4',5,5,5',5'-octamethyl-2,2'-bi(1,3,2-dioxaborolane) (89 mg, 0.35 mmol), PdCl$_2$dppf. DCM (31 mg, 0.038 mmol), and potassium acetate (74 mg, 0.75 mmol) in dioxane (2.5 ml) was heated at 85° C. for 20 hrs. The reaction mixture was then cooled to r.t. and filtered through celite, washed with EtOAc, and concentrated. The residue was then purified by silica gel chromatography to afford the desired product. LCMS calculated for $C_{15}H_{22}BN_2O_4$ $(M-C_6H_9)^+$: m/z=305.2; Found: 305.1.

Step 4. 3-(6-(3-Azabicyclo[3.1.0]hexan-1-yl)pyridin-3-yl)-5-(2,3-dihydro-1H-inden-4-yl)-6-methoxy-1H-pyrazolo[4,3-b]pyridine

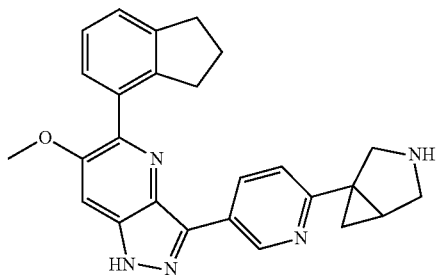 [SMILES: COc1cc2[nH]nc(-c3ccc(C45CNCC4C5)nc3)c2nc1-c1cccc2c1CCC2]

A mixture of tert-butyl 5-(2,3-dihydro-1H-inden-4-yl)-3-iodo-6-methoxy-1H-pyrazolo[4,3-b]pyridine-1-carboxylate (450 mg, 0.916 mmol), tert-butyl 1-(5-(4,4,5,5-tetramethyl-1,3,2-dioxaborolan-2-yl)pyridin-2-yl)-3-azabicyclo[3.1.0]hexane-3-carboxylate (531 mg, 1.374 mmol), SPhos Pd G3 (107 mg, 0.137 mmol), and cesium carbonate (895 mg, 2.75 mmol) in dioxane (5 ml) and water (0.5 ml) was heated to 80° C. for 20 hrs. After this time, the solution was cooled to r.t., diluted with water, and the product was extracted with EtOAc. The combined organic layers were washed with sat. aq. NaCl and dried over $Na_2SO_4$, then filtered and concentrated to dryness. The residue was then dissolved in DCM (3 mL), and TFA (2 mL) was added. The solution was stirred at r.t. for 1 h. The solvent was then removed in vacuo, and the residue was purified by silica gel chromatography to afford the desired product. LCMS calculated for $C_{26}H_{26}N_5O$ $(M+H)^+$: m/z=424.2; Found: 424.4.

Step 5. 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one A mixture of 3-(6-(3-azabicyclo[3.1.0]hexan-1-yl)pyridin-3-yl)-5-(2,3-dihydro-1H-inden-4-yl)-6-methoxy-1H-pyrazolo[4,3-b]pyridine (20 mg, 0.047 mmol), 2-hydroxyacetic acid (4 mg, 0.052 mmol), HATU (20 mg, 0.052 mmol), and N,N-diisopropylethylamine (25 µl, 0.142 mmol) in DMF (0.5 ml) was stirred at r.t. for 2 hrs. The mixture was then diluted with MeCN and purified by prep-LCMS (XBridge C18 column, eluting with a gradient of acetonitrile/water containing 0.1% TFA, at flow rate of 60 mL/min). LCMS calculated for $C_{28}H_{28}N_5O_3$ $(M+H)^+$: m/z=482.2; found 482.4.

Example 191B and Example 191C. 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one, two enantiomers Example 191B, peak 1

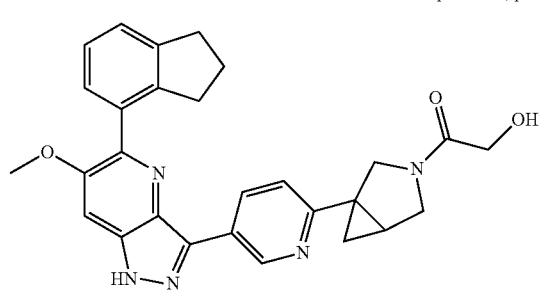

Example 191C, peak 2

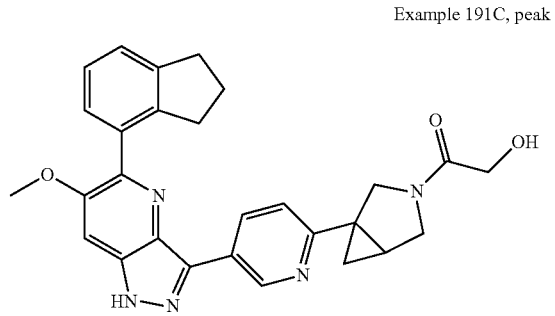

The two enantiomers of 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one were separated with chiral SFC (Phenomenex Cellulose-3, 2×250 mm, eluting with 40% MeOH in $CO_2$, at flow rate of 65 mL/min). Example 191B: peak 1, $t_R$=3.4 min. Example 191C: peak 2, $t_R$=4.1 min. LCMS calculated for $C_{28}H_{28}N_5O_3$ $(M+H)^+$: m/z=482.2; found 482.4.

Example 192. (1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)((R)-4-methylmorpholin-3-yl)methanone

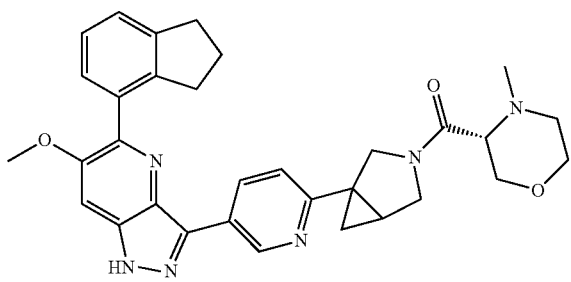 [SMILES: COc1cc2[nH]nc(-c3ccc(C45CC4CN(C(=O)[C@H]4COCCN4C)C5)nc3)c2nc1-c1cccc2c1CCC2]

This compound was prepared according to the procedure described in Example 191, using (R)-4-methylmorpholine-3-carboxylic acid hydrochloride instead of 2-hydroxyacetic acid. LC-MS calculated for $C_{32}H_{35}N_6O_3$ $(M+H)^+$: m/z=551.3; found 551.3.

Example 193. 5-(2,3-Dihydro-1H-inden-4-yl)-6-methoxy-3-(6-(3-(tetrahydro-2H-pyran-4-yl)-3-azabicyclo[3.1.0]hexan-1-yl)pyridin-3-yl)-1H-pyrazolo[4,3-b]pyridine

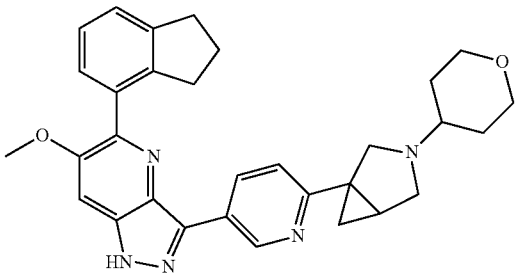 [SMILES: COc1cc2[nH]nc(-c3ccc(C45CC4CN(C4CCOCC4)C5)nc3)c2nc1-c1cccc2c1CCC2]

A mixture of 3-(6-(3-azabicyclo[3.1.0]hexan-1-yl)pyridin-3-yl)-5-(2,3-dihydro-1H-inden-4-yl)-6-methoxy-1H-pyrazolo[4,3-b]pyridine (20 mg, 0.047 mmol), tetrahydro-4H-pyran-4-one (14 mg, 0.142 mmol), and sodium triacetoxyhydroborate (20 mg, 0.094 mmol) in DCM (1 ml) was stirred at r.t. for 20 hrs. After this time, the solution was quenched with TFA (0.5 mL). The mixture was diluted with MeCN and purified by prep-LCMS (XBridge C18 column, eluting with a gradient of acetonitrile/water containing 0.1% TFA, at flow rate of 60 mL/min). LCMS calculated for $C_{31}H_{34}N_5O_2$ $(M+H)^+$: m/z=508.3; found 508.4.

Example 194A. 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol

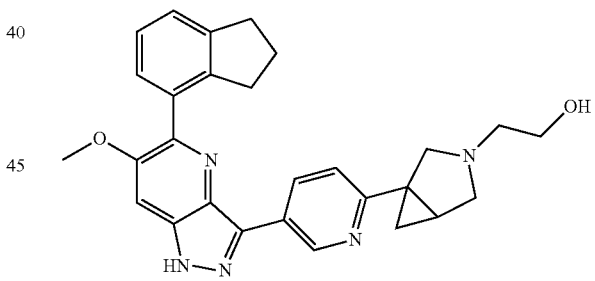

A mixture of 3-(6-(3-azabicyclo[3.1.0]hexan-1-yl)pyridin-3-yl)-5-(2,3-dihydro-1H-inden-4-yl)-6-methoxy-1H-pyrazolo[4,3-b]pyridine (30 mg, 0.071 mmol), 2-((tert-butyldimethylsilyl)oxy)acetaldehyde (37 mg, 0.213 mmol), and sodium triacetoxyhydroborate (30 mg, 0.142 mmol) in DCM (1 ml) was stirred at r.t. for 20 hrs. After this time, the solution was diluted with water, and the product was extracted with DCM. The combined organic layers were washed with sat. aq. NaCl and dried with $Na_2SO_4$, then filtered and concentrated to dryness. The residue was then dissolved in DCM (1 mL) and TFA (1 mL) was added. The mixture was stirred at r.t. for 1 h and purified by prep-LCMS (XBridge C18 column, eluting with a gradient of acetonitrile/water containing 0.1% TFA, at flow rate of 60 mL/min). LCMS calculated for $C_{28}H_{30}N_5O_2$ $(M+H)^+$: m/z=468.2; found 468.4.

Example 194B and Example 194C. 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol, two enantiomers Example 194B, peak 1

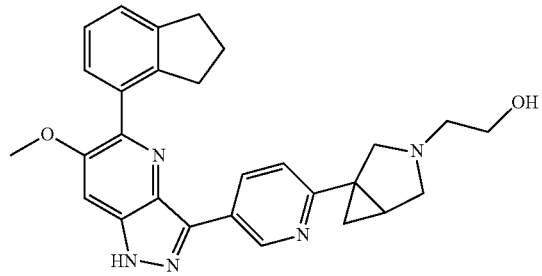 [SMILES: COc1cc2[nH]nc(-c3ccc(C45CC4CN(CCO)C5)nc3)c2nc1-c1cccc2c1CCC2]

Example 194C, peak 2

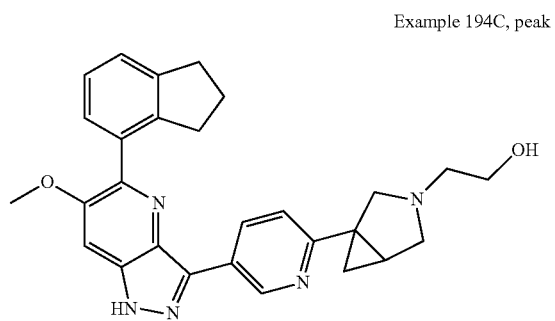

The two enantiomers of 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol were separated with chiral prep-HPLC (Phenomenex Lux Sum Cellulose-2, 21.2×250 mm, eluting with 30% EtOH in hexanes, at flow rate of 20 mL/min). Example 194B: peak 1, $t_R$=14.4 min. Example 194C: peak 2, $t_R$=16.1 min. LCMS calculated for $C_{28}H_{30}N_5O_2$ (M+H)$^+$: m/z=468.2; found 468.4.

Example 195. 3-(5-(5-(2,3-Dihydro-1H-inden-4-yl)-6-methoxy-1H-pyrazolo[4,3-b]pyridin-3-yl)pyridin-2-yl)-1-((R)-4-methylmorpholine-3-carbonyl)pyrrolidine-3-carbonitrile

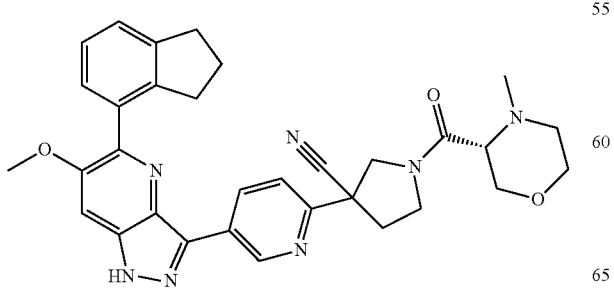

Step 1. tert-Butyl 3-(5-bromopyridin-2-yl)-3-cyano-pyrrolidine-1-carboxylate

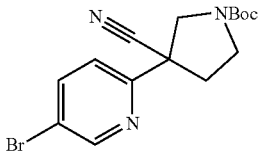 [SMILES: CC(C)(C)OC(=O)N1CCC(C#N)(c2ccc(Br)cn2)C1]

To a solution of tert-butyl 3-cyanopyrrolidine-1-carboxylate (1.18 g, 6.01 mmol) and 5-bromo-2-fluoropyridine (1.06 g, 6.01 mmol) in THF (30 ml) at 0° C. was added sodium bis(trimethylsilyl)amide (6.6 ml, 6.6 mmol) dropwise. The resulting solution was stirred at 0° C. for 1 hr, then warm to r.t. and stirred for additional 2 hrs. After this time, the solution was quenched with water, and the product was extracted with DCM. The combined organic layers were washed with sat. aq. NaCl and dried with $Na_2SO_4$, then filtered and concentrated to dryness. The residue was then purified by silica gel chromatography to afford the desired product. LCMS calculated for $C_{11}H_{11}BrN_3O_2$ (M-C4H7)$^+$: m/z=296.0; Found: 296.0.

Step 2. tert-Butyl 3-cyano-3-(5-(4,4,5,5-tetramethyl-1,3,2-dioxaborolan-2-yl)pyridin-2-yl)pyrrolidine-1-carboxylate

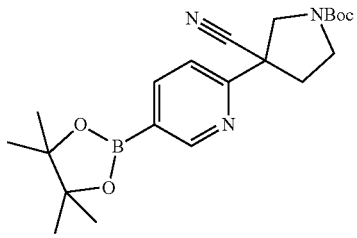 [SMILES: CC(C)(C)OC(=O)N1CCC(C#N)(c2ccc(B3OC(C)(C)C(C)(C)O3)cn2)C1]

A mixture of tert-butyl 3-(5-bromopyridin-2-yl)-3-cyano-pyrrolidine-1-carboxylate (1.72 g, 4.88 mmol), 4,4,4',4',5,5,5',5'-octamethyl-2,2'-bi(1,3,2-dioxaborolane) (1.74 g, 6.84 mmol), PdCl₂dppf. DCM (0.6 g, 0.732 mmol), and potassium acetate (1.44 g, 14.65 mmol) in dioxane (30 ml) was heated at 85° C. for 20 hrs. The reaction mixture was then filtered through celite, washed with EtOAc, and concentrated. The residue was then purified by silica gel chromatography to afford the desired product. LCMS calculated for $C_{17}H_{23}BN_3O_4$ (M-C4H7)$^+$: m/z=344.2; Found: 344.1.

Step 3. 3-(5-(5-(2,3-dihydro-1H-inden-4-yl)-6-methoxy-1H-pyrazolo[4,3-b]pyridin-3-yl)pyridin-2-yl)pyrrolidine-3-carbonitrile

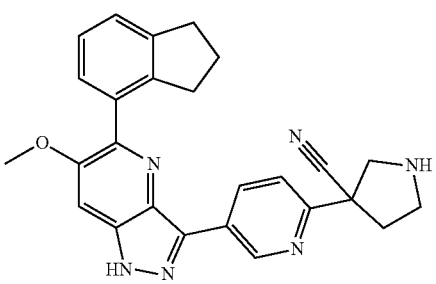 [SMILES: COc1cc2[nH]nc(-c3ccc(C4(C#N)CCNC4)nc3)c2nc1-c1cccc2c1CCC2]

A mixture of tert-butyl 5-(2,3-dihydro-1H-inden-4-yl)-3-iodo-6-methoxy-1H-pyrazolo[4,3-b]pyridine-1-carboxylate (500 mg, 1.02 mmol), tert-butyl 3-cyano-3-(5-(4,4,5,5-tetramethyl-1,3,2-dioxaborolan-2-yl)pyridin-2-yl)pyrrolidine-1-carboxylate (813 mg, 2.04 mmol), SPhos Pd G3 (159 mg, 0.204 mmol), and cesium carbonate (995 mg, 3.05 mmol) in dioxane (6 ml) and water (0.6 ml) was heated to 80° C. for 2 hrs. After this time, the solution was cooled to r.t., diluted with water, and the product was extracted with EtOAc. The combined organic layers were washed with sat. aq. NaCl and dried with $Na_2SO_4$, then filtered and concentrated to dryness. The residue was then dissolved in DCM (3 mL) and TFA (2 mL) was added. The solution was stirred at r.t. for 1 h. The solvent was then removed in vacuo, and the residue was purified by silica gel chromatography to afford the desired product. LCMS calculated for $C_{26}H_{25}N_6O$ $(M+H)^+$: m/z=437.2; Found: 437.4.

Step 4. 3-(5-(5-(2,3-Dihydro-1H-inden-4-yl)-6-methoxy-1H-pyrazolo[4,3-b]pyridin-3-yl)pyridin-2-yl)-1-((R)-4-methylmorpholine-3-carbonyl)pyrrolidine-3-carbonitrile A mixture of 3-(5-(5-(2,3-dihydro-1H-inden-4-yl)-6-methoxy-1H-pyrazolo[4,3-b]pyridin-3-yl)pyridin-2-yl)pyrrolidine-3-carbonitrile (20 mg, 0.046 mmol), (R)-4-methylmorpholine-3-carboxylic acid hydrochloride (9 mg, 0.050 mmol), HATU (19 mg, 0.050 mmol), and N,N-diisopropylethylamine (24 µl, 0.137 mmol) in DMF (0.5 ml) was stirred at r.t. for 20 hrs. The mixture was then diluted with MeCN and purified by prep-LCMS (XBridge C18 column, eluting with a gradient of acetonitrile/water containing 0.1% TFA, at flow rate of 60 mL/min). LCMS calculated for $C_{32}H_{34}N_7O_3$ $(M+H)^+$: m/z=564.3; found 564.3.

Example 196. (R)-4-(5-(5-(2,3-Dihydro-1H-inden-4-yl)-6-methoxy-1H-pyrazolo[4,3-b]pyridin-3-yl)pyridin-2-yl)-1-(4-methylmorpholine-3-carbonyl)piperidine-4-carbonitrile

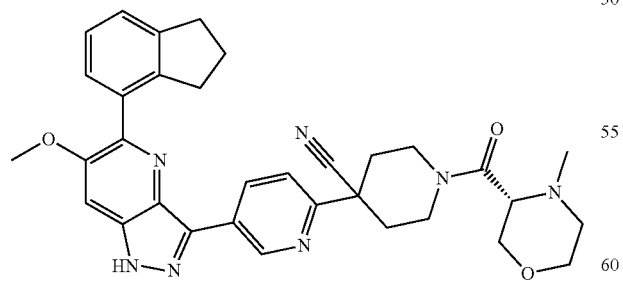

This compound was prepared according to the procedure described in Example 165, using (R)-4-methylmorpholine-3-carboxylic acid hydrochloride instead of 2-hydroxyacetic acid. LC-MS calculated for $C_{33}H_{36}N_7O_3$ $(M+H)^+$: m/z=578.3; found 578.3.

Example 197. 1-(1-(4-(5-(2,3-Dihydro-1H-inden-4-yl)-6-methoxy-1H-pyrazolo[4,3-b]pyridin-3-yl)-1H-pyrazol-1-yl)-3-azabicyclo[3.1.0]hexan-3-yl)-2-hydroxyethan-1-one

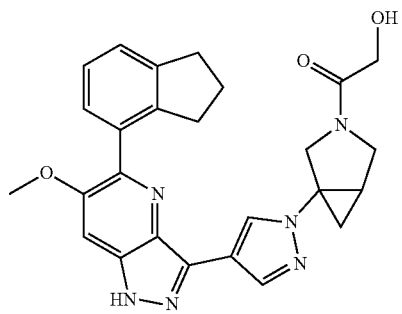 [SMILES: COc1cc2[nH]nc(-c3cnn(C45CC4CN(C(=O)CO)C5)c3)c2nc1-c1cccc2c1CCC2]

Step 1. tert-Butyl 1-(4-(4,4,5,5-tetramethyl-1,3,2-dioxaborolan-2-yl)-1H-pyrazol-1-yl)-3-azabicyclo[3.1.0]hexane-3-carboxylate

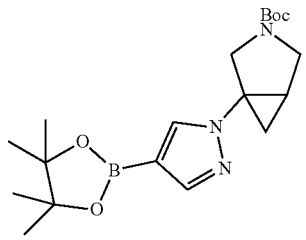 [SMILES: CC(C)(C)OC(=O)N1CC2CC2(n2cc(B3OC(C)(C)C(C)(C)O3)cn2)C1]

A mixture of tert-butyl 1-(4-chloro-1H-pyrazol-1-yl)-3-azabicyclo[3.1.0]hexane-3-carboxylate (150 mg, 0.529 mmol), 4,4,4',4',5,5,5',5'-octamethyl-2,2'-bi(1,3,2-dioxaborolane) (188 mg, 0.740 mmol), $Pd_2dba_3$ (48 mg, 0.053 mmol), XPhos (50 mg, 0.106 mmol), and potassium acetate (156 mg, 1.586 mmol) in dioxane (5.3 ml) was heated at 100° C. for 20 hrs.

The reaction mixture was then filtered through celite, washed with EtOAc, and concentrated. The residue was then purified by silica gel chromatography to afford the desired product. LCMS calculated for $C_{15}H_{23}BN_3O_4$ $(M-C_4H_7)^+$: m/z=320.2; Found: 320.1.

Step 2. 3-(1-(3-Azabicyclo[3.1.0]hexan-1-yl)-1H-pyrazol-4-yl)-5-(2,3-dihydro-1H-inden-4-yl)-6-methoxy-1H-pyrazolo[4,3-b]pyridine

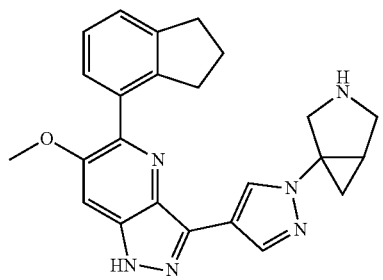 [SMILES: COc1cc2[nH]nc(-c3cnn(C45CNCC4C5)c3)c2nc1-c1cccc2c1CCC2]

A mixture of tert-butyl 5-(2,3-dihydro-1H-inden-4-yl)-3-iodo-6-methoxy-1H-pyrazolo[4,3-b]pyridine-1-carboxylate (150 mg, 0.305 mmol), tert-butyl 1-(4-(4,4,5,5-tetramethyl-1,3,2-dioxaborolan-2-yl)-1H-pyrazol-1-yl)-3-azabicyclo[3.1.0]hexane-3-carboxylate (172 mg, 0.458 mmol), SPhos Pd G3 (48 mg, 0.061 mmol), and cesium carbonate (298 mg, 0.916 mmol) in dioxane (2 ml) and water (0.200 ml) was heated at 80° C. for 2 hrs. After this time, the solution was cooled to r.t., diluted with water, and the product was extracted with EtOAc. The combined organic layers were washed with sat. aq. NaCl and dried with $Na_2SO_4$, then filtered and concentrated to dryness. The residue was then dissolved in DCM (3 mL) and TFA (2 mL) was added. The solution was stirred at r.t. for 1 h. The solvent was then removed and the residue was purified by silica gel chromatography to afford the desired product. LCMS calculated for $C_{24}H_{25}N_6O$ $(M+H)^+$: m/z=413.2; Found: 413.4.

Step 3. 1-(1-(4-(5-(2,3-Dihydro-1H-inden-4-yl)-6-methoxy-1H-pyrazolo[4,3-b]pyridin-3-yl)-1H-pyrazol-1-yl)-3-azabicyclo[3.1.0]hexan-3-yl)-2-hydroxyethan-1-one A mixture of 3-(1-(3-azabicyclo[3.1.0]hexan-1-yl)-1H-pyrazol-4-yl)-5-(2,3-dihydro-1H-inden-4-yl)-6-methoxy-1H-pyrazolo[4,3-b]pyridine (10 mg, 0.024 mmol), 2-hydroxyacetic acid (2 mg, 0.024 mmol), HATU (14 mg, 0.036 mmol), and N,N-diisopropylethylamine (9 µl, 0.048 mmol) in DMF (0.5 ml) was stirred at r.t. for 1 hr. The mixture was then diluted with MeCN and purified by prep-LCMS (XBridge C18 column, eluting with a gradient of acetonitrile/water containing 0.1% TFA, at flow rate of 60 mL/min). LCMS calculated for $C_{26}H_{27}N_6O_3$ $(M+H)^+$: m/z=471.2; found 471.2.

Example 198. 3-(5-(5-(2,3-Dihydro-1H-inden-4-yl)-6-methoxy-1H-pyrazolo[4,3-b]pyridin-3-yl)pyridin-2-yl)-1(2-hydroxyacetyl)pyrrolidine-3-carbonitrile

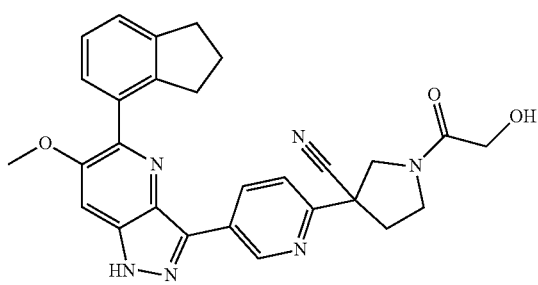 [SMILES: COc1cc2[nH]nc(-c3ccc(C4(C#N)CCN(C(=O)CO)C4)nc3)c2nc1-c1cccc2c1CCC2]

This compound was prepared according to the procedure described in Example 195, using 2-hydroxyacetic acid instead of (R)-4-methylmorpholine-3-carboxylic acid hydrochloride. LC-MS calculated for $C_{28}H_{27}N_6O_3$ $(M+H)^+$: m/z=495.2; found 495.1.

Example 199. (S)-4-((5-(5-(2,3-Dihydro-1H-inden-4-yl)-6-methoxy-1H-pyrazolo[4,3-b]pyridin-3-yl)pyridin-2-yl)methyl)-1,3-dimethylpiperazin-2-one

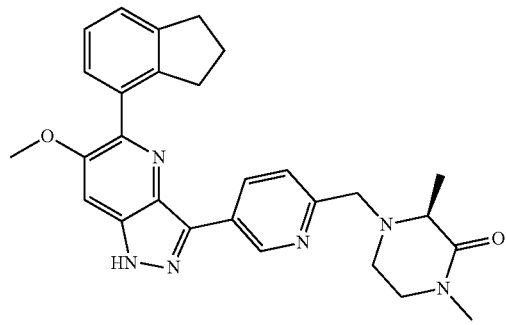 [SMILES: COc1cc2[nH]nc(-c3ccc(CN4CCN(C)C(=O)[C@@H]4C)nc3)c2nc1-c1cccc2c1CCC2]

This compound was prepared according to the procedure described in Example 160, using (S)-1,3-dimethylpiperazin-2-one instead of piperidin-4-ol. LC-MS calculated for $C_{28}H_{31}N_6O_2$ $(M+H)^+$: m/z=483.2; found 483.2.

Example 200. (1R,4R)-5-((5-(5-(2,3-Dihydro-1H-inden-4-yl)-6-methoxy-1H-pyrazolo[4,3-b]pyridin-3-yl)pyridin-2-yl)methyl)-2-oxa-5-azabicyclo[2.2.1]heptane

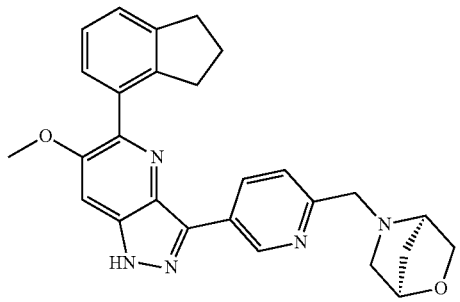 [SMILES: COc1cc2[nH]nc(-c3ccc(CN4C[C@H]5C[C@@H]4CO5)nc3)c2nc1-c1cccc2c1CCC2]

This compound was prepared according to the procedure described in Example 160, using (1R,4R)-2-oxa-5-azabicyclo[2.2.1]heptane instead of piperidin-4-ol. LC-MS calculated for $C_{27}H_{28}N_5O_2$ $(M+H)^+$: m/z=454.2; found 454.4.

Example a

FGFR Enzymatic Assay

The inhibitor potency of the exemplified compounds was determined in an enzyme discontinuous assay that measures peptide phosphorylation using FRET measurements to detect product formation. Inhibitors were serially diluted in DMSO and a volume of 0.2 µL was transferred to the wells of a 384-well plate. A 5 µL/well volume of enzyme isoforms of FGFR (-1, -2, -3 wild-type and mutant isoforms, -4) including phosphorylated and un-phosphorylated proteins diluted in assay buffer (50 mM HEPES, 10 mM $MgCl_2$, 1 mM EGTA, 0.01% Tween-20, 5 mM DTT, pH 7.5) was added to the plate and pre-incubated with inhibitor for 5 to 15 minutes at ambient temperature. Appropriate controls (enzyme blank and enzyme with no inhibitor) were included on the plate. The reaction was initiated by the addition of a 5 µL/well volume containing both biotinylated EQEDE- PEGDYFEWLE peptide substrate (SEQ ID NO. 1) and ATP in assay buffer. The 10 μL/well reaction concentration of the peptide substrate was 500 nM whereas the ATP concentration was maintained near or below the ATP Km. The ATP Km values were pre-determined in a separate series of experiments. The reaction plate was incubated at 25° C. for 1 hr and the reactions were ended with the addition of 5 μL/well of quench solution (50 mM Tris, 150 mM NaCl, 0.5 mg/mL BSA, pH 7.8; 45 mM EDTA, 600 nM staurosporin, with Perkin Elmer Lance Reagents at 3.75 nM Eu-antibody PY20 and 180 nM APC-Streptavidin). The plate was allowed to equilibrate for ~10 minutes at ambient temperature before scanning on a PheraStar plate reader (BMG Labtech) instrument.

Either GraphPad prism or XLfit was used to analyze the data. The $IC_{50}$ values were derived by fitting the data to a four parameter logistic equation producing a sigmoidal dose-response curve with a variable Hill coefficient. Prism equation: Y=Bottom+(Top−Bottom)/(1+10^((Log $IC_{50}$−X)*Hill slope)); XLfit equation: Y=(A+((B−A)/(1+((X/C)^D)))) where X is the logarithm of inhibitor concentration and Y is the response. Compounds having an $IC_{50}$ of 1 μM or less are considered active.

GraphPad prism3 was used to analyze the data. The $IC_{50}$ values were derived by fitting the data to the equation for a sigmoidal dose-response with a variable slope. Y=Bottom+(Top−Bottom)/(1+10^((Log $IC_{50}$−X)*HillSlope)) where X is the logarithm of concentration and Y is the response. Compounds having an $IC_{50}$ of 1 μM or less are considered active.

Table 1 provides $IC_{50}$ data for compounds of the invention assayed in the FGFR Enzymatic Assay after dilution in assay buffer, added to the plate and pre-incubated for 4 hours. The symbol: "+" indicates an $IC_{50}$ less than 6 nM; "++" indicates an $IC_{50}$ greater than or equal to 6 nM but less than 40 nM; "+++" indicates an $IC_{50}$ greater than or equal to 40 nM but less than 100 nM; and "++++" indicates an $IC_{50}$ greater than or equal to 100 nM.

The data in Table 1 was measured in wild-type unphosphorylated FGFR1, FGFR2, FGFR3, and FGFR4 proteins.

TABLE 1

| Example No. | FGFR3 | FGFR1 | FGFR4 | FGFR2 |
| --- | --- | --- | --- | --- |
| 1 | + | ++++ | ++++ | ++ |
| 2 | + | +++ | +++ | + |
| 3 | + | +++ | | + |
| 4 | + | ++++ | ++++ | ++ |
| 5 | + | ++++ | ++++ | ++ |
| 6 | + | ++++ | | + |
| 7 | + | +++ | | |
| 8 | + | ++++ | | |
| 9 | + | +++ | | |
| 10 | + | +++ | ++++ | ++ |
| 11 | + | +++ | | + |
| 12 | + | +++ | | + |
| 13 | + | ++++ | | |
| 14 | + | +++ | | |
| 15 | + | +++ | | |
| 16 | + | +++ | ++++ | + |
| 17 | + | +++ | ++++ | + |
| 18 | + | +++ | ++++ | + |
| 19 | + | +++ | ++++ | + |
| 20 | + | +++ | ++++ | + |
| 21 | + | +++ | +++ | + |
| 22 | + | +++ | +++ | + |
| 23 | + | ++++ | ++++ | + |
| 24 | + | ++ | ++ | + |
| 25 | + | ++ | +++ | + |
| 26 | + | ++++ | | |
| 27 | + | +++ | +++ | + |
| 28 | + | +++ | ++++ | + |
| 29 | + | +++ | +++ | + |
| 30 | + | ++++ | +++ | ++ |
| 31 | + | +++ | +++ | + |
| 32 | + | ++++ | | |
| 33 | + | +++ | ++++ | + |
| 34 | + | +++ | ++++ | + |
| 35 | + | +++ | | |
| 36 | + | +++ | ++++ | ++ |
| 37 | + | ++++ | | |
| 38 | + | ++++ | ++++ | ++ |
| 39 | + | +++ | | ++ |
| 40 | + | ++++ | ++++ | ++ |
| 41 | + | +++ | +++ | + |
| 42 | + | +++ | ++++ | + |
| 43 | + | ++++ | | + |
| 44 | + | ++++ | ++++ | ++ |
| 45 | + | ++++ | | + |
| 46 | + | ++++ | | + |
| 47 | + | +++ | | |
| 48 | + | +++ | | + |
| 49 | + | +++ | | |
| 50 | + | ++++ | | + |
| 51 | + | +++ | | + |
| 52 | + | ++++ | ++++ | ++ |
| 53 | + | +++ | | |
| 54 | + | +++ | | |
| 55 | + | ++++ | | |
| 56 | + | ++++ | ++++ | ++ |
| 57 | + | ++++ | ++++ | + |
| 58 | + | +++ | +++ | + |
| 59 | + | ++ | ++ | + |
| 60 | + | ++ | ++ | + |
| 61 | + | +++ | ++++ | + |
| 62 | + | ++ | ++++ | + |
| 63 | + | ++ | +++ | + |
| 64 | + | ++ | | |
| 65 | + | ++++ | | + |
| 66 | + | ++++ | ++++ | + |
| 67 | + | ++++ | | |
| 68 | + | +++ | | + |
| 69 | + | ++++ | | |
| 70 | + | ++++ | | |
| 71 | + | ++++ | | |
| 72 | + | +++ | +++ | + |
| 73 | + | +++ | | ++ |
| 74 | + | ++ | ++++ | + |
| 75 | + | ++ | | + |
| 76 | + | ++ | | + |
| 77 | + | ++++ | ++++ | + |
| 78 | + | ++++ | ++++ | + |
| 79 | + | +++ | | + |
| 80 | + | +++ | | + |
| 81 | + | ++ | | + |
| 82 | + | ++ | | + |
| 83 | + | ++ | | + |
| 84 | + | +++ | ++++ | + |
| 85 | + | +++ | +++ | + |
| 86 | + | ++++ | | + |
| 87 | + | +++ | +++ | + |
| 88 | + | +++ | | |
| 89 | + | ++++ | | + |
| 90 | + | ++++ | | ++ |
| 91 | + | ++++ | | ++ |
| 92 | + | ++++ | | ++ |
| 93 | + | ++++ | | ++ |
| 94 | + | ++++ | | ++ |
| 95 | + | +++ | ++++ | ++ |
| 96 | + | +++ | ++++ | ++ |
| 97 | + | +++ | ++++ | ++ |
| 98 | + | +++ | ++++ | + |
| 99 | + | ++ | ++ | + |
| 100 | + | ++ | ++ | + |
| 101 | + | ++ | ++ | + |
| 102 | + | ++ | ++ | + |
| 103 | + | ++ | ++ | + |
| 104 | + | ++ | ++ | + |
| 105 | + | ++ | ++ | + |

TABLE 1-continued

| Example No. | FGFR3 | FGFR1 | FGFR4 | FGFR2 |
|---|---|---|---|---|
| 106 | + | ++ | ++ | + |
| 107 | + | ++ | ++ | + |
| 108 | + | ++ | ++ | + |
| 109 | + | ++ | ++ | + |
| 110 | + | ++ | ++ | + |
| 111 | + | + | +++ | + |
| 112 | + | +++ | +++ | + |
| 113 | + | ++ | +++ | + |
| 114 | + | ++ | ++ | + |
| 115 | + | ++ | ++ | + |
| 116 | + | ++ | +++ | + |
| 117 | + | ++ | +++ | + |
| 118 | + | ++ | +++ | + |
| 119 | + | ++ | +++ | + |
| 120 | + | ++ | +++ | + |
| 121 | + | ++ | +++ | + |
| 122 | + | ++ | +++ | + |
| 123 | + | ++ | ++ | + |
| 124 | + | ++ | +++ | + |
| 125 | + | ++ | ++ | + |
| 126 | + | ++ | ++ | + |
| 127 | + | ++ | +++ | + |
| 128 | + | ++ | +++ | + |
| 129 | + | ++ | ++ | + |
| 130 | + | ++ | ++ | + |
| 131 | + | ++ | ++ | + |
| 132 | + | ++ | +++ | + |
| 133 | + | ++ | +++ | + |
| 134 | + | ++ | +++ | + |
| 135 | + | ++ | ++ | + |
| 136 | + | ++ | ++ | + |
| 137 | + | ++ | +++ | + |
| 138 | + | ++ | +++ | + |
| 139 | + | ++ | ++ | + |
| 140 | + | ++ | +++ | + |
| 141 | + | ++ | ++ | + |
| 142 | + | ++ | +++ | + |
| 143 | + | ++ | ++ | + |
| 144 | + | ++ | ++ | + |
| 145 | + | ++ | ++ | + |
| 146 | + | ++ | ++ | + |
| 147 | + | ++ | +++ | + |
| 148 | + | ++ | +++ | + |
| 149 | + | ++ | ++ | + |
| 150 | + | +++ | +++ | + |
| 151 | + | ++ | +++ | + |
| 152 | + | +++ | +++ | + |
| 153 | + | ++ | +++ | + |
| 154 | + | +++ | ++++ | + |
| 155 | + | ++ | ++ | + |
| 156 | + | ++ | ++ | + |
| 157 | + | +++ | +++ | + |
| 158 | + | ++ | +++ | + |
| 159 | + | ++ | ++ | + |
| 160 | + | +++ | +++ | + |
| 161 | + | +++ | +++ | + |
| 162 | + | +++ | ++++ | + |
| 163 | + | +++ | +++ | + |
| 164 | + | +++ | +++ | + |
| 165 | + | ++ | ++ | + |
| 166 | + | +++ | +++ | + |
| 167 | + | +++ | +++ | + |
| 168 | + | ++ | ++ | + |
| 169 | + | ++ | +++ | + |
| 170 | + | ++ | ++ | + |
| 171 | + | ++ | ++ | + |
| 172 | + | +++ | +++ | + |
| 173 | + | ++ | ++ | + |
| 174 | + | ++ | +++ | + |
| 175 | + | ++ | ++ | + |
| 176 | + | ++ | +++ | + |
| 177 | + | +++ | +++ | + |
| 178 | + | ++ | ++ | + |
| 179 | + | ++ | ++ | + |
| 180 | + | +++ | +++ | + |
| 181 | + | ++ | ++ | + |
| 182 | + | ++ | ++ | + |
| 183 | + | ++ | ++ | + |
| 184 | + | ++ | ++ | + |
| 185 | + | +++ | ++ | + |
| 186 | + | ++ | ++ | + |
| 187 | + | ++ | ++ | + |
| 188 | + | ++ | ++ | + |
| 189 | + | ++ | ++ | + |
| 190 | + | ++ | +++ | + |
| 191A | + | ++ | ++ | + |
| 191B | + | ++ |  | + |
| 191C | + | ++ |  | + |
| 192 | + | ++ |  | + |
| 193 | + | ++ | ++ | + |
| 194A | + | ++ | ++ | + |
| 194B | + | ++ |  | + |
| 194C | + | ++ |  | + |
| 195 | + | ++ |  | + |
| 196 | + | ++ |  | + |
| 197 | + | ++ |  | + |
| 198 | + | ++ | +++ | + |
| 199 | + | +++ | +++ | + |
| 200 | + | +++ | +++ | + |

* Blank entries were not tested.

Compounds disclosed in US 2018/0072718 were also evaluated for FGFR3 inhibitory activity according to the protocol described above. Accordingly, Table 2 provides $IC_{50}$ data for compounds of US 2018/0072718. The symbol: "+" indicates an $IC_{50}$ less than 6 nM; "++" indicates an $IC_{50}$ greater than or equal to 6 nM but less than 60 nM; "+++" indicates an $IC_{50}$ greater than or equal to 60 nM but less than 200 nM; and "++++" indicates an $IC_{50}$ greater than or equal to 200 nM.

TABLE 2

| Example No. from US2018/0072718 | Structure | Inhibition of FGFR3 |
|---|---|---|
| 2 | 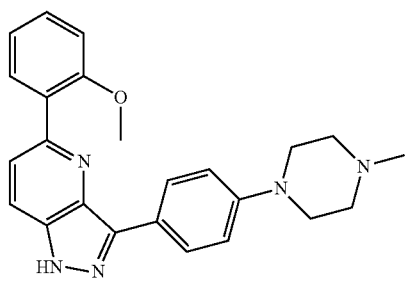 [SMILES: COc1ccccc1-c1ccc2[nH]nc(-c3ccc(N4CCN(C)CC4)cc3)c2n1] | +++ |

TABLE 2-continued

| Example No. from US2018/0072718 | Structure | Inhibition of FGFR3 |
|---|---|---|
| 3 | 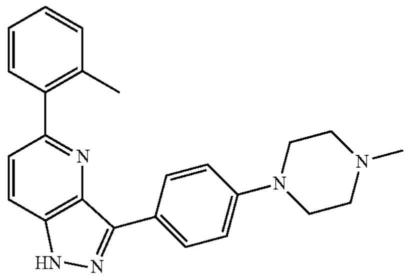 [SMILES: Cc1ccccc1-c1ccc2[nH]nc(-c3ccc(N4CCN(C)CC4)cc3)c2n1] | +++ |
| 4 | 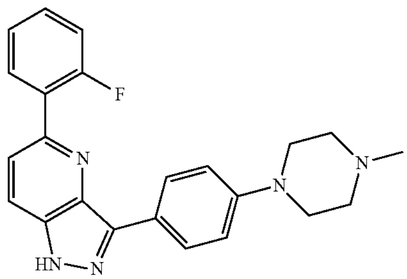 [SMILES: CN1CCN(c2ccc(-c3n[nH]c4ccc(-c5ccccc5F)nc34)cc2)CC1] | ++++ |
| 19 | 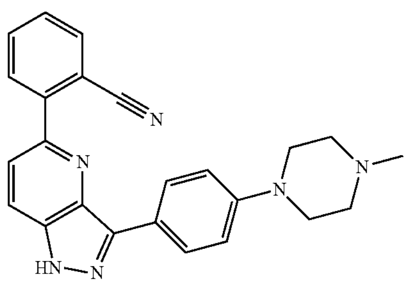 [SMILES: CN1CCN(c2ccc(-c3n[nH]c4ccc(-c5ccccc5C#N)nc34)cc2)CC1] | ++++ |
| 54 | 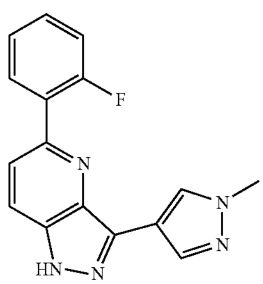 [SMILES: Cn1cc(-c2n[nH]c3ccc(-c4ccccc4F)nc23)cn1] | ++++ |
| 62 | 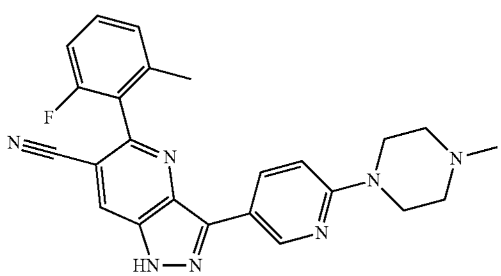 [SMILES: Cc1cccc(F)c1-c1nc2c(-c3ccc(N4CCN(C)CC4)nc3)n[nH]c2cc1C#N] | ++++ |

TABLE 2-continued

| Example No. from US2018/0072718 | Structure | Inhibition of FGFR3 |
|---|---|---|
| 64 | 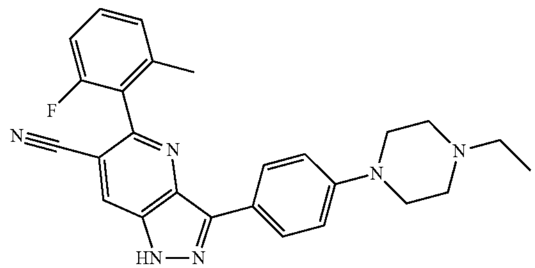 [SMILES: CCN1CCN(c2ccc(-c3n[nH]c4cc(C#N)c(-c5c(C)cccc5F)nc34)cc2)CC1] | ++++ |
| 74 | 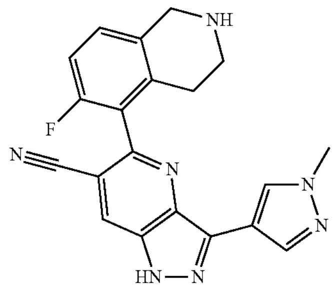 [SMILES: Cn1cc(-c2n[nH]c3cc(C#N)c(-c4c(F)ccc5c4CCNC5)nc23)cn1] | ++++ |
| 75 | 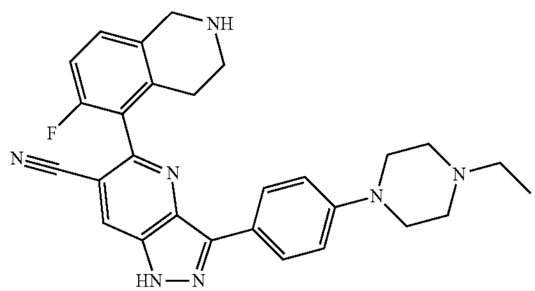 [SMILES: CCN1CCN(c2ccc(-c3n[nH]c4cc(C#N)c(-c5c(F)ccc6c5CCNC6)nc34)cc2)CC1] | ++++ |
| 76 | 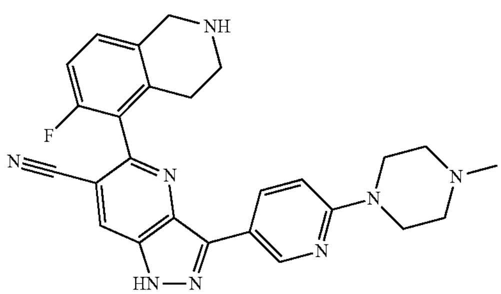 [SMILES: CN1CCN(c2ccc(-c3n[nH]c4cc(C#N)c(-c5c(F)ccc6c5CCNC6)nc34)cn2)CC1] | ++++ |
| 77 | 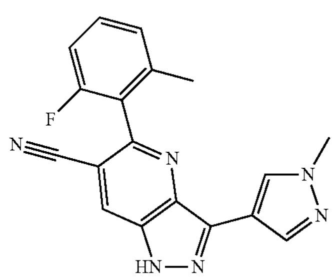 [SMILES: Cc1cccc(F)c1-c1nc2c(-c3cnn(C)c3)n[nH]c2cc1C#N] | ++++ |

Example B: Luminescent Viability Assay

RT112 cells (cell lines and genetic profiles further detailed in Table 3) are purchased from ATCC (Manassas, Va.) and maintained in RPMI, 10% FBS (Gibco/Life Technologies). To measure the effect of test compounds on the viability of cells, the cells are plated with RPMI 10% FBS (5×103 cells/well/in 50 µL) into black 96-well Greiner polystyrene in the presence or absence of 50 ul of a concentration range of test compounds. After 3 days, 100 ul of CellTiter-Glo Reagent (Promega) is added. Luminescence is read with a TopCount (PerkinElmer). $IC_{50}$ determination is performed by fitting the curve of percent inhibition versus the log of the inhibitor concentration using the GraphPad Prism 5.0 software.

TABLE 3

| Cell line | Histology | FGFR2/3 alteration |
|---|---|---|
| RT-112/84 | Bladder | FGFR3-TACC3 |
| RT112 | Bladder | FGFR3-TACC3 |
| RT-112 V555M* | Bladder | FGFR3-TACC3 V555M |
| UM-UC-14 | Bladder | FGFR3 S249C |
| RT-4 | Bladder | FGFR3-TACC3 |
| SW-780 | Bladder | FGFR3-BAIAP2L1 |
| KMS-11 | Multiple Myeloma | IgH-FGFR3 translocation + FGFR3 Y373C |
| OPM-2 | Multiple Myeloma | IgH-FGFR3 translocation + FGFR3 K650E |
| KATO-III | Stomach | FGFR2 amplification |
| SNU-16 | Stomach | FGFR2 amplification |
| AN3CA | Endometrial | FGFR2 N310R/N549K |
| Ba/F3-FGFR2-BICC1 | Engineered system | FGFR2-BICC1** |
| Ba/F3-TEL-FGFR3 | Engineered system | TEL-FGFR3 |
| Ba/F3-TEL-FGFR3 V555M | Engineered system | TEL-FGFR3 V555M |
| Ba/F3-TEL-FGFR3 V555L | Engineered system | TEL-FGFR3 V555L |

*RT112 V555M: V555M mutation was engineered using CRISPR-mediated genome editing.
**FGFR2-BICC1 fusion represents the most prevalent FGFR2 alteration in cholangiocarcinoma Example C: pFGFR2 and pFGFR1,3 Functional Cell HTRF Assay To measure phosphorylated Fibroblast Growth Factor Receptor 2 (FGFR2), KATOIII cells (Human Gastric Carcinoma) are purchased from ATCC and maintained in Iscoves with 20% FBS (Gibco/Life Technologies). For the pFGFR2 assay, KATOIII cells are plated overnight in 5% FBS and Iscove's medium at $5 \times 10^4$ cells/well into Corning 96-well flat-bottom tissue culture treated plates. The next morning, 50 µl of fresh media with 0.5% FBS is incubated in the presence or absence of a concentration range of test compounds also at 50 ul, for 1 hour at 37° C., 5% $CO_2$. Cell are washed with PBS, lysed with Cell Signaling Lysis Buffer with standard Protease inhibitors for 45 min at room temperature. 4 µl total of Cis Bio Anti Phospho-YAP d2 and Cis Bio Anti Phospho-YAP Cryptate together are added to the lysate and mixed well (following directions of the kit). 16 µl is then transferred to 384 well Greiner white plates and stored at 4° C. overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

To measure phosphorylated Fibroblast Growth Factor Receptor 3 (FGFR3), in house stable cell lines BAF3-TEL-FGFR1 or BAF3-TEL-FGFR3 are maintained in RPMI with 10% FBS and 1 ug/ml puromycin (Gibco/Life Technologies). For the assay, 12 nl of BAF3-TEL-FGFR1 or BAF3-TEL-FGFR3 cells in serum free and puromycin free RPMI media at $1 \times 10^6$ cell/ml are added to 384 Greiner white plate already containing 20 nl dots of compounds at a concentration range. The plates are gently shaken (100 rpm) for 2 minutes at room temperature to mix well and incubate for 2 hours in a single layer at 37° C., 5% $CO_2$. 4 µl/well of ⅕ dilution of lysis buffer #3 (Cis Bio) is added with standard Protease inhibitors and shaken at 200 rpm at room temperature for 20 minutes. 4 µl total of the Cis Bio Tb-pFGFR Ab (10 ng) and d2-FGFR3 (1 ng) together are added to the lysate and mixed well. The plates are sealed and incubated at room temperature overnight in the dark. The plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example D: pFGFR3 Functional Whole Blood HTRF Assay

To measure phosphorylated Fibroblast Growth Factor Receptor 3 (FGFR3) in a whole blood assay, in house stable cell lines BAF3-TEL-FGFR3 are maintained in RPMI with 10% FBS and 1 pg/ml puromycin (Gibco/Life Technologies). For the assay, 100 ul BAF3-TEL-FGFR3 cells in 10% FBS and puromycin free RPMI media at $5 \times 10^4$ cell/well are added to fibronectin coated 96 well tissue culture plate (5 ug/ml) overnight at 37° C., 5% $CO_2$. The next day, serum is separated from the top of the blood by a low speed spin, 1200, RPM, and heat inactivated by incubating at 56° C. for 15 minutes. 30 µl of the cooled serum is added to a 96 well plate pre dotted with 70 nM dots of compounds at a concentration range. Cell plates are washed gently with media, all the blood/compound mixture is added to the plates, and the plates are incubated for 2 hours at 37° C., 5% $CO_2$. Blood from the plate is gently washed twice by adding media to the side of the wells and then dumping media from the plate, and allowing the plate to briefly sit on a paper towel to drain. 70 µl/well of 1× of lysis buffer #1 (Cis Bio) are added with standard Protease inhibitors, and are shaken at 400 rpm at room temperature for 30 minutes. Following lysis, the plate is spun down for 5 minutes and 16 uL of lysate is transferred into a 384-well small volume plate. 4 µl total of the Cis Bio Tb-pFGFR Ab (10 ng) and d2-FGFR3 (1 ng) together are added to the lysate and mixed well. The plates are sealed and incubated at room temperature overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example E: KATOIII Whole Blood pFGFR2α ELISA Assay

To measure tyrosine-phosphorylated Fibroblast Growth Factor Receptor 2 alpha (FGFR2a) in KATO III spiked whole blood assay, KATO III cells are purchased from ATCC and maintained in Iscove's medium with 20% FBS (Gibco/Life Technologies). To measure the inhibition of FGFR2a activity of test compounds, the cells are resuspended with Iscove's, 0.2% FBS at $5 \times 10^6$ cells/ml. 50 µL of the cells are then spiked into a 96-deep well 2 ml polypropylene assay block (Costar) in the presence or absence of a concentration range of test compounds and 300 ul human heparinized whole blood (Biological Specialty Corp, Colmar Pa.). After 4 hours incubation in 37° C., the red cells are lysed using Qiagen EL buffer and the cell lysates are resuspended in lysis buffer (Cell Signaling) containing standard protease inhibitor cocktail (Calbiochem/EMD) and PMSF (Sigma) for 30 minutes on ice. The lysates are transferred to a standard V bottom propylene tissue culture plate and frozen overnight at −80° C. Samples are tested an in an R & D Systems DuoSet IC Human Phospho-FGF R2α

ELISA and the plate is measured using a SpectraMax M5 microplate set to 450 nm with a wavelength correction of 540. $IC_{50}$ determination is performed by fitting the curve of inhibitor percent inhibition versus the log of the inhibitor concentration using the GraphPad Prism 5.0 software.

Example F: Inhibition of FGFR Pathway

The cellular potency of compounds was determined by measuring phosphorylation of FGFR or FGFR downstream effectors Fibroblast growth factor receptor substrate 2 (FRS2) and extracellular-signal-regulated kinase (ERK) in cell lines with FGFR2/3 alterations.

To measure phosphorylated Fibroblast growth factor receptor, Fibroblast growth factor receptor substrate 2 (FRS2) and extracellular-signal-regulated kinase (ERK), cells (details regarding the cell lines and types of data produced are further detailed in Table 4) were seeded in 6 well plates overnight in 10% FBS and RPMI medium at $5\text{-}7.5 \times 10^5$ cells/well into Corning 6-well tissue culture treated plates. The next morning, 2 ml of fresh media with 10% FBS is incubated in the presence or absence of a concentration range of test compounds for 4 hours at 37° C., 5% $CO_2$. Cells were washed with PBS and lysed with Cell Signaling Lysis Buffer with standard Protease inhibitors. 20-40 µg of total protein lysates were applied to western blot analysis using antibodies: phosphor-FRS2 Tyr436 (AF5126) from R&D Systems (Minneapolis, Minn.)), phosphor-FGFR-Tyr653/654 (#2476S), phospho-ERK1/2-Thr202/Tyr204 (#9101L) and total-ERK1/2 (#9102L) from Cell Signaling Technologies (Danvers, Mass.)).

TABLE 4

| Cell line | Histology | FGFR2/3 alteration | Readout |
| --- | --- | --- | --- |
| RT-112/84 | Bladder | FGFR3-TACC3 | pFRS2, pERK |
| RT112 V555M | Bladder | FGFR3-TACC3 V555M | pFRS2, pERK |
| UM-UC-14 | Bladder | FGFR3 S249C | pFRS2, pERK |
| KMS-11 | Multiple Myeloma | IgH-FGFR3 translocation + FGFR3 Y373C | pFRS2, pERK |
| KATO-III | Stomach | FGFR2 amplification | pFGFR, pERK |
| SNU-16 | Stomach | FGFR2 amplification | pFGFR, pERK |

Example G: Activity on In Vivo Tumor Models Harboring FGFR2/3 Alteration

In vivo activity of compounds was determined by measuring tumor growth when treated with various doses of compounds in FGFR2/3 altered models.

RT112/84 tumor cells (85061106, ECACC, UK) were maintained as recommended by the source (tumor models are further detailed in Table 5). On Day 0 of the experiments, $2.0 \times 10^6$ RT112/84 cells were inoculated with a 1:1 PBS to Matrigel (354263, Corning) subcutaneously into the right hind flank of female NSG mice (Jackson). Treatment with compounds at 0 (Vehicle), 100 mg/kg, 30 mg/kg or 10 mg/kg PO QD was initiated on Day 7 after tumor inoculation, when tumors averaged approximately 200 mm$^3$, and continued until the end of study. Mice were monitored for tumor growth and overt tolerability over the course of the experiment. Tumor volume was calculated using the formula $(L \times W^2)/2$, where L and W refer to the length and width dimensions, respectively. Tumor growth inhibition (TGI) was calculated using the formula $(1-(V_T/V_C))*100$ where $V_T$ is the tumor volume of the treatment group on the last day of treatment, and $V_C$ is the tumor volume of the control group on the last day of treatment. One-way ANOVA was used to determine statistical differences between treatment groups at the end of the study.

TABLE 5

| Tumor model | Histology | FGFR2/3 alteration |
| --- | --- | --- |
| RT-112/84 | Bladder | FGFR3-TACC3 |
| RT112 V555M | Bladder | FGFR3-TACC3 V555M |
| UM-UC-14 | Bladder | FGFR3 S249C |
| KMS-11 | Multiple Myeloma | IgH-FGFR3 translocation + FGFR3 Y373C |
| KATO-III | Stomach | FGFR2 amplification |
| SNU-16 | Stomach | FGFR2 amplification |
| Ba/F3-TEL-FGFR3 V555M | Engineered system | TEL-FGFR3 V555M |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound having Formula (I):

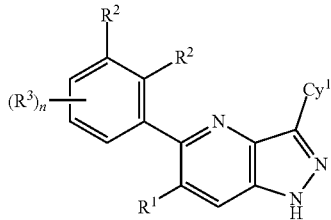

or a pharmaceutically acceptable salt thereof, wherein:

$Cy^1$ is selected from phenyl and 5-6 membered heteroaryl; wherein each 5-6 membered heteroaryl has at least one ring-forming carbon atom and 1, 2, or 3 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1, 2, 3 or 4 substituents independently selected from $R^{10}$;

$R^1$ is selected from halo, $C_{1-6}$ alkyl, $C_{2-6}$ alkenyl, $C_{2-6}$ alkynyl, $C_{1-6}$ haloalkyl, $C_{3-6}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, $C_{1-6}$ alkylamino, di($C_{1-6}$ alkyl)amino, $C_{1-6}$ alkylthio, $C_{1-6}$ alkylsulfonyl, $C_{1-6}$ alkylcarbonyl, and $C_{1-6}$ alkoxycarbonyl; wherein optionally one or more H atoms of the $C_{1-6}$ alkyl, $C_{2-6}$ alkenyl, $C_{2-6}$ alkynyl, $C_{1-6}$ haloalkyl, $C_{3-6}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, $C_{1-6}$ alkylamino, di($C_{1-6}$ alkyl)amino, $C_{1-6}$ alkylthio, $C_{1-6}$ alkylsulfonyl, $C_{1-6}$ alkylcarbonyl, and $C_{1-6}$ alkoxycarbonyl are replaced by one or more D atoms;

each $R^2$ and $R^3$ are independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$ $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

or two adjacent $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming heteroatoms independently selected from N, O, and S; wherein a ring-forming carbon atom of each fused 5- or 6-membered heterocycloalkyl ring is optionally substituted by oxo to form a carbonyl group; and wherein the fused 5- or 6-membered cycloalkyl ring, and the fused 5- or 6-membered heterocycloalkyl ring are each optionally substituted with 1, 2, 3 or 4 substituents independently selected from $R^{21}$;

n is selected from 0, 1, 2, and 3;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$ $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl, are each optionally substituted with 1, 2, 3, or 4 substituents independently selected from $R^g$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a6}$, $SR^{a6}$, $C(O)R^{b6}$, $C(O)NR^{c6}R^{d6}$, $C(O)OR^{a6}$ $NR^{c6}R^{d6}$ $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{36}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein Cy1 is selected from phenyl, pyridinyl and pyrazolyl; wherein the phenyl, pyridinyl, and pyrazolyl are each optionally substituted with 1, 2, 3 or 4 substituents independently selected from R10.

3. The compound of claim 1, or a pharmaceutically acceptable salt thereof, wherein Cy1 is selected from phenyl, pyridin-3-yl and pyrazol-4-yl; wherein the phenyl, pyridin-3-yl, and pyrazol-4-yl are each optionally substituted with 1 substituent selected from R10.

4. The compound of claim 1, or a pharmaceutically acceptable salt thereof, wherein $Cy^1$ is 5-6 membered heteroaryl optionally substituted with 1 or 2 substituents selected from $R^{10}$.

5. The compound of claim 1, or a pharmaceutically acceptable salt thereof, wherein $Cy^1$ is selected from pyrazol-4-yl and pyridin-3-yl; wherein the pyrazol-4-yl and pyridin-3-yl are each optionally substituted with 1 or 2 substituents selected from $R^{10}$.

6. The compound of claim 1, or a pharmaceutically acceptable salt thereof, wherein $R^1$ is selected from halo, $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$ alkyl)amino; wherein optionally one or more H atoms of the $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$ alkyl)amino are replaced by one or more D atoms.

7. The compound of claim 1, or a pharmaceutically acceptable salt thereof, wherein $R^1$ is selected from Cl, $C_{1-2}$ alkyl, $C_{1-2}$ haloalkyl, hydroxymethyl, $C_{1-2}$ alkoxy, $C_{1-2}$ haloalkoxy and $C_{1-2}$ alkylamino; wherein optionally one or more H atoms of the $C_{1-2}$ alkyl, $C_{1-2}$ haloalkyl, hydroxymethyl, $C_{1-2}$ alkoxy, $C_{1-2}$ haloalkoxy and $C_{1-2}$ alkylamino are replaced by one or more D atoms.

8. The compound of claim 1, or a pharmaceutically acceptable salt thereof, wherein $R^1$ is selected from Cl, $CH_3$, $OCH_3$, $OCD_3$, $OCH_2CH_3$, $OCHF_2$, $NHCH_3$, $CHF_2$, and $CH_2OH$.

9. The compound of claim 1, or a pharmaceutically acceptable salt thereof, wherein $R^1$ is $OCH_3$.

10. The compound of claim 1, or a pharmaceutically acceptable salt thereof, wherein each $R^2$ is independently selected from $C_{1-6}$ alkyl, $C_{3-6}$ cycloalkyl, halo, and $OR^{a2}$; wherein said $C_{1-6}$ alkyl and $C_{3-6}$ cycloalkyl are each optionally substituted with 1, 2, 3, or 4 substituents independently selected from $R^{21}$.

11. The compound of claim 1, or a pharmaceutically acceptable salt thereof, wherein two adjacent $R^2$ substituents on the phenyl ring, taken together with the atoms to which they are attached, form a fused 5-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5-membered cycloalkyl ring, and the fused 5- or 6-membered heterocycloalkyl ring are each optionally substituted with 1 or 2 substituents independently selected from $R^{21}$.

12. The compound of claim 1, or a pharmaceutically acceptable salt thereof, wherein each $R^2$ is independently selected from $C_{1-3}$ alkyl, $C_{1-3}$ haloalkyl, $C_{3-6}$ cycloalkyl, F, Cl, CN, and $OR^{a2}$; wherein said $C_{1-3}$ alkyl, and $C_{3-6}$ cycloalkyl, are each optionally substituted with 1, 2 or 3 substituents independently selected from $R^{21}$.

13. The compound of claim 1, or a pharmaceutically acceptable salt thereof, wherein each $R^2$ is independently selected from F, methyl, $CH_2CN$, $CD_3$, OH, $OCH_3$, and cyclopropyl.

14. The compound of claim 1, or a pharmaceutically acceptable salt thereof, wherein the $R^2$ substituents, taken together with the atoms to which they are attached, form a fused cyclopentyl group, a fused tetrahydrofuranyl group, a fused 1,4-dioxanyl group, or a fused tetrahydropyranyl group, each of which is optionally substituted with 1 or 2 substituents selected from $R^{21}$.

15. The compound of claim 1, or a pharmaceutically acceptable salt thereof, wherein the $R^2$ substituents, taken together with the atoms to which they are attached, form a fused cyclopentyl group optionally substituted with 1 or 2 substituents independently selected from D, OH, CN, $CH_2OH$, and F.

16. The compound of claim 1, or a pharmaceutically acceptable salt thereof, wherein the $R^2$ substituents, taken together with the atoms to which they are attached, form a fused cyclopentyl group or a fused cyclohexyl group; wherein the fused cyclopentyl group and the fused cyclohexyl group have at least one ring-forming carbon atom and each optionally have 1 or 2 ring-forming O atoms; and wherein the fused cyclopentyl group and the fused cyclohexyl group are each optionally substituted with 1 or 2 substituents independently selected from D, OH, CN, $CH_2OH$, and F.

17. The compound of claim 1, or a pharmaceutically acceptable salt thereof, wherein the $R^2$ substituents, taken together with the atoms to which they are attached, form a fused cyclopentyl group.

18. The compound of claim 1, or a pharmaceutically acceptable salt thereof, wherein n is selected from 0 and 1.

19. The compound of claim 1, or a pharmaceutically acceptable salt thereof, wherein n is 0.

20. The compound of claim 1, or a pharmaceutically acceptable salt thereof, wherein each $R^{10}$ is independently selected from $C_{1-6}$ alkyl, $C_{1-6}$ haloalkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $S(O)_2R^{b1}$; wherein said $C_{1-6}$ alkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$.

21. The compound of claim 1, or a pharmaceutically acceptable salt thereof, wherein each $R^{10}$ is independently selected from $C_{1-3}$ alkyl, $C_{1-3}$ haloalkyl, $C_{3-6}$ cycloalkyl, 4-6 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, $C(O)NR^{c1}R^{d1}$, and $NR^{c1}R^{d1}$; wherein the $C_{1-3}$ alkyl, $C_{3-6}$ cycloalkyl, 4-6 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from $R^{11}$.

22. The compound of claim 1, or a pharmaceutically acceptable salt thereof, wherein each $R^{10}$ is independently selected from $C_{1-3}$ alkyl, $C_{1-3}$ haloalkyl, $C_{3-6}$ cycloalkyl, 4-10 membered heterocycloalkyl, 5-6 membered heteroaryl, 4-6 membered heterocycloalkyl-$C_{1-2}$ alkylene, 5-6 membered heteroaryl-$C_{1-2}$ alkylene, halo, D, CN, $OR^{a1}$, $C(O)NR^{c1}R^{d1}$, and $NR^{c1}R^{d1}$; wherein the $C_{1-3}$ alkyl, $C_{3-6}$ cycloalkyl, 4-10 membered heterocycloalkyl, 5-6 membered heteroaryl, 4-6 membered heterocycloalkyl-$C_{1-2}$ alkylene, and 5-6 membered heteroaryl-$C_{1-2}$ alkylene are each optionally substituted with 1 or 2 substituents independently selected from $R^{11}$.

23. The compound of claim 1, or a pharmaceutically acceptable salt thereof, wherein each $R^{10}$ is independently selected from $C_{1-2}$ alkyl, $C_{1-2}$ haloalkyl, F, Cl, D, CN, $OR^{a1}$ and $NR^{c1}R^{d1}$; wherein the $C_{1-2}$ alkyl is optionally substituted with 1 or 2 substituents independently selected from $R^{11}$.

24. The compound of claim 1, or a pharmaceutically acceptable salt thereof, wherein each $R^{10}$ is independently selected from methyl, (1-methyl-1H-1,2,4-triazol-5-yl)methyl, pyrrolidin-3-yl, pyrrolidin-1-yl, 1-ethylpyrrolidin-3-yl, 1-methylazetidin-3-yl, 1-ethylazetidin-3-yl, 4-acetylpiperazin-1-yl, 3-cyanocyclobutyl, 1-(dimethylcarbamoyl)piperidin-4-yl, 1-(methoxycarbonyl)piperidin-4-yl, 1-(methoxycarbonyl)azetidin-3-yl, 1-acetylazetidin-3-yl, 1-(methylsulfonyl)azetidin-3-yl, 1-(dimethylcarbamoyl)azetidin-3-yl, 1-(cyclopropanecarbonyl)azetidin-3-yl, pyridin-4-ylmethyl, 2-morpholinoethyl, cyclopropyl, 2-cyanoethyl, 2-hydroxyethyl, pyridin-4-yl, 4-hydroxycyclohexyl, 4-methylpiperazin-1-yl, 4-ethylpiperazin-1-yl, morpholino, 4-methyl-3-oxopiperazin-1-yl, 4-hydroxypiperidin-1-yl, (R)-3,4-dimethylpiperazin-1-yl, (1S,4S)-5-methyl-2,5-diazabicyclo[2.2.1]heptan-2-yl, 4-(dimethylcarbamoyl)piperidin-1-yl, 4-carboxy-4-methylpiperidin-1-yl, (1S,4S)-4-acetamidocyclohexyl, 2,4-dimethylpiperazin-1-yl, 4-(ethylcarbamoyl)piperazin-1-yl, 4-carbamoylpiperazin-1-yl, 4-isopropylpiperazin-1-yl, 4-ethylpiperazin-1-yl, 2-oxo-1-oxa-3,8-diazaspiro[4.5]decan-8-yl, pyridin-2-ylmethyl, 1-acetylpiperidin-4-yl), 1-(methoxycarbonyl)piperidin-4-yl, (tetrahydrofuran-3-yl)oxy, 1-methyl-5-oxopyrrolidin-3-yl, 1-(2-hydroxypropanoyl)piperidin-4-yl, 1-(2-hydroxyacetyl)piperidin-4-yl, 4-carboxycyclohexyl, 3-amino-4-fluoropyrrolidin-1-yl, (7R,8aS)-7-hydroxyhexahydropyrrolo[1,2-a]pyrazin-2(1H)-yl, (7R,8aS)-7-hydroxyhexahydropyrrolo[1,2-a]pyrazin-2(1H)-yl, 4-imino-4-oxo-4$\lambda^6$-piperazin-1-yl, (2-hydroxy-N-methylacetamido)pyrrolidin-1-yl, 4-(2-hydroxyethyl)piperazin-1-yl, 2-methoxyethoxy, (tetrahydro-2H-pyran-4-yl)oxy, cyclopropyl, and 3-(2-hydroxy-N-methylacetamido)azetidin-1-yl, 1-(2-hydroxyacetyl)pyrrolidin-3-yl, 1-acetylpiperidin-3-yl, 1-(3'-pyrrolidin-2'-one)pyrrolidin-3-yl, 1-(1'-methyl-(3'-pyrrolidin-2'-one)) pyrrolidin-3-yl, 1-(2-propanamide)pyrrolidin-3-yl, 1-(methyl-L-prolyl)piperidin-4-yl, 1-(4-methylmorpholin-3-yl)pyrrolidin-3-yl, 3-cyanocyclobut-1-yl, 1-(hydroxymethylcarbonyl)azetidin-3-yl, 1-(2-(dimethylamino)ethanecarbonyl)azetidin-3-yl, 1-(dimethylamino-methyl-acetyl)azetidin-3-yl, 1-((1-methylazetidin-2-yl)carbonyl)azetidin-3-yl, 1-(2-(4-methylpiperazin-1-yl)ethan-1-one)azetidin-3-yl, 1-(2-(4-hydroxypiperazin-1-yl)ethan-1-one)azetidin-3-yl, 1-((1-methylazetidin-2-yl)carbonyl)azetidin-3-yl, 1-(hydroxy-methyl-acetyl)azetidin-3-yl, 1-((trans)-3-hydroxycyclobutylcarbonyl)azetidin-3-yl, 1-((cis)-3-hydroxycyclobutylcarbonyl)azetidin-3-yl, 1-((4-methylmorpholin-3-yl)carbonyl)azetidin-3-yl, 1-(hydroxyl-acetyl)pyrrolidin-3-yl, 1-((tetrahydrofuran-2-yl)carbonyl)azetidin-3-yl, 1-((tetrahydrofuran-3-yl)carbonyl)azetidin-3-yl, 1-(hydroxy-methyl-acetyl)pyrrolidin-3-yl, 1-(3-hydroxybutanoyl)azetidin-3-yl, 1-((-3-hydroxy-3-methylcyclobutyl)carbonyl)azetidin-3-yl, 1-(4-methylmorpholin-3-yl)carbonyl)pyrrolidin-3-yl, 1-((hydroxymethyl)cyclobutylcarbonyl)azetidin-3-yl, 1-((1-ethylazetidin-2-yl)carbonyl)azetidin-3-yl, 1-((1-(2-fluoroethyl)azetidin-2-yl)carbonyl)azetidin-3-yl, 1-((1-isopropylazetidin-2-yl)carbonyl)azetidin-3-yl, 1-((1-(2-fluoroethyl)azetidin-2-yl)carbonyl)pyrrolidin-3-yl, 1-((trans)-3-hydroxycyclobutylcarbonyl)pyrrolidin-3-yl, 1-((cis)-3-hydroxycyclobutylcarbonyl)pyrrolidin-3-yl, 1-((3-hydroxy-3-methylcyclobutyl)carbonyl)pyrrolidin-3-yl, 1-(2-methoxyethan-1-one)azetidin-3-yl, 1-(2-(dimethylamino)-2-methylpropan-1-one)azetidin-3-yl, 1-((cyclopropane-1-carbonitrile)carbonyl)azetidin-3-yl, 1-((ethan-1-ol)sulfonyl)azetidin-3-yl, 1-((N,N-dimethylethan-1-amine)sulfonyl)azetidin-3-yl, 1-((2-methoxyethyl)carboxylate)azetidin-3-yl, 1-((3-methoxycyclobutyl)carbonyl)azetidin-3-yl, 3-(2-hydroxy-N-methylacetamide)cyclopentyl, 3-(2-hydroxypropanamid)cyclopentyl, 3-(2-hydroxyacetamide)cyclopentyl, 3-(2-hydroxyethyl)-3-azabicyclo[3.1.0]hexan-1-yl, (4-hydroxypiperidin-1-yl)methyl, (2-oxa-5-azabicyclo[2.2.1]heptan-5-yl)methyl, 1-(morpholin-4-yl)ethyl, (5,6,7,8-tetrahydro-[1,2,4]triazolo[1,5-a]pyrazine-7-yl)methyl, 1-(2-hydroxyethyl)piperidin-4-yl-4-carbonitrile, 1-(2-hydroxyacetyl)piperidin-4-yl-4-carbonitrile, 2-methoxyethylpiperazin-1-yl, 1-(tetrahydro-2H-pyran-4-carbonyl)piperidin-4-yl-4-d, 1-(2-methoxyacetyl)pyrrolidin-3-yl, 1-(tetrahydrofuran-2-carbonyl)pyrrolidin-3-yl, 3-(2-hydroxy-N-methylacetamide)azetidin-1-yl, 1-((tetrahydrofuran-2-yl)carbonyl)azetidin-3-yl, 1-((1-methylpiperidin-2-yl)carbonyl)azetidin-3-yl, 1-(2-(dimethylamino)ethan-1-one)azetidin-3-yl, 1-(3-hydroxypropan-1-one)azetidin-3-yl, 1-(2-hydroxyethan-1-one)azetidin-3-yl, 1-(2-hydroxypropan-1-one)azetidin-3-yl, 1-(2-hydroxy-N-methylacetamide)cyclobut-3-yl, 1-(2-hydroxyethan-1-one)-3-d-azetidin-3-yl, 1-carboxylatepiperidin-4-yl, 1-(morpholine-4-carbonyl)piperidin-4-yl, 1-acetylpyrrolidin-3-yl, 1-(morpholine-4-carbonyl)pyrrolidin-3-yl, cyanomethyl, 1-propanenitrile-azetidin-3-yl, 1-(2-methoxy-N-methylacetamide)cyclobut-3-yl, 1-(3-hydroxy-N-methylpropanamide)cyclobut-3-yl, 1-(2-hydroxy-N-methylpropanamide)cyclobut-3-yl, 1-(2-hydroxyethan-1-one)azabicyclo[3.1.0]hexan-3-yl, 1-((4-methylmorpholin-3-yl)carbonyl)azabicyclo[3.1.0]hexan-3-yl, 1-(tetrahydro-2H-pyran-4-yl)azabicyclo[3.1.0]hexan-3-yl, 1-(ethan-1-ol)azabicyclo[3.1.0]hexan-3-yl, 1-(4-methylmorpholine-3-carbonyl)-3-carbonitrile-pyrrolidin-3- yl, 1-(4-methylmorpholine-3-carbonyl)-4-carbonitrile-piperdin-4-yl, 1-(2-hydroxyacetyl)-3-carbonitrile-pyrrolidin-3-yl, (1,3-dimethylpiperazin-4-yl-2-one)methyl, and (2-oxa-5-azabicyclo[2.2.1]heptan-5-yl)methyl.

25. The compound of claim 1, or a pharmaceutically acceptable salt thereof, wherein each $R^{11}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $NR^{c3}S(O)_2NR^{c3}R^{d3}$ $S(O)_2R^{b3}$, and $S(O)_2NR^{c3}R^{d3}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{12}$.

26. The compound of claim 1, or a pharmaceutically acceptable salt thereof, wherein each $R^{11}$ is independently selected from $C_{1-3}$ alkyl, $C_{1-3}$ haloalkyl, $C_{3-4}$ cycloalkyl, 5-6 membered heteroaryl, 4-6 membered heterocycloalkyl, halo, D, CN, $OR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $S(O)_2R^{b3}$; and $NR^{c3}S(O)_2R^{b3}$, wherein said $C_{1-3}$ alkyl, $C_{3-4}$ cycloalkyl, 5-6 membered heteroaryl, and 4-6 membered heterocycloalkyl are each optionally substituted with 1 substituent selected from $R^{12}$.

27. The compound of claim 1, or a pharmaceutically acceptable salt thereof, wherein each $R^{11}$ is independently selected from halo, $C_{1-2}$ alkyl, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $S(O)_2R^{b3}$, 1-methyl-pyrrolidin-3-yl-2-one, pyrrolidin-3-yl-2-one, 2-propanamide, $NR^{c3}S(O)_2R^{b3}$, D, and tetrahydropyran-4-yl, wherein said $C_{1-2}$ alkyl is optionally substituted with $OR^{a5}$.

28. The compound of claim 1, or a pharmaceutically acceptable salt thereof, wherein each $R^{11}$ is independently selected from $C_{1-3}$ alkyl, 4-10 membered heterocycloalkyl, F, D, CN, $OR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$ $NR^{c3}S(O)_2R^{b3}$, and $S(O)_2R^{b3}$; wherein said $C_{1-3}$ alkyl, and 4-10 membered heterocycloalkyl, are each optionally substituted with 1 or 2 substituents independently selected from $R^{12}$.

29. The compound of claim 1, or a pharmaceutically acceptable salt thereof, wherein each $R^{11}$ is independently selected from D, methyl, ethyl, isopropyl, CN, OH, oxo, (1-methyl-1H-1,2,4-triazol-5-yl)methyl, $CH_2CH_2OH$, $C(O)CH_3$, $C(O)N(CH_3)_2$, $C(O)NH_2$, $C(O)NHCH_2CH_3$, $C(O)CH_2CH_2N(CH_3)_2$, $C(O)CH(CH_3)N(CH_3)_2$, $C(O)OCH_3$, $C(O)CH_2OH$, $CH(CH_3)C(O)NH_2$, $C(O)OH$, $NHC(O)CH_3$, $S(O)_2CH_3$, cyclopropanecarbonyl, pyridin-4-yl, pyridin-2-yl, morpholino, 2-hydroxypropanoyl, 2-hydroxyacetyl, 2-hydroxyethyl, F, $NH_2$, $N(CH_3)C(O)CH_2OH$, 3'-pyrrolidin-2'-one, methyl-3'-pyrrolidin-2'-one, 1-methyl-prolyl, (4-methylmorpholin-3-yl)methyl-1-one, (1-methylazetidin-2-yl)methyl-1-one, 2-(4-methylpiperazin-1-yl)ethyl-1-one, 2-(4-hydroxypiperidin-1-yl)ethyl-1-one, 2-hydroxypropyl-1-one, (trans)-3-hydroxycyclobutyl)methyl-1-one, (cis)-3-hydroxycyclobutyl)methyl-1-one, (4-methylmorpholin-3-yl)methyl-1-one, (tetrahydrofuran-2-yl)methyl-1-one, 2-hydroxypropyl-1-one, 3-hydroxybutyl-1-one, 3-hydroxy-3-methylcyclobutyl)methyl-1-one, (hydroxymethyl)cyclobutyl)methyl-one, (1-ethylazetidin-2-yl)methyl-1-one, (2-fluoroethyl)azetidin-2-yl)methyl-1-one, (1-isopropylazetidin-2-yl)methyl-1-one, 2-methoxyethyl-1-one, 2-(dimethylamino)-2-methylpropyl-1-one, (cyclopropane-1-carbonitrile)methyl-1-one, $S(O)_2CH_2CH_2OH$, $S(O)_2CH_2CH_2N(CH_3)_2$, 2-methoxyethyl-N-carboxyl, N-methylmethanesulfonamido, 2-hydroxy-N-methylacetamido, 2-hydroxypropanamido, tetrahydro-2H-pyran-4-methyl-1-one, 2-methoxyacetyl, 2-hydroxy-N-methylacetamido, tetrahydrofuran-2-methyl-1-one, (1-methylpiperidin-2-yl)methyl-1-one, 2-(dimethylamino)ethyl-1-one, 3-hydroxypropyl-1-one, methoxymethyl-carboxyl, morpholine-4-carbonyl, propylnitrile, 2-methoxy-N-methylacetamido, 3-hydroxy-N-methylpropanamido, 2-hydroxy-N-methylpropanamido, tetrahydro-2H-pyran-4-yl, and 1,3-dimethylpiperazinyl-2-one.

30. The compound of claim 1, or a pharmaceutically acceptable salt thereof, wherein each $R^{b3}$ is independently selected from $C_{1-3}$ alkyl, $C_{1-3}$ haloalkyl, $C_{3-6}$ cycloalkyl, and 4-6 membered heterocycloalkyl; wherein said $C_{1-3}$ alkyl $C_{3-6}$ cycloalkyl, and 4-6 membered heterocycloalkyl, are each optionally substituted with 1 or 2 substituents independently selected from $R^{12}$.

31. The compound of claim 1, or a pharmaceutically acceptable salt thereof, wherein any $R^{c3}$ and $R^{d3}$ attached to the same N atom, together with the N atom to which they are attached, form a 4-, 5- or 6-membered heterocycloalkyl group optionally substituted with 1 or 2 substituents independently selected from $R^{12}$.

32. The compound of claim 1, or a pharmaceutically acceptable salt thereof, wherein each $R^{12}$ is independently selected from $C_{1-6}$ alkyl, $C_{1-6}$ haloalkyl, $C_{3-6}$ cycloalkyl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$, $S(O)_2R^{b5}$, and $S(O)_2NR^{c5}R^{d5}$; wherein said $C_{1-6}$ alkyl, $C_{3-6}$ cycloalkyl, and 4-7 membered heterocycloalkyl, are each optionally substituted with 1, 2, 3, or 4 substituents independently selected from $R^9$.

33. The compound of claim 1, or a pharmaceutically acceptable salt thereof, wherein each $R^{12}$ is independently selected from $C_{1-3}$ alkyl, $C_{1-3}$ haloalkyl, $C_{3-6}$ cycloalkyl, 4-7 membered heterocycloalkyl, F, Cl, D, CN, $OR^{a5}$, $C(O)R^{b5}$, $C(O)NR^{c5}R^{d5}$, and $NR^{c5}R^{d5}$; wherein said $C_{1-3}$ alkyl, $C_{3-6}$ cycloalkyl, and 4-7 membered heterocycloalkyl, are each optionally substituted with 1 substituent independently selected from $R^9$.

34. The compound of claim 1, or a pharmaceutically acceptable salt thereof, wherein each $R^{21}$ is independently selected from $C_{1-6}$ alkyl, $C_{1-6}$ haloalkyl, halo, D, CN, $OR^{a4}$, $C(O)R^{b4}$, $C(O)NR^{c4}R^{d4}$, $C(O)OR^{a4}$, $NR^{c4}R^{d4}$ and $S(O)_2R^{b4}$; wherein said $C_{1-6}$ alkyl is optionally substituted with 1, 2, or 3 substituents independently selected from $R^{22}$.

35. The compound of claim 1, or a pharmaceutically acceptable salt thereof, wherein each $R^{21}$ is independently selected from $C_{1-3}$ alkyl, halo, D, CN, and $OR^{a4}$; wherein said $C_{1-3}$ alkyl, is optionally substituted with 1 or 2 substituents independently selected from $R^{22}$.

36. The compound of claim 1, or a pharmaceutically acceptable salt thereof, wherein each $R^{21}$ is independently selected from $C_{1-3}$ alkyl, F, Cl, D, CN, and $OR^{a4}$; wherein said $C_{1-3}$ alkyl, is optionally substituted with 1 or 2 substituents independently selected from $R^{22}$.

37. The compound of claim 1, or a pharmaceutically acceptable salt thereof, wherein each $R^{22}$ is independently selected from halo, D, CN, and $OR^{a6}$.

38. The compound of claim 1, or a pharmaceutically acceptable salt thereof, wherein each $R^{22}$ is independently selected from F, Cl, D, CN, and $OR^{a6}$.

39. The compound of claim 1, or a pharmaceutically acceptable salt thereof, wherein $R^{22}$ is $OR^{a6}$.

40. The compound of claim 1, or a pharmaceutically acceptable salt thereof, wherein each $R^9$ is independently selected from OH, CN, F, Cl, $C_{1-3}$ alkyl, and $C_{1-3}$ haloalkyl.

41. The compound of claim 1, or a pharmaceutically acceptable salt thereof, having Formula IIb:

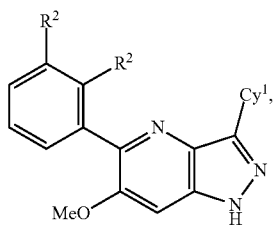

IIb or a pharmaceutically acceptable salt thereof.

42. The compound of claim 1, or a pharmaceutically acceptable salt thereof, having Formula IIIa:

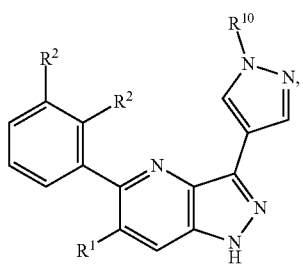

IIIa or a pharmaceutically acceptable salt thereof.

43. The compound of claim 1, or a pharmaceutically acceptable salt thereof, having Formula IIIb:

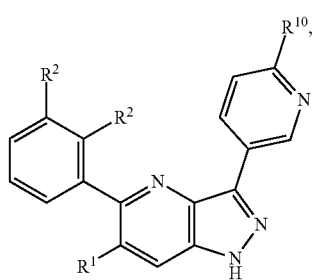

IIIb or a pharmaceutically acceptable salt thereof.

44. The compound of claim 1, or a pharmaceutically acceptable salt thereof, having Formula IIIc:

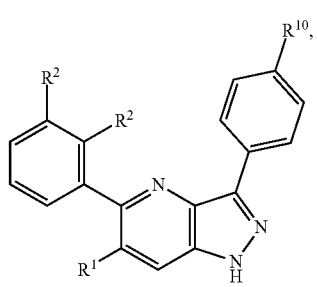

IIIc or a pharmaceutically acceptable salt thereof.

45. The compound of claim 1, or a pharmaceutically acceptable salt thereof, having Formula IVa:

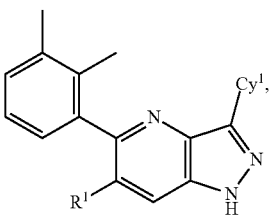

IVa or a pharmaceutically acceptable salt thereof.

46. The compound of claim 1, or a pharmaceutically acceptable salt thereof, having Formula Va:

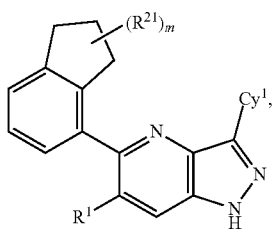

Va or a pharmaceutically acceptable salt thereof, wherein m is 0, 1, or 2.

47. The compound of claim 1, or a pharmaceutically acceptable salt thereof,
wherein:
  $Cy^1$ is selected from phenyl, pyridinyl and pyrazolyl; wherein the phenyl pyridinyl and pyrazolyl are each optionally substituted with 1, 2, 3 or 4 substituents independently selected from $R^{10}$;
  $R^1$ is selected from halo, $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$ alkyl)amino; wherein any of the H atoms of the $C_{1-6}$ alkyl, $C_{1-6}$ haloalkyl, $C_{3-5}$ cycloalkyl, 4-5 membered heterocycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, $C_{1-6}$ alkylamino, and di($C_{1-6}$ alkyl)amino can be replaced by D atoms;
  each $R^2$ and $R^3$ are independently selected from $C_{1-6}$ alkyl, $C_{2-6}$ alkenyl, $C_{1-6}$ haloalkyl, $C_{3-6}$ cycloalkyl, 4-6 membered heterocycloalkyl, halo, CN, $OR^{a2}$, $C(O)R^{b2}$, $C(O)NR^{c2}R^{d2}$, $C(O)OR^{a2}$, $NR^{c2}R^{d2}$, and $S(O)_2R^{b2}$; wherein said $C_{1-6}$ alkyl, $C_{2-6}$ alkenyl, $C_{3-6}$ cycloalkyl, and 4-6 membered heterocycloalkyl are each optionally substituted with 1, 2, 3, or 4 substituents independently selected from $R^{21}$;
  or two adjacent $R^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming heteroatoms independently selected from O and N; wherein a ring-forming carbon atom of each fused 5- or 6-membered heterocycloalkyl ring is optionally substituted by oxo to form a carbonyl group; and wherein the fused 5- or 6-membered cycloalkyl ring, and the fused 5- or 6-membered heterocycloalkyl ring are each optionally substituted with 1, 2, 3 or 4 substituents independently selected from $R^{21}$;

n is selected from 0 and 1;

each $R^{10}$ is independently selected from $C_{1-6}$ alkyl, $C_{1-6}$ haloalkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $S(O)_2R^{b1}$; wherein said $C_{1-6}$ alkyl, $C_{3-10}$ cycloalkyl, 4-12 membered heterocycloalkyl, $C_{6-10}$ aryl, 5-10 membered heteroaryl, $C_{3-10}$ cycloalkyl-$C_{1-3}$ alkylene, 4-12 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$ $NR^{c3}C(O)OR^{a3}$, $NR^{c3}S(O)_2R^{b3}$, $NR^{c3}S(O)_2NR^{c3}R^{d3}$ $S(O)_2R^{b3}$, and $S(O)_2NR^{c3}R^{d3}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{12}$;

each $R^{12}$ is independently selected from $C_{1-6}$ alkyl, $C_{1-6}$ haloalkyl, $C_{3-6}$ cycloalkyl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$, $S(O)_2R^{b5}$, and $S(O)_2NR^{c5}R^{d5}$; wherein said $C_{1-6}$ alkyl, $C_{3-6}$ cycloalkyl, and 4-7 membered heterocycloalkyl, are each optionally substituted with 1, 2, 3, or 4 substituents independently selected from $R^g$;

each $R^{21}$ is independently selected from $C_{1-6}$ alkyl, $C_{1-6}$ haloalkyl, halo, D, CN, $OR^{a4}$, $C(O)R^{b4}$, $C(O)NR^{c4}R^{d4}$, $C(O)OR^{a4}$, $NR^{c4}R^{d4}$ and $S(O)_2R^{b4}$; wherein said $C_{1-6}$ alkyl, is optionally substituted with 1, 2, or 3 substituents independently selected from $R^{22}$;

each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1 or 2 substituents independently selected from $R^g$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{b1}$ is independently selected from $C_{1-6}$ alkyl, $C_{1-6}$ haloalkyl, $C_{3-10}$ cycloalkyl, and 4-10 membered heterocycloalkyl, wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{a2}$, $R^{c2}$ and $R^{d2}$, is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, or 6-membered heterocycloalkyl group optionally substituted with 1, 2 or 3 substituents independently selected from $R^{21}$;

each $R^{b2}$ is independently selected from $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{21}$;

each $R^{a3}$, $R^{c3}$ and $R^{d3}$, is independently selected from H, $C_{1-6}$ alkyl, $C_{1-6}$ haloalkyl, $C_{3-6}$ cycloalkyl, and 4-7 membered heterocycloalkyl; wherein said $C_{1-6}$ alkyl $C_{3-6}$ cycloalkyl, and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{1-6}$ haloalkyl, $C_{3-6}$ cycloalkyl, and 4-7 membered heterocycloalkyl; wherein said $C_{1-6}$ alkyl $C_{3-6}$ cycloalkyl, and 4-7 membered heterocycloalkyl, are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, and $C_{1-6}$ haloalkyl;

wherein said $C_{1-6}$ alkyl is optionally substituted with 1, 2, 3, or 4 substituents independently selected from $R^{22}$;

each $R^{b4}$ is independently selected from $C_{1-6}$ alkyl, and $C_{1-6}$ haloalkyl; wherein said $C_{1-6}$ alkyl is optionally substituted with 1, 2, 3, or 4 substituents independently selected from $R^{22}$;

each $R^{a5}$, $R^{c5}$ and $R^{d5}$, is independently selected from H, $C_{1-6}$ alkyl, and $C_{1-6}$ haloalkyl;

wherein said $C_{1-6}$ alkyl, is optionally substituted with 1, 2, 3, or 4 substituents independently selected from $R^g$;

each $R^b5$ is independently selected from $C_{1-6}$ alkyl, and $C_{1-6}$ haloalkyl; wherein said $C_{1-6}$ alkyl is optionally substituted with 1, 2, 3, or 4 substituents independently selected from $R^g$;

each $R^{a6}$, $R^{c6}$ and $R^{d6}$, is independently selected from H, $C_{1-6}$ alkyl, and $C_{1-6}$ haloalkyl;

wherein said $C_{1-6}$ alkyl, is optionally substituted with 1, 2, 3, or 4 substituents independently selected from $R^g$;

each $R^{b6}$ is independently selected from $C_{1-6}$ alkyl, and $C_{1-6}$ haloalkyl; wherein said $C_{1-6}$ alkyl, is optionally substituted with 1, 2, 3, or 4 substituents independently selected from $R^g$; and each $R^g$ is independently selected from OH, CN, halo, $C_{1-6}$ alkyl, $C_{1-6}$ haloalkyl, $C_{3-6}$ cycloalkyl, $C_{1-6}$ alkoxy, $C_{1-6}$ haloalkoxy, $C_{1-3}$ alkoxy-$C_{1-3}$ alkyl, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, $C_{1-6}$ alkylthio, $C_{1-6}$ alkylsulfonyl, carboxy, $C_{1-6}$ alkylcarbonyl, $C_{1-6}$ alkoxycarbonyl, and $C_{1-6}$ alkylcarbonylamino.

48. The compound of claim 1, or a pharmaceutically acceptable salt thereof, wherein:

or a pharmaceutically acceptable salt thereof, wherein:

$Cy^1$ is selected from phenyl, pyridine-3-yl and pyrazol-4-yl; wherein the phenyl, pyridine-3-yl and pyrazol-4-yl of $Cy^1$ are each optionally substituted with 1 substituent selected from $R^{10}$;

R$^1$ is selected from Cl, C$_{1-3}$ alkyl, C$_{1-3}$ haloalkyl, cyclopropyl, azedinyl, hydroxymethyl, C$_{1-3}$ alkoxy, C$_{1-3}$ haloalkoxy and C$_{1-3}$ alkylamino; wherein the C$_{1-3}$ alkyl, C$_{1-3}$ haloalkyl, cyclopropyl, azedinyl, hydroxymethyl, C$_{1-3}$ alkoxy, C$_{1-3}$ haloalkoxy and C$_{1-3}$ alkylamino are each optionally substituted with 1, 2, 3, 4, 5, 6, or 7 deuteriums;

each R$^2$ is independently selected from C$_{1-3}$ alkyl, C$_{1-3}$ haloalkyl, C$_{3-6}$ cycloalkyl, F, Cl, CN, and OR$^{a2}$; wherein said C$_{1-3}$ alkyl, and C$_{3-6}$ cycloalkyl, are each optionally substituted with 1, 2 or 3 substituents independently selected from R$^{21}$;

or the R$^2$ substituents on the phenyl ring, taken together with the atoms to which they are attached, form a fused 5- or 6-membered cycloalkyl ring, or a fused 5- or 6-membered heterocycloalkyl ring; wherein each fused 5- or 6-membered heterocycloalkyl ring has at least one ring-forming carbon atom and 1 or 2 ring-forming O atoms; and wherein the fused 5- or 6-membered cycloalkyl ring, and the fused 5- or 6-membered heterocycloalkyl ring are each optionally substituted with 1 or 2 substituents independently selected from R$^{21}$;

n is 0;

each R$^{10}$ is independently selected from C$_{1-3}$ alkyl, C$_{1-3}$ haloalkyl, C$_{3-6}$ cycloalkyl, 4-10 membered heterocycloalkyl, 5-6 membered heteroaryl, 4-10 membered heterocycloalkyl-C$_{1-2}$ alkylene, 5-6 membered heteroaryl-C$_{1-2}$ alkylene, F, Cl, D, CN, OR$^{a1}$, C(O)NR$^{c1}$R$^{d1}$, and NR$^{c1}$R$^{d1}$; wherein said C$_{1-3}$ alkyl, C$_{3-6}$ cycloalkyl, 4-10 membered heterocycloalkyl, 5-6 membered heteroaryl, 4-10 membered heterocycloalkyl-C$_{1-2}$ alkylene, and 5-6 membered heteroaryl-C$_{1-2}$ alkylene are each optionally substituted with 1 or 2 substituents independently selected from R$^{11}$;

each R$^{11}$ is independently selected from C$_{1-3}$ alkyl, C$_{1-3}$ haloalkyl, C$_{3-6}$ cycloalkyl, 4-10 membered heterocycloalkyl, 5-6 membered heteroaryl, F, Cl, D, CN, OR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$S(O)$_2$R$^{b3}$, S(O)$_2$R$^{b3}$, and S(O)$_2$NR$^{c3}$R$^{d3}$; wherein said C$_{1-3}$ alkyl, C$_{3-6}$ cycloalkyl, 4-10 membered heterocycloalkyl, and 5-6 membered heteroaryl, are each optionally substituted with 1 or 2 substituents independently selected from R$^{12}$;

each R$^{12}$ is independently selected from C$_{1-3}$ alkyl, C$_{1-3}$ haloalkyl, C$_{3-6}$ cycloalkyl, 4-7 membered heterocycloalkyl, F, Cl, D, CN, OR$^{a5}$, C(O)R$^{b5}$, C(O)NR$^{c5}$R$^{d5}$, and NR$^{c5}$R$^{d5}$; wherein said C$_{1-3}$ alkyl, C$_{3-6}$ cycloalkyl, and 4-7 membered heterocycloalkyl, are each optionally substituted with 1 substituent independently selected from R$^g$;

R$^{21}$ is independently selected from C$_{1-3}$ alkyl, F, Cl, D, CN, and OR$^{a4}$; wherein said C$_{1-3}$ alkyl, is optionally substituted with 1 or 2 substituents independently selected from R$^{22}$;

each R$^{22}$ is independently selected from F, Cl, D, CN, and OR$^{a6}$;

each R$^{a1}$, R$^{c1}$ and R$^{d1}$ is independently selected from H, C$_{1-3}$ alkyl, C$_{1-3}$ haloalkyl, and 4-6 membered heterocycloalkyl; wherein said C$_{1-3}$ alkyl, and 4-6 membered heterocycloalkyl, are each optionally substituted with 1 substituent independently selected from R$^{11}$;

each R$^{a2}$ is independently selected from H, C$_{1-3}$ alkyl, and C$_{1-3}$ haloalkyl;

each R$^{a3}$, R$^{c3}$ and R$^{d3}$, is independently selected from H, C$_{1-3}$ alkyl, C$_{1-3}$ haloalkyl, C$_{3-6}$ cycloalkyl, and 4-6 membered heterocycloalkyl; wherein said C$_{1-3}$ alkyl C$_{3-6}$ cycloalkyl, and 4-6 membered heterocycloalkyl are each optionally substituted with 1 or 2 substituents independently selected from R$^{12}$;

or any R$^{c3}$ and R$^{d3}$ attached to the same N atom, together with the N atom to which they are attached, form a 4-, 5- or 6-membered heterocycloalkyl group optionally substituted with 1 or 2 substituents independently selected from R$^{12}$;

each R$^{b3}$ is independently selected from C$_{1-3}$ alkyl, C$_{1-3}$ haloalkyl, C$_{3-6}$ cycloalkyl, and 4-6 membered heterocycloalkyl; wherein said C$_{1-3}$ alkyl C$_{3-6}$ cycloalkyl, and 4-6 membered heterocycloalkyl, are each optionally substituted with 1 or 2 substituents independently selected from R$^{12}$;

each R$^{a4}$ is independently selected from H, C$_{1-3}$ alkyl, and C$_{1-3}$ haloalkyl;

each R$^{a5}$, R$^{c5}$ and R$^{d5}$, is independently selected from H, C$_{1-3}$ alkyl, and C$_{1-3}$ haloalkyl;

wherein said C$_{1-3}$ alkyl, is optionally substituted with 1 substituent independently selected from R$^g$;

each R$^{b5}$ is independently selected from C$_{1-3}$ alkyl, and C$_{1-3}$ haloalkyl; wherein said C$_{1-3}$ alkyl is optionally substituted with 1 substituents independently selected from R$^g$;

each R$^{a6}$ is independently selected from H, and C$_{1-3}$ alkyl; and each R$^g$ is independently selected from OH, CN, F, Cl, C$_{1-3}$ alkyl, and C$_{1-3}$ haloalkyl.

49. The compound of claim 1, selected from:

5-(2,3-dimethylphenyl)-6-methoxy-3-(1-methyl-1H-pyrazol-4-yl)-1H-pyrazolo[4,3-b]pyridine;

5-(2,3-dihydro-1H-inden-4-yl)-6-methoxy-3-(1-methyl-1H-pyrazol-4-yl)-1H-pyrazolo[4,3-b]pyridine;

5-(2,3-dimethylphenyl)-6-methoxy-3-(1-((1-methyl-1H-1,2,4-triazol-5-yl)methyl)-1H-pyrazol-4-yl)-1H-pyrazolo[4,3-b]pyridine;

5-(2,3-dihydrobenzofuran-7-yl)-6-methoxy-3-(1-methyl-1H-pyrazol-4-yl)-1H-pyrazolo[4,3-b]pyridine;

2-(3-(6-methoxy-3-(1-methyl-1H-pyrazol-4-yl)-1H-pyrazolo[4,3-b]pyridin-5-yl)-2-methylphenyl)acetonitrile;

1-(4-(5-(6-(difluoromethoxy)-5-(2,3-dimethylphenyl)-1H-pyrazolo[4,3-b]pyridin-3-yl)pyridin-2-yl)piperazin-1-yl)ethan-1-one;

4-(6-methoxy-3-(1-methyl-1H-pyrazol-4-yl)-1H-pyrazolo[4,3-b]pyridin-5-yl)-2,3-dihydro-1H-inden-1-ol;

4-(6-methoxy-3-(1-methyl-1H-pyrazol-4-yl)-1H-pyrazolo[4,3-b]pyridin-5-yl)-2,3-dihydro-1H-indene-1-carbonitrile;

4-(6-methoxy-3-(1-methyl-1H-pyrazol-4-yl)-1H-pyrazolo[4,3-b]pyridin-5-yl)-2,3-dihydro-1H-inden-2-ol;

(4-(6-methoxy-3-(1-methyl-1H-pyrazol-4-yl)-1H-pyrazolo[4,3-b]pyridin-5-yl)-2,3-dihydro-1H-inden-1-yl)methanol;

2-fluoro-4-(6-methoxy-3-(1-methyl-1H-pyrazol-4-yl)-1H-pyrazolo[4,3-b]pyridin-5-yl)-2,3-dihydro-1H-inden-1-ol;

5-(2,3-dihydro-1H-inden-4-yl)-6-methoxy-3-(1-(pyrrolidin-3-yl)-1H-pyrazol-4-yl)-1H-pyrazolo[4,3-b]pyridine;

5-(2,3-dihydro-1H-inden-4-yl)-3-(1-(1-ethylpyrrolidin-3-yl)-1H-pyrazol-4-yl)-6-methoxy-1H-pyrazolo[4,3-b]pyridine;

3-(4-(5-(2,3-dihydro-1H-inden-4-yl)-6-methoxy-1H-pyrazolo[4,3-b]pyridin-3-yl)-1H-pyrazol-1-yl)cyclobutanecarbonitrile;

5-(2,3-dihydro-1H-inden-4-yl)-6-methoxy-3-(1-(1-methylazetidin-3-yl)-1H-pyrazol-4-yl)-1H-pyrazolo[4,3-b]pyridine;

5-(2,3-dihydro-1H-inden-4-yl)-3-(1-(1-ethylazetidin-3-yl)-1H-pyrazol-4-yl)-6-methoxy-1H-pyrazolo[4,3-b]pyridine;
4-(4-(5-(2,3-dihydro-1H-inden-4-yl)-6-methoxy-1H-pyrazolo[4,3-b]pyridin-3-yl)-1H-pyrazol-1-yl)-N,N-dimethylpiperidine-1-carboxamide;
methyl 4-(4-(5-(2,3-dihydro-1H-inden-4-yl)-6-methoxy-1H-pyrazolo[4,3-b]pyridin-3-yl)-1H-pyrazol-1-yl)piperidine-1-carboxylate;
methyl 3-(4-(5-(2,3-dihydro-1H-inden-4-yl)-6-methoxy-1H-pyrazolo[4,3-b]pyridin-3-yl)-1H-pyrazol-1-yl)azetidine-1-carboxylate;
1-(3-(4-(5-(2,3-dihydro-1H-inden-4-yl)-6-methoxy-1H-pyrazolo[4,3-b]pyridin-3-yl)-1H-pyrazol-1-yl)azetidin-1-yl)ethan-1-one;
5-(2,3-dihydro-1H-inden-4-yl)-6-methoxy-3-(1-(1-(methylsulfonyl)azetidin-3-yl)-1H-pyrazol-4-yl)-1H-pyrazolo[4,3-b]pyridine;
3-(4-(5-(2,3-dihydro-1H-inden-4-yl)-6-methoxy-1H-pyrazolo[4,3-b]pyridin-3-yl)-1H-pyrazol-1-yl)-N,N-dimethylazetidine-1-carboxamide;
cyclopropyl(3-(4-(5-(2,3-dihydro-1H-inden-4-yl)-6-methoxy-1H-pyrazolo[4,3-b]pyridin-3-yl)-1H-pyrazol-1-yl)azetidin-1-yl)methanone;
5-(2,3-dihydro-1H-inden-4-yl)-6-ethoxy-3-(1-methyl-1H-pyrazol-4-yl)-1H-pyrazolo[4,3-b]pyridine;
5-(2,3-dihydro-1H-inden-4-yl)-6-methoxy-3-(1-(pyridin-4-ylmethyl)-1H-pyrazol-4-yl)-1H-pyrazolo[4,3-b]pyridine;
4-(2-(4-(5-(2,3-dihydro-1H-inden-4-yl)-6-methoxy-1H-pyrazolo[4,3-b]pyridin-3-yl)-1H-pyrazol-1-yl)ethyl)morpholine;
3-(1-cyclopropyl-1H-pyrazol-4-yl)-5-(2,3-dihydro-1H-inden-4-yl)-6-methoxy-1H-pyrazolo[4,3-b]pyridine;
3-(4-(5-(2,3-dihydro-1H-inden-4-yl)-6-methoxy-1H-pyrazolo[4,3-b]pyridin-3-yl)-1H-pyrazol-1-yl)propanenitrile;
2-(4-(5-(2,3-dihydro-1H-inden-4-yl)-6-methoxy-1H-pyrazolo[4,3-b]pyridin-3-yl)-1H-pyrazol-1-yl)ethan-1-ol;
5-(2,3-dihydro-1H-inden-4-yl)-6-methoxy-3-(1-(pyridin-4-yl)-1H-pyrazol-4-yl)-1H-pyrazolo[4,3-b]pyridine;
(trans)-4-(4-(5-(2,3-dihydro-1H-inden-4-yl)-6-methoxy-1H-pyrazolo[4,3-b]pyridin-3-yl)-1H-pyrazol-1-yl)cyclohexan-1-ol;
5-(2, 3-dimethylphenyl)-N-methyl-3-(1-methyl-1H-pyrazol-4-yl)-1H-pyrazolo[4,3-b]pyridin-6-amine;
6-(difluoromethyl)-5-(2,3-dihydro-1H-inden-4-yl)-3-(1-methyl-1H-pyrazol-4-yl)-1H-pyrazolo[4,3-b]pyridine;
(5-(2,3-dihydro-1H-inden-4-yl)-3-(1-methyl-1H-pyrazol-4-yl)-1H-pyrazolo[4,3-b]pyridin-6-yl)methanol;
5-(2,3-dihydro-1H-inden-4-yl)-N-methyl-3-(1-methyl-1H-pyrazol-4-yl)-1H-pyrazolo[4,3-b]pyridin-6-amine;
(5-(2,3-dimethylphenyl)-3-(1-methyl-1H-pyrazol-4-yl)-1H-pyrazolo[4,3-b]pyridin-6-yl)methanol;
4-(6-chloro-3-(1-methyl-1H-pyrazol-4-yl)-1H-pyrazolo[4,3-b]pyridin-5-yl)-2,3-dihydro-1H-inden-2-ol;
5-(2,3-dimethylphenyl)-6-methyl-3-(1-methyl-1H-pyrazol-4-yl)-1H-pyrazolo[4,3-b]pyridine;
5-(2,3-dimethylphenyl)-6-methoxy-3-(6-(4-methylpiperazin-1-yl)pyridin-3-yl)-1H-pyrazolo[4,3-b]pyridine;
5-(2,3-dimethylphenyl)-3-(6-(4-ethylpiperazin-1-yl)pyridin-3-yl)-6-methoxy-1H-pyrazolo[4,3-b]pyridine;
1-(4-(5-(5-(2,3-dimethylphenyl)-6-methoxy-1H-pyrazolo[4,3-b]pyridin-3-yl)pyridin-2-yl)piperazin-1-yl)ethan-1-one;
4-(5-(5-(2,3-dimethylphenyl)-6-methoxy-1H-pyrazolo[4,3-b]pyridin-3-yl)pyridin-2-yl)morpholine;
4-(5-(5-(2,3-dimethylphenyl)-6-methoxy-1H-pyrazolo[4,3-b]pyridin-3-yl)pyridin-2-yl)-1-methylpiperazin-2-one;
1-(5-(5-(2,3-dimethylphenyl)-6-methoxy-1H-pyrazolo[4,3-b]pyridin-3-yl)pyridin-2-yl)piperidin-4-ol;
(R)-5-(2,3-dimethylphenyl)-3-(6-(3,4-dimethylpiperazin-1-yl)pyridin-3-yl)-6-methoxy-1H-pyrazolo[4,3-b]pyridine;
5-(2,3-dimethylphenyl)-6-(methoxy-d3)-3-(6-(4-methylpiperazin-1-yl)pyridin-3-yl)-1H-pyrazolo[4,3-b]pyridine;
5-(2,3-dimethylphenyl)-6-methoxy-3-(6-((1S,4S)-5-methyl-2,5-diazabicyclo[2.2.1]heptan-2-yl)pyridin-3-yl)-1H-pyrazolo[4,3-b]pyridine;
1-(5-(5-(2,3-dimethylphenyl)-6-methoxy-1H-pyrazolo[4,3-b]pyridin-3-yl)pyridin-2-yl)-N,N-dimethylpiperidine-4-carboxamide;
1-(5-(5-(2,3-dimethylphenyl)-6-methoxy-1H-pyrazolo[4,3-b]pyridin-3-yl)pyridin-2-yl)-4-methylpiperidine-4-carboxylic acid;
3-(4-(5-(2-fluoro-3-methylphenyl)-6-methoxy-1H-pyrazolo[4,3-b]pyridin-3-yl)-1H-pyrazol-1-yl)-N,N-dimethylazetidine-1-carboxamide;
N-((cis)-4-(4-(5-(2,3-dihydro-1H-inden-4-yl)-6-methoxy-1H-pyrazolo[4,3-b]pyridin-3-yl)-1H-pyrazol-1-yl)cyclohexyl)acetamide;
5-(2,3-dihydro-1H-inden-4-yl)-3-(6-(2,4-dimethylpiperazin-1-yl)pyridin-3-yl)-6-methoxy-1H-pyrazolo[4,3-b]pyridine;
2-(3-(3-(6-(4-acetylpiperazin-1-yl)pyridin-3-yl)-6-methoxy-1H-pyrazolo[4,3-b]pyridin-5-yl)-2-methylphenyl)acetonitrile;
2-(3-(6-methoxy-3-(6-morpholinopyridin-3-yl)-1H-pyrazolo[4,3-b]pyridin-5-yl)-2-methylphenyl)acetonitrile;
5-(2,3-dihydro-1H-inden-4-yl)-6-methoxy-3-(6-(pyrrolidin-1-yl)pyridin-3-yl)-1H-pyrazolo[4,3-b]pyridine;
4-(5-(5-(2,3-dihydro-1H-inden-4-yl)-6-methoxy-1H-pyrazolo[4,3-b]pyridin-3-yl)pyridin-2-yl)morpholine;
4-(5-(5-(2,3-dihydro-1H-inden-4-yl)-6-methoxy-1H-pyrazolo[4,3-b]pyridin-3-yl)pyridin-2-yl)-N-ethylpiperazine-1-carboxamide;
4-(5-(5-(2,3-dihydro-1H-inden-4-yl)-6-methoxy-1H-pyrazolo[4,3-b]pyridin-3-yl)pyridin-2-yl)piperazine-1-carboxamide;
1-(4-(4-(5-(2,3-dihydro-1H-inden-4-yl)-6-methoxy-1H-pyrazolo[4,3-b]pyridin-3-yl)phenyl)piperazin-1-yl)ethan-1-one;
5-(2,3-dihydro-1H-inden-4-yl)-3-(4-(4-isopropylpiperazin-1-yl)phenyl)-6-methoxy-1H-pyrazolo[4,3-b]pyridine;
5-(2,3-dihydro-1H-inden-4-yl)-3-(4-(4-ethylpiperazin-1-yl)phenyl)-6-methoxy-1H-pyrazolo[4,3-b]pyridine;
1-(4-(5-(5-(2,3-dihydro-1H-inden-4-yl)-6-methoxy-1H-pyrazolo[4,3-b]pyridin-3-yl)pyridin-2-yl)piperazin-1-yl)ethan-1-one;
8-(5-(5-(2,3-dimethylphenyl)-6-methoxy-1H-pyrazolo[4,3-b]pyridin-3-yl)pyridin-2-yl)-1-oxa-3,8-diazaspiro[4.5]decan-2-one;
5-(2,3-dimethylphenyl)-6-methoxy-3-(1-(pyridin-2-ylmethyl)-1H-pyrazol-4-yl)-1H-pyrazolo[4,3-b]pyridine;
3-(1-cyclopropyl-1H-pyrazol-4-yl)-5-(2,3-dimethylphenyl)-6-methoxy-1H-pyrazolo[4,3-b]pyridine;
6-methoxy-5-(2-methyl-3-(methyl-d3)phenyl)-3-(6-(4-methylpiperazin-1-yl)pyridin-3-yl)-1H-pyrazolo[4,3-b]pyridine;

1-(4-(4-(5-(2,3-dimethylphenyl)-6-methoxy-1H-pyrazolo [4,3-b]pyridin-3-yl)-1H-pyrazol-1-yl)piperidin-1-yl) ethan-1-one;
methyl 4-(4-(5-(2,3-dimethylphenyl)-6-methoxy-1H-pyrazolo[4,3-b]pyridin-3-yl)-1H-pyrazol-1-yl)piperidine-1-carboxylate;
methyl 3-(4-(5-(2,3-dimethylphenyl)-6-methoxy-1H-pyrazolo[4,3-b]pyridin-3-yl)-1H-pyrazol-1-yl)azetidine-1-carboxylate; and
3-(4-(5-(2,3-dimethylphenyl)-6-methoxy-1H-pyrazolo[4,3-b]pyridin-3-yl)-1H-pyrazol-1-yl)-N,N-dimethylazetidine-1-carboxamide;
or a pharmaceutically acceptable salt of any of the aforementioned.

50. The compound of claim 1, selected from:
2-fluoro-4-(6-methoxy-3-(1-methyl-1H-pyrazol-4-yl)-1H-pyrazolo[4,3-b]pyridin-5-yl)-2,3-dihydro-1H-inden-1-ol;
5-(2,3-dimethylphenyl)-6-methoxy-3-(6-(4-methylpiperazin-1-yl)pyridin-3-yl)-1H-pyrazolo[4,3-b]pyridine;
4-(6-methoxy-3-(6-((tetrahydrofuran-3-yl)oxy)pyridin-3-yl)-1H-pyrazolo[4,3-b]pyridin-5-yl)-2,3-dihydro-1H-inden-2-ol;
4-(6-methoxy-3-(1-methyl-1H-pyrazol-4-yl)-1H-pyrazolo[4,3-b]pyridin-5-yl) 2,3-dihydro-1H-inden-2-d-2-ol;
4-(6-methoxy-3-(6-(1-methyl-5-oxopyrrolidin-3-yl)pyridin-3-yl)-1H-pyrazolo[4,3-b]pyridin-5-yl)-2,3-dihydro-1H-indene-1-carbonitrile;
(S)-1-(4-(5-(5-(2,3-dimethylphenyl)-6-methoxy-1H-pyrazolo[4,3-b]pyridin-3-yl)pyridin-2-yl)piperidin-1-yl)-2-hydroxypropan-1-one;
1-(4-(5-(5-(2,3-dimethylphenyl)-6-methoxy-1H-pyrazolo[4,3-b]pyridin-3-yl)pyridin-2-yl)piperidin-1-yl)-2-hydroxyethan-1-one;
4-(5-(5-(2,3-dimethylphenyl)-6-methoxy-1H-pyrazolo[4,3-b]pyridin-3-yl)pyridin-2-yl)cyclohexane-1-carboxylic acid;
(3S,4R)-1-(5-(5-(2,3-dimethylphenyl)-6-methoxy-1H-pyrazolo[4,3-b]pyridin-3-yl)pyridin-2-yl)-4-fluoropyrrolidin-3-amine;
(2S)-1-(4-(5-(5-(2-fluoro-2,3-dihydro-1H-inden-4-yl)-6-methoxy-1H-pyrazolo[4,3-b]pyridin-3-yl)pyridin-2-yl) piperidin-1-yl)-2-hydroxypropan-1-one;
1-(4-(5-(5-(2-fluoro-2,3-dihydro-1H-inden-4-yl)-6-methoxy-1H-pyrazolo[4,3-b]pyridin-3-yl)pyridin-2-yl) piperidin-1-yl)-2-hydroxyethan-1-one;
(7R,8aS)-2-(5-(5-(2-fluoro-2,3-dihydro-1H-inden-4-yl)-6-methoxy-1H-pyrazolo[4,3-b]pyridin-3-yl)pyridin-2-yl)octahydropyrrolo[1,2-a]pyrazin-7-ol;
5-(2-fluoro-2,3-dihydro-1H-inden-4-yl)-6-methoxy-3-(1-methyl-1H-pyrazol-4-yl)-1H-pyrazolo[4,3-b]pyridine;
(7S,8aR)-2-(5-(5-(2,3-dimethylphenyl)-6-methoxy-1H-pyrazolo[4,3-b]pyridin-3-yl)pyridin-2-yl)octahydropyrrolo[1,2-a]pyrazin-7-ol;
4-(5-(5-(2,3-dimethylphenyl)-6-methoxy-1H-pyrazolo[4,3-b]pyridin-3-yl)pyridin-2-yl)-1-imino-1W$^6$-thiomorpholine 1-oxide;
(7R,8aS)-2-(5-(5-(2,3-dimethylphenyl)-6-methoxy-1H-pyrazolo[4,3-b]pyridin-3-yl)pyridin-2-yl)octahydropyrrolo[1,2-a]pyrazin-7-ol;
(S)—N-(1-(5-(5-(2,3-dimethylphenyl)-6-methoxy-1H-pyrazolo[4,3-b]pyridin-3-yl)pyridin-2-yl)pyrrolidin-3-yl)-2-hydroxy-N-methylacetamide;
2-(3-(3-(6-(4-(2-hydroxyethyl)piperazin-1-yl)pyridin-3-yl)-6-methoxy-1H-pyrazolo[4,3-b]pyridin-5-yl)-2-methylphenyl)acetonitrile;
(7R,8aS)-2-(5-(6-methoxy-5-(3-methoxy-2-methylphenyl)-1H-pyrazolo[4,3-b]pyridin-3-yl)pyridin-2-yl)octahydropyrrolo[1,2-a]pyrazin-7-ol;
(7R,8aS)-2-(5-(5-(2,3-dihydrobenzo[b][1,4]dioxin-5-yl)-6-methoxy-1H-pyrazolo[4,3-b]pyridin-3-yl)pyridin-2-yl)octahydropyrrolo[1,2-a]pyrazin-7-ol;
(7R,8aS)-2-(5-(5-(2-cyclopropylphenyl)-6-methoxy-1H-pyrazolo[4,3-b]pyridin-3-yl)pyridin-2-yl)octahydropyrrolo[1,2-a]pyrazin-7-ol;
(7R,8aS)-2-(5-(5-(chroman-5-yl)-6-methoxy-1H-pyrazolo[4,3-b]pyridin-3-yl)pyridin-2-yl)octahydropyrrolo[1,2-a]pyrazin-7-ol;
(7R,8aS)-2-(5-(5-(2-fluoro-3-methylphenyl)-6-methoxy-1H-pyrazolo[4,3-b]pyridin-3-yl)pyridin-2-yl)octahydropyrrolo[1,2-a]pyrazin-7-ol;
4-(6-methoxy-3-(6-(2-methoxyethoxy)pyridin-3-yl)-1H-pyrazolo[4,3-b]pyridin-5-yl)-2,3-dihydro-1H-inden-2-ol;
4-(6-methoxy-3-(6-((tetrahydro-2H-pyran-4-yl)oxy)pyridin-3-yl)-1H-pyrazolo[4,3-b]pyridin-5-yl)-2,3-dihydro-1H-inden-2-ol;
4-(3-(6-cyclopropylpyridin-3-yl)-6-methoxy-1H-pyrazolo[4,3-b]pyridin-5-yl)-2,3-dihydro-1H-inden-2-ol; and
N-(1-(5-(5-(2,3-dimethylphenyl)-6-methoxy-1H-pyrazolo[4,3-b]pyridin-3-yl)pyridin-2-yl)azetidin-3-yl)-2-hydroxy-N-methylacetamide;
or a pharmaceutically acceptable salt of any of the aforementioned.

51. The compound of claim 1, selected from:
1-(4-(5-(5-(2,3-Dihydro-1H-inden-4-yl)-6-methoxy-1H-pyrazolo[4,3-b]pyridin-3-yl)pyridin-2-yl)piperidin-1-yl)ethan-1-one;
1-(4-(5-(5-(2, 3-Dihydro-1H-inden-4-yl)-6-methoxy-1H-pyrazolo[4,3-b]pyridin-3-yl)pyridin-2-yl)piperidin-1-yl)-2-hydroxyethan-1-one;
1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)-2-hydroxyethan-1-one (Peak 1);
1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)-2-hydroxyethan-1-one (Peak 2);
1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)ethan-1-one (Peak 1);
1-(3-(5-(5-(2,3-Dihydro-1H-inden-4-yl)-6-methoxy-1H-pyrazolo[4,3-b]pyridin-3-yl)pyridin-2-yl)pyrrolidin-1-yl)ethan-1-one (Peak 2);
3-(5-(5-(2,3-Dihydro-1H-inden-4-yl)-6-methoxy-1H-pyrazolo[4,3-b]pyridin-3-yl)pyridin-2-yl)-[1,3'-bipyrrolidin]-2'-one (Peak 1);
3-(5-(5-(2,3-Dihydro-1H-inden-4-yl)-6-methoxy-1H-pyrazolo[4,3-b]pyridin-3-yl)pyridin-2-yl)-1'-methyl-[1,3'-bipyrrolidin]-2'-one (Peak 1);
2-(3-(5-(5-(2,3-Dihydro-1H-inden-4-yl)-6-methoxy-1H-pyrazolo[4,3-b]pyridin-3-yl)pyridin-2-yl)pyrrolidin-1-yl)propanamide (Peak 1);
5-(2,3-Dihydro-1H-inden-4-yl)-6-methoxy-3-(6-(1-(methyl-L-prolyl)piperidin-4-yl)pyridin-3-yl)-1H-pyrazolo[4,3-b]pyridine;
(3-(5-(5-(2,3-Dihydro-1H-inden-4-yl)-6-methoxy-1H-pyrazolo[4,3-b]pyridin-3-yl)pyridin-2-yl)pyrrolidin-1-yl)((R)-4-methylmorpholin-3-yl)methanone (Peak 2);
4-(6-Methoxy-3-(6-(4-methylpiperazin-1-yl)pyridin-3-yl)-1H-pyrazolo[4,3-b]pyridin-5-yl)-2,3-dihydro-1H-indene-1-carbonitrile;

4-(3-(1-(3-Cyanocyclobutyl)-1H-pyrazol-4-yl)-6-methoxy-1H-pyrazolo[4,3-b]pyridin-5-yl)-2,3-dihydro-1H-indene-1-carbonitrile;
4-(3-(1-(1-Acetylpiperidin-4-yl)-1H-pyrazol-4-yl)-6-methoxy-1H-pyrazolo[4,3-b]pyridin-5-yl)-2,3-dihydro-1H-indene-1-carbonitrile;
4-(3-(6-(4-Hydroxycyclohexyl)pyridin-3-yl)-6-methoxy-1H-pyrazolo[4,3-b]pyridin-5-yl)-2,3-dihydro-1H-indene-1-carbonitrile;
4-(3-(6-(4-(2-Hydroxyethyl)piperazin-1-yl)pyridin-3-yl)-6-methoxy-1H-pyrazolo[4,3-b]pyridin-5-yl)-2,3-dihydro-1H-indene-1-carbonitrile;
4-(3-(6-(1-(2-Hydroxyacetyl)piperidin-4-yl)pyridin-3-yl)-6-methoxy-1H-pyrazolo[4,3-b]pyridin-5-yl)-2,3-dihydro-1H-indene-1-carbonitrile;
1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxyethan-1-one;
1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-3-(dimethylamino)propan-1-one;
(S)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(dimethylamino)propan-1-one;
(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-methylazetidin-2-yl)methanone;
1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(4-methylpiperazin-1-yl)ethan-1-one;
1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(4-hydroxypiperidin-1-yl)ethan-1-one;
(R)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-methylazetidin-2-yl)methanone;
(R)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxypropan-1-one;
(S)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-hydroxypropan-1-one;
(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((trans)-3-hydroxycyclobutyl)methanone;
(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((cis)-3-hydroxycyclobutyl)methanone;
(R)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(4-methylmorpholin-3-yl)methanone;
(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(4-methylmorpholin-3-yl)methanone;
(S)-1-(3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxyethan-1-one;
(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(tetrahydrofuran-2-yl)methanone;
(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(tetrahydrofuran-3-yl)methanone;
(R)-1-((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxypropan-1-one;
(S)-1-((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)-2-hydroxypropan-1-one;
(R)-1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-3-hydroxybutan-1-one;
(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1r,3r)-3-hydroxy-3-methylcyclobutyl)methanone;
(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1s,3s)-3-hydroxy-3-methylcyclobutyl)methanone;
((R)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((S)-4-methylmorpholin-3-yl)methanone;
((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((R)-4-methylmorpholin-3-yl)methanone;
(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-(hydroxymethyl)cyclobutyl)methanone;
(S)-(3-(4-(5-(2,3-dihydro-1H-inden-4-yl)-6-methoxy-1H-pyrazolo[4,3-b]pyridin-3-yl)-1H-pyrazol-1-yl)azetidin-1-yl)(1-ethylazetidin-2-yl)methanone;
(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-(2-fluoroethyl)azetidin-2-yl)methanone;
(S)-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)(1-isopropylazetidin-2-yl)methanone;
((S)-3-(4-(5-(2,3-dihydro-1H-inden-4-yl)-6-methoxy-1H-pyrazolo[4,3-b]pyridin-3-yl)-1H-pyrazol-1-yl)pyrrolidin-1-yl)((S)-1-(2-fluoroethyl)azetidin-2-yl)methanone;
((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((trans)-3-hydroxycyclobutyl)methanone;
((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((cis)-3-hydroxycyclobutyl)methanone;
((S)-3-(4-(5-(2,3-Dihydro-1H-inden-4-yl)-6-methoxy-1H-pyrazolo[4,3-b]pyridin-3-yl)-1H-pyrazol-1-yl)pyrrolidin-1-yl)((1s,3r)-3-hydroxy-3-methylcyclobutyl)methanone;
1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-methoxyethan-1-one;
1-(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)-2-(dimethylamino)-2-methylpropan-1-one;
1-(3-(4-(5-(2,3-Dihydro-1H-inden-4-yl)-6-methoxy-1H-pyrazolo[4,3-b]pyridin-3-yl)-1H-pyrazol-1-yl)azetidine-1-carbonyl)cyclopropane-1-carbonitrile;
2-((3-(4-(5-(2,3-Dihydro-1H-inden-4-yl)-6-methoxy-1H-pyrazolo[4,3-b]pyridin-3-yl)-1H-pyrazol-1-yl)azetidin-1-yl)sulfonyl)ethan-1-ol;
2-((3-(4-(5-(2,3-Dihydro-1H-inden-4-yl)-6-methoxy-1H-pyrazolo[4,3-b]pyridin-3-yl)-1H-pyrazol-1-yl)azetidin-1-yl)sulfonyl)-N,N-dimethylethan-1-amine;
2-Methoxyethyl 3-(4-(5-(2,3-dihydro-1H-inden-4-yl)-6-methoxy-1H-pyrazolo[4,3-b]pyridin-3-yl)-1H-pyrazol-1-yl)azetidine-1-carboxylate;
(3-(4-(5-(2,3-Dihydro-1H-inden-4-yl)-6-methoxy-1H-pyrazolo[4,3-b]pyridin-3-yl)-1H-pyrazol-1-yl)azetidin-1-yl)((1s,3s)-3-methoxycyclobutyl)methanone;

N-(3-(5-(5-(2,3-Dihydro-1H-inden-4-yl)-6-methoxy-1H-pyrazolo[4,3-b]pyridin-3-yl)pyridin-2-yl)cyclopentyl)-N-methylmethanesulfonamide;

N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxy-N-methylacetamide (Peak 1);

(2S)—N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxypropanamid;

N-(3-(5-(5-(2,3-Dihydro-1H-inden-4-yl)-6-methoxy-1H-pyrazolo[4,3-b]pyridin-3-yl)pyridin-2-yl)cyclopentyl)-2-hydroxyacetamide;

2-(1-(4-(5-(2,3-Dihydro-1H-inden-4-yl)-6-methoxy-1H-pyrazolo[4,3-b]pyridin-3-yl)phenyl)-3-azabicyclo[3.1.0]hexan-3-yl)ethan-1-ol;

4-(3-(4-((1R,5S)-3-(2-Hydroxyethyl)-3-azabicyclo[3.1.0]hexan-1-yl)phenyl)-6-methoxy-1H-pyrazolo[4,3-b]pyridin-5-yl)-2,3-dihydro-1H-indene-1-carbonitrile;

1-((5-(5-(2,3-Dihydro-1H-inden-4-yl)-6-methoxy-1H-pyrazolo[4,3-b]pyridin-3-yl)pyridin-2-yl)methyl)piperidin-4-ol;

5-((5-(5-(2,3-Dihydro-1H-inden-4-yl)-6-methoxy-1H-pyrazolo[4,3-b]pyridin-3-yl)pyridin-2-yl)methyl)-2-oxa-5-azabicyclo[2.2.1]heptane;

4-(1-(5-(5-(2,3-Dihydro-1H-inden-4-yl)-6-methoxy-1H-pyrazolo[4,3-b]pyridin-3-yl)pyridin-2-yl)ethyl)morpholine;

7-((5-(5-(2,3-Dihydro-1H-inden-4-yl)-6-methoxy-1H-pyrazolo[4,3-b]pyridin-3-yl)pyridin-2-yl)methyl)-5,6,7,8-tetrahydro-[1,2,4]triazolo[1,5-a]pyrazine;

4-(5-(5-(2,3-Dihydro-1H-inden-4-yl)-6-methoxy-1H-pyrazolo[4,3-b]pyridin-3-yl)pyridin-2-yl)-1-(2-hydroxyethyl)piperidine-4-carbonitrile;

4-(5-(5-(2,3-Dihydro-1H-inden-4-yl)-6-methoxy-1H-pyrazolo[4,3-b]pyridin-3-yl)pyridin-2-yl)-1-(2-hydroxyacetyl)piperidine-4-carbonitrile;

2-(3-(6-Methoxy-3-(6-(4-(2-methoxyethyl)piperazin-1-yl)pyridin-3-yl)-1H-pyrazolo[4,3-b]pyridin-5-yl)-2-methylphenyl)acetonitrile;

4-(6-Methoxy-3-(1-(1-(tetrahydro-2H-pyran-4-carbonyl)piperidin-4-yl-4-d)-1H-pyrazol-4-yl)-1H-pyrazolo[4,3-b]pyridin-5-yl)-2,3-dihydro-1H-indene-1-carbonitrile;

4-(6-Methoxy-3-(1-((S)-1-(2-methoxyacetyl)pyrrolidin-3-yl)-1H-pyrazol-4-yl)-1H-pyrazolo[4,3-b]pyridin-5-yl)-2,3-dihydro-1H-indene-1-carbonitrile;

4-(6-Methoxy-3-(1-((S)-1-((S)-tetrahydrofuran-2-carbonyl)pyrrolidin-3-yl)-1H-pyrazol-4-yl)-1H-pyrazolo[4,3-b]pyridin-5-yl)-2,3-dihydro-1H-indene-1-carbonitrile;

(7R,8aS)-2-(5-(5-(2,3-Dihydro-1H-inden-4-yl)-6-methoxy-1H-pyrazolo[4,3-b]pyridin-3-yl)pyridin-2-yl)octahydropyrrolo[1,2-a]pyrazin-7-ol;

N-(1-(5-(5-(2,3-Dihydro-1H-inden-4-yl)-6-methoxy-1H-pyrazolo[4,3-b]pyridin-3-yl)pyridin-2-yl)azetidin-3-yl)-2-hydroxy-N-methylacetamide;

(3-(5-(5-(2,3-Dihydro-1H-inden-4-yl)-6-methoxy-1H-pyrazolo[4,3-b]pyridin-3-yl)pyridin-2-yl)azetidin-1-yl)(tetrahydrofuran-2-yl)methanone;

(S)-(3-(5-(5-(2,3-Dihydro-1H-inden-4-yl)-6-methoxy-1H-pyrazolo[4,3-b]pyridin-3-yl)pyridin-2-yl)azetidin-1-yl)(1-methylpiperidin-2-yl)methanone;

1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-(dimethylamino)ethan-1-one;

1-(3-(5-(5-(2,3-Dihydro-1H-inden-4-yl)-6-methoxy-1H-pyrazolo[4,3-b]pyridin-3-yl)pyridin-2-yl)azetidin-1-yl)-3-hydroxypropan-1-one;

1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-hydroxyethan-1-one;

(S)-1-(3-(5-(5-(2,3-Dihydro-1H-inden-4-yl)-6-methoxy-1H-pyrazolo[4,3-b]pyridin-3-yl)pyridin-2-yl)azetidin-1-yl)-2-hydroxypropan-1-one;

N-(3-(5-(5-(2,3-Dihydro-1H-inden-4-yl)-6-methoxy-1H-pyrazolo[4,3-b]pyridin-3-yl)pyridin-2-yl)cyclobutyl)-2-hydroxy-N-methylacetamide;

1-(3-(5-(5-(2,3-Dihydro-1H-inden-4-yl)-6-methoxy-1H-pyrazolo[4,3-b]pyridin-3-yl)pyridin-2-yl)azetidin-1-yl-3-d)-2-hydroxyethan-1-one;

Methyl 4-(5-(5-(1-Cyano-2,3-dihydro-1H-inden-4-yl)-6-methoxy-1H-pyrazolo[4,3-b]pyridin-3-yl)pyridin-2-yl)piperidine-1-carboxylate;

4-(6-Methoxy-3-(6-(1-(morpholine-4-carbonyl)piperidin-4-yl)pyridin-3-yl)-1H-pyrazolo[4,3-b]pyridin-5-yl)-2,3-dihydro-1H-indene-1-carbonitrile, Peak 2;

4-(3-(6-(1-Acetylpiperidin-4-yl)pyridin-3-yl)-6-methoxy-1H-pyrazolo[4,3-b]pyridin-5-yl)-2,3-dihydro-1H-indene-1-carbonitrile, Peak 2;

4-(3-(6-(1-Acetylpyrrolidin-3-yl)pyridin-3-yl)-6-methoxy-1H-pyrazolo[4,3-b]pyridin-5-yl)-2,3-dihydro-1H-indene-1-carbonitrile;

4-(6-Methoxy-3-(6-(1-(morpholine-4-carbonyl)pyrrolidin-3-yl)pyridin-3-yl)-1H-pyrazolo[4,3-b]pyridin-5-yl)-2,3-dihydro-1H-indene-1-carbonitrile;

4-(3-(1-(Cyanomethyl)-1H-pyrazol-4-yl)-6-methoxy-1H-pyrazolo[4,3-b]pyridin-5-yl)-2,3-dihydro-1H-indene-1-carbonitrile;

4-(6-Methoxy-3-(6-(4-methylpiperazin-1-yl)pyridin-3-yl)-1H-pyrazolo[4,3-b]pyridin-5-yl)-2,3-dihydro-1H-indene-1-carbonitrile;

3-(3-(5-(5-(2,3-Dihydro-1H-inden-4-yl)-6-methoxy-1H-pyrazolo[4,3-b]pyridin-3-yl)pyridin-2-yl)azetidin-1-yl)propanenitrile;

N-(3-(5-(5-(2,3-Dihydro-1H-inden-4-yl)-6-methoxy-1H-pyrazolo[4,3-b]pyridin-3-yl)pyridin-2-yl)cyclobutyl)-2-methoxy-N-methylacetamide;

N-(3-(5-(5-(2,3-Dihydro-1H-inden-4-yl)-6-methoxy-1H-pyrazolo[4,3-b]pyridin-3-yl)pyridin-2-yl)cyclobutyl)-3-hydroxy-N-methylpropanamide;

(S)—N-(3-(5-(5-(2,3-Dihydro-1H-inden-4-yl)-6-methoxy-1H-pyrazolo[4,3-b]pyridin-3-yl)pyridin-2-yl)cyclobutyl)-2-hydroxy-N-methylpropanamide;

1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one;

(R) 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one, two enantiomers;

(S) 1-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)-2-hydroxyethan-1-one, two enantiomers;

(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)((R)-4-methylmorpholin-3-yl)methanone;

5-(2,3-Dihydro-1H-inden-4-yl)-6-methoxy-3-(6-(3-(tetrahydro-2H-pyran-4-yl)-3-azabicyclo[3.1.0]hexan-1-yl)pyridin-3-yl)-1H-pyrazolo[4,3-b]pyridine 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol;

(R) 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol, two enantiomers;

(S) 2-(1-(5-(5-(2,3-Dihydro-1H-inden-4-yl)-6-methoxy-1H-pyrazolo[4,3-b]pyridin-3-yl)pyridin-2-yl)-3-azabicyclo[3.1.0]hexan-3-yl)ethan-1-ol, two enantiomers;

3-(5-(5-(2,3-Dihydro-1H-inden-4-yl)-6-methoxy-1H-pyrazolo[4,3-b]pyridin-3-yl)pyridin-2-yl)-1-((R)-4-methylmorpholine-3-carbonyl)pyrrolidine-3-carbonitrile;

(R)-4-(5-(5-(2,3-Dihydro-1H-inden-4-yl)-6-methoxy-1H-pyrazolo[4,3-b]pyridin-3-yl)pyridin-2-yl)-1-(4-methylmorpholine-3-carbonyl)piperidine-4-carbonitrile;

1-(1-(4-(5-(2,3-Dihydro-1H-inden-4-yl)-6-methoxy-1H-pyrazolo[4,3-b]pyridin-3-yl)-1H-pyrazol-1-yl)-3-azabicyclo[3.1.0]hexan-3-yl)-2-hydroxyethan-1-one;

3-(5-(5-(2,3-Dihydro-1H-inden-4-yl)-6-methoxy-1H-pyrazolo[4,3-b]pyridin-3-yl)pyridin-2-yl)-1-(2-hydroxyacetyl)pyrrolidine-3-carbonitrile;

(S)-4-((5-(5-(2,3-Dihydro-1H-inden-4-yl)-6-methoxy-1H-pyrazolo[4,3-b]pyridin-3-yl)pyridin-2-yl)methyl)-1,3-dimethylpiperazin-2-one; and (1R,4R)-5-((5-(5-(2,3-Dihydro-1H-inden-4-yl)-6-methoxy-1H-pyrazolo[4,3-b]pyridin-3-yl)pyridin-2-yl)methyl)-2-oxa-5-azabicyclo[2.2.1]heptane;

or a pharmaceutically acceptable salt of any of the aforementioned.

52. A pharmaceutical composition comprising a compound of claim 1 or a pharmaceutically acceptable salt thereof, and a pharmaceutically acceptable carrier or excipient.

* * * * *